(12) United States Patent
Weisser et al.

(10) Patent No.: US 12,215,166 B2
(45) Date of Patent: *Feb. 4, 2025

(54) BISPECIFIC ANTIGEN BINDING CONSTRUCTS TARGETING HER2

(71) Applicant: ZYMEWORKS BC INC., Vancouver (CA)

(72) Inventors: Nina E. Weisser, Delta (CA); Gordon Yiu Kon Ng, Vancouver (CA); Grant Raymond Wickman, Vancouver (CA); Surjit Bhimarao Dixit, Richmond (CA); Eric Escobar-Cabrera, Vancouver (CA); Mario Sanches, Vancouver (CA)

(73) Assignee: Zymeworks BC Inc., Vancouver (CA)

( * ) Notice: Subject to any disclaimer, the term of this patent is extended or adjusted under 35 U.S.C. 154(b) by 28 days.

This patent is subject to a terminal disclaimer.

(21) Appl. No.: 17/728,491

(22) Filed: Apr. 25, 2022

(65) Prior Publication Data

US 2023/0118302 A1 Apr. 20, 2023

Related U.S. Application Data

(60) Continuation of application No. 16/011,048, filed on Jun. 18, 2018, now Pat. No. 11,325,981, which is a continuation of application No. 15/863,464, filed on Jan. 5, 2018, now Pat. No. 10,000,576, which is a division of application No. 15/036,176, filed as application No. PCT/CA2014/051140 on Nov. 27, 2014, now Pat. No. 10,947,319.

(60) Provisional application No. 62/009,125, filed on Jun. 6, 2014, provisional application No. 62/000,908, filed on May 20, 2014, provisional application No. 61/910,026, filed on Nov. 27, 2013.

(51) Int. Cl.
| | | |
|---|---|---|
| *C07K 16/32* | (2006.01) | |
| *A61K 39/395* | (2006.01) | |
| *A61K 45/06* | (2006.01) | |
| *A61K 47/68* | (2017.01) | |
| *C07K 16/30* | (2006.01) | |
| *G01N 33/574* | (2006.01) | |
| *A61K 39/00* | (2006.01) | |

(52) U.S. Cl.
CPC ........ *C07K 16/32* (2013.01); *A61K 39/39558* (2013.01); *A61K 45/06* (2013.01); *A61K 47/68033* (2023.08); *A61K 47/6851* (2017.08); *A61K 47/6855* (2017.08); *A61K 47/6869* (2017.08); *C07K 16/3015* (2013.01); *C07K 16/3069* (2013.01); *G01N 33/57492* (2013.01); *A61K 2039/505* (2013.01); *C07K 2317/24* (2013.01); *C07K 2317/31* (2013.01); *C07K 2317/35* (2013.01); *C07K 2317/41* (2013.01); *C07K 2317/52* (2013.01); *C07K 2317/524* (2013.01); *C07K 2317/526* (2013.01); *C07K 2317/55* (2013.01); *C07K 2317/622* (2013.01); *C07K 2317/73* (2013.01); *C07K 2317/732* (2013.01); *C07K 2317/77* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,194,551 A | 3/1993 | Clavier | |
| 5,571,894 A | 11/1996 | Wels et al. | |
| 5,587,458 A | 12/1996 | King et al. | |
| 5,624,821 A | 4/1997 | Winter et al. | |
| 5,731,168 A | 3/1998 | Carter et al. | |
| 5,737,056 A | 4/1998 | Martin | |
| 5,807,706 A | 9/1998 | Carter et al. | |
| 5,821,333 A | 10/1998 | Carter et al. | |
| 5,821,337 A * | 10/1998 | Carter ..................... | A61P 35/00 530/387.3 |
| 5,885,573 A | 3/1999 | Bluestone et al. | |
| 5,937,158 A | 8/1999 | Uranaka | |
| 5,968,509 A | 10/1999 | Gorman et al. | |
| 6,054,297 A * | 4/2000 | Carter ..................... | G06F 15/00 435/69.6 |
| 6,331,415 B1 | 12/2001 | Cabilly et al. | |
| 6,627,196 B1 | 9/2003 | Baughman et al. | |
| 6,809,185 B1 | 10/2004 | Schoonjans et al. | |
| 6,949,245 B1 | 9/2005 | Sliwkowski | |

(Continued)

FOREIGN PATENT DOCUMENTS

| | | |
|---|---|---|
| EP | 0368684 A1 | 5/1990 |
| RU | 2420537 C2 | 6/2011 |

(Continued)

OTHER PUBLICATIONS

Von Kreudenstein et al (mAbs, 2013, 5:646-654; published online Jul. 8, 2013) (IDS).*

(Continued)

*Primary Examiner* — Laura B Goddard

(74) *Attorney, Agent, or Firm* — DLA Piper LLP (US)

(57) ABSTRACT

Provided herein are biparatopic antigen-binding constructs that specifically bind HER2. The biparatopic antigen-binding constructs comprise one antigen-binding moiety that binds to ECD2 of HER2, a second antigen-binding moiety that binds to ECD4 of HER2, and an Fc. At least one of the antigen-binding moieties is an scFv. The biparatopic antigen-binding constructs can be used in the treatment of cancer.

23 Claims, 70 Drawing Sheets

Specification includes a Sequence Listing.

(56) References Cited

U.S. PATENT DOCUMENTS

| | | | |
|---|---|---|---|
| 7,183,076 B2 | 2/2007 | Arathoon et al. | |
| 7,498,142 B2 | 3/2009 | Yarden et al. | |
| 7,635,472 B2 | 12/2009 | Kufer et al. | |
| 7,642,228 B2 | 1/2010 | Carter et al. | |
| 7,695,936 B2 | 4/2010 | Carter et al. | |
| 7,862,817 B2 | 1/2011 | Adams et al. | |
| 7,923,221 B1 | 4/2011 | Cabilly et al. | |
| 7,951,917 B1 | 5/2011 | Arathoon | |
| 8,193,322 B2 | 6/2012 | Yan et al. | |
| 8,592,562 B2 | 11/2013 | Kannan et al. | |
| 8,609,095 B2 | 12/2013 | Pedersen et al. | |
| 8,771,988 B2 | 7/2014 | Goepfert et al. | |
| 9,499,634 B2 | 11/2016 | Dixit et al. | |
| 9,574,010 B2 | 2/2017 | Von Kreudenstein et al. | |
| 10,000,576 B1 | 6/2018 | Weisser et al. | |
| 2003/0086924 A1 | 5/2003 | Sliwkowski | |
| 2004/0071696 A1 | 4/2004 | Adams et al. | |
| 2004/0110226 A1 | 6/2004 | Lazar et al. | |
| 2005/0027109 A1 | 2/2005 | Mezo et al. | |
| 2006/0165702 A1 | 7/2006 | Allison et al. | |
| 2007/0196363 A1 | 8/2007 | Arathoon et al. | |
| 2007/0274985 A1 | 11/2007 | Dubel et al. | |
| 2008/0050370 A1 | 2/2008 | Glaser et al. | |
| 2009/0010840 A1 | 1/2009 | Adams et al. | |
| 2009/0162360 A1 | 6/2009 | Klein et al. | |
| 2009/0182127 A1 | 8/2009 | Kjaergaard et al. | |
| 2009/0232811 A1 | 9/2009 | Klein et al. | |
| 2009/0263392 A1 | 10/2009 | Igawa et al. | |
| 2010/0104564 A1 | 4/2010 | Hansen et al. | |
| 2010/0105874 A1 | 4/2010 | Schuurman et al. | |
| 2010/0166749 A1 | 7/2010 | Presta | |
| 2010/0196265 A1 | 8/2010 | Adams et al. | |
| 2010/0256338 A1 | 10/2010 | Brinkmann et al. | |
| 2010/0286374 A1 | 11/2010 | Kannan et al. | |
| 2010/0322934 A1 | 12/2010 | Imhof-Jung et al. | |
| 2010/0331527 A1 | 12/2010 | Davis et al. | |
| 2011/0008345 A1 | 1/2011 | Ashman et al. | |
| 2011/0059090 A1 | 3/2011 | Revets et al. | |
| 2011/0117097 A1 | 5/2011 | Kao et al. | |
| 2011/0275787 A1 | 11/2011 | Kufer et al. | |
| 2011/0287009 A1 | 11/2011 | Scheer et al. | |
| 2011/0293613 A1 | 12/2011 | Brinkmann et al. | |
| 2012/0076728 A1 | 3/2012 | Wu et al. | |
| 2012/0149876 A1 | 6/2012 | Von Kreudenstein et al. | |
| 2012/0244578 A1 | 9/2012 | Kannen et al. | |
| 2012/0270801 A1 | 10/2012 | Frejd et al. | |
| 2013/0078249 A1 | 3/2013 | Ast et al. | |
| 2013/0171148 A1 | 7/2013 | De Goeij et al. | |
| 2013/0189271 A1 | 7/2013 | De Goeij et al. | |
| 2013/0195849 A1 | 8/2013 | Von Kreudenstein et al. | |
| 2013/0216523 A1 | 8/2013 | Wallweber et al. | |
| 2013/0245233 A1 | 9/2013 | Lei et al. | |
| 2014/0051835 A1 | 2/2014 | Dixit et al. | |
| 2014/0199294 A1 | 7/2014 | Mimoto et al. | |
| 2014/0322217 A1* | 10/2014 | Moore | C07K 16/2896 435/69.6 |
| 2017/0158779 A1 | 6/2017 | Dixit et al. | |
| 2017/0355779 A1 | 12/2017 | Wickman et al. | |
| 2018/0016347 A1 | 1/2018 | Von Kreudenstein et al. | |
| 2018/0273635 A1 | 9/2018 | Escobar-Cabrera et al. | |
| 2018/0282429 A1 | 10/2018 | Weisser et al. | |
| 2020/0087414 A1 | 3/2020 | Kreudenstein et al. | |

FOREIGN PATENT DOCUMENTS

| | | | | |
|---|---|---|---|---|
| WO | WO 1994/004690 A1 | 3/1994 | | |
| WO | WO 1996/026964 A1 | 9/1996 | | |
| WO | WO 1997/034631 A1 | 9/1997 | | |
| WO | WVO 1999/058572 A1 | 11/1999 | | |
| WO | WO 2001/00245 A2 | 1/2001 | | |
| WO | WO-0100245 A2 * | 1/2001 | ........... | A61K 31/282 |
| WO | WO 2004/029207 A2 | 4/2004 | | |
| WO | WO 2004/032961 A1 | 4/2004 | | |
| WO | WO 2007/093630 A1 | 8/2007 | | |
| WO | WO 2007/110205 A2 | 10/2007 | | |
| WO | WO 2009/068625 A2 | 6/2009 | | |
| WO | WO 2009/068631 A1 | 6/2009 | | |
| WO | WO 2009/088805 A2 | 7/2009 | | |
| WO | WO 2009/089004 A1 | 7/2009 | | |
| WO | WO 2009/111707 A1 | 9/2009 | | |
| WO | WO 2009/134776 A2 | 11/2009 | | |
| WO | WO 2009/154651 A1 | 12/2009 | | |
| WO | WO 2010/085682 A2 | 7/2010 | | |
| WO | WO 2010/115553 A1 | 10/2010 | | |
| WO | WO 2011/005621 A1 | 1/2011 | | |
| WO | WO 2011/028952 A1 | 3/2011 | | |
| WO | WO 2011/117330 | 9/2011 | | |
| WO | WO 2011/133886 A2 | 10/2011 | | |
| WO | WO 2011/143545 A1 | 11/2011 | | |
| WO | WO 2011/147982 A2 | 12/2011 | | |
| WO | WO 2011/147986 A1 | 12/2011 | | |
| WO | WO 2012/006635 A1 | 1/2012 | | |
| WO | WO 2012/058768 A1 | 5/2012 | | |
| WO | WO 2012/131555 | 10/2012 | | |
| WO | WO 2012/143524 A2 | 10/2012 | | |
| WO | WO-2012143523 A1 * | 10/2012 | ........... | A61K 39/395 |
| WO | WO 2013/002362 A1 | 1/2013 | | |
| WO | WO 2013/055958 | 4/2013 | | |
| WO | WO 2013/135588 A1 | 9/2013 | | |
| WO | WO 2013/063702 A1 | 10/2013 | | |
| WO | WO 2013/166604 A1 | 11/2013 | | |
| WO | WO 2014/004586 | 1/2014 | | |
| WO | WO 2014/060365 A1 | 4/2014 | | |
| WO | WO 2014/083208 A1 | 6/2014 | | |
| WO | WO 2014/144722 A2 | 9/2014 | | |
| WO | WO 2015/077891 | 6/2015 | | |
| WO | WO 2015/091738 A1 | 6/2015 | | |
| WO | WO 2016/082044 A1 | 6/2016 | | |
| WO | WO 2016/179707 A1 | 11/2016 | | |
| WO | WO 2017/185177 A1 | 11/2017 | | |

OTHER PUBLICATIONS

U.S. Appl. No. 15/355,019 Non-Final Office Action dated Jan. 8, 2019.

U.S. Appl. No. 15/355,019 Notice of Allowance dated Jul. 29, 2019.

U.S. Appl. No. 15/355,019 Notice of Allowance dated May 22, 2018.

Adams et al., "Humanization of a Recombinant Monoclonal Antibody to Produce a Therapeutic HER Dimerization Inhibitor, Pertuzumab," Cancer Immunol Immunother, 2006, pp. 717-727, vol. 55, No. 6.

Australian Notice of Acceptance for Australian Patent Application No. Au2014357292 dated Jun. 10, 2020 3 pages.

Bargou et al. "Tumor Regression in Cancer Patients by Very Low Doses of a T Cell-Engaging Antibody" Science Aug. 15, 2008 pp. 974-977 vol. 321.

Bendig "Humanization of Rodent Monoclonal Antibodies by CDR Grafting" Methods: A Companion to Methods in Enzymology 1995; 8:83-93.

Bohua et al., "Bispecific Antibody to ErbB2 Overcomes Trastuzumab Resistance through Comprehensive Blockade of ErbB2 Heterodimerization," Cancer Research, vol. 73, No. 21, pp. 6471-6483, Sep. 17, 2013.

Brodowicz et al., "Soluble HER-2/Neu Neutralizes Biologic Effects Of Anti-HER-2/Neu Antibody on Breast Cancer Cells In Vitro," Int. J. Cancer, 1997, pp. 875-879, vol. 73.

Brown et al. "Tolerance to Single but not Multiple Amino Acid Replacements in Antibody VHCDR2" The Journal of Immunology 1996 156:3285-3291.

Bunn et al., "Expression of Her-2/neu in Human Lung Cancer Cell Lines by Immunohistochemistry and Fluorescence in Situ Hybridization and its Relationship to in Vitro Cytotoxicity by Trastuzumab and Chemotherapeutic Agents," Clinical Cancer Research, Oct. 2001, pp. 3239-3250, vol. 7.

Campiglio et al., "Inhibition of Proliferation and Induction of Apoptosis in Breast Cancer Cells by the Epidermal Growth Factor Receptor (EGFR) Tyrosine Kinase Inhibitor ZD1839 ('Iressa') is

(56) References Cited

OTHER PUBLICATIONS

Independent of EGFR Expression Level," Journal of Cellular Physiology, Feb. 2004, pp. 259-268, vol. 198, No. 2.
Carter et al., "Humanization of an Anti-p18SHERz Antibody for Human Cancer Therapy," Proc. Natl. Acad. Sci. USA, May 15, 1992, pp. 4285-4289, vol. 89, No. 10.
Casset et al. "A peptide mimetic of an anti-CD4 monoclonal antibody by rational design" BBRC 2003 307: 198-205.
Cavazzoni et al., "Combined Use of Anti-ErbB Monoclonal Antibodies and Erlotinib Enhances Antibody-Dependent Cellular Cytotoxicity of Wild-Type Erlotinib-Sensitive NSCLC Cell Lines," Molecular Cancer, 2012, pp. 91-115, vol. 11.
Chavez-Blanco et al., "HER2 Expression in Cervical Cancer as a Potential Therapeutic Target," BMC Cancer, 2004, pp. 1-6, vol. 4:59.
Chinese Office Action for Chinese Application No. 201480074300.2 dated Apr. 2, 2020 with English Translation 19 pages.
Chmielewski et al., "T Cell Activation by Antibody-Like Immunoreceptors: Increase in Affinity of the Single-Chain Fragment Domain Above Threshold Does Not Increase T Cell Activation Against Antigen-Positive Target Cells but Decreases Selectivity," The Journal of Immunology, Dec. 15, 2004, pp. 7647-7653, vol. 173, No. 12.
Cho et al., "Structure of the Extracellular Region of HER2 Alone and in Complex with the Herceptin Fab," Nature, Feb. 13, 2003, pp. 756-760, vol. 421, No. 6924.
Coldren et al., "Baseline Gene Expression Predicts Sensitivity to Gefitinib in Non-Small Cell Lung Cancer Cell Lines," Mol Cancer Res., Jul. 28, 2006, pp. 521-528, vol. 4, No. 8.
Collins et al., "Trastuzumab Induces Antibody-Dependent Cell-Mediated Cytotoxicity (ADCC) in HER-2-Non Amplifiedbreast Cancer Cell Lines," Annals Oncology, 2001, pp. 1788-1795, vol. 23.
Colman "Effects of amino acid sequence changes on antibody-antigen interactions" Research in Immunology1994 vol. 145: pp. 33-36.
Cretella et al., "Trastuzumab Emtansine is Active on HER-2 Overexpressing NSCLC Cell Lines and Overcomes Gefitinib Resistance," Molecular Cancer, 2014, pp. 143-155, vol. 13.
Davis et al. "SEEDbodies: fusion proteins based on a strand-exchange engineered domain (SEED) Ch3 heterodimers in an Fc analogue platform for asymmetric binders or immunofusions and bispecific antibodies" Protein Engineering Design & Selection Feb. 4, 2010 pp. 195-202 vol. 23 No. 4.
Decision to Grant Patent Application for Japanese Patent Application No. 2019-105971.
Franklin et al., "Insights into ErbB Signaling from the Structure of the ErbB2-Pertuzumab Complex," Cancer Cell, Apr. 2004, pp. 317-328, vol. 5.
Fujimoto-Ouchi et al., "Antitumor Activity of Trastuzumab in Combination with Chemotherapy in Human Gastric Cancer Xenograft Models," Cancer Chemother Pharmacol, 2007, pp. 795-805, vol. 59.
Gaborit et al., "Time-Resolved Fluorescence Resonance Energy Transfer (TRFRET) to Analyze the Disruption of EGFR/HER2 Dimers: a New Method to Evaluate the Efficiency of Targeted Therapy Using Monoclonal Antibodies," The Journal of Biological Chemistry, Apr. 1, 2011, pp. 11337-11345, vol. 286, No. 13.
Garrett et al., "The Crystal Structure of a Truncated ErbB2 Ectodomain Reveals an Active Conformation, Poised to Interact with Other ErbB Receptors," Molecular Cell, Feb. 2003, pp. 495-505, vol. 11, No. 2.
Ghasemi et al., "Dual Targeting of ErbB-2/ErbB-3 Results in Enhanced Antitumor Activity in Preclinical Models of Pancreatic Cancer," Oncogenesis, 2014, pp. 1-6, vol. 3.8, e117.
Grazette et al., "Inhibition of ErbB2 Causes Mitochondrial Dysfunction in Cardiomyocytes," Journal of the American College of Cardiology, Dec. 7, 2004, pp. 2231-2238, vol. 44, No. 11.
Hayashi et al., :MP28-14: Targeting HER2 with Trastuzumab-DM1 (T-DM1) in HER2-overexpressing Bladder Cancer, Journal of Urology, May 18, 2014, 191 (4S) Supplement: e301.
Hendriks et al., "Impact of Tumor HER2/ERBB2 Expression Level on HER-Targeted Liposomal Doxorubicin-Mediated Drug Delivery: Multiple Low-Affinity Interactions Lead to a Threshold Effect," Molecular Cancer Therapeutics, Sep. 2013, pp. 1816-1828, vol. 12, No. 9.
HER2: Basic Research, Prognosis and Therapy, Yarden, Y, (ed.), IOS Press, 2000, 162 pages.
Indian Examination Report for Indian Application No. 201647021238 dated Mar. 3, 2020 8 pages.
Japanese Office Action for Japanese Patent Application No. 2017-528442 dated Nov. 8, 2019 with English translation 6 pages.
Jost et al., "Structural Basis for Eliciting a Cytotoxic Effect in HER2-Overexpressing Cancer Cells Via Binding to the Extracellular Domain of HER2," Structure, Nov. 5, 2013, pp. 1979-1991, vol. 21.
Khantasup et al. "Design and Generation of Humanized Single-chain Fv Derived from Mouse Hybridoma for Potential Targeting Application" Monoclonal Antibodies in Immunodiagnosis and Immunotherapy 2015 34(6): 404-417.
Kimura et al., "Antitumor Effect of Trastuzumab for Pancreatic Cancer with High HER-2 Expression and Enhancement of Effect by Combined Therapy with Gemcitabine," Clin Cancer Res, Aug. 15, 2006, pp. 4925-4932, vol. 12, No. 16.
Komoto et al., "In Vitro and In Vivo Evidence That a Combination of Lapatinib plus S-1 is a Promising Treatment for Pancreatic Cancer—Komoto," Cancer Science, Wiley Online Libra., Feb. 2010, pp. 468-473, vol. 101, No. 2.
Kontermann, "Dual Targeting Strategies with Bispecific Antibodies," mAbs, 2012, pp. 182-197, vol. 4, No. 2.
Kuwada et al., "Effects of Trastuzumab on Epidermal Growth Factor Receptor-Dependent and -Independent Human Colon Cancer Cells," Int J Cancer, 2004, pp. 291-301, vol. 109.
Labrijn et al. "Efficient Generation of Stable Bispecific IgG1 by Controlled Fab-Arm Exchange," Proc. Natl. Acad. Sci. USA, Mar. 26, 2013, pp. 5145-5150, vol. 110, No. 13.
Larbouret et al., "In Pancreatic Carcinoma, Dual EGFR/HER2 Targeting with Cetuximab/Trastuzumab Is More Effective than Treatment with Trastuzumab/ Erlotinib or Lapatinib Alone: Implication of Receptors' Down-Regulation and Dimers' Disruption," Neoplasia, Feb. 2012, pp. 121-130, vol. 14, No. 2.
Lazar et al. "Chapter 15: Engineering the Antibody Fc Region for Optimal Effector Function Therapeutic Monoclonal Antibodies: From Bench to Clinic" Z. An ed. John Wiley & Sons 2009 pp. 349-370.
Lehmann et al., "Identification of Human Triple-Negative Breast Cancer Subtypes and Preclinical Models for Selection of Targeted Therapies," The Journal of Clinical Investigation, 2011, pp. 2750-2767, vol. 121, No. 7.
Li et al. "Genomic Analysis of Head and Neck Squamous Cell Carcinoma Cell Lines and Human Tumors: A Rational Approach to Preclinical Model Selection," Mol Cancer Res, Apr. 2014, pp. 571-582, vol. 12, No. 4.
Li et al., "Bispecific Antibody to ErbB2 Overcomes Trastuzumab Resistance Through Comprehensive Blockade of ErbB2 Heterodimerization," Cancer Research, Sep. 17, 2013, pp. 6471-6483, vol. 73, No. 21.
Ma et al., "HER2 as a Promising Target for Cytotoxicity T Cells in Human Melanoma Therapy," PLOS One, Aug. 2013, pp. e73261-e73261, vol. 8, Issue 8.
MacCallum et al., "Antibody-Antigen Interactions: Contact Analysis and Binding Site Topography," J. Mol. Biol., 1996, pp. 732-745, vol. 262.
Makhja et al., "Clinical Activity of Gemcitabine Plus Pertuzumab in Platinum-Resistant Ovarian Cancer, Fallopian Tube Cancer, or Primary Peritoneal Cancer," Journal ofClincal Oncology, Mar. 1, 2010, pp. 1215-1223, vol. 28, No. 7.
McDonagh et al., "Antitumor Activity of a Novel Bispecific Antibody That Targets the ErbB2/ErbB3 Oncogenic Unit and Inhibits Heregulin-Induced Activation of ErbB3," Molecular Cancer Therapeutics, Mar. 2012, pp. 582-593, vol. 11, No. 3.
Meira et al., "Combination of Cetuximab with Chemoradiation, Trastuzumab or MAPK Inhibitors: Mechanisms of Sensitisation of Cervical Cancer Cells," British Journal of Cancer, 2009, pp. 782-791, vol. 101.

(56) References Cited

OTHER PUBLICATIONS

Mexican Office Action for Mexican Application No. MX/a/2016006572 dated Jun. 1, 2020 with English Translation 7 pages.
Nordstrom, "Anti-Tumor Activity and Toxicokinetics Analysis of MGAH22, and anti-HER2 Monoclonal Antibody with Enhanced Fe-Gamma Receptor Binding Properties," Breast Cancer Research, Nov. 30, 2011, pp. 1-14, vol. 13, No. 6, R123.
Ohno et al. "Antigen-binding specificities of antibodies are primarily determined by seven residues of VH" Proc. Natl. Acad. Sci. USA May 1985 vol. 82: pp. 2945-2949.
Patent Cooperation Treaty International Preliminary Report on Patentability International Patent Application No. PCT/CA2014/051140 Jun. 9, 2016.
Patent Cooperation Treaty International Search Report and Written Opinion of the International Searching Authority International Patent Application No. PCT/CA2015/051238 Feb. 15, 2016 13 Pages.
Patent Cooperation Treaty International Search Report and Written Opinion of the International Searching Authority International Patent Application No. PCT/CA2016/050546 Aug. 4, 2016 22 pages.
Patent Cooperation Treaty International Search Report and Written Opinion of the International Searching Authority International Patent Application No. PCT/CA2017/050507 Aug. 16, 2017.
Patent Cooperation Treaty, International Search Report and Written Opinion of the International Searching Authority, International Patent Application No. PCT/US2014/051140, Feb. 18, 2015, 18 Pages.
Paul Fundamental Immunology 3rd Edition 1993 pp. 292-295.
PCT/CA2014/051140 International Preliminary Report on Patentability issued Jun. 9, 2016.
Phillips et al., "Dual Targeting of HER2-Positive Cancer with Trastuzumab-Emtansine (T-DM1) and Pertuzumab: Critical Role for Neuregulin Blockade in Anti-Tumor Response to Combination Therapy," Clinical Cancer Research, Jan. 15, 2014, pp. 456-468, vol. 20, No. 2.
Plowman et al. "Ligand-Specific Activation of HER4/p180erbs4, a Fourth Member of the Epidermal Growth Factor Receptor Family," Proc. Natl. Acad. Sci., Mar. 1993, pp. 1746-1750, vol. 90.
Prang et al., "Cellular and Complement-Dependent Cytotoxicity of Ep-CAMSpecific Monoclonal Antibody MT201 Against Breast Cancer Cell Lines," British Journal of Cancer Research, 2005, pp. 342-349, vol. 92.
Reddy et al. "Elimination of Fe receptor-dependent effector functions of a modified IgG4 monoclonal antibody to human CD4" J Immunol Feb. 15, 2000; 164(4): 1925-33.
Repp et al. "Combined Fc-Protein and Fc-Glyco-Engineering of scFv-Fc Fusion Proteins Synergistically Enhances CD16a Binding but does not further enhance NK-Cell Mediated ADCC" Journal of Immunological Methods 2011 pp. 57-78 vol. 373 No. 1.
Ridgway et al. "'Knobs-into-holes' engineering of antibody Ch3 domains for heavy chain heterodimerization" Protein Engineering Jul. 1996 pp. 617-621 vol. 9 No. 7.
Rudikoff et al., "Cellular and Complement-Dependent Cytotoxicity of Ep-CAMSpecific Monoclonal Antibody MT201 Against Breast Cancer Cell Lines," British Journal of Cancer Research, 2005, pp. 342-349, vol. 92.
Rudnick et al. "Influence of Affinity and Antigen Internalization on the Uptake and Penetration of anti-HER2 Antibodies in Solid Tumors," Cancer Research, 2011, pp. 2250-2259, vol. 71, No. 6.
Rusnack et al., "Assessment of Epidermal Growth Factor Receptor (EGFR, ErbB1) and HER2 (ErbB2) Protein Expression Levels and Response to Lapatinib (Tykerb®, GW572016) in an Expanded Panel of Human Normal and Rumour Cell Lines," Cell Prolif, 2007, pp. 580-594, vol. 40.
Seidman et al., "Cardiac Dysfunction in the Trastuzumab Clinical Trials Experience," Journal of Clinical Oncology, Mar. 1, 2002, pp. 1215-1221, vol. 20, No. 5.
Semba et al., "A v-erbB-Related Protooncogene, c-erbB-2, is Distinct from the cerbB-1/Epidermal Growth Factor-Receptor Gene and is Amplified in a Human Salivary Gland Adenocarcinoma," Proc. Natl. Acad. Sci., Oct. 1, 1985, pp. 6497-6501, vol. 82, No. 19.

Shields et al. "High resolution mapping of the binding site on the human IgG1 for FcyRI FcyRIII and FcRn and design of IgG1 variants with improved binding to FcyR" Journal of Biological Chemistry Mar. 2, 2001 pp. 5591-6604 vol. 276 No. 9.
Spreter Von Kreudenstein et al. "Protein engineering and the use of molecular modeling and simulation: The case of Heterodimeric Fe engineering" Methods 65(1): 77-94 (2014).
Subik et al., "The Expression Patterns of ER, PR, HER2, CKS/6, EGFR, Ki-67 and AR by Immunohistochemical Analysis in Breast Cancer Cell Lines," Breast Cancer: Basic Clinical Research, 2010, pp. 35-41, vol. 4.
Suresh et al. "Bispecific monoclonal antibodies from hybrid hybridomas" Methods In Enzymol 121:210-28 (1983).
Takai et al., "2C4, a Monoclonal Antibody Against HER2, Disrupts the HER Kinase Signaling Pathway and Inhibits Ovarian Carcinoma Cell Growth," Cancer, Dec. 15, 2005, pp. 2701-2708, vol. 104, No. 12.
Trail "Antibody Drug Conjugates as Cancer Therapeutics," Antibodies, 2013, pp. 113-129, vol. 2.
Traunecker et al. "Bispecific single chain molecules (Janusins) target cytotoxic lymphocytes on HIV infected cells" EMBO J. Dec. 1991;10(12):3655-9.
Tse et al., "HER2 Shedding and Serum HER2 Extracellular Domain: Biology and Clinical Utility in Breast Cancer," Cancer Treatment Reviews, Apr. 2012, pp. 133-142, vol. 38, No. 2.
U.S. Appl. No. 15/355,019 Notice of Allowance dated May 22, 2018 26 pages.
U.S. Appl. No. 15/036,176—Non-Final Office Action dated Mar. 14, 2018 21 pages.
U.S. Appl. No. 15/036,176—Non-Final Office Action dated Nov. 26, 2019.
U.S. Appl. No. 15/036,176—Restriction Requirement dated Jul. 28, 2017.
U.S. Appl. No. 15/036,176 Final Office Action dated Dec. 17, 2018.
U.S. Appl. No. 15/411,799 Restriction Requirement dated Jan. 25, 2019.
U.S. Appl. No. 15/526,888 Final Office Action Mar. 25, 2020 33 pages.
U.S. Appl. No. 15/526,888 Non-Final Office Action Aug. 1, 2019 33 pages.
U.S. Appl. No. 15/526,888 Restriction Requirement dated Oct. 9, 2018.
U.S. Appl. No. 15/572,364—Restriction Requirement dated Feb. 7, 2020.
U.S. Appl. No. 15/863,464—Notice of Allowance dated Apr. 20, 2018.
U.S. Appl. No. 16/011,048 Non-Final Office Action Apr. 28, 2020 101 pages.
U.S. Appl. No. 13/668,098—Final Office Action issued Nov. 17, 2015.
U.S. Appl. No. 13/668,098—Non-final Office Action issued Apr. 3, 2015.
U.S. Appl. No. 13/668,098—Notice of Allowance issued Sep. 23, 2016.
U.S. Appl. No. 13/668,098—Restriction Requirement issued Dec. 5, 2014.
U.S. Appl. No. 13/927,065—Final Office Action issued Feb. 22, 2016.
U.S. Appl. No. 13/927,065—Non-final Office Action issued Oct. 7, 2015.
U.S. Appl. No. 13/927,065—Notice of Allowance issued Aug. 26, 2016.
U.S. Appl. No. 13/927,065—Restriction Requirement issued Apr. 15, 2015.
U.S. Appl. No. 15/355,019—Non-Final Office Action issued Jul. 21, 2017.
U.S. Appl. No. 15/355,019—Notice of Allowance issued Nov. 17, 2017.
Vajdos et al. "Comprehensive Functional Maps of the Antigen-binding Site of an Anti-ErbB2 Antibody Obtained with Shotgun Scanning Mutagenesis" J. Mol. Biol. 320:415-28 (Year: 2002)_.

(56) References Cited

OTHER PUBLICATIONS

Von Kreudenstein et al., "Improving Biophysical Properties of a Bispecific Antibody Scaffold to Aid Developability Quality by Molecular Design," MAPBS, Landes Bioscience, Sep. 1, 2013, pp. 646-654, vol. 5, No. 5.

Von Kreudenstein et al., "Supplemental Material to: Improving Biophysical Properties of a Bispecific Antibody Scaffold to Aid Developability Quality by Molecular Design," MAPBS, Landes Bioscience, Sep. 1, 2013, pp. 646-654, vol. 5, No. 5.

Wang et al., Effect of Trastuzumab in Combination with IFN alpha-2b on HER2 and-MRP1 of ACHN. J Huazhong Univ Sci Technolog Med Sci. Jun. 2005; 25(3):326-8.

Weidle et al., "The Intriguing Options of Multispecific Antibody Formats for Treatment of Cancer", Cancer Genomics & Proteomics. 2013; 10(1):1-18.

Winkler et al. "Changing the Antigen Binding Specificity by Single Point Mutations of an Anti-p24 (HIV-1) Antibody" The Journal of Immunology 2000 165: 4505-4514.

Woods et al. "LC-MS characterization and purity assessment of a prototype bispecific antibody" MABS 5(5): 711-722 (2013).

Xu et al.' ' "Diversity in the CDR3 Region of VH Is Sufficient for Most Antibody Specificities," Immunity, Jul. 2000, pp. 37-45, vol. 13.

Yamamoto et al., "Similarity of Protein Encoded by the Human c-erb-B-2 Gene to Epidermal Growth Factor Receptor," Nature, Jan. 16-22, 1986, pp. 230-234, vol. 319, No. 6050.

Zhou et al._' "Remodeling domain interfaces to enhance heterodimer formation" Protein Science vol. 6 No. 4 Apr. 1997 pp. 781-788.

\* cited by examiner

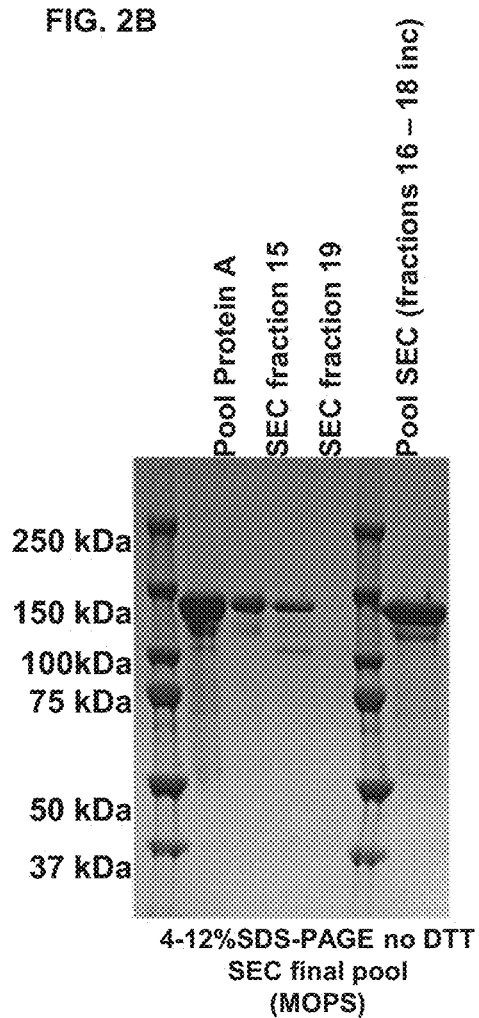

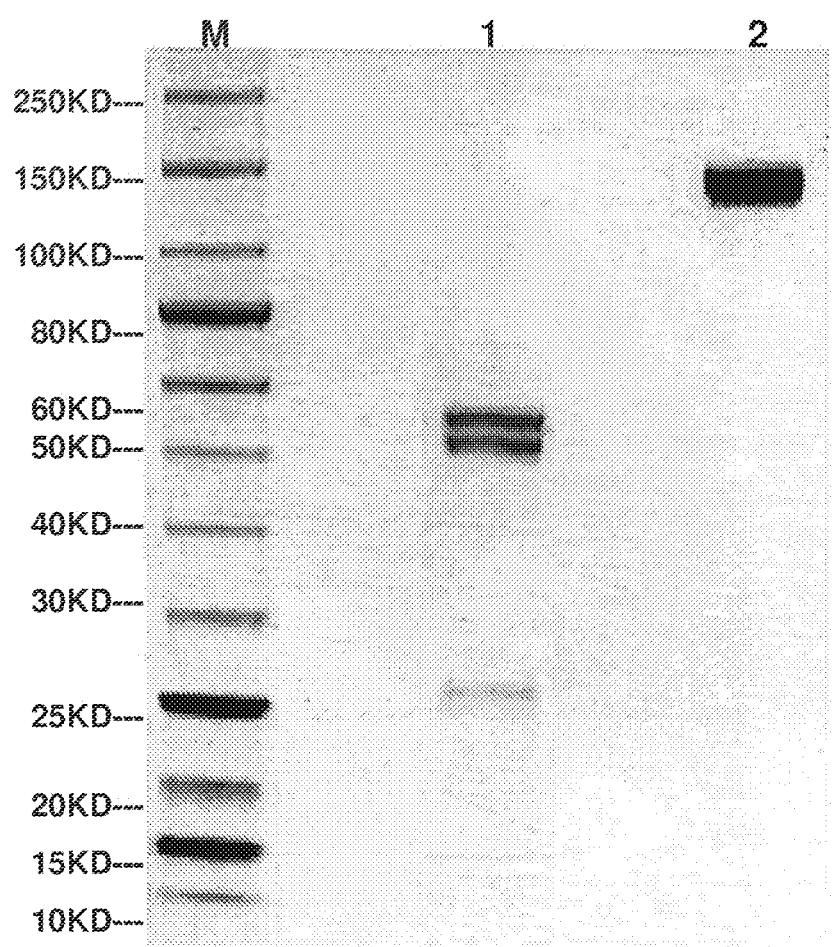

| Peak # | RT (min) | Type | Height | Area | Area% |
|---|---|---|---|---|---|
| 1 | 8.022 | MF R | 0.183 | 22.103 | 1.508 |
| 2 | 11.059 | MF R | 0.179 | 9.708 | 0.662 |
| 3 | 12.961 | MF R | 30.701 | 1416.498 | 96.619 |
| 4 | 15.419 | FM R | 0.299 | 17.759 | 1.211 |

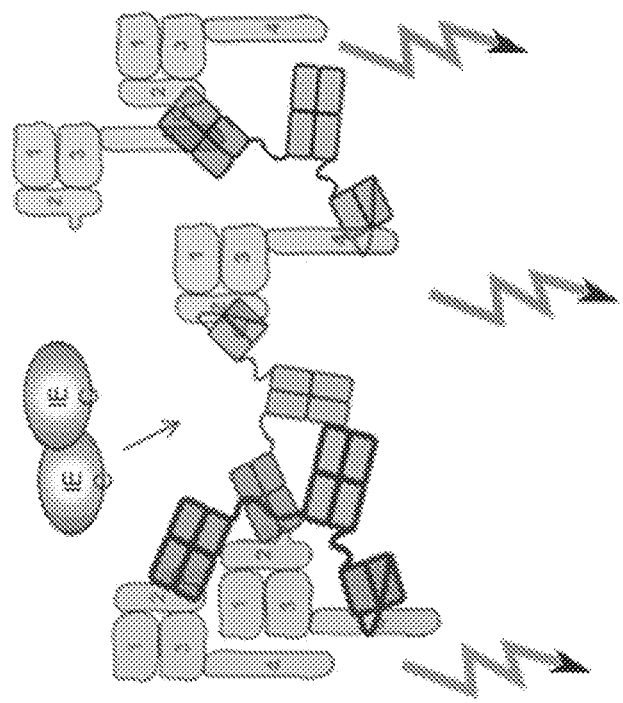
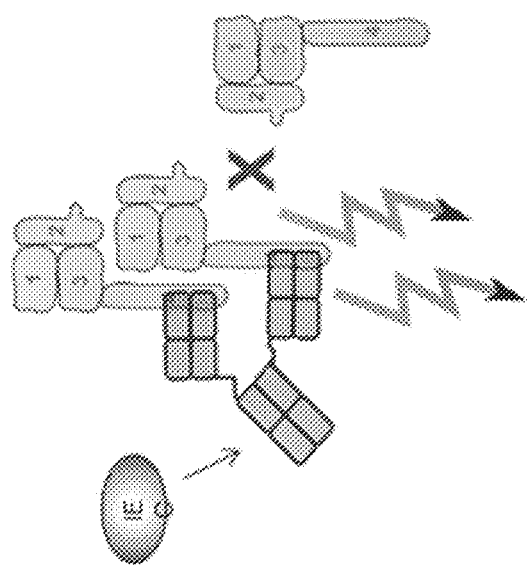
FIG. 14

| Cell Line | Cell Line Description | IHC Receptor | | | v10000 activity | v10553 activity | Ref |
|---|---|---|---|---|---|---|---|
| | | HER2 | EGFR | HER3 | | | |
| BxPC3 | human pancreas adenocarcinoma | 1 | 2 | 1 | + | + | 1,2,3 |
| Capan-1 | human pancreatic adenocarcinoma | 1/3 | 1 | 0 | + | + | 1,4,5 |
| MiaPaca2 | human pancreas carcinoma | 2 | 1/2 | 0 | + | + | 3,4 |
| SW 1990 | human pancreas adenocarcinoma, metastatic | 2 | 1 | 0 | - | + | 2,4 |
| Panc1 | human pancreas carcinoma | 1 | 1/2 | | - | + | 4 |
| A549 | human lung carcinoma | 0/1 | 1 | | - | + | 6,7 |
| Calu-3 | human lung adenocarcinoma | 3 | 2 | 1 | + | + | 6,8,9 |
| Calu-6 | human lung anaplastic carcinoma | 0 | | | - | + | 6 |
| NCI-H2126 | human adenocarcinoma; non-small cell lung cancer | | | | - | + | 10 |
| NCI-H322 | human Caucasian bronchioalveolar carcinoma | 2 | 2 | | + | + | 6,7,11 |
| Detroit 562 | human pharyngeal carcinoma | | | | + | + | 12 |
| SCC-15 | human tongue squamous cell carcinoma | | 2 | | - | + | 12 |
| SCC-25 | human tongue squamous cell carcinoma | | 2 | | + | + | 12 |
| FaDu | squamous cell carcinoma, pharynx | 2 | 2 | | + | + | |

FIG. 38

| Cell Line | Cell Line Description | IHC Receptor | | | v10000 activity | v10553 activity | Ref |
| --- | --- | --- | --- | --- | --- | --- | --- |
| | | HER2 | EGFR | HER3 | | | |
| Colo201 | human colorectal adenocarcinoma | 2 | 1 | | - | + | 13 |
| DLD-1 | human colorectal adenocarcinoma, Dukes' type C | 1 | 0/1 | | - | + | 14 |
| HCT116 | human colorectal carcinoma | 1 | 0/1 | | - | + | 14 |
| HT 29 | human colorectal adenocarcinoma; | 1 | 0 | | + | + | 14 |
| SNU-C2B | humancecum colorectal carcinoma | 2* | | | + | + | |
| SNU-1 | human gastric carcinoma | 0 | | | - | + | 15 |
| SNU-16 | human gastric carcinoma | 1 | | | + | + | 15 |
| NCI-N87 | human gastric carcinoma | 3 | 2 | 1 | + | + | 15 |
| MDAMB175 | human breast ductal carcinoma, ER+ | 1 | 1 | 0/1 | + | + | 8,16 |
| MDAMB361 | human breast adenocarcinoma, ER+, HER2 amp | 2/3 | 1 | 1 | + | + | 9,15,17 |
| ZR-75-1 | human breast duct epithelial ductal carcinoma, ER+ luminal A | 2 | 1 | 1 | - | + | 9 |
| BT-20 | human breast carcinoma, Basal A TNBC | 0/1 | 2 | 1 | + | + | 18 |
| BT549 | human breast ductal carcinoma, Basal B, Mesenchymal-like TNBC, ER- | 0 | 0/1 | 0 | - | + | 18 |
| CAMA-1 | human breast adenocarcinoma, ER+ | 2 | 0 | 1 | - | + | |
| MDAMB453 | human breast metastatic carcinoma, ER-, HER2amp luminal A TNBC | 0 | 0/1 | 0 | - | + | 18 |
| T47D | human breast ductal carcinoma, ER+ | 1 | 0 | 1 | - | + | 19 |
| SK-UT-1 | human uterus mesodermal tumor (mixed) grade III | | | | - | + | |
| TOV-112D | human primary malignant adenocarcinoma; endometrioid carcinoma | 2 | 1 | 2 | + | + | 20 |

FIG. 38 (con.)

| Cell Line | Cell Line Description | IHC Receptor | | | v10000 activity | v10553 activity | Ref |
| --- | --- | --- | --- | --- | --- | --- | --- |
| | | HER2 | EGFR | HER3 | | | |
| A431 | human skin epidermoid carcinoma | 1 | 3 | | - | + | 21 |
| Malme-3M | human malignant melanoma, metastatic lung | 1 | 1 | 1 | + | + | 9, 22 |
| SKMEL28 | human malignant melanoma | 1 | 0 | | - | + | 22 |
| Caski | human cervix carcinoma | 1 | | | + | + | 23 |
| MS751 | human cervix epidermoid carcinoma | | | | + | + | |
| T24 | human urinary bladder carcinoma | 1 | 0 | | - | + | 19, 21, 24 |
| ACHN | human renal cell adenocarcinoma | 1 | 2 | 0/1 | + | + | 9, 25 |
| CaOV3 | human ovary adenocarcinoma | 1 | 1 | | + | + | 26 |
| Ovcar-3 | human ovary adenocarcinoma | 1/2 | 2 | 2 | - | + | 20, 26 |
| SKOV3 | human ovary adenocarcinoma | 2/3 | 2 | 0/1 | - | + | |

FIG. 38 (con.)

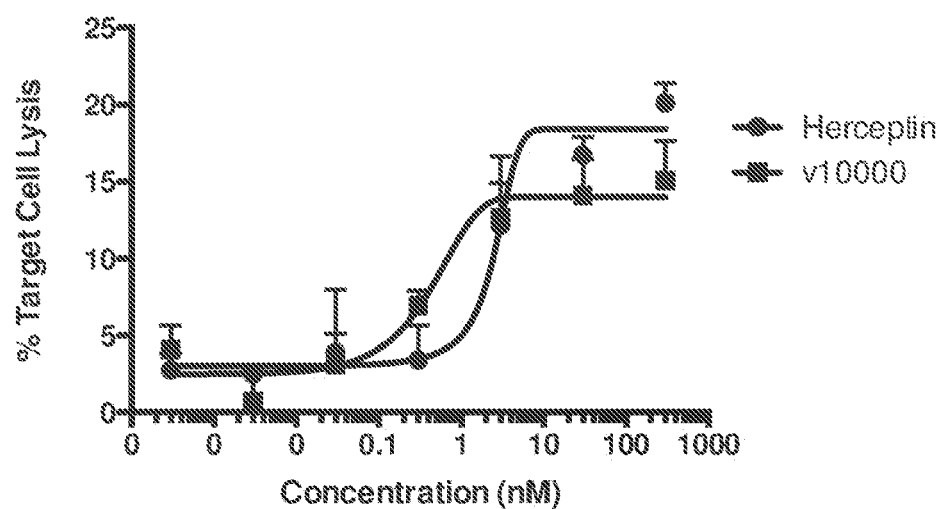
FIG. 39A Fadu
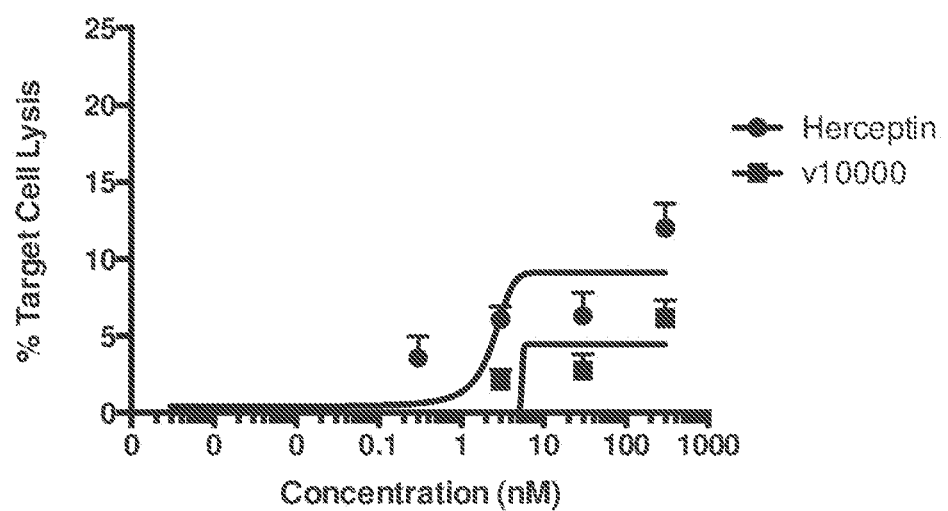
FIG. 39B A549

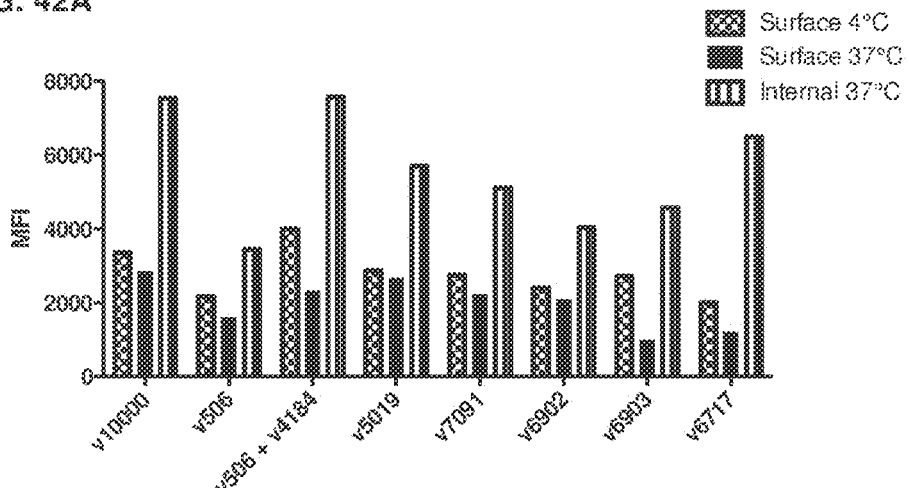
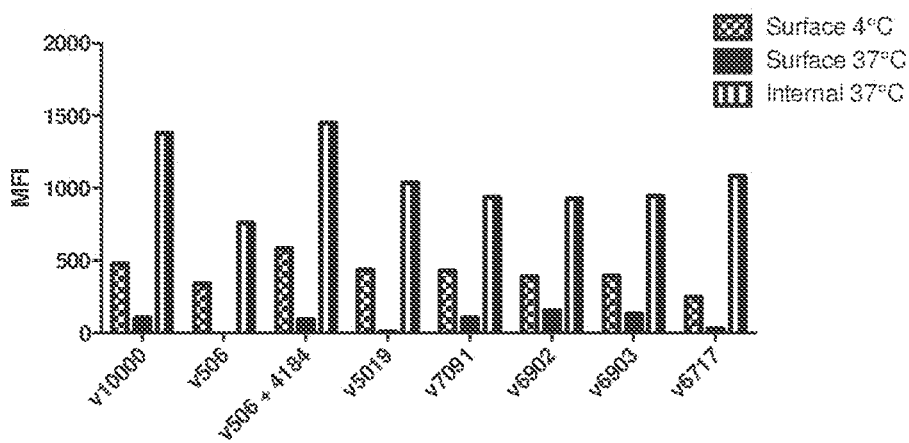
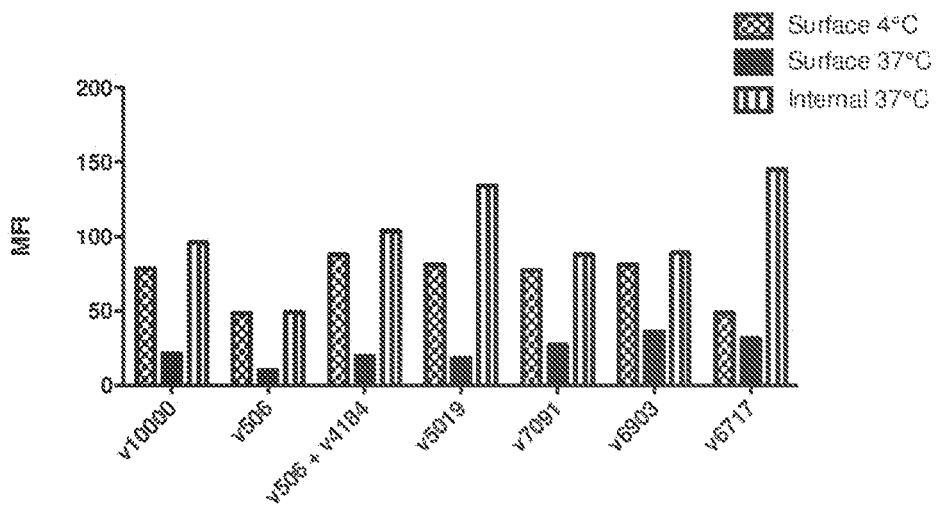

BISPECIFIC ANTIGEN BINDING CONSTRUCTS TARGETING HER2

CROSS REFERENCE TO RELATED APPLICATIONS

This application is a continuation of U.S. patent application Ser. No. 16/011,048, filed Jun. 18, 2018, which is a continuation of U.S. patent application Ser. No. 15/863,464, filed Jan. 5, 2018, now U.S. Pat. No. 10,000,576, which is a divisional of U.S. patent application Ser. No. 15/036,176, filed May 12, 2016, now U.S. Pat. No. 10,947,319, which is a 371 National Phase Application of PCT/CA2014/051140, filed Nov. 27, 2014, which claims priority to U.S. Provisional Application No. 61/910,026, filed Nov. 27, 2013, U.S. Provisional Application No. 62/000,908, filed May 20, 2014, and U.S. Provisional Application No. 62/009,125, filed Jun. 6, 2014, which are all hereby incorporated in their entirety by reference, for all purposes.

SEQUENCE LISTING

The instant application contains a Sequence Listing which will be submitted via EFS-Web and is hereby incorporated by reference in its entirety. Said ASCII copy, created on Apr. 25, 2022, is named ZWI-017C3_sequencelisting.txt, and is 275,217 bytes in size.

BACKGROUND

The majority of current marketed antibody therapeutics are bivalent monospecific antibodies optimized and selected for high affinity binding and avidity conferred by the two antigen binding domains. Defucosylation or enhancement of FcgR binding by mutagenesis have been employed to render antibodies more efficacious via antibody Fc dependent cell cytotoxicity FIG. 8FIG. 8fimechanisms. Afucyosylated antibodies or antibodies with enhanced FcgR binding still suffer from incomplete therapeutic efficacy in clinical testing and marketed drug status has yet to be achieved for any of these antibodies.

Therapeutic antibodies would ideally possess certain minimal characteristics, including target specificity, biostability, bioavailability and biodistribution following administration to a subject patient, and sufficient target binding affinity and high target occupancy to maximize antibody dependent therapeutic effects. Typically therapeutic antibodies are monospecific. Monospecific targeting however does not address other target epitopes that may be relevant in signaling and disease pathogenesis, allowing for drug resistance and escape mechanism. Some of the current therapeutic paradigms call for the use of combination of two therapeutic monospecific antibodies targeting two different epitopes of the same target antigen. One example is the use of a combination of Trastuzumab and Pertuzumab, both targeting the Her2 receptor protein on the surface of some cancer cells. Therapeutic antibodies targeting HER2 are disclosed in WO 2012/143523 to GenMab and WO 2009/154651 to Genentech. Antibodies are also described in WO 2009/068625 and WO 2009/068631.

Co-owned patent applications PCT/CA2011/001238, filed Nov. 4, 2011, PCT/CA2012/050780, filed Nov. 2, 2012, PCT/CA2013/00471, filed May 10, 2013, and PCT/CA2013/050358, filed May 8, 2013 describe therapeutic antibodies. Each is hereby incorporated by reference in their entirety for all purposes.

SUMMARY OF THE INVENTION

Described herein are bivalent antigen binding constructs that binding HER2. The antigen binding constructs comprise a first antigen binding polypeptide construct which monovalently and specifically binds a HER2 (human epidermal growth factor receptor 2) ECD2 (extracellular domain 2) antigen on a HER2-expressing cell and a second antigen-binding polypeptide construct which monovalently and specifically binds a HER2 ECD4 (extracellular domain 4) antigen on a HER2-expressing cell, wherein at least one of the ECD2- or the ECD4-binding polypeptide constructs is an scFv. In certain embodiments, the ECD2-binding polypeptide construct is an scFv, and the ECD2-binding polypeptide construct is a Fab. In certain embodiments, the ECD2-binding polypeptide construct is a Fab and the ECD4 binding polypeptide construct is an scFv. In some embodiments, both the ECD2- and ECD4-binding polypeptide constructs are scFvs. In some embodiments, the antigen binding constructs have a dimeric Fc comprising a CH3 sequence. In some embodiments, the Fc is a heterodimer having one or more modifications in the CH3 sequence that promote the formation of a heterodimer with stability comparable to a wild-type homodimeric Fc. In some embodiments, the heterodimeric CH3 sequence has a melting temperature (Tm) of 68° C. or higher. Also described are nucleic acids encoding antigen binding constructs, and vectors and cells. Also described are methods of treating a disorder, e.g., cancer, using the antigen binding constructs described herein.

BRIEF DESCRIPTION OF THE DRAWINGS

In FIG. 1B, antigen-binding domain 1 is an scFv, fused to Chain A, while antigen-binding domain 2 is a Fab, fused to Chain B.

In FIG. 1C, antigen-binding domain 1 is a Fab, fused to Chain A, while antigen-binding domain 2 is an scFv, fused to Chain B.

In FIG. 1D, antigen-binding domain 2 is a Fab, fused to Chain A, while antigen-binding domain 1 is an scFv, fused to Chain B.

In FIG. 1E, antigen-binding domain 2 is an scFv, fused to Chain A, while antigen-binding domain 1 is a Fab, fused to Chain B.

In FIG. 1F, both antigen-binding domains are scFvs.

FIG. 2A depicts the SEC chromatograph of the protein A purified antibody, and non-reducing SDS-PAGE analysis of 10 L expression and purification of v5019.

FIG. 2B depicts the characterization of expression and purification of exemplary anti-HER2 biparatopic antibodies. FIG. 2B depicts the SEC chromatograph of the protein A purified antibody, and non-reducing SDS-PAGE analysis of 10 L expression and purification of v5019.

FIG. 2C depicts the characterization of expression and purification of exemplary anti-HER2 biparatopic antibodies.

FIG. 2C depicts the SDS-PAGE analysis of a 25 L expression and purification of v10000.

FIG. 3A shows the results for v5019, where the upper panel shows the results of the purification and the lower panel shows the same result with an expanded scale for the y-axis. A summary of the data obtained is provided below the UPLC-SEC results.

FIG. 3B shows the results for v10000.

FIG. 4A depicts results from LC-MS analysis of the pooled SEC fractions of v5019.

FIG. 4B depicts the results from LC-MS analysis of the pooled protein A fractions of v10000.

FIG. 5A depicts the SDS-PAGE profile of an exemplary anti-HER2 biparatopic following MabSelect™ and HiTrap™ SP FF purification.

FIG. 5B depicts LCMS analysis of the purified antibody.

FIG. 6A depict binding to SKOV3 cells.

FIG. 6B depicts binding to JIMT1 cells.

FIG. 6C and FIG. 6F depict binding to MCF7 cells.

FIG. 6D depicts binding to MDA-MB-231 cells.

FIG. 6E depict binding to SKOV3 cells.

FIG. 6F compares the ability of an exemplary biparatopic anti-HER2 antibodies to bind to HER2+ whole cells displaying different HER2 receptor density compared to control antibodies, as measured by FACS. FIG. 6F depict binding to MCF7 cells.

FIG. 6G depicts binding to WI-38 cells.

FIG. 7A shows growth inhibition in SKOV3 cells.

FIG. 7B shows growth inhibition in BT-474 cells.

FIG. 7C shows growth inhibition in SKBR3 cells.

FIG. 7D shows growth inhibition in SKOV3 cells.

FIG. 7E shows growth inhibition in JIMT-1 cells.

FIG. 8A illustrates the $K_D$ values (nM) of a monovalent anti-Her2 antibody (v1040; representing the antigen binding domain on CH-B of exemplary anti-Her2 biparatopic antibody), for binding to immobilized Her2 ECD or dimeric Her2-Fc.

FIG. 8B illustrates the $K_D$ values (nM) of a monovalent anti-Her2 antibody (v4182; representing the antigen binding domain on CH-A of exemplary anti-Her2 biparatopic antibody) for binding to immobilized Her2 ECD or dimeric Her2-Fc.

FIG. 9A depicts internalization in BT-474 cells.

FIG. 9B depicts internalization in JIMT-1 cells.

FIG. 10A (v5019) depicts the result in BT-474 cells.

FIG. 10B (v5019) depict the result in JIMT1 cells.

FIG. 10C (v5019) depict the result in SKOV3 cells.

FIG. 10D (v5019) depicts the result in MCF7 cells.

FIG. 10E (v5019 and v10000) depict the result in SKOV3 cells.

FIG. 10F (v5019 and v10000) depict the result in JIMT1 cells.

In FIG. 11A, the assay was carried out using an effector to target cell ratio of 5:1.

In FIG. 11B, the assay was carried out using an effector to target cell ratio of 3:1.

In FIG. 11C, the assay was carried out using an effector to target cell ratio of 1:1.

FIG. 12A shows the measurement of ka (1/Ms).

FIG. 12B shows the measurement of kd (1/s).

FIG. 12C shows the measurement of $K_D$ (M).

FIG. 13A depicts the measurement of kd (1/s) to HER2 ECD determined over a range of antibody capture levels for exemplary biparatopic anti-Her2 antibody (v5019).

FIG. 13B depicts the measurement of kd (1/s) to HER2 ECD determined over a range of antibody capture levels for monovalent anti-Her2 antibody (v4182).

FIG. 13C depicts the measurement of kd (1/s) to HER2 ECD determined over a range of antibody capture levels for monovalent anti-Her2 antibody (v630).

FIG. 14 shows a comparison of the mechanism of binding of a monospecific anti-ECD4 HER2 antibody (left), and a Fab-scFv biparatopic anti-ECD2×ECD4 HER2 antibody (right). The monospecific anti-ECD4 HER2 antibody is capable of binding one antibody molecule to two HER2 molecules; whereas the biparatopic anti-ECD2×ECD4 HER2 antibody is capable of binding one antibody to two HER2 molecule, as well as 2 antibodies to one HER2 molecule and combinations therein which results in HER2 receptor cross-linking and lattice formation followed by downstream biological effects such as internalization and/or growth inhibition as indicated by the arrows. IEC represents "immune effector cells." The four extracellular domains of HER2 are numbered as 1, 2, 3, or 4 where 1=ECD1, 2=ECD2, 3=ECD3, and 4=ECD4.

FIG. 16A depicts the effect of v5019 and the corresponding ADC v6363 on cardiomyocyte viability.

FIG. 16B depicts the effect of v5019, v7091, and v10000 and corresponding ADCs v6363, 7148, 10553 on cardiomyocyte viability.

FIG. 16C depicts the effect of v5019, v7091, and v10000 and corresponding ADCs v6363, 7148, 10553 on the viability of doxorubicin-pretreated cardiomyocytes.

FIG. 17A shows the ability of the ADC v6363 to inhibit the growth of JIMT1 cells.

FIG. 17B shows the ability of the ADC v6363 to inhibit the growth of SKOV3 cells.

FIG. 17C shows the ability of the ADC v6363 to inhibit the growth of MCF7 cells.

FIG. 17D shows the ability of the ADC v6363 to inhibit the growth of MDA-MB-231 cells.

FIG. 17E shows the ability of ADCs v6363, v10553, and v1748 to inhibit the growth of SKOV3 cells.

FIG. 17F shows the ability of ADCs v6363, v10553, and v1748 to inhibit the growth of JIMT-1 cells.

FIG. 17G shows the ability of ADCs v6363, v10553, and v1748 to inhibit the growth of NCI-N87 cells.

FIG. 18A shows the effect of the antibody on mean tumor volume.

FIG. 18B shows the effect of the antibody on percent survival of the animals.

FIG. 19A shows the effect of the antibody on mean tumor volume.

FIG. 19B shows the effect of the antibody on percent survival of the animals.

FIG. 25A depicts the thermal stability of v5019.

FIG. 25B depicts the thermal stability of v10000.

FIG. 26A depicts the thermal stability of v6363.

FIG. 26B depicts the thermal stability of v10553.

FIG. 26C depicts the thermal stability of v7148.

FIG. 27A depicts this ability in SKBR3 cells, FIG. 27B depicts this ability in JIMT-1 cells, FIG. 27C depicts this ability in MDA-MB-231 cells.

FIG. 27D depicts this ability in WI-38 cells.

FIG. 28A compares the ability of an afucosylated version of v5019 to mediate ADCC to that of Herceptin™ in SKOV3 cells.

FIG. 28B compares the ability of an afucosylated version of v5019 to mediate ADCC to that of Herceptin™ in MDA-MB-231 cells.

FIG. 28C compares the ability of v10000 and an afucosylated version of v10000 to mediate ADCC against that of Herceptin™ in ZR-75-1 cells.

FIG. 31A compares the binding of v6363 to a T-DM1 analog, v6246, in SKOV3 cells.

FIG. 31B compares the binding of v6363 to a T-DM1 analog, v6246, in JIMT-1 cells.

FIG. 31C compares the binding of several exemplary anti-HER2 biparatopic antibodies and anti-HER2 biparatopic-ADCs to controls, in SKOV3 cells.

FIG. 31D compares the binding of several exemplary anti-HER2 biparatopic antibodies and anti-HER2 biparatopic-ADCs to controls, in JIMT-1 cells.

FIG. 32A shows the effect of v6363 on tumor volume.

FIG. 32B shows the effect on percent survival.

FIG. 33A depicts the effect of treatment on tumor volume.

FIG. 33B depicts the effect of treatment on survival.

FIG. 35A depicts the effect of treatment on tumor volume.

FIG. 35B depicts the effect of treatment on survival.

FIG. 37A depicts the ability of v10000 to inhibit growth selected cell lines.

FIG. 37B depicts the ability of v10553 to inhibit growth of selected cell lines.

FIG. 38 depicts a summary of the ability of v10000 and v10553 to inhibit growth in a panel of cell lines. Hyphenated values (e.g. 1/2) indicate discrepant erbb receptor levels as reported in the literature; Erbb IHC values were obtained internally or from the literature. Where no value is reported the receptor quantities are unknown and/or not reported. * IHC level estimate based on erBb2 gene expression data (Crown BioSciences). Numbered references are described below.

FIG. 39A depicts the ability of v10000 to mediate ADCC in HER2+ cells.

FIG. 39A depicts the results in FaDu cells.

FIG. 39B depicts the ability of v10000 to mediate ADCC in HER2+ cells.

FIG. 39B depicts the results in A549 cells.

FIG. 39C depicts the results in BxPC3 cells.

FIG. 39D depicts the results in MiaPaca2 cells.

FIG. 40A depicts the results in A549 cells.

FIG. 40B depicts the results in NCI-N87 cells.

FIG. 40C depicts the results in HCT-116 cells.

FIG. 41A depicts the effect of format on binding to BT-474 cells.

FIG. 41B depicts the effect of format on binding to JIMT-1 cells.

FIG. 41C depicts the effect of format on binding to MCF7 cells.

FIG. 41D depicts the effect of format on binding to MDA-MB-231 cells.

FIG. 42A depicts the effect of anti-HER2 biparatopic antibody format on internalization of antibody in HER2+ cells. FIG. 42A depicts the effect on internalization in BT-474 cells.

FIG. 42B depicts the effect of anti-HER2 biparatopic antibody format on internalization of antibody in HER2+ cells. FIG. 42B depicts the effect on internalization in JIMT-1 cells.

FIG. 42C depicts the effect of anti-HER2 biparatopic antibody format on internalization of antibody in HER2+ cells. FIG. 42C depicts the effect on internalization in MCF7 cells.

FIG. 43A depicts the effect in JIMT-1 cells.

FIG. 43B depicts the effect in MCF7 cells.

FIG. 43C depicts the effect in HER2 0/1+ MDA-MB-231 breast tumor cells.

FIG. 46A depicts growth inhibition in SKOV3 cells.

FIG. 46B depicts growth inhibition in JIMT-1 cells.

FIG. 46C depicts growth inhibition in MCF7 cells.

FIG. 47A depicts a comparison of binding characteristics of anti-HER2 biparatopic antibodies of differing format as measured by SPR. FIG. 47A depicts the plot and linear regression analysis for the kd (1/s) at different antibody capture levels with v6903 and v7091.

FIG. 47B depicts a comparison of binding characteristics of anti-HER2 biparatopic antibodies of differing format as measured by SPR. FIG. 47B depicts the plot and linear regression analysis for the KD (M) at different antibody capture levels with v6903 and v7091.

Figure 1A:
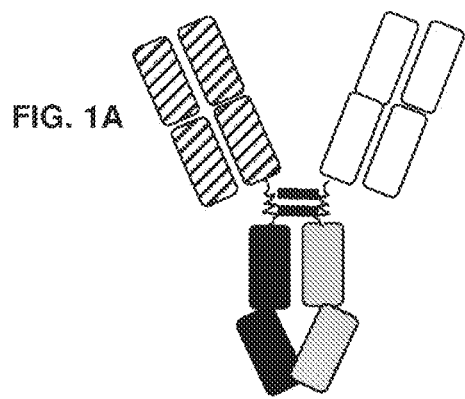
FIG. 1A depicts the structure of a biparatopic antibody in a Fab-Fab format.

References found in FIG. 38 are as follows: 1. Labouret et al. 2012, Neoplasia 14:121-130; 2. Ghasemi et al. 2014, Oncogenesis doi:10.1038/oncsis.2014.31; 3. Gaborit et al. 2011 J Bio Chem, 286:1133-11345; 4. Kimura et al. 2006, Clin Cancer Res; 12:4925-4932; 5. Komoto et al. 2009, Canc Sci; 101:468-473; 6. Cretella et al. 2014, Molecular Cancer 13:143-155; 7. Bunn et al. 2001, Clin Cancer Res; 7:3239-3250; 8. Lewis Phillips et al. 2013, Clin Cancer Res, 20:456-468; 9. McDonagh et al. 2012, 11:582-593; 10. Coldren et al. 2006, Mol Cancer Res:521-528; 11. Cavazzoni et al. 2012 Mol Cancer, 11:91-115; 12. Li et al. 2014, Mol Cancer Res, doi:10.1158/1541-7786.MCR-13-0396; 13. Chmielewski et al. 2004, Immunology, 173:7647-7653; 14. Kuwada et al. 2004, Int J Cancer, 109:291-301; 15. Fujimoto-Ouchi et al. 2007, Clin Chemother Pharmacol, 59:795-805; 16. Chavez-Blanco et al. 2004, BMC Cancer, 4:59; 17. Campiglio et al. 2004, J Cellular Physiology. 198:259-268; 18. Lehmann et al. 2011, J Clin Investigation, 121:2750-2767; 19. Collins et al. 2011, Annals Oncology, 23:1788-1795; 20. Takai et al. 2005, Cancer, 104:2701-2708; 21. Rusnack et al. 2007, Cell Prolif, 40:580-594; 22. Ma et al. 2013, PLOS ONE, 8:e73261-e73261; 23. Meira et al. 2009, British J Cancer, 101:782-791; 24. Hayashi MP28-14 poster; 25. Wang et al. 2005 J Huazhong Univ Sci Technolog Med Sci. 25:326-8; 26. Makhja et al. 2010. J Clinc Oncolo 28:1215-1223.

DETAILED DESCRIPTION

Described herein are antigen binding constructs comprising a first antigen binding polypeptide construct which monovalently and specifically binds a HER2 (human epidermal growth factor receptor 2) ECD2 (extracellular domain 2) antigen on a HER2-expressing cell and a second antigen-binding polypeptide construct which monovalently and specifically binds a HER2 ECD4 (extracellular domain 4) antigen on a HER2-expressing cell, wherein at least one of the ECD2- or the ECD4-binding polypeptide constructs is an scFv. In certain embodiments, the ECD2-binding polypeptide construct is an scFv, and the ECD2-binding polypeptide construct is a Fab. In certain embodiments, the ECD2-binding polypeptide construct is a Fab and the ECD4 binding polypeptide construct is an scFv. In some embodiments, both the ECD2- and ECD4-binding polypeptide constructs are scFvs. In some embodiments, the antigen binding constructs have a dimeric Fc comprising a CH3 sequence. In some embodiments, the Fc is a heterodimer having one or more modifications in the CH3 sequence that promote the formation of a heterodimer with stability comparable to a wild-type homodimeric Fc. In some embodiments, the heterodimeric CH3 sequence has a melting temperature (Tm) of 68° C. or higher.

The antigen binding constructs exhibit anti-tumor activities in vitro, such as (i) the ability to inhibit cancer cell growth both in the presence or absence of stimulation by epidermal growth factor or heregulin, (ii) the ability to be internalized in cancer cells and (iii) the ability to mediate antibody-directed effector cell killing (ADCC). These in vitro activities are observed both with the naked antigen binding construct, and with the antigen binding construct conjugated to maytansine, and at varying levels of HER2 expression (1+, 2+ and 3+).

It is shown herein that the format (scFv/scFv, scFv/Fab or Fab/Fab) of the antigen-binding constructs is important in determining its functional profile. In certain embodiments, the anti-HER2 binding constructs exhibit an increased ability to be internalized by HER2-expressing tumor cells compared to a reference biparatopic antigen-binding construct in which both the ECD2- and ECD4-binding polypeptide constructs are Fabs. One embodiment, in which both the ECD2 and ECD4-binding polypeptides are scFvs, is internalized to a greater extent by tumor cells expressing HER2 at a level of 1+, 2+ or 3+ than constructs of equivalent affinity that have a Fab/scFv format, which in turn are internalized more efficiently than constructs of equivalent affinity that have a Fab/Fab format. Embodiments that are readily internalized are good candidates for antibody-drug conjugates, which require internalization by a tumor cell to effect killing.

In certain embodiments, the antigen-binding constructs exhibit an increased potency in ADCC killing of tumor cells that express low levels of HER2 compared to constructs of equivalent affinity that have a Fab/Fab format. In one embodiment, an antigen binding construct having a Fab/scFv format is more potent in ADCC killing of tumor cells expressing low levels of HER2 (HER2 0-1+ or 1+) than an anti-HER2 construct having a Fab/Fab format, which in turn is more potent than an antigen binding construct having a scFv/scFv format.

In some embodiments, the anti-HER2 binding constructs are afucosylated. In some embodiments, the anti-HER2 binding constructs are coupled to a drug. In some embodiments, the anti-HER2 binding constructs are coupled to maytansine (DM1) through an SMCC linker.

Also described herein are methods of treating a subject having a HER2+ tumor by administering an anti-HER2 antigen binding construct to the subject. In some embodiments, the level of HER2 expression on the tumor is 2+ or lower. In some embodiments, the antigen-binding construct is conjugated to maytansine. In certain embodiments, the tumor is pancreatic cancer, head and neck cancer, gastric cancer, colorectal cancer, breast cancer, renal cancer, cervical cancer, ovarian cancer, endometrial cancer or epidermal-derived cancer. In some embodiments, the tumor is (i) a HER2 3+ estrogen receptor negative (ER−), progesterone receptor negative (PR−), trastuzumab resistant, chemotherapy resistant invasive ductal breast cancer, (ii) a HER2 3+ER−, PR−, trastuzumab resistant inflammatory breast cancer, (iii) a HER2 3+, ER−, PR−, invasive ductal carcinoma or (iv) a HER2 2+ HER2 gene amplified trastuzumab and pertuzumab resistant breast cancer.

Also provided herein are methods of inhibiting the growth of tumor cells or killing tumor cells by administering the antigen binding constructs.

Also provided herein is a modified pertuzumab construct comprising a having mutations Y96A in the VL region and T30A/A49G/L70F in the VH region. In one embodiment, the modified pertuzumab construct is monovalent, and has a 7 to 9-fold higher affinity for HER2 ECD2 than pertuzumab. In certain embodiments, the modified pertuzumab construct has an Fab/Fab, an Fab/scFv or an scFv/scFv format.

Bispecific Antigen-Binding Constructs

Provided herein are bispecific antigen binding constructs that bind HER2. The bispecific antigen-binding construct includes two antigen binding polypeptide constructs, each specifically binding a different epitope of HER2. In some embodiments, the antigen-binding construct is derived from known antibodies or antigen-binding constructs. As described in more detail below, the antigen binding polypeptide constructs can be, but are not limited to, protein wdomain antibody). Typically the antigen-binding construct includes an Fc.

The term "antigen binding construct" refers to any agent, e.g., polypeptide or polypeptide complex capable of binding to an antigen. In some aspects an antigen binding construct is a polypeptide the specifically binds to an antigen of interest. An antigen binding construct can be a monomer, dimer, multimer, a protein, a peptide, or a protein or peptide complex; an antibody, an antibody fragment, or an antigen binding fragment thereof; an scFv and the like. An antigen binding construct can be a polypeptide construct that is monospecific, bispecific, or multispecific. In some aspects, an antigen binding construct can include, e.g., one or more antigen binding components (e.g., Fabs or scFvs) linked to one or more Fc. Further examples of antigen binding constructs are described below and provided in the Examples.

The term "bispecific" is intended to include any agent, e.g., an antigen binding construct, which has two antigen binding moieties (e.g. antigen binding polypeptide constructs), each with a unique binding specificity. For example, a first antigen binding moiety binds to an epitope on a first antigen, and a second antigen binding moiety binds to an epitope on a second antigen. The term "biparatopic" as used herein, refers to a bispecific antibody where the first antigen binding moiety and the second antigen binding moiety bind to different epitopes on the same antigen.

A monospecific antigen binding construct refers to an antigen binding construct with one binding specificity. In other words, both antigen binding moieties bind to the same epitope on the same antigen. Examples of monospecific antigen binding constructs include trastuzumab, pertuzumab, for example.

An antigen binding construct can be an antibody or antigen binding portion thereof. As used herein, an "antibody" or "immunoglobulin" refers to a polypeptide substantially encoded by an immunoglobulin gene or immunoglobulin genes, or fragments thereof, which specifically bind and recognize an analyte (e.g., antigen). The recognized immunoglobulin genes include the kappa, lambda, alpha, gamma, delta, epsilon and mu constant region genes, as well as the myriad immunoglobulin variable region genes. Light chains are classified as either kappa or lambda. The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., IgGi, $IgG_2$, $IgG_3$, $IgG_4$, $IgA_i$, and $IgA_2$. The heavy chain constant domains that correspond to the different classes of immunoglobulins are called α, δ, ε, γ, and μ, respectively.

An exemplary immunoglobulin (antibody) structural unit is composed of two pairs of polypeptide chains, each pair having one "light" (about 25 kD) and one "heavy" chain (about 50-70 kD). The N-terminal domain of each chain defines a variable region of about 100 to 110 or more amino acids primarily responsible for antigen recognition. The terms variable light chain (VL) and variable heavy chain (VH) refer to these light and heavy chain domains respectively. The IgG1 heavy chain comprises of the VH, CH1, CH2 and CH3 domains respectively from the N to C-terminus. The light chain comprises of the VL and CL domains from N to C terminus. The IgG1 heavy chain comprises a hinge between the CH1 and CH2 domains. In certain embodiments, the immunoglobulin constructs comprise at least one immunoglobulin domain from IgG, IgM, IgA, IgD, or IgE connected to a therapeutic polypeptide. In some embodiments, the immunoglobulin domain found in an antigen binding construct provided herein, is from or derived from an immunoglobulin based construct such as a diabody, or a nanobody. In certain embodiments, the immunoglobulin constructs described herein comprise at least one immunoglobulin domain from a heavy chain antibody such as a camelid antibody. In certain embodiments, the immunoglobulin constructs provided herein comprise at least one immunoglobulin domain from a mammalian antibody such as a bovine antibody, a human antibody, a camelid antibody, a mouse antibody or any chimeric antibody.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as "complementarity determining regions" (CDRs), and these terms are used herein interchangeably in reference to portions of the variable region that form the antigen binding regions. This particular region has been described by Kabat et al., U.S. Dept. of Health and Human Services, Sequences of Proteins of Immunological Interest (1983) and by Chothia et al., J Mol Biol 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table 1 as a comparison. The exact residue numbers which encompass a particular CDR will vary depending on the sequence and size of the CDR. Those skilled in the art can routinely determine which residues comprise a particular CDR given the variable region amino acid sequence of the antibody.

As used herein, the term "single-chain" refers to a molecule comprising amino acid monomers linearly linked by peptide bonds. In certain embodiments, one of the antigen binding polypeptide constructs is a single-chain Fab molecule, i.e. a Fab molecule wherein the Fab light chain and the Fab heavy chain are connected by a peptide linker to form a single peptide chain. In a particular such embodiment, the C-terminus of the Fab light chain is connected to the N-terminus of the Fab heavy chain in the single-chain Fab molecule. In certain other embodiments, one of the antigen binding polypeptide constructs is a single-chain Fv molecule (scFv). As described in more detail herein, an scFv has a variable domain of light chain (VL) connected from its C-terminus to the N-terminal end of a variable domain of heavy chain (VH) by a polypeptide chain. Alternately the scFv comprises of polypeptide chain where in the C-terminal end of the VH is connected to the N-terminal end of VL by a polypeptide chain.

Antigen-Binding Polypeptide Construct

The bispecific antigen binding construct comprises two antigen-binding polypeptide constructs that each bind to a particular domain or epitope of HER2. In one embodiment, each antigen-binding polypeptide construct binds to an extracellular domain of HER2, e.g., ECD2, or ECD4. The antigen binding polypeptide construct can be, e.g., a Fab, or an scFv, depending on the application.

The format of the bispecific antigen-binding construct determines the functional characteristics of the bispecific antigen-binding construct. In one embodiment, the bispecific antigen-binding construct has an scFv-Fab format (i.e. one antigen-binding polypeptide construct is an scFv and the other antigen-binding polypeptide construct is a Fab). In another embodiment, the bispecific antigen-binding construct has an scFv-scFv format (i.e. both antigen-binding polypeptide constructs are scFvs.

The "Fab fragment" (also referred to as fragment antigen binding) contains the constant domain (CL) of the light chain and the first constant domain (CH1) of the heavy chain along with the variable domains VL and VH on the light and heavy chains respectively. The variable domains comprise the complementarity determining loops (CDR, also referred to as hypervariable region) that are involved in antigen binding. Fab' fragments differ from Fab fragments by the addition of a few residues at the carboxy terminus of the heavy chain CH1 domain including one or more cysteines from the antibody hinge region.

The "Single-chain Fv" or "scFv" includes the VH and VL domains of an antibody, wherein these domains are present in a single polypeptide chain. In one embodiment, the Fv polypeptide further comprises a polypeptide linker between the VH and VL domains which enables the scFv to form the desired structure for antigen binding. For a review of scFv see Pluckthun in *The Pharmacology of Monoclonal Antibodies*, vol. 113, Rosenburg and Moore eds., Springer-Verlag, New York, pp. 269-315 (1994). HER2 antibody scFv fragments are described in WO93/16185; U.S. Pat. Nos. 5,571,894; and 5,587,458.

The "Single domain antibodies" or "sdAb" format is an individual immunoglobulin domain. Sdabs are fairly stable and easy to express as fusion partner with the Fc chain of an antibody (Harmsen M M, De Haard H J (2007). "Properties, production, and applications of camelid single-domain antibody fragments". Appl. Microbiol Biotechnol. 77(1): 13-22).

Format and Function of Antigen Binding Constructs

Provided herein are biparatopic HER2 antigen binding constructs having two antigen binding polypeptide constructs, the first of which specifically binds to HER2 ECD2, and the second of which specifically binds to HER2 ECD4. The format of the antigen binding construct is such that at least one of the first or the second antigen-binding polypeptide is an scFv. The format of the antigen binding construct may be scFv-scFv, or Fab-scFv or scFv-Fab (first antigen binding polypeptide construct-second antigen-binding polypeptide respectively).

In certain embodiments, the antigen binding constructs exhibit anti-tumor activities in vitro, such as (i) the ability to inhibit cancer cell growth both in the presence or absence of stimulation by epidermal growth factor or heregulin, (ii) the ability to be internalized in cancer cells (through binding to the HER2 antigen and causing it to be internalized) and (iii) the ability to mediate antibody-directed effector cell killing (ADCC). These in vitro activities are observed both with the naked antigen binding construct, and with the antigen binding construct conjugated to maytansine, and at varying levels of HER2 expression (1+, 2+ and 3+).

Examples herein show that the format (scFv/scFv, scFv/Fab or Fab/Fab) of the antigen-binding constructs is important in determining its functional profile. In certain embodiments, the anti-HER2 binding constructs exhibit an increased ability to be internalized by HER2-expressing tumor cells compared to a reference antigen-binding construct in which both the ECD2- and ECD4-binding polypeptide constructs are Fabs. One embodiment, in which both the ECD2 and ECD4-binding polypeptides are scFvs, is internalized to a greater extent by tumor cells expressing HER2 at a level of 1+, 2+ or 3+ than constructs of equivalent affinity that have a Fab/scFv format, which in turn are internalized more efficiently than constructs of equivalent affinity that have a Fab/Fab format. Embodiments that are readily internalized are good candidates for antibody-drug conjugates, which require internalization by a tumor cell to effect killing. Conversely, in certain embodiments, antigen-binding constructs which are not as readily internalized exhibit an increased potency in ADCC killing of tumor cells that express low levels of HER2 compared to constructs of equivalent affinity that have a Fab/Fab format. In one embodiment, an antigen binding construct having a Fab/scFv format is more potent in ADCC killing of tumor cells expressing low levels of HER2 (HER2 0-1+ or 1+) than an anti-HER2 construct having a Fab/Fab format, which in turn is more potent than an antigen binding construct having a scFv/scFv format. The enhanced ADCC potency of some embodiments may be due to their increased ability to remain on the cell surface (rather than causing internalization) and hence are more available for cell-mediated effector killing.

HER2

The antigen binding constructs described herein have antigen binding polypeptide constructs that bind to ECD2 and ECD4 of HER2

The expressions "ErbB2" and "HER2" are used interchangeably herein and refer to human HER2 protein described, for example, in Semba et al., *PNAS (USA)* 82:6497-6501 (1985) and Yamamoto et al. *Nature* 319:230-234 (1986) (Genebank accession number X03363). The term "erbB2" and "neu" refers to the gene encoding human ErbB2 protein. p185 or p185neu refers to the protein product of the neu gene.

HER2 is a HER receptor. A "HER receptor" is a receptor protein tyrosine kinase which belongs to the human epidermal growth factor receptor (HER) family and includes EGFR, HER2, HER3 and HER4 receptors. A HER receptor will generally comprise an extracellular domain, which may bind an HER ligand; a lipophilic transmembrane domain; a conserved intracellular tyrosine kinase domain; and a carboxyl-terminal signaling domain harboring several tyrosine residues which can be phosphorylated. By "HER ligand" is meant a polypeptide which binds to and/or activates an HER receptor.

The extracellular (ecto) domain of HER2 comprises four domains, Domain I (ECD1, amino acid residues from about 1-195), Domain II (ECD2, amino acid residues from about 196-319), Domain III (ECD3, amino acid residues from about 320-488), and Domain IV (ECD4, amino acid residues from about 489-630) (residue numbering without signal peptide). See Garrett et al. *Mol. Cell.* 11: 495-505 (2003), Cho et al. *Nature* 421: 756-760 (2003), Franklin et al. *Cancer Cell* 5:317-328 (2004), Tse et al. Cancer Treat Rev. 2012 April; 38(2):133-42 (2012), or Plowman et al. *Proc. Natl. Acad. Sci.* 90:1746-1750 (1993).

The sequence of HER2 is as follows; ECD boundaries are Domain I: 1-165; Domain II: 166-322; Domain III: 323-488; Domain IV: 489-607.

(SEQ ID NO: 349)

```
  1  tqvctgtdmk lrlpaspeth ldmlrhlyqg cqvvqgnlel tylptnasls flqdiqevqg
 61  yvliahnqvr qvplqrlriv rgtqlfedny alavldngdp lnnttpvtga spgglrelql
121  rsltellkgg vliqrnpqlc yqdtilwkdi fhknnqlalt lidtnrsrac hpcspmckgs
181  rcwgessedc qsltrtvcag gcarckgplp tdccheqcaa gctgpkhsdc laclhfnhsg
241  icelhcpalv tyntdtfesm pnpegrytfg ascvtacpyn ylstdvgsct lvcplhnqev
301  taedgtqrce kcskpcarvc yglgmehlre vravtsaniq efagckkifg slaflpesfd
361  gdpasntapl qpeqlqvfet leeitgylyi sawpdslpdl svfqnlqvir grilhngays
421  ltlqglgisw lglrslrelg sglalihhnt hlcfvhtvpw dqlfrnphqa llhtanrped
481  ecvgeglach qlcarghcwg pgptqcvncs qflrgqecve ecrvlqglpr eyvnarhclp
541  chpecqpqng svtcfgpead qcvacahykd ppfcvarcps gvkpdlsymp iwkfpdeega
601  cqpcpin
```

The "epitope 2C4" is the region in the extracellular domain of HER2 to which the antibody 2C4 binds. Epitope 2C4 comprises residues from domain II in the extracellular domain of HER2. 2C4 and Pertuzumab bind to the extracellular domain of HER2 at the junction of domains I, II and III. Franklin et al. *Cancer Cell* 5:317-328 (2004). In order to screen for antibodies which bind to the 2C4 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to assess whether the antibody binds to the 2C4 epitope of HER2 using methods known in the art and/or one can study the antibody-HER2 structure (Franklin et al. *Cancer Cell* 5:317-328 (2004)) to see what domain(s) of HER2 is/are bound by the antibody.

The "epitope 4D5" is the region in the extracellular domain of HER2 to which the antibody 4D5 (ATCC CRL 10463) and Trastuzumab bind. This epitope is close to the transmembrane domain of HER2, and within Domain IV of HER2. To screen for antibodies which bind to the 4D5 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to assess whether the antibody binds to the 4D5 epitope of HER2 (e.g. any one or more residues in the region from about residue 529 to about residue 625, inclusive, see FIG. 1 of US Patent Publication No. 2006/0018899).

"Specifically binds", "specific binding" or "selective binding" means that the binding is selective for the antigen and can be discriminated from unwanted or non-specific interactions. The ability of an antigen binding construct to bind to a specific antigenic determinant can be measured either through an enzyme-linked immunosorbent assay (ELISA) or other techniques familiar to one of skill in the art, e.g. surface plasmon resonance (SPR) technique (analyzed on a BIAcore instrument) (Liljeblad et al, Glyco J 17, 323-329 (2000)), and traditional binding assays (Heeley, Endocr Res 28, 217-229 (2002)). In one embodiment, the extent of binding of an antigen binding moiety to an unrelated protein is less than about 10% of the binding of the antigen binding construct to the antigen as measured, e.g., by SPR. In certain embodiments, an antigen binding construct that binds to the antigen, or an antigen binding molecule comprising that antigen binding moiety, has a dissociation constant ($K_D$) of <1 µM, <100 nM, <10 nM, <1 nM, <0.1 nM, <0.01 nM, or <0.001 nM (e.g. $10^{-8}$ M or less, e.g. from $10^{-8}$ M to $10^{-13}$ M, e.g., from $10^{-9}$ M to $10^{-13}$ M).

"Heregulin" (HRG) when used herein refers to a polypeptide encoded by the heregulin gene product as disclosed in U.S. Pat. No. 5,641,869 or Marchionni et al., *Nature*, 362:312-318 (1993). Examples of heregulins include heregulin-α, heregulin-β1, heregulin-β2 and heregulin-β3 (Holmes et al., Science, 256:1205-1210 (1992); and U.S. Pat. No. 5,641,869); neu differentiation factor (NDF) (Peles et al. Cell 69: 205-216 (1992)); acetylcholine receptor-inducing activity (ARIA) (Falls et al. Cell 72:801-815 (1993)); glial growth factors (GGFs) (Marchionni et al., Nature, 362:312-318 (1993)); sensory and motor neuron derived factor (SMDF) (Ho et al. J. Biol. Chem. 270:14523-14532 (1995)); γ-heregulin (Schaefer et al. Oncogene 15:1385-1394 (1997)). The term includes biologically active fragments and/or amino acid sequence variants of a native sequence HRG polypeptide, such as an EGF-like domain fragment thereof (e.g. HRGβ1177-244).

"HER activation" or "HER2 activation" refers to activation, or phosphorylation, of any one or more HER receptors, or HER2 receptors. Generally, HER activation results in signal transduction (e.g. that caused by an intracellular kinase domain of a HER receptor phosphorylating tyrosine residues in the HER receptor or a substrate polypeptide). HER activation may be mediated by HER ligand binding to a HER dimer comprising the HER receptor of interest. HER ligand binding to a HER dimer may activate a kinase domain of one or more of the HER receptors in the dimer and thereby results in phosphorylation of tyrosine residues in one or more of the HER receptors and/or phosphorylation of tyrosine residues in additional substrate polypeptides(s), such as Akt or MAPK intracellular kinases.

Derived Antigen Binding Polypeptide Constructs

The antigen-binding polypeptide constructs can be derived from known anti-HER2 antibodies or anti-HER2 binding domains regardless of the type of domain Examples of types of domains include Fab fragments, scFvs, and sdAbs. Furthermore, if the antigen binding moieties of a known anti-HER2 antibody or binding domain is a Fab, the Fab can be converted to an scFv. Likewise, if the antigen binding moiety of a known anti-HER2 antibody or binding domain is an scFv, the scFv can be converted to a Fab. Methods of converting between types of antigen binding domains are known in the art (see for example methods for converting an scFv to a Fab format described at, e.g., Zhou et al (2012) Mol Cancer Ther 11:1167-1476. The methods described therein are incorporated by reference).

The antigen-binding constructs described herein can be derived from known anti-HER2 antibodies that bind to ECD2 or ECD4. As described elsewhere herein, antibodies that bind to ECD2 or ECD4 are known in the art and include for example, 2C4 or pertuzumab (which bind ECD2), 4D5 or trastuzumab (which bind ECD4). Other antibodies that bind to ECD2 or ECD4 of HER2 have also been described in the art, for example in WO 2011/147982 (Genmab A/S).

In some embodiments the antigen-binding polypeptide construct of the antigen binding construct is derived from an antibody that blocks by 50% or greater the binding of antibody 4D5 or trastuzumab to ECD4 of HER2. In some embodiments, the antigen-binding polypeptide construct of the antigen binding construct is derived from an antibody that that blocks by 50% or greater the binding of antibody 2C4 or pertuzumab to ECD2 of HER2.

In one embodiment, the antigen-binding polypeptide construct is derived from a Fab fragment of trastuzumab or pertuzumab. In one embodiment, the antigen-binding polypeptide is derived from an scFv.

In certain embodiments the antigen-binding polypeptide is derived from humanized, or chimeric versions of these antibodies.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

Humanized HER2 antibodies include huMAb4D5-1, huMAb4D5-2, huMAb4D5-3, huMAb4D5-4, huMAb4D5-5, huMAb4D5-6, huMAb4D5-7 and huMAb4D5-8 or Trastuzumab (HERCEPTIN®) as described in Table 3 of U.S. Pat. No. 5,821,337 expressly incorporated herein by reference; humanized 520C9 (WO93/21319) and 20' humanized 2C4 antibodies as described in US Patent Publication No. 2006/0018899.

Affinity Maturation

In some embodiments, the antigen binding construct is derived from known HER2 binding antibodies using affinity maturation.

In instances where it is desirable to increase the affinity of the antigen-binding polypeptide for its cognate antigen, methods known in the art can be used to increase the affinity of the antigen-binding polypeptide for its antigen. Examples of such methods are described in the following references, Birtalan et al. (2008) *JMB* 377, 1518-1528; Gerstner et al. (2002) *JMB* 321, 851-862; Kelley et al. (1993) *Biochem* 32(27), 6828-6835; Li et al. (2010) *JBC* 285(6), 3865-3871, and Vajdos et al. (2002) JMB 320, 415-428.

One exemplary method for affinity maturation of HER2 antigen-binding domains is described as follows. Structures of the trastuzumab/HER2 (PDB code 1N8Z) complex and pertuzumab/HER2 complex (PDB code 1S78) are used for modeling. Molecular dynamics (MD) can be employed to evaluate the intrinsic dynamic nature of the WT complex in an aqueous environment. Mean field and dead-end elimination methods along with flexible backbones can be used to optimize and prepare model structures for the mutants to be screened. Following packing a number of features will be scored including contact density, clash score, hydrophobicity and electrostatics. Generalized Born method will allow accurate modeling of the effect of solvent environment and compute the free energy differences following mutation of specific positions in the protein to alternate residue types. Contact density and clash score will provide a measure of complementarity, a critical aspect of effective protein packing. The screening procedure employs knowledge-based potentials as well as coupling analysis schemes relying on pair-wise residue interaction energy and entropy computations. Literature mutations known to enhance HER2 binding, and combinations of thereof are summarized in the following tables:

TABLE A4

Trastuzumab mutations known to increase binding to HER2 for the Trastuzumab-HER2 system.

| Mutation | Reported Improvement |
|---|---|
| H_D102W (H_D98W) | 3.2× |
| H_D102Y | 3.1× |
| H_D102K | 2.3× |
| H_D102T | 2.2× |
| H_N55K | 2.0× |
| H_N55T | 1.9× |
| L_H91F | 2.1× |
| L_D28R | 1.9× |

TABLE A5

Pertuzumab mutations known to increase binding to HER2 for the Pertuzumab-HER2 system.

| Mutation | Reported Improvement |
|---|---|
| L_I31A | 1.9× |
| L_Y96A | 2.1× |
| L_Y96F | 2.5× |
| H_T30A | 2.1× |
| H_G56A | 8.3× |
| H_F63V | 1.9× |

Fc of Antigen Binding Constructs.

In some embodiments, the antigen-binding constructs described herein comprise an Fc, e.g., a dimeric Fc.

The term "Fc domain" or "Fc region" herein is used to define a C-terminal region of an immunoglobulin heavy chain that contains at least a portion of the constant region. The term includes native sequence Fc regions and variant Fc regions. Unless otherwise specified herein, numbering of amino acid residues in the Fc region or constant region is according to the EU numbering system, also called the EU index, as described in Kabat et al, Sequences of Proteins of Immunological Interest, 5th Ed. Public Health Service, National Institutes of Health, Bethesda, MD, 1991. An "Fc polypeptide" of a dimeric Fc as used herein refers to one of the two polypeptides forming the dimeric Fc domain, i.e. a polypeptide comprising C-terminal constant regions of an immunoglobulin heavy chain, capable of stable self-association. For example, an Fc polypeptide of a dimeric IgG Fc comprises an IgG CH2 and an IgG CH3 constant domain sequence.

An Fc domain comprises either a CH3 domain or a CH3 and a CH2 domain. The CH3 domain comprises two CH3 sequences, one from each of the two Fc polypeptides of the dimeric Fc. The CH2 domain comprises two CH2 sequences, one from each of the two Fc polypeptides of the dimeric Fc.

In some aspects, the Fc comprises at least one or two CH3 sequences. In some aspects, the Fc is coupled, with or without one or more linkers, to a first antigen-binding construct and/or a second antigen-binding construct. In some aspects, the Fc is a human Fc. In some aspects, the Fc is a human IgG or IgG1 Fc. In some aspects, the Fc is a heterodimeric Fc. In some aspects, the Fc comprises at least one or two CH2 sequences.

In some aspects, the Fc comprises one or more modifications in at least one of the CH3 sequences. In some aspects, the Fc comprises one or more modifications in at least one of the CH2 sequences. In some aspects, an Fc is a single polypeptide. In some aspects, an Fc is multiple peptides, e.g., two polypeptides.

In some aspects, an Fc is an Fc described in patent applications PCT/CA2011/001238, filed Nov. 4, 2011 or PCT/CA2012/050780, filed Nov. 2, 2012, the entire disclosure of each of which is hereby incorporated by reference in its entirety for all purposes.

Modified CH3 Domains

In some aspects, the antigen-binding construct described herein comprises a heterodimeric Fc comprising a modified CH3 domain that has been asymmetrically modified. The heterodimeric Fc can comprise two heavy chain constant domain polypeptides: a first Fc polypeptide and a second Fc polypeptide, which can be used interchangeably provided that Fc comprises one first Fc polypeptide and one second Fc polypeptide. Generally, the first Fc polypeptide comprises a first CH3 sequence and the second Fc polypeptide comprises a second CH3 sequence.

Two CH3 sequences that comprise one or more amino acid modifications introduced in an asymmetric fashion generally results in a heterodimeric Fc, rather than a homodimer, when the two CH3 sequences dimerize. As used herein, "asymmetric amino acid modifications" refers to any modification where an amino acid at a specific position on a first CH3 sequence is different from the amino acid on a second CH3 sequence at the same position, and the first and second CH3 sequence preferentially pair to form a heterodimer, rather than a homodimer. This heterodimerization can be a result of modification of only one of the two amino acids at the same respective amino acid position on each sequence; or modification of both amino acids on each sequence at the same respective position on each of the first and second CH3 sequences. The first and second CH3 sequence of a heterodimeric Fc can comprise one or more than one asymmetric amino acid modification.

Table A provides the amino acid sequence of the human IgG1 Fc sequence, corresponding to amino acids 231 to 447 of the full-length human IgG1 heavy chain. The CH3 sequence comprises amino acid 341-447 of the full-length human IgG1 heavy chain.

Typically an Fc can include two contiguous heavy chain sequences (A and B) that are capable of dimerizing. In some aspects, one or both sequences of an Fc include one or more mutations or modifications at the following locations: L351, F405, Y407, T366, K392, T394, T350, S400, and/or N390, using EU numbering. In some aspects, an Fc includes a mutant sequence shown in Table X. In some aspects, an Fc includes the mutations of Variant 1 A-B. In some aspects, an Fc includes the mutations of Variant 2 A-B. In some aspects, an Fc includes the mutations of Variant 3 A-B. In some aspects, an Fc includes the mutations of Variant 4 A-B. In some aspects, an Fc includes the mutations of Variant 5 A-B.

TABLE A

IgG1 Fc sequences

| Human IgG1 Fc sequence 231-447 (EU-numbering) | APELLGGPSVFLFPPKPKDTLMISRTPEVTCVVV DVSHEDPEVKFNWYVDGVEVHNAKTKPREEQYNS TYRVVSVLTVLHQDWLNGKEYKCKVSNKALPAPI EKTISKAKGQPREPQVYTLPPSRDELTKNQVSLT CLVKGFYPSDIAVEWESNGQPENNYKTTPPVLDS DGSFFLYSKLTVDKSRWQQGNVFSCSVMHEA LHNHYTQKSLSLSPGK (SEQ ID NO: 350) | |
|---|---|---|

| Variant IgG1 Fc sequence (231-447) | Chain | Mutations |
|---|---|---|
| 1 | A | L351Y_F405A_Y407V |
| 1 | B | T366L_K392M_T394W |
| 2 | A | L351Y_F405A_Y407V |
| 2 | B | T366L_K392L_T394W |
| 3 | A | T350V_L351Y_F405A_Y407V |
| 3 | B | T350V_T366L_K392L_T394W |
| 4 | A | T350V_L351Y_F405A_Y407V |
| 4 | B | T350V_T366L_K392M_T394W |
| 5 | A | T350V_L351Y_S400E_F405A_Y407V |
| 5 | B | T350V_T366L_N390R_K392M_T394W |

The first and second CH3 sequences can comprise amino acid mutations as described herein, with reference to amino acids 231 to 447 of the full-length human IgG1 heavy chain. In one embodiment, the heterodimeric Fc comprises a modified CH3 domain with a first CH3 sequence having amino acid modifications at positions F405 and Y407, and a second CH3 sequence having amino acid modifications at position T394. In one embodiment, the heterodimeric Fc comprises a modified CH3 domain with a first CH3 sequence having one or more amino acid modifications selected from L351Y, F405A, and Y407V, and the second CH3 sequence having one or more amino acid modifications selected from T366L, T366I, K392L, K392M, and T394W.

In one embodiment, a heterodimeric Fc comprises a modified CH3 domain with a first CH3 sequence having amino acid modifications at positions L351, F405 and Y407, and a second CH3 sequence having amino acid modifications at positions T366, K392, and T394, and one of the first or second CH3 sequences further comprising amino acid modifications at position Q347, and the other CH3 sequence further comprising amino acid modification at position K360. In another embodiment, a heterodimeric Fc comprises a modified CH3 domain with a first CH3 sequence having amino acid modifications at positions L351, F405 and Y407, and a second CH3 sequence having amino acid modifications at position T366, K392, and T394, one of the first or second CH3 sequences further comprising amino acid modifications at position Q347, and the other CH3 sequence further comprising amino acid modification at position K360, and one or both of said CH3 sequences further comprise the amino acid modification T350V.

In one embodiment, a heterodimeric Fc comprises a modified CH3 domain with a first CH3 sequence having amino acid modifications at positions L351, F405 and Y407, and a second CH3 sequence having amino acid modifica-tions at positions T366, K392, and T394 and one of said first and second CH3 sequences further comprising amino acid modification of D399R or D399K and the other CH3 sequence comprising one or more of T411E, T411D, K409E, K409D, K392E and K392D. In another embodiment, a heterodimeric Fc comprises a modified CH3 domain with a first CH3 sequence having amino acid modifications at positions L351, F405 and Y407, and a second CH3 sequence having amino acid modifications at positions T366, K392, and T394, one of said first and second CH3 sequences further comprises amino acid modification of D399R or D399K and the other CH3 sequence comprising one or more of T411E, T411D, K409E, K409D, K392E and K392D, and one or both of said CH3 sequences further comprise the amino acid modification T350V.

In one embodiment, a heterodimeric Fc comprises a modified CH3 domain with a first CH3 sequence having amino acid modifications at positions L351, F405 and Y407, and a second CH3 sequence having amino acid modifica-tions at positions T366, K392, and T394, wherein one or both of said CH3 sequences further comprise the amino acid modification of T350V.

In one embodiment, a heterodimeric Fc comprises a modified CH3 domain comprising the following amino acid modifications, where "A" represents the amino acid modi-fications to the first CH3 sequence, and "B" represents the amino acid modifications to the second CH3 sequence: A:L351Y_F405A_Y407V, B:T366L_K392M_T394W, A:L351Y_F405A_Y407V, B:T366L_K392L_T394W, A:T350V_L315Y_F405A_Y407V, B:T350V_T366L_K392L_T394W, A:T350V_L351Y_F405A_Y407V, B:T350V_T366L_K392M_T394W, A:T350V_L351Y_S400E_F405A_Y407V, and/or B:T350V_T366L_N390R_K392M_T394W.

The one or more asymmetric amino acid modifications can promote the formation of a heterodimeric Fc in which the heterodimeric CH3 domain has a stability that is com-parable to a wild-type homodimeric CH3 domain. In an embodiment, the one or more asymmetric amino acid modi-fications promote the formation of a heterodimeric Fc domain in which the heterodimeric Fc domain has a stability that is comparable to a wild-type homodimeric Fc domain. In an embodiment, the one or more asymmetric amino acid modifications promote the formation of a heterodimeric Fc domain in which the heterodimeric Fc domain has a stability observed via the melting temperature (Tm) in a differential scanning calorimetry study, and where the melting tempera-ture is within 4° C. of that observed for the corresponding symmetric wild-type homodimeric Fc domain. In some aspects, the Fc comprises one or more modifications in at least one of the $C_{H3}$ sequences that promote the formation of a heterodimeric Fc with stability comparable to a wild-type homodimeric Fc.

In one embodiment, the stability of the CH3 domain can be assessed by measuring the melting temperature of the CH3 domain, for example by differential scanning calorim-etry (DSC). Thus, in a further embodiment, the CH3 domain has a melting temperature of about 68° C. or higher. In another embodiment, the CH3 domain has a melting tem-perature of about 70° C. or higher. In another embodiment, the CH3 domain has a melting temperature of about 72° C. or higher. In another embodiment, the CH3 domain has a melting temperature of about 73° C. or higher. In another embodiment, the CH3 domain has a melting temperature of about 75° C. or higher. In another embodiment, the CH3 domain has a melting temperature of about 78° C. or higher.

In some aspects, the dimerized CH3 sequences have a melting temperature (Tm) of about 68, 69, 70, 71, 72, 73, 74, 75, 76, 77, 77.5, 78, 79, 80, 81, 82, 83, 84, or 85° C. or higher.

In some embodiments, a heterodimeric Fc comprising modified CH3 sequences can be formed with a purity of at least about 75% as compared to homodimeric Fc in the expressed product. In another embodiment, the heterodimeric Fc is formed with a purity greater than about 80%. In another embodiment, the heterodimeric Fc is formed with a purity greater than about 85%. In another embodiment, the heterodimeric Fc is formed with a purity greater than about 90%. In another embodiment, the heterodimeric Fc is formed with a purity greater than about 95%. In another embodiment, the heterodimeric Fc is formed with a purity greater than about 97%. In some aspects, the Fc is a heterodimer formed with a purity greater than about 75, 76, 77, 78, 79, 80, 81, 82, 83, 84, 85, 86, 87, 88, 89, 90, 91, 92, 93, 94, 95, 96, 97, 98, or 99% when expressed. In some aspects, the Fc is a heterodimer formed with a purity greater than about 75, 76, 77, 78, 79, 80, 81, 82, 83, 84, 85, 86, 87, 88, 89, 90, 91, 92, 93, 94, 95, 96, 97, 98, or 99% when expressed via a single cell.

Additional methods for modifying monomeric Fc polypeptides to promote heterodimeric Fc formation are described in International Patent Publication No. WO 96/027011 (knobs into holes), in Gunasekaran et al. (Gunasekaran K. et al. (2010) J Biol Chem. 285, 19637-46, electrostatic design to achieve selective heterodimerization), in Davis et al. (Davis, J H. et al. (2010) Prot Eng Des Sel; 23(4): 195-202, strand exchange engineered domain (SEED) technology), and in Labrijn et al [Efficient generation of stable bispecific IgG1 by controlled Fab-arm exchange. Labrijn A F, Meesters J I, de Goeij B E, van den Bremer E T, Neijssen J, van Kampen M D, Strumane K, Verploegen S, Kundu A, Gramer M J, van Berkel P H, van de Winkel J G, Schuurman J, Parren P W. Proc Natl Acad Sci USA. 2013 Mar. 26; 110(13):5145-50.

CH2 Domains

In some embodiments, the Fc of the antigen-binding construct comprises a CH2 domain. One example of an CH2 domain of an Fc is amino acid 231-340 of the sequence shown in Table A. Several effector functions are mediated by Fc receptors (FcRs), which bind to the Fc of an antibody.

The terms "Fc receptor" and "FcR" are used to describe a receptor that binds to the Fc region of an antibody. For example, an FcR can be a native sequence human FcR. Generally, an FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Immunoglobulins of other isotypes can also be bound by certain FcRs (see, e.g., Janeway et al., Immuno Biology: the immune system in health and disease, (Elsevier Science Ltd., NY) (4th ed., 1999)). Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (reviewed in Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976); and Kim et al., J. Immunol. 24:249 (1994)).

Modifications in the CH2 domain can affect the binding of FcRs to the Fc. A number of amino acid modifications in the Fc region are known in the art for selectively altering the affinity of the Fc for different Fcgamma receptors. In some aspects, the Fc comprises one or more modifications to promote selective binding of Fc-gamma receptors.

Exemplary mutations that alter the binding of Fcrs to the Fc are listed below:

S298A/E333A/K334A, S298A/E333A/K334A/K326A (Lu Y, Vernes J M, Chiang N, et al. J Immunol Methods. 2011 Feb. 28; 365(1-2):132-41);

F243L/R292P/Y300L/V305I/P396L, F243L/R292P/Y300L/L235V/P396L (Stavenhagen J B, Gorlatov S, Tuaillon N, et al. Cancer Res. 2007 Sep. 15; 67(18):8882-90; Nordstrom J L, Gorlatov S, Zhang W, et al. Breast Cancer Res. 2011 Nov. 30; 13(6):R123);

F243L (Stewart R, Thom G, Levens M, et al. Protein Eng Des Sel. 2011 September; 24(9):671-8), S298A/E333A/K334A (Shields R L, Namenuk A K, Hong K, et al. J Biol Chem. 2001 Mar. 2; 276(9):6591-604);

S239D/I332E/A330L, S239D/I332E (Lazar G A, Dang W, Karki S, et al. Proc Natl Acad Sci USA. 2006 Mar. 14; 103(11):4005-10);

S239D/S267E, S267E/L328F (Chu S Y, Vostiar I, Karki S, et al. Mol Immunol. 2008 September; 45(15):3926-33); S239D/D265S/S298A/I332E, S239E/S298A/K326A/A327H, G237F/S298A/A330L/I332E, S239D/I332E/S298A, S239D/K326E/A330L/I332E/S298A, G236A/S239D/D270L/I332E, S239E/S267E/H268D, L234F/S267E/N325L, G237F/V266L/S267D and other mutations listed in WO2011/120134 and WO2011/120135, herein incorporated by reference. Therapeutic Antibody Engineering (by William R. Strohl and Lila M. Strohl, Woodhead Publishing series in Biomedicine No 11, ISBN 1 907568 37 9, October 2012) lists mutations on page 283.

In some embodiments an antigen-binding construct described herein comprises an antigen binding polypeptide construct which binds an antigen; and a dimeric Fc that has superior biophysical properties like stability and ease of manufacture relative to an antigen binding construct which does not include the same dimeric Fc. In some embodiments a CH2 domain comprises one or more asymmetric amino acid modifications. Exemplary asymmetric mutations are described in International Patent Application No. PCT/CA2014/050507.

Additional Modifications to Improve Effector Function.

In some embodiments an antigen binding construct described herein includes modifications to improve its ability to mediate effector function. Such modifications are known in the art and include afucosylation, or engineering of the affinity of the Fc towards an activating receptor, mainly FCGR3a for ADCC, and towards C1q for CDC. The following Table B summarizes various designs reported in the literature for effector function engineering.

Thus, in one embodiment, a construct described herein can include a dimeric Fc that comprises one or more amino acid modifications as noted in Table B that confer improved effector function. In another embodiment, the construct can be afucosylated to improve effector function.

TABLE B

CH2 domains and effector function engineering.

| Reference | Mutations | Effect |
| --- | --- | --- |
| Lu, 2011, Ferrara 2011, Mizushima 2011 | Afucosylated | Increased ADCC |
| Lu, 2011 | S298A/E333A/K334A | Increased ADCC |
| Lu, 2011 | S298A/E333A/K334A/K326A | Increased ADCC |
| Stavenhagen, 2007 | F243L/R292P/Y300L/V305I/P396L | Increased ADCC |
| Nordstrom, 2011 | F243L/R292P/Y300L/L235V/P396L | Increased ADCC |
| Stewart, 2011 | F243L | Increased ADCC |
| Shields, 2001 | S298A/E333A/K334A | Increased ADCC |
| Lazar, 2006 | S239D/I332E/A330L | Increased ADCC |
| Lazar, 2006 | S239D/I332E | Increased ADCC |
| Bowles, 2006 | AME-D, not specified mutations | Increased ADCC |
| Heider, 2011 | 37.1, mutations not disclosed | Increased ADCC |
| Moore, 2010 | S267E/H268F/S324T | Increased CDC |

Fc modifications reducing FcγR and/or complement binding and/or effector function are known in the art. Recent publications describe strategies that have been used to engineer antibodies with reduced or silenced effector activity (see Strohl, WR (2009), Curr Opin Biotech 20:685-691, and Strohl, WR and Strohl L M, "Antibody Fc engineering for optimal antibody performance" In Therapeutic Antibody Engineering, Cambridge: Woodhead Publishing (2012), pp 225-249). These strategies include reduction of effector function through modification of glycosylation, use of IgG2/IgG4 scaffolds, or the introduction of mutations in the hinge or CH2 regions of the Fc. For example, US Patent Publication No. 2011/0212087 (Strohl), International Patent Publication No. WO 2006/105338 (Xencor), US Patent Publication No. 2012/0225058 (Xencor), US Patent Publication No. 2012/0251531 (Genentech), and Strop et al ((2012) J. Mol. Biol. 420: 204-219) describe specific modifications to reduce FcγR or complement binding to the Fc.

Specific, non-limiting examples of known amino acid modifications to reduce FcγR or complement binding to the Fc include those identified in the following table:

TABLE C modifications to reduce FcγR or complement binding to the Fc

| Company | Mutations |
| --- | --- |
| GSK | N297A |
| Ortho Biotech | L234A/L235A |
| Protein Design labs | IGG2 V234A/G237A |
| Wellcome Labs | IGG4 L235A/G237A/E318A |
| GSK | IGG4 S228P/L236E |
| Alexion | IGG2/IGG4combo |
| Merck | IGG2 H268Q/V309L/A330S/A331S |
| Bristol-Myers | C220S/C226S/C229S/P238S |
| Seattle Genetics | C226S/C229S/E3233P/L235V/L235A |
| Amgen | E. coli production, non glyco |
| Medimune | L234F/L235E/P331S |
| Trubion | Hinge mutant, possibly C226S/P230S |

In one embodiment, the Fc comprises at least one amino acid modification identified in the above table. In another embodiment the Fc comprises amino acid modification of at least one of L234, L235, or D265. In another embodiment, the Fc comprises amino acid modification at L234, L235 and D265. In another embodiment, the Fc comprises the amino acid modification L234A, L235A and D265S.

Linkers and Linker Polypeptides

Each of the antigen binding polypeptide constructs of the antigen-binding construct are operatively linked to to a linker polypeptide wherein the linker polypeptides are capable of forming a covalent linkage with each other. The spatial conformation of the antigen-binding construct comprising a first and second antigen-binding polypeptide constructs with the linker polypeptides is similar to the relative spatial conformation of the paratopes of a F(ab')2 fragment generated by papain digestion, albeit in the context of the bispecific antigen-binding constructs described herein, the two antigen-binding polypeptide constructs are in the Fab-scFv or scFv-scFv format.

Thus, the linker polypeptides are selected such that they maintain the relative spatial conformation of the paratopes of a F(ab') fragment, and are capable of forming a covalent bond equivalent of the disulphide bond in the core hinge of IgG. Suitable linker polypeptides include IgG hinge regions such as, for example those from IgG1, IgG2, or IgG4. Modified versions of these exemplary linkers can also be used. For example, modifications to improve the stability of the IgG4 hinge are known in the art (see for example, Labrijn et al. (2009) Nature Biotechnology 27, 767-771).

In one embodiment, the linker polypeptides are operatively linked to a scaffold as described here, for example an Fc. In some aspects, an Fc is coupled to the one or more antigen binding polypeptide constructs with one or more linkers. In some aspects, Fc is coupled to the heavy chain of each antigen binding polypeptide by a linker.

In other embodiments, the linker polypeptides are operatively linked to scaffolds other than an Fc. A number of alternate protein or molecular domains are know in the art and can be used to form selective pairs of two different antigen binding polypeptides. An example is the leucine zipper domains such as Fos and Jun that selectively pair together [S A Kostelny, M S Cole, and J Y Tso. Formation of a bispecific antibody by the use of leucine zippers J Immunol 1992 148:1547-53; Bernd J. Wranik, Erin L. Christensen, Gabriele Schaefer, Janet K. Jackman, Andrew C. Vendel, and Dan Eaton. LUZ-Y, a Novel Platform for the Mammalian Cell Production of Full-length IgG-bispecific AntibodiesJ. Biol. Chem. 2012 287: 43331-43339]. Alternately, other selectively pairing molecular pairs such as the barnase barstar pair [Deyev, S. M., Waibel, R., Lebedenko, E. N., Schubiger, A. P., and Plückthun, A. (2003). Design of multivalent complexes using the barnase*barstar module. Nat Biotechnol 21, 1486-1492], DNA strand pairs [Zahida N. Chaudri, Michael Bartlet-Jones, George Panayotou, Thomas Klonisch, Ivan M. Roitt, Torben Lund, Peter J. Delves, Dual specificity antibodies using a double-stranded oligonucleotide bridge, FEBS Letters, Volume 450, Issues 1-2, 30 Apr. 1999, Pages 23-26], split fluorescent protein pairs [Ulrich Brinkmann, Alexander Haas. Fluorescent antibody fusion protein, its production and use, WO 2011135040 A1] can also be employed.

Dissociation Constant ($K_D$) and Maximal Binding (Bmax)

In some embodiments, an antigen binding construct is described by functional characteristics including but not limited to a dissociation constant and a maximal binding.

The term "dissociation constant ($K_D$)" as used herein, is intended to refer to the equilibrium dissociation constant of a particular ligand-protein interaction. As used herein, ligand-protein interactions refer to, but are not limited to protein-protein interactions or antibody-antigen interactions. The $K_D$ measures the propensity of two proteins (e.g. AB) to dissociate reversibly into smaller components (A+B), and is define as the ratio of the rate of dissociation, also called the "off-rate ($k_{off}$)", to the association rate, or "on-rate ($k_{on}$)". Thus, $K_D$ equals $k_{off}/k_{on}$ and is expressed as a molar concentration (M). It follows that the smaller the $K_D$, the stronger the affinity of binding. Therefore, a $K_D$ of 1 mM indicates weak binding affinity compared to a $K_D$ of 1 nM. $K_D$ values for antigen binding constructs can be determined using methods well established in the art. One method for determining the $K_D$ of an antigen binding construct is by using surface plasmon resonance (SPR), typically using a biosensor system such as a Biacore® system. Isothermal titration calorimetry (ITC) is another method that can be used to determine.

The binding characteristics of an antigen binding construct can be determined by various techniques. One of which is the measurement of binding to target cells expressing the antigen by flow cytometry (FACS, Fluorescence-activated cell sorting). Typically, in such an experiment, the target cells expressing the antigen of interest are incubated with antigen binding constructs at different concentrations, washed, incubated with a secondary agent for detecting the antigen binding construct, washed, and analyzed in the flow cytometer to measure the median fluorescent intensity (MFI) representing the strength of detection signal on the cells, which in turn is related to the number of antigen binding constructs bound to the cells. The antigen binding construct concentration vs. MFI data is then fitted into a saturation binding equation to yield two key binding parameters, Bmax and apparent $K_D$.

Apparent $K_D$, or apparent equilibrium dissociation constant, represents the antigen binding construct concentration at which half maximal cell binding is observed. Evidently, the smaller the $K_D$ value, the smaller antigen binding construct concentration is required to reach maximum cell binding and thus the higher is the affinity of the antigen binding construct. The apparent $K_D$ is dependent on the conditions of the cell binding experiment, such as different receptor levels expressed on the cells and incubation conditions, and thus the apparent $K_D$ is generally different from the $K_D$ values determined from cell-free molecular experiments such as SPR and ITC. However, there is generally good agreement between the different methods.

The term "Bmax", or maximal binding, refers to the maximum antigen binding construct binding level on the cells at saturating concentrations of antigen binding construct. This parameter can be reported in the arbitrary unit MFI for relative comparison, or converted into an absolute value corresponding to the number of antigen binding constructs bound to the cell with the use of a standard curve. In some embodiments, the antigen binding constructs display a Bmax that is 1.1, 1.2, 1.3, 1.4, 1.5, 1.6, 1.7, 1.8, 1.9, or 2.0 times the Bmax of a reference antigen binding construct.

For the antigen binding constructs described herein, the clearest separation in Bmax versus FSA occurs at saturating concentrations and where Bmax can no longer be increased with a FSA. The significance is less at non-saturating concentrations. In one embodiment the increase in Bmax and $K_D$ of the antigen binding construct compared to a reference antigen binding construct is independent of the level of target antigen expression on the target cell.

In some embodiments is an isolated antigen binding construct described herein, wherein said antigen binding construct displays an increase in Bmax (maximum binding) to a target cell displaying said antigen as compared to a corresponding reference antigen binding construct. In some embodiments said increase in Bmax is at least about 125% of the Bmax of the corresponding reference antigen binding construct. In certain embodiments, the increase in Bmax is at least about 150% of the Bmax of the corresponding reference antigen binding construct. In some embodiments, the increase in Bmax is at least about 200% of the Bmax of the corresponding reference antigen binding construct. In some embodiments, the increase in Bmax is greater than about 110% of the Bmax of the corresponding reference antigen binding construct.

Increased Effector Functions

In one embodiment, the bispecific antigen-binding construct described herein displays increased effector functions compared to each corresponding monospecific bivalent antigen-binding construct (i.e., compared to a monospecific bivalent antigen-binding construct that binds to ECD2 or a monospecific bivalent antigen-binding construct that binds to ECD4) and/or compared to a combination the two monospecific bivalent antigen-binding constructs. Antibody "effector functions" refer to those biological activities attributable to the Fc domain (a native sequence Fc domain or amino acid sequence variant Fc domain) of an antibody. Examples of antibody effector functions include C1q binding; complement dependent cytotoxicity (CDC); Fc receptor binding; antibody-dependent cell-mediated cytotoxicity (ADCC); antibody dependent cellular phagocytosis (ADCP); down regulation of cell surface receptors (e.g. B cell receptor; BCR), etc.

ADCC

Thus, in one embodiment, the bispecific antigen-binding construct is in a Fab-scFv format and displays a higher potency in an ADCC assay than a format reference antigen-binding construct that is in a Fab-Fab format in cells expressing HER2 at the 1+ level.

In one embodiment, the bispecific antigen-binding construct displays greater maximum cell lysis in an ADCC assay than a reference antigen-binding construct that is trastuzumab or analog thereof. In one embodiment, the bispecific antigen-binding construct is in a Fab-scFv format and displays greater maximum cell lysis in an ADCC assay than a reference antigen-binding construct that is trastuzumab or analog thereof, or a combination of trastuzumab or pertuzumab analogs. In one embodiment, the bispecific antigen-binding construct is in a Fab-scFv format and displays greater maximum cell lysis in an ADCC assay than a reference antigen-binding construct that is trastuzumab or analog thereof in cells expressing HER2 at the 1+ or greater level. In one embodiment, the bispecific antigen-binding construct is in a Fab-scFv format and displays a higher potency in an ADCC assay than a reference antigen-binding construct that is trastuzumab or analog thereof in HER2 2+/3+ cells.

Internalization

The bispecific antigen-binding constructs described herein are internalized in HER2+ cells, through binding to the receptor HER2. Thus, the bispecific antigen-binding constructs described herein are able to induce receptor internalization in HER2+ cells. In one embodiment, the bispecific antigen-binding construct is in a Fab-scFv format and induces greater HER2 internalization than a format reference antigen-binding construct that is in a Fab-Fab format in cells expressing HER2 at the 3+ level. In one embodiment, the bispecific antigen-binding construct is in a Fab-scFv format and induces greater HER2 internalization than a format reference antigen-binding construct that is in a Fab-Fab format in cells expressing HER2 at the 2+ or 3+ level. In one embodiment, the bispecific antigen-binding construct is in an scFv-scFv format and induces greater HER2 internalization than a format reference antigen-binding construct that is in a Fab-Fab format in cells expressing HER2 at the 1+, 2+ or 3+ level.

Cellular Cytotoxicity

The bispecific antigen-binding construct can be prepared as ADCs as described elsewhere herein and are cytotoxic to cells. In one embodiment, the bispecific antigen-binding construct ADC is displays a higher potency in a cytotoxicity or cell survival assay in HER2+ breast cancer cells than a reference antigen-binding construct that is trastuzumab or analog thereof, or a reference antigen-binding construct that is a combination of T-DM1 and pertuzumab in HER2 1+, 2+, 2+/3+, or 3+ cells.

Increased Binding Capacity to FcγRs

In some embodiments, the bispecific antigen-binding constructs exhibit a higher binding capacity (Rmax) to one or more FcγRs. In one embodiment the bispecific antigen-binding construct exhibits an increase in Rmax to one or more FcγRs over a reference antigen-binding construct that is v506 or v6246, having a homodimeric Fc, of between about 1.3- to 2-fold. In one embodiment, the bispecific antigen-binding construct exhibits an increase in Rmax to a CD16 FcγR of between about 1.3- to 1.8-fold over the reference bivalent antigen-binding construct. In one embodiment, the bispecific antigen-binding construct exhibits an increase in Rmax to a CD32 FcγR of between about 1.3- to 1.8-fold over the reference bivalent antigen-binding construct. In one embodiment, the bispecific antigen-binding construct exhibits an increase in Rmax to a CD64 FcγR of between about 1.3- to 1.8-fold over the reference bivalent antigen-binding construct.

Increased Affinity for FcγRs

The bispecific antigen-binding constructs provided herein have an increased affinity for FcγR as compared to corresponding bivalent antigen-binding constructs. The increased Fc concentration resulting from the decoration is consistent with increased ADCC, ADCP, CDC activity.

In some embodiments, the bispecific antigen-binding constructs exhibit an increased affinity for one or more FcγRs. In one embodiment, where the bispecific antigen-binding construct comprises an antigen-binding polypeptide that binds to HER2, the bispecific antigen-binding constructs exhibit an increased affinity for at least one FcγR. In accordance with this embodiment, the bispecific antigen-binding construct exhibits an increased affinity for CD32.

FcRn Binding and PK Parameters

In some embodiments, the antigen-binding constructs of the described herein are able to bind FcRn. As is known in the art, binding to FcRn recycles endocytosed antibody from the endosome back to the bloodstream (Raghavan et al., 1996, Annu Rev Cell Dev Biol 12:181-220; Ghetie et al., 2000, Annu Rev Immunol 18:739-766). This process, coupled with preclusion of kidney filtration due to the large size of the full-length molecule, results in favorable antibody serum half-lives ranging from one to three weeks. Binding of Fc to FcRn also plays a key role in antibody transport.

Pharmacokinetic Parameters

In certain embodiments, a bispecific antigen-binding construct provided herein exhibits pharmacokinetic (PK) properties comparable with commercially available therapeutic antibodies. In one embodiment, the bispecific antigen-binding constructs described herein exhibit PK properties similar to known therapeutic antibodies, with respect to serum concentration, t1/2, beta half-life, and/or CL. In one embodiment, the bispecific antigen-binding constructs display in vivo stability comparable to or greater than said monospecific bivalent antigen-binding construct. Such in vivo stability parameters include serum concentration, t1/2, beta half-life, and/or $C_L$.

Testing of the Bispecific Antigen-Binding Constructs. FcγR, FcRn and C1q Binding The effector functions of the bispecific antigen-binding constructs can be tested as follows. In vitro and/or in vivo cytotoxicity assays can be conducted to assess ADCP, CDC and/or ADCC activities. For example, Fc receptor (FcR) binding assays can be conducted to measure FcγR binding. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). An example of an in vitro assay to assess ADCC activity of a molecule of interest is described in U.S. Pat. No. 5,500,362 or 5,821,337. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998). C1q binding assays may also be carried out to determine if the bispecific antigen-binding constructs are capable of binding C1q and hence activating CDC. To assess complement activation, a CDC assay, e.g. as described in Gazzano-Santoro et al., J. Immunol. Methods 202:163 (1996), may be performed. FcRn binding such as by SPR and in vivo PK determinations of antibodies can also be performed using methods well known in the art.

Testing of Antigen Binding Constructs: HER2 Binding

The antigen binding constructs or pharmaceutical compositions described herein are tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific antigen-binding construct is indicated, include in vitro cell culture assays, or in vitro assays in which a patient tissue sample is grown in culture, and exposed to or otherwise administered antigen binding construct, and the effect of such antigen binding construct upon the tissue sample is observed.

Candidate antigen binding constructs can be assayed using cells, e.g., breast cancer cell lines, expressing HER2. The following Table D describes the expression level of HER2 in several representative cancer cell lines.

TABLE D

Relative expression levels of HER2 in cell lines of interest.

| Cell Line | Description | IHC scoring | HER2 receptors/cell |
|---|---|---|---|
| NCI-N87 | Human gastric carcinoma | 3+ | Not assessed |
| A549 | Human lung alveolar carcinoma (non-small cell lung cancer) | 0/1+ | Not assessed |
| BxPC-3 | Human pancreatic adenocarcinoma | 1+ | Not assessed |
| MIA PaCa-2 | Human pancreatic ductal adenocarcinoma | 2+ | Not assessed |
| FaDu | Human pharyngeal squamous cell carcinoma | 2+ | Not assessed |
| HCT-116 | Human colorectal epithelial carcinoma | 1+ | Not assessed |
| WI-38 | Normal fetal lung | 0 | $1.0 \times 10E4$ |
| MDA-MB-231 | Human triple negative breast epithelial adenocarcinoma | 0/1+ | $1.7 \times 10E4 – 2.3 \times 10E4$ |
| MCF-7 | Human estrogen receptor positive breast epithelial adenocarcinoma | 1+ | $4 \times 10E4 – 7 \times 10E4$ |
| JIMT-1 | Trastuzumab resistant breast epithelial carcinoma, amplified HER2 oncogene, insensitive to HER2-inhibiting drugs (i.e. Herceptin™) | 2+ | $2 \times 10E5 – 8 \times 10E5$ |
| ZR-75-1 | Estrogen receptor positive breast ductal carcinoma | 2+ | $3 \times 10E5$ |
| SKOV-3 | Human ovarian epithelial adenocarcinoma, HER2 gene amplified | 2/3+ | $5 \times 10E5 – 1 \times 10E6$ |
| SK-BR-3 | Human breast epithelial adenocarcinoma | 3+ | $>1 \times 10E6$ |
| BT-474 | Human breast epithelial ductal carcinoma, | 3+ | $>1 \times 10E6$ |

McDonagh et al Mol Cancer Ther. 2012 March; 11(3): 582-93; Subik et al. (2010) Breast Cancer: Basic Clinical Research:4; 35-41; Carter et al. PNAS, 1994:89; 4285-4289; Yarden 2000, HER2: Basic Research, Prognosis and Therapy; Hendricks et al Mol Cancer Ther 2013; 12:1816-28.

As is known in the art, a number of assays may be employed in order to identify antigen-binding constructs suitable for use in the methods described herein. These assays can be carried out in cancer cells expressing HER2. Examples of suitable cancer cells are identified in Table A5. Examples of assays that may be carried out are described as follows.

For example, to identify growth inhibitory candidate antigen-binding constructs that bind HER2, one may screen for antibodies which inhibit the growth of cancer cells which express HER2. In one embodiment, the candidate antigen-binding construct of choice is able to inhibit growth of cancer cells in cell culture by about 20-100% and preferably by about 50-100% at compared to a control antigen-binding construct.

To select for candidate antigen-binding constructs which induce cell death, loss of membrane integrity as indicated by, e.g., PI (phosphatidylinositol), trypan blue or 7AAD uptake may be assessed relative to control.

In order to select for candidate antigen-binding constructs which induce apoptosis, an annexin binding assay may be employed. In addition to the annexin binding assay, a DNA staining assay may also be used.

In one embodiment, the candidate antigen-binding construct of interest may block heregulin dependent association of ErbB2 with ErbB3 in both MCF7 and SK-BR-3 cells as determined in a co-immunoprecipitation experiment substantially more effectively than monoclonal antibody 4D5, and preferably substantially more effectively than monoclonal antibody 7F3.

To screen for antigen-binding constructs which bind to an epitope on ErbB2 bound by an antibody of interest, a routine cross-blocking assay such as that described in Antibodies, *A Laboratory Manual*, Cold Spring Harbor Laboratory, Ed Harlow and David Lane (1988), can be performed. Alternatively, or additionally, epitope mapping can be performed by methods known in the art.

In some embodiments, antigen binding constructs described herein are assayed for function in vivo, e.g., in animal models. In some embodiments, the animal models are those described in Table E. In some embodiments, the antigen binding constructs display increase <InsertFunctionHere> in an animal model compared to a control antigen binding construct.

TABLE E

Animal models for testing HER2 binding antigen binding constructs

| Xenograft Model | Description | Reference |
|---|---|---|
| SKOV3 human ovarian cancer | HER2+/3+, gene amplified, moderately sensitive to trastuzumab | Rhodes et al. 2002. American Journal of Pathology 118: 408-417; Sims et al. 2012. British Journal of Cancer 106: 1779-1789 |
| HBCx-13b human metastatic breast cancer | HER2 3+, estrogen receptor negative, progesterone receptor negative; Invasive ductal breast carcinoma; Chemotherapy resistant, Trastuzumab resistant | Marangoni et al. 2007. Clinical Cancer Research 13: 3989-3998; Reyal et al. 2012. Breast Cancer Research 14: R11 |

TABLE E-continued

Animal models for testing HER2 binding antigen binding constructs

| Xenograft Model | Description | Reference |
| --- | --- | --- |
| T226 human breast cancer | HER2 3+, estrogen receptor negative, progesterone receptor negative; Inflammatory breast cancer; Trastuzumab resistant, Docetaxel and capecitabine moderately sensitive, Adriamycin/cyclophosphamide sensitive | |
| HBCx-5 human breast cancer | HER2 3+, estrogen receptor negative, progesterone receptor negative; Invasive ductal carcinoma, luminal B; Trastuzumab resistant, Docetaxel moderately sensitive, Capecitabine, Adriamycin/Cyclophosphamide sensitive | Marangoni et al. 2007. Clinical Cancer Research 13: 3989-3998; Reyal et al. 2012. Breast Cancer Research 14: R11 |
| JIMT-1 human breast cancer | HER2 2+, HER2 gene amplified, Trastuzumab and pertuzumab resistant | Tanner et al. 2004. Molecular Cancer Therapeutics 3: 1585-1592 |

Reference Antigen-Binding Construct

In some embodiments, the functional characteristics of the bispecific antigen-binding constructs described herein are compared to those of a reference antigen-binding construct. The identity of the reference antigen-binding construct depends on the functional characteristic being measured or the distinction being made. For example, when comparing the functional characteristics of exemplary bispecific antigen-binding constructs, the reference antigen-binding construct may be a trastuzumab analog such as, for example v506, or may be a combination of antibodies such as trastuzumab and pertuzumab (v4184). In embodiments where the format of the bispecific antigen-binding construct is being compared, the reference antigen-binding construct is, e.g., a biparatopic anti-HER2 antibody where both antigen-binding moieties are in the Fab-Fab format (format reference antigen-binding construct). Examples of the latter construct include v6902 and v6903.

Antigen Binding Constructs and Antibody Drug Conjugates (ADC)

In certain embodiments an antigen binding construct is conjugated to a drug, e.g., a toxin, a chemotherapeutic agent, an immune modulator, or a radioisotope. Several methods of preparing ADCs (antibody drug conjugates or antigen binding construct drug conjugates) are known in the art and are described in U.S. Pat. No. 8,624,003 (pot method), 8,163,888 (one-step), and 5,208,020 (two-step method) for example.

In some embodiments, the drug is selected from a maytansine, auristatin, calicheamicin, or derivative thereof. In other embodiments, the drug is a maytansine selected from DM1 and DM4. Further examples are described below.

In some embodiments the drug is conjugated to the isolated antigen binding construct with an SMCC linker (DM1), or an SPDB linker (DM4). Additional examples are described below. The drug-to-antigen binding protein ratio (DAR) can be, e.g., 1.0 to 6.0 or 3.0 to 5.0 or 3.5-4.2.

In some embodiments the antigen binding construct is conjugated to a cytotoxic agent. The term "cytotoxic agent" as used herein refers to a substance that inhibits or prevents the function of cells and/or causes destruction of cells. The term is intended to include radioactive isotopes (e.g. At211, I131, I125, Y90, Re186, Re188, Sm153, Bi212, P32, and Lu177), chemotherapeutic agents, and toxins such as small molecule toxins or enzymatically active toxins of bacterial, fungal, plant or animal origin, including fragments and/or variants thereof. Further examples are described below.

Drugs

Non-limiting examples of drugs or payloads used in various embodiments of ADCs include DM1 (maytansine, N2'-deacetyl-N2'-(3-mercapto-1-oxopropyl)- or N2'-deacetyl-N2'-(3-mercapto-1-oxopropyl)-maytansine), me-MMAD (6-maleimidocaproyl-monomethylauristatin-D or N-methyl-L-valyl-N-[(1S,2R)-2-methoxy-4-[(2S)-2-[(1R,2R)-1-methoxy-2-methyl-3-oxo-3-[[(1S)-2-phenyl-1-(2-thiazolyl)ethyl]amino]propyl]-1-pyrrolidinyl]-1-[(1S)-1-methylpropyl]-4-oxobutyl]-N-methyl-(9Cl)-L-valinamide), me-MMAF (maleimidocaproyl-monomethylauristatin F or N-[6-(2,5-dihydro-2,5-dioxo-1H-pyrrol-1-yl)-1-oxohexyl]-N-methyl-L-valyl-L-valyl-(3R,4S,5S)-3-methoxy-5-methyl-4-(methylamino)heptanoyl-(αR,βR,2S)-β-methoxy-α-methyl-2-pyrrolidinepropanoyl-L-phenylalanine) and mc-Val-Cit-PABA-MMAE (6-maleimidocaproyl-ValcCit-(p-aminobenzyloxycarbonyl)-monomethylauristatin E or N-[[[4-[[N-[6-(2,5-dihydro-2,5-dioxo-1H-pyrrol-1-yl)-1-oxohexyl]-L-valyl-N5-(aminocarbonyl)-L-ornithyl]amino]phenyl]methoxy]carbonyl]-N-meth yl-L-valyl-N-[(1S,2R)-4-[(2S)-2-[(1R,2R)-3-[[(1R,2S)-2-hydroxy-1-methyl-2-phenylethyl]amino]-1-methoxy-2-methyl-3-oxopropyl]-1-pyrrolidinyl]-2-methoxy-1-[(1S)-1-methylpropyl]-4-oxobutyl]-N-methyl-L-valinamide). DM1 is a derivative of the tubulin inhibitor maytansine while MMAD, MMAE, and MMAF are auristatin derivatives.

Maytansinoid Drug Moieties

As indicated above, in some embodiments the drug is a maytansinoid. Exemplary maytansinoids include DM1, DM3 ($N^{2'}$-deacetyl-$N^{2'}$-(4-mercapto-1-oxopentyl) maytansine), and DM4 ($N^{2'}$-deacetyl-$N^{2'}$-(4-iiethyl-4-mercapto-1-oxopentyl)methylmaytansine) (see US20090202536).

Many positions on maytansine compounds are known to be useful as the linkage position, depending upon the type of link. For example, for forming an ester linkage, the C-3 position having a hydroxyl group, the C-14 position modified with hydroxymethyl, the C-15 position modified with a hydroxyl group and the C-20 position having a hydroxyl group are all suitable.

All stereoisomers of the maytansinoid drug moiety are contemplated for the ADCs described herein, i.e. any combination of R and S configurations at the chiral carbons of D.

Auristatins

In some embodiments, the drug is an auristatin, such as auristatin E (also known in the art as a derivative of dolastatin-10) or a derivative thereof. The auristatin can be, for example, an ester formed between auristatin E and a keto acid. For example, auristatin E can be reacted with paraacetyl benzoic acid or benzoylvaleric acid to produce AEB and AEVB, respectively. Other typical auristatins include AFP, MMAF, and MMAE. The synthesis and structure of exemplary auristatins are described in U.S. Pat. Nos. 6,884,869, 7,098,308, 7,256,257, 7,423,116, 7,498,298 and 7,745,394, each of which is incorporated by reference herein in its entirety and for all purposes.

Chemotherapeutic Agents

In some embodiments the antigen binding construct is conjugated to a chemotherapeutic agent. Examples include but are not limited to Cisplantin and Lapatinib. A "chemotherapeutic agent" is a chemical compound useful in the treatment of cancer.

Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK7; razoxane; sizofiran; spirogermanium; tenuazonic acid; triaziquone; 2,2',2''-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

Conjugate Linkers

In some embodiments, the drug is linked to the antigen binding construct, e.g., antibody, by a linker. Attachment of a linker to an antibody can be accomplished in a variety of ways, such as through surface lysines, reductive-coupling to oxidized carbohydrates, and through cysteine residues liberated by reducing interchain disulfide linkages. A variety of ADC linkage systems are known in the art, including hydrazone-, disulfide- and peptide-based linkages.

Suitable linkers include, for example, cleavable and non-cleavable linkers. A cleavable linker is typically susceptible to cleavage under intracellular conditions. Suitable cleavable linkers include, for example, a peptide linker cleavable by an intracellular protease, such as lysosomal protease or an endosomal protease. In exemplary embodiments, the linker can be a dipeptide linker, such as a valine-citrulline (val-cit), a phenylalanine-lysine (phe-lys) linker, or maleimidocapronic-valine-citruline-p-aminobenzyloxycarbonyl (mc-Val-Cit-PABA) linker. Another linker is Sulfosuccinimidyl-44N-maleimidomethyllcyclohexane-1-carboxylate (SMCC). Sulfo-smcc conjugation occurs via a maleimide group which reacts with sulfhydryls (thiols, —SH), while its Sulfo-NHS ester is reactive toward primary amines (as found in Lysine and the protein or peptide N-terminus). Yet another linker is maleimidocaproyl (MC). Other suitable linkers include linkers hydrolyzable at a specific pH or a pH range, such as a hydrazone linker. Additional suitable cleavable linkers include disulfide linkers. The linker may be covalently bound to the antibody to such an extent that the antibody must be degraded intracellularly in order for the drug to be released e.g. the MC linker and the like.

Preparation of ADCs

The ADC may be prepared by several routes, employing organic chemistry reactions, conditions, and reagents known to those skilled in the art, including: (1) reaction of a nucleophilic group or an electrophilic group of an antibody with a bivalent linker reagent, to form antibody-linker intermediate Ab-L, via a covalent bond, followed by reaction with an activated drug moiety D; and (2) reaction of a nucleophilic group or an electrophilic group of a drug moiety with a linker reagent, to form drug-linker intermediate D-L, via a covalent bond, followed by reaction with the nucleophilic group or an electrophilic group of an antibody. Conjugation methods (1) and (2) may be employed with a variety of antibodies, drug moieties, and linkers to prepare the antibody-drug conjugates described here.

Several specific examples of methods of preparing ADCs are known in the art and are described in U.S. Pat. No. 8,624,003 (pot method), 8,163,888 (one-step), and 5,208,020 (two-step method).

Methods of Preparation of Antigen Binding Constructs

Antigen-binding constructs described herein may be produced using recombinant methods and compositions, e.g., as described in U.S. Pat. No. 4,816,567.

In one embodiment, isolated nucleic acid encoding an antigen-binding construct described herein is provided. Such nucleic acid may encode an amino acid sequence comprising the VL and/or an amino acid sequence comprising the VH of the antigen-binding construct (e.g., the light and/or heavy chains of the antigen-binding construct). In a further embodiment, one or more vectors (e.g., expression vectors) comprising such nucleic acid are provided. In one embodiment, the nucleic acid is provided in a multicistronic vector. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antigen-binding construct and an amino acid sequence comprising the VH of the antigen-binding polypeptide construct, or (2) a first vector comprising a nucleic acid that encodes an amino acid sequence comprising the VL of the antigen-binding polypeptide construct and a second vector comprising a nucleic acid that encodes an amino acid sequence comprising the VH of the antigen-binding polypeptide construct. In one embodiment, the host cell is eukaryotic, e.g. a Chinese Hamster Ovary (CHO) cell, or human embryonic kidney (HEK) cell, or lymphoid cell (e.g., Y0, NS0, Sp20 cell). In one embodiment, a method of making an antigen-binding construct is provided, wherein the method comprises culturing a host cell comprising nucleic acid encoding the antigen-binding construct, as provided above, under conditions suitable for expression of the antigen-binding construct, and optionally recovering the antigen-binding construct from the host cell (or host cell culture medium).

For recombinant production of the antigen-binding construct, nucleic acid encoding an antigen-binding construct, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antigen-binding construct).

The term "substantially purified" refers to a construct described herein, or variant thereof that may be substantially or essentially free of components that normally accompany or interact with the protein as found in its naturally occurring environment, i.e. a native cell, or host cell in the case of recombinantly produced heteromultimer that in certain embodiments, is substantially free of cellular material includes preparations of protein having less than about 30%, less than about 25%, less than about 20%, less than about 15%, less than about 10%, less than about 5%, less than about 4%, less than about 3%, less than about 2%, or less than about 1% (by dry weight) of contaminating protein. When the heteromultimer or variant thereof is recombinantly produced by the host cells, the protein in certain embodiments is present at about 30%, about 25%, about 20%, about 15%, about 10%, about 5%, about 4%, about 3%, about 2%, or about 1% or less of the dry weight of the cells. When the heteromultimer or variant thereof is recombinantly produced by the host cells, the protein, in certain embodiments, is present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less of the dry weight of the cells. In certain embodiments, "substantially purified" heteromultimer produced by the methods described herein, has a purity level of at least about 30%, at least about 35%, at least about 40%, at least about 45%, at least about 50%, at least about 55%, at least about 60%, at least about 65%, at least about 70%, specifically, a purity level of at least about 75%, 80%, 85%, and more specifically, a purity level of at least about 90%, a purity level of at least about 95%, a purity level of at least about 99% or greater as determined by appropriate methods such as SDS/PAGE analysis, RP-HPLC, SEC, and capillary electrophoresis.

Suitable host cells for cloning or expression of antigen-binding construct-encoding vectors include prokaryotic or eukaryotic cells described herein.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome.

As used herein, the term "eukaryote" refers to organisms belonging to the phylogenetic domain Eucarya such as animals (including but not limited to, mammals, insects, reptiles, birds, etc.), ciliates, plants (including but not limited to, monocots, dicots, algae, etc.), fungi, yeasts, flagellates, microsporidia, protists, etc.

As used herein, the term "prokaryote" refers to prokaryotic organisms. For example, a non-eukaryotic organism can belong to the Eubacteria (including but not limited to, *Escherichia coli, Thermus thermophilus, Bacillus stearothermophilus, Pseudomonas fluorescens, Pseudomonas aeruginosa, Pseudomonas putida*, etc.) phylogenetic domain, or the Archaea (including but not limited to, *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix*, etc.) phylogenetic domain.

For example, antigen-binding construct may be produced in bacteria, in particular when glycosylation and Fc effector function are not needed. For expression of antigen-binding construct fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli.*) After expression, the antigen-binding construct may be isolated from the bacterial cell paste in a soluble fraction and can be further purified.

In addition to prokaryotes, eukaryotic microbes such as filamentous fungi or yeast are suitable cloning or expression hosts for antigen-binding construct-encoding vectors, including fungi and yeast strains whose glycosylation pathways have been "humanized," resulting in the production of an antigen-binding construct with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antigen-binding constructs are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antigen-binding constructs in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in *Mather, Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antigen-binding construct production, see, e.g., Yazaki and Wu, *Methods in Molecular Biology,* Vol. 248 (B. K. C. Lo, ed., Humana Press, Totowa, N.J.), pp. 255-268 (2003).

In one embodiment, the antigen-binding constructs described herein are produced in stable mammalian cells, by a method comprising: transfecting at least one stable mammalian cell with: nucleic acid encoding the antigen-binding construct, in a predetermined ratio; and expressing the nucleic acid in the at least one mammalian cell. In some embodiments, the predetermined ratio of nucleic acid is determined in transient transfection experiments to determine the relative ratio of input nucleic acids that results in the highest percentage of the antigen-binding construct in the expressed product.

In some embodiments is the method of producing a antigen-binding construct in stable mammalian cells as described herein wherein the expression product of the at least one stable mammalian cell comprises a larger percentage of the desired glycosylated antigen binding construct as compared to the monomeric heavy or light chain polypeptides, or other antibodies.

In some embodiments is the method of producing a glycosylated antigen-binding construct in stable mammalian cells described herein, said method comprising identifying and purifying the desired glycosylated antigen binding construct. In some embodiments, the said identification is by one or both of liquid chromatography and mass spectrometry.

If required, the antigen-binding constructs can be purified or isolated after expression. Proteins may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. As is well known in the art, a variety of natural proteins bind Fc and antibodies, and these proteins can find use in the present invention for purification of antigen-binding constructs. For example, the bacterial proteins A and G bind to the Fc region. Likewise, the bacterial protein L binds to the Fab region of some antibodies. Purification can often be enabled by a particular fusion partner. For example, antibodies may be purified using glutathione resin if a GST fusion is employed, $Ni^{+2}$ affinity chromatography if a His-tag is employed, or immobilized anti-flag antibody if a flag-tag is used. For general guidance in suitable purification techniques, see, e.g. incorporated entirely by reference Protein Purification: Principles and Practice, $3^{rd}$ Ed., Scopes, Springer-Verlag, NY, 1994, incorporated entirely by reference. The degree of purification necessary will vary depending on the use of the antigen-binding constructs. In some instances no purification is necessary.

In certain embodiments the antigen-binding constructs are purified using Anion Exchange Chromatography including, but not limited to, chromatography on Q-sepharose, DEAE sepharose, poros HQ, poros DEAF, Toyopearl Q, Toyopearl QAE, Toyopearl DEAE, Resource/Source Q and DEAE, Fractogel Q and DEAE columns.

In specific embodiments the proteins described herein are purified using Cation Exchange Chromatography including, but not limited to, SP-sepharose, CM sepharose, poros HS, poros CM, Toyopearl SP, Toyopearl CM, Resource/Source S and CM, Fractogel S and CM columns and their equivalents and comparables.

In addition, antigen-binding constructs described herein can be chemically synthesized using techniques known in the art (e.g., see Creighton, 1983, Proteins: Structures and Molecular Principles, W. H. Freeman & Co., N.Y and Hunkapiller et al., Nature, 310:105-111 (1984)). For example, a polypeptide corresponding to a fragment of a polypeptide can be synthesized by use of a peptide synthesizer. Furthermore, if desired, nonclassical amino acids or chemical amino acid analogs can be introduced as a substitution or addition into the polypeptide sequence. Nonclassical amino acids include, but are not limited to, to the D-isomers of the common amino acids, 2,4diaminobutyric acid, alpha-amino isobutyric acid, 4aminobutyric acid, Abu, 2-amino butyric acid, g-Abu, e-Ahx, 6amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, □-alanine, fluoro-amino acids, designer amino acids such as □-methyl amino acids, C □-methyl amino acids, N□-methyl amino acids, and amino acid analogs in general. Furthermore, the amino acid can be D (dextrorotary) or L (levorotary).

Post-Translational Modifications:

In certain embodiments antigen-binding constructs described herein are differentially modified during or after translation.

The term "modified," as used herein refers to any changes made to a given polypeptide, such as changes to the length of the polypeptide, the amino acid sequence, chemical structure, co-translational modification, or post-translational modification of a polypeptide. The form "(modified)" term means that the polypeptides being discussed are optionally modified, that is, the polypeptides under discussion can be modified or unmodified.

The term "post-translationally modified" refers to any modification of a natural or non-natural amino acid that occurs to such an amino acid after it has been incorporated into a polypeptide chain. The term encompasses, by way of example only, co-translational in vivo modifications, co-translational in vitro modifications (such as in a cell-free translation system), post-translational in vivo modifications, and post-translational in vitro modifications.

In some embodiments, the modification is at least one of: glycosylation, acetylation, phosphorylation, amidation, derivatization by known protecting/blocking groups, proteolytic cleavage and linkage to an antibody molecule or antigen binding construct or other cellular ligand. In some embodiments, the antigen-binding construct is chemically modified by known techniques, including but not limited, to specific chemical cleavage by cyanogen bromide, trypsin, chymotrypsin, papain, V8 protease, $NaBH_4$; acetylation, formylation, oxidation, reduction; and metabolic synthesis in the presence of tunicamycin.

Additional post-translational modifications of antigen-binding constructs described herein include, for example, N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The antigen-binding constructs described herein are modified with a detectable label, such as an enzymatic, fluorescent, isotopic or affinity label to allow for detection and isolation of the protein. In certain embodiments, examples of suitable enzyme labels include horseradish peroxidase, alkaline phosphatase, beta-galactosidase, or acetylcholinesterase; examples of suitable prosthetic group complexes include streptavidin biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include iodine, carbon, sulfur, tritium, indium, technetium, thallium, gallium, palladium, molybdenum, xenon, fluorine.

In specific embodiments, antigen-binding constructs described herein are attached to macrocyclic chelators that associate with radiometal ions.

In some embodiments, the antigen-binding constructs described herein are modified by either natural processes, such as post-translational processing, or by chemical modification techniques which are well known in the art. In certain embodiments, the same type of modification may be present in the same or varying degrees at several sites in a given polypeptide. In certain embodiments, polypeptides from antigen-binding constructs described herein are branched, for example, as a result of ubiquitination, and in some embodiments are cyclic, with or without branching. Cyclic, branched, and branched cyclic polypeptides are a result from posttranslation natural processes or made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POST-TRANSLATIONAL COVALENT MODIFICATION OF PROTEINS, B. C. Johnson, Ed., Academic Press, New York, pgs. 1-12 (1983); Seifter et al., Meth. Enzymol. 182:626-646 (1990); Rattan et al., Ann. N.Y. Acad. Sci. 663:48-62 (1992)).

In certain embodiments, antigen-binding constructs described herein are attached to solid supports, which are particularly useful for immunoassays or purification of polypeptides that are bound by, that bind to, or associate with proteins described herein. Such solid supports include, but are not limited to, glass, cellulose, polyacrylamide, nylon, polystyrene, polyvinyl chloride or polypropylene.

Pharmaceutical Compositions

Also provided herein are pharmaceutical compositions comprising an antigen binding construct described herein. Pharmaceutical compositions comprise the construct and a pharmaceutically acceptable carrier.

The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. In some aspects, the carrier is a man-made carrier not found in nature. Water can be used as a carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In certain embodiments, the composition comprising the construct is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In certain embodiments, the compositions described herein are formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxide isopropylamine, triethylamine, 2-ethylamino ethanol, histidine, procaine, etc.

Methods of Treatment

In certain embodiments, provided is a method of treating a disease or disorder comprising administering to a subject in which such treatment, prevention or amelioration is desired, an antigen binding construct described herein, in an amount effective to treat, prevent or ameliorate the disease or disorder.

"Disorder" refers to any condition that would benefit from treatment with an antigen binding construct or method described herein. This includes chronic and acute disorders or diseases including those pathological conditions which predispose the mammal to the disorder in question. In some embodiments, the disorder is cancer, as described in more detail below.

The term "subject" refers to an animal, in some embodiments a mammal, which is the object of treatment, observation or experiment. An animal may be a human, a non-human primate, a companion animal (e.g., dogs, cats, and the like), farm animal (e.g., cows, sheep, pigs, horses, and the like) or a laboratory animal (e.g., rats, mice, guinea pigs, and the like).

The term "mammal" as used herein includes but is not limited to humans, non-human primates, canines, felines, murines, bovines, equines, and porcines.

"Treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishing of any direct or indirect pathological consequences of the disease, preventing metastasis, decreasing the rate of disease progression, amelioration or palliation of the disease state, and remission or improved prognosis. In some embodiments, antigen binding constructs described herein are used to delay development of a disease or disorder. In one embodiment, antigen binding constructs and methods described herein effect tumor regression. In one embodiment, antigen binding constructs and methods described herein effect inhibition of tumor/cancer growth.

Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, construct constructs described herein are used to delay development of a disease or to slow the progression of a disease.

The term "effective amount" as used herein refers to that amount of construct being administered, which will accomplish the goal of the recited method, e.g., relieve to some extent one or more of the symptoms of the disease, condition or disorder being treated. The amount of the composition described herein which will be effective in the treatment, inhibition and prevention of a disease or disorder associated with aberrant expression and/or activity of a therapeutic protein can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses are extrapolated from dose-response curves derived from in vitro or animal model test systems.

The antigen binding construct is administered to the subject. Various delivery systems are known and can be used to administer an antigen binding construct formulation described herein, e.g., encapsulation in liposomes, microparticles, microcapsules, recombinant cells capable of expressing the compound, receptor-mediated endocytosis (see, e.g., Wu and Wu, J. Biol. Chem. 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, in certain embodiments, it is desirable to introduce the antigen binding construct compositions described herein into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it is desirable to administer the antigen binding constructs, or compositions described herein locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antigen binding construct, described herein, care must be taken to use materials to which the protein does not absorb.

In another embodiment, the antigen binding constructs or composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the antigen binding constructs or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, e.g., the brain, thus requiring only a fraction of the systemic dose (see, e.g., Goodson, in Medical Applications of Controlled Release, vol. 2, pp. 115-138 (1984)).

In a specific embodiment comprising a nucleic acid encoding antigen binding constructs described herein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

In certain embodiments an antigen binding construct described herein is administered as a combination with antigen binding constructs with non-overlapping binding target epitopes.

The amount of the antigen binding construct which will be effective in the treatment, inhibition and prevention of a disease or disorder can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses are extrapolated from dose-response curves derived from in vitro or animal model test systems.

The antigen binding constructs described herein may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in an embodiment, human antigen binding constructs, fragments derivatives, analogs, or nucleic acids, are administered to a human patient for therapy or prophylaxis.

Methods of Treating Cancers

Described herein are methods of treating a HER2+ cancer or a tumor in a subject, and methods of inhibiting the growth of a HER2+ tumor cell or killing a HER2+ tumor cell using the antigen binding constructs described herein.

By a HER2+ cancer is meant a cancer that expresses HER2 such that the antigen binding constructs described herein are able to bind to the cancer. As is known in the art, HER2+ cancers express HER2 at varying levels. To determine ErbB, e.g. ErbB2 (HER2) expression in the cancer, various diagnostic/prognostic assays are available. In one embodiment, ErbB2 overexpression may be analyzed by IHC, e.g. using the HERCEPTEST® (Dako). Parrafin embedded tissue sections from a tumor biopsy may be subjected to the IHC assay and accorded a ErbB2 protein staining intensity criteria as follows: Score 0 no staining is observed or membrane staining is observed in less than 10% of tumor cells.

Score 1+ a faint/barely perceptible membrane staining is detected in more than 10% of the tumor cells. The cells are only stained in part of their membrane.

Score 2+ a weak to moderate complete membrane staining is observed in more than 10% of the tumor cells.

Score 3+ a moderate to strong complete membrane staining is observed in more than 10% of the tumor cells.

Those tumors with 0 or 1+ scores for ErbB2 overexpression assessment may be characterized as not overexpressing ErbB2, whereas those tumors with 2+ or 3+ scores may be characterized as overexpressing ErbB2.

Alternatively, or additionally, fluorescence in situ hybridization (FISH) assays such as the INFORM™ (sold by Ventana, Ariz.) or PATHVISION™ (Vysis, Ill.) may be carried out on formalin-fixed, paraffin-embedded tumor tissue to determine the extent (if any) of ErbB2 overexpression in the tumor. In comparison with IHC assay, the FISH assay, which measures HER2 gene amplification, seems to correlate better with response of patients to treatment with HERCEPTIN®, and is currently considered to be the preferred assay to identify patients likely to benefit from HERCEPTIN® treatment.

Table D describes the expression level of HER2 on several representative breast cancer and other cancer cell lines (Subik et al. (2010) Breast Cancer: Basic Clinical Research:4; 35-41; Prang et a. (2005) British Journal of Cancer Research:92; 342-349). As shown in the table, MCF-7 and MDA-MB-231 cells are considered to be low HER2 expressing cells; JIMT-1, and ZR-75-1 cells are considered to be medium HER2 expressing cells, and SKBR3 and BT-474 cells are considered to be high HER2 expressing cells. SKOV3 (ovarian cancer) cells are considered to be medium HER2 expressing cells.

Described herein are methods of treating a subject having a HER2+ cancer or a tumor comprising providing to the subject an effective amount of a pharmaceutical composition comprising an antigen binding construct described herein.

Also described herein is the use of an HER2 antigen-binding construct described herein for the manufacture of a medicament for treating a cancer or a tumor. Also described herein are HER2 antigen-binding constructs for use in the treatment of cancer or a tumor.

In specific embodiments, the antigen binding construct is v10000, v5019 or v7091, v5019 or v5020. In one embodiment, the antigen binding construct is v10000. In some embodiments, the antigen binding construct is conjugated to maytansine, (DM1). When the antigen binding construct conjugated to DM1 is internalized into tumor cells, the DM1 is cleaved from the construct intracellularly, and kills the tumor cells.

In some embodiments, the subject being treated has pancreatic cancer, head and neck cancer, gastric cancer, colorectal cancer, breast cancer, renal cancer, cervical cancer, ovarian cancer, brain cancer, endometrial cancer, bladder cancer, non-small cell lung cancer or an epidermal-derived cancer. In some embodiments, the tumor is metastatic.

In general, the tumor in the subject being treated expresses an average of 10,000 or more copies of HER2 per tumor cell. In certain embodiments the tumor is HER2 0-1+, 1+, HER2 2+ or HER2 3+ as determined by IHC. In some embodiments the tumor is HER2 2+ or lower, or HER2 1+ or lower.

In some embodiments, the tumor of the subject being treated with the antigen binding constructs is a breast cancer. In a specific embodiment, the breast cancer expresses HER2 at a 2+ level or lower. In a specific embodiment, the breast cancer expresses HER2 at a 1+ level or lower. In some embodiments, the breast cancer expresses estrogen receptors (ER+) and/or progesterone receptors (PR+). In some embodiments, the breast cancer is ER– and or PR–. In some embodiments the breast cancer has an amplified HER2 gene. In some embodiments, the breast cancer is a HER2 3+ estrogen receptor negative (ER–), progesterone receptor negative (PR–), trastuzumab resistant, chemotherapy resistant invasive ductal breast cancer. In another embodiment, the breast cancer is a HER2 3+ER–, PR–, trastuzumab resistant inflammatory breast cancer. In another embodiment, the breast cancer is a HER2 3+, ER–, PR–, invasive ductal carcinoma. In another embodiment, the breast cancer is a HER2 2+ HER2 gene amplified trastuzumab and pertuzumab resistant breast cancer. In some embodiments, the breast cancer is triple negative (ER–, PR– and low HER2-expressing).

In one embodiment, the tumor is an HER2 2/3+ ovarian epithelial adenocarcinoma having an amplified HER2 gene.

Provided herein are methods for treating a subject having a HER2+ tumor that is resistant or becoming resistant to other standard-of-care therapies comprising administering to the subject a pharmaceutical composition comprising the antigen binding constructs described herein. In certain embodiments the antigen-binding constructs described herein are provided to subjects that are unresponsive to current therapies, optionally in combination with one or more current anti-HER2 therapies. In some embodiments the current anti-HER2 therapies include, but are not limited to, anti-HER2 or anti-HER3 monospecific bivalent antibodies, trastuzumab, pertuzumab, T-DM1, a bi-specific HER2/HER3 scFv, or combinations thereof. In some embodiments, the cancer is resistant to various chemotherapeutic agents such as taxanes. In some embodiments the cancer is resistant to trastuzumab. In some embodiment the cancer is resistant to pertuzumab. In one embodiment, the cancer is resistant to TDM1 (trastuzumab conjugated to DM1). In some embodiments, the subject has previously been treated with an anti-HER2 antibody such as trastuzumab, pertuzumab or DM1. In some embodiments, the subject has not been previously treated with an anti-HER2 antibody. In one embodiment, the antigen binding construct is provided to a subject for the treatment of metastatic cancer when the patient has progressed on previous anti-HER2 therapy.

Provided herein are methods of treating a subject having a HER2+ tumor comprising providing an effective amount of a pharmaceutical composition comprising an antigen binding construct described herein in conjunction with an additional anti-tumor agent. The additional anti tumor agent may be a therapeutic antibody as noted above, or a chemotherapeutic agent. Chemotherapeutic agents useful for use in combination with the antigen-binding constructs of the invention include cisplatin, carboplatin, paclitaxel, albumin-bound paclitaxel, docetaxel, gemcitabine, vinorelbine, irinotecan, etoposide, vinblastine, pemetrexed, 5-fluorouracil (with or without folinic acid), capecitabine, carboplatin, epirubicin, oxaliplatin, folfirinox, abraxane, and cyclophosphamide.

In some embodiments, the tumor is non-small cell lung cancer, and the additional agent is one or more of cisplatin, carboplatin, paclitaxel, albumin-bound paclitaxel, docetaxel, gemcitabine, vinorelbine, irinotecan, etoposide, vinblastine or pemetrexed. In embodiments, the tumor is gastric or stomach cancer, and the additional agent is one or more of 5-fluorouracil (with or without folinic acid), capecitabine, carboplatin, cisplatin, docetaxel, epirubicin, irinotecan, oxaliplatin, or paclitaxel. In other embodiments the tumor is pancreatic cancer, and the additional agent is one or more of gemcitabine, folfirinox, abraxane, or 5-fluorouracil. In other embodiments the tumor is a estrogen and/or progesterone positive breast cancer, and the additional agent is one or more of a combination of (a) doxorubicin and epirubicin, (b) a combination of paclitaxel and docetaxel, or (c) a combination of 5-fluorouracil, cyclophosphamide and carboplatin. In other embodiments, the tumor is head and neck cancer, and the additional agent is one or more of paclitaxel, carboplatin, doxorubicin or cisplatin. In other embodiments, the tumor is ovarian cancer and the additional agent may be one or more of cisplatin, carboplatin, or a taxane such as paclitaxel or docetaxel.

The additional agents may be administered to the subject being treated concurrently with the antigen binding constructs or sequentially.

The subject being treated with the antigen-binding constructs may be a human, a non-human primate or other mammal such as a mouse.

In some embodiments, the result of providing an effective amount of the antigen binding construct to a subject having a tumor is shrinking the tumor, inhibiting growth of the tumor, increasing time to progression of the tumor, prolonging disease-free survival of the subject, decreasing metastases, increasing the progression-free survival of the subject, or increasing overall survival of the subject or increasing the overall survival of a group of subjects receiving the treatment.

Also described herein are methods of killing or inhibiting the growth of a HER2-expressing tumor cell comprising contacting the cell with the antigen binding construct provided herein.

In various embodiments, a tumor cell may be a HER2 1+ or 2+ human pancreatic carcinoma cell, a HER2 3+ human lung carcinoma cell, a HER2 2+ human Caucasian bronchioaveolar carcinoma cell, a human pharyngeal carcinoma cell, a HER2 2+ human tongue squamous cell carcinoma cell, a HER2 2+ squamous cell carcinoma cell of the pharynx, a HER2 1+ or 2+ human colorectal carcinoma cell, a HER2 3+ human gastric carcinoma cell, a HER2 1+ human breast ductal ER+ (estrogen receptor-positive) carcinoma cell, a HER2 2+/3+ human ER+, HER2-amplified breast carcinoma cell, a HER2 0+/1+ human triple negative breast carcinoma cell, a HER2 2+ human endometrioid carcinoma cell, a HER2 1+ lung-metastatic malignant melanoma cell, a HER2 1+ human cervix carcinoma cell, Her2 1+ human renal cell carcinoma cell, or a HER2 1+ human ovary carcinoma cell.

In embodiments in which the antigen binding constructs are conjugated to DM1, the tumor cell may be a HER2 1+ or 2+ or 3+ human pancreatic carcinoma cell, a HER2 2+ metastatic pancreatic carcinoma cell, a HER2 0+/1+, +3+ human lung carcinoma cell, a HER2 2+ human Caucasian bronchioaveolar carcinoma cell, a HER2 0+ anaplastic lung carcinoma, a human non-small cell lung carcinoma cell, a human pharyngeal carcinoma cell, a HER2 2+ human tongue squamous cell carcinoma cell, a HER2 2+ squamous cell carcinoma cell of the pharynx, a HER2 1+ or 2+ human colorectal carcinoma cell, a HER2 0+, 1+ or 3+ human gastric carcinoma cell, a HER2 1+ human breast ductal ER+ (estrogen receptor-positive) carcinoma cell, a HER2 2+/3+ human ER+, HER2-amplified breast carcinoma cell, a HER2 0+/1+ human triple negative breast carcinoma cell, a HER2 0+ human breast ductal carcinoma (Basal B, Mesenchymal-like triple negative) cell, a HER2 2+ER+ breast carcinoma, a HER2 0+ human metastatic breast carcinoma cell (ER−, HER2-amplified, luminal A, TN), a human uterus mesodermal tumor (mixed grade III) cell, a 2+ human endometrioid carcinoma cell, a HER2 1+ human skin epidermoid carcinoma cell, a HER2 1+ lung-metastatic malignant melanoma cell, a HER2 1+ malignant melanoma cell, a human cervix epidermoid carcinoma vcell, a HER2 1+ human urinary bladder carcinoma cell, a HER2 1+ human cervix carcinoma cell, Her2 1+ human renal cell carcinoma cell, or a HER2 1+, 2+ or 3+ human ovary carcinoma cell.

In some embodiments the tumor cell may be one or more of the following cell lines (shown in FIGS. 37 and 38): pancreatic tumor cell lines BxPC3, Capan-1, MiaPaca2; lung tumor cell lines Calu-3, NCI-H322; head and neck tumor cells lines Detroit 562, SCC-25, FaDu; colorectal tumor cell lines HT29, SNU-C2B; gastric tumor cell line NCI-N87; breast tumor cell lines MCF-7, MDAMB175, MDAMB361, MDA-MB-231, BT-20, JIMT-1, SkBr3, BT-474; uterine tumor cell line TOV-112D; skin tumor cell line Malme-3M; cervical tumor cell lines Caski, MS751; bladder tumor cell line T24, ovarian tumor cell lines CaOV3, and SKOV3.

In some embodiments in which the antigen-binding constructs are conjugated to DM1, the tumor cell may be one or more of the following cell lines (shown in FIGS. 37 and 38): pancreatic tumor cell lines BxPC3, Capan-1, MiaPaca2, SW 1990, Panc1; lung tumor cell lines A549, Calu-3, Calu-6, NCI-H2126, NCI-H322; head and neck tumor cells lines Detroit 562, SCC-15, SCC-25, FaDu; colorectal tumor cell lines Colo201, DLD-1, HCT116, HT29, SNU-C2B; gastric tumor cell lines SNU-1, SNU-16, NCI-N87; breast tumor cell lines SkBr3, MCF-7, MDAMB175, MDAMB361, MDA-MB-231, ZR-75-1, BT-20, BT549, BT-474, CAMA-1, MDAMB453, JIMT-1, T47D; Uterine tumor cell lines SK-UT-1, TOV-112D; skin tumor cell lines A431, Malme-3M, SKEMEL28; cervical tumor cell lines Cash, MS751; bladder tumor cell line T24, renal tumor cell line ACHN; ovarian tumor cell lines CaOV3, Ovar-3, and SKOV3.

Kits and Articles of Manufacture

Also described herein are kits comprising one or more antigen binding constructs. Individual components of the kit would be packaged in separate containers and, associated with such containers, can be a notice in the form prescribed by a governmental agency regulating the manufacture, use or sale of pharmaceuticals or biological products, which notice reflects approval by the agency of manufacture, use or sale. The kit may optionally contain instructions or directions outlining the method of use or administration regimen for the antigen binding construct.

When one or more components of the kit are provided as solutions, for example an aqueous solution, or a sterile aqueous solution, the container means may itself be an inhalant, syringe, pipette, eye dropper, or other such like apparatus, from which the solution may be administered to a subject or applied to and mixed with the other components of the kit.

The components of the kit may also be provided in dried or lyophilized form and the kit can additionally contain a suitable solvent for reconstitution of the lyophilized components. Irrespective of the number or type of containers, the kits described herein also may comprise an instrument for assisting with the administration of the composition to a patient. Such an instrument may be an inhalant, nasal spray device, syringe, pipette, forceps, measured spoon, eye dropper or similar medically approved delivery vehicle.

In another aspect described herein, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is a T cell activating antigen binding construct described herein. The label or package insert indicates that the composition is used for treating the condition of choice. Moreover, the article of manufacture may comprise (a) a first container with a composition contained therein, wherein the composition comprises an antigen-binding construct described herein; and (b) a second container with a composition contained therein, wherein the composition comprises a further cytotoxic or otherwise therapeutic agent. The article of manufacture in this embodiment described herein may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Polypeptides and Polynucleotides

The antigen binding constructs described herein comprise at least one polypeptide. Also described are polynucleotides encoding the polypeptides described herein. The antigen-binding constructs are typically isolated.

As used herein, "isolated" means an agent (e.g., a polypeptide or polynucleotide) that has been identified and separated and/or recovered from a component of its natural cell culture environment. Contaminant components of its natural environment are materials that would interfere with diagnostic or therapeutic uses for the antigen-binding construct, and may include enzymes, hormones, and other proteinaceous or non-proteinaceous solutes. Isolated also refers to an agent that has been synthetically produced, e.g., via human intervention.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally encoded amino acid. As used herein, the terms encompass amino acid chains of any length, including full length proteins, wherein the amino acid residues are linked by covalent peptide bonds.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, praline, serine, threonine, tryptophan, tyrosine, and valine) and pyrrolysine and selenocysteine Amino acid analogs refers to compounds that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid. Reference to an amino acid includes, for example, naturally occurring proteogenic L-amino acids; D-amino acids, chemically modified amino acids such as amino acid variants and derivatives; naturally occurring non-proteogenic amino acids such as α-alanine, ornithine, etc.; and chemically synthesized compounds having properties known in the art to be characteristic of amino acids. Examples of non-naturally occurring amino acids include, but are not limited to, α-methyl amino acids (e.g. α-methyl alanine), D-amino acids, histidine-like amino acids (e.g., 2-amino-histidine, β-hydroxy-histidine, homohistidine), amino acids having an extra methylene in the side chain ("homo" amino acids), and amino acids in which a carboxylic acid functional group in the side chain is replaced with a sulfonic acid group (e.g., cysteic acid). The incorporation of non-natural amino acids, including synthetic non-native amino acids, substituted amino acids, or one or more D-amino acids into the proteins of the present invention may be advantageous in a number of different ways. D-amino acid-containing peptides, etc., exhibit increased stability in vitro or in vivo compared to L-amino acid-containing counterparts. Thus, the construction of peptides, etc., incorporating D-amino acids can be particularly useful when greater intracellular stability is desired or required. More specifically, D-peptides, etc., are resistant to endogenous peptidases and proteases, thereby providing improved bioavailability of the molecule, and prolonged lifetimes in vivo when such properties are desirable. Additionally, D-peptides, etc., cannot be processed efficiently for major histocompatibility complex class II-restricted presentation to T helper cells, and are therefore, less likely to induce humoral immune responses in the whole organism.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

Also included in the invention are polynucleotides encoding polypeptides of the antigen binding constructs. The term "polynucleotide" or "nucleotide sequence" is intended to indicate a consecutive stretch of two or more nucleotide molecules. The nucleotide sequence may be of genomic, cDNA, RNA, semisynthetic or synthetic origin, or any combination thereof.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)).

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of ordinary skill in the art will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the deletion of an amino acid, addition of an amino acid, or substitution of an amino acid with a chemically similar amino acid. Conservative substitution tables providing functionally similar amino acids are known to those of ordinary skill in the art. Such conservatively modified variants are in addition to and do not exclude polymorphic variants, interspecies homologs, and alleles described herein.

Conservative substitution tables providing functionally similar amino acids are known to those of ordinary skill in the art. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and [0139] 8) Cysteine (C), Methionine (M) (see, e.g., Creighton, Proteins: Structures and Molecular Properties (W H Freeman & Co.; 2nd edition (December 1993))

The terms "identical" or percent "identity," in the context of two or more nucleic acids or polypeptide sequences, refer to two or more sequences or subsequences that are the same. Sequences are "substantially identical" if they have a percentage of amino acid residues or nucleotides that are the same (i.e., about 60% identity, about 65%, about 70%, about 75%, about 80%, about 85%, about 90%, or about 95% identity over a specified region), when compared and aligned for maximum correspondence over a comparison window, or designated region as measured using one of the following sequence comparison algorithms (or other algorithms available to persons of ordinary skill in the art) or by manual alignment and visual inspection. This definition also refers to the complement of a test sequence. The identity can exist over a region that is at least about 50 amino acids or nucleotides in length, or over a region that is 75-100 amino acids or nucleotides in length, or, where not specified, across the entire sequence of a polynucleotide or polypeptide. A polynucleotide encoding a polypeptide of the present invention, including homologs from species other than human, may be obtained by a process comprising the steps of screening a library under stringent hybridization conditions with a labeled probe having a polynucleotide sequence described herein or a fragment thereof, and isolating full-length cDNA and genomic clones containing said polynucleotide sequence. Such hybridization techniques are well known to the skilled artisan.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are known to those of ordinary skill in the art. Optimal alignment of sequences for comparison can be conducted, including but not limited to, by the local homology algorithm of Smith and Waterman (1970) Adv. Appl. Math. 2:482c, by the homology alignment algorithm of Needleman and Wunsch (1970) J. Mol. Biol. 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)).

One example of an algorithm that is suitable for determining percent sequence identity and sequence similarity are the BLAST and BLAST 2.0 algorithms, which are described in Altschul et al. (1997) Nuc. Acids Res. 25:3389-3402, and Altschul et al. (1990) J. Mol. Biol. 215:403-410, respectively. Software for performing BLAST analyses is publicly available through the National Center for Biotechnology Information available at the World Wide Web at ncbi nlm nih gov. The BLAST algorithm parameters W, T, and X determine the sensitivity and speed of the alignment. The BLASTN program (for nucleotide sequences) uses as defaults a wordlength (W) of 11, an expectation (E) or 10, $M=5$, $N=-4$ and a comparison of both strands. For amino acid sequences, the BLASTP program uses as defaults a wordlength of 3, and expectation (E) of 10, and the BLOSUM62 scoring matrix (see Henikoff and Henikoff (1992) Proc. Natl. Acad. Sci. USA 89:10915) alignments (B) of 50, expectation (E) of 10, $M=5$, $N=-4$, and a comparison of both strands. The BLAST algorithm is typically performed with the "low complexity" filter turned off.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, or less than about 0.01, or less than about 0.001.

The phrase "selectively (or specifically) hybridizes to" refers to the binding, duplexing, or hybridizing of a molecule only to a particular nucleotide sequence under stringent hybridization conditions when that sequence is present in a complex mixture (including but not limited to, total cellular or library DNA or RNA).

The phrase "stringent hybridization conditions" refers to hybridization of sequences of DNA, RNA, or other nucleic acids, or combinations thereof under conditions of low ionic strength and high temperature as is known in the art. Typically, under stringent conditions a probe will hybridize to its target subsequence in a complex mixture of nucleic acid (including but not limited to, total cellular or library DNA or RNA) but does not hybridize to other sequences in the complex mixture. Stringent conditions are sequence-dependent and will be different in different circumstances. Longer sequences hybridize specifically at higher temperatures. An extensive guide to the hybridization of nucleic acids is found in Tijssen, Laboratory Techniques in Biochemistry and Molecular Biology—Hybridization with Nucleic Probes, "Overview of principles of hybridization and the strategy of nucleic acid assays" (1993).

As used herein, the terms "engineer, engineered, engineering", are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches. The engineered proteins are expressed and produced by standard molecular biology techniques.

By "isolated nucleic acid molecule or polynucleotide" is intended a nucleic acid molecule, DNA or RNA, which has been removed from its native environment. For example, a recombinant polynucleotide encoding a polypeptide contained in a vector is considered isolated. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extra-chromosomally or at a chromosomal location that is different from its natural chromosomal location. Isolated RNA molecules include in vivo or in vitro RNA transcripts, as well as positive and negative strand forms, and double-stranded forms. Isolated polynucleotides or nucleic acids described herein, further include such molecules produced synthetically, e.g., via PCR or chemical synthesis. In addition, a polynucleotide or a nucleic acid, in certain embodiments, include a regulatory element such as a promoter, ribosome binding site, or a transcription terminator.

The term "polymerase chain reaction" or "PCR" generally refers to a method for amplification of a desired nucleotide sequence in vitro, as described, for example, in U.S. Pat. No. 4,683,195. In general, the PCR method involves repeated cycles of primer extension synthesis, using oligonucleotide primers capable of hybridising preferentially to a template nucleic acid.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g. ALIGN-2).

A derivative, or a variant of a polypeptide is said to share "homology" or be "homologous" with the peptide if the amino acid sequences of the derivative or variant has at least 50% identity with a 100 amino acid sequence from the original peptide. In certain embodiments, the derivative or variant is at least 75% the same as that of either the peptide or a fragment of the peptide having the same number of amino acid residues as the derivative. In certain embodiments, the derivative or variant is at least 85% the same as that of either the peptide or a fragment of the peptide having the same number of amino acid residues as the derivative. In certain embodiments, the amino acid sequence of the derivative is at least 90% the same as the peptide or a fragment of the peptide having the same number of amino acid residues as the derivative. In some embodiments, the amino acid sequence of the derivative is at least 95% the same as the peptide or a fragment of the peptide having the same number of amino acid residues as the derivative. In certain embodiments, the derivative or variant is at least 99% the same as that of either the peptide or a fragment of the peptide having the same number of amino acid residues as the derivative.

The term "modified," as used herein refers to any changes made to a given polypeptide, such as changes to the length of the polypeptide, the amino acid sequence, chemical structure, co-translational modification, or post-translational modification of a polypeptide. The form "(modified)" term means that the polypeptides being discussed are optionally modified, that is, the polypeptides under discussion can be modified or unmodified.

In some aspects, an antigen-binding construct comprises an amino acids sequence that is at least 80, 85, 90, 91, 92, 93, 94, 95, 96, 97, 98, 99, or 100% identical to a relevant amino acid sequence or fragment thereof set forth in the Table(s) or accession number(s) disclosed herein. In some aspects, an isolated antigen-binding construct comprises an amino acids sequence encoded by a polynucleotide that is at least 80, 85, 90, 91, 92, 93, 94, 95, 96, 97, 98, 99, or 100% identical to a relevant nucleotide sequence or fragment thereof set forth in Table(s) or accession number(s) disclosed herein.

It is to be understood that this invention is not limited to the particular protocols; cell lines, constructs, and reagents described herein and as such may vary. It is also to be understood that the terminology used herein is for the purpose of describing particular embodiments only, and is not intended to limit the scope of the present invention All publications and patents mentioned herein are incorporated herein by reference for the purpose of describing and disclosing, for example, the constructs and methodologies that are described in the publications, which might be used in connection with the presently described invention. The publications discussed herein are provided solely for their disclosure prior to the filing date of the present application. Nothing herein is to be construed as an admission that the inventors are not entitled to antedate such disclosure by virtue of prior invention or for any other reason.

REFERENCES

Bowles J A, Wang S Y, Link B K, Allan B, Beuerlein G, Campbell M A, Marquis D, Ondek B, Wooldridge J E, Smith B J, Breitmeyer J B, Weiner G J. Anti-CD20 monoclonal antibody with enhanced affinity for CD16 activates N K cells at lower concentrations and more effectively than rituximab. Blood. 2006 Oct. 15; 108(8): 2648-54. Epub 2006 Jul. 6.

Desjarlais J R, Lazar G A. Modulation of antibody effector function. Exp Cell Res. 2011 May 15; 317(9):1278-85.

Ferrara C, Grau S, Jäger C, Sondermann P, Brünker P, Waldhauer I, Hennig M, Ruf A, Rufer A C, Stihle M, Umaña P, Benz J. Unique carbohydrate-carbohydrate interactions are required for high affinity binding between FcgammaRIII and antibodies lacking core fucose. Proc Natl Acad Sci USA. 2011 Aug. 2; 108(31):12669-74.

Heider K H, Kiefer K, Zenz T, Volden M, Stilgenbauer S, Ostermann E, Baum A, Lamche H, Küpcü Z, Jacobi A, Müller S, Hirt U, Adolf G R, Borges E. A novel Fc-engineered monoclonal antibody to CD37 with enhanced ADCC and high proapoptotic activity for treatment of B-cell malignancies. Blood. 2011 Oct. 13; 118(15):4159-68. Epub 2011 Jul. 27. Blood. 2011 Oct. 13; 118(15): 4159-68. Epub 2011 Jul. 27.

Lazar G A, Dang W, Karki S, Vafa O, Peng J S, Hyun L, Chan C, Chung H S, Eivazi A, Yoder S C, Vielmetter J, Carmichael D F, Hayes R J, Dahiyat B I. Engineered antibody Fc variants with enhanced effector function. Proc Natl Acad Sci USA. 2006 Mar. 14; 103(11):4005-10. Epub 2006 Mar. 6.

Lu Y, Vernes J M, Chiang N, Ou Q, Ding J, Adams C, Hong K, Truong B T, Ng D, Shen A, Nakamura G, Gong Q, Presta L G, Beresini M, Kelley B, Lowman H, Wong W L, Meng Y G. Identification of IgG(1) variants with increased affinity to FcγRIIIa and unaltered affinity to FcγRI and FcRn: comparison of soluble receptor-based and cell-based binding assays. J Immunol Methods. 2011 Feb. 28; 365(1-2):132-41. Epub 2010 Dec. 23.

Mizushima T, Yagi H, Takemoto E, Shibata-Koyama M, Isoda Y, Lida S, Masuda K, Satoh M, Kato K. Structural basis for improved efficacy of therapeutic antibodies on defucosylation of their Fc glycans. Genes Cells. 2011 November; 16(11):1071-1080.

Moore G L, Chen H, Karki S, Lazar G A. Engineered Fc variant antibodies with enhanced ability to recruit complement and mediate effector functions. MAbs. 2010 March-April; 2(2):181-9.

Nordstrom J L, Gorlatov S, Zhang W, Yang Y, Huang L, Burke S, Li H, Ciccarone V, Zhang T, Stavenhagen J, Koenig S, Stewart S J, Moore P A, Johnson S, Bonvini E. Anti-tumor activity and toxicokinetics analysis of MGAH22, an anti-HER2 monoclonal antibody with enhanced Fc-gamma receptor binding properties. Breast Cancer Res. 2011 Nov. 30; 13(6):R123. [Epub ahead of print]

Richards J O, Karki S, Lazar G A, Chen H, Dang W, Desjarlais J R. Optimization of antibody binding to FcgammaRIIa enhances macrophage phagocytosis of tumor cells. Mol Cancer Ther. 2008 August; 7(8):2517-27.

Schneider S, Zacharias M. Atomic resolution model of the antibody Fc interaction with the complement C1q component. Mol Immunol. 2012 May; 51(1):66-72.

Shields R L, Namenuk A K, Hong K, Meng Y G, Rae J, Briggs J, Xie D, Lai J, Stadlen A, Li B, Fox J A, Presta L G. High resolution mapping of the binding site on human IgG1 for Fc gamma RI, Fc gamma RII, Fc gamma RIII, and FcRn and design of IgG1 variants with improved binding to the Fc gamma R. J Biol Chem. 2001 Mar. 2; 276(9):6591-604.

Stavenhagen J B, Gorlatov S, Tuaillon N, Rankin C T, Li H, Burke S, Huang L, Vijh S, Johnson S, Bonvini E, Koenig S. Fc optimization of therapeutic antibodies enhances their ability to kill tumor cells in vitro and controls tumor expansion in vivo via low-affinity activating Fcgamma receptors. Cancer Res. 2007 Sep. 15; 67(18):8882-90.

Stewart R, Thom G, Levens M, Güler-Gane G, Holgate R, Rudd P M, Webster C, Jermutus L, Lund J. A variant human IgG1-Fc mediates improved ADCC. *Protein Eng Des Sel.* 2011 September; 24(9):671-8. Epub 2011 May 18.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pennsylvania: Mack Publishing Company, 1990); Carey and Sundberg *Advanced Organic Chemistry* $3^{rd}$ Ed. (Plenum Press) Vols A and B (1992).

Example 1: Preparation of Exemplary Anti-HER2 Bispecific Antibodies and Controls A number of exemplary anti-HER2 biparatopic antibodies (or antigen-binding constructs) and controls were prepared as described below. The antibodies and controls have been prepared in different formats, and representations of exemplary biparatopic formats are shown in FIG. 1. In all of the formats shown in FIG. 1, the heterodimeric Fc is depicted with one chain (Chain A) shown in black and the other (Chain B) shown in grey, while one antigen-binding domain (1) is shown in hatched fill, while the other antigen-binding domain (2) is shown in white.

Figure 1B:
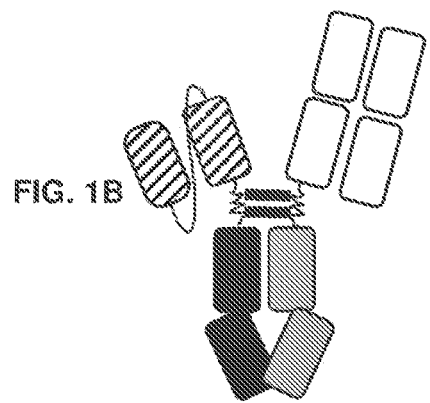
FIG. 1B depicts the structure of a possible version of a biparatopic antibody in an scFv-Fab format.
Figure 1C:
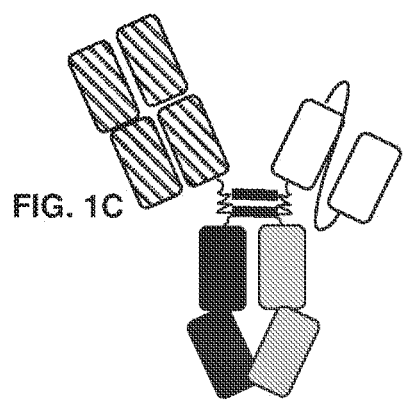
FIG. 1C depicts the structure of a possible version of a biparatopic antibody in an scFv-Fab format.
Figure 1D:
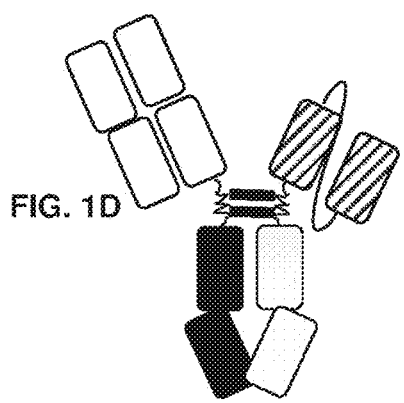
FIG. 1D depicts the structure of a possible version of a biparatopic antibody in an scFv-Fab format.
Figure 1E:
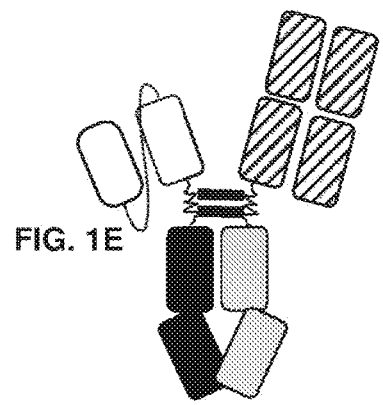
FIG. 1E depicts the structure of a possible version of a biparatopic antibody in an scFv-Fab format.
Figure 1F:
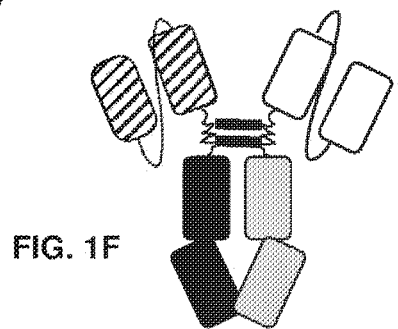
FIG. 1F depicts the structure of a possible version of a biparatopic antibody in an scFv-Fab format.

FIG. 1A depicts the structure of a biparatopic antibody in a Fab-Fab format. FIGS. 1B to 1E depict the structure of possible versions of a biparatopic antibody in an scFv-Fab format. In FIG. 1B, antigen-binding domain 1 is an scFv, fused to Chain A, while antigen-binding domain 2 is a Fab, fused to Chain B. In FIG. 1C, antigen-binding domain 1 is a Fab, fused to Chain A, while antigen-binding domain 2 is an scFv, fused to Chain B. In FIG. 1D, antigen-binding domain 2 is a Fab, fused to Chain A, while antigen-binding domain 1 is an scFv, fused to Chain B. In FIG. 1E, antigen-binding domain 2 is an scFv, fused to Chain A, while antigen-binding domain 1 is a Fab, fused to Chain B. In FIG. 1F, both antigen-binding domains are scFvs.

The sequences of the following variants are provided in the Sequence Table found after the Examples. CDR regions were identified using a combination of the Kabat and Chothia methods. Regions may vary slightly based on method used for identification.

Exemplary Anti-HER2 Biparatopic Antibodies

Exemplary anti-HER2 biparatopic antibodies were prepared as shown in Table 1.

TABLE 1

Exemplary anti-HER2 biparatbopic antibodies

| Variant | | Chain A | Chain B |
|---|---|---|---|
| 5019 | domain containing the epitope | ECD2 | ECD4 |
| | Format | Fab | scFv |
| | Antibody name | Pertuzumab | Trastuzumab |

TABLE 1-continued

Exemplary anti-HER2 biparatopic antibodies

| Variant | | Chain A | Chain B |
|---|---|---|---|
| | CH3 sequence substitutions | T350V_L351Y_F405A_Y407V | T366I_N390R_K392M_T394W |
| 5020 | domain containing the epitope | ECD4 | ECD2 |
| | format | scFv | Fab |
| | Antibody name | Trastuzumab | Pertuzumab |
| | CH3 sequence substitutions | L351Y_S400E_F405A_Y405V | T350V_T366L_K392L_T394W |
| 7091 | domain containing the epitope | ECD2 | ECD4 |
| | format | Fab | scFv |
| | Antibody name | Pertuzumab | Trastuzumab |
| | CH3 sequence substitutions | T350V_L351Y_F405A_Y405V | T350V_T366L_K392L_T394W |
| 10000 | domain containing the epitope | ECD2 | ECD4 |
| | format | Fab | scFv |
| | Antibody name | Pertuzumab-with Y96A in VL region and T30A/A49G/L69F in VH region | Trastuzumab |
| | CH3 sequence substitutions | T350V_L351Y_F405A_Y405V | T350V_T366L_K392L_T394W |
| 6902 | domain containing the epitope | ECD2 | ECD4 |
| | format | Fab | Fab |
| | Antibody name | Trastuzumab | Pertuzumab |
| | Fab substitutions | HC: L143E_K145T LC: Q124R | HC: D146G_Q179K LC: Q124E_Q160E_T180E |
| | CH3 sequence substitutions | T350V_L351Y_F405A_Y405V | T350V_T366L_K392L_T394W |
| 6903 | domain containing the epitope | ECD2 | ECD4 |
| | format | Fab | Fab |
| | Fab substitutions | HC: L143E_K145T LC: Q124R_Q1160K_T178R | HC: D146G_Q179K LC: Q124E_Q160E_T180E |
| | Antibody name | Trastuzumab | Pertuzumab |
| | CH3 sequence substitutions | T350V_L351Y_F405A_Y405V | T350V_T366L_K392L_T394W |
| 6717 | domain containing the epitope | ECD4 | ECD2 |
| | format | scFv | scFv |
| | Antibody name | Pertuzumab | Trastuzumab |
| | CH3 sequence substitutions | T350V_L351Y_F405A_Y405V | T366I_N390R_K392M_T394W |

Notes:
CH3 numbering according to EU; Fab or variable domain numbering according to Kabat;
"domain containing the epitope" = domain of HER2 to which antigen binding moiety binds;
"Antibody name" = antibody from which antigen binding moiety is derived, includes substitutions compared to wild-type when present;
"Fab substitutions" = substitutions in Fab that promote correct light chain pairing;
"CH3 sequence substitutions" = substitutions in CH3 domain that promote formation of heterodimeric Fc Exemplary Anti-HER2 Monovalent Control Antibodies v1040: a monovalent anti-HER2 antibody, where the HER2 binding domain is a Fab derived from trastuzumab on chain A, and the Fc region is a heterodimer having the mutations T350V_L351Y_F405A_Y407V in Chain A, T350V_T366L_K392L_T394W in Chain B, and the hinge region of Chain B having the mutation C226S; the antigen binding domain binds to domain 4 of HER2.

v630—a monovalent anti-HER2 antibody, where the HER2 binding domain is an scFv derived from trastuzumab on Chain A, and the Fc region is a heterodimer having the mutations L351Y_S400E_F405A_Y407V in Chain A, T366I_N390R_K392M_T394W in Chain B; and the hinge region having the mutation C226S (EU numbering) in both chains; the antigen binding domain binds to domain 4 of HER2.

v4182: a monovalent anti-HER2 antibody, where the HER2 binding domain is a Fab derived from pertuzumab on chain A, and the Fc region is a heterodimer having the mutations T350V_L351Y_F405A_Y407V in Chain A, T350V_T366L_K392L_T394W in Chain B, and the hinge region of Chain B having the mutation C226S; the antigen binding domain binds to domain 2 of HER2.

Exemplary Anti-HER2 Monospecific Bivalent Antibody Controls (Full-Sized Antibodies, FSAs)

v506 is a wild-type anti HER2 produced in-house in Chinese Hamster Ovary (CHO) cells, as a control. Both HER2 binding domains are derived from trastuzumab in the Fab format and the Fc is a wild type homodimer; the antigen binding domain binds to domain 4 of HER2. This antibody is also referred to as a trastuzumab analog.

v792, is wild-type trastuzumab with a IgG1 hinge, where both HER2 binding domains are derived from trastuzumab in the Fab format, and the and the Fc region is a heterodimer having the mutations T350V_L351Y_F405A_Y407V in Chain A, and T350V_T366L_K392L_T394W Chain B; the antigen binding domain binds to domain 4 of HER2. This antibody is also referred to as a trastuzumab analog.

v4184, a bivalent anti-HER2 antibody, where both HER2 binding domains are derived from pertuzumab in the Fab format, and the Fc region is a heterodimer having the mutations T350V_L351Y_F405A_Y407V in Chain A, and T350V_T366L_K392L_T394W Chain B. The antigen binding domain binds to domain 2 of HER2. This antibody is also referred to as a pertuzumab analog.

hIgG, is a commercial non-specific polyclonal antibody control (Jackson ImmunoResearch, #009-000-003).

These antibodies and controls (other than human IgG) were cloned and expressed as follows. The genes encoding the antibody heavy and light chains were constructed via gene synthesis using codons optimized for human/mammalian expression. The Trastuzumab Fab sequence was generated from a known HER2/neu domain 4 binding antibody (Carter P. et al. (1992) Humanization of an anti p185 HER2 antibody for human cancer therapy. *Proc Natl Acad Sci* 89, 4285.) And the Fc was an IgG1 isotype. The scFv sequence was generated from the VH and VL domains of Trastuzumab using a glycine-serine linker (Carter P. et al. (1992) Humanization of an anti p185 her2 antibody for human cancer therapy. *Proc Natl Acad Sci* 89, 4285). The Pertuzumab Fab sequence was generated from a known HER2/neu domain 2 binding Ab (Adams C W et al. (2006) Humanization of a recombinant monoclonal antibody to produce a therapeutic her dimerization inhibitor, Pertuzumab. *Cancer Immunol Immunother.* 2006; 55(6):717-27).

The final gene products were sub-cloned into the mammalian expression vector PTTS (NRC-BRI, Canada) and expressed in CHO cells (Durocher, Y., Perret, S. & Kamen, A. High-level and high-throughput recombinant protein production by transient transfection of suspension-growing CHO cells. *Nucleic acids research* 30, e9 (2002)).

The CHO cells were transfected in exponential growth phase (1.5 to 2 million cells/ml) with aqueous 1 mg/ml 25 kDa polyethylenimine (PEI, polysciences) at a PEI:DNA ratio of 2.5:1. (Raymond C. et al. A simplified polyethylenimine-mediated transfection process for large-scale and high-throughput applications. Methods. 55(1):44-51 (2011)). To determine the optimal concentration range for forming heterodimers, the DNA was transfected in optimal DNA ratios of the heavy chain a (HC-A), light chain (LC), and heavy chain B (HC-B) that allow for heterodimer formation (e.g. HC-A/HC-B/LC ratios=30:30:40 (v5019). Transfected cells were harvested after 5-6 days with the culture medium collected after centrifugation at 4000 rpm and clarified using a 0.45 μm filter.

The clarified culture medium was loaded onto a MabSelect SuRe (GE Healthcare) protein-A column and washed with 10 column volumes of PBS buffer at pH 7.2. The antibody was eluted with 10 column volumes of citrate buffer at pH 3.6 with the pooled fractions containing the antibody neutralized with TRIS at pH 11.

The protein-A antibody eluate was further purified by gel filtration (SEC). For gel filtration, 3.5 mg of the antibody mixture was concentrated to 1.5 mL and loaded onto a Sephadex 200 HiLoad 16/600 200 pg column (GE Healthcare) via an AKTA Express FPLC at a flow-rate of 1 mL/min. PBS buffer at pH 7.4 was used at a flow-rate of 1 mL/min. Fractions corresponding to the purified antibody were collected, concentrated to ~1 mg/mL.

Exemplary anti-HER2 ECD2×ECD4 biparatopic antibodies with different molecular formats (e.g. v6717, scFv-scFv IgG1; v6903 and v6902 Fab-Fab IgG1; v5019, v7091 and v10000 Fab-scFv IgG1) were cloned, expressed and purified as described above.

To quantify antibody purity and to determine the amount of target heterodimer protein and possible homodimer and/or half antibody and/or mispaired light chain contaminant, LC-MS intact mass analysis was performed. The LC-MS intact mass analysis was performed as described in Example 2, excluding DAR analysis calculations used for ADC molecules.

The data is shown in Table 2. Table 2 shows that expression and purification of these biparatopic antibodies resulted in 100% of the desired product for v6717, 91% of the desired heterodimeric product for v6903, and 62% of the desired product for v6902. The numbers in brackets indicate the quantities of the main peak plus a side peak of +81 Da. This side peak is typically detected with variants that contain C-terminal HA tags (such of v6903 and v6902). Adding the main and side peaks yields heterodimer purities of approximately 98% and 67% for v6903 and v6903. Based on the high heterodimer purity, v6903 was identified as the representative Fab-Fab anti-HER2 biparatopic variant for direct comparison to the scFv-scFv and Fab-scFv formats. v6903 was included in all format comparison assays.

TABLE 2

Expression and purification of antibodies

| Variant | Desired heterodimer species (+side peak) |
|---|---|
| 6717 | 100.0 |
| 6903 | 90.9 (97.7) |
| 6902 | 62.4 (67.4) |

Example 2: Preparation of Exemplary Anti-HER2 Biparatopic Antibody Drug Conjugates (ADCs)

The following anti-HER2 biparatopic antibody drug conjugates (anti-HER2 biparatopic-ADCs) were prepared. ADCs of variants 5019, 7091, 10000 and 506 were prepared. These ADCs are identified as follows:
- v6363 (v5019 conjugated to DM1)
- v7148 (v7091 conjugated to DM1)
- v10553 (v10000 conjugated to DM1)
  - v6246 (v506 conjugated to DM1, analogous to T-DM1, trastuzumab-emtansine)
- v6249 (human IgG conjugated to DM1)

The ADCs were prepared via direct coupling to maytansine. Antibodies purified by Protein A and SEC, as described in Example 1 (>95% purity), were used in the preparation of the ADC molecules. ADCs were conjugated following the method described in Kovtun Y V, Audette C A, Ye Y, et al. Antibody-drug conjugates designed to eradicate tumors with homogeneous and heterogeneous expression of the target antigen. Cancer Res 2006; 66:3214-21. The ADCs had an average molar ratio of 3.0 maytansinoid molecules per antibody as determined by LC/MS and described below.

Details of the reagents used in the ADC conjugation reaction are as follows: Conjugation Buffer 1: 50 mM Potassium Phosphate/50 mM Sodium Chloride, pH 6.5, 2 mM EDTA. Conjugation Buffer 2: 50 mM Sodium Succinate, pH 5.0. ADC formulation buffer: 20 mM Sodium Succinate, 6% (w/v) Trehalose, 0.02% polysorbate 20, pH 5.0. Dimethylacetamide (DMA); 10 mM SMCC in DMA (prepared before conjugation), 10 mM DM1-SH in DMA (prepared before conjugation), 1 mM DTNB in PBS, 1 mM Cysteine in buffer, 20 mM Sodium Succinate, pH 5.0. UV-VIS spectrophotometer (Nano drop 100 from Fisher Scientific), PD-10 columns (GE Healthcare).

The ADCs were prepared as follows. The starting antibody solution was loaded onto the PD-10 column, previously equilibrated with 25 mL of Conjugation Buffer 1, followed by 0.5 ml Conjugation Buffer 1. The antibody eluate was collect and the concentration measured at $A_{280}$ and the concentration was adjusted to 20 mg/mL. The 10 mMS MCC-DM1 solution in DMA was prepared. A 7.5 molar equivalent of SMCC-DM1 to antibody was added to the antibody solution and DMA was added to a final DMA volume of 10% v/v. The reaction was briefly mixed and incubated at RT for 2 h. A second PD-10 column was equilibrated with 25 ml of Conjugation Buffer 1 and the antibody-MCC-DM1 solution was added to the column follow by 0.5 ml of Buffer 1. The antibody-MCC-DM1 eluate was collected and the A252 and A280 of antibody solution was measured. The Antibody-MCC-DM1 concentration was calculated ($\square$=1.45 mg$^{-1}$cm$^{-1}$, or 217500 M$^{-1}$cm$^{-1}$). The ADCs were analyzed on a SEC-HPLC column for high MW analysis (SEC-HPLC column TOSOH, G3000-SWXL, 7.8 mm×30 cm, Buffer, 100 mM Sodium phosphate, 300 mM Sodium Chloride, pH 7.0, flow rate: 1 ml/min).

ADC drug to antibody ratio (DAR) was analysed by HIC-HPLC_using the Tosoh TSK gel Butyl-NPR column (4.6 mm×3.5 mm×2.5 mm). Elution was performed at 1 ml/min using a gradient of 10-90% buffer B over 25 min followed by 100% buffer B for 4 min Buffer A comprises 20 mM sodium phosphate, 1.5 M ammonium sulphate, pH 7.0. Buffer B comprises 20 mM sodium phosphate, 25% v/v isopropanol, pH 7.0.

ADC drug to antibody ratio (DAR) was determined by LC-MS by the following method. The antibodies were deglycosylated with PNGase F prior to loading on the LC-MS. Liquid chromatography was carried out on an Agilent 1100 Series HPLC under the following conditions:

Flow rate: 1 mL/min split post column to 100 uL/min to MS. Solvents: A=0.1% formic acid in ddH2O, B=65% acetonitrile, 25% THF, 9.9% ddH2O, 0.1% formic acid. Column: 2.1×30 mm PorosR2. Column Temperature: 80° C.; solvent also pre-heated. Gradient: 20% B (0-3 min), 20-90% B (3-6 min), 90-20% B (6-7 min), 20% B (7-9 min).

Mass Spectrometry (MS) was subsequently carried out on an LTQ-Orbitrap XL mass spectrometer under the following conditions: Ionization method using Ion Max Electrospray. Calibration and Tuning Method: 2 mg/mL solution of CsI is infused at a flowrate of 10 µL/min. The Orbitrap was tuned on m/z 2211 using the Automatic Tune feature (overall CsI ion range observed: 1690 to 2800). Cone Voltage: 40V; Tube Lens: 115V; FT Resolution: 7,500; Scan range m/z 400-4000; Scan Delay: 1.5 min. A molecular weight profile of the data was generated using Thermo's Promass deconvolution software. Average DAR of the sample was determined as a function of DAR observed at each fractional peak (using the calculation: Σ(DAR×fractional peak intensity)).

Table 3 summarizes the average DAR for the ADC molecules. The average DAR for the exemplary anti-HER2 biparatopic antibody and control was approximately 3.

TABLE 3

Average DAR for ADCs

| | DAR (LC-MS) | DAR (HIC) | n |
|---|---|---|---|
| v6246 | 2.9 | 3.0 | 5 |
| v6363 | 2.6 | 3.3 | 5 |
| v7148 | 3.4 | 3.9 | 1 |
| v10553 | 4.0 | 4.0 | 1 |

Example 3: Expression and Bench-Scale Purification of Anti-HER2 Biparatopic Antibody The anti-HER2 biparatopic antibodies (v5019, v7091 and v10000) described in Example 1 were expressed in 10 and/or 25 L volumes and purified by protein A and size exclusion chromatography (SEC) as follows.

The clarified culture medium was loaded onto a MabSelect SuRe (GE Healthcare) protein-A column and washed with 10 column volumes of PBS buffer at pH 7.2. The antibody was eluted with 10 column volumes of citrate buffer at pH 3.6 with the pooled fractions containing the antibody neutralized with Tris at pH 11.

The protein-A antibody eluate was further purified by gel filtration (SEC). For gel filtration, 3.5 mg of the antibody mixture was concentrated to 1.5 mL and loaded onto a Sephadex 200 HiLoad 16/600 200 pg column (GE Healthcare) via an AKTA Express FPLC at a flow-rate of 1 mL/min. PBS buffer at pH 7.4 was used at a flow-rate of 1 mL/min. Fractions corresponding to the purified antibody were collected, concentrated to ~1 mg/mL. The purified proteins were analyzed by LC-MS as described in Example 2.

Figure 2A:
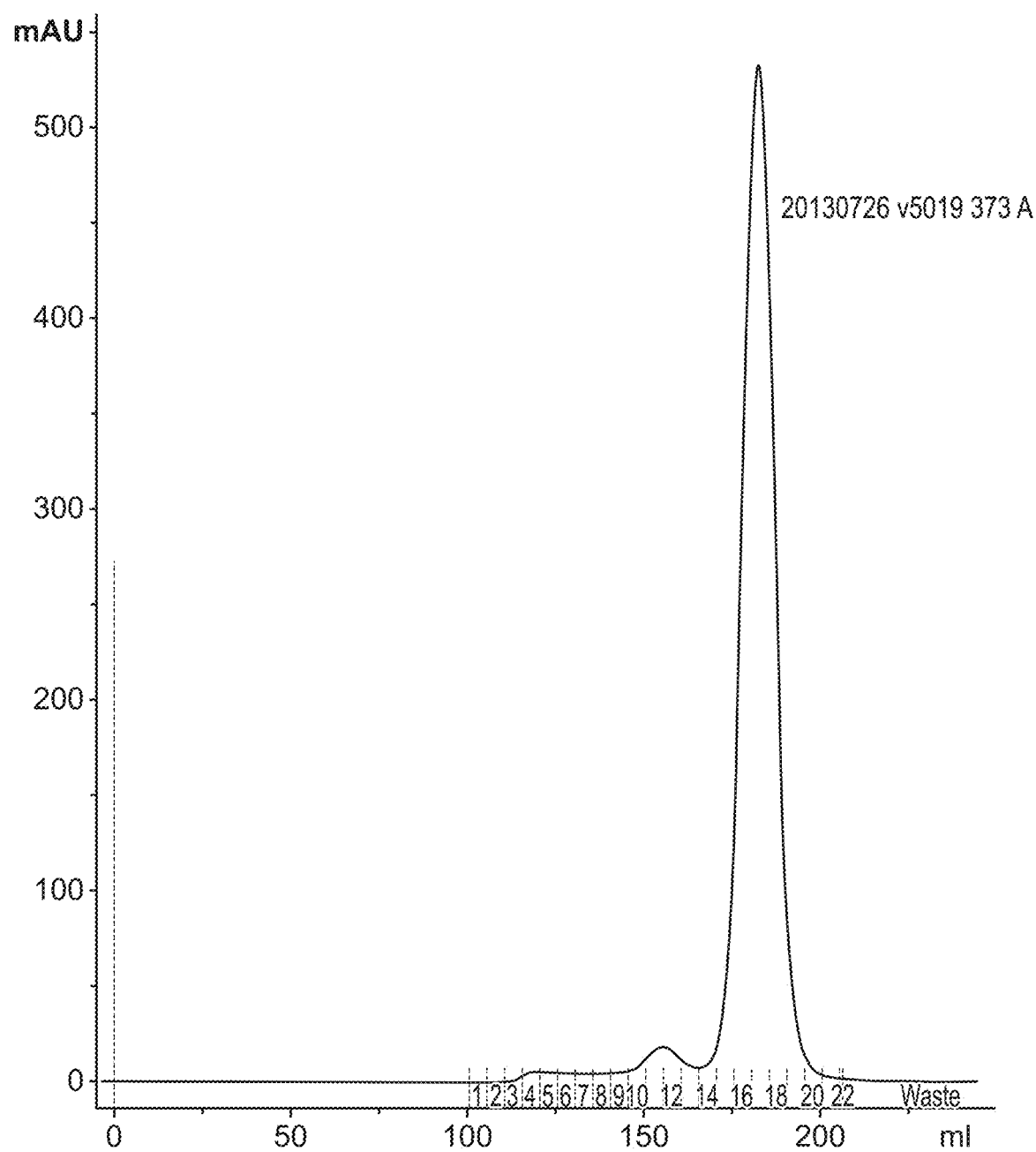
FIG. 2A depicts the characterization of expression and purification of exemplary anti-HER2 biparatopic antibodies.

The results of the 10 L expression and bench-scale protein A and SEC purification are shown in FIGS. 2A and 2B. FIG. 2A shows the SEC chromatograph of the protein A purified v5019 and FIG. 2B shows the non-reducing SDS-PAGE gel that compares the relative purity of a protein A pooled fraction as well as SEC fractions 15 and 19 and pooled SEC fractions 16-18. These results show that the anti-HER2 biparatopic antibody was expressed and that purification by protein A and SEC yielded a pure protein sample. Further quantification was performed by UPLC-SEC and LC-MS analysis and is described in Example 4.

The results of the 25 L expression and bench-scale protein A purification is shown in FIG. 2C. FIG. 2C shows SDS-PAGE gel that compares the relative purity of a protein A purified v10000. Lane M contains: protein marker; lane 1 contains: v10000 under reducing conditions; lane 2 contains v10000 under non-reducing conditions. The SDS-PAGE gel shows that v10000 is pure and runs at the correct predicted MW of approximately 125 kDa under non-reducing conditions. Under reducing conditions two heavy chains bands are visible corresponding to the CH-A heavy chain (approximately 49 kDa) and the CH-B heavy chain (approximately 52.5 kDa); the CH-A light chain is visible and runs at the correct predicted mass of approximately 23.5 kDa. These results show that the anti-HER2 biparatopic antibody was expressed and that one-step purification by protein A yielded a pure protein sample. Further quantification was performed by UPLC-SEC and LC-MS analysis and is described in Example 4.

Example 4: Analysis of Biparatopic Anti-HER2 Antibody Purity by UPLC-SEC and LC-MS The purity and percent aggregation of exemplary protein A and SEC purified biparatopic anti-HER2 heteromultimers was determined by UPLC-SEC by the method described.

UPLC-SEC analysis was performed using a Waters BEH200 SEC column set to 30° C. (2.5 mL, 4.6×150 mm, stainless steel, 1.7 µm particles) at 0.4 ml/min Run times consisted of 7 min and a total volume per injection of 2.8 mL with running buffers of 25 mM sodium phosphate, 150 mM sodium acetate, pH 7.1; and, 150 mM sodium phosphate, pH 6.4-7.1. Detection by absorbance was facilitated at 190-400 nm and by fluorescence with excitation at 280 nm and emission collected from 300-360 nm. Peak integration was analyzed by Empower 3 software.

Figure 3A:
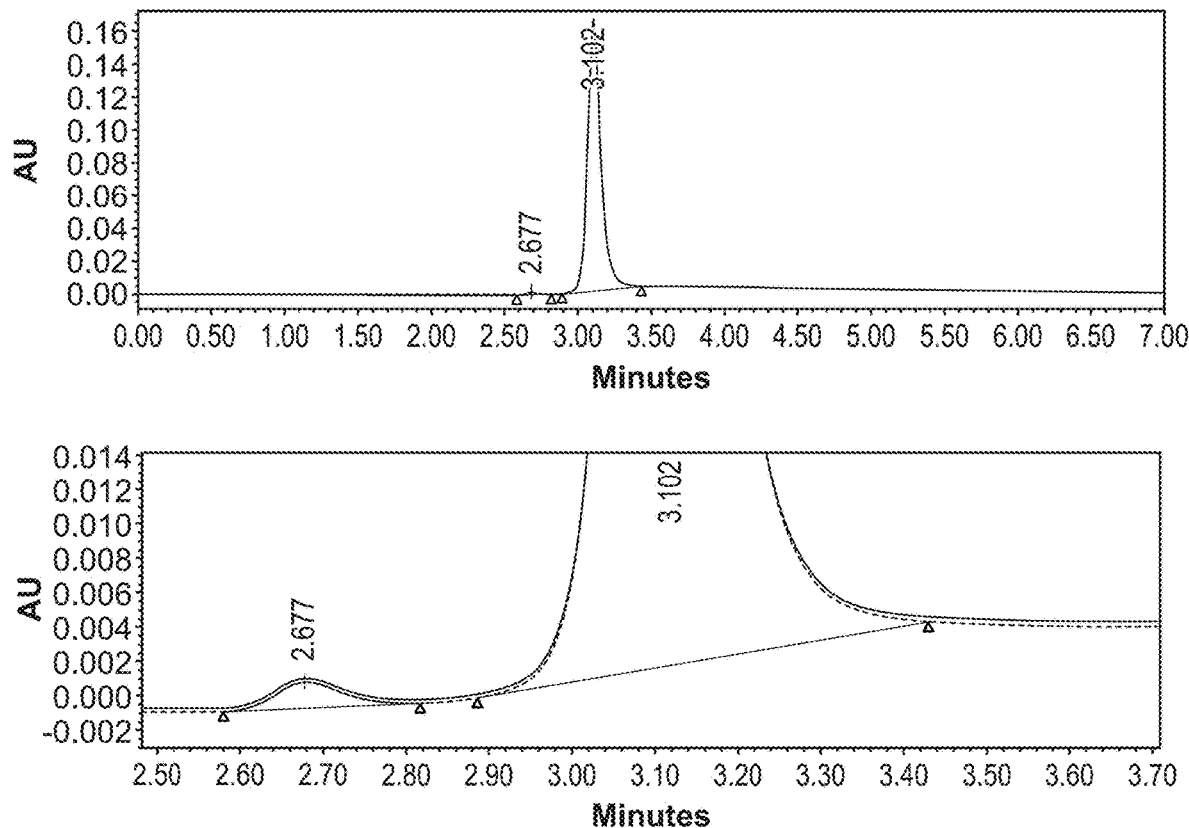
FIG. 3A depicts the results of UPLC-SEC analysis of exemplary anti-HER2 biparatopic antibodies purified by protein A and SEC.

UPLC-SEC results of the pooled v5019 SEC fractions are shown in FIG. 3A. These results indicate that the exemplary anti-HER2 biparatopic antibody was purified to >99% purity with less than 1% HMW species by protein A and SEC chromatography.

Figure 3B:
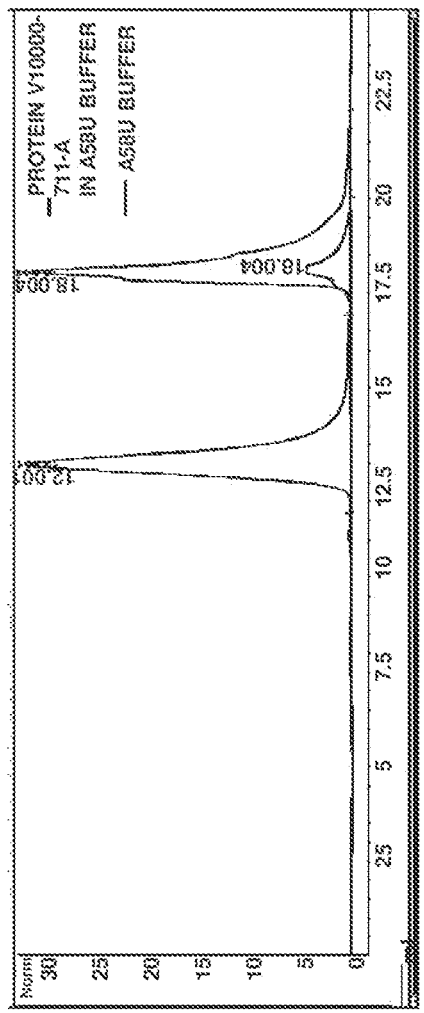
FIG. 3B depicts the results of UPLC-SEC analysis of exemplary anti-HER2 biparatopic antibodies purified by protein A and SEC.

UPLC-SEC results of the v10000 pooled Protein A fractions are shown in FIG. 3B. These results indicate that the exemplary anti-HER2 biparatopic antibody was purified to >96% purity with less than 1% HMW species by protein A chromatography.

Figure 4A:
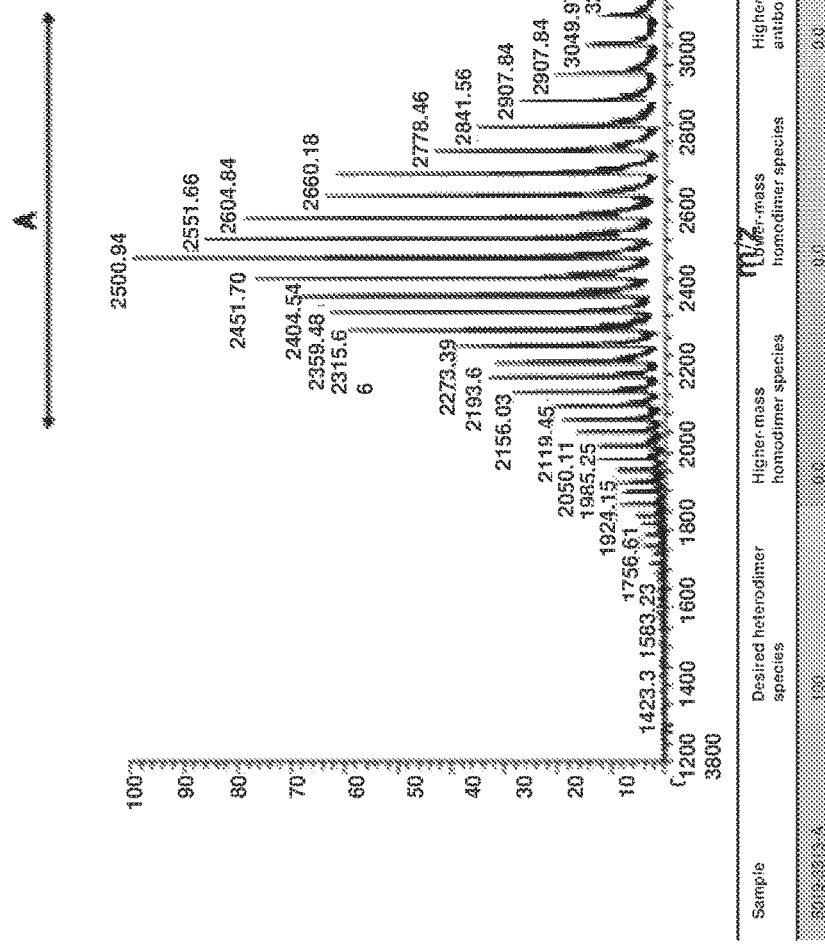
FIG. 4A depicts LCMS analysis of the heterodimer purity of exemplary anti-HER2 biparatopic antibodies.
Figure 4B:
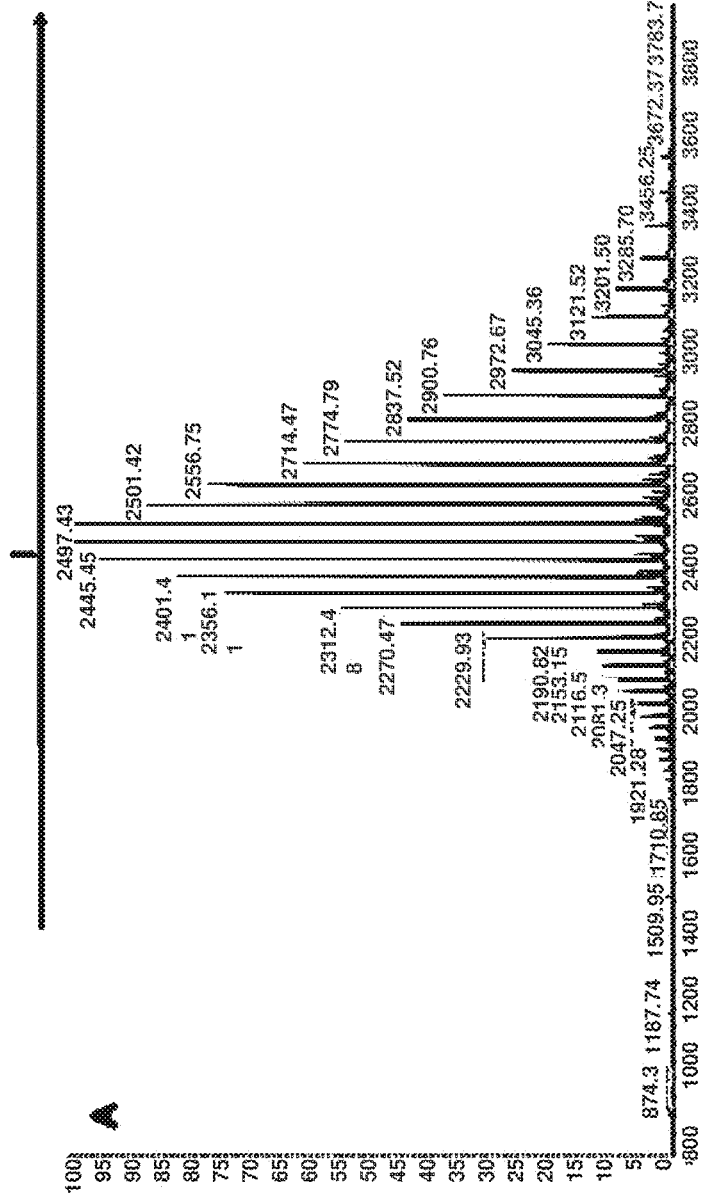
FIG. 4B depicts LCMS analysis of the heterodimer purity of exemplary anti-HER2 biparatopic antibodies.

The purity of exemplary biparatopic anti-HER2 antibodies was determined using LC-MS under standard conditions by the method described in Example 2. Results from LC-MS analysis of the pooled SEC fractions of v5019 are shown in FIG. 4A. This data shows that the exemplary biparatopic anti-HER2 heterodimer has a heterodimer purity of 100%. Results from LC-MS analysis of the pooled protein A fractions of v10000 are shown in FIG. 4B. This data shows that the exemplary biparatopic anti-HER2 heterodimer has a heterodimer purity of 98% following a one-step protein A purification.

Antibodies purified by protein A chromatography and/or protein A and SEC were used for the assays described in the following Examples.

Example 5. Large-Scale Expression and Manufacturability Assessment of Biparatopic Anti-HER2 Antibody Purified by Protein a and CEX Chromatography The exemplary anti-HER2 biparatopic antibody v5019 described in Example 1 was expressed in a 25 L scale and purified as follows.

Antibody was obtained from supernatant followed by a two-step purification method that consisted of Protein A purification (MabSelect™ resin; GE Healthcare) followed by cation exchange chromatography (HiTrap™ SP FF resin; GE Healthcare) by the protocol described.

CHO-3E7 cells were maintained in serum-free Freestyle CHO expression medium (Invitrogen, Carlsbad, CA, USA) in Erlenmeyer Flasks at 37° C. with 5% CO2 (Corning Inc., Acton, MA) on an orbital shaker (VWR Scientific, Chester, PA). Two days before transfection, the cells were seeded at an appropriate density in a 50 L CellBag with a volume of 25 L using the Wave Bioreactor System 20/50 (GE Healthcare Bio-Science Corp). On the day of transfection, DNA and PEI (Polysciences, Eppelheim, Germany) were mixed at an optimal ratio and added to the cells using the method described in Example 1. Cell supernatants collected on day 6 was used for further purification.

Cell culture broth was centrifuged and filtered before loading onto 30 mL MabSelect™ resin packed in XK26/20 (GE Healthcare, Uppsala, Sweden) at 10.0 mL/min. After washing and elution with appropriate buffer, the fractions were collected and neutralized with 1 M Tris-HCl, pH 9.0. The target protein was further purified via 20 mL SP FF resin packed in XK16/20 (GE Healthcare, Uppsala, Sweden). MabSelect™ purified sample was diluted with 20 mM NaAC, pH5.5 to adjust the conductivity to <5 ms/cm and 50 mM citrate acid (pH3.0) was added adjust the sample pH value to 5.5. Sample was loaded at a 1 mL/min onto the HiTrap™ SP FF resin (GE Healthcare) and washed with 20 mM NaAC. Protein was eluted using a gradient elution 0-100% of 20 mM NaAC, 1 M NaCl, pH5.5, 10 CV at 1 mL/min.

Figure 5A:
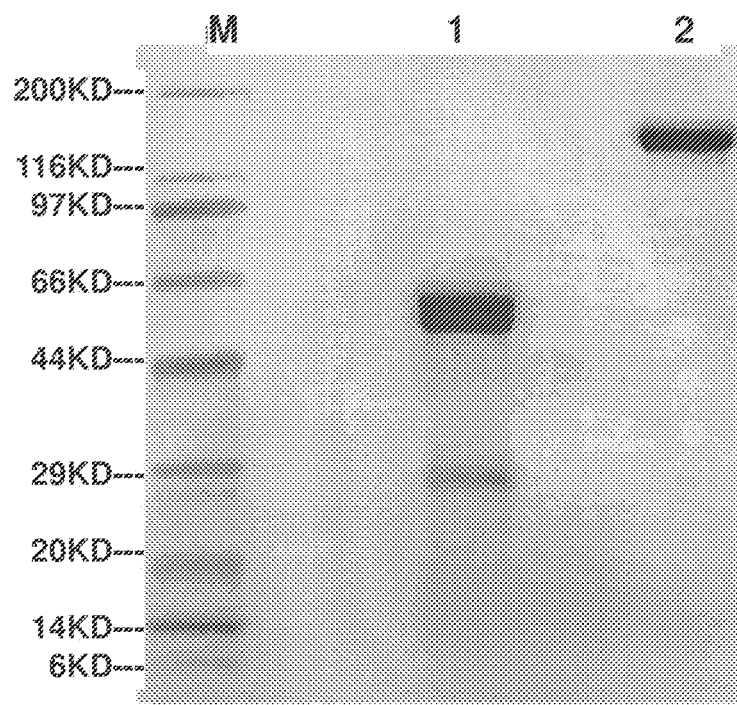
FIG. 5A depicts analysis of a 25 L-scale preparation of an exemplary anti-HER2 biparatopic antibody.
Figure 5B:
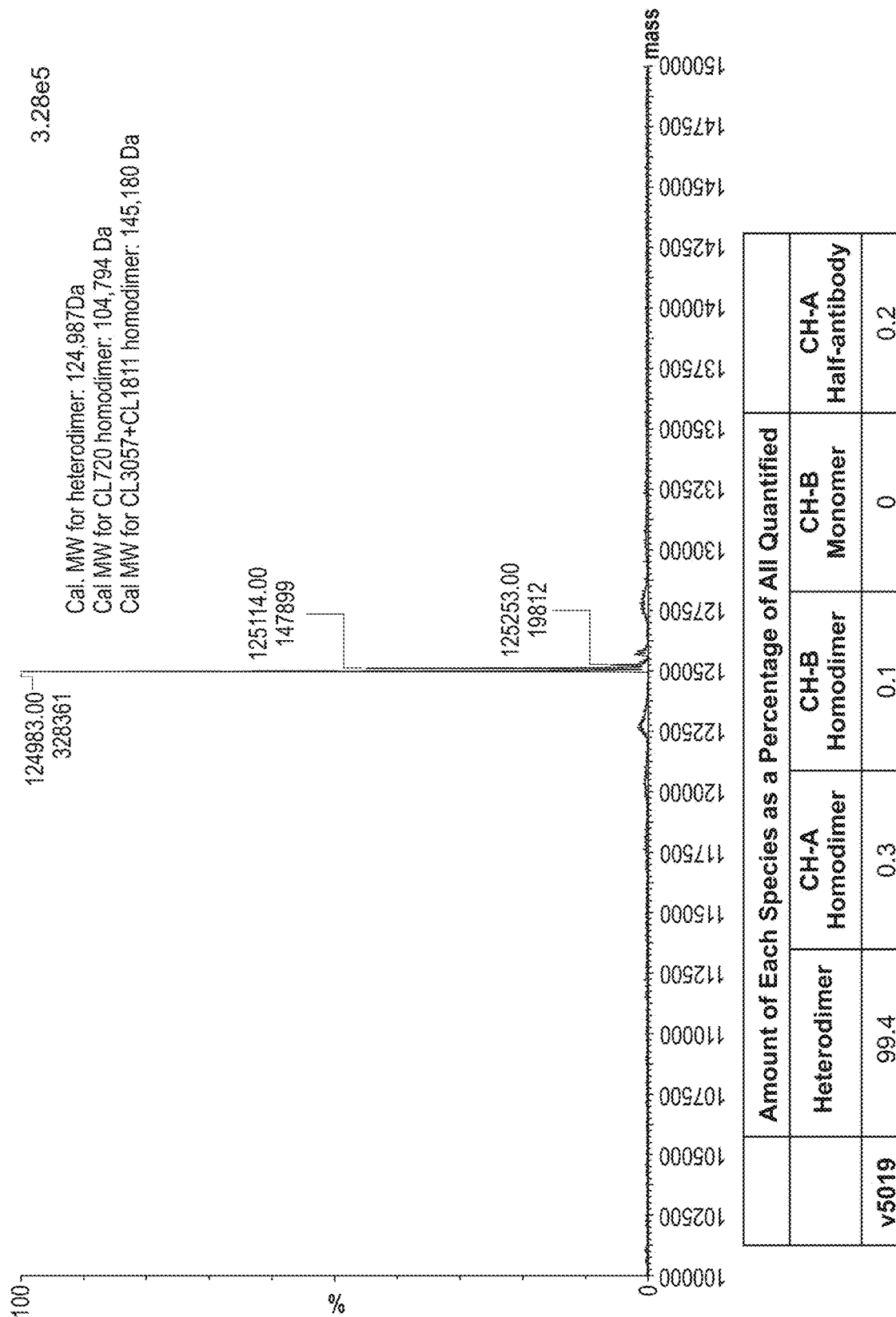
FIG. 5B depicts analysis of a 25 L-scale preparation of an exemplary anti-HER2 biparatopic antibody.

The purified protein was analyzed by SDS-PAGE as described in Example 1, and LC-MS for heterodimer purity by the method described in example 4. The results are shown in FIGS. 5A and 5B. FIG. 5A shows the SDS-PAGE results of v5019 following MabSelect™ and HiTrap™ SP FF purification; lane M contains: protein marker; lane 1: v5019 under reducing conditions (3 µg); Lane 2: v5019 under non-reducing conditions (2.5 µg). The SDS-PAGE gel shows that v5019 is relatively pure following MabSelect™ and HiTrap™ SP FP purification and, under non-reducing conditions, runs at the correct predicted MW of approximately 125 kDa. Under reducing conditions two heavy chains bands are visible corresponding to the CH-A heavy chain (approximately 49 kDa) and the CH-B heavy chain (approximately 52.5 kDa); the CH-A light chain is visible and runs at the correct predicted mass of approximately 23.5 kDa.

LC-MS analysis of the MabSelect™ and HiTrap™ SP FF purified v5019 was performed to determine heterodimer purity using the method described in Example 4. Results from the LC-MS analysis are shown in FIG. 5B. These results show that v5019 purification using MabSelect™ and HiTrap™ SP FF yields protein with >99% heterodimer purity and with little (<1%) or undetectable homodimer or half antibody contamination.

Example 6: Comparison of Bmax of a Biparatopic Anti-HER2 Antibody Against Bmax of Controls in Cell Lines Expressing Low to High Levels of HER2

The following experiment was performed to measure the ability of an exemplary biparatopic anti-HER2 antibody to bind to cells expressing varying levels of HER2 in comparison to controls. The cell lines used were SKOV3 (HER2 2+/3+), JIMT-1 (HER2 2+), MDA-MB-231 (HER2 0/1+), and MCF7 (HER2 1+). The biparatopic anti-HER2 antibodies tested include v5019, v7091 and v10000. The ability of the biparatopic anti-HER2 antibodies to bind to the HER2 expressing (HER2+) cells was determined as described below, with specific measurement of $B_{max}$ and apparent $K_D$ (equilibrium dissociation constant).

Binding of the test antibodies to the surface of HER2+ cells was determined by flow cytometry. Cells were washed with PBS and resuspended in DMEM at $1\times10^5$ cells/100 µl. 100 µl cell suspension was added into each microcentrifuge tube, followed by 10 µl/tube of the antibody variants. The tubes were incubated for 2 hr 4° C. on a rotator. The microcentrifuge tubes were centrifuged for 2 min 2000 RPM at room temperature and the cell pellets washed with 500 µl media. Each cell pellet was resuspended 100 µl of fluorochrome-labelled secondary antibody diluted in media to 2 µg/sample. The samples were then incubated for 1 hr at 4° C. on a rotator. After incubation, the cells were centrifuged for 2 min at 2000 rpm and washed in media. The cells were resuspended in 500 µl media, filtered in tube containing 5 µl propidium iodide (PI) and analyzed on a BD LSR II flow cytometer according to the manufacturer's instructions. The $K_D$ of exemplary biparatopic anti-HER2 heterodimer antibody and control antibodies were assessed by FACS with data analysis and curve fitting performed in GraphPad Prism.

The results are shown in FIGS. 6A-6G. These results demonstrate that exemplary biparatopic anti-HER2 antibodies (v5019, v7091 and v10000) can bind to HER2+ cells with approximately a 1.5-fold higher Bmax compared to an anti-HER2 FSA (v506). The results in FIG. 6A-6G also show that biparatopic anti-HER2 antibodies (v5019, v7091 and v10000) can bind to HER2+ cells with a similar Bmax compared to a combination of two anti-HER2 FSAs (v506+v4184).

Figure 6A:
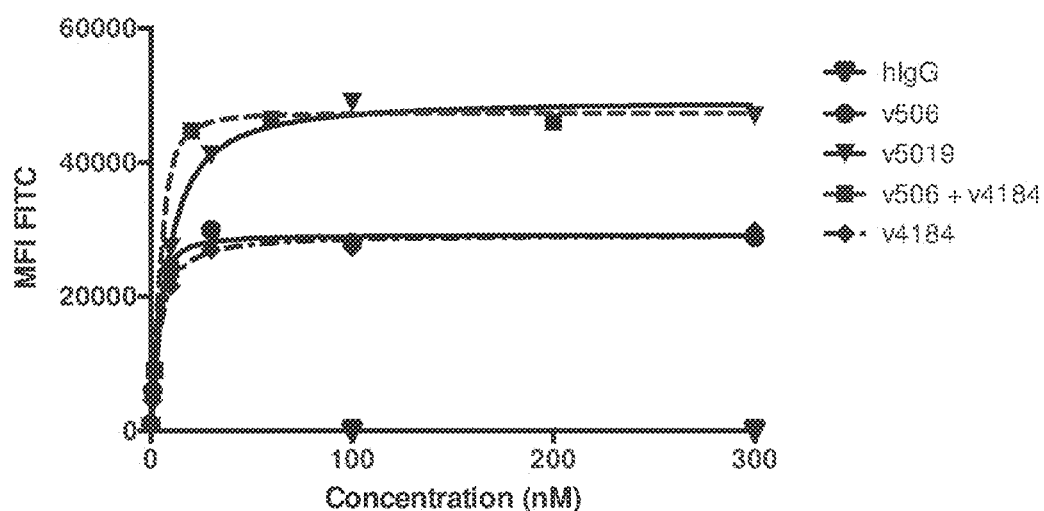
FIG. 6A compares the ability of an exemplary biparatopic anti-HER2 antibodies to bind to HER2+ whole cells displaying different HER2 receptor density compared to control antibodies, as measured by FACS.
Figure 6B:
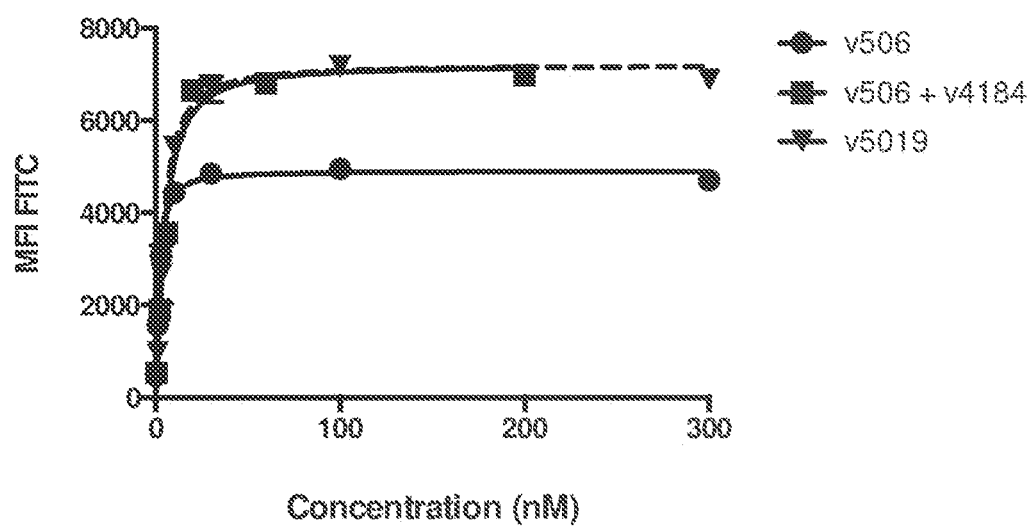
FIG. 6B compares the ability of an exemplary biparatopic anti-HER2 antibodies to bind to HER2+ whole cells displaying different HER2 receptor density compared to control antibodies, as measured by FACS.
Figure 6C:
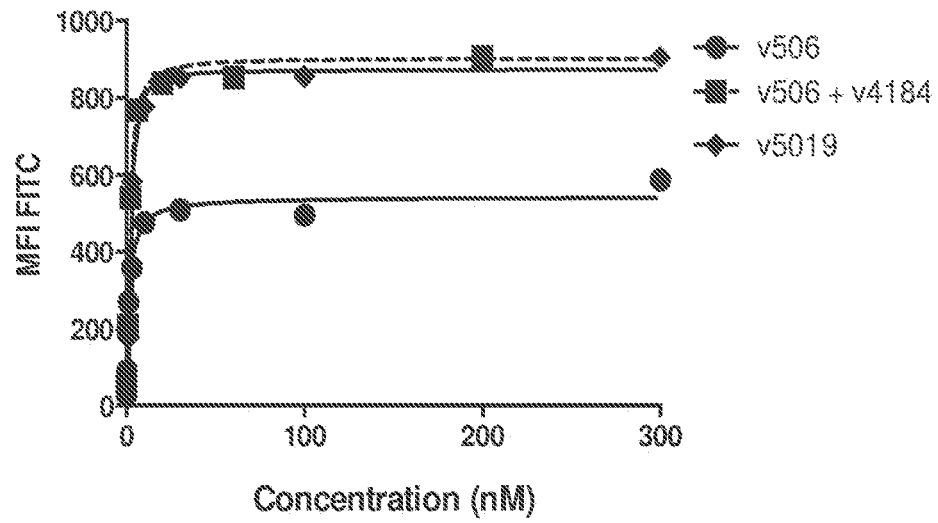
FIG. 6C compares the ability of an exemplary biparatopic anti-HER2 antibodies to bind to HER2+ whole cells displaying different HER2 receptor density compared to control antibodies, as measured by FACS.
Figure 6D:
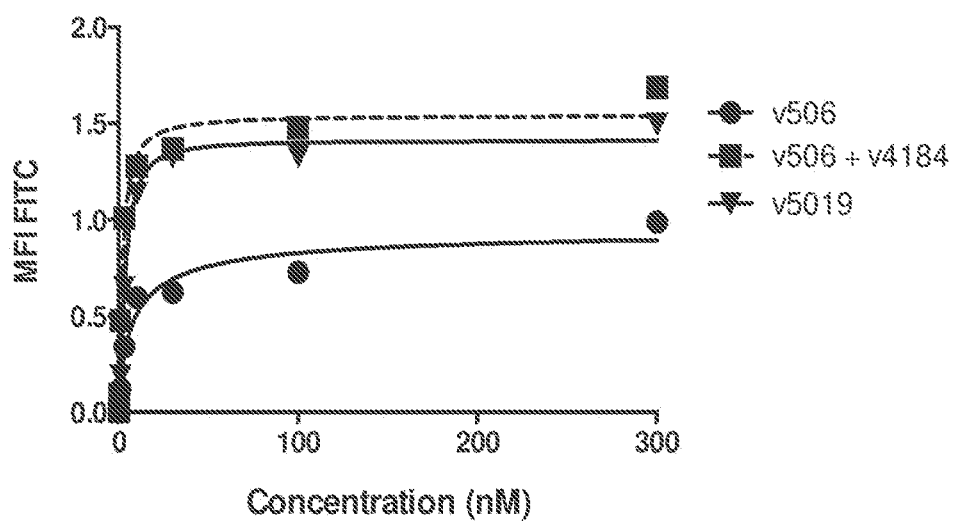
FIG. 6D compares the ability of an exemplary biparatopic anti-HER2 antibodies to bind to HER2+ whole cells displaying different HER2 receptor density compared to control antibodies, as measured by FACS.
Figure 6E:
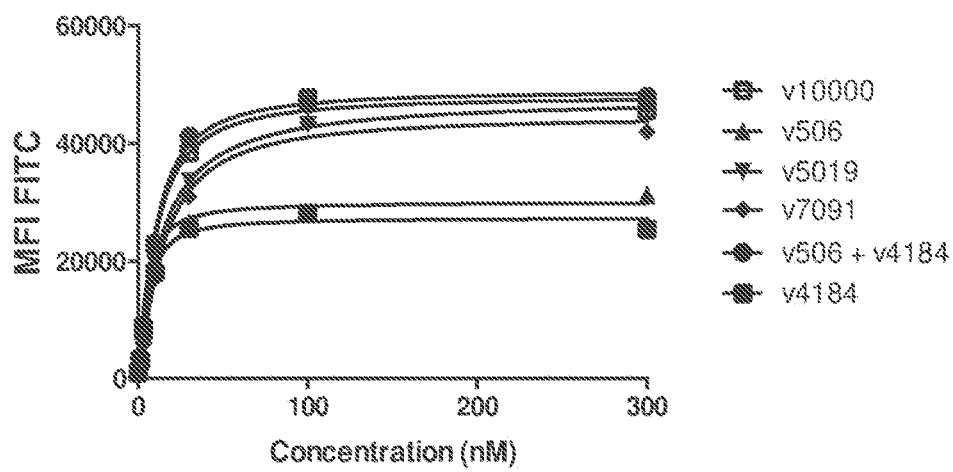
FIG. 6E compares the ability of an exemplary biparatopic anti-HER2 antibodies to bind to HER2+ whole cells displaying different HER2 receptor density compared to control antibodies, as measured by FACS.

The binding results for HER2+ SKOV3 cells (HER2 2/3+) are shown in FIGS. 6A, 6E and Table 4 and Table 5. The results in FIG. 6A and Table 4 show that exemplary biparatopic anti-HER2 antibody (v5019) displays approximately a 1.5-fold higher Bmax in binding to SKOV3 cells compared to two different anti-HER2 FSAs (v506 or v4184). The results also show that exemplary biparatopic anti-HER2 antibody (v5019) displays equivalent Bmax compared to the combination of two anti-HER2 FSAs (v506+v4184). The apparent $K_D$ of v5019 for binding to SKOV3 was approximately 2 to 4-fold higher compared to either anti-HER2 FSA alone (v506 or v4184), or the combination of two anti-HER2 FSAs (v506+v4184).

TABLE 4

| Binding to SKOV3 cells | | |
| --- | --- | --- |
| Antibody variant | $K_D$ (nM) | Bmax |
| v506 | 2.713 | 29190 |
| v4184 | 4.108 | 29204 |

TABLE 4-continued

| Binding to SKOV3 cells | | |
| --- | --- | --- |
| Antibody variant | $K_D$ (nM) | Bmax |
| v5019 | 8.084 | 47401 |
| v506 + v4184 | 4.414 | 49062 |

The results in FIG. 6E and Table 5 show that exemplary biparatopic anti-HER2 antibodies (v5019, 7091 and v10000) display approximately a 1.5 to 1.6-fold higher Bmax in binding to SKOV3 cells compared to two different anti-HER2 FSAs (v506 or v4184). The results also show that exemplary biparatopic anti-HER2 antibodies (v5019, 7091 and v10000) display equivalent Bmax compared to the combination of two anti-HER2 FSAs (v506+v4184). The apparent $K_D$ of v5019, v7091, v10000 and the combination of two anti-HER2 FSAs (v506+ v4184) for binding to SKOV3 was approximately 2 to 3-fold higher compared to either anti-HER2 FSA alone (v506 or v4184).

TABLE 5

| Binding to SKOV3 | | |
| --- | --- | --- |
| Antibody Variant | $K_D$ (nM) | Bmax |
| v506 | 4.8 | 30007 |
| v4184 | 5.6 | 27628 |
| v506 + v4184 | 10.0 | 49014 |
| v5019 | 13.6 | 47693 |
| v7091 | 14.5 | 44737 |
| v10000 | 10.3 | 48054 |

Binding curves in the JIMT-1 cell line (HER2 2+) are shown in FIG. 6B and Table 6. These results show that exemplary biparatopic anti-HER2 antibody (v5019) displays approximately a 1.5-fold higher Bmax in binding to JIMT-1 cells compared to an anti-HER2 FSAs (v506). The results also show that exemplary biparatopic anti-HER2 antibody (v5019) displays equivalent Bmax compared to the combination of two anti-HER2 FSAs (v506+v4184). The apparent $K_D$ of v5019 for binding to JIMT-1 was approximately 2-fold higher compared to the anti-HER2 FSA (v506), and was similar (approximately 1.2 fold greater) compared to the combination of two anti-HER2 FSAs (v506+v4184).

TABLE 6

| Binding to JIMT-1 cells | | |
| --- | --- | --- |
| Antibody variant | $K_D$ (nM) | Bmax |
| v506 | 1.875 | 4905 |
| v5019 | 4.317 | 7203 |
| v506 + v4184 | 5.057 | 7200 |

Figure 6F:
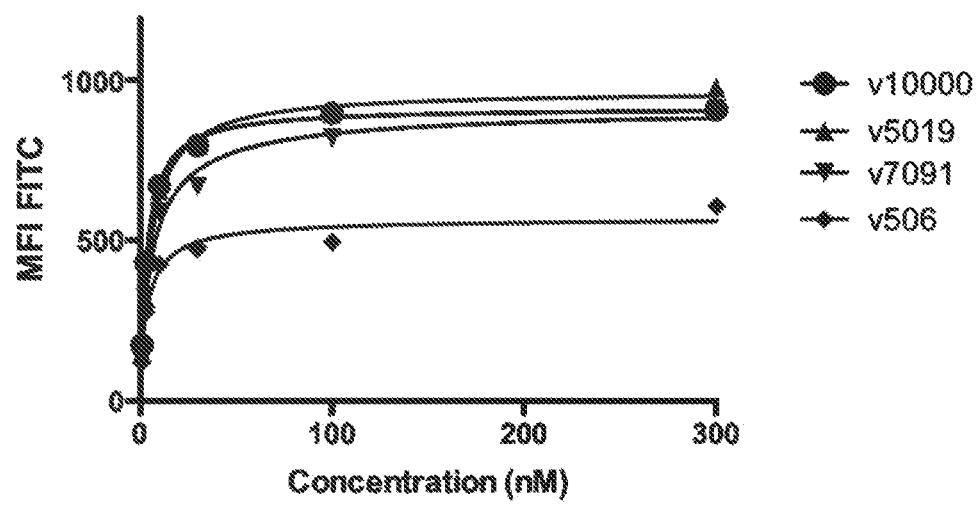

Binding curves in the MCF7 cell line (HER2 1+) are shown in FIG. 6C, 6F and Tables 7 and 8. These results show that exemplary biparatopic anti-HER2 antibodies (v5019, 7091 and v10000) display approximately a 1.5-fold higher Bmax in binding to MCF7 cells compared to an anti-HER2 FSAs (v506). The results in FIG. 6C also show that exemplary biparatopic anti-HER2 antibody (v5019) displays equivalent Bmax compared to the combination of two anti-HER2 FSAs (v506+v4184). The apparent $K_D$ of v5019 for binding to MCF7 was similar to the anti-HER2 FSA (v506) and the combination of two anti-HER2 FSAs (v506+ v4184).

TABLE 7

Binding to MCF7 cells

| Antibody variant | $K_D$ (nM) | Bmax |
|---|---|---|
| v506 | 1.301 | 542 |
| v5019 | 1.506 | 872 |
| v506 + v4184 | 2.095 | 903 |

The results in FIG. 6F and Table 8 show that exemplary biparatopic anti-HER2 antibodies (v5019, v7091 and v10000) display approximately 1.6 to 1.7-fold greater Bmax compared to the FSA monospecific v506. The apparent $K_D$ of v5019, v7091 and v10000 was similar to the anti-HER2 FSA (v506).

TABLE 8

Binding to MCF7 cells

| Antibody variant | $K_D$ (nM) | Bmax |
|---|---|---|
| v506 | 3.5 | 571 |
| v5019 | 5.6 | 968 |
| v7091 | 6.5 | 918 |
| v10000 | 3.7 | 915 |

Binding curves in the MDA-MB-231 cell line (HER2 0/1+) are shown in FIG. 6D and Table 9. These results show that exemplary biparatopic anti-HER2 antibody (v5019) displays approximately a 1.5-fold higher Bmax in binding to MDA-MB-231 cells compared to an anti-HER2 FSA (v506). The results also show that exemplary biparatopic anti-HER2 antibody (v5019) displays equivalent Bmax compared to the combination of two anti-HER2 FSAs (v506+v4184). The apparent $K_D$ of v5019 for binding to MDA-MB-231 was approximately 2.4-fold lower compared to the anti-HER2 FSA (v506) and was approximately 1.7-fold higher compared to the combination of two anti-HER2 FSAs (v506+v4184).

TABLE 9

Binding to MDA-MB-231 cells

| Antibody variant | $K_D$ (nM) | Bmax |
|---|---|---|
| v506 | 8.364 | 0.9521 |
| v5019 | 3.543 | 1.411 |
| v506 + v4184 | 2.040 | 1.542 |

Figure 6G:
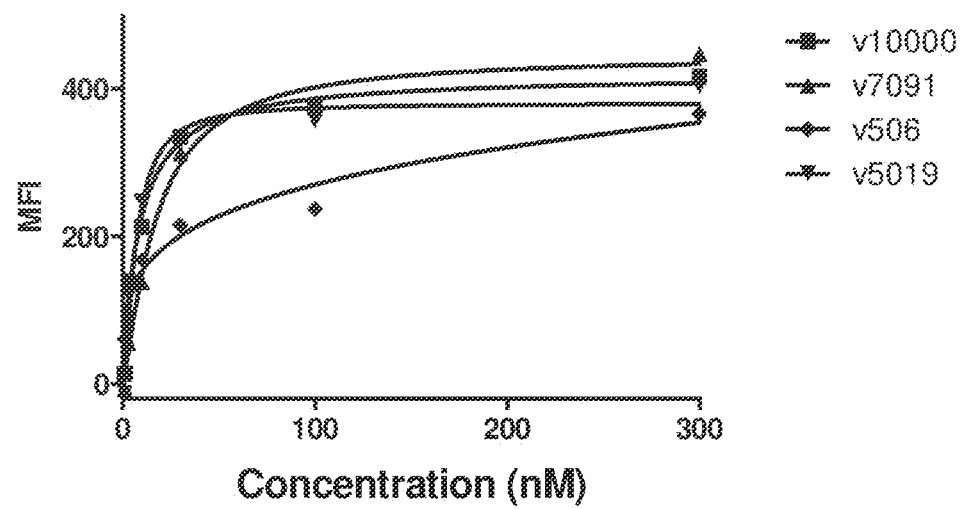
FIG. 6G compares the ability of an exemplary biparatopic anti-HER2 antibodies to bind to HER2+ whole cells displaying different HER2 receptor density compared to control antibodies, as measured by FACS.

Binding curves in the WI-38 lung fibroblast cell line are shown in FIG. 6G and Table 10. The WI-38 cell line is a normal lung epithelium that expresses basal levels (HER2 0+, 10,000 receptors/cell) of HER2 (Carter et al. 1992, PNAS, 89:4285-4289; Yarden 2000, HER2: Basic Research, Prognosis and Therapy). These results show that exemplary biparatopic anti-HER2 antibodies (v5019, v7091, v10000) displays equivalent cell surface decoration (Bmax) in binding to WI-38 cells compared to an anti-HER2 FSAs (v506); however, note that binding for v506 did not appear to reach saturation, and thus $K_D$ could not be determined. The apparent $K_D$ among the exemplary biparatopic anti-HER2 antibodies was equivalent.

TABLE 10

Binding to WI-38 cells

| Antibody Variant | $K_D$ (nM) | Bmax |
|---|---|---|
| v506 | Not determined | ~366 |
| v5019 | 7.0 | 380 |
| v7091 | 8.3 | 371 |
| v10000 | 8.4 | 418 |

These results show that an exemplary biparatopic anti-HER2 antibody can bind to HER2 1+, 2+ and 3+ tumor cells to levels that are approximately 1.5 to 1.6-fold greater than an anti-HER2 monospecific FSA, and that exemplary biparatopic anti-HER2 antibodies can bind to HER2 1+, 2+ and 3+ tumor cells to equivalent levels compared to the combination of two unique monospecific anti-HER2 FSAs with different epitope specificities. These results also show that the biparatopic anti-HER2 antibodies do not show increased binding (i.e. compared to monospecific anti-HER2 antibody, v506) to basal HER2 expressing cells that express approximately 10,000 HER2 receptors/cell or less, and that a threshold for increased cell surface binding to the biparatopic anti-HER2 antibodies occurs when the HER2 receptor level is approximately >10,000 receptors/cell. Based on this data it would be expected that the exemplary biparatopic anti-HER2 antibodies would have increased cell surface binding to HER2 3+, 2+ and 1+ tumor cells but would not have increased cell surface binding to non-tumor cells that express basal levels of the HER2 receptor at approximately 10,000 receptors or less.

Example 7: Ability of Biparatopic Anti-HER2 Antibody to Inhibit Growth of HER2+ Cells The ability of an exemplary biparatopic anti-HER2 antibody to inhibit growth of cells expressing HER2 at the 3+ and 2+ level was measured. The experiment was carried out in the HER2 3+ cell lines BT-474, SKBr3, SKOV3, and HER2 2+ JIMT-1. The biparatopic anti-HER2 antibodies v5019, v7091 and v10000 were tested. The ability of the biparatopic anti-HER2 antibodies to inhibit the growth of BT-474 cells (200 nM antibody); SKOV3, SKBr3 and JIMT-1 cells (300 nM antibody) was measured as described below.

Test antibodies were diluted in media and added to the cells at 10 μl/well in triplicate. The plates were incubated for 3 days 37° C. Cell viability was measured using either AlamarBlue™ (Biosource #da11100), or Celltiter-Glo® and absorance read as per the manufacturer's instructions. Data was normalized to untreated control and analysis was performed in GraphPad prism.

Figure 10A:
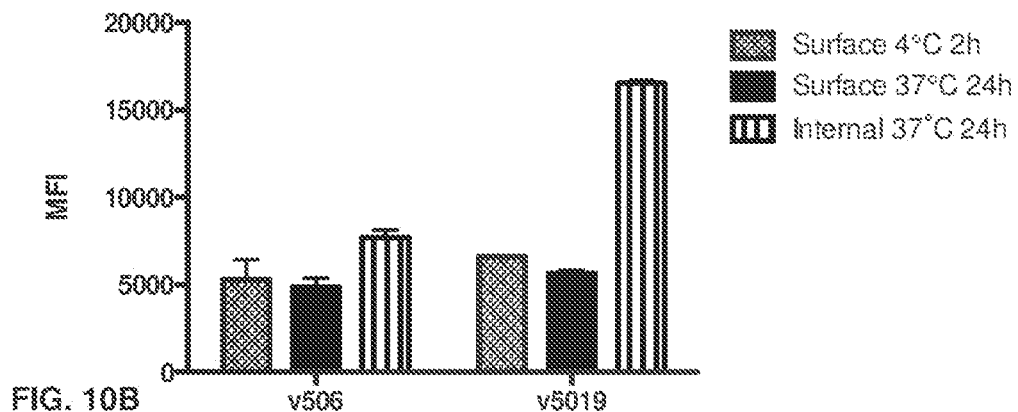
FIG. 10A depicts surface binding and internalization of exemplary anti-HER2 biparatopic antibodies.

The growth inhibition results are shown in FIG. 7A-E. A summary of the results is provided in Tables 11A and 11B. The results FIGS. 7A-B and Table 11A indicate that exemplary anti-HER2 biparatopic (v5019) is capable of growth inhibition of HER2+ SKOV3 and BT-474 cell lines. FIG. 10A shows that anti-HER2 biparatopic antibody mediated the greatest growth inhibition of SKOV3 when compared to anti-HER2 FSA (v506) and when compared to the combination of two anti-HER2 FSA antibodies (v506+v4184).

TABLE 11A

Growth Inhibition of HER2 3+ Cancer Cells

| Treatment | % Survival | |
|---|---|---|
| | SKOV3 HER2 2+/3+ | BT-474 HER2 3+ |
| v506 | 88 | 37 |
| v506 + v4184 | 96 | 32 |
| v5019 | 77 | 43 |

Figure 7A:
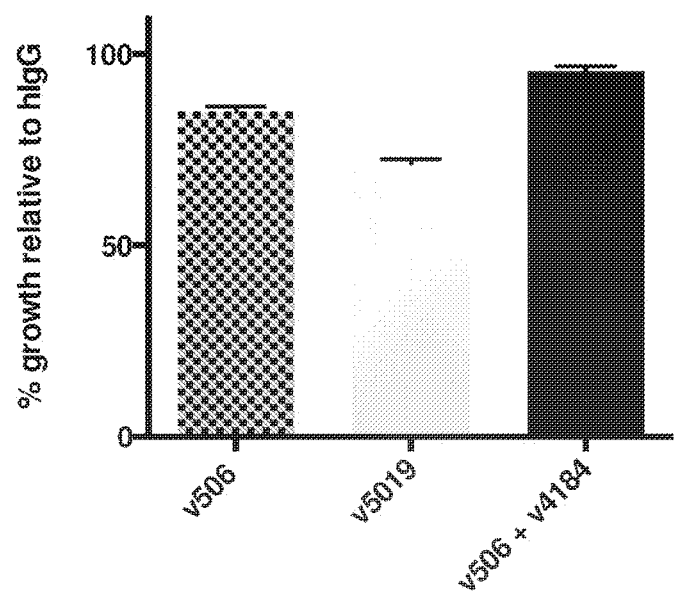
FIG. 7A depicts the ability of exemplary anti-HER2 biparatopic antibodies to inhibit the growth of HER2+ cells.
Figure 7B:
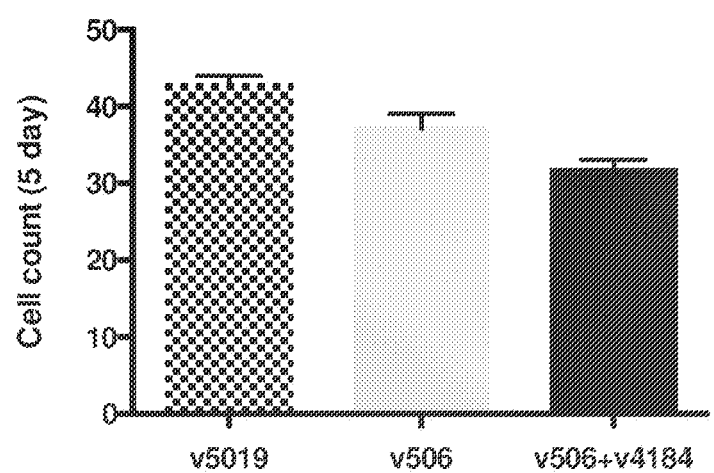
FIG. 7B depicts the ability of exemplary anti-HER2 biparatopic antibodies to inhibit the growth of HER2+ cells.
Figure 7C:
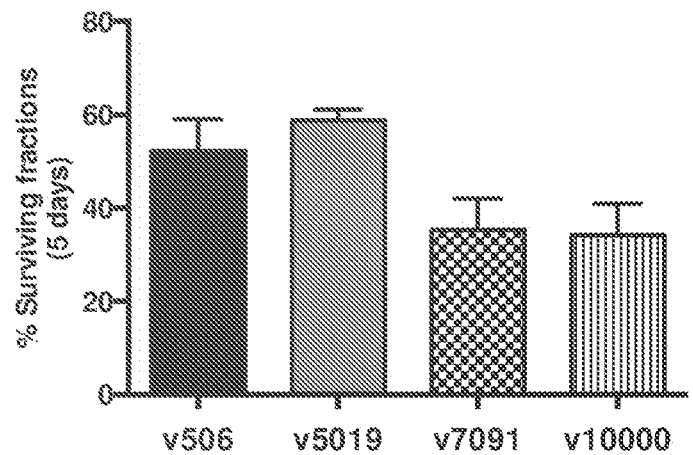
FIG. 7C depicts the ability of exemplary anti-HER2 biparatopic antibodies to inhibit the growth of HER2+ cells.
Figure 7D:
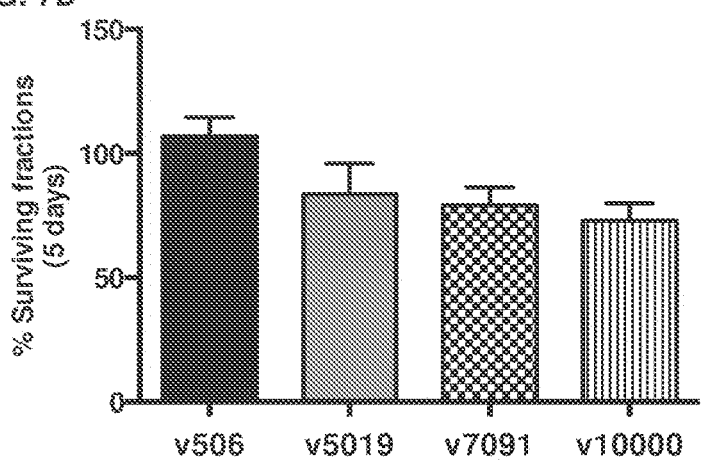
FIG. 7D depicts the ability of exemplary anti-HER2 biparatopic antibodies to inhibit the growth of HER2+ cells.
Figure 7E:
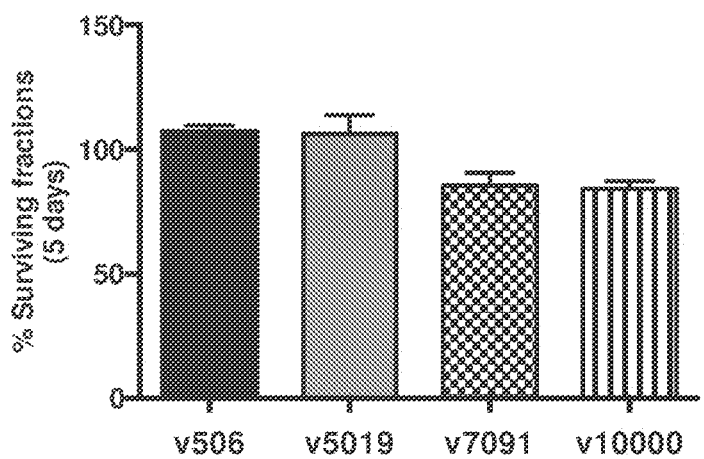
FIG. 7E depicts the ability of exemplary anti-HER2 biparatopic antibodies to inhibit the growth of HER2+ cells.

The results in FIGS. 7C-E and Table 11B indicate that exemplary anti-HER2 biparatopic antibodies (v5019, v7091 and v10000) can inhibit growth of HER2 3+ SKBR3, HER2 2+/3+ SKOV3, and HER2 2+ JIMT-1 tumor cell lines. FIG. 7C shows that anti-HER2 biparatopic antibodies v7091 and v10000 mediated the greatest growth inhibition of HER2 3+ SKBr3 breast tumor cells. FIG. 7D shows that anti-HER2 biparatopic antibodies (v7091 and v10000) mediated the greatest growth inhibition of HER2 3+ SKOV3 ovarian tumor cells. FIG. 7E shows that anti-HER2 biparatopic antibodies (v7091 and v10000) mediated the greatest growth inhibition of HER2 2+ Herceptin-resistant JIMT-1 tumor cells. In all cell lines tested, exemplary anti-HER2 biparatopic antibodies (v7091 and v10000) mediated greater growth inhibition compared to the anti-HER2 FSA monospecific antibody (v506).

TABLE 11B

Growth inhibition of HER2 3+ Cancer Cells

| Treatment | % Survival | | |
|---|---|---|---|
| | SKBr3 HER2 3+ | SKOV3 HER2 2+/3+ | JIMT-1 HER2 2+ |
| v506 | 52 | 107 | 107 |
| v5019 | 59 | 83 | 106 |
| v7091 | 35 | 79 | 85 |
| v10000 | 34 | 73 | 84 |

These results show that exemplary saturating concentrations of biparatopic anti-HER2 antibodies can growth inhibit HER2 3+ and 2+ breast and ovarian and HER2 2+ Trastuzumab resistant tumor cells approximately 20% greater than a FSA anti-HER2 monospecific antibody.

Example 8: Preferential Binding of Paratopes of Biparatopic Anti-HER2 Antibodies to Dimeric HER2 Compared to HER2 ECD This experiment was performed to determine the ability of the individual paratopes of exemplary biparatopic anti-HER2 antibodies to bind to dimeric HER2 and the HER2 ECD as a surrogate for differential binding between membrane bound HER2 (HER2-Fc) and the shed HER2 ECD. The experiment was carried out as follows.

Surface plasmon resonance (SPR) analysis: affinity of monovalent anti-HER2 antibodies (v1040 or v4182) for binding to the HER2 extracellular domain (sHER-2, Ebioscience BMS362, encoding amino acid 23-652 of the full length protein) and HER2-Fc (dimeric HER2-Fc fusion encoding the amino acid 1-652 of the extracellular domain; Sino Biological Inc., 10004-H02H) was measured by SPR using the T200 system from Biacore (GE Healthcare). Binding to the HER2 ECD was determined by the following method. HER2 ECD in 10 mm Hepes pH 6.8, was immobilized on CMS chip through amine coupling to a level of 44 RU (response units). Monovalent anti-HER2 antibodies were passed over the surface of the HER2 immobilized chip at concentrations ranging from 0.76-60 nM. Binding to the HER2-Fc was determined by the following method. HER2-Fc in 10 mm Hepes pH 6.8, was immobilized on CMS chip through amine coupling to a level of 43 RU. Monovalent anti-HER2 antibodies were passed over the surface of the HER2 immobilized chip at concentrations ranging from 0.76-60 nM. Antibody concentrations were analyzed for binding in triplicate. Equilibrium dissociation binding constants ($K_D$) and kinetics (ka and kd) were determined using the single cycle kinetics method. Sensograms were fit globally to a 1:1 Langmuir binding model. All experiments were conducted at room temperature.

Figure 8A:
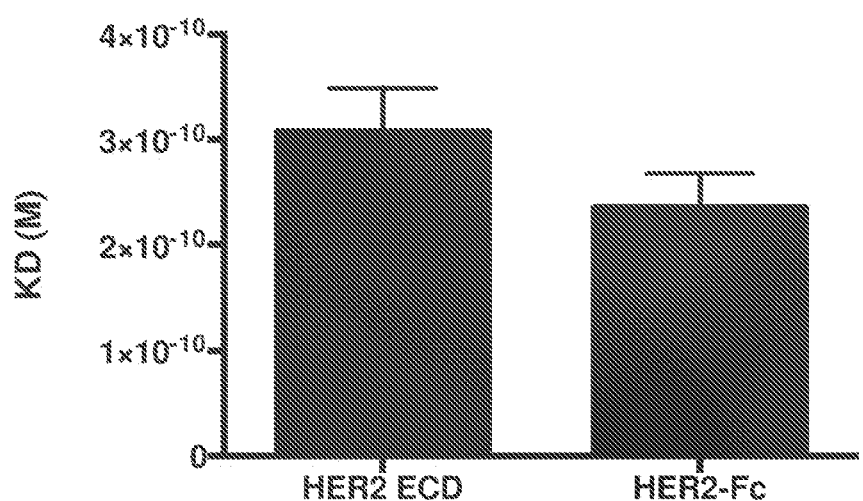
FIG. 8A depicts the SPR binding data relating to the paratopes of an exemplary anti-HER2 biparatopic antibodies.
Figure 8B:
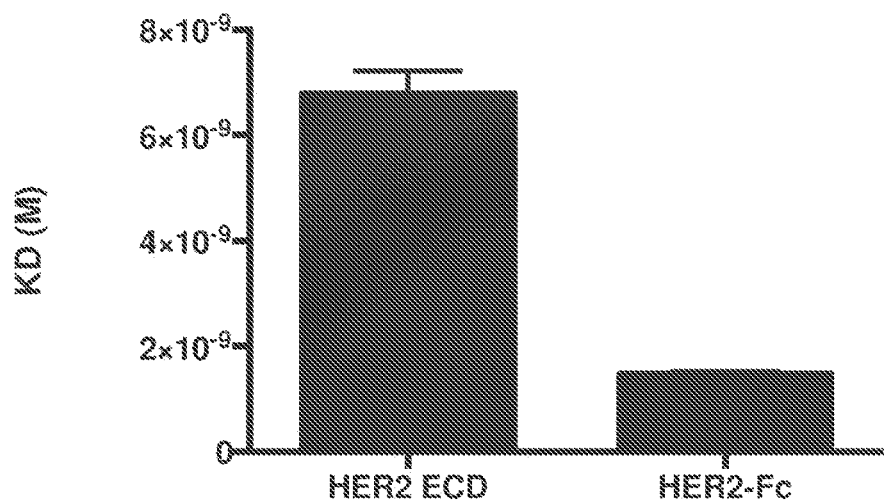
FIG. 8B depicts the SPR binding data relating to the paratopes of an exemplary anti-HER2 biparatopic antibodies.

Results are shown in FIG. 8A, FIG. 8B, Table 11C and Table 11D. The results in FIG. 8A and Table 11C show SPR binding data of the monovalent anti-HER2 antibody (v1040; representing the antigen binding domain on CH-B of exemplary anti-HER2 biparatopic antibody). FIG. 8A illustrates the $K_D$ values (nM) of v1040 binding to immobilized HER2 ECD or HER2-Fc and shows that monovalent anti-HER2 antibody has a lower $K_D$ for binding to the HER2-Fc compared to the HER2 ECD. Table 11C shows the ka (1/M s) and kd (1/s) values of the monovalent anti-HER2 antibody (OA) compared to the full-sized anti-HER2 antibody (FSA) in binding to the HER2 ECD and HER2-FC ('HER2 mem'). This data shows comparable on (ka) and off (kd) rates of the OA and FSA for binding to the HER2 ECD and HER2-Fc.

TABLE 11C

Ka (1/M s) and kd (1/s) values of the monovalent anti-HER2 antibody (OA) compared to the full-sized anti-HER2 antibody (FSA) in binding to the HER2 ECD and HER2-FC ('HER2 mem'

| | ka (1/Ms) | kd (1/s) |
|---|---|---|
| OA vs. HER2 ECD | 2.00E+05 | 6.15E−05 |
| FSA vs. HER2 ECD | 4.14E+05 | 2.01E−05 |
| OA vs. HER2 mem | 1.88E+05 | 4.38E−05 |
| FSA vs. HER2 mem | 3.41E+05 | 4.94E−06* |

Results in FIG. 8B and Table 11D show the SPR binding data of the monovalent anti-HER2 antibody (v4182; representing the antigen binding domain on CH-A of exemplary anti-HER2 biparatopic antibody). FIG. 8B illustrates the $K_D$ values (nM) of v4182 binding to immobilized HER2 ECD or HER2-Fc and shows that monovalent anti-HER2 antibody has a lower $K_D$ for binding to the HER2-Fc compared to the HER2 ECD. Table 11D shows the ka (1/M s) and kd (1/s) values of the monovalent anti-HER2 antibody (OA) compared to the full-sized anti-HER2 antibody (FSA) in binding to the HER2 ECD and HER2-FC ('HER2 mem'). This data shows comparable on rates (ka) and off rates (kd) of the OA and FSA for binding to the HER2 ECD and HER2-Fc.

TABLE 11D

| | ka (1/Ms) | kd (1/s) |
|---|---|---|
| OA vs. HER2 ECD | 9.08E+04 | 6.17E−04 |
| FSA vs. HER2 ECD | 9.55E+04 | 3.93E−04 |
| OA vs. HER2 mem | 1.39E+05 | 2.04E−04 |
| FSA vs. HER2 mem | 1.77E+05 | 6.84E−05 |

These data show that each of the paratopes of the exemplary anti-HER2 biparatopic antibody have lower $K_D$ values for binding to the dimeric HER2 antigen, a representative of membrane bound HER2, as compared to the HER2 ECD. Based on this data it would be expected that the exemplary anti-HER2 antibody would have a higher binding affinity for the membrane bound HER2 antigen as compared to the shed HER2 ECD that is present in the serum of diseased patients and can act as a sink for the therapeutic antibody (Brodowicz T, et al. Soluble HER-2/neu neutralizes biologic effects of anti-HER-2/neu antibody on breast cancer cells in vitro. Int J Cancer. 1997; 73:875-879). For example, baseline HER2 ECD levels ≤15 ng/mL; whereas patients with progressive disease have HER2 ECD≥38 ng/mL.

Example 9: Whole Cell Loading and Internalization of Biparatopic Anti-HER2 Antibody in HER2+ Cells This experiment was performed to assess the ability of an exemplary biparatopic anti-HER2 antibody to be internalized in HER2 2+ cells. The direct internalization method was followed according to the protocol detailed in Schmidt, M. et al., *Kinetics of anti-carcinoembryonic antigen antibody internalization: effects of affinity, bivalency, and stability*. Cancer Immunol Immunother (2008) 57:1879-1890. Specifically, the antibodies were directly labeled using the AlexaFluor® 488 Protein Labeling Kit (Invitrogen, cat. no. A10235), according to the manufacturer's instructions.

For the internalization assay, 12 well plates were seeded with 1×10$^5$ cells/well and incubated overnight at 37° C.+5% CO2. The following day, the labeled antibodies were added at 200 nM in DMEM+10% FBS and incubated 24 hours at 37° C.+5% CO2. Under dark conditions, media was aspirated and wells were washed 2×500 µL PBS. To harvest cells, cell dissociation buffer was added (250 µL) at 37° C. Cells were pelleted and resuspended in 100 µL DMEM+10% PBS without or with anti-Alexa Fluor 488, rabbit IgG fraction (Molecular Probes, A11094) at 50 µg/mL, and incubated on ice for 30 min Prior to analysis 300 µL DMEM+10% FBS the samples filtered 4 µl propidium iodide was added. Samples were analyzed using the LSRII flow cytometer.

Figure 9A:
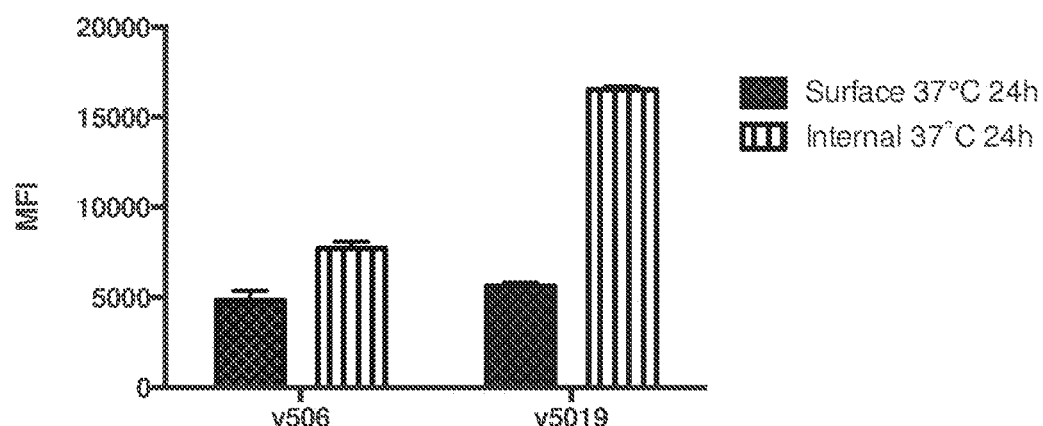
FIG. 9A depicts the ability of exemplary anti-HER2 biparatopic antibody to internalize in HER2+ cells.
Figure 9B:
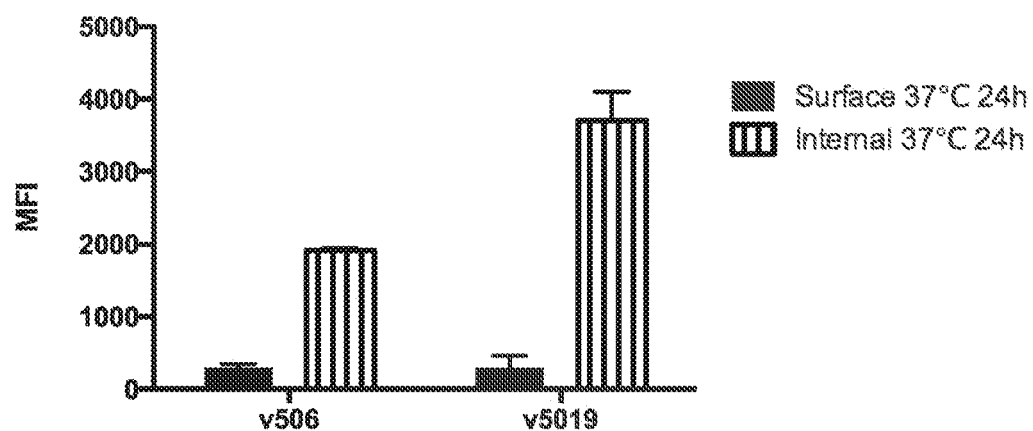
FIG. 9B depicts the ability of exemplary anti-HER2 biparatopic antibody to internalize in HER2+ cells.

The ability of exemplary anti-HER2 biparatopic antibody to internalize in HER2+ cells is shown in FIG. 9A and FIG. 9B. FIG. 9A shows the results of detectable surface and internal antibody in BT-474 cells following 24 h incubation with the exemplary anti-HER2 biparatopic antibody and anti-HER2 FSA control. These results show that incubation with exemplary anti-HER2 biparatopic antibody (v5019) results in approximately 2-fold more internalized antibody in BT-474 cells compared to the anti-HER2 FSA control. FIG. 9B shows the results of detectable surface and internal antibody in JIMT-1 cells following 24 h incubation with the exemplary anti-HER2 biparatopic antibody and anti-HER2 FSA control. These results show that incubation with exemplary anti-HER2 biparatopic antibody (v5019) results in approximately 2-fold more internalized antibody in JIMT-1 cells compared to the anti-HER2 FSA control. The amount of surface staining post 24 h was comparable among the biparatopic anti-HER2 and anti-HER2 FSA in both BT-474 and JIMT-1 cells.

The results in FIG. 10A-F show a comparison of detectable antibody bound to the surface of whole cells after 2 h at 4° C., compared to antibody bound to the surface following incubation for 24 h at 37° C.; in addition to the amount of internalized antibody following 24 h at 37° C. FIG. 10A shows the results in BT-474 cells following incubation with the exemplary anti-HER2 biparatopic antibody and anti-HER2 FSA control. These results show that incubation of exemplary anti-HER2 biparatopic antibody with BT-474 cells for 24 h results in approximately a 15% reduction of antibody detected on the surface of whole cells. FIG. 10A also shows that incubation with exemplary anti-HER2 biparatopic antibody (v5019) results in approximately 2-fold more internalized antibody in BT-474 cells compared to the anti-HER2 FSA control.

Figure 10B:
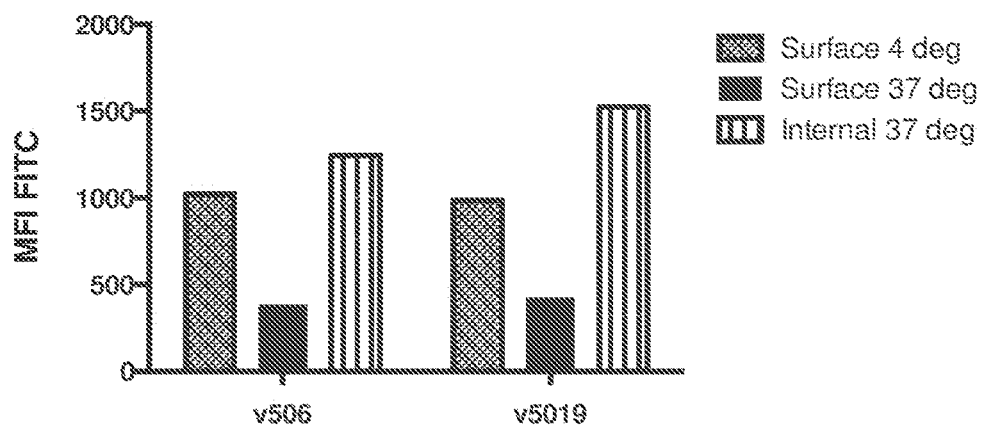
FIG. 10B depicts surface binding and internalization of exemplary anti-HER2 biparatopic antibodies.

FIG. 10B shows the results in JIMT-1 cells following incubation with the exemplary anti-HER2 biparatopic antibody and anti-HER2 FSA control. FIG. 10B is a repeat of the experiment shown in FIG. 9B with the addition of surface staining following 2 h at 4° C. These results show that incubation of exemplary anti-HER2 biparatopic antibody with JIMT-1 cells for 24 h results in approximately a 57% reduction of antibody detected on the surface of whole cells. FIG. 10B also shows that incubation with exemplary anti-HER2 biparatopic antibody (v5019) results more internalized antibody in BT-474 cells following 24 incubation at 37° C., compared to the anti-HER2 FSA control.

Figure 10C:
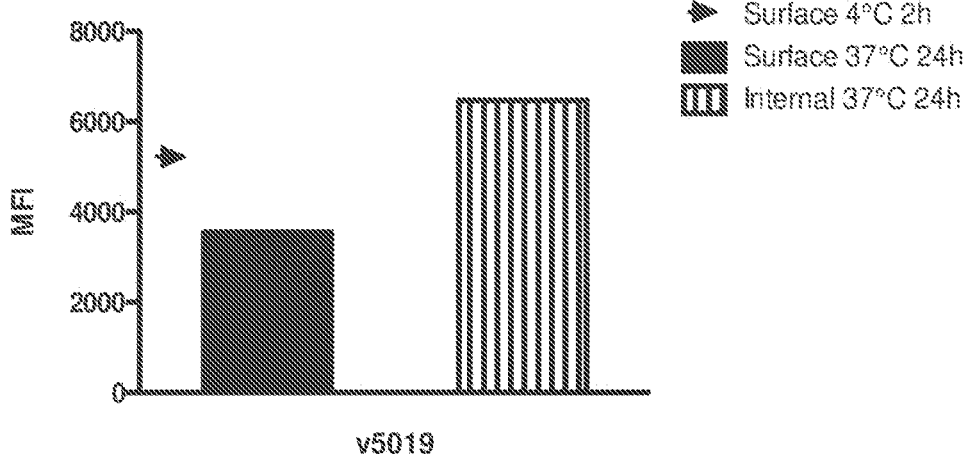
FIG. 10C depicts surface binding and internalization of exemplary anti-HER2 biparatopic antibodies.

FIG. 10C shows the results in SKOV3 cells following incubation with the exemplary anti-HER2 biparatopic antibody. These results show that incubation of exemplary anti-HER2 biparatopic antibody with SKOV3 cells for 24 h results in approximately a 32% reduction of antibody detected on the surface of whole cells.

Figure 10D:
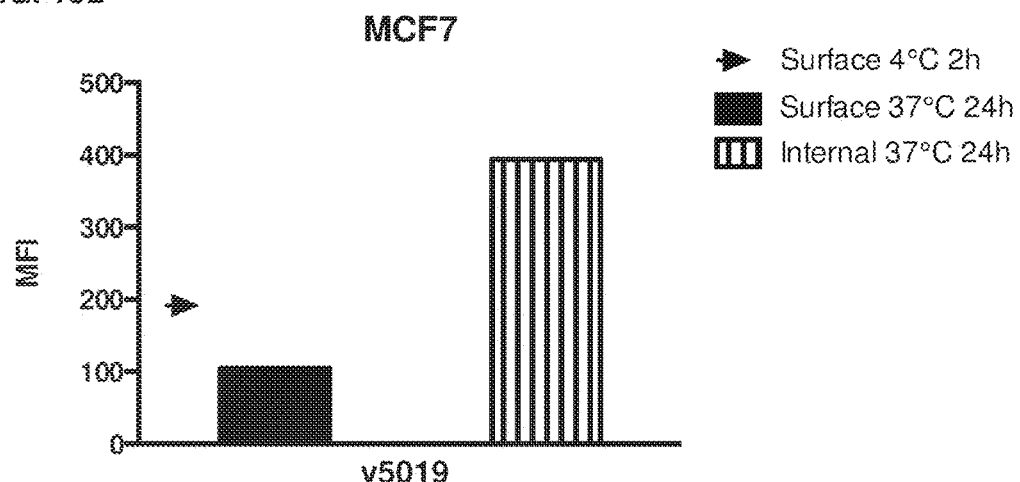
FIG. 10D depicts surface binding and internalization of exemplary anti-HER2 biparatopic antibodies.

FIG. 10D shows the results in MCF7 cells following incubation with the exemplary anti-HER2 biparatopic antibody. These results show that incubation of exemplary anti-HER2 biparatopic antibody with MCF7 cells for 24 h results in approximately a 45% reduction of antibody detected on the surface of whole cells.

Figure 10E:
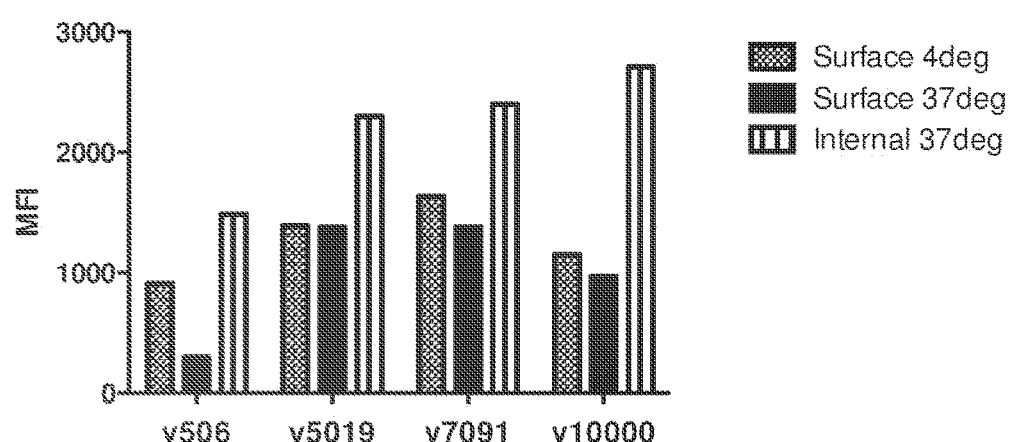
FIG. 10E depicts surface binding and internalization of exemplary anti-HER2 biparatopic antibodies.

FIG. 10E shows the results in SKOV3 cells following incubation with the exemplary anti-HER2 biparatopic antibodies, v5019, v7091 and v10000. These results show that incubation of exemplary anti-HER2 biparatopic antibodies results in 1.5 to 1.8-fold more internalized antibody with SKOV3 cells compared to the anti-HER2 FSA control. Incubation with the anti-HER2 FSA control for 24 h resulted in the greatest reduction (~77%) of antibody detected on the surface of whole cells.

Figure 10F:
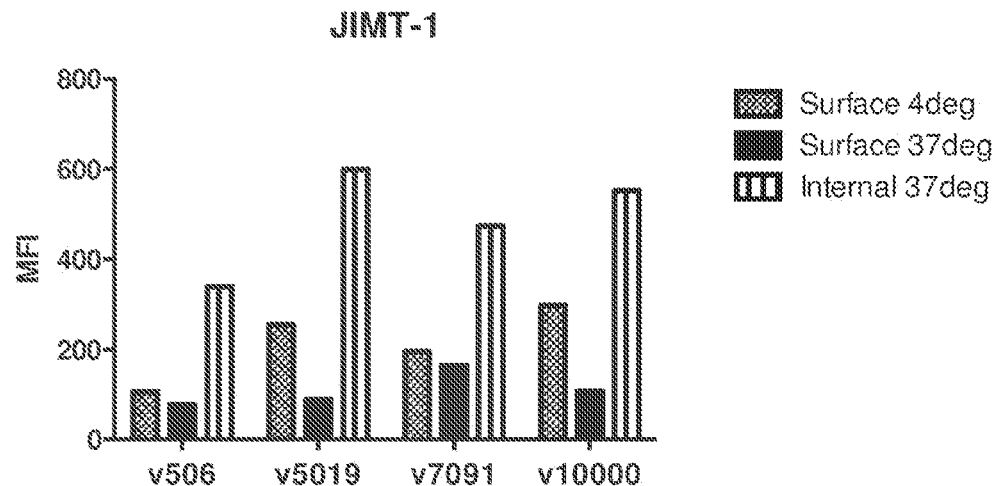
FIG. 10F depicts surface binding and internalization of exemplary anti-HER2 biparatopic antibodies.

FIG. 10F shows the results in JIMT-1 cells following incubation with the exemplary anti-HER2 biparatopic antibodies, v5019, v7091 and v10000. These results show that incubation of exemplary anti-HER2 biparatopic antibodies results in 1.4 to 1.8-fold more internalized antibody with JIMT-1 cells compared to the anti-HER2 FSA control. Incubation with the anti-HER2 biparatopic antibodies (v5019 and v10000) for 24 h resulted in the greatest reduction (~64%) of antibody detected on the surface of whole cells.

These results show that exemplary anti-HER2 biparatopic antibodies have superior internalization properties in HER2+ cells compared to a monospecific anti-HER2 FSA. The reduction of surface antibody detected following 24 h incubation at 37° C. shows that an exemplary anti-HER2 biparatopic antibody is capable of reducing the amount of cell surface HER2 receptor following incubation in HER2+ cells and that surface HER2 reduction post incubation is greatest in HER2 2+ tumor cells.

Example 10: Cellular Staining and Location of an Anti-HER2 Biparatopic Antibody Following Incubation with HER2+ Cells at 1, 3 and 16 Hours This experiment was performed to analyze internalization of the exemplary anti-HER2 biparatopic antibody in HER2+ JIMT-1 cells at different time points and as an orthogonal method to that presented in Example 9 to analyze whole cell loading and internalization.

JIMT-1 cells were incubated with the antibody (v506, v4184, v5019, or a combination of v506 and v4184) at 200 nM in serum-free DMEM, 37° C.+5% $CO_2$ for 1 h, 3 h and 16 h. Cells were gently washed two times with warmed sterile PBS (500 ml/well). Cells were fixed with 250 ml of 10% formalin/PBS solution for 10 min at RT. The fixed cells were washed three times with PBS (500 µl/well), permeabilized with 250 µl/well of PBS containing 0.2% Triton X-100 for 5 min, and washed three times with 500 µl/well PBS. Cells were blocked with 500 µl/well of PBS+5% goat serum for 1 h at RT. Blocking buffer was removed, and 300 µl/well secondary antibody (Alexa Fluor 488-conjugated AffiniPure Fab Fragment Goat anti-Human IgG (H+L); Jackson ImmunoResearch Laboritories, Inc.; 109-547-003) was incubated for 1 h at RT. Cells were washed three times with 500 µl/well of PBS and the coverslips containing fixed cells were then mounted on a slide using Prolong gold anti-fade with DAPI (Life Technologies; #P36931). 60λ single images were acquired using Olympus FV1000 Confocal microscope.

The results indicated that the exemplary anti-HER2 biparatopic antibody (v5019) was internalized into JIMT-1 cells at 3 h and was primarily located close to the nuclei. Comparing images at the 3 h incubation showed a greater amount of internal staining associated with the anti-HER2 biparatopic antibody compared to the combination of two anti-HER2 FSAs (v506+v4184) and compared to the individual anti-HER2 FSA (v506 or v4184). Differences in the cellular location of antibody staining were seen when the anti-HER2 biparatopic antibody (v5019) results were compared with the anti-HER2 FSA (v4184); where the anti-HER2 FSA (v4184) showed pronounced plasma membrane staining at the 1, 3 and 16 h time points. The amount of detectable antibody was reduced at the 16 h for the anti-HER2 FSA (v506), the combination of two anti-HER2 FSAs (v506+v4184) and anti-HER2 biparatopic antibody treatments (data not shown).

These results show that the exemplary anti-HER2 biparatopic antibody v5019 was internalized in HER2+ cells and the internalized antibody was detectable after 3 h incubation. These results are consistent with the results presented in Example 9 that show exemplary anti-HER2 biparatopic antibody can internalize to greater amounts in HER2+ cells compared to an anti-HER2 FSA.

Example 11: ADCC of HER2+ Cells Mediated by Biparatopic Anti-HER2 Antibody Compared to Controls This experiment was performed in order to measure the ability of an exemplary biparatopic anti-HER2 antibody to mediate ADCC in SKOV3 cells (ovarian cancer, HER2 2+/3+).

Target cells were pre-incubated with test antibodies (10-fold descending concentrations from 45 µg/ml) for 30 min followed by adding effector cells with effector/target cell ratio of 5:1 and the incubation continued for 6 hours at 37° C.+5% $CO_2$. Samples were tested with 8 concentrations, 10 fold descending from 45 µg/ml. LDH release was measured using LDH assay kit.

Dose-response studies were performed with various concentrations of the samples with a effector/target (E/T) ratios of 5:1, 3:1 and 1:1. Half maximal effective concentration ($EC_{50}$) values were analyzed with the sigmoidal dose-response non-linear regression fit using GraphPad prism.

Cells were maintained in McCoy's 5a complete medium at 37° C./5% $CO_2$ and regularly sub-cultured with suitable medium supplemented with 10% FBS according to protocol from ATCC. Cells with passage number fewer than p10 were used in the assays. The samples were diluted to concentrations between 0.3-300 nM with phenol red free DMEM medium supplemented with 1% FBS and 1% pen/strep prior to use in the assay.

Figure 11A:
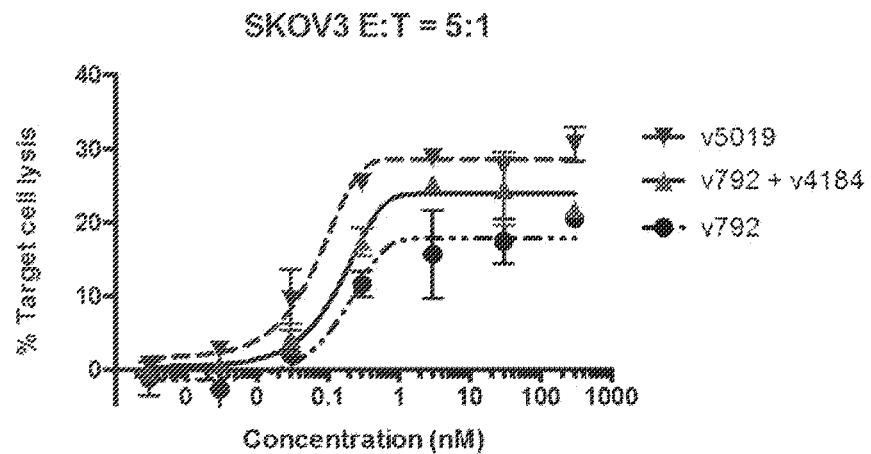
FIG. 11A depicts the ability of an exemplary anti-HER2 biparatopic antibody to mediate ADCC in SKOV3 cells.

The ADCC results in HER2+ SKOV3 cells at an effector to target cell ratio of 5:1 are shown in FIG. 11A and Table 12. These results show that the exemplary biparatopic anti-HER2 antibody (v5019) mediated the greatest percentage of maximum target cell lysis by ADCC when compared to the anti-HER2 FSA (v792) and combination of two different anti-HER2 FSAs (v792+v4184). The difference in maximum cell lysis mediated by the exemplary biparatopic anti-HER2 antibody was approximately 1.6-fold greater compared to the anti-HER2 FSA, and approximately 1.2-fold greater compared to a combination of two different anti-HER2 FSAs (v792+v4184).

TABLE 12

| Antibody variant | $EC_{50}$ (nM) | % Max Cell Lysis |
|---|---|---|
| v792 | ~0.032 | 17.82 |
| v5019 | ~0.164 | 28.57 |
| v792 + v4184 | ~0.042 | 23.85 |

Figure 11B:
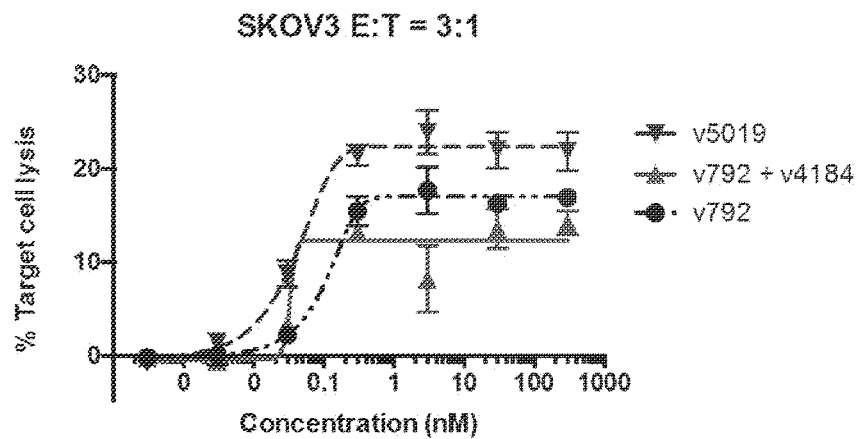
FIG. 11B depicts the ability of an exemplary anti-HER2 biparatopic antibody to mediate ADCC in SKOV3 cells.

The ADCC results in HER2+ SKOV3 cells at an effector to target cell ratio of 3:1 are shown in FIG. 11B and Table 13. These results show that the exemplary biparatopic anti-HER2 antibody (v5019) mediated the greatest percentage of maximum target cell lysis by ADCC when compared to the anti-HER2 FSA (v792) and combination of two different anti-HER2 FSAs (v792+v4184). The difference in maximum cell lysis mediated by the exemplary biparatopic anti-HER2 antibody was approximately 1.3-fold greater compared to the anti-HER2 FSA, and approximately 1.8-fold greater compared to a combination of two different anti-HER2 FSAs (v792+v4184).

TABLE 13

| Antibody variant | $EC_{50}$ (nM) | % Max Cell Lysis |
|---|---|---|
| v792 | 1.064 | 16.9 |
| v5019 | ~0.4608 | 22.3 |
| v792 + v4184 | ~1.078 | 12.3 |

Figure 11C:
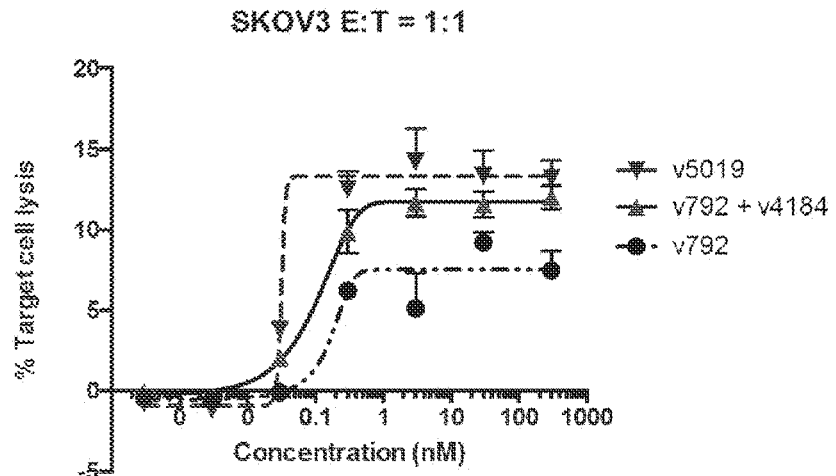
FIG. 11C depicts the ability of an exemplary anti-HER2 biparatopic antibody to mediate ADCC in SKOV3 cells.

The ADCC results in HER2+ SKOV3 cells at an effector to target cell ratio of 1:1 are shown in FIG. 11C and Table 14. These results show that the exemplary biparatopic anti-HER2 antibody (v5019) mediated the greatest percentage of maximum target cell lysis by ADCC when to compared to the anti-HER2 FSA (v792) and combination of two different anti-HER2 FSAs (v792+v4184). The difference in maximum cell lysis mediated by the exemplary biparatopic anti-HER2 antibody was approximately 1.8-fold greater compared to the anti-HER2 FSA, and approximately 1.13-fold greater compared to a combination of two different anti-HER2 FSAs (v792+v4184).

TABLE 14

| Antibody variant | $EC_{50}$ (nM) | % Max Cell Lysis |
|---|---|---|
| v792 | 1.429 | 7.529 |
| v5019 | ~1.075 | 13.29 |
| v792 + v4184 | ~0.1121 | 11.73 |

The results in FIG. 11 and Tables 12-14 show that the exemplary biparatopic HER2 antibody mediates the greatest ADCC of SKOV3 cells at different E:T ratios when compared to an anti-HER2 FSA and combination of two anti-HER2 FSAs. The observation of increased ADCC mediated by the anti-HER2 biparatopic antibody would be expected in HER2+ diseased patients who express variable and/or reduced circulating effector cells following chemotherapy (Suzuki E. et al. Clin Cancer Res 2007; 13:1875-1882). The observations in FIG. 11 are consistent with the whole cell binding Bmax data presented in Example 6, that shows an approximate 1.5-fold increase in cell binding to the exemplary anti-HER2 biparatopic antibody compared to the anti-HER2 FSA.

Example 12: Ability of Exemplary Anti-HER2 Antibody to Bind to HER2 ECD

An SPR assay was used to evaluate the mechanism by which an exemplary anti-HER2 biparatopic antibody binds to HER2 ECD; specifically, to understand whether both paratopes of one biparatopic antibody molecule can bind to one HER2 ECD (Cis binding; 1:1 antibody to HER2 molecules) or if each paratope of one biparatopic antibody can bind two different HER2 ECDs (Trans binding; 1:2 antibody to HER2 molecules). A representation of cis vs. trans binding is illustrated in FIG. 14. The correlation between a reduced (slower) off-rate with increasing antibody capture levels (surface density) is an indication of Trans binding (i.e. one antibody molecule binding to two HER2 molecules.

Affinity and binding kinetics of the exemplary biparatopic anti-HER2 antibody (v5019) to recombinant human HER2 were measured and compared to that of monovalent anti-HER2 antibodies (v630 or v4182; comprising the individual paratopes of v5019) was measured by SPR using the T200 system from Biacore (GE Healthcare). Between 2000 and 4000 RU of anti-human Fc injected at concentration between 5 and 10 µg/ml was immobilized on a CMS chip using standard amine coupling. Monovalent anti-HER2 antibody (v630 or v4182) and exemplary biparatopic anti-HER2 antibody (v5019) were captured on the anti-human Fc (injected at concentration ranging 0.08 to 8 µg/ml in PBST, 1 min at 10 ul/min) at response levels ranging from 350-15 RU. Recombinant human HER2 was diluted in PBST and injected at starting concentration of either 120 nM, 200 nM or 300 nM with 3-fold dilutions and injected at a flow rate of 50 µl/min for 3 minutes, followed by dissociation for another 30 minutes at the end of the last injection. HER2 dilutions were analyzed in duplicate. Sensograms were fit globally to a 1:1 Langmuir binding model. All experiments were conducted at 25° C.

The results are shown in FIG. 12 and FIG. 13.

Figure 12A:
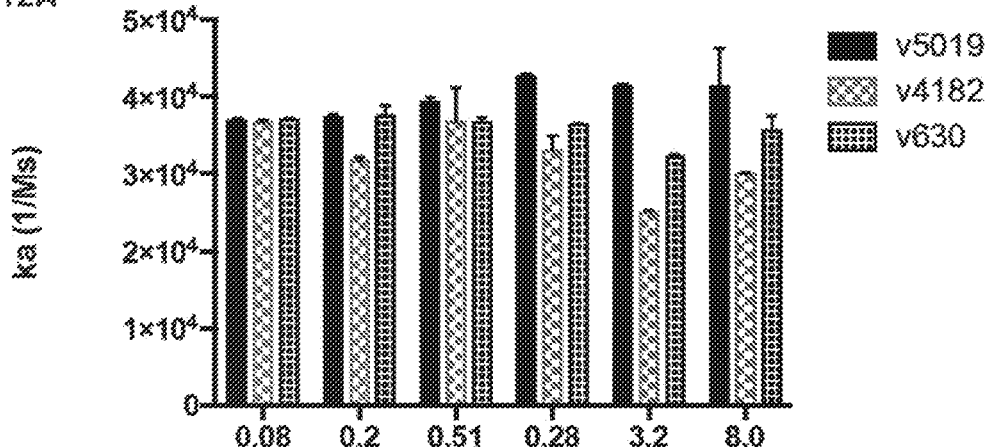
FIG. 12A depicts the characterization of affinity and binding kinetics of monovalent anti-HER2 (v630 and v4182) and an exemplary biparatopic anti-Her2 antibody (v5019) to recombinant human HER2.

The results in FIG. 12A show the ka (1/Ms) of monovalent anti-HER2 (v630 and v4182) and exemplary biparatopic anti-HER2 antibody (v5019) for binding to recombinant human HER2 over a range of injected and captured antibody concentrations on the surface of the chip. These results show that ka does not change when for v630, v4182 and v5019 at different antibody capture levels.

Figure 12B:
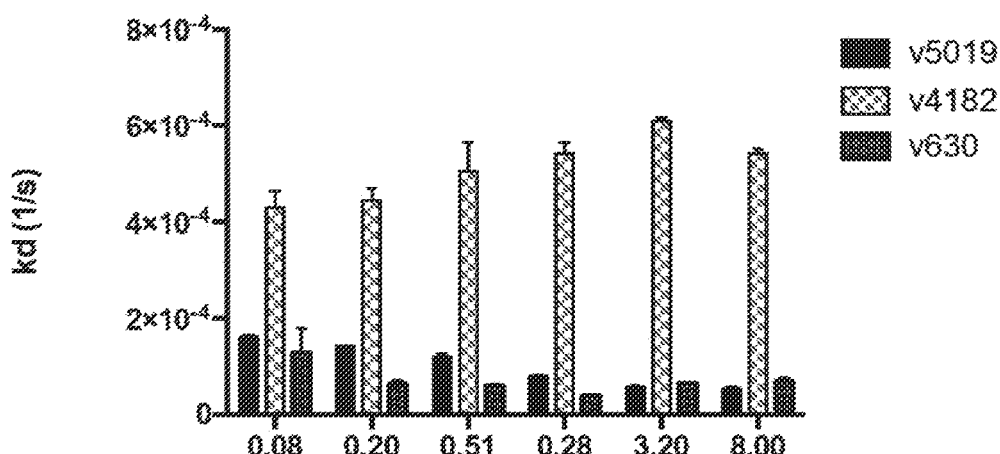
FIG. 12B depicts the characterization of affinity and binding kinetics of monovalent anti-HER2 (v630 and v4182) and an exemplary biparatopic anti-Her2 antibody (v5019) to recombinant human HER2.

The results in FIG. 12B show the kd (1/s) of monovalent anti-HER2 (v630 and v4182) and exemplary biparatopic anti-HER2 antibody (v5019) for binding to recombinant human HER2 over a range of injected and captured antibody concentrations on the surface of the chip. These results show that kd decreased only for the exemplary anti-HER2 biparatopic antibody (v5019) at increasing antibody capture levels.

Figure 12C:
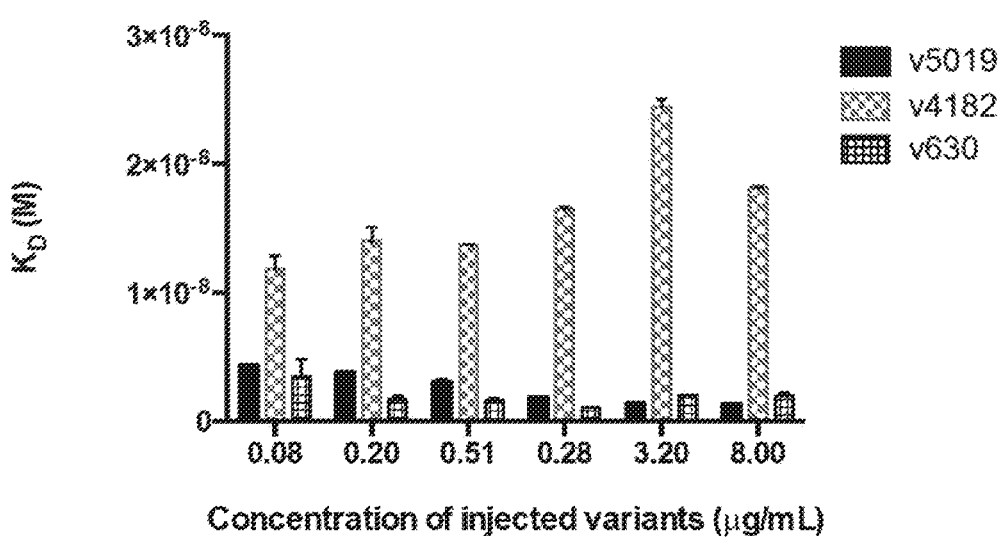
FIG. 12C depicts the characterization of affinity and binding kinetics of monovalent anti-HER2 (v630 and v4182) and an exemplary biparatopic anti-Her2 antibody (v5019) to recombinant human HER2.

The results in FIG. 12C show the $K_D$ (M) of monovalent anti-HER2 (v630 and v4182) and exemplary biparatopic anti-HER2 antibody (v5019) for binding to recombinant human HER2 over a range of injected and captured antibody concentrations on the surface of the chip. These results show that $K_D$ decreased only for the exemplary anti-HER2 biparatopic antibody (v5019) at increasing antibody capture levels. This result correlated to the decreasing kd values shown in FIG. 15B.

Figure 13A:
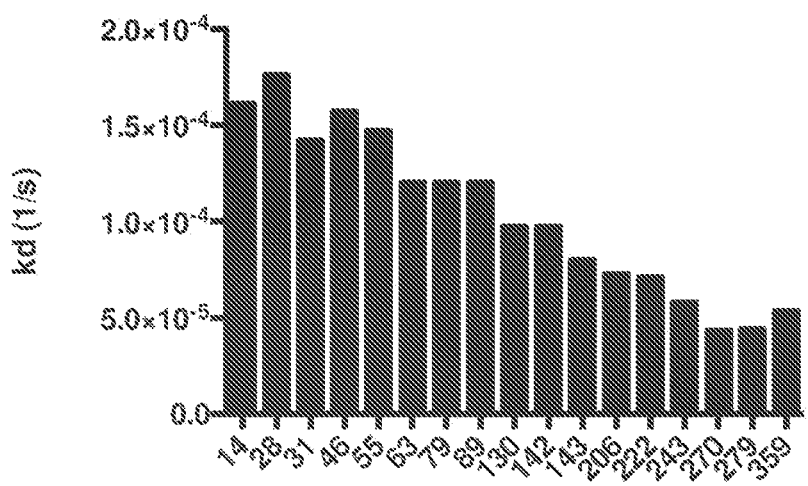
FIG. 13A depicts affinity and binding characteristics of an exemplary biparatopic anti-HER2 antibody to recombinant human HER2 over a range of antibody capture levels.

The results in FIG. 13A show the kd (1/s) of exemplary biparatopic anti-HER2 antibody (v5019) for binding to recombinant human HER2 over a range of antibody capture levels. These results show kd values are inversely proportional to higher RUs of antibody captured on the surface of the chip (i.e slower off-rates at higher antibody capture levels). The results indicate that exemplary biparatopic anti-HER2 antibody (v5019) is capable of binding HER2 ECD2 and HER2 ECD4 on two separate HER2 molecules (i.e. trans binding) as is evidenced by the reduction in off-rate at higher antibody capture levels. This data is supported by a similar experiment presented in FIG. 47 and discussed in Example 43, where bivalent monospecific anti-HER2 FSA (v506) demonstrated Cis binding (1:1 antibody to HER2) where the kd (1/s) and $K_D$ (M) values remained constant at increasing antibody capture levels as is expected for this molecule.

Figure 13B:
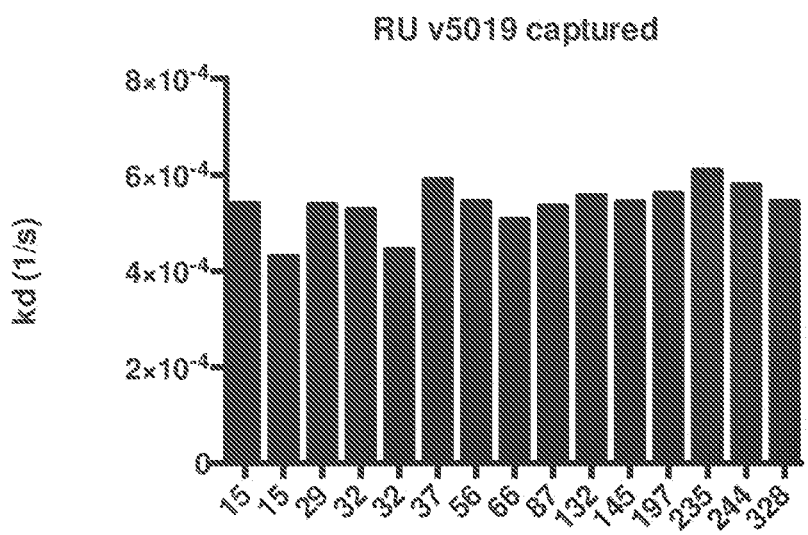
FIG. 13B depicts affinity and binding characteristics of an exemplary biparatopic anti-HER2 antibody to recombinant human HER2 over a range of antibody capture levels.

The results in FIG. 13B show the kd (1/s) of monovalent anti-HER2 antibody (v4182) for binding to recombinant human HER2 over a range of antibody capture levels. These results show no change in kd values over the range of different antibody RUs captured on the surface of the chip. These results show that monovalent anti-HER2 antibody (v4182) is binding monovalently 1:1 (cis binding).

Figure 13C:
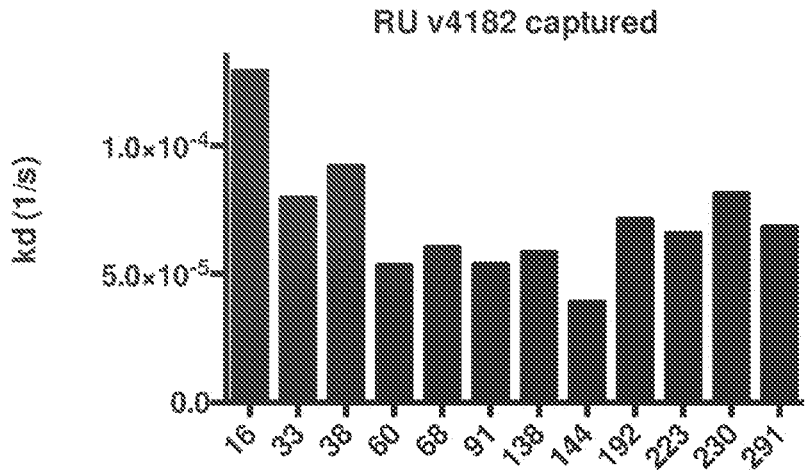
FIG. 13C depicts affinity and binding characteristics of an exemplary biparatopic anti-HER2 antibody to recombinant human HER2 over a range of antibody capture levels.

The results in FIG. 13C show the kd (1/s) of monovalent anti-HER2 antibody (v630) for binding to recombinant human HER2 over a range of antibody capture levels. These results show no change in kd values over the range of different antibody RUs captured on the surface of the chip. These results show that monovalent anti-HER2 antibody (v630) is binding monovalently 1:1 (cis binding). This data is supported by the experiment presented in FIG. 47 and discussed in Example 43X, where the bivalent monospecific anti-HER2 FSA (v506) showed no change in kd (1/s).

The results in FIG. 12, and FIG. 13 indicate that exemplary biparatopic anti-HER2 antibody (v5019) is capable of simultaneously binding to two HER2 molecules in trans (antibody to HER2 ratio 1:2). The trans mechanism of binding detected by SPR is consistent with the higher cell surface saturation binding data (Bmax), presented in Example 6, in combination with the internalization data presented in Examples 9 and 10.

Example 13: Effect of Exemplary Biparatopic Anti-HER2 Antibody Incubation on AKT Phosphorylation in BT-474 Cells The ability of an exemplary anti-HER2 biparatopic antibody to reduce pAKT signaling in BT-474 cells was tested using the AKT Colorimetric In-Cell ELISA Kit (Thermo Scientifiic; cat no. 62215) according to the manufacturer's instructions with the following modifications. Cells were seeded at $5 \times 10^3$/well and incubated 24 h at 37° C.+5% $CO_2$. Cells were incubated with 100 nM antibody for with 30 min followed by a 15 min incubation with rhHRG-β1. Cells were washed, fixed, and permeabilized according to the instructions. Secondary antibodies (1:5000; Jackson ImmunoReasearch, HRP-donkey anti-mouse IgG, JIR, Cat #715-

036-150, HRP-donkey anti-rabbit IgG, JIR, Cat #711-036-452) were added and the assay processed according to the manufacturer's instructions.

Figure 15:
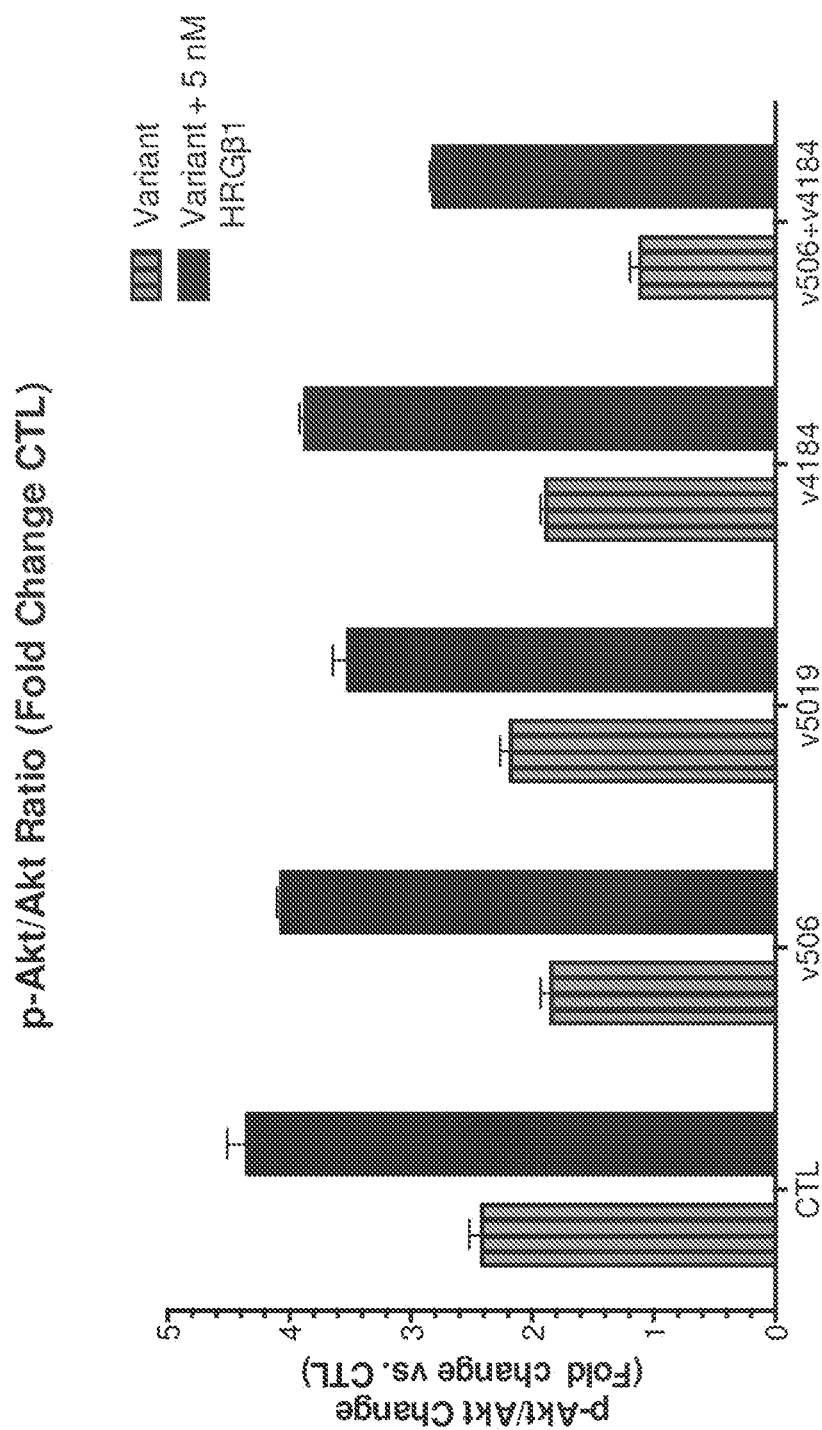
FIG. 15 depicts the effect of an exemplary anti-HER2 biparatopic antibody on AKT phosphorylation in BT-474 cells.

The results in FIG. 15 show that incubation with exemplary anti-HER2 biparatopic antibody mediated an approximate 1.2-fold reduction in p-Akt levels in the presence of HRGβ1 relative to the human IgG control (CTL). The combination of two anti-HER2 FSAs (v506+v4184) mediated the greatest reduction in p-Akt levels in the presence HRGβ1 that was approximately 1.5-fold less compared to the human IgG control. A modest reduction in p-Akt was detected with the exemplary anti-HER2 biparatopic antibody in the absence of ligand (HRGβ1) compared to the human IgG control antibody.

These data show that exemplary anti-HER2 biparatopic antibody can block ligand-activated signaling in HER2+ cells.

Example 14: Effect of Biparatopic Anti-HER2 Antibody on Cardiomyocyte Viability

The effect of exemplary biparatopic anti-HER2 antibodies and ADCs on cardiomyocyte viability was measured in order to obtain a preliminary indication of potentially cardiotoxic effects.

iCell cardiomyocytes (Cellular Dynamics International, CMC-100-010), that express basal levels of the HER2 receptor, were grown according the manufacturer's instructions and used as target cells to assess cardiomyocyte health following antibody treatment. The assay was performed as follows. Cells were seeded in 96-well plates (15,000 cells/well) and maintained for 48 h. The cell medium was replaced with maintenance media and cells were maintained for 72 h. To access the effects of antibody-induced cardiotoxicity, cells were treated for 72 h with 10 and 100 nM of, variants alone or in combinations. To access the effects of anthracycline-induced cardiotoxicity (alone or in combination with the exemplary biparatopic anti-HER2 antibodies), cells were treated with 3 uM (~$IC_{20}$) of doxorubicin for 1 hr followed by 72 h with 10 and 100 nM of, antibody variants alone or in combinations. Cell viability was assessed by quantitating cellular ATP levels with the CellTiter-Glo® Luminescent Cell Viability Assay (Promega, G7570) and/or Sulphorhodamine (Sigma 230162-5G) as per the manufacturer's instructions.

Figure 16A:
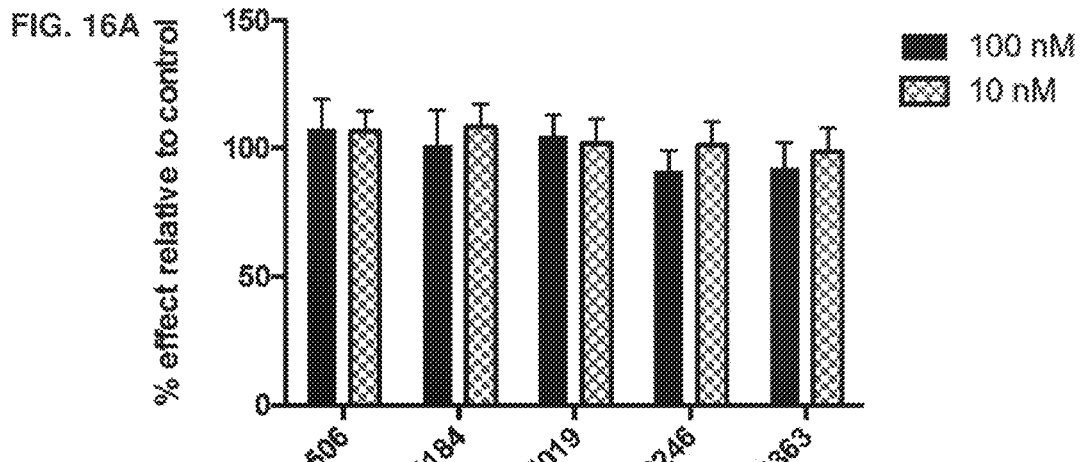
FIG. 16A depicts the effect of an exemplary anti-HER2 biparatopic antibody on cardiomyocyte viability.
Figure 16B:
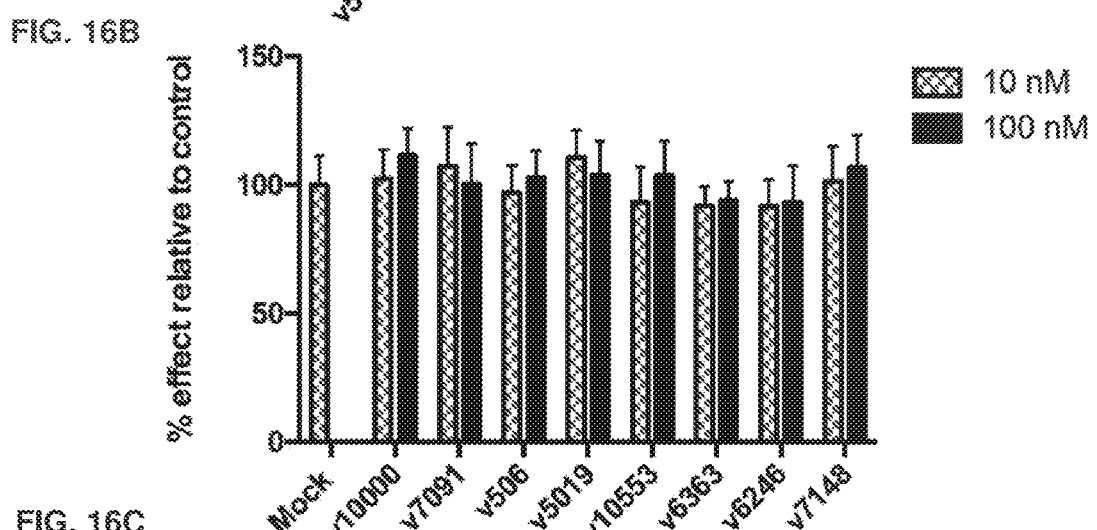
FIG. 16B depicts the effect of an exemplary anti-HER2 biparatopic antibody on cardiomyocyte viability.
Figure 16C:
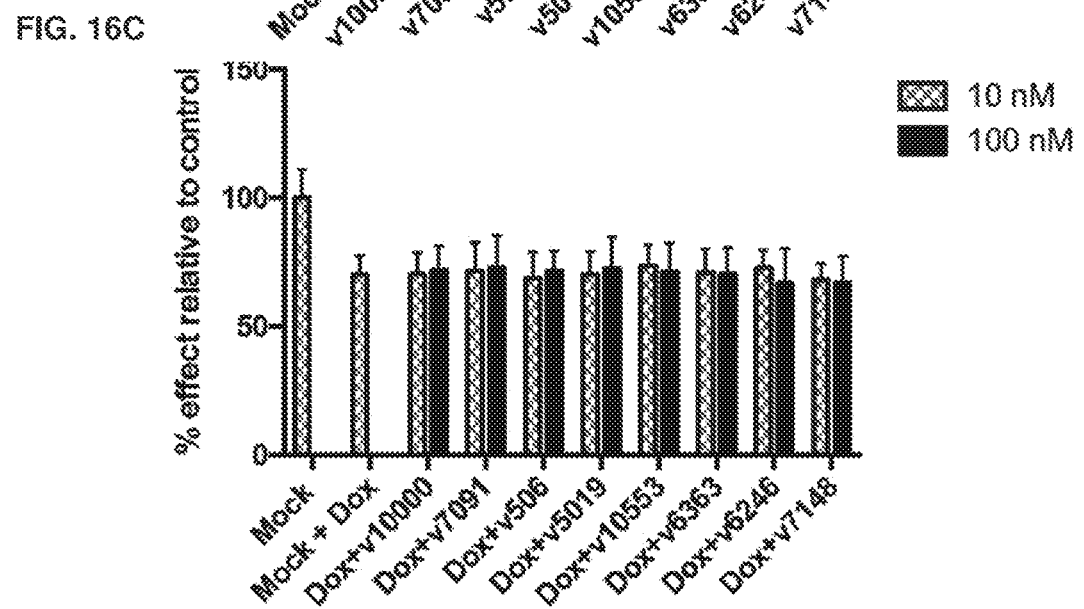
FIG. 16C depicts the effect of an exemplary anti-HER2 biparatopic antibody on cardiomyocyte viability.

The results are shown in FIG. 16A-C. The results in FIG. 16A show that incubation of the cardiomyocytes with therapeutically relevant concentrations of exemplary anti-HER2 biparatopic antibody (v5019) and exemplary anti-HER2 biparatopic-ADC (v6363), did not affect cardiomyocyte viability relative to the untreated control ('mock').

The results in FIG. 16B show that incubation of the cardiomyocytes with therapeutically relevant concentrations of exemplary anti-HER2 biparatopic antibodies (v5019, v7091 and v10000), and exemplary anti-HER2 biparatopic-ADCs (v6363, v7148 and v10553), had no effect on cardiomyocyte viability relative to the untreated control ('mock'). Based on the results in FIGS. 16A and 16B it is expected that exemplary anti-HER2 biparatopic antibodies and exemplary anti-HER2 biparatopic-ADCs should not induce cardiomyopathy, for example through mitochondrial dysfunction, as is reported with other anti-HER2 targeting antibodies (Grazette L. P. et al. Inhibition of ErbB2 Causes Mitochondrial Dysfunction in Cardiomyocytes; Journal of the American College of Cardiology: 2004; 44:11).

The results in FIG. 16C show that pretreatment of the cardiomyocytes with doxorubicin followed by incubation with therapeutically relevant concentrations of exemplary anti-HER2 biparatopic antibodies (v5019, v7091 and v10000) and exemplary anti-HER2 biparatopic-ADCs (v6363, v7148 and v10553), had no effect on cardiomyocyte viability relative to the untreated control+doxorubicin ('Mock+Dox'). Based on the results in FIG. 16C it is expected that exemplary anti-HER2 biparatopic antibodies and exemplary anti-HER2 biparatopic-ADCs should not result in an increased risk of cardiac dysfunction in patients receiving concurrent anthracycline treatment (Seidman A, Hudis C, Pierri M K, et al. Cardiac dysfunction in the trastuzumab clinical trials experience. J Clin Oncol (2002) 20:1215-1221).

FIGS. 16A-C show that incubation of cardiomyocytes with the anti-HER2 biparatopic antibodies and ADCs had equivalent effects compared to monospecific anti-HER2 FSA antibody (v506), anti-HER2 FSA combination (v506+v4184) and ADC (v6246) when treated either alone, or in combination with doxorubicin. Based on these results, it is expected that exemplary anti-HER2 biparatopic antibodies and ADCs would not have greater cardiotoxic effects compared to anti-monospecific anti-HER2 FSA, trastuzumab or ADC, T-DM1.

Example 15: Cytotoxicity of Exemplary Biparatopic Anti-HER2-ADCs in HER2+ Cells

The ability of exemplary biparatopic anti-HER2-ADC antibodies (v6363, v7148 and v10553) to mediate cellular cytotoxicity in HER2+ cells was measured. Human IgG conjugated to DM1 (v6249) was used as a control in some cases. The experiment was carried out in HER2+ breast tumor cell lines JIMT-1, MCF7, MDA-MB-231, the HER2+ ovarian tumor cell line SKOV3, and HER2+ gastric cell line NCI-N87. The cytotoxicity of exemplary biparatopic anti-HER2-ADC antibodies in HER2+ cells was evaluated and compared to the monospecific anti-HER2 FSA-ADC (v6246) and anti-HER2-FSA-ADC+anti-HER2-FSA controls (v6246+v4184). The method was conducted as described in Example 7 with the following modifications. The anti-HER2 ADCs were incubated with the target SKOV3 and JIMT-1 (FIGS. 17A and B) cells for 24 h, cells washed, media replaced and cell survival was evaluated after 5 day incubation at 37° C. The anti-HER2 ADCs were incubated with target MCF7 and MDA-MB-231 target cells for 6 h (FIGS. 17C and D), cells washed media replaced and cell survival was evaluated at 5 days incubation at 37° C. In FIG. 17E-G, anti-HER2 ADCs were incubated continuously with target SKOV3, JIMT-1, NCI-N87 cells for 5 days. Cell viability was measured as described in Example 7 using either AlamarBlue™ (FIGS. 17A-D) or Celltiter-Glo® (FIGS. 17E-G).

The results are shown in FIG. 17A-G and the data is summarized in Tables 15 and 16.

Figure 17A:
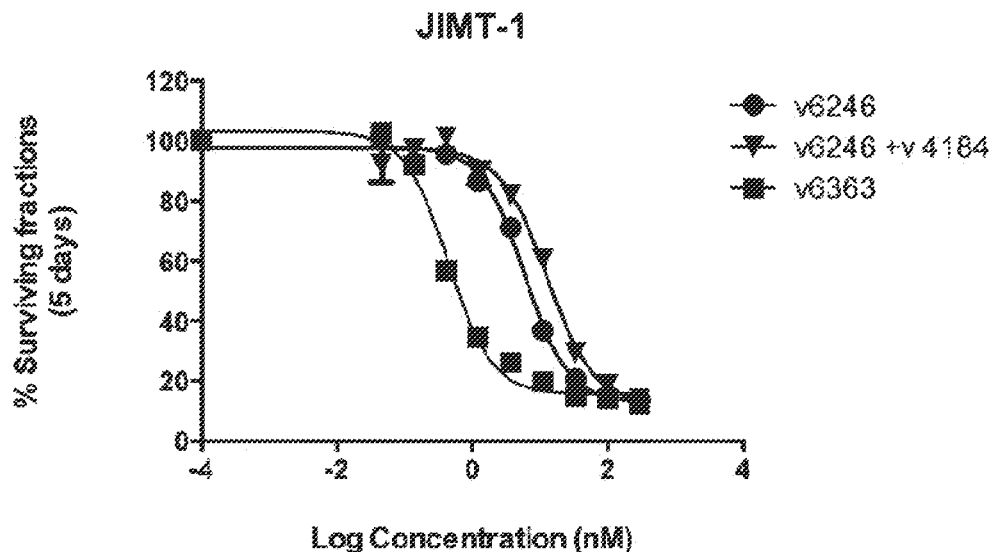
FIG. 17A depicts the ability of exemplary anti-HER2 biparatopic antibody drug conjugates to inhibit the growth of HER2+ cells.

The results in FIG. 17A and Table 15 and 16 show that exemplary anti-HER2 biparatopic-ADC (v6363) is more cytotoxic in JIMT-1 compared to the anti-HER2-FSA-ADC (v6246) and the combination of anti-HER2-FSA-ADC+anti-HER2 FSA (v6246+v4184). The exemplary anti-HER2 biparatopic-ADC had a superior $EC_{50}$ that was approximately 13-fold lower compared to the anti-HER2 FSA-ADC control.

Figure 17B:
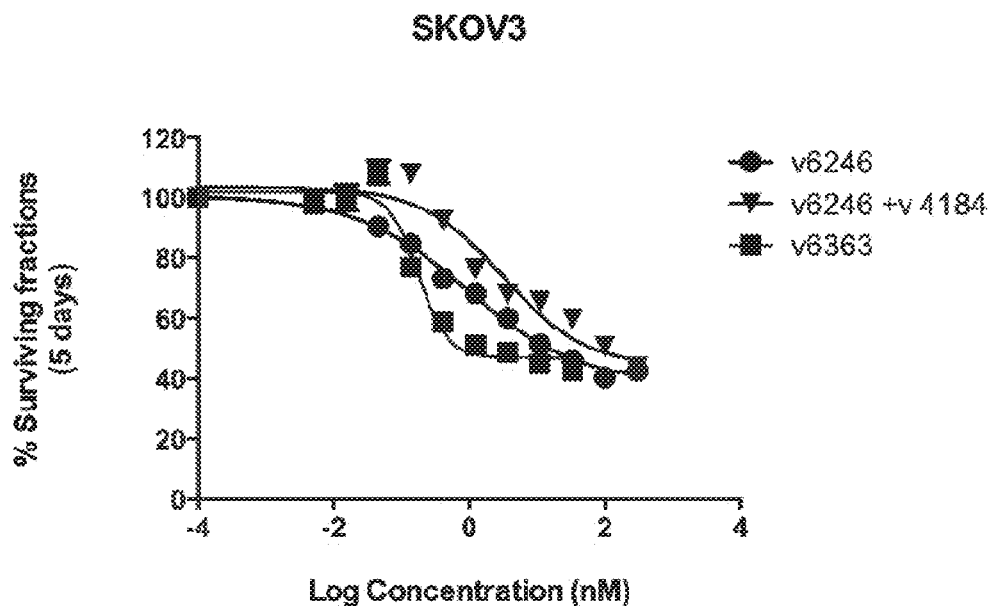
FIG. 17B depicts the ability of exemplary anti-HER2 biparatopic antibody drug conjugates to inhibit the growth of HER2+ cells.

The results in FIG. 17B and Table 15 show that exemplary anti-HER2 biparatopic-ADC (v6363) is more cytotoxic in SKOV3 compared to the anti-HER2-FSA-ADC (v6246) and the combination of anti-HER2-FSA-ADC+anti-HER2 FSA (v6246+v4184). The exemplary anti-HER2 biparatopic- ADC had a superior $EC_{50}$ that was approximately 5-fold lower compared to the anti-HER2 FSA-ADC control.

Figure 17C:
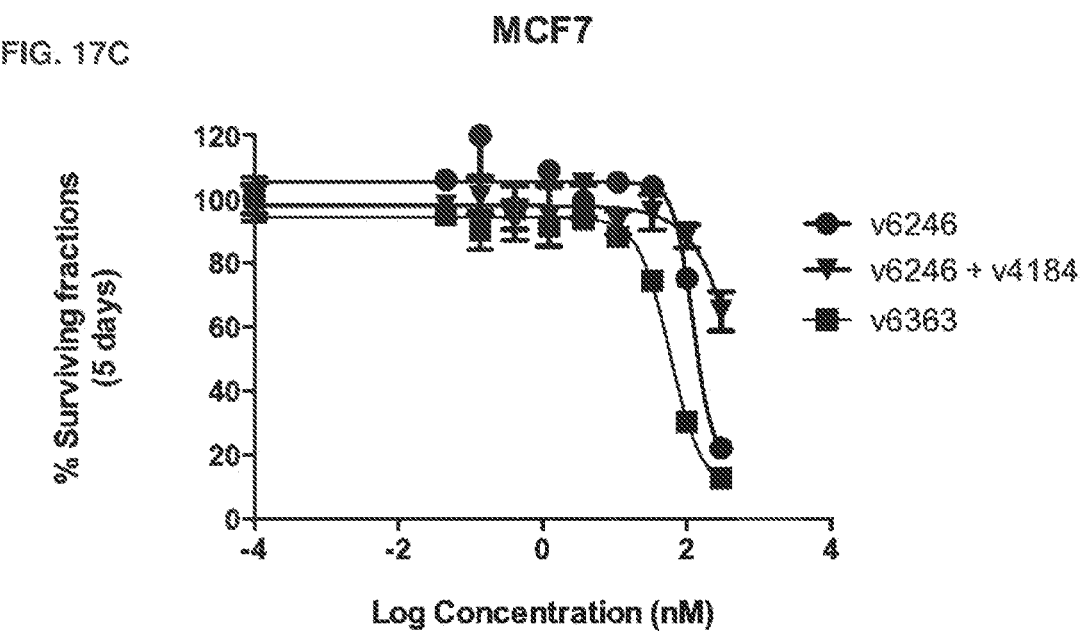
FIG. 17C depicts the ability of exemplary anti-HER2 biparatopic antibody drug conjugates to inhibit the growth of HER2+ cells.

The results in FIG. 17C and Table 15 show that exemplary anti-HER2 biparatopic-ADC (v6363) is more cytotoxic in MCF7 compared to the anti-HER2-FSA-ADC (v6246) and the combination of anti-HER2-FSA-ADC+anti-HER2 FSA (v6246+v4184). The exemplary anti-HER2 biparatopic-ADC had a superior $EC_{50}$ that was approximately 2-fold lower compared to the anti-HER2 FSA-ADC control.

Figure 17D:
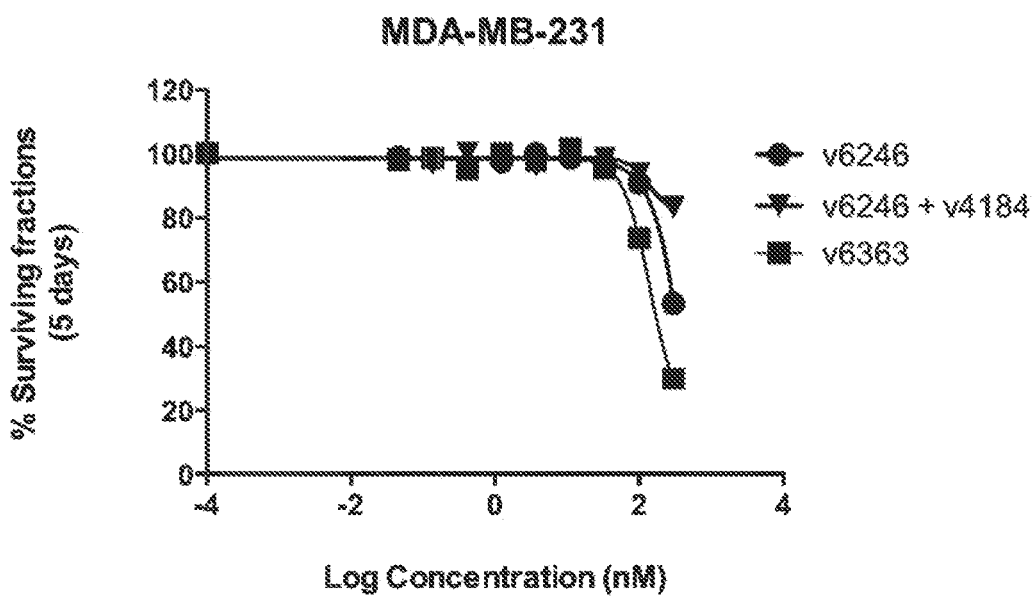
FIG. 17D depicts the ability of exemplary anti-HER2 biparatopic antibody drug conjugates to inhibit the growth of HER2+ cells.
Figure 17E:
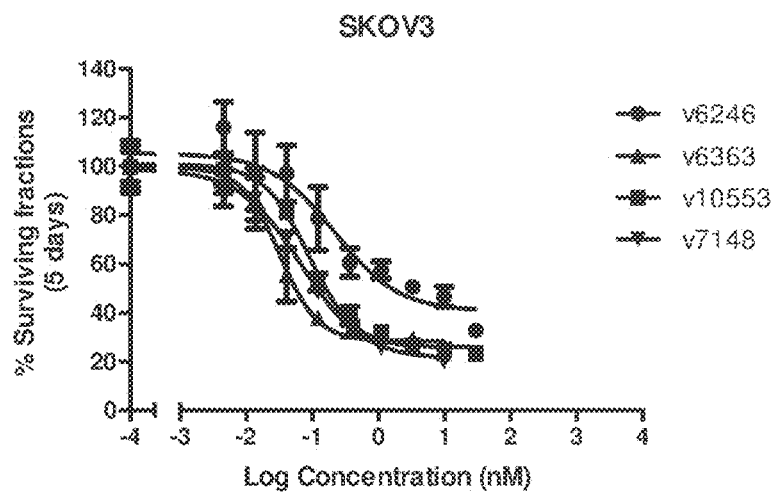
FIG. 17E depicts the ability of exemplary anti-HER2 biparatopic antibody drug conjugates to inhibit the growth of HER2+ cells.
Figure 17F:
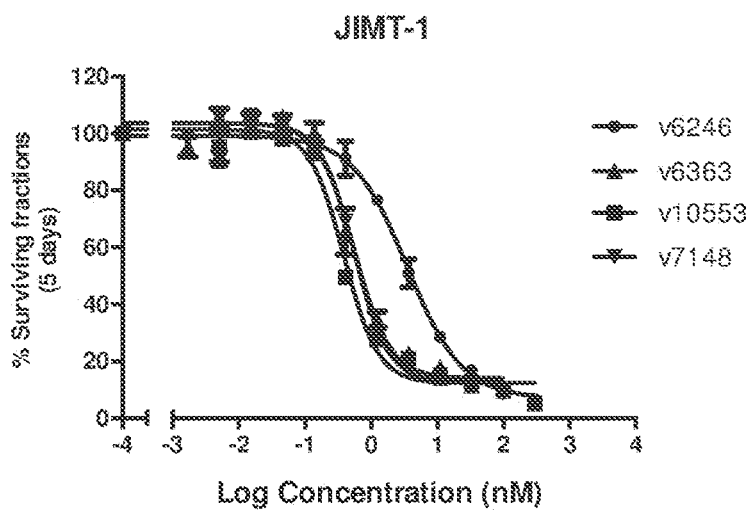
FIG. 17F depicts the ability of exemplary anti-HER2 biparatopic antibody drug conjugates to inhibit the growth of HER2+ cells.
Figure 17G:
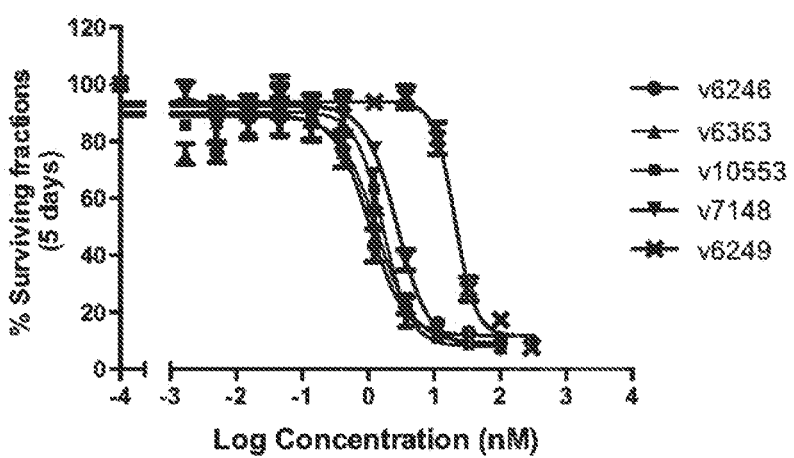
FIG. 17G depicts the ability of exemplary anti-HER2 biparatopic antibody drug conjugates to inhibit the growth of HER2+ cells.

The results in FIG. 17D and Table 15 show that exemplary anti-HER2 biparatopic-ADC (v6363) is more cytotoxic in MDA-MB-231 compared to the anti-HER2-FSA-ADC (v6246) and the combination of anti-HER2-FSA-ADC+anti-HER2 FSA (v6246+v4184). The exemplary anti-HER2 biparatopic-ADC had a superior $EC_{50}$ that was approximately 2-fold lower compared to the anti-HER2 FSA-ADC control.

TABLE 15

| Antibody variant | $EC_{50}$ (nM) | | | |
|---|---|---|---|---|
| | SKOV3 | JIMT-1 | MCF7 | MDA-MB-231 |
| v6246 | 0.9225 | 5.942 | 122.0 | ~1075 |
| v6246 + 4184 | 3.146 | 12.68 | ~24432 | 136.4 |
| v6363 | 0.1776 | 0.4443 | 58.55 | 141.0 |

The results in FIG. 17E and Table 16 show that exemplary anti-HER2 biparatopic-ADCs (v6363, v7148 and v10553) are more cytotoxic in SKOV3 ovarian tumor cells compared to the anti-HER2-FSA-ADC (v6246). The exemplary anti-HER2 biparatopic-ADCs had a superior $EC_{50}$ values that were approximately 2 to 7-fold lower compared to the anti-HER2 FSA-ADC control.

The results in FIG. 17F and Table 16 show that exemplary anti-HER2 biparatopic-ADCs (v6363, v7148 and v10553) are more cytotoxic in JIMT-1 breast tumor cells compared to the anti-HER2-FSA-ADC (v6246). The exemplary anti-HER2 biparatopic-ADCs had a superior $EC_{50}$ values were approximately 6 to 9-fold lower compared to the anti-HER2 FSA-ADC control.

The results in FIG. 17G and Table 16 show that exemplary anti-HER2 biparatopic-ADCs (v6363, v7148 and v10553) are cytotoxic in NCI-N87 gastric tumor cells. The exemplary anti-HER2 biparatopic-ADCs had has approximately equivalent $EC_{50}$ values compared to the anti-HER2 FSA-ADC control.

TABLE 16

| Antibody variant | $EC_{50}$ (nM) | | |
|---|---|---|---|
| | SKOV3 | JIMT-1 | NCI-N87 |
| v6246 | 0.22 | 3.52 | 1.04 |
| v6363 | 0.03 | 0.56 | 1.33 |
| v7148 | 0.06 | 0.56 | 2.74 |
| v10553 | 0.09 | 0.39 | 1.69 |

These results show that exemplary anti-HER2 biparatopic-ADCs (v6363, v7148 and v10553) are more cytotoxic compared to anti-HER-FSA-ADC control in HER2 3+, 2+, and 1+ breast tumor cells. These results also show that exemplary anti-HER2 biparatopic-ADCs (v6363, v7148 and v10553) are cytotoxic in HER2 2/3+ gastric tumor cells. These results are consistent with the internalization results presented in Example 9.

Example 16: Effect of a Biparatopic Anti-HER2 Antibody in a Human Ovarian Cancer Cell Xenograft Model The established human ovarian cancer cell derived xenograft model SKOV3 was used to assess the anti-tumor efficacy of an exemplary biparatopic anti-HER2 antibody.

Female athymic nude mice were inoculated with the tumor via the insertion of a 1 mm$^3$ tumor fragment subcutaneously. Tumors were monitored until they reached an average volume of 220 mm$^3$; animals were then randomized into 3 treatment groups: IgG control, anti-HER2 FSA (v506), and biparatopic anti-HER2 antibody (v5019).

Fifteen animals were included in each group. Dosing for each group is as follows:

A) IgG control was dosed intravenously with a loading dose of 30 mg/kg on study day 1 then with maintenance doses of 20 mg/kg twice per week to study day 39.

B) Anti-HER2 FSA (v506) was dosed intravenously with a loading dose of 15 mg/kg on study day 1 then with maintenance doses of 10 mg/kg twice per week to study day 18. On days 22 through 39, 5 mg/kg anti-HER2 FSA was dosed intravenously twice per week. Anti-HER2 FSA (v4184) was dosed simultaneously at 5 mg/kg intraperitoneally twice per week.

C) Biparatopic anti-HER2 antibody was dosed intravenously with a loading dose of 15 mg/kg on study day 1 then with maintenance doses of 10 mg/kg twice per week to study day 39.

Tumor volume was measured twice weekly over the course of the study, number of responders and median survival was assessed at day 22. The results are shown in FIG. 18 and Table 17.

Figure 18A:
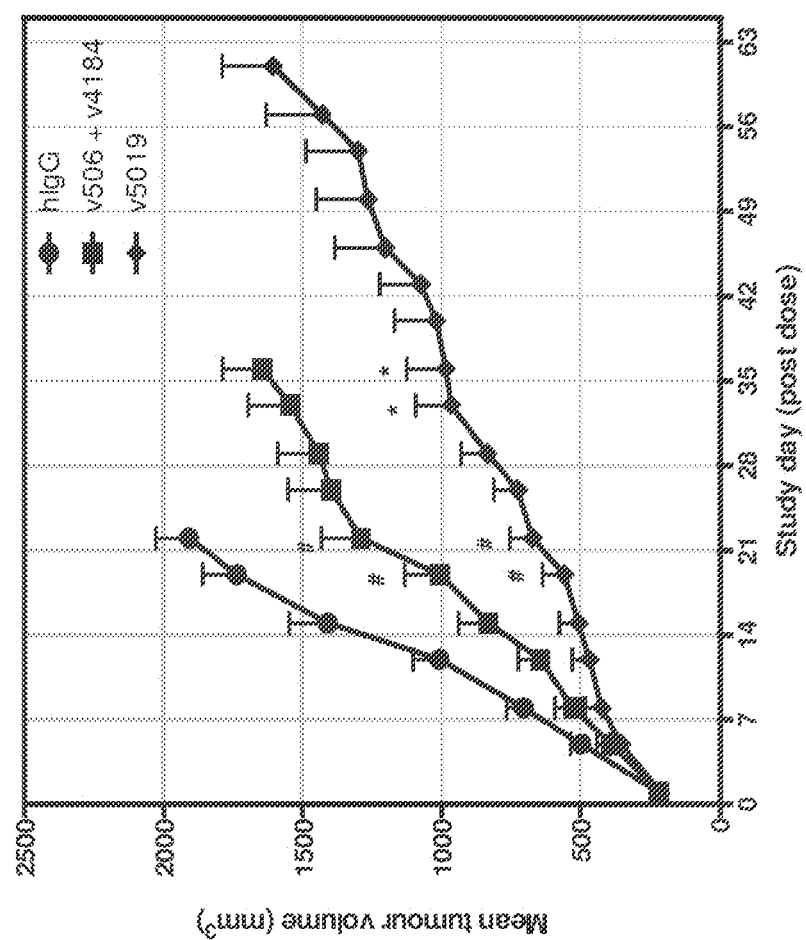
FIG. 18A depicts the effect of a biparatopic anti-HER2 antibody in a human ovarian cancer line xenograft model (SKOV3).
Figure 18B:
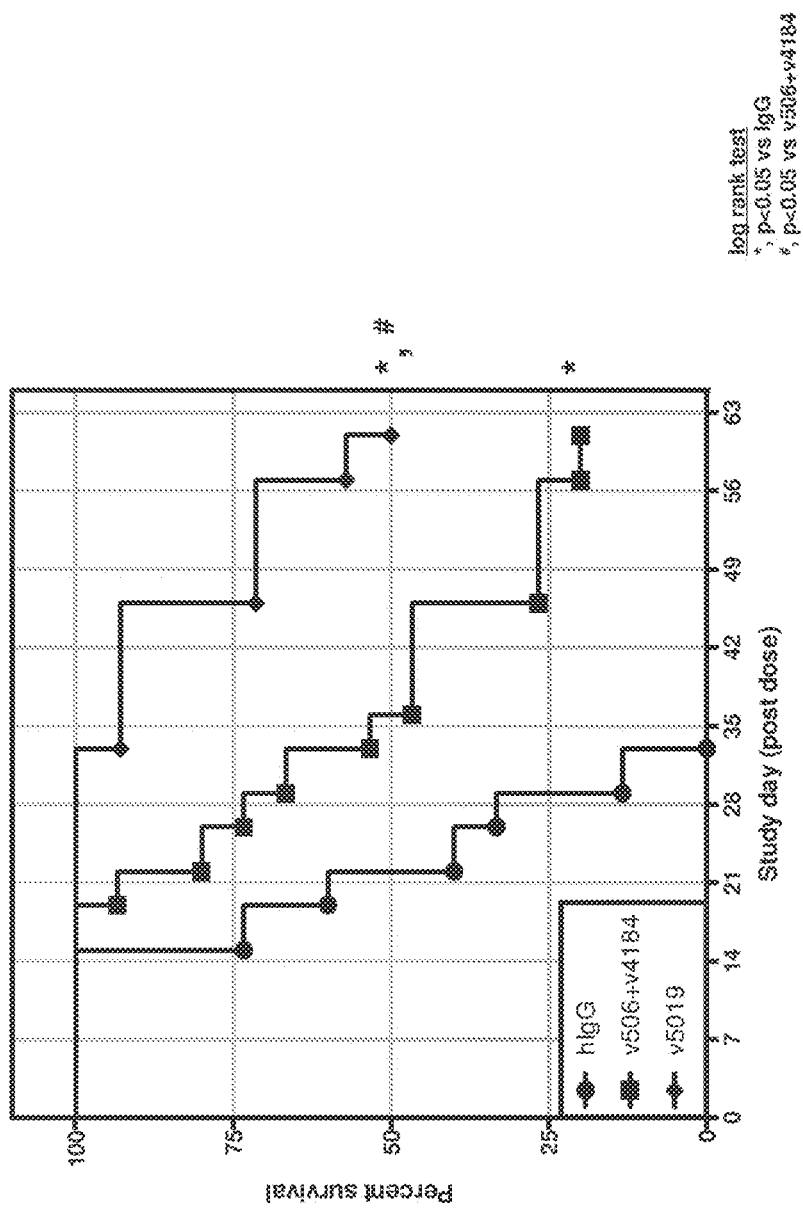
FIG. 18B depicts the effect of a biparatopic anti-HER2 antibody in a human ovarian cancer line xenograft model (SKOV3).

The biparatopic anti-HER2 and anti-HER2 FSA demonstrated superior tumor growth inhibition compared to IgG control. The biparatopic anti-HER2 antibody induced superior tumor growth inhibition compared to anti-HER2 FSA combination (FIG. 18A). The biparatopic anti-HER2 antibody was associated with an increase in the number of responding tumors compared to anti-HER2 FSA v506 at day 22 (11 and 5, respectively)(Table 17). The exemplary biparatopic anti-HER2 antibody and anti-HER2 FSA demonstrated superior survival compared to IgG control. The biparatopic anti-HER2 antibody had a superior median survival (61 days) compared to anti-HER2 FSA (36 days) (FIG. 18B and Table 17). On study day 22 a second anti-HER2 FSA (v4184) was added in combination to the anti-HER2 FSA (v506). The combination of two anti-HER2 FSAs induced a further tumour growth inhibition compared to anti-HER2 FSA (v506) alone.

TABLE 17

| n = 15, Day 22 | IgG | v506 | v5019 |
|---|---|---|---|
| Mean TV (mm3) | 1908 | 1291 | 697 |
| (% change from Baseline) | (+766%) | (+486%) | (+217%) |
| % TGI | 0 | 32 | 63 |
| Responders (TV <50% of control) | 0/15 | 5/15 | 11/15 |
| Median Survival (days) | 22 | 36 | 61 |

Example 17: Effect of a Biparatopic Anti-HER2 Antibody Drug Conjugate (ADC) in a Human Ovarian Cancer Cell Line Xenograft Model The established human ovarian cancer cell derived xenograft model SKOV3 was used to assess the anti-tumor efficacy of an exemplary biparatopic anti-HER2 antibody conjugated to DM1 (v6363).

Female athymic nude mice were inoculated with the tumor via the insertion of a 1 mm$^3$ tumor fragment subcutaneously. Tumors were monitored until they reached an average volume of 220 mm$^3$; animals were then randomized into 3 treatment groups: IgG control, anti-HER2 FSA-ADC, and a biparatopic anti-HER2-ADC.

Fifteen animals were included in each group. Dosing for each group is as follows:

A) IgG control was dosed intravenously with a loading dose of 30 mg/kg on study day 1 then with maintenance doses of 20 mg/kg twice per week to study day 39.

B) Anti-HER2 FSA-ADC (v6246) was dosed intravenously with a loading dose of 10 mg/kg on study day 1 then with a maintenance dose of 5 mg/kg on day 15 and 29.

C) Biparatopic anti-HER2 antibody-ADC (v6363) was dosed intravenously with a loading dose of 10 mg/kg on study day 1 then with a maintenance dose of 5 mg/kg on day 15 and 29.

Tumor volume was measured throughout the study, and the number of responders and median survival was assessed at day 22. The results are shown in FIG. 19. A summary of the results is shown in Table 18.

Figure 19A:
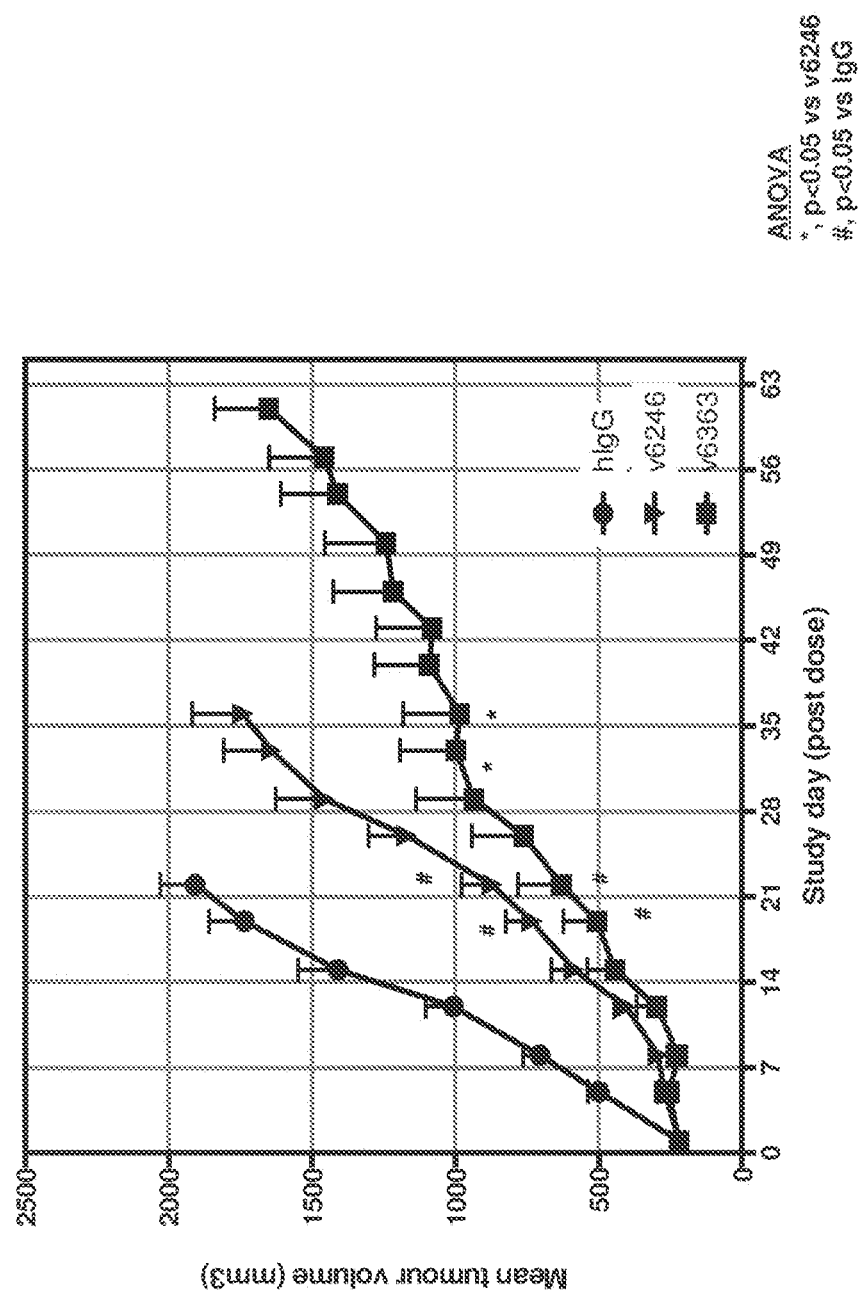
FIG. 19A depicts the effect of a biparatopic anti-HER2 antibody drug conjugate (ADC) in a human ovarian cancer line xenograft model (SKOV3).
Figure 19B:
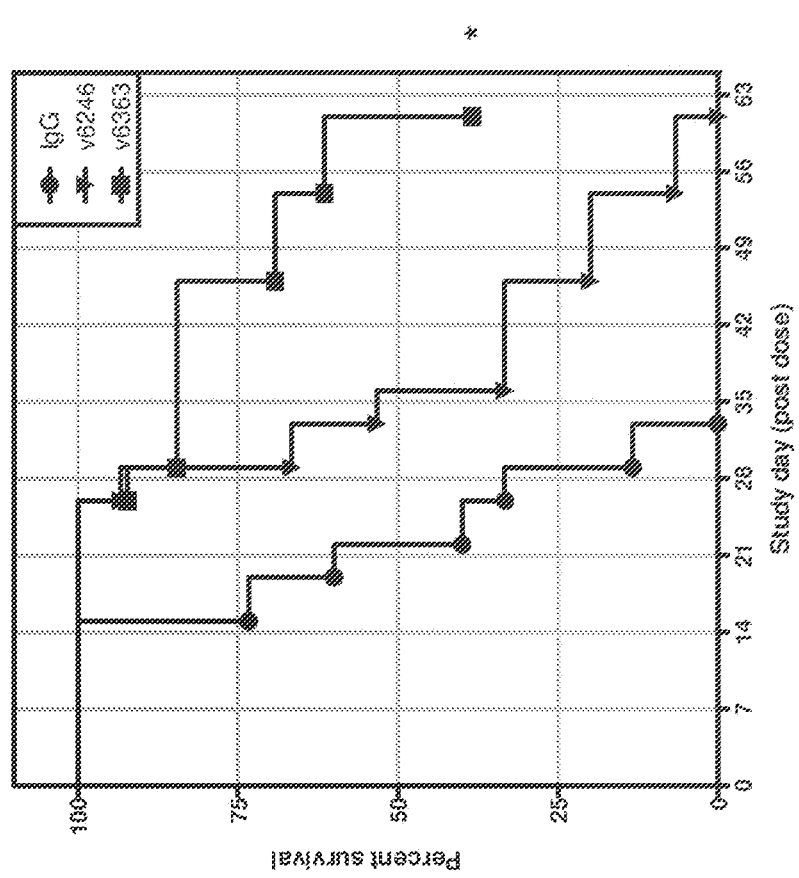
FIG. 19B depicts the effect of a biparatopic anti-HER2 antibody drug conjugate (ADC) in a human ovarian cancer line xenograft model (SKOV3).

The biparatopic anti-HER2-ADC and anti-HER2 FSA-ADC inhibited tumor growth better than IgG control (FIG. 19A and Table 18). The biparatopic anti-HER2-ADC inhibited tumor growth to a greater degree than did the anti-HER2 FSA-ADC. The biparatopic anti-HER2-ADC group was associated with an increase in the number of responding tumors compared to anti-HER2 FSA-ADC (11 and 9, respectively). The biparatopic anti-HER2-ADC and anti-HER2 FSA-ADC groups demonstrated superior survival compared to IgG control (FIG. 19B and Table 18). The biparatopic anti-HER2 antibody group demonstrated median survival of 61 days compared to the anti-HER2 FSA-ADC which had a median survival of 36 days (FIG. 19B and Table 18).

TABLE 18

| n = 15, Day 22 | IgG | v6246 | v6363 |
| --- | --- | --- | --- |
| Mean TV (mm3) | 1908 | 873 | 632 |
| (% change from Baseline) | (+766%) | (+297%) | (+187%) |
| % TGI | 0 | 54% | 67% |
| Responders (TV <50% of control) | 0/15 | 9/15 | 11/15 |
| Median survival (days) | 22 | 36 | 61 |

Example 18: Effect of a Biparatopic Anti-HER2 Antibody Drug Conjugate (ADC) in a Human Primary Cell Xenograft Model (HBCx-13b)

The trastuzumab resistant patient derived xenograft model from human breast cancer, HBCx-13B, was used to assess the anti-tumor efficacy of an exemplary biparatopic anti-HER2 antibody conjugated to DM1.

Female athymic nude mice were inoculated with the tumor via the insertion of a 20 mm$^3$ tumor fragment subcutaneously. Tumors were monitored until they reached an average volume of 100 mm$^3$; animals were then randomized into 3 treatment groups: anti-HER2 FSA (v506), anti-HER2 FSA-ADC (v6246), and the biparatopic anti-HER2-ADC (v6363). Seven animals were included in each group. Dosing for each group was as follows:

A) Anti-HER2 FSA was dosed intravenously with a loading dose of 15 mg/kg on study day 1 and maintenance doses of 10 mg/kg administered on study days 4, 8, 11, 15, 18, 22, and 25.

B) Anti-HER2 FSA-ADC was dosed intravenously with a loading dose of 10 mg/kg on study day 1 then with a maintenance dose of 5 mg/kg on day 22.

C) Biparatopic anti-HER2 antibody-ADC was dosed intravenously with a loading dose of 10 mg/kg on study day 1 then with a maintenance dose of 5 mg/kg on day 22.

Figure 20:
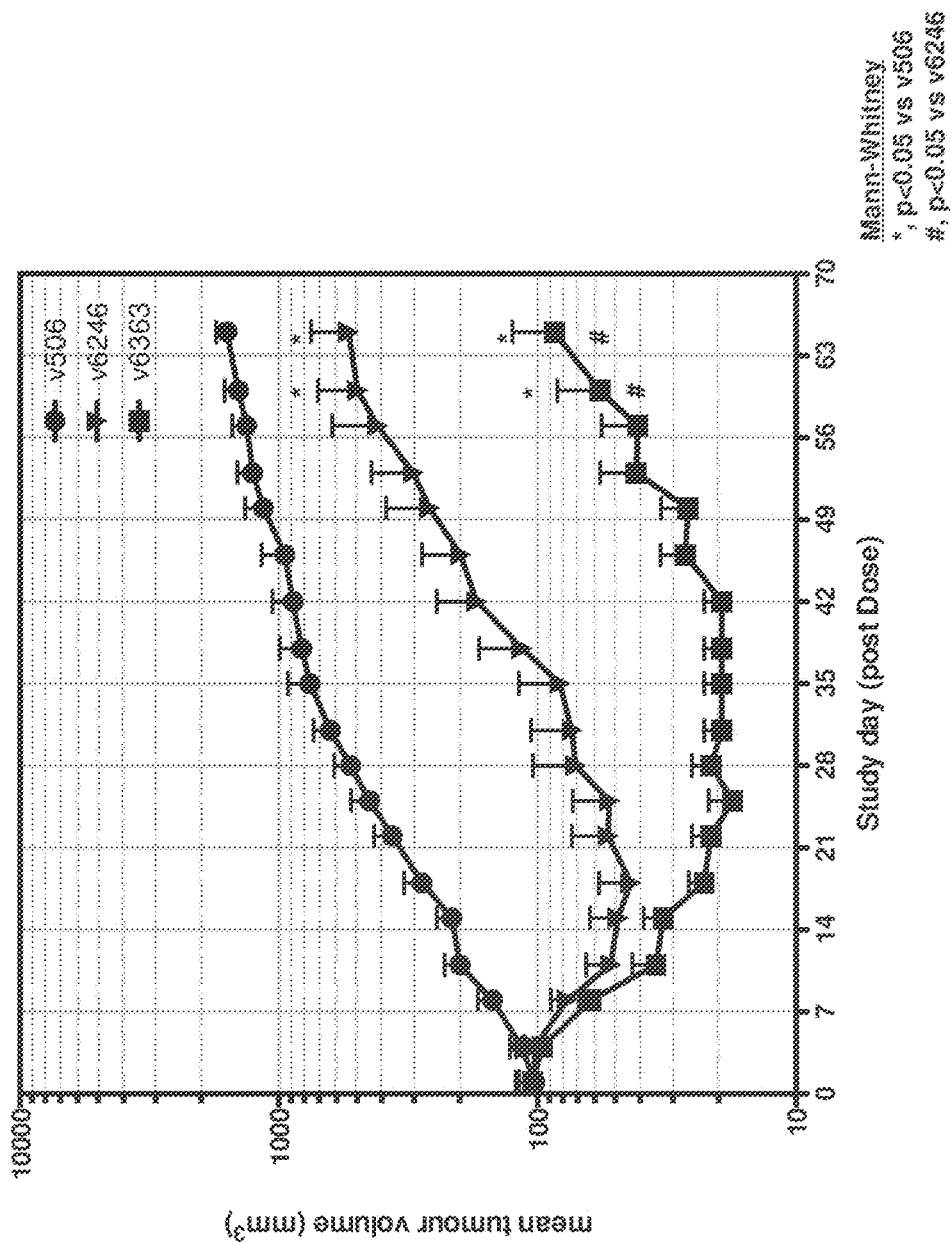
FIG. 20 depicts the effect of a biparatopic anti-HER2 antibody drug conjugate (ADC) on mean tumour volume in a human breast primary cell xenograft model (HBCx-13b).

Tumor volume was measured throughout the study, and mean tumor volume, complete response, and zero residual disease parameters were assessed at Day 50. The results are shown in FIG. 20. A summary of the results is shown in Table 19.

The biparatopic anti-HER2-ADC and anti-HER2 FSA-ADC demonstrated greater tumor growth inhibition compared to an anti-HER2 FSA (v506). The biparatopic anti-HER2-ADC inhibited tumor growth better than the anti-HER2 FSA-ADC. The biparatopic anti-HER2-ADC group as compared to the anti-HER2 FSA-ADC group was associated with an increase in the number of tumors showing complete responses (more than a 10% decrease below baseline), 7 and 4 respectively, and showing zero residual disease, 5 and 2 respectively.

TABLE 19

| n = 7, Day 50 | v506 | v6246 | v6363 |
| --- | --- | --- | --- |
| Mean TV (mm3) | 1149 | 262 | 26 |
| (% change from Baseline) | (+1018%) | (+153%) | (−75%) |
| % TGI | 0% | 77% | 98% |
| Complete response (>10% baseline regression) | 0 | 4/7 | 7/7 |
| Zero residual disease (TV <20 mm3) | 0 | 2/7 | 5/7 |

Example 19: Effect of a Biparatopic Anti-HER2 Antibody Drug Conjugate (ADC) in a Human Primary Cell Xenograft Model (T226)

The patient derived trastuzumab resistant xenograft model from human breast cancer, T226, was used to assess the anti-tumor efficacy of an exemplary biparatopic anti-HER2-ADC.

Female athymic nude mice were inoculated with the tumor via the insertion of a 20 mm$^3$ tumor fragment subcutaneously. Tumors were monitored until they reached an average volume of 100 mm$^3$; animals were then randomized into 4 treatment groups: IgG control (n=15), anti-HER2 FSA (v506; n=15), anti-HER2 FSA-ADC (v6246; n=16), and the biparatopic anti-HER2-ADC conjugate (v6363; n=16). Dosing for each group was as follows:

A) IgG control was dosed intravenously with a loading dose of 15 mg/kg on study day 1 and maintenance doses of 10 mg/kg administered on study days 4, 8, 11, 15, 18, 22, and 25

B) Anti-HER2 FSA was dosed intravenously with a loading dose of 15 mg/kg on study day 1 and maintenance doses of 10 mg/kg administered on study days 4, 8, 11, 15, 18, 22, and 25

C) Anti-HER2 FSA-ADC was dosed intravenously with 5 mg/kg on study days 1 and 15

D) Biparatopic anti-HER2-ADC conjugate was dosed intravenously with 5 mg/kg on study days 1 and 15.

Figure 21:
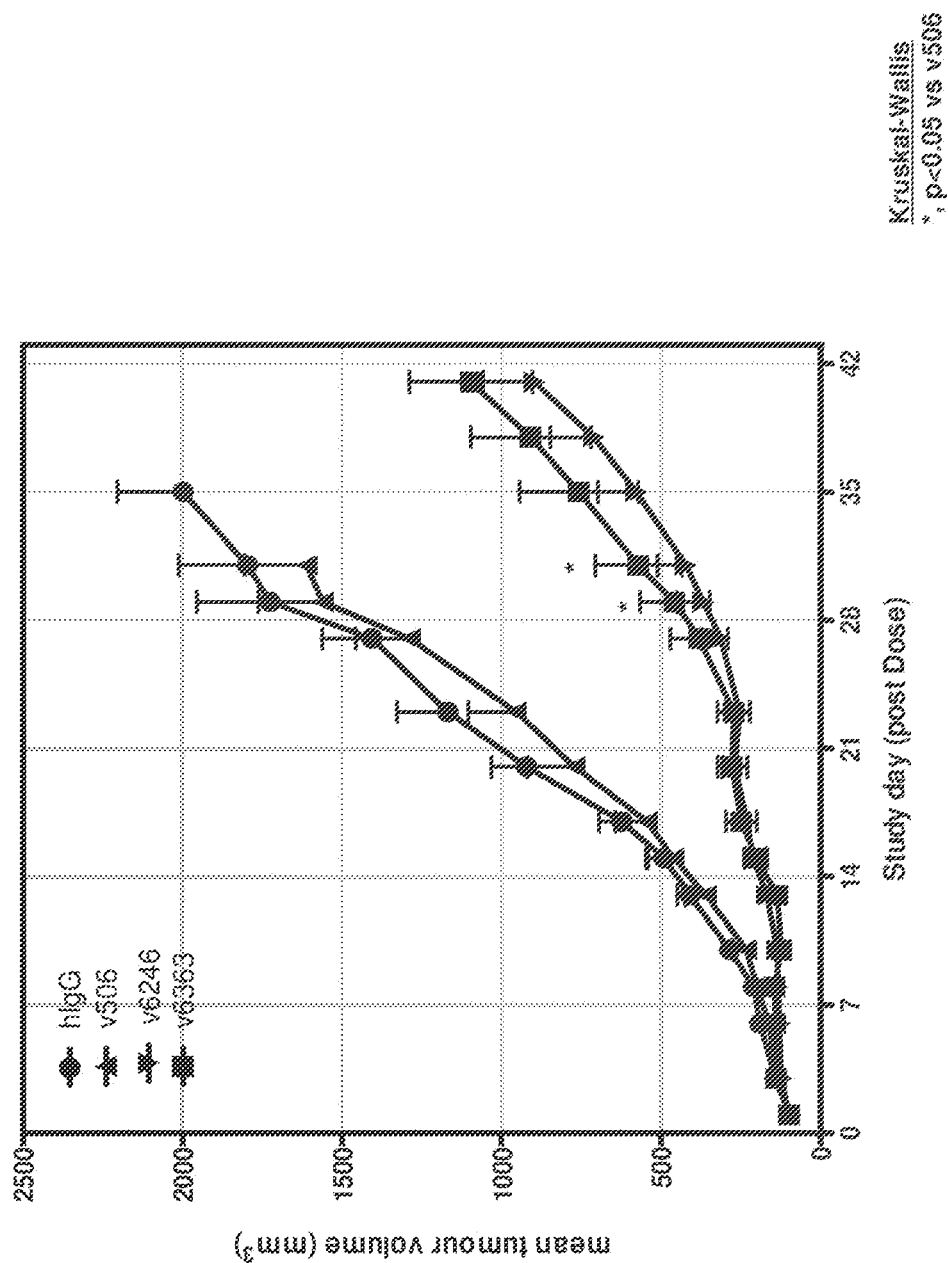
FIG. 21 depicts the effect of a biparatopic anti-HER2 antibody drug conjugate (ADC) on mean tumour volume in a human breast primary cell xenograft model (T226).

Tumor volume was measured throughout the course of the study, and mean tumor volume and complete response parameters were assessed at day 31. The results are shown in FIG. 21. A summary of the results is shown in Table 20.

The biparatopic anti-HER2-ADC and anti-HER2 FSA-ADC demonstrated better tumor growth inhibition compared to the anti-HER2 FSA (v506) and IgG control. The exemplary biparatopic anti-HER2-ADC induced equivalent tumor growth inhibition and complete baseline regression compared to anti-HER2 FSA-ADC (FIG. 21 and Table 20) in this model.

TABLE 20

| Day 31 | IgG (n = 13) | v506 (n = 13) | v6246 (n = 16) | v6363 (n = 16) |
| --- | --- | --- | --- | --- |
| Mean TV (mm3) | 1797 | 1611 | 422 | 572 |
| (% change from Baseline) | (+1728%) | (+1573%) | (+332%) | (+483%) |
| % TGI (vs. hIgG) | 0% | 11% | 77% | 68% |
| Complete response (>10% baseline regression) | 0/13 | 0/14 | 1/16 | 1/16 |

Example 20: Effect of a Biparatopic Anti-HER2 Antibody Drug Conjugate (ADC) in a Human Primary Cell Xenograft Model (HBCx-5)

The patient derived trastuzumab resistant xenograft model from human breast cancer, HBCx-5 (invasive ductal carcinoma, luminal B), was used to assess the anti-tumor efficacy of an exemplary biparatopic anti-HER2-ADC.

Female athymic nude mice were inoculated with the tumor via the insertion of a 20 mm$^3$ tumor fragment subcutaneously. Tumors were monitored until they reached an average volume of 100 mm$^3$; animals were then randomized into 4 treatment groups: IgG control (n=15), anti-HER2 FSA (v506; n=15), anti-HER2 FSA-ADC (v6246; n=16), and the biparatopic anti-HER2-ADC (v6363; n=16). Dosing for each group was as follows:

A) IgG control was dosed intravenously with a loading dose of 15 mg/kg on study day 1 and maintenance doses of 10 mg/kg administered on study days 4, 8, 11, 15, 18, 22, and 25

B) Anti-HER2 FSA was dosed intravenously with a loading dose of 15 mg/kg on study day 1 and maintenance doses of 10 mg/kg administered on study days 4, 8, 11, 15, 18, 22, and 25

C) Anti-HER2 FSA-ADC was dosed intravenously with 10 mg/kg on study days 1 and 15, 22, 29, 36

D) Biparatopic anti-HER2-ADC was dosed intravenously with 10 mg/kg on study days 1 and 15, 22, 29, 36.

Figure 22:
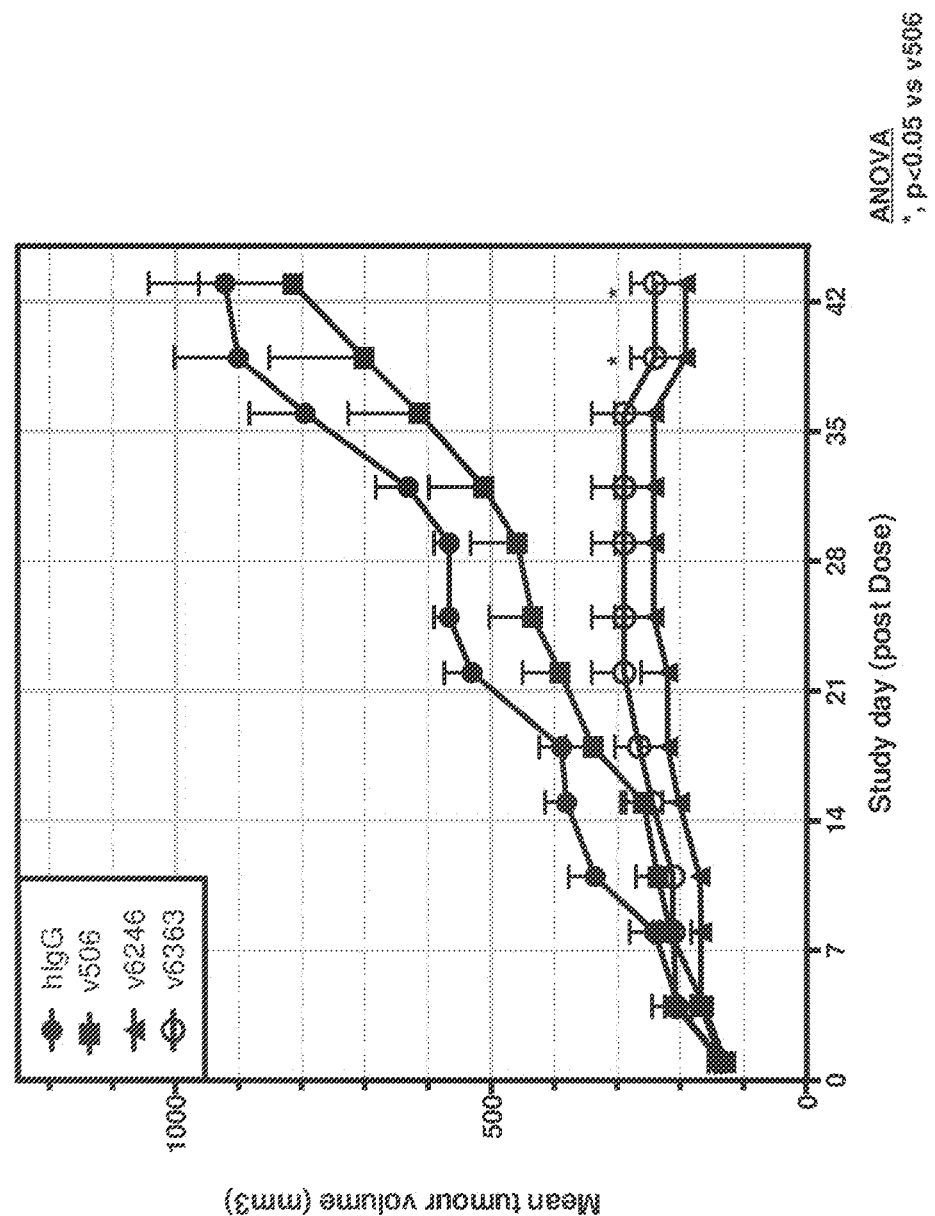
FIG. 22 depicts the effect of a biparatopic anti-HER2 antibody drug conjugate (ADC) on mean tumour volume in a human breast primary cell xenograft model (HBCx-5).

Tumor volume was measured throughout the course of the study, and the mean tumor volume, T/C ratio, number of responders, complete response, and zero residual disease parameters were assessed at day 43. The results are shown in FIG. 22. A summary of the results is shown in Table 21.

The biparatopic anti-HER2-ADC and anti-HER2 FSA-ADC demonstrated better tumor growth inhibition compared to an anti-HER2 FSA (v506) and IgG control. The exemplary biparatopic anti-HER2-ADC induced equivalent tumor growth inhibition and had an increased number of responders compared to anti-HER2 FSA-ADC (FIG. 22 and Table 21) in the trastuzumab resistant HBCx-5 human breast cancer xenograft model.

TABLE 21

| Day 43 | IgG (n = 4) | Herceptin (n = 5) | T-DM1 (n = 7) | 6363 (n = 7) |
| --- | --- | --- | --- | --- |
| Mean TV (mm3) | 922 | 815 | 193 | 241 |
| (% change from Baseline) | (+693%) | (+598%) | (+65%) | (+106%) |
| T/C (IgG) ratio | 1 | 0.88 | 0.21 | 0.26 |

TABLE 21-continued

| Day 43 | IgG (n = 4) | Herceptin (n = 5) | T-DM1 (n = 7) | 6363 (n = 7) |
| --- | --- | --- | --- | --- |
| Responders (TV <50% of control) | 0/4 | 1/5 | 6/7 | 7/7 |
| Complete response (>10% baseline regression) | 0/4 | 0/5 | 1/7 | 0/7 |
| Zero residual disease (TV <20 mm3) | 0/4 | 0/5 | 0/7 | 0/7 |

Example 21: Effect of a Biparatopic Anti-HER2 Antibody Drug Conjugate (ADC) to Anti-HER2 Treatment Resistant Tumors in a Human Cell Line Xenograft Model (SKOV3)

The established human ovarian cancer cell derived xenograft model SKOV3, described in Example 17, was used to assess the anti-tumor efficacy of an exemplary biparatopic anti-HER2-ADC in anti-HER2 treatment resistant tumors.

The methods were followed as described in Example 17 with the following modifications. A cohort of animals was dosed with an anti-HER2 antibody intravenously with 15 mg/kg on study day 1 and with 10 mg/kg on day 4, 8, 15; however, this treatment failed to demonstrate an efficacious response by day 15 in this model. This treatment group was then converted to treatment with the exemplary biparatopic anti-HER2 antibody drug conjugate (v6363) and was dosed with 5 mg/kg and on study day 19 and 27 and 15 mg/kg on study day 34, 41 and 48.

Tumor volume was measured twice weekly throughout the course of the experiment.

Figure 23:
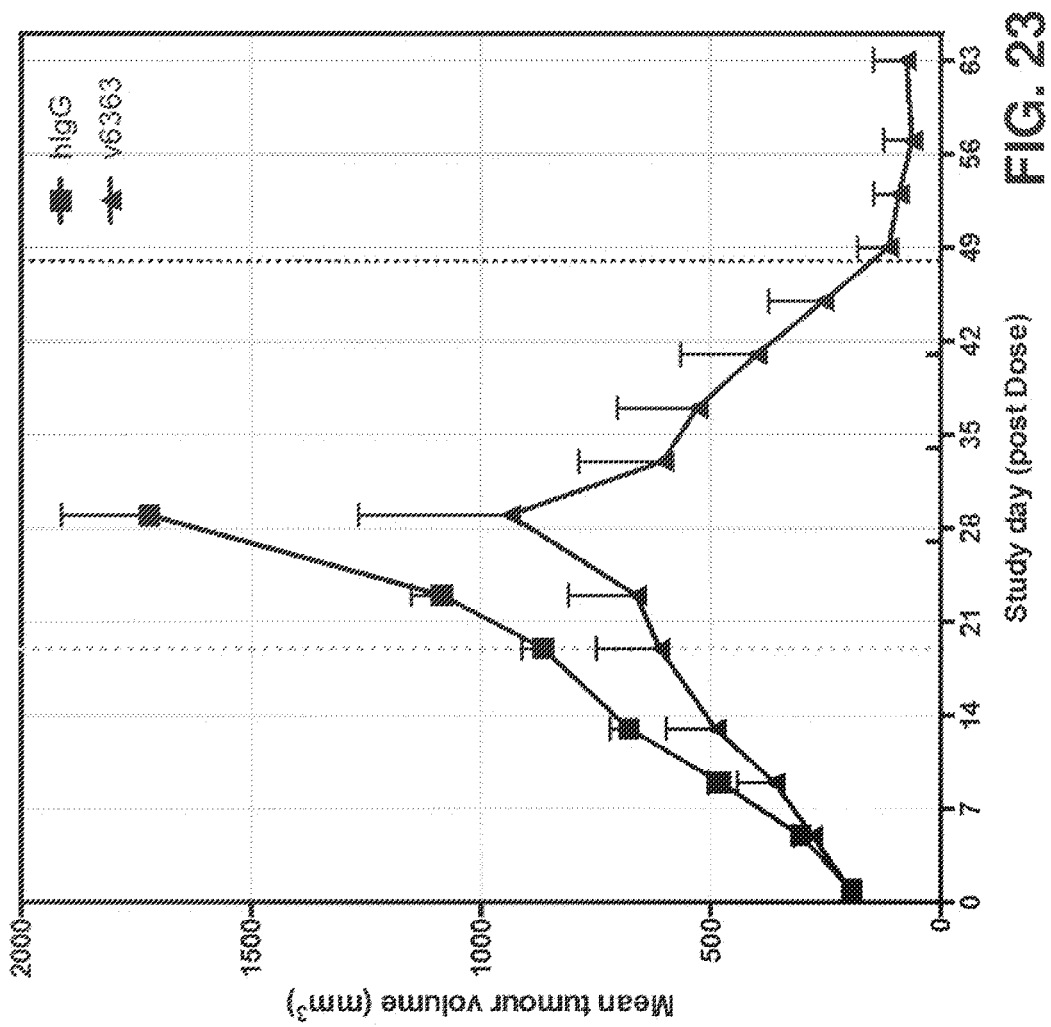
FIG. 23 depicts the effect of a biparatopic anti-HER2 antibody drug conjugate (ADC) on anti-HER2 treatment resistant tumors in a human cell line xenograft model (SKOV3).

The results are shown in FIG. 23 and indicate that the group treated with exemplary biparatopic anti-HER2-ADC (v6363) showed tumor regression to a mean tumor volume less than the initial mean starting volume of 220 mm$^3$.

Example 22: Effect of a Biparatopic Anti-HER2 Antibody Drug Conjugate (ADC) on Anti-HER2 Treatment Resistant Tumors in Human Primary Cell Xenograft Model (HBCx-13b)

The trastuzumab resistant patient derived xenograft model from human breast cancer, HBCx-13B, was used to assess the anti-tumor efficacy of an exemplary biparatopic anti-HER2 antibody conjugated to DM1.

The methods were followed as described in Example 18 with the following modifications. A cohort of animals was dosed with a bi-specific anti-ErbB family targeting antibody intravenously with 15 mg/kg on study day 1 and with 10 mg/kg on day 4, 8, 15, 18, 22, and 25; however, this treatment failed to demonstrate an efficacious response. This treatment group was then converted to treatment with the exemplary biparatopic anti-HER2 antibody drug conjugate (v6363) and was dosed with 10 mg/kg on days 31, 52 and with 5 mg/kg on day 45. Tumor volume was measured throughout the duration of the study.

Figure 24:
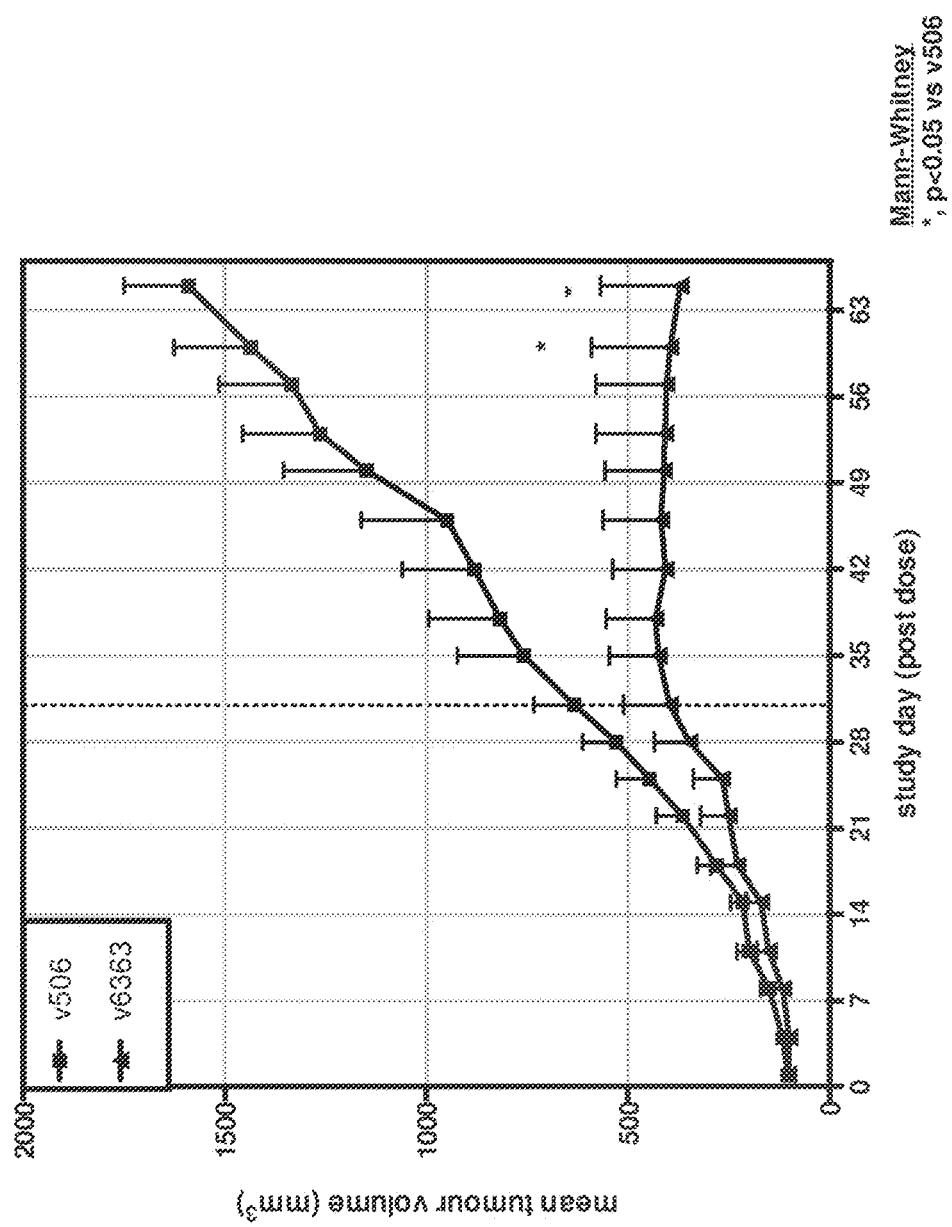
FIG. 24 depicts the effect of a biparatopic anti-HER2 antibody drug conjugate (ADC) to anti-HER2 treatment resistant tumors in human primary cell xenograft model (HBCx-13b).

The results are shown in FIG. 24. These results show that the exemplary biparatopic anti-HER2-ADC (v6363) prevented tumour progression. From the first dose to day 57 the tumour volume of the v6363 treated group increased by less than 2% while in the same interval the v506 treated group grew by more than 110%.

Example 23: Analysis of Fucose Content of an Exemplary Biparatopic Anti-HER2 Antibody Glycopeptide analysis was performed to quantify the fucose content of the N-linked glycan of the exemplary biparatopic anti-HER2 antibodies (v5019, v7091 and v10000).

The glycopeptide analysis was performed as follows. Antibody samples were reduced with 10 mM DTT at 56° C. 1 h and alkylated with 55 mM iodoacetamide at RT 1 h and digested in-solution with trypsin in 50 mM ammonium bicarbonate overnight at 37° C. Tryptic digests were analyzed by nanoLC-MS/MS on a QTof-Ultima. The NCBI database was searched with Mascot to identify protein sequences. MaxEnt3 (MassLynx) was used to deconvolute the glycopeptide ions and to quantify the different glycoforms.

A summary of the glycopeptide analysis results is in Table 22. The N-linked glycans of exemplary biparatopic anti-HER2 antibodies (v5019, v7091 and v10000) are, approximately 90% fucosylated (10% N-linked glycans without fucose). The N-linked glycans of monospecific anti-HER2 FSA (v506) are, approximately 96% fucosylated (4% N-linked glycans without fucose) and Herceptin is approximately 87% fucosylated (4% N-linked glycans without fucose).

TABLE 22

Fc N-linked Glycopeptide Analysis

| Antibody Variant | Average % of Glycopeptides Observed With Fucose | Average % of Glycopeptides Observed Without Fucose | n |
|---|---|---|---|
| v506 | 96.4 | 3.6 | 5 |
| Herceptin ® | 86.5 | 13.4 | 4 |
| v5019 | 90.5 | 9.4 | 6 |
| v7091 | 89.9 | 26.9 | 3 |
| v10000 | 89.2 | 10.7 | 5 |

These results show that biparatopic anti-HER2 antibodies (with a heterodimeric Fc), expressed transiently in CHO cells, have approximately 3% higher fucose content in the N-glycan compared to commercial Herceptin®. The homodimeric anti-HER2 FSA (v506), expressed transiently in CHO cells, has the highest fucose content of approximately 96%.

Example 24: Thermal Stability of an Exemplary Biparatopic Anti-HER2 Antibody Thermal stability of exemplary biparatopic anti-HER2 antibodies (v5019, v7091 and v10000) and ADCs (v6363, v7148 and v10533) was measured by DSC as described below.

DSC was performed in the MicroCal™ VP-Capillary DSC (GE Healthcare) using a purified protein sample (anti-HER2 biparatopic antibodies and anti-HER2 biparatopic-ADCs) adjusted to about 0.3 mg/ml in PBS. The sample was scanned from 20 to 100° C. at a 60° C./hr rate, with low feedback, 8 sec filter, 5 min preTstat, and 70 psi nitrogen pressure. The resulting thermogram was analyzed using Origin 7 software.

Figure 25A:
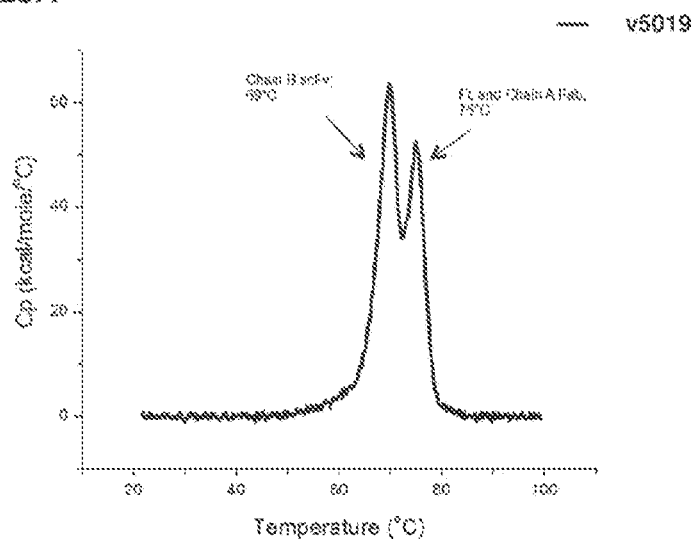
FIG. 25A depicts the thermal stability of exemplary anti-HER2 biparatopic antibodies.
Figure 25B:
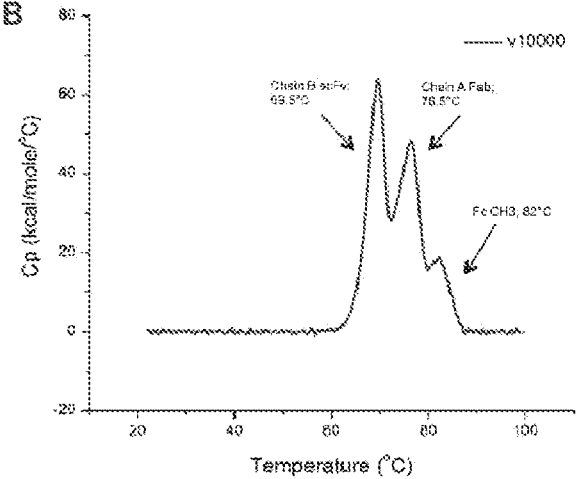
FIG. 25B depicts the thermal stability of exemplary anti-HER2 biparatopic antibodies.
Figure 25C:
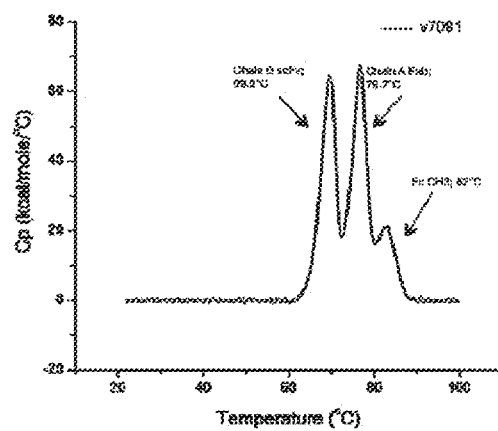
FIG. 25C depicts the thermal stability of v7091.

The thermal stability results of exemplary biparatopic anti-HER2 antibodies (v5019, v7091 and v10000) are shown in FIG. 25A-C. FIG. 25A shows the thermogram for v5019; the Fc and chain A Fab of each have a $T_m$ of 75° Celsius and the chain B scFv of 5019 has a $T_m$ of 69° Celsius. FIG. 25B shows the thermogram for v10000; the Fc CH3 domain has a $T_m$ 82° Celsius, Fab chain A has $T_m$ of 76.5° Celsius and the chain B scFv has a $T_m$ of 69.5° Celsius. FIG. 25C shows the thermogram for v7091; the Fc CH3 domain has a $T_m$ 82° Celsius, Fab chain A has $T_m$ of 76.7° Celsius and the chain B scFv has a $T_m$ of 69.5° Celsius.

Figure 26A:
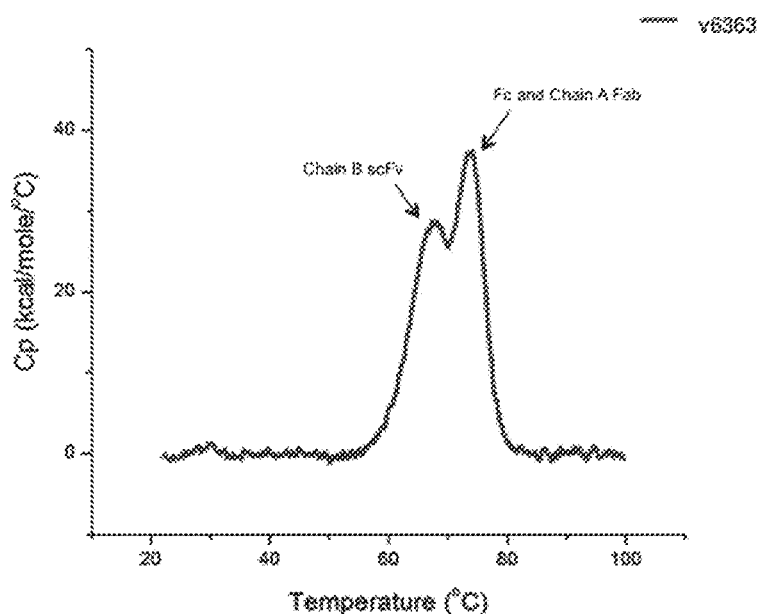
FIG. 26A depicts the thermal stability of exemplary anti-HER2 biparatopic antibody drug conjugates.
Figure 26B:
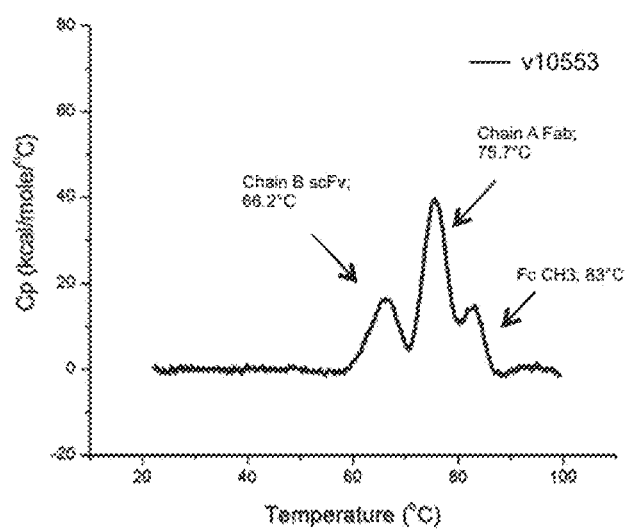
FIG. 26B depicts the thermal stability of exemplary anti-HER2 biparatopic antibody drug conjugates.
Figure 26C:
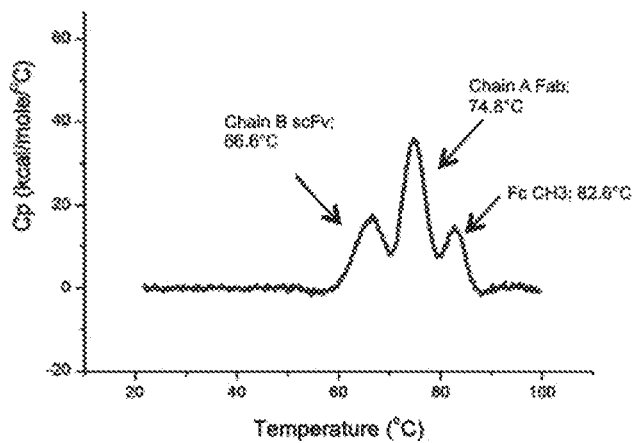
FIG. 26C depicts the thermal stability of exemplary anti-HER2 biparatopic antibody drug conjugates.

The thermal stability results of exemplary biparatopic anti-HER2 ADCs (v6363, v7148 and v10533) are shown in FIG. 26A-C. FIG. 26A shows the thermogram for v6363; the Fc has a $T_m$ of 75° Celsius and the chain A Fab and Fc CH3 domain have a $T_m$ of 75° Celsius. The chain B scFv of 6363 has a $T_m$ of 69° Celsius. FIG. 26B shows the thermogram for v10553; the Fc CH3 domain has a $T_m$ of 83° Celsius, the chain A Fab has a $T_m$ of 75.7° Celsius and the chain B scFv has a $T_m$ of 66.2° Celsius. FIG. 26C shows the thermogram for v7148; the Fc CH3 domain has a $T_m$ of 82.6° Celsius, the chain A Fab has a $T_m$ of 74.8° Celsius and the chain B scFv has a $T_m$ of 66.6° Celsius.

The exemplary biparatopic antibodies and ADCs have thermal stability comparable to wildtype IgG.

Example 25: Ability of an Exemplary Biparatopic Anti-HER2 Antibody to Elicit ADCC of Breast Tumor Cells Expressing Varying Levels of HER2

The ability of exemplary biparatopic antibody (v5019) to elicit dose-dependent ADCC of HER2 positive 3+, 2+, and 0/1+ HER2 expressing (triple-negative) breast cancer cell lines was examined. The ADCC experiments were performed as described in Example 11 with the exception that NK effector cell to target cell ratio remained constant at 5:1.

The ADCC results are shown in FIG. 27 and Table 23. The results in FIG. 27A-C show that exemplary biparatopic antibody (v5019) elicits approximately 1.2 to 1.3-fold greater maximum cell lysis of HER2 positive 3+, 2+ and 0/1+ HER2 expressing breast cancer cells compared to Herceptin®. The results also show that v5019 (90% N-glycans with fucose) more effectively mediates ADCC of HER2 positive 3+, 2+ and 0/1+ HER2 expressing breast cancer despite having approximately a 4% higher fucose content in the N-glycan (resulting in lower binding affinity to CD16 on NK cells) compared to Herceptin® (86% N-glycans with fucose; Example 23). The higher target cell killing elicited by v5019 is presumably due to increased tumor cell decoration as described in Example 6.

TABLE 23

ADCC of HER2 3+, 2+ and 0/1+ HER2 expressing breast cancer cells

| | SKBr3 HER2 3+ | | JIMT-1 HER2 2+ | | MDA-MB-231 HER2 0/1+ | |
|---|---|---|---|---|---|---|
| Treatment | Max % Target Cell Lysis | EC$_{50}$ (nM) | Max % Target Cell Lysis | EC$_{50}$ (nM) | Max % Target Cell Lysis | EC$_{50}$ (nM) |
| v5019 | 30 | −0.9 | 60 | 0.001 | 53 | 0.9 |
| Herceptin ® | 23 | −0.9 | 51 | 0.002 | 44 | 0.9 |

Figure 27A:
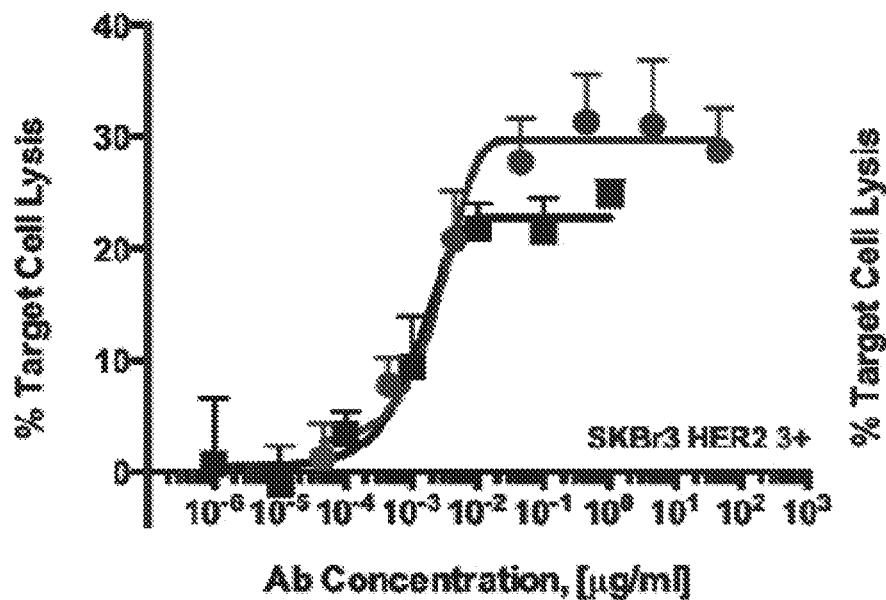
FIG. 27A depicts the ability of anti-HER2 biparatopic antibodies to mediate ADCC in HER2+ cells. The legend shown in FIG. 27C applies to FIG. 27A.
Figure 27B:
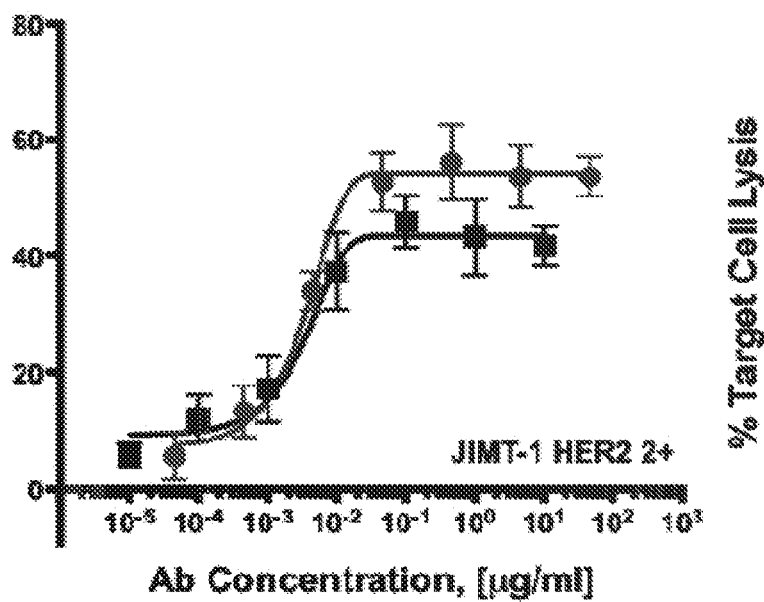
FIG. 27B depicts the ability of anti-HER2 biparatopic antibodies to mediate ADCC in HER2+ cells. The legend shown in FIG. 27C applies to FIG. 27B.
Figure 27C:
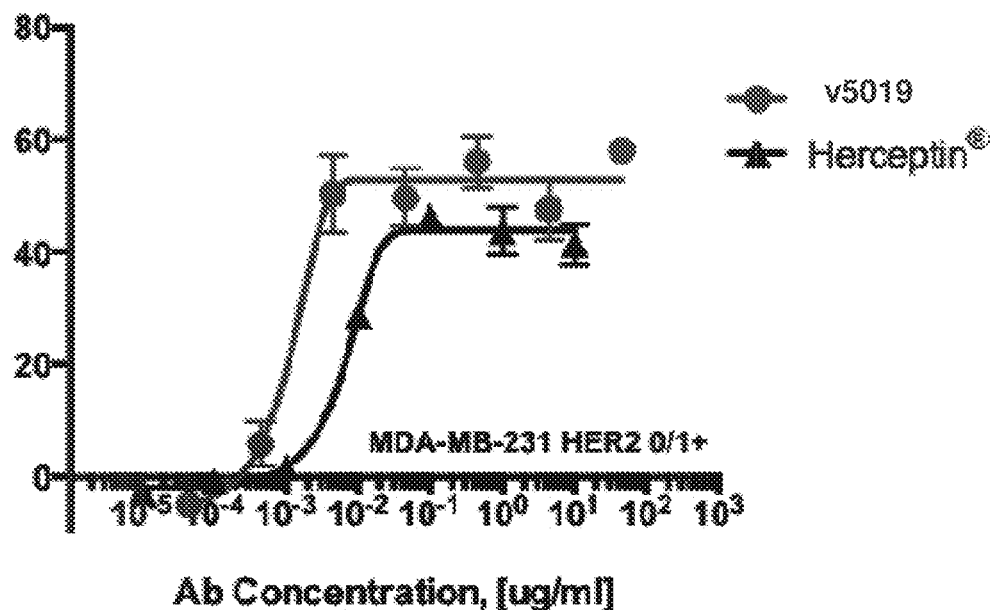
FIG. 27C depicts the ability of anti-HER2 biparatopic antibodies to mediate ADCC in HER2+ cells.
Figure 27D:
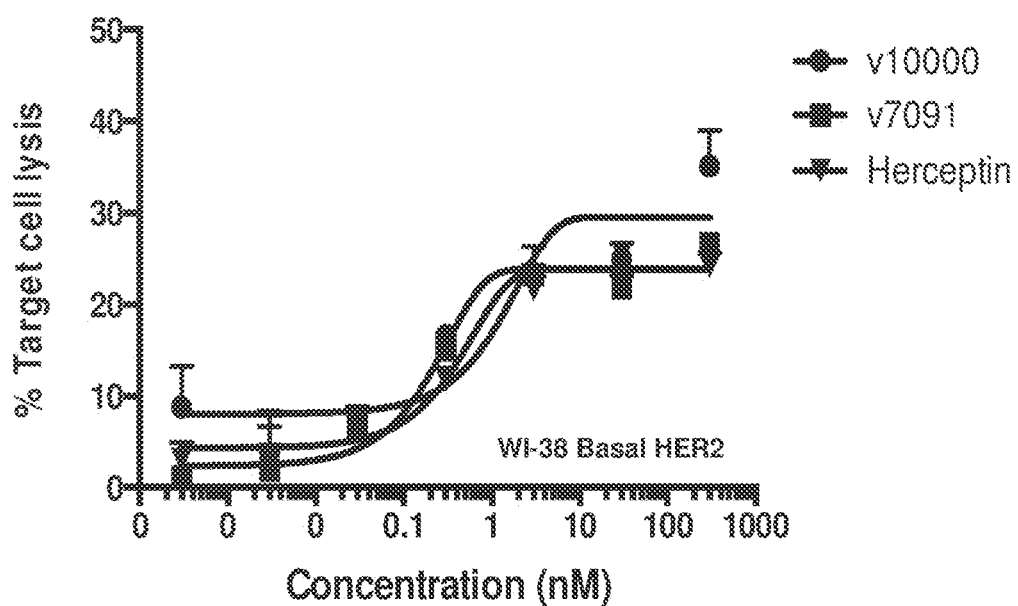
FIG. 27D depicts the ability of anti-HER2 biparatopic antibodies to mediate ADCC in HER2+ cells.

The ADCC results in FIG. 27D show that exemplary biparatopic antibodies (v7091 and v10000) elicit similar maximal cell lysis compared to Herceptin® in the basal HER2 expressing WI-38 cell line. The ADCC results support the cell binding data (Example 6), showing that a threshold for increased binding and ADCC occurs when the HER2 receptor levels are greater than 10,000 HER2/cell. Based on this data it would be expected that the exemplary biparatopic anti-HER2 antibodies would have increased cell surface binding and ADCC of HER2 3+, 2+ and 1+ tumor cells but would not have increase cell surface binding and ADCC of non-tumor cells that express basal levels of the HER2 receptor at approximately 10,000 receptors or less.

Example 26: Effect of Antibody Afucosylation on ADCC

The ability of afucosylated exemplary biparatopic antibodies (v5019-afuco, 10000-afuco) to elicit dose-dependent ADCC of HER2 positive 2/3+, 2+ and 0/1+ HER2 expressing (triple-negative) breast cancer cell lines, was examined ADCC experiments were performed as described in Example 11, in SKOV3 cells, MDA-MB-231 cells and ZR75-1 cells with the exception that a constant NK effector cell or PBMC effector to target (E:T) cell ratio of 5:1 was used. Afucosylated exemplary biparatopic antibodies were produced transiently in CHO cells as described in Example 1, using the transiently expressed RMD enzyme as described in von Horsten et al. 2010 Glycobiology 20:1607-1618. The fucose content of v5019-afuco and v10000-afuco were measured as described in Example 23 and determined to be less <2% fucosylated (data not shown). Data using NK effector cells is shown in FIG. 28A-B, while data using PBMCs is shown in FIG. 28C.

Figure 28A:
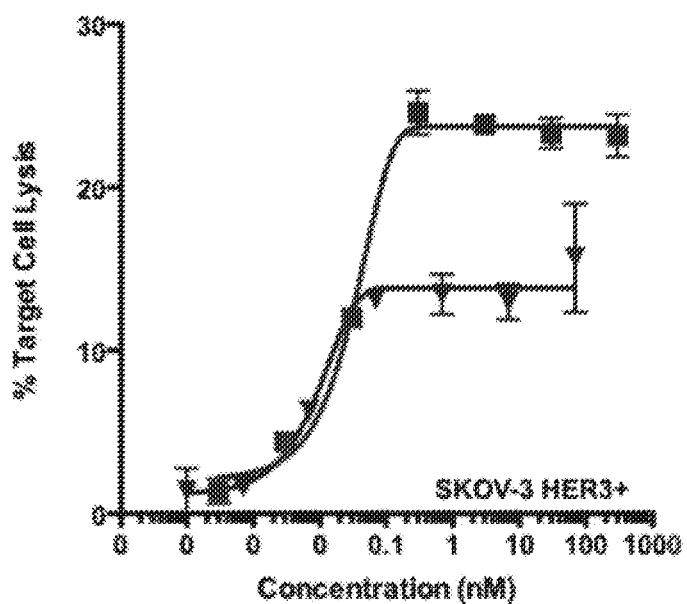
FIG. 28A depicts the effect of afucosylation on the ability of anti-HER2 biparatopic antibodies to mediate ADCC. The legend shown in FIG. 28B applies to FIG. 28A as well.
Figure 28B:
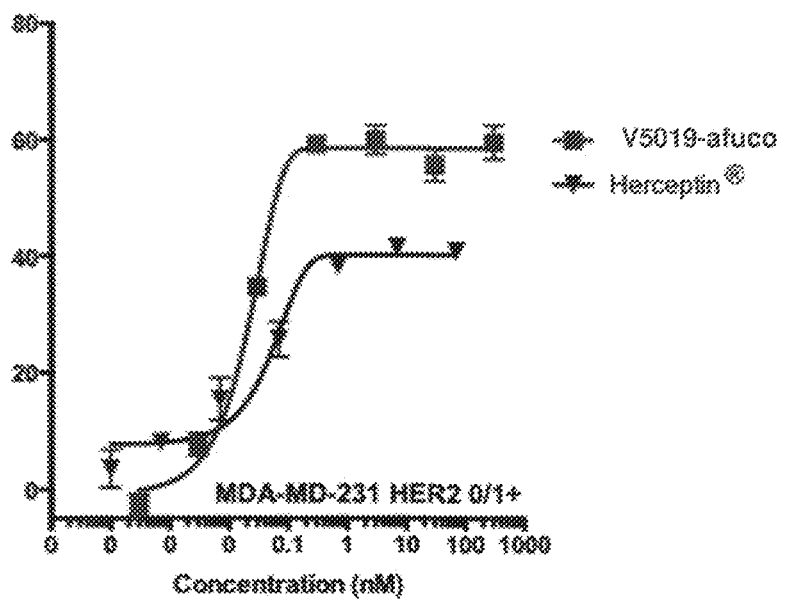
FIG. 28B depicts the effect of afucosylation on the ability of anti-HER2 biparatopic antibodies to mediate ADCC.
Figure 28C:
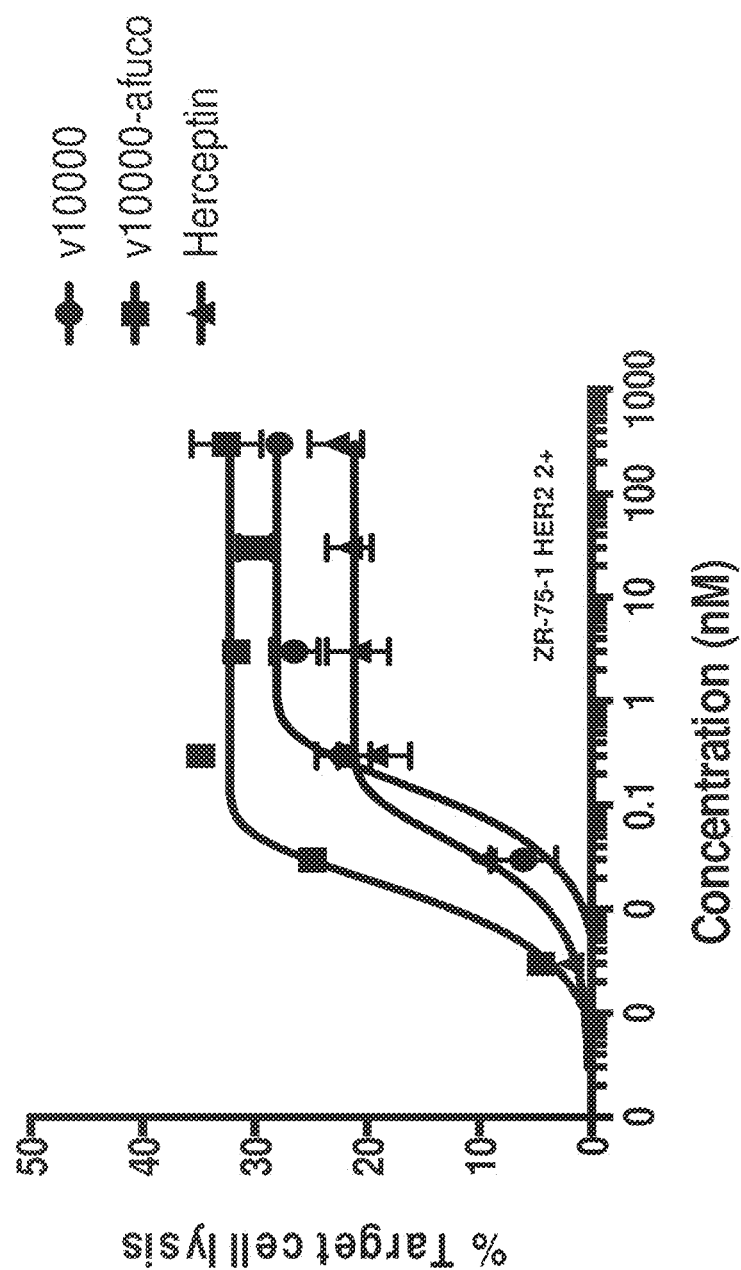
FIG. 28C depicts the effect of afucosylation on the ability of anti-HER2 biparatopic antibodies to mediate ADCC.

FIG. 28A, FIG. 28B and Table 24 show that afucosylated v5019 (v5019-afuco) elicits ADCC of HER 2/3+ and 0/1+ HER2 expressing breast cancer cells with approximately 1.5 to 1.7-fold higher maximum cell lysis than Herceptin®.

TABLE 24

ADCC of HER2 2/3+ and basal HER2 expressing (triple-negative) breast cancer cells

| | SKOV3 HER2 2+/3+ | | MDA-MD-231 HER2 0/1+ | |
|---|---|---|---|---|
| Treatment | Max % Target Cell Lysis | $EC_{50}$ (nM) | Max % Target Cell Lysis | $EC_{50}$ (nM) |
| v5019-afucosylated | 24 | ~0.6 | 58 | ~0.6 |
| Herceptin ® | 14 | ~0.6 | 40 | ~0.3 |

The results in FIG. 28C and Table 25 show that v10000 elicits ADCC of HER2 2+ ZR-75-1 breast cancer cells with approximately 1.3-fold greater maximal cell lysis than Herceptin®, and v10000-afuco elicits approximately 1.5-fold greater maximal cell lysis than Herceptin®.

TABLE 25

ADCC of HER2 2/3+ breast cancer cells

| | ZR-751 HER2 2+ | |
|---|---|---|
| Treatment | Max % Target Cell Lysis | $EC_{50}$ (nM) |
| v10000 | 28 | ~0.06 |
| v10000-afucosylated | 32 | ~0.7 |
| Herceptin ® | 21 | ~0.5 |

The ADCC results show that the exemplary afucosylated biparatopic antibodies (v5019-afuco, v10000-afuco) elicit approximately 15-25% greater maximum cell lysis compared to the fucosylated antibodies (v5019 Example 25, v10000) when Herceptin® is used as a benchmark. These results show that reducing the fucose content of the Fc N-glycan results in increased maximal cell lysis by ADCC.

Example 27: Ability of Exemplary Biparatopic Anti-HER2 Antibody to Inhibit Growth of HER2 3+ Breast Cancer Cells in the Presence of Exogenous Growth-Stimulatory Ligands (EGF and HRG)

The ability of 5019 to inhibit growth of HER2 3+ breast cancer cells in the presence of exogenous growth-stimulatory ligands (EGF and HRG) was examined.

Test antibodies and exogenous ligand (10 ng/mL HRG or 50 ng/mL EGF) were added to the target BT-474 HER2 3+ cells in triplicate and incubated for 5 days at 37° C. Cell viability was measured using AlamarBlue™ (37° C. for 2 hr), absorbance read at 530/580 nm. Data was normalised to untreated control and analysis was performed using Graph-Pad Prism.

Figure 29:
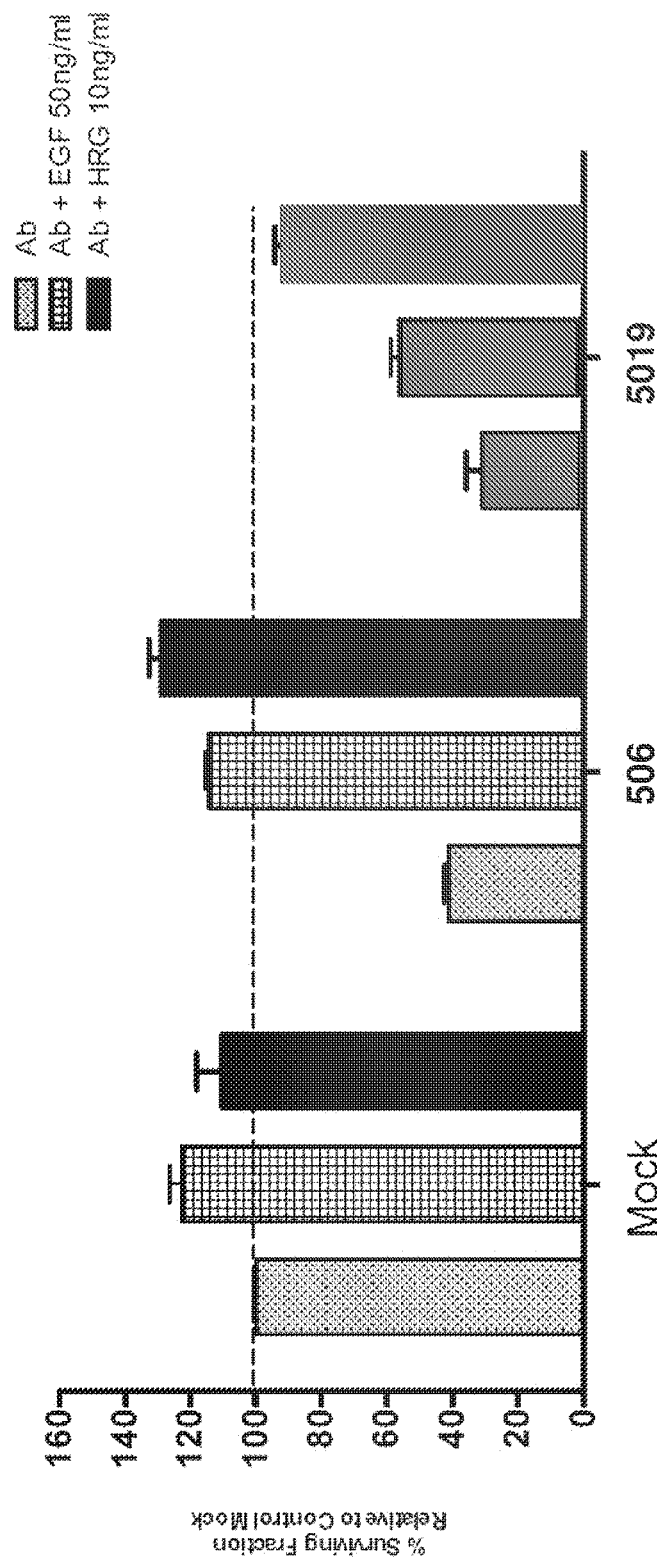
FIG. 29 depicts the ability of v5019 to inhibit growth of BT-474 cells in the presence or absence of growth-stimulatory ligands.

The results are shown in FIG. 29 and Table 26. The results show that exemplary biparatopic antibody v5019 inhibits the growth of HER2 3+ breast cancer cells in the absence of growth stimulatory ligand (70% inhibition), as well as in the presence of EGF (40% inhibition) or HRG (~10% inhibition). The anti-HER2 monospecific FSA (v506) does not block EGF or HRG induced tumor cell growth via other erbB receptors EGFR and HER3. v5019 is superior to v506 in inhibiting HER2 and ligand-dependent dimerization and growth via other companion erbB receptors.

TABLE 26

Growth Inhibition of HER2 3+ Cancer Cells

| | % Survival | | |
|---|---|---|---|
| Treatment | Antibody only | +EGF | +HRG |
| Mock | 100 | 122 | 110 |
| v506 | 41 | 114 | 129 |
| v5019 | 31 | 56 | 92 |

These results show that exemplary biparatopic antibody is capable of reducing ligand-dependent growth of HER2+ cells, presumably due binding of the anti-ECD2 chain A Fab arm and subsequent blocking of ligand stimulated receptor homo- and heterodimerization, and erbB signaling.

Example 28: Effect of a Biparatopic Anti HER2 Antibody in a Trastuzumab-Resistant and Chemotherapy Resistant HER2 3+ Patient-Derived (PDX) Metastatic Breast Cancer Xenograft Model of Invasive Ductal Breast Carcinoma The HER2 3+ (ER-PR negative) patient derived xenograft model from invasive ductal human breast cancer, HBCx-13B, was used to assess the anti-tumor efficacy of an exemplary biparatopic anti-HER2 antibody, v7187. v7187 is an afucosylated version of v5019. The model is resistant to single agent trastuzumab, the combination of trastuzumab and pertuzumab (see example 31), capecitabine, docetaxel, and adriamycin/cyclophosphamide.

Female athymic nude mice were inoculated subcutaneously with a 20 mm$^3$ tumor fragment. Tumors were then monitored until reaching an average volume of 140 mm3. Animals were then randomized into 2 treatment groups: vehicle control and v7187 with eight animals in each group. IV Dosing was as follows. Vehicle control was dosed intravenously with 5 ml/kg of formulation buffer twice per week to study day 43. v7187 was dosed intravenously with 10 mg/kg twice per week to study day 43. Tumor volume was measured throughout the study, and other parameters assessed at day 43 as shown in Table 27.

Figure 30:
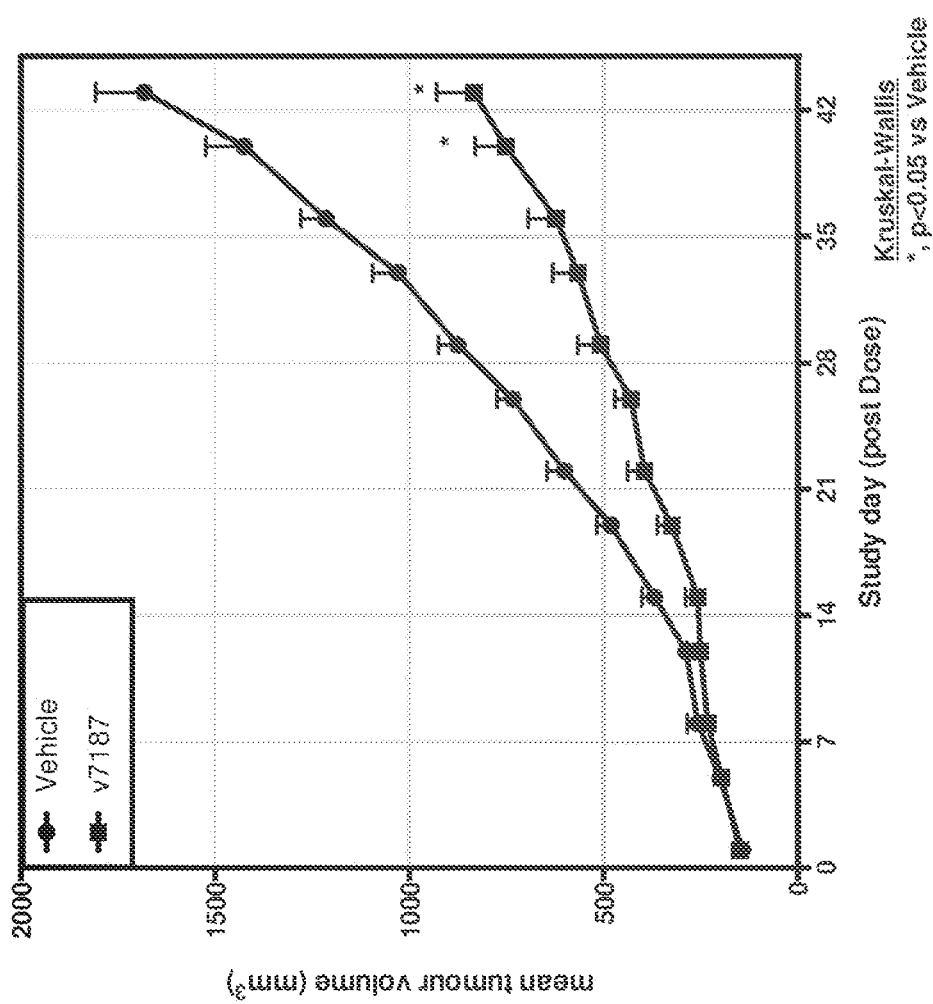
FIG. 30 depicts the effect of an afucosylated version of v5019 (v7187) on tumor volume in a human breast cancer xenograft model (HBCx13B).

The results are shown in FIG. 30 and Table 27. The results show that tumors treated with vehicle control showed continual progression and exceeded 1600 mm$^3$ by study day 43. Mice treated with v7187 showed significantly greater tumor growth inhibition (T/C—0.44) with a mean tumor volume of 740 mm$^3$ on day 43. v7187 induced responses in 5/8 tumors with a single tumor showing complete regression with zero residual disease on study day 43. Animals treated with v7187 had a superior response rate with 5/8 tumors responding to therapy compared to 0/8 mice treated with vehicle control. In addition, treatment with v7187 significantly delayed tumor progression compared to vehicle control with doubling times of 19 and 11 days respectively.

TABLE 27

| | Tumour Response | Vehicle | V7087 |
|---|---|---|---|
| Day 43 | Mean TV (mm3) | 1683 | 740 |
| | (% Change from Baseline) | (+1079%) | (+422%) |
| | T/C ratio | 1 | 0.44 |
| | Responders (TV <50% of control) | 0/8 | 5/8 |
| | PR (>10% baseline regression) | 0/8 | 1/8 |
| | ZRD (TV <20 mm3) | 0/8 | 1/8 |
| Time to progression | Doubling time (days) | 11 | 19 |

These data show that the exemplary anti-HER2 biparatopic (v7187) is efficacious in a Trastuzumab+Pertuzumab resistant HER2 3+ metastatic breast cancer tumor xenograft model. V7187 treatment has a high response rate and can significantly impair tumor progression of standard of care treatment resistant HER2 3+ breast cancers.

Example 29: Assessment of Biparatopic Anti-HER2 ADC Binding to HER2+ Tumor Cell Lines The ability of exemplary biparatopic anti-HER2 ADCs to bind and saturate HER2 positive 3+, 2+, breast and ovarian tumor cell lines was analyzed by FACS as described in Example 6.

The data is shown in FIG. 31. FIG. 31A shows v6363 binding to SKOV3 tumor cell lines with approximately a 2.0-fold greater Bmax (MFI) than T-DM1 (v6246) at saturating concentrations. FIG. 31B shows v6363 binds to JIMT-1 tumor cell lines with approximately a 1.6-fold greater Bmax (MFI) than T-DM1 (v6246) at saturating concentrations. These data show that v6363 (ADC) has similar tumor cell binding properties of increased cell surface binding compared to the parent unconjugated v5019 antibody (Example 6). Conjugation of v5019 with SMCC-DM1 (v6363) does not alter the antigen binding properties of the antibody.

Figure 31A:
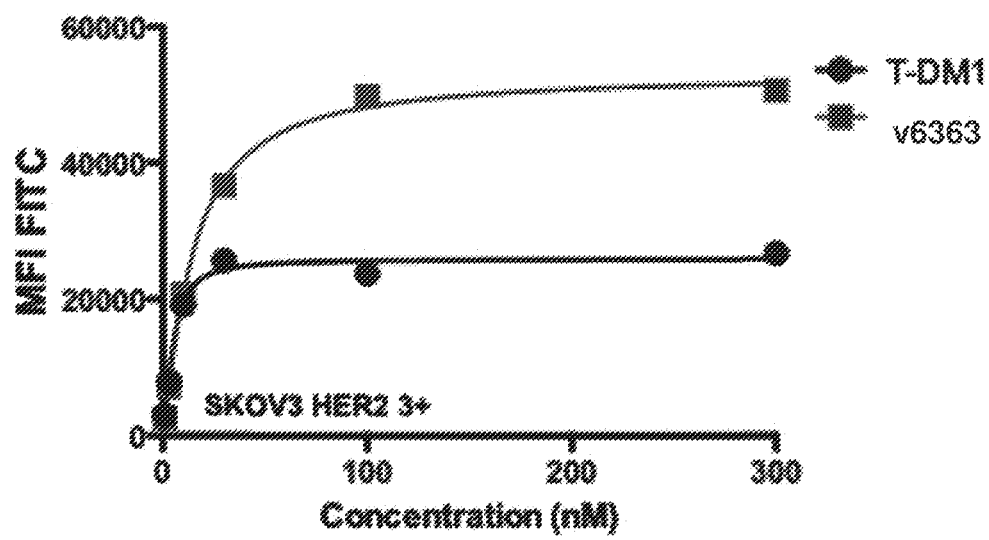
FIG. 31A depicts the ability of anti-HER2 biparatopic antibodies and anti-HER2 biparatopic-ADCs to bind to HER2+ tumor cells.
Figure 31B:
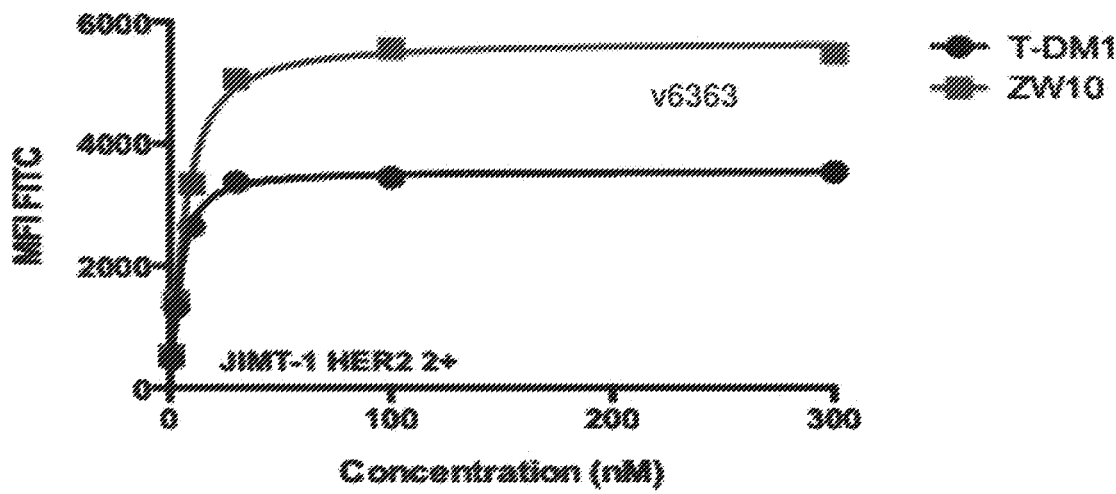
FIG. 31B depicts the ability of anti-HER2 biparatopic antibodies and anti-HER2 biparatopic-ADCs to bind to HER2+ tumor cells.
Figure 31C:
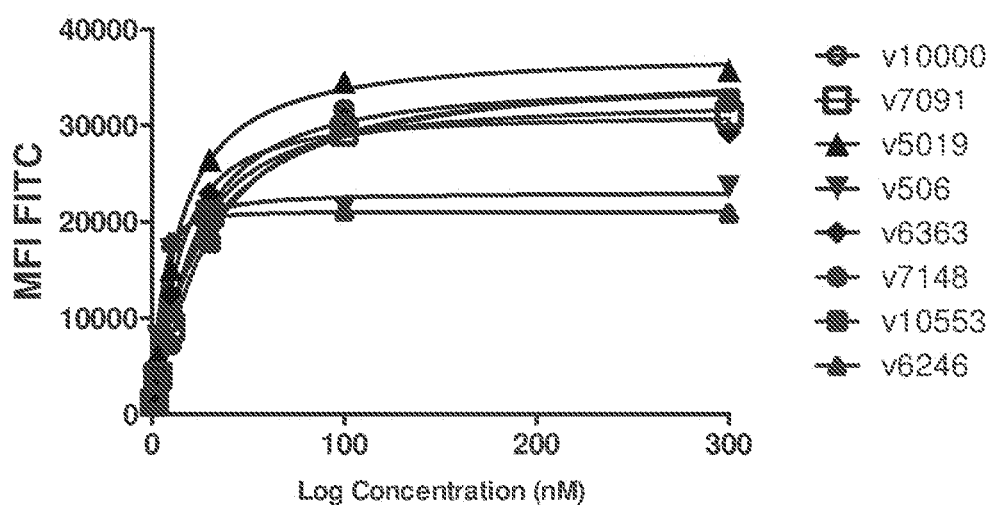
FIG. 31C depicts the ability of anti-HER2 biparatopic antibodies and anti-HER2 biparatopic-ADCs to bind to HER2+ tumor cells.
Figure 31D:
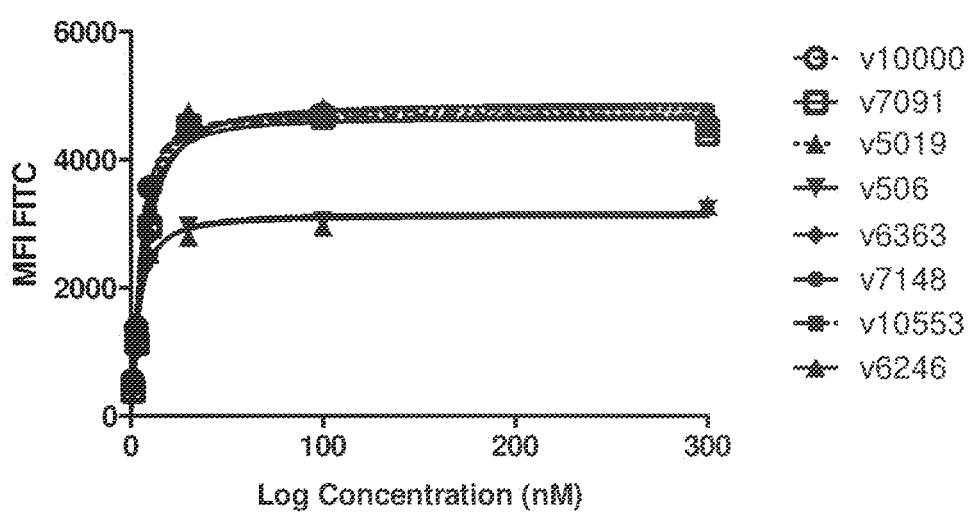
FIG. 31D depicts the ability of anti-HER2 biparatopic antibodies and anti-HER2 biparatopic-ADCs to bind to HER2+ tumor cells.

The FACS binding assay was repeated to include direct comparison to the exemplary biparatopic antibodies (v5019, v7091 and v10000) and ADCs (v6363, v7148 and v10553). The data is shown in FIG. 31C and FIG. 31D. The exemplary biparatopic anti-HER2 ADCs (v6363, v7148 and v10553) have equivalent cell surface saturation (Bmax) compared to the unlabeled biparatopic antibodies (v5019, v7091 and v10000).

These data show that conjugation of exemplary biparatopic antibodies (v5019, v7091 and v10000) with SMCC-DM1 does not alter the binding properties. The exemplary anti-HER2 biparatopic anti-HER2 ADCs (v6363, v7148 and v10553) have approximately 1.5-fold (or greater) increased cell surface binding compared to a monospecific anti-HER2 ADC (v6246, T-DM1).

Example 30: Dose-Dependent Tumour Growth Inhibition of an Exemplary Anti-HER2 Biparatopic-ADC in a HER2 3+ (ER-PR Negative) Patient Derived Xenograft Model The HER2 3+ (ER-PR negative) patient derived xenograft model from invasive ductal human breast cancer, HBCx-13B, was used to assess the anti-tumor efficacy of an exemplary biparatopic anti-HER2 ADC, v6363. The model is resistant to single agent trastuzumab, the combination of trastuzumab and pertuzumab (see example 31), capecitabine, docetaxel, and adriamycin/cyclophosphamide.

Female athymic nude mice were inoculated with the tumor via the subcutaneous insertion of a 20 mm$^3$ tumor fragment. Tumors were monitored until they reached an average volume of 160 mm$^3$; animals were then randomized into 5 treatment groups: non-specific human IgG control, and 4 escalating doses of v6363. 8-10 animals were included in each group. Dosing for each group was as follows. IgG control was dosed intravenously with 10 mg/kg twice per week to study day 29. v6363 was dosed intravenously with 0.3, 1, 3, or 10 mg/kg on study days 1, 15, and 29. Tumor volume was assessed throughout the study and parameters assessed as indicated in Table 29.

Figure 32B:
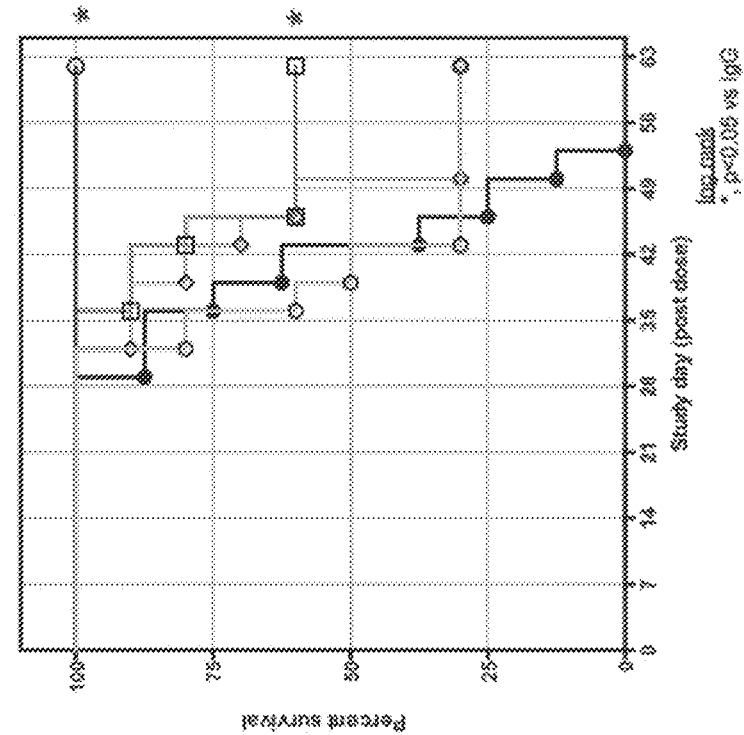
FIG. 32B depicts Dose-Dependent Tumour Growth Inhibition of an exemplary anti-HER2 biparatopic-ADC in a HER2 3+ (ER-PR negative) patient derived xenograft model (HBCx13b).
Figure 32A:
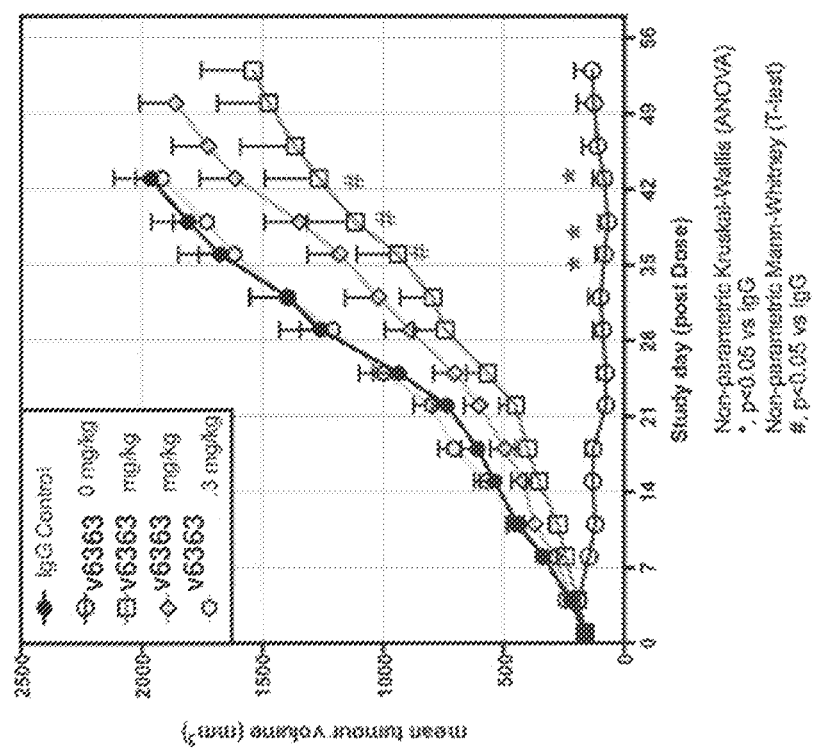
FIG. 32A depicts Dose-Dependent Tumour Growth Inhibition of an exemplary anti-HER2 biparatopic-ADC in a HER2 3+ (ER-PR negative) patient derived xenograft model (HBCx13b).

The results are shown in FIG. 32 and Table 28. These results show that the exemplary anti-HER2 biparatopic ADC (v6363) mediated dose-dependent tumor growth inhibition in the Trastuzumab-resistant HBCx-13b PDX model (FIG. 32A). In addition, v6363 improved overall survival in a dose-dependent manner, with median survival time of more than 63 days for 3 mg/kg and 10 mg/kg doses compared to 43 days for IgG control (FIG. 32B and Table 28). The 3 mg/kg dose was associated with an increased response rate (5/10) compared to control (0/8). All mice treated with v6363 at 10 mg/kg dose not only responded to therapy (9/9) but also showed prevention of tumor progression. Moreover, the majority of tumors had objective partial responses (7/9) and, at the end of the study, many had zero residual disease (6/9). v6363 was well tolerated at all doses, no adverse events were observed and no body weight loss was observed.

TABLE 28

| | Tumour Response | IgG | 6363 0.3 mg/kg | 6363 1 mg/kg | 6363 3 mg/kg | 6363 10 mg/kg |
|---|---|---|---|---|---|---|
| Day 43 | Mean TV (mm3) (% change from Baseline) | 1963 (+1119%) | 1916 (+1073%) | 1613 (+895%) | 1268 (+682%) | 84 (−49%) |

TABLE 28-continued

| Tumour Response | | IgG | 6363 0.3 mg/kg | 6363 1 mg/kg | 6363 3 mg/kg | 6363 10 mg/kg |
|---|---|---|---|---|---|---|
| | T/C (IgG) ratio | 1 | 0.97 | 0.82 | 0.64 | 0.04 |
| | Responders (TV <50% of control) | 0/8 | 0/10 | 2/10 | 5/10 | 9/9 |
| | PR (>10% baseline regression) | 0/8 | 0/10 | 0/10 | 0/10 | 7/9 |
| | ZRD (TV <20 mm3) | 0/8 | 0/10 | 0/10 | 0/10 | 6/9 |
| Time to progression | Tumor doubling time (days) | 9 | 9 | 14 | 17 | 52 |
| Survival Response | Median Survival (Days) | 43 | 41 | 50 | >63 | >63 |
| Body Weight | % Change from Baseline | +10% | +10% | +9% | +5% | +0% |

These data show that the exemplary anti-HER2 biparatopic ADC (v6363) is efficacious in a Trastuzumab+ Pertuzumab resistant HER2 3+ metastatic breast cancer tumor xenograft model. v6363 treatment is associated with a high response rate, significantly impairs tumor progression, and prolongs survival in a standard of care resistant HER2 3+ breast cancers.

Example 31: Biparatopic Anti-HER2-ADC Compared to Standard of Care Combinations in the Trastuzumab Resistant PDX HBCx-13b The efficacy of v6363 in a HER2 3+, ER-PR negative Trastuzumab resistant patient-derived breast cancer xenograft model (HBCx-13b), was evaluated and compared to to the combination of: Herceptin™+Perjeta™; and Herceptin™+Docetaxel.

Female athymic nude mice were inoculated with the tumor via the subcutaneous insertion of a 20 mm3 tumor fragment. Tumors were monitored until they reached an average volume of 100 mm3; animals were then randomized into 4 treatment groups (8-10 animals/group): non-specific human IgG control, Herceptin™+Docetaxel, Herceptin™+Perjeta™, and v6363. Dosing for each group was as follow.

IgG control was dosed intravenously with 10 mg/kg twice per week to study day 29. Herceptin™+Docetaxel combination Herceptin™ was dosed intravenously with 10 mg/kg IV twice weekly to study day 29 and Docetaxel was dosed intraperitoneally with 20 mg/kg on study day 1 and 22. Herceptin™+Perjeta™ combination Herceptin was dosed intravenously with 5 mg/kg twice per week to study day 29 and Perjeta™ was dosed intravenously with 5 mg/kg twice per week to study day 29. The dosing of Herceptin™ and Perjeta™ was concurrent. v6363 was dosed intravenously with 10 mg/kg on study day 1, 15, and 29.

Figure 33A:
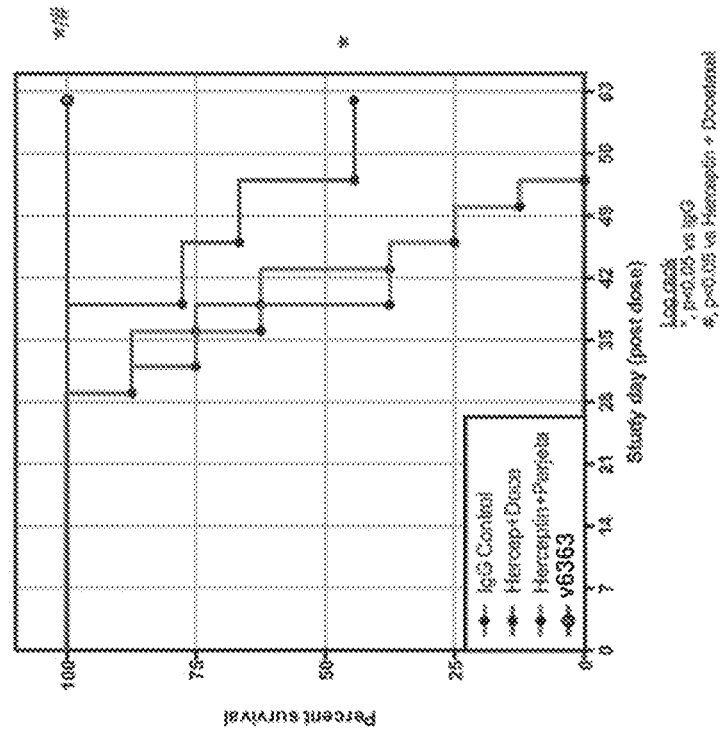
FIG. 33A depicts the effect of Biparatopic anti-HER2-ADC v6363 compared to Standard of Care Combinations in a Trastuzumab Resistant PDX HBCx-13b xenograft model.
Figure 33B:
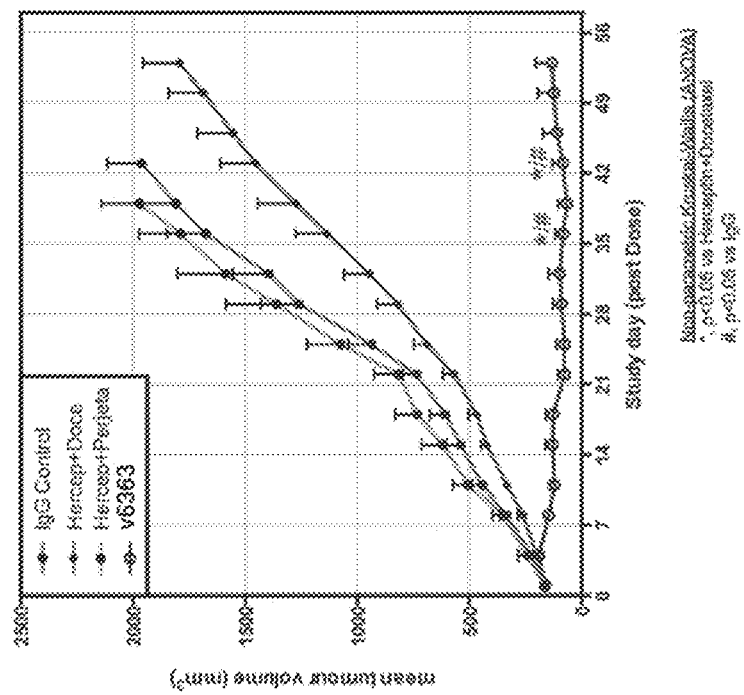
FIG. 33B depicts the effect of Biparatopic anti-HER2-ADC v6363 compared to Standard of Care Combinations in a Trastuzumab Resistant PDX HBCx-13b xenograft model.

The results are shown in FIG. 33 and Table 29. FIG. 33A shows tumor volume over time, and FIG. 33B shows a survival plot. These results show that the combination of Herceptin™+Perjeta™ did not produce any tumor growth inhibition compared to control IgG and exceeded 1800 mm³ on day 39. The combination of Herceptin™+Docetaxel did not significantly reduce tumor growth but did prolong median survival to 53 days compared to 43 days for IgG control. v6363 produced significant tumor growth inhibition (T/C—0.04), where, all tumors responded to therapy and 7/10 tumors experienced complete regressions (zero residual disease). v6363 significantly prolonged survival compared to both combination therapies. Body weights across cohorts were not significantly affected by treatments.

TABLE 29

| | Tumour Response | IgG | Herceptin ™ + Perjeta ™ | Herceptin ™ + Docetaxel | v6363 10 mg/kg |
|---|---|---|---|---|---|
| Day 39 | Mean TV (mm3) | 1809 | 1975 | 1328 | 76 |
| | (% change from Baseline) | (+1023%) | (+1085%) | (+714%) | (−54%) |
| | T/C (IgG) ratio | 1.0 | 1.10 | 0.73 | 0.04 |
| | Responders (TV <50% of control) | 0/8 | 0/8 | 1/10 | 9/9 |
| | PR (>10% baseline regression) | 0/8 | 0/8 | 0/10 | 8/9 |
| | ZRD (TV <20 mm3) | 0/8 | 0/8 | 0/10 | 6/9 |
| Survival Response | Median Survival (days) | 43 | 39 | 53 | >63 |
| Body Weight | % Change from Baseline | +10% | +7% | +3% | −2% |

These results show that exemplary anti-HER2 biparatopic ADC (v6363) is superior to standard of care combinations with respect to all parameters tested in this xenograft model.

Example 32: Efficacy of a Biparatopic Anti-HER2-ADC in HER2+ Trastuzumab-Resistant Breast Cancer Cell Derived Tumour Xenograft Model The efficacy of v6363 in a HER2 3+ Trastuzumab resistant breast cancer cell-derived (JIMT-1, HER2 2+) xenograft model was evaluated (Tanner et al. 2004. Molecular Cancer Therapeutics 3: 1585-1592).

Female RAG2 mice were inoculated with the tumor subcutaneously. Tumors were monitored until they reached an average volume of 115 $mm^3$; animals were then randomized into 2 treatment groups: Trastuzumab (n=10) and v6363. Dosing for each group was as follows. Trastuzumab was dosed intravenously with 15 mg/kg on study day 1 and 10 mg/kg twice per week to study day 26. v6363 was dosed intravenously with 5 mg/kg on study days 1 and 15 and with 10 mg/kg on day 23 and 30 and 9 mg/kg on day 37 and 44.

Figure 34:
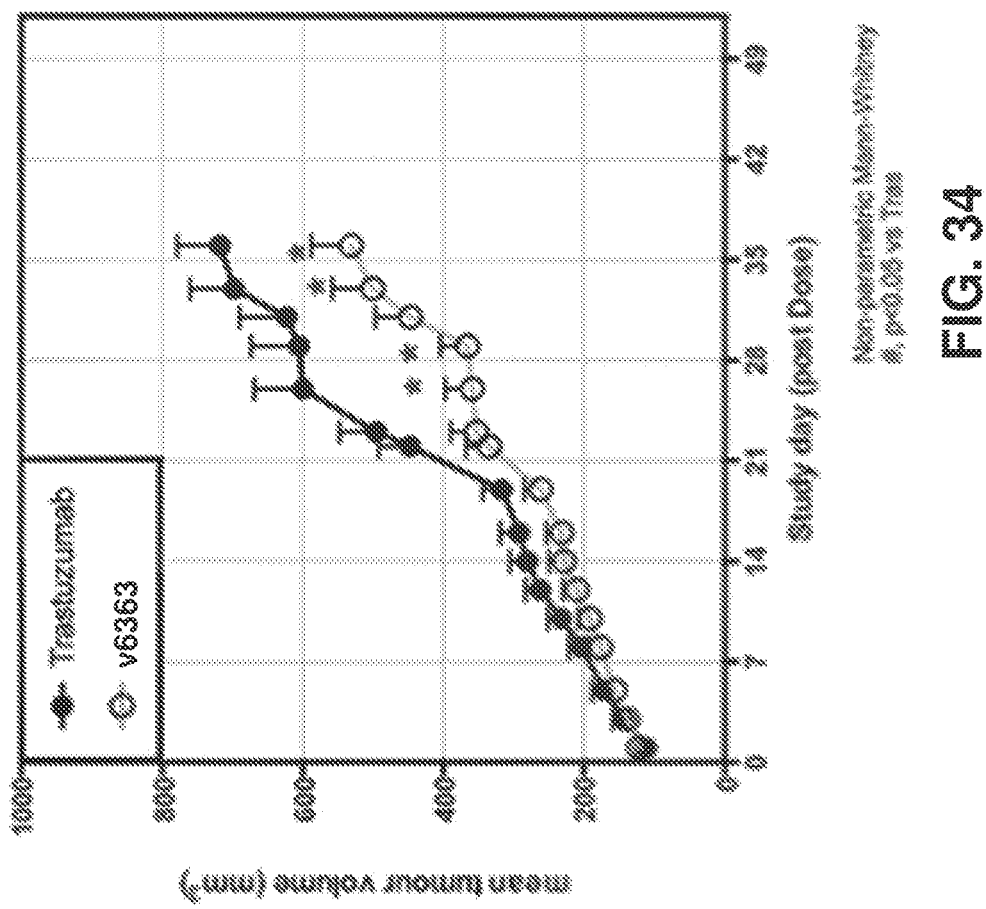
FIG. 34 depicts the efficacy of a biparatopic anti-HER2-ADC in HER2+ trastuzumab-resistant breast cancer cell derived tumour xenograft model (JIMT-1).

The results are shown in FIG. 34 and Table 30. These results show that v6363 significantly inhibited tumor growth (T/C—0.74) compared to Trastuzumab on study day 36. v6363 and Trastuzumab treatment did not significantly change body weight. v6363 serum exposure was 17.9 µg/ml 7 days after the first 10 mg/kg dose.

TABLE 30

| Tumour Response | | Trastuzumab | 6363 |
|---|---|---|---|
| Day 36 | Mean TV (mm3) (% change from Baseline) | 718 (+541) | 532 (+335%) |
| | T/C (Tras) ratio | 1 | 0.74 |
| | Responders (TV <50% of control) | 1/10 | 2/13 |
| | PR (>10% baseline regression) | 0/10 | 0/13 |
| | ZRD (TV <20 mm3) | 0/10 | 0/13 |
| Body Weight | % Change from Baseline | +5.8% | +3.1% |
| Drug Exposure (day 7) | Mean Serum Concentration (ug/ml) | 187.2 | 17.9 |

These results show that exemplary anti-HER2 biparatopic ADC (v6363) is efficacious in a Trastuzumab-resistant breast cancer and has a potential utility in treating breast cancers that are resistant to current standards of care.

Example 33: FcγR Binding to Heterodimeric Fc of Anti-HER2 Biparatopic Antibodies and Anti-HER2 Biparatopic-ADCs The binding of anti-HER2 biparatopic antibody (v5019, v7019 v10000) and ADC (v6363, v7148 and v10553) having a heterodimeric Fc, to human FcγRs was assessed and compared to anti-HER2 FSA (v506) and ADC (v6246) having a homodimeric Fc.

Affinity of FcγR to antibody Fc region was measured by SPR using a ProteOn XPR36 (BIO-RAD). HER2 was immobilized (3000 RU) on CM5 chip by standard amine coupling. Antibodies were antigen captured on the HER2 surface. Purified FcγR was injected various concentration (20-30 µl/min) for 2 minutes, followed by 4 minute dissociation. Sensograms were fit globally to a 1:1 Langmuir binding model. Experiments were conducted at 25° C.

The results are shown in Table 31. The exemplary heterodimeric anti-HER2 biparatopic antibodies and ADCs bound to CD16aF, CD16aV158, CD32aH, CD32aR131, CD32bY163 and CD64A with comparable affinities. Conjugation of the antibodies with SMCC-DM1 does not negatively affect FcγR binding. The heterodimeric anti-HER2 biparatopic antibodies have approximately 1.3 to 2-fold higher affinity to CD16aF, CD32aR131, CD32aH compared to homodimeric anti-HER2 FSA (v506) and ADC (v6246). These results show that the heterodimeric anti-HER2 biparatopic antibodies and ADCs bind different polymorphic forms of FcγRs on immune effector cells with similar or greater affinity than a WT homodimeric IgG1.

TABLE 31

Human FcγR Binding by SPR

| Variant | 10 uM CD16a v158 | | 10 uM CD16aF | | 10 uM CD32aR131 | | 10 uM CD32aH | | 10 uM CD32b Y163 | | 100 nM CD64A | |
|---|---|---|---|---|---|---|---|---|---|---|---|---|
| | KD Ave | SD | KD Ave | SD | KD Ave | SD | KD Ave | SD | KD Ave | SD | KD Ave | SD |
| v506 | 1.5E−07 | 2E−08 | 7.1E−07 | 1.E−08 | 7.6E−07 | 1.E−07 | 6.3E−07 | 2E−08 | 2.4E−06 | 1.E−07 | 8.64E−10 | 4.33E−10 |
| v6246 | 1.6E−07 | 2E−08 | 7.0E−07 | 9.E−09 | 7.4E−07 | 7.E−08 | 6.3E−07 | 2E−08 | 2.1E−06 | 7.E−08 | 1.08E−09 | 5.13E−10 |
| v10000 | 1.2E−07 | 1E−08 | 4.8E−07 | 2.E−08 | 5.1E−07 | 9.E−08 | 4.6E−07 | 2E−08 | 1.5E−06 | 7.E−08 | 8.41E−10 | 4.74E−10 |
| v10553 | 1.2E−07 | 2E−08 | 4.9E−07 | 2.E−07 | 3.5E−07 | 1.E−07 | 3.6E−07 | 4E−09 | 1.2E−06 | 7E−08 | 4.95E−10 | 1.41E−10 |
| v7091 | 1.2E−07 | 1E−08 | 5.1E−07 | 2.E−08 | 5.6E−07 | 9.E−08 | 5.0E−07 | 3E−08 | 1.7E−06 | 8E−08 | 9.68E−10 | 5.05E−10 |
| v7148 | 1.2E−07 | 2E−08 | 5.4E−07 | 2.E−07 | 3.7E−07 | 1.E−07 | 4.2E−07 | 1E−08 | 1.5E−06 | 1.E−07 | 5.77E−10 | 2.02E−10 |
| v5019 | 1.3E−07 | 1E−08 | 5.2E−07 | 1.E−07 | 5.6E−07 | 6.E−08 | 4.7E−07 | 2E−08 | 1.6E−06 | 2.E−08 | 8.44E−10 | 4.88E−10 |
| V6363 | 1.2E−07 | 2E−08 | 4.5E−07 | 1.E−07 | 3.5E−07 | 1.E−07 | 3.4E−07 | 1E−08 | 1.2E−06 | 5.E−08 | 4.58E−10 | 1.13E−10 |

Example 34: Efficacy of Exemplary Anti-HER2 Biparatopic Antibodies In Vivo in a Trastuzumab Sensitive Ovarian Cancer Cell Derived Tumour Xenograft Model The established human ovarian cancer cell derived xenograft model SKOV3, described in Example 17, was used to assess the anti-tumor efficacy of the exemplary biparatopic anti-HER2 antibodies, v5019, v7091 and v10000.

Female athymic nude mice were inoculated with a tumor suspension of 325,000 cells in HBSS subcutaneously on the left flank. Tumors were monitored until they reached an average volume of 190 mm$^3$ and enrolled in a randomized and staggered fashion into 4 treatment groups: non-specific human IgG control, v5019, v7091, and v10000. Dosing for each group was as follows. Non-specific human IgG was dosed intravenously with 10 mg/kg starting on study day 1 twice per week to study day 26. V5019, v7091, and v10000 were dosed intravenously with 3 mg/kg starting on study day 1 twice per week to study day 26. Tumor volume was measured throughout the study, and the parameters listed in Table 32 were measured at day 29.

Figure 35B:
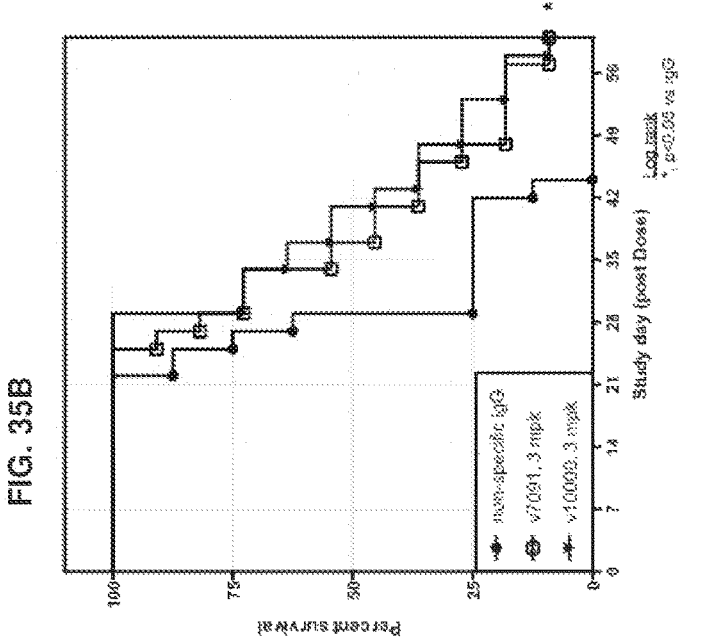
FIG. 35B depicts the efficacy of exemplary anti-HER2 biparatopic antibodies in vivo in a trastuzumab sensitive ovarian cancer cell derived tumour xenograft model (SKOV3).
Figure 35A:
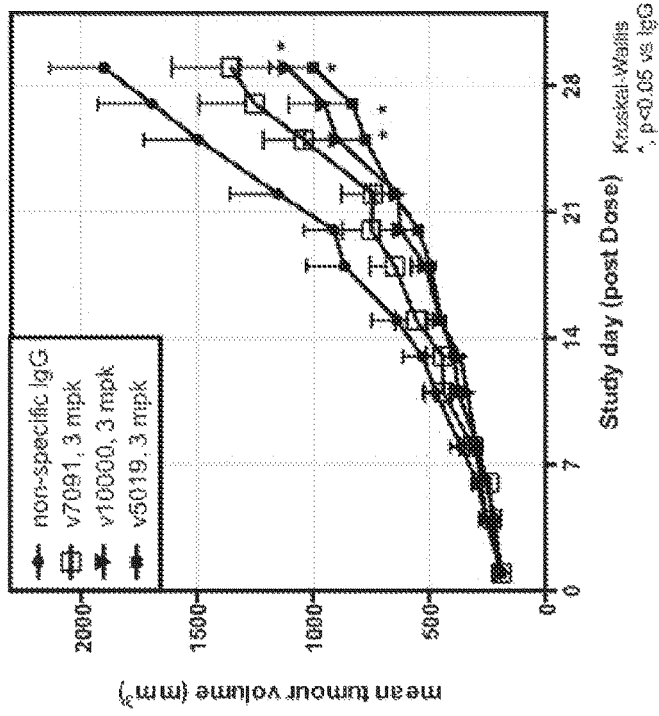
FIG. 35A depicts the efficacy of exemplary anti-HER2 biparatopic antibodies in vivo in a trastuzumab sensitive ovarian cancer cell derived tumour xenograft model (SKOV3).

The data are presented in FIG. 35A (tumor growth), FIG. 35B (survival plot) and Table 32 and show that treatment with v5019, v7091 and v10000 resulted in comparable tumor growth inhibition (T/C: 0.53-0.71), number of responding tumors, time to progression, and survival on study day 29 compared to IgG control. The serum exposure of v5019, v7091, and v10000 was similar (31-41 microg/ml) on study day 7.

TABLE 32

| Tumour Response | | IgG (n = 8) | v5019 (n = 11) | V7091 (n = 11) | V10000 (n = 11) |
|---|---|---|---|---|---|
| Day 29 | Mean TV (mm3) (% change from Baseline) | 1903 (+899%) | 1001 (+416%) | 1354 (+618%) | 1114 (+503%) |
| | T/C (Tras) ratio | 1 | 0.53 | 0.71 | 0.58 |
| | Responders (TV <50% of control) | 1/8 | 5/11 | 4/11 | 6/11 |
| | PR (>10% baseline regression) | 0/8 | 1/11 | 0/11 | 0/11 |
| | ZRD (TV <20 mm3) | 0/8 | 0/11 | 0/11 | 0/11 |
| Time to progression | Tumor doubling time (days) | 12 | 15 | 16 | 15 |
| Survival | Median survival (days) | 29 | Na | 37 | 41 |
| Drug Exposure (day 7) | Mean Serum Concentration (ug/ml) | na | 31.2 | 41.0 | 31.2 |

These results show that the exemplary anti-HER2 biparatopic antibodies, v5019, v7091, and v10000) have potential utility in treating moderately Trastuzumab sensitive HER2 overexpressing ovarian cancers.

Example 35: Exemplary Biparatopic Anti-Her2 Antibodies Dose-Dependently Inhibit Tumour Growth in the Trastuzumab-Sensitive Ovarian Cancer Cell Derived Tumour Xenograft The established human ovarian cancer cell derived xenograft model SKOV3, described in Example 17, was used to assess the dose-dependent efficacy of an exemplary biparatopic anti-HER2 antibody, v10000.

Female athymic nude mice were inoculated with a tumor suspension of 325,000 cells in HBSS subcutaneously on the left flank. Tumors were monitored until they reached an average volume of 190 mm$^3$ and enrolled in a randomized and staggered fashion into 6 treatment groups: non-specific human IgG control and 5 escalating doses of v10000. 9-13 animals were included in each group. Dosing for each group was as follows. IgG control was dosed intravenously with 10 mg/kg twice per week to study day 26. V10000 was dosed intravenously with 0.1, 0.3, 1, 3, or 10 mg/kg twice per week.

Figure 36:
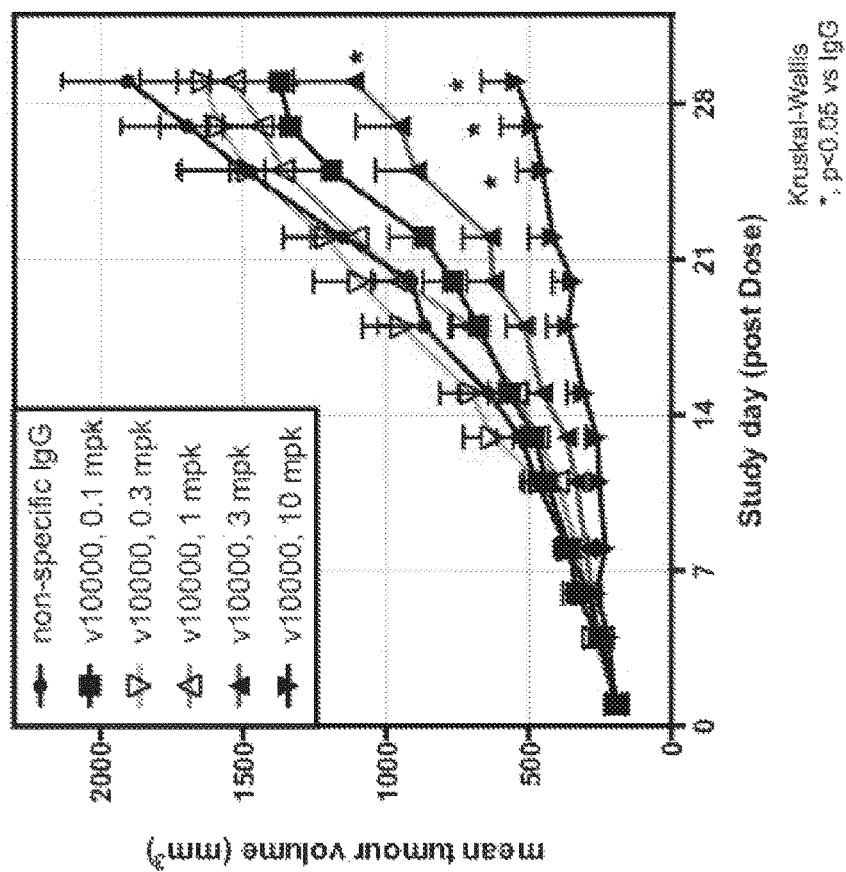
FIG. 36 depicts the dose-dependent efficacy of exemplary anti-HER2 biparatopic antibodies in vivo in a trastuzumab sensitive ovarian cancer cell derived tumour xenograft model (SKOV3).

The data are presented in FIG. 36 and Table 33 and show that treatment with v10000 dose dependently induces tumor growth inhibition (T/C: 0.28-0.73) compared to control IgG. In addition, v10000 was dose-dependently associated with responding tumors (7/9 at 10 mg/kg and 3/11 at 0.1 mg/kg) increased time to progression (24 days at 10 mg/kg and 12 days at 0.1 mg/kg) on study day 29. The serum exposure of v10000 on day 7 was dose dependent and increased from 0.46 microg/ml with a 0.1 mg/kg dose to 79.3 microg/ml with a 10 mg/kg dose.

TABLE 33

| Tumor Response | | IgG (n = 8) | V10000, 10 mg/kg (n = 9) | V10000, 3 mg/kg (n = 11) | V10000, 1 mg/kg (n = 11) | V10000, 0.3 mg/kg (n = 13) | V10000, 0.1 mg/kg (n = 11) |
|---|---|---|---|---|---|---|---|
| Day 29 | Mean TV (mm3) (% change from Baseline) | 1903 (+899%) | 543 (+281%) | 1114 (+503%) | 1534 (+688%) | 1535 (+694%) | 1385 (+643%) |
| | T/C ratio | 1 | 0.28 | 0.58 | 0.81 | 0.81 | 0.73 |
| | Responders (TV <50% of control) | 1/8 | 7/9 | 6/11 | 2/11 | 3/13 | 3/11 |
| | PR (>10% baseline regression) | 0/8 | 1/9 | 0/11 | 0/11 | 0/13 | 0/11 |
| | ZRD (TV <20 mm3) | 0/8 | 0/9 | 0/11 | 0/11 | 0/13 | 0/11 |
| Time to Progression | Tumor doubling time (days) | 12 | 24 | 15 | 14 | 12 | 12 |
| Drug Exposure (Day7) | Mean Serum Concentration (ug/ml) | na | 79.3 | 31.2 | 4.7 | 1.5 | 0.46 |

These results show that the exemplary anti-HER2 biparatopic antibody, v10000, inhibits tumor progression in a dose-dependent manner.

Example 36: Ability of Anti-HER2 Biparatopic Antibody and Anti-HER2 Biparatopic-ADC to Inhibit Growth of Cell Lines Expressing HER2, and EGFR and/or HER3 at the 3+, 2+ or 1+ Levels The following experiment was performed to measure the ability of an exemplary biparatopic anti-HER2 antibody (v10000) and corresponding biparatopic anti-HER2 ADC (v10553) to inhibit growth of a selection of breast, colorectal, gastric, lung, skin, ovarian, renal, pancreatic, head and neck, uterine and bladder tumor cell lines that express HER2, and EGFR and/or HER3 at the 3+, 2+, 1+ or 0+ level as defined by IHC.

The experiment was conducted as follows. The optimal seeding density for each cell line was uniquely determined to identify a seeding density that yielded approximately 60-90% confluency after the 72 hr duration of the assay. Each cell line was seeded at the optimal seeding density, in the appropriate growth medium per cell line, in a 96-well plate and incubated for 24° C. at 36° C. and 5% $CO_2$. Antibodies were added at three concentrations (v10000 at 300, 30 and 0.3 nM; v10553 at 300, 1, 0.1 nM), along with the positive and vehicle controls. The positive control chemococktail drug combination of 5-FU (5-fluorouracil), paclitaxel, cisplatin, etoposide (25 microM), the vehicle control consisted of PBS. The antibody treatments and controls were incubated with the cells for 72 h in a cell culture incubator at 36° C. and 5% $CO_2$. The plates were centrifuged at 1200 RPM for 10 min and culture medium completely removed by aspiration. RPMI SFM medium (200 microL) and MTS (20 microL) was added to each well and incubated at 36° C. and 5% $CO_2$ for 3 h. Optical density was read at 490 nM and percent growth inhibition was determined relative to the vehicle control.

Figure 37A:
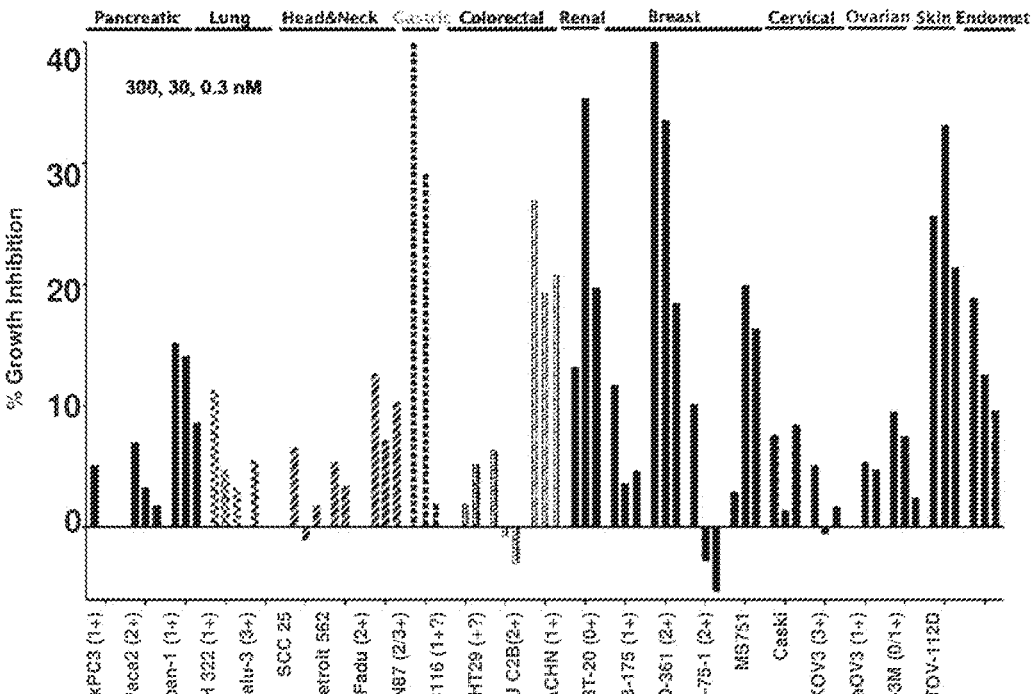
FIG. 37A depicts the ability of an anti-HER2 biparatopic antibody and an anti-HER2 biparatopic-ADC to inhibit growth of cell lines expressing HER2, and EGFR and/or HER3 at the 3+, 2+ or 1+ levels.

The results are shown in FIG. 37 and a summary of all test results are shown in FIG. 38. FIG. 37A shows the growth inhibition results of v10000. These results show that v10000 can inhibit growth of breast, colorectal, gastric, lung, skin, ovarian, renal, pancreatic, head and neck, uterine, and endometrial tumor cell lines that express HER2 and coexpress EGFR and/or HER3 at the 3+, 2+, 1+ or 0+ level. The activity of v10000 and v10553 at 300 nM is summarized in FIG. 38, where '+' indicates cell lines that showed a reduction in cell viability at 300 nM that was >5% of the vehicle control, and '−' indicates <5% viability of the vehicle control.

Figure 37B:
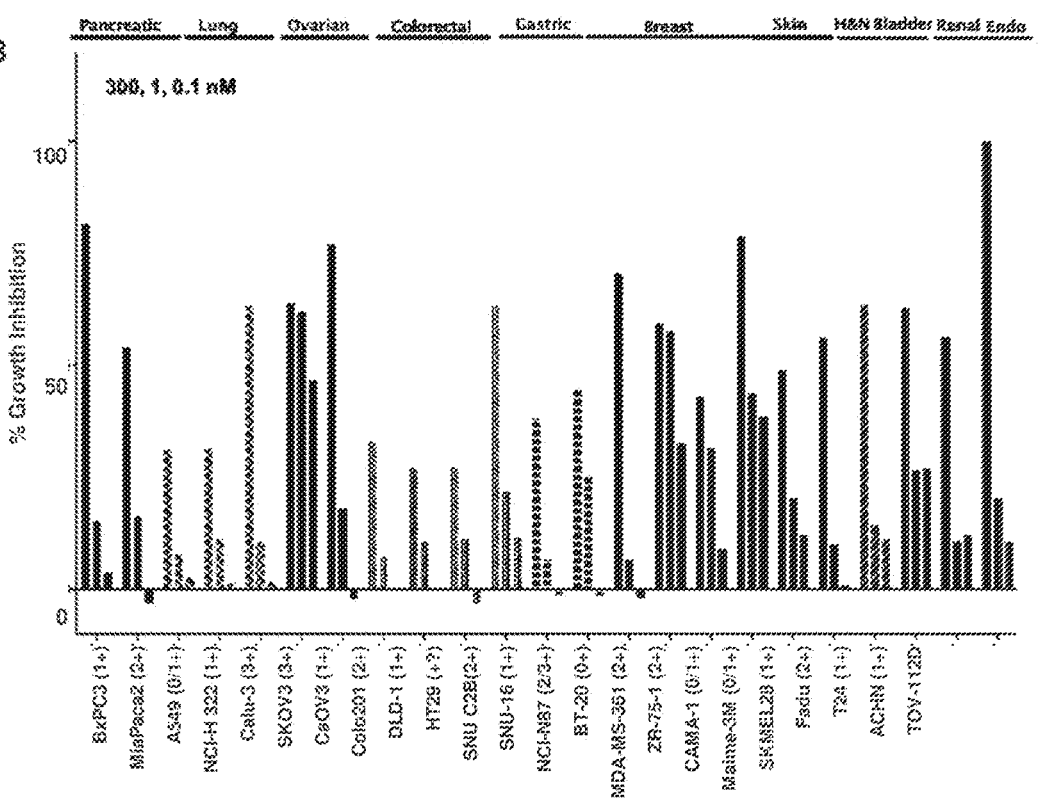
FIG. 37B depicts the ability of an anti-HER2 biparatopic antibody and an anti-HER2 biparatopic-ADC to inhibit growth of cell lines expressing HER2, and EGFR and/or HER3 at the 3+, 2+ or 1+ levels.

FIG. 37B shows the growth inhibition results of v10553. These results show that v10553 can inhibit growth of breast, colorectal, gastric, lung, skin, ovarian, renal, pancreatic, head and neck, uterine and bladder tumor cell lines that express HER2 and coexpress EGFR and/or HER3 at the 3+, 2+, 1+ or 0+ level (see also FIG. 38). The results plotted in FIG. 37B are defined by cell lines that showed a minimum of dose-dependent growth inhibition at 300 and 1 nM, and where the growth inhibition at 1 nM is equal or greater than 5% (FIG. 37B).

These results show that exemplary biparatopic antibody v10000 and ADC v10553 can inhibit growth of tumor cells originating from breast, colorectal, gastric, lung, skin, ovarian, renal, pancreatic, head and neck, uterine and bladder histologies that express HER2 at the 3+, 2/3+, 2+, 1+ and 0/1+ levels and that coexpress EGFR and/or HER3 at the 2+, 1+ levels.

Example 37: Ability of Anti-HER2 Biparatopic Antibodies to Mediate ADCC of HER2 2+, 1+ and 0/1+ Cancer Cells The following experiment was conducted to determine the ability of anti-HER2 biparatopic antibodies to mediate ADCC of tumor cells that express HER2 at the 2+, 1+ and/or 0/1+ levels and that coexpress EGFR and/or HER3 at the 2+ or 1+ level. The anti-HER2 biparatopic antibodies tested were 5019, 10000, and 10154 (an afucosylated version of v10000), with Herceptin™ and v506 as controls.

The ADCC experiment was conducted as described in Example 11 and Example 25 with E/T: 5:1 with NK-92 effector cells (FIG. 39), and as described in Example 26 with E/T 30:1 with PBMC effector cells.

Figure 39C:
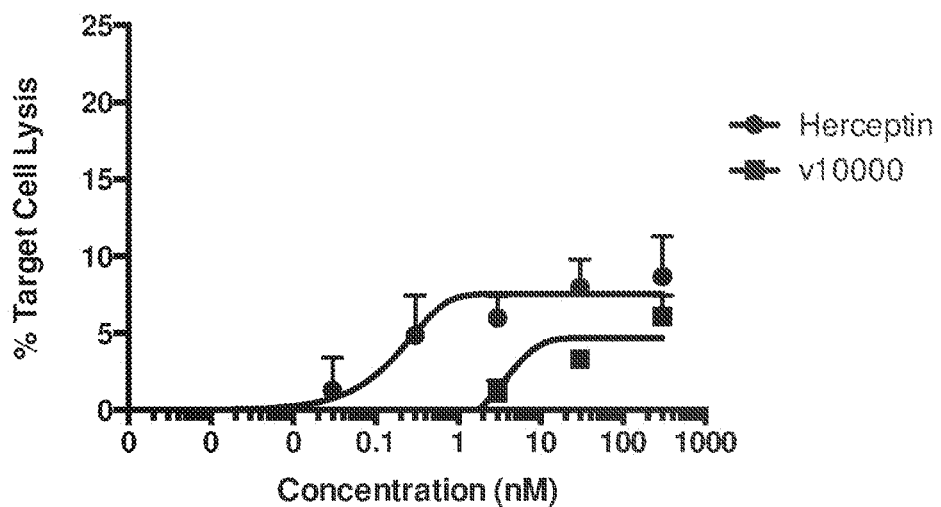
FIG. 39C depicts the ability of v10000 to mediate ADCC in HER2+ cells.
Figure 39D:
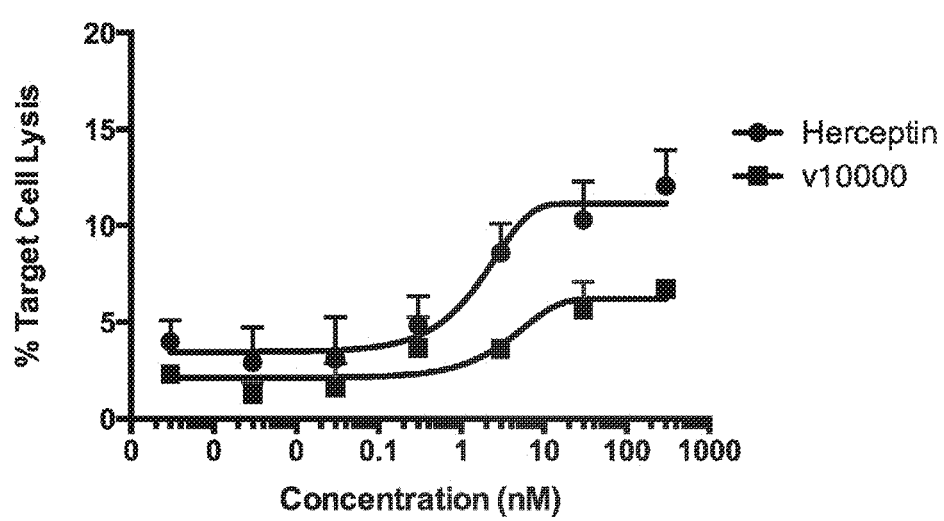
FIG. 39D depicts the ability of v10000 to mediate ADCC in HER2+ cells.

The results are shown in FIG. 39 (NK-92 effector cells) and FIG. 40 (PBMC effector cells). FIG. 39A shows the ADCC results of the HER2 2+ head and neck tumor cell line (hypopharyngeal carcinoma), FaDu, where the anti-HER2 biparatopic elicits approximately 15% maximal cell lysis. FIG. 39C shows the ADCC results of the HER2 1+ BxPC3 pancreatic tumor cell line, and FIG. 39D the results of the HER2 2+ MiaPaca2 pancreatic tumor cell line. FIG. 39B shows the ADCC results of the HER2 0/1+ A549 NSCLC (non-small cell lung cancer) tumor cell line. In the BxPC3, MiaPaca2 and A549 tumor cell lines, v10000 mediated approximately 5% maximal tumor cell lysis.

Figure 40A:
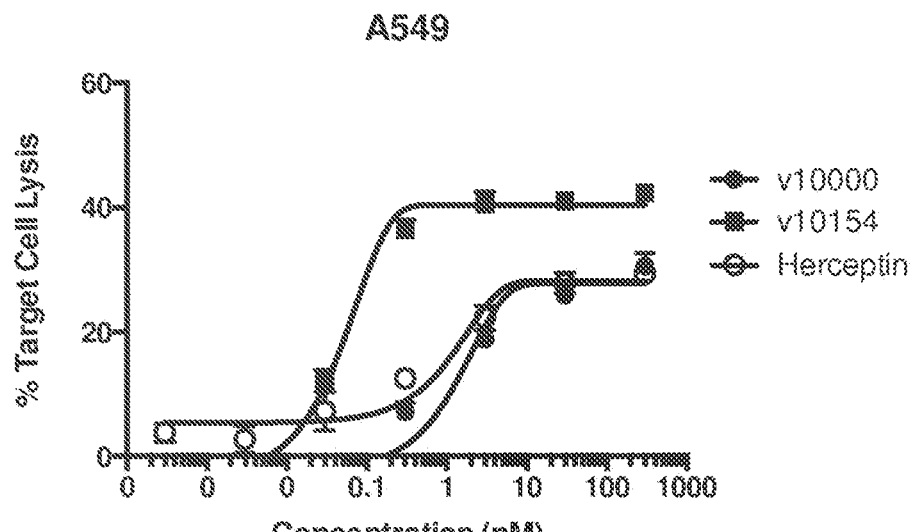
FIG. 40A depicts the ability of anti-HER2 biparatopic antibodies to mediate ADCC in HER2+ cells.

FIG. 40 shows the ADCC results in A549, NCI-N87, and HCT-116 cells, where PBMCs were used as the effector cells. FIG. 40A shows the ADCC results of the HER2 0/1+ A549 NSCLC tumor cell line, where v10000 elicited ~28% maximum cell lysis and this was comparable to Herceptin™ that has equivalent level of fucose content in the N-linked glycan. The exemplary 100% afucosylated (0% fucose) biparatopic v10154 shows an increase in maximal cell lysis (40% maximum cell lysis) and increased potency compared to v10000 and Herceptin that have approximately 88% fucose in the N-linked glycan.

Figure 40B:
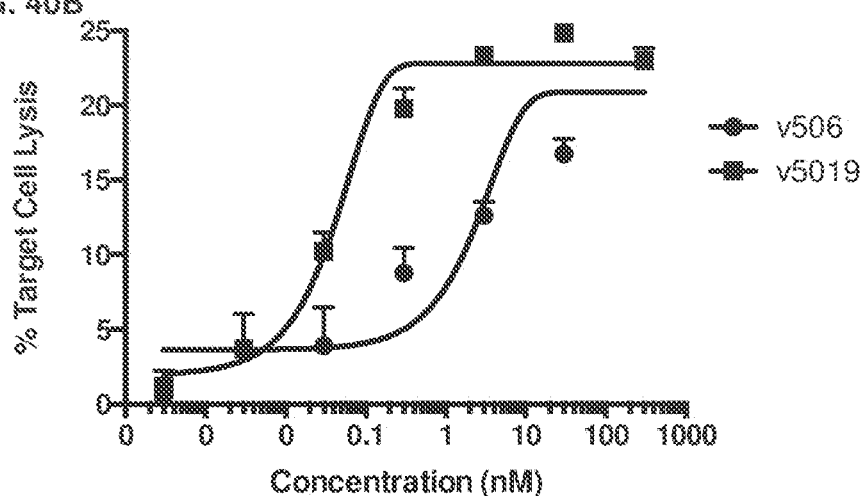
FIG. 40B depicts the ability of anti-HER2 biparatopic antibodies to mediate ADCC in HER2+ cells.

FIG. 40B shows the ADCC results of the HER2 3+ gastric tumor cell line, NCI-N87. FIG. 40B shows that exemplary biparatopic v5019 (approximately 88% fucosylated) mediates approximately 23% maximal cell lysis and has a lower EC50 compared to Trastuzumab v506 (approximately 98% fucosylated).

Figure 40C:
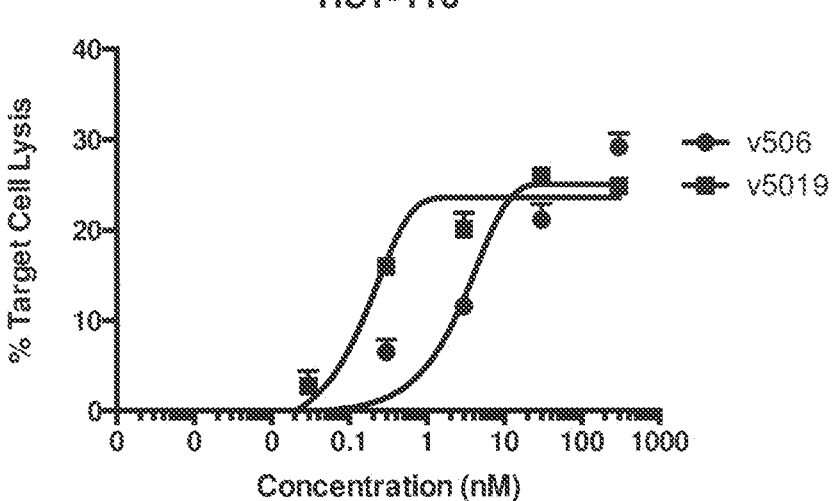
FIG. 40C depicts the ability of anti-HER2 biparatopic antibodies to mediate ADCC in HER2+ cells.

FIG. 40C shows the ADCC results of the HER2 1+ HCT-116 colorectal tumor cell line. FIG. 40C shows that exemplary biparatopic v5019 (approximately 88% fucosylated) mediates approximately 25% maximal cell lysis and is more potent compared to Trastuzumab v506 (approximately 98% fucosylated).

These results show that exemplary anti-HER2 biparatopic antibodies can elicit ADCC of HER2 01/+, 2+ and 3+ tumor cells that originate from head and neck, gastric, NSCLC, and pancreatic tumor histologies. ADCC in the presence of NK-92 cells as the effector cells had an apparent HER2 2+ receptor level requirement (i.e. 2+ or greater) to show higher (>5%) percentage of maximum cell lysis. However, when PBMC cells were used as effector cells higher levels of maximum cell lysis were achieved (>5% and up to 28% or 40%; v10000 and v10154, respectively) and were independent of HER2 receptor density as ADCC >5% was seen at the 0/1+, 1+ and 3+ HER2 receptor density levels.

Example 38: HER2 Binding Affinity and Kinetics as Measured by SPR

As indicated in Example 1, anti-HER2 biparatopic antibodies having different antigen-binding moiety formats were constructed, as described in Table 1. The formats included scFv-scFv format (v6717), Fab-Fab format (v6902 and v6903), along with Fab-scFv format (v5019, v7091, and v10000). The following experiment was conducted to compare HER2 binding affinity and kinetics of these exemplary anti-HER2 biparatopic antibody formats.

Affinity and binding kinetics to murine HER2 ECD (Sino Biological 50714-M08H) was measured by single cycle kinetics with the T200 SPR system from Biacore (GE Healthcare). Between 2000-4000 RU of anti-human Fc was immobilized on a CM5 chip using standard amine coupling. 5019 was captured on the anti-human Fc surface at 50 RU. Recombinant HER2 ECD (1.8-120 nM) was injected at 50 µl/min for 3 minutes, followed by a 30 minute dissociation after the last injection. HER2 dilutions were analyzed in duplicate. Sensorgrams were fit globally to a 1:1 Langmuir binding model. All experiments were conducted at room temperature, 25° C.

The results in Table 34 show that Fab-scFv biparatopic antibodies (v5019 and v7091), Fab-Fab variants (v6902 and v6903) and the scFv-scFv variant (v6717) have comparable binding affinity (1-4 nM). The Fab-scFv variant v10000 had higher binding affinity (lower KD) of approximately 0.6 nM. The monspecific anti-HER2 ECD4 antibody (v506) and anti-HER2 ECD2 antibody (v4184) were included in the assay as controls. These results indicate that the molecular formats including v6717, v6902, v6903, v5019 and/or v7091 have equivalent binding affinities, and thus differences in function between these antibodies may be considered to result from differences in format.

TABLE 34

| Antibody Variant | AVERAGE | | | STD DEV | | |
|---|---|---|---|---|---|---|
| | Ka (1/Ms) | Kd (1/s) | KD (M) | Ka (1/Ms) | Kd (1/s) | KD (M) |
| v506 | 7.34E+04 | 4.08E−05 | 5.56E−10 | 1.13E+03 | 3.04E−06 | 3.28E−11 |
| v4184 | 3.61E+04 | 5.46E−04 | 1.56E−08 | 7.78E+03 | 2.80E−05 | 4.12E−09 |
| v5019 | 6.01E+04 | 7.77E−05 | 1.29E−09 | 1.30E+03 | 8.56E−07 | 4.24E−11 |
| v7091 | 5.17E+04 | 1.19E−04 | 2.31E−09 | 2.70E+03 | 1.49E−05 | 4.09E−10 |
| v10000 | 6.44E+04 | 3.69E−05 | 5.79E−10 | 6.18E+03 | 6.72E−06 | 1.42E−10 |
| v6902 | 6.83E+04 | 1.72E−04 | 2.72E−09 | 1.93E+04 | 4.49E−05 | 1.43E−09 |
| v6903 | 7.10E+04 | 1.71E−04 | 2.75E−09 | 3.60E+04 | 3.96E−06 | 1.34E−09 |
| v6717 | 1.50E+05 | 5.33E−04 | 4.45E−09 | 1.28E+05 | 2.54E−04 | 211E−09 |

Example 39: Effect of Anti-HER2 Biparatopic Antibody Format on Binding to HER2+ Tumor Cells The following experiment was conducted to compare the whole cell binding properties (Bmax and apparent $K_D$) of exemplary anti-HER2 ECD2×ECD4 biparatopic antibodies that have different molecular formats (e.g. v6717, scFv-scFv IgG1; v6903 and v6902 Fab-Fab IgG1; v5019, v7091 and v10000 Fab-scFv IgG1).

Figure 41A:
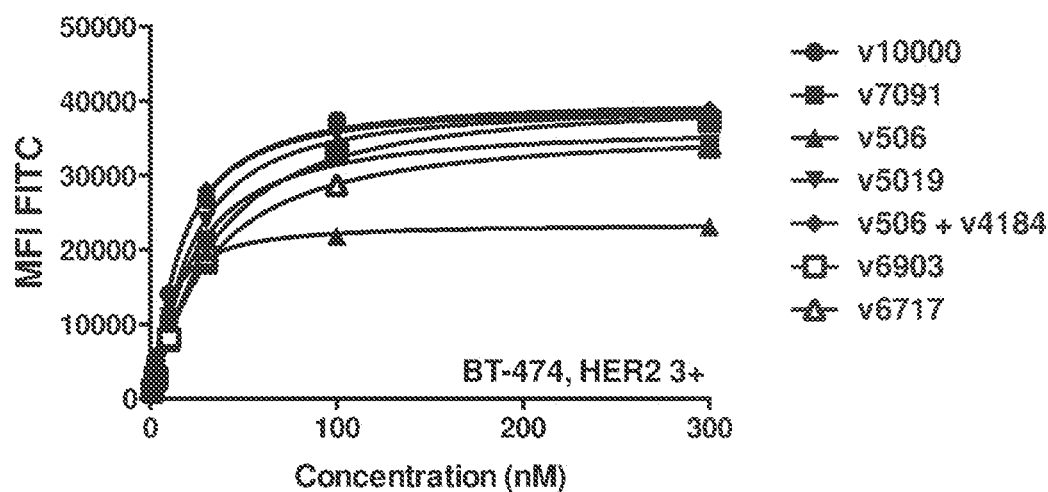
FIG. 41A depicts the effect of anti-HER2 biparatopic antibody format on binding HER2+ cells.

The experiment was conducted as described in Example 6. The results are shown in FIG. 41 and Tables 35-38. FIG. 41A and Table 35 shows the FACS binding results of the exemplary biparatopic antibodies to the BT474 HER2 3+ breast tumor cell line. The results show that all anti-HER2 antibodies have a higher Bmax (1.5 to 1.7-fold greater) when compared to the monospecific bivalent anti-HER2 antibody v506. The Fab-scFv (v5019, v7091 and v10000) and the Fab-Fab (v6903) formats had approximately a 1.7-fold increased Bmax and the scFv-scFv format (v6717) had a 1.5-fold increased Bmax compared to v506. An equimolar combination of FSAs v506 and v4184 resulted in a 1.7-fold increase in Bmax. The apparent $K_D$ of the exemplary anti-HER2 biparatopic antibodies was approximately 2 to 3-fold higher compared to the monospecific v506.

TABLE 35

FACS binding BT-474

| Antibody Variant | $K_D$ (nM) | Bmax |
|---|---|---|
| v506 | 9.0 | 23536 |
| v10000 | 16 | 39665 |
| v506 + v4184 | 16 | 40320 |
| v5019 | 21 | 39727 |
| v7091 | 22 | 36718 |
| v6717 | 30 | 36392 |
| v6903 | 31 | 40321 |

Figure 41B:
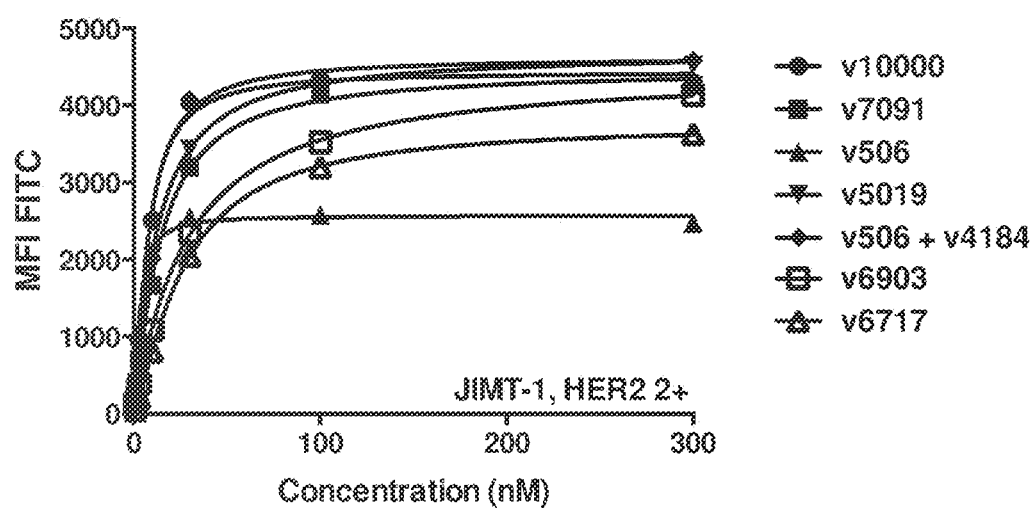
FIG. 41B depicts the effect of anti-HER2 biparatopic antibody format on binding HER2+ cells.

FIG. 41B and Table 36 shows the FACS binding results to the JIMT-1 HER2 2+ breast tumor cell line. The results show that all anti-HER2 antibodies have a higher Bmax (1.5 to 1.8-fold greater) when compared to the monospecific bivalent anti-HER2 antibody v506. The Fab-scFv (v7091 and v10000) and the Fab-Fab (v6903) formats had approximately a 1.7-fold increased Bmax, the scFv-scFv format (v6717) had a 1.5-fold increased Bmax and the Fab-scFv (v5019) and FSA combination (v506+v4184) had a 1.8-fold increased Bmax compared to v506. The apparent $K_D$ of the exemplary anti-HER2 biparatopic Fab-scFv antibodies was approximately 2 to 4-fold higher compared to the monospecific v506; whereas the $K_D$ of the Fab-Fab (v6903) and scFv-scFv (v6717) were approximately 8-fold higher compared to v506.

TABLE 36

FACS Binding JIMT-1

| Antibody Variant | $K_D$ (nM) | Bmax |
|---|---|---|
| v506 | 3.5 | 2574 |
| v10000 | 7.6 | 4435 |
| v506 + v4184 | 8.0 | 4617 |
| v5019 | 12 | 4690 |
| v7091 | 14 | 4456 |
| v6717 | 26 | 3769 |
| v6903 | 28 | 4452 |

Figure 41C:
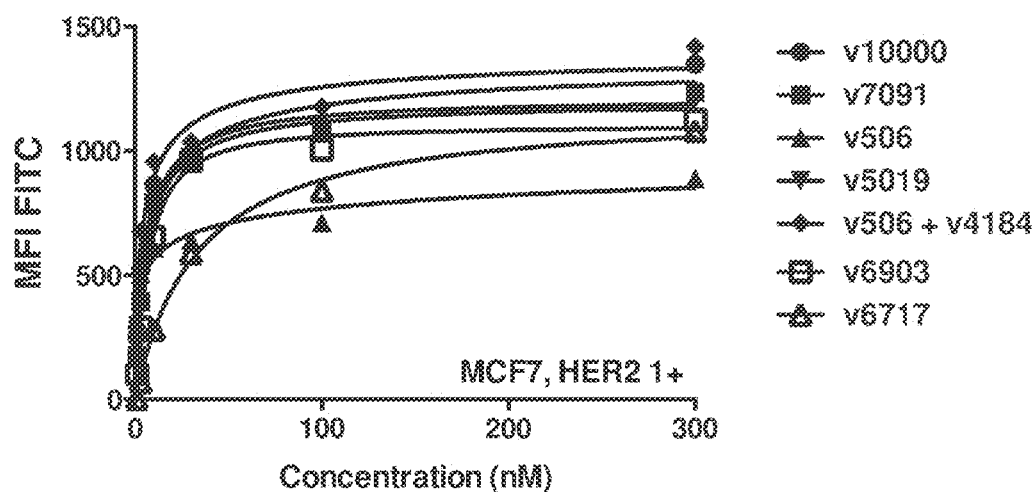
FIG. 41C depicts the effect of anti-HER2 biparatopic antibody format on binding HER2+ cells.

FIG. 41C and Table 37 shows the FACS binding results of the exemplary biparatopic antibodies to the HER2 1+ MCF7 breast tumor cell line. The results show that anti-HER2 antibody v10000 and FSA combination (v506+v4184) have a 1.6-fold higher Bmax compared to the monospecific bivalent anti-HER2 antibody v506. The Fab-scFv (v5019, v7091) had approximately a 1.4-fold; the scFv-scFv format (v6717) a 1.3-fold, and the Fab-Fab format (v6903) had a 1.2-fold increased Bmax compared to v506. The apparent $K_D$ of the exemplary anti-HER2 biparatopic Fab-scFv, Fab-Fab (v6903) and FSA combination (v506+v4184) was approximately 2 to 3-fold lower compared to v506; whereas the $K_D$ of the scFv-scFv (v6717) was approximately 3-fold higher compared to v506.

TABLE 37

FACS Binding MCF7

| Antibody Variant | $K_D$ (nM) | Bmax |
|---|---|---|
| v506 + v4184 | 4.5 | 1410 |
| v7091 | 6.1 | 1216 |
| v5019 | 6.3 | 1201 |
| v10000 | 6.8 | 1381 |
| v6903 | 7.1 | 1105 |
| v506 | 12 | 889 |
| v6717 | 32 | 1167 |

Figure 41D:
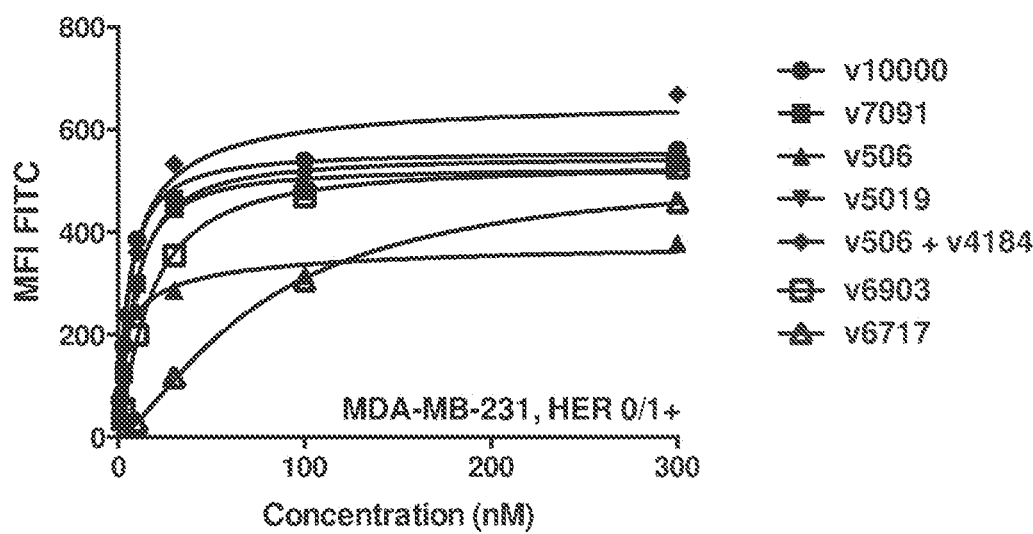
FIG. 41D depicts the effect of anti-HER2 biparatopic antibody format on binding HER2+ cells.

FIG. 41D and Table 38 shows the FACS binding results of the exemplary biparatopic antibodies to the HER2 0/1+ MDA-MD-231 breast tumor cell line. The results show that exemplary biparatopic anti-HER2 antibodies had approximately 1.3 to 1.4-fold increased Bmax compared to the monospecific bivalent anti-HER2 antibody v506. The FSA combination (v506+v4184) had a 1.7-fold increased Bmax The apparent $K_D$ of the exemplary anti-HER2 biparatopic Fab-scFv antibodies (v5019, v7091, v10000) and FSA combination (v506+v4184) had an approximate equivalent KD compared to v506; whereas Fab-Fab (v6903) and scFv-scFv (v6717) was approximately 4 and 16-fold higher $K_D$ respectively, compared to v506.

TABLE 38

FACS Binding MDA-MB-231

| Antibody Variant | $K_D$ (nM) | Bmax |
|---|---|---|
| v506 | 4.8 | 395 |
| v10000 | 5.6 | 558 |
| v506 + v4184 | 7.3 | 662 |
| v7091 | 7.9 | 525 |
| v5019 | 8.7 | 548 |
| v6903 | 17 | 534 |
| v6717 | 77 | 524 |

The tumor cell binding results show that anti-HER2 biparatopic antibodies with different molecular formats have an increased Bmax on HER2 3+, 2+, 1+ and 0/1+ tumor cells compared to a bivalent monospecific anti-HER2 antibody. Of the different anti-HER2 biparatopic antibodies, the scFv-scFv format had the lowest Bmax gain relative to v506 on HER2 3+, 2+, 1+ and 0/1+ tumor cells These results also show that scFv-scFv and Fab-Fab formats have the greatest increase in $K_D$ on HER2 3+, 2+, 1+ and 0/1+ tumor cells compared monospecific v506 (3 to 16-fold increase) and the biparatopic Fab-scFv formats (approximately 2-fold or greater). The increase in $K_D$ is an indication of a reduction in avid binding and suggests that different biparatopic formats have unique mechanisms of binding to HER2 on the cell surface.

Example 40: Effect of Anti-HER2 Biparatopic Antibody Format on Internalization in HER2+ Cells The following experiment was conducted to compare the ability of exemplary anti-HER2 ECD2×ECD4 biparatopic antibodies that have different molecular formats (e.g. v6717, scFv-scFv IgG1; v6903 and v6902 Fab-Fab IgG1; v5019, v7091 and v10000 Fab-scFv IgG1) to internalize in HER2+ cells expressing HER2 at varying levels.

The experiment was conducted as detailed in Example 9. The results are shown in FIG. 42 and Tables 39-41. FIG. 42A and Table 39 show the internalization results in HER2 3+ BT-474. These results show that the Fab-scFv format (v10000) and the FSA combination (v506+v4184) have 2.2-fold greater quantities of intracellular antibody, compared to the monospecific anti-HER2 v506. The scFv-scFv format (v6717) had 1.9-fold greater; the Fab-scFv formats (v5019 and v7091) had 1.5 to 1.7-fold greater; and the Fab-Fab formats (v6902 and v6903) had 1.2 to 1.3-fold greater quantities of intracellular antibody accumulation compared to v506.

TABLE 39

Internalization BT-474

| Antibody Variant | Surface 4° C. | Surface 37° C. | Internal 37° C. |
|---|---|---|---|
| v506 | 2156 | 1590 | 3453 |
| v6902 | 2407 | 2077 | 4035 |
| v6903 | 2717 | 986 | 4573 |
| v7091 | 2759 | 2227 | 5111 |
| v5019 | 2867 | 2675 | 5710 |
| v6717 | 2006 | 1212 | 6498 |
| v10000 | 3355 | 2851 | 7528 |
| v506 + v4184 | 3998 | 2326 | 7569 |

FIG. 42B and Table 40 show the internalization results in HER2 2+ JIMT-1. These results show that the Fab-scFv format (v10000) and the FSA combination (v506+v4184) have respectively 1.8 and 1.9-fold greater quantities of intracellular antibody, compared to the monospecific anti-HER2 v506. The scFv-scFv (v6717) and the Fab-scFv formats (v5019) have 1.4-fold greater; and the Fab-scFv (v7091) and Fab-Fab formats (v6902 and v6903) had 1.2-fold greater quantities of intracellular antibody accumulation compared to v506.

TABLE 40

Internalization JIMT-1

| Antibody Variant | Surface 4° C. | Surface 37° C. | Internal 37° C. |
|---|---|---|---|
| v506 | 337 | −7.1 | 759 |
| v6902 | 389 | 152 | 926 |
| v7091 | 426 | 102 | 935 |
| v6903 | 392 | 130 | 945 |
| v5019 | 437 | 5.2 | 1035 |
| v6717 | 247 | 31 | 1082 |
| v10000 | 474 | 103 | 1375 |
| v506 + v4184 | 583 | 89 | 1449 |

FIG. 42C and Table 41 show the internalization results in HER2 1+ MCF7. These results show that the scFv-scFv format and Fab-scFv formats have 3.0 and 2.8-fold greater quantities of intracellular antibody, compared to the monospecific anti-HER2 v506. The Fab-scFv format (v10000)

and the FSA combination (v506+v4184) have approximately 2.0-fold; the Fab-scFv (v7091) and Fab-Fab (v6903) formats have 1.8-fold greater quantities of intracellular antibody accumulation compared to v506.

TABLE 41

Internalization MCF7

| Antibody Variant | Surface 4° C. | Surface 37° C. | Internal 37° C. |
|---|---|---|---|
| v506 | 48 | 10 | 48 |
| v7091 | 77 | 27 | 87 |
| v6903 | 81 | 35 | 89 |
| v10000 | 78 | 20 | 96 |
| v506 + v4184 | 87 | 19 | 103 |
| v5019 | 81 | 17 | 134 |
| v6717 | 48 | 31 | 145 |

These results show that anti-HER2 biparatopic antibodies with different molecular formats have unique degrees of internalization in HER2 3+, 2+ and 1+ tumor cells that varies with respect to the structure and format of the antigen binding domains. In general, the monospecific FSA combination of v506 and v4184, the Fab-scFv (v10000, v7091 and v5019) and the scFv-scFv (v6717) biparatopic formats had the higher internalization values in the HER2 3+, 2+ and 1+ tumor cells. Whereas, the Fab-Fab biparatopic formats (v6902 and v6903) had the lowest internalization values in the HER2 3+, 2+ and 1+ tumor cells. These data suggest that the molecular format and geometric spacing of the antigen binding domains has an influence on the ability of the biparatopic antibodies to cross-link HER2 receptors, and subsequently to internalize in HER2+ tumor cells. The Fab-Fab biparatopic format, having the greatest distance between the two antigen binding domains, resulted in the lowest degree of internalization, whereas the Fab-scFv and scFv-scFv formats, having shorter distances between the antigen binding domains, had greater internalization in HER2+ cells. This is consistent with the correlation of potency and shorter linker length as described in Jost et al 2013, Structure 21, 1979-1991).

Example 41: Effect of Anti-HER2 Biparatopic Antibody Format on ADCC in HER2+ Cells The following experiment was conducted to compare the ability of exemplary anti-HER2 ECD2×ECD4 biparatopic antibodies that have different molecular formats (e.g. v6717, scFv-scFv IgG1; v6903 and v6902 Fab-Fab IgG1; v5019, v7091 and v10000 Fab-scFv IgG1) to mediate ADCC in HER2+ cells expressing HER2 at varying levels.

Prior to performing the ADCC assay, glycopeptide analysis was performed on the antibody samples to quantify the fucose content in the N-linked glycopeptide. The method was followed as described in Example 23. The results are shown in Table 42; the data shows that exemplary biparatopic variants v5019, v6717, v6903 have equivalent fucose content in the N-linked glycan (91-93%). Antibody samples with equivalent levels of fucose in the N-glycan were selected for the ADCC assay to normalize for fucose content in the interpretation of the ADCC assay results.

TABLE 42

LC-MS Tryptic peptide analysis

| Variant | Percentage of Glycopeptides Observed WITH Fucose | Percentage of Glycopeptides Observed WITHOUT Fucose |
|---|---|---|
| v6903 | 90.7 | 9.3 |
| v6717 | 92.8 | 7.2 |
| v5019 | 91.3 | 8.7 |

Figure 43A:
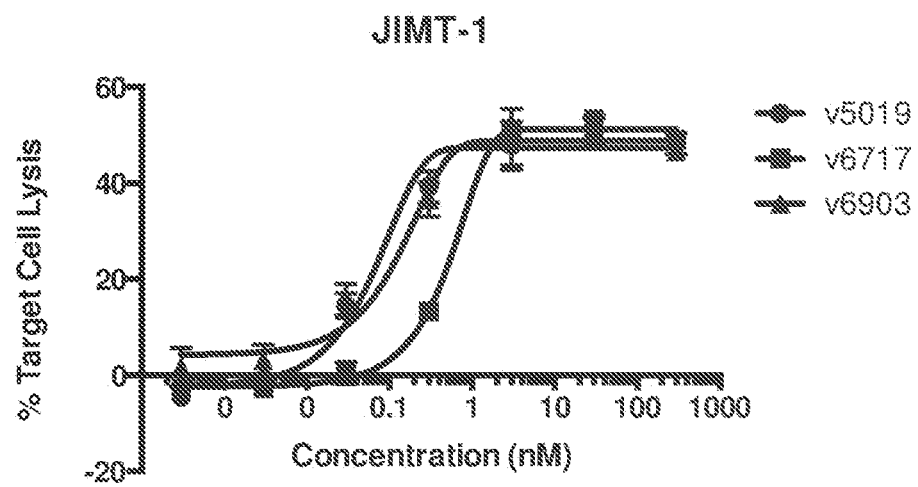
FIG. 43A depicts the effect of anti-HER2 biparatopic antibody format on the ability to mediate ADCC in HER2+ cells.

The ADCC experiment was conducted as described in Example 11 with E/T: 5:1 with NK-92 effector cells. The ADCC results are shown in FIG. 43 and Tables 43-45. FIG. 43A and Table 43 show the ADCC results in HER2 2+ JIMT-1 breast tumor cells. These data show that v5019, v6717 and v6903 elicit similar levels of maximum cell lysis and that the scFv-scFv format (v6717) is less potent compared to v5019 and v6903 when HER2 2+ tumor cells are targets.

TABLE 43

JIMT-1 ADCC

| Antibody variant | EC50 (nM) | % Max Cell Lysis |
|---|---|---|
| v6903 | ~0.03 | 48 |
| v5019 | ~0.16 | 47 |
| v6717 | ~0.72 | 51 |

Figure 43B:
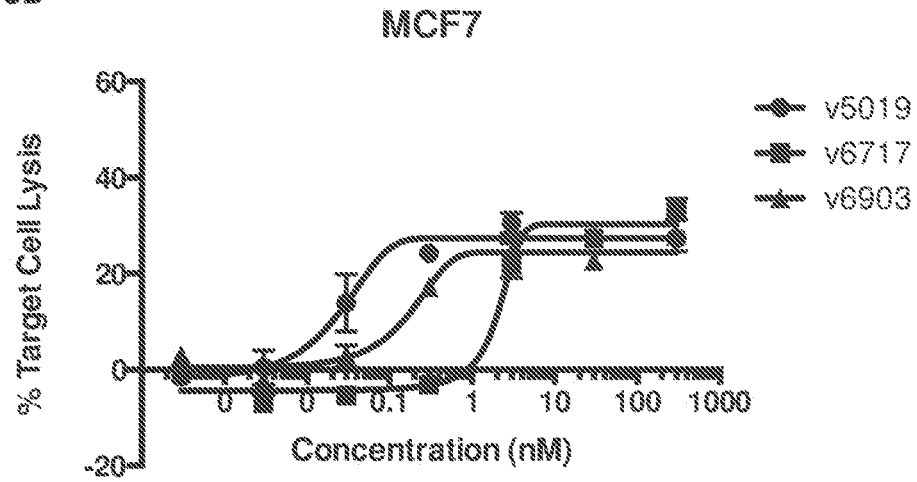
FIG. 43B depicts the effect of anti-HER2 biparatopic antibody format on the ability to mediate ADCC in HER2+ cells.

FIG. 43B and Table 44 show the ADCC results in HER2 1+ MCF7 breast tumor cells. These data show that v5019 and v6717 have slightly higher maximum cell lysis (27-30%) compared to v6903 (24%). These data also show that v6717 is the least potent, followed by v6903 and v5019, which have lower EC50 values.

TABLE 44

MCF7 ADCC

| Antibody variant | $EC_{50}$ (nM) | % Max Cell Lysis |
|---|---|---|
| v5019 | ~0.69 | 27 |
| v6717 | 109 | 30 |
| v6903 | 0.94 | 24 |

Figure 43C:
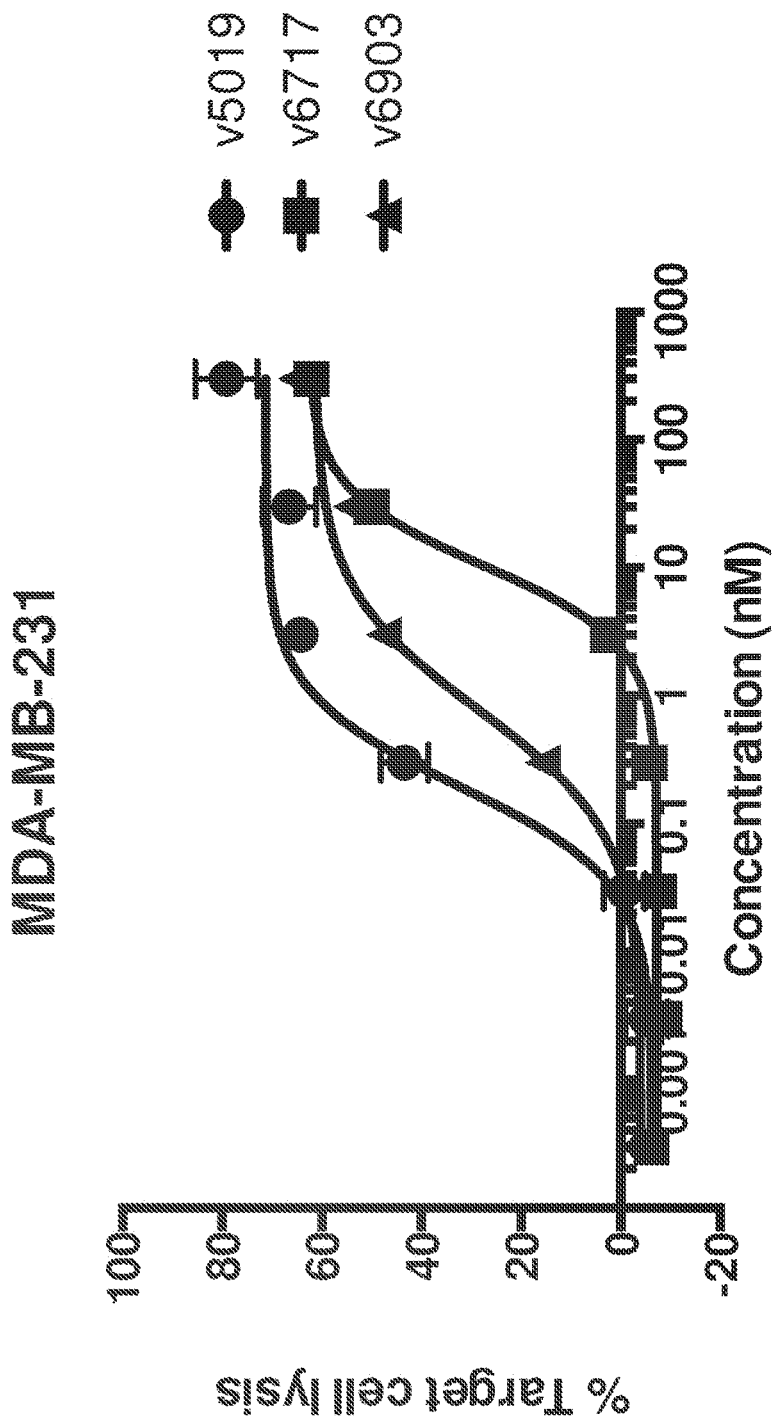
FIG. 43C depicts the effect of anti-HER2 biparatopic antibody format on the ability to mediate ADCC in HER2+ cells.

FIG. 43C and Table 45 show the ADCC results in HER2 0/1+ MDA-MB-231 breast tumor cells. These data show that v5019 shows slightly higher maximum cell lysis (77%) compared to v6903 (62%) and v6717 (63%). These data also show that v6717 is the least potent, followed by v6903 and v5019, which have lower $EC_{50}$ values.

TABLE 45

MDA-MB-231 ADCC

| Antibody variant | $EC_{50}$ (nM) | % Max Cell Lysis(top only) |
|---|---|---|
| v5019 | 0.20 | 71 |
| v6717 | 10 | 63 |
| v6903 | 0.79 | 62 |

These data show that exemplary anti-HER2 ECD2×ECD4 biparatopic antibodies elicit similar levels of maximum cell lysis by ADCC in HER2 2+ and 1+ tumor cells. Despite similarities in maximal cell lysis, these data also show that the different molecular formats have unique ADCC potencies. The scFv-scFv was the least potent (greatest $EC_{50}$ values) in the HER2 2+ and HER2 1+. Differential potencies among the three formats was seen in the ADCC data targeting HER2 1+ cells, where the EC50 values for v6717>v6903>v5019. These data are consistent with the observations presented in Example 40 (FACS binding), where an increase in $K_D$ (reduced affinity) was seen with the Fab-Fab and scFv-scFv formats.

Example 42: Effect of Anti-HER2 Biparatopic Antibody Format on Growth of HER2+ Tumor Cells The following experiment was conducted to compare the effect of anti-HER2 biparatopic antibody format on growth of HER2 3+, 2+ and 1+ tumor cells, either basal growth or ligand-stimulated. Basal growth was measured as described in Example 15, while ligand-stimulated growth was measured as described in Example 27. In both types of experiments, growth was measured as % survival with respect to control treatment.

Figure 44:
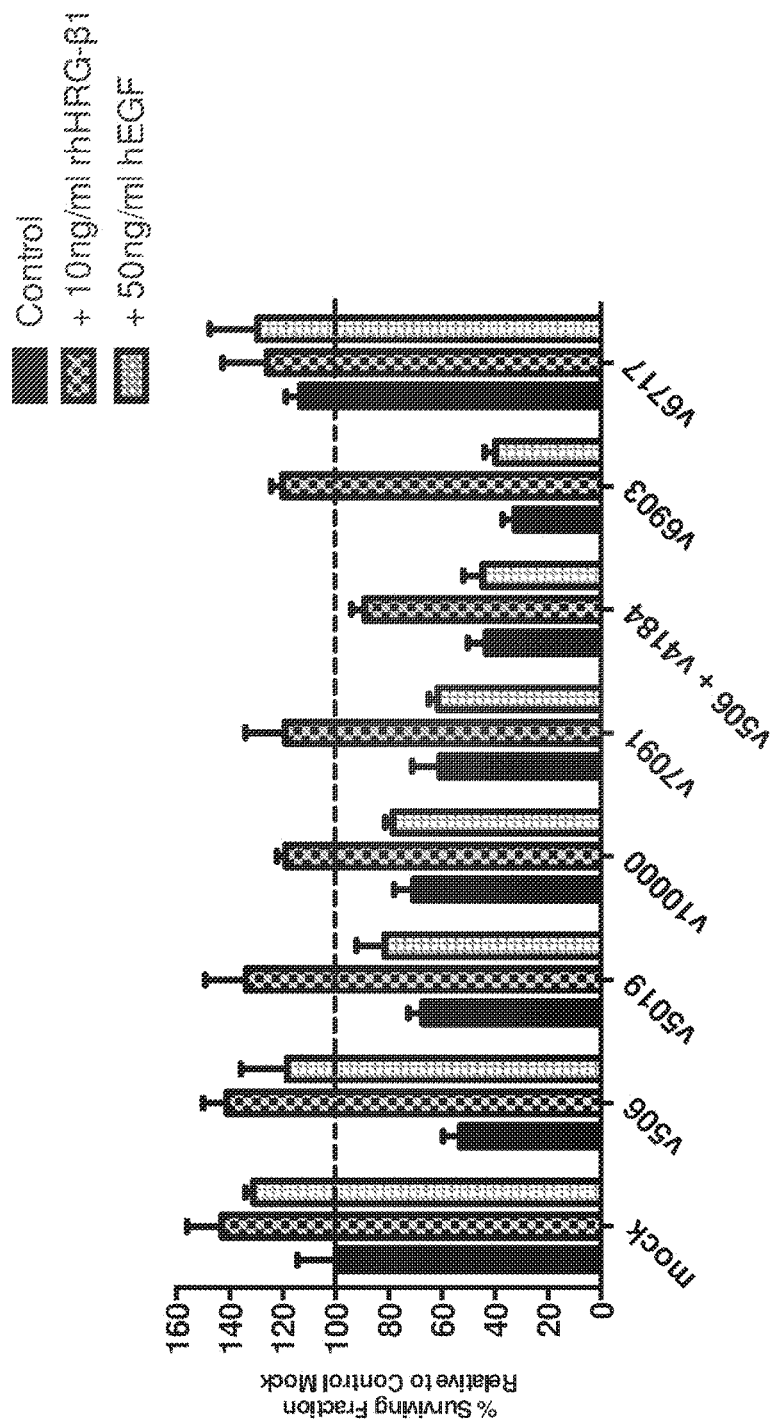
FIG. 44 depicts the effect of anti-HER2 biparatopic antibody format on the ability of the antibodies to inhibit HER2+ tumor cell growth in BT-474 cells in the presence or absence of growth-stimulatory ligands.

FIG. 44 and Table 46 show the effect of exemplary anti-HER2 ECD2×ECD4 biparatopic antibodies on growth of HER2 3+ breast cancer cells (BT-474) in the presence of exogenous growth-stimulatory ligands (EGF and HRG). In the absence of EGF or HRG, the anti-HER2 biparatopic antibodies were able to inhibit growth of BT-474 cells, where % survival of each treatment group ranked as follows: v6903<v506+v4184<506<v7091<v5019<v10000<v6717. In the presence of HRG, growth inhibition relative to the mock control was achieved only with the FSA combination of v506+v4184. In the presence of EGF, growth inhibition relative to the mock control was achieved, where % survival of each treatment group ranked as follows: v6903<v506+v4184<7091<v10000<5019.

TABLE 46

| Treatment | % Survival | | |
|---|---|---|---|
| | Antibody only | +HRG | +EGF |
| Mock | 100 | 143 | 131 |
| v6717 | 113 | 126 | 129 |
| v10000 | 70 | 118 | 78 |
| v5019 | 67 | 133 | 81 |
| v7091 | 61 | 119 | 61 |
| v506 | 53 | 141 | 118 |
| v506 + v4184 | 43 | 89 | 45 |
| v6903 | 32 | 120 | 39 |

Figure 45:
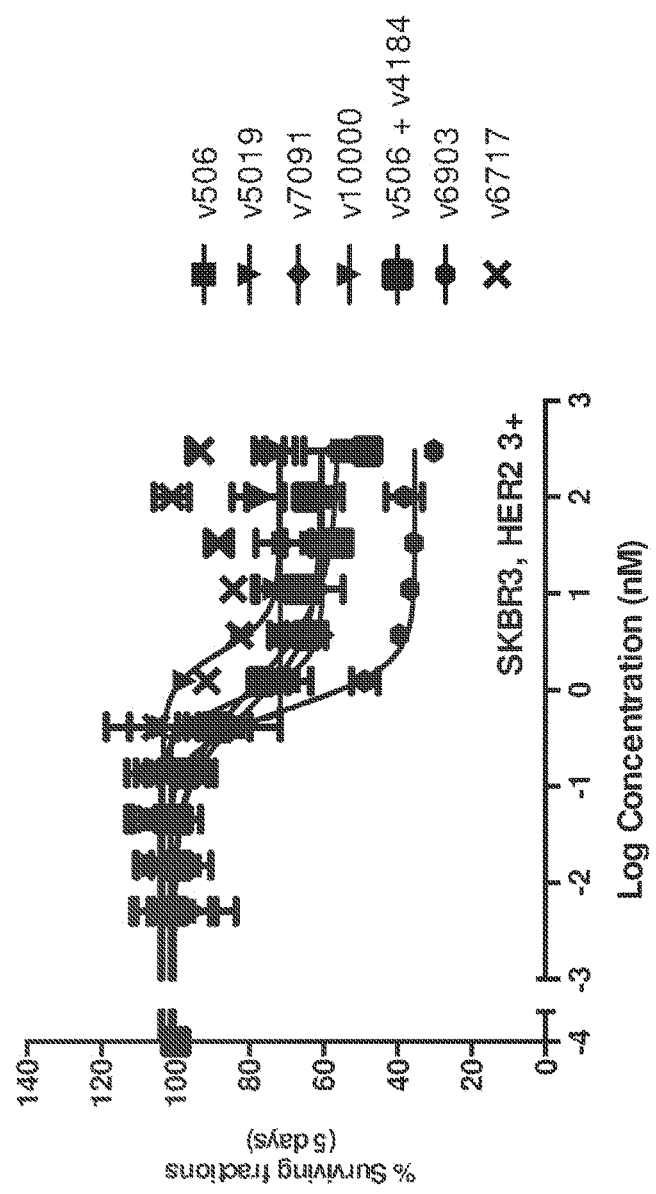
FIG. 45 depicts the effect of anti-HER2 biparatopic antibody format on the ability of the antibodies to inhibit growth of SKBR3 cells.

FIG. 45 shows the dose-dependent effect of the anti-HER2 biparatopic antibody formats on growth inhibition of the SKBr3 HER2 3+ cell line. The data is consistent with the results presented in FIG. 44, where the rank order potency/efficacy of the biparatopic formats is as follows Fab-Fab>Fab-scFv>scFv-scFv in HER2 3+ tumor cells.

Figure 46A:
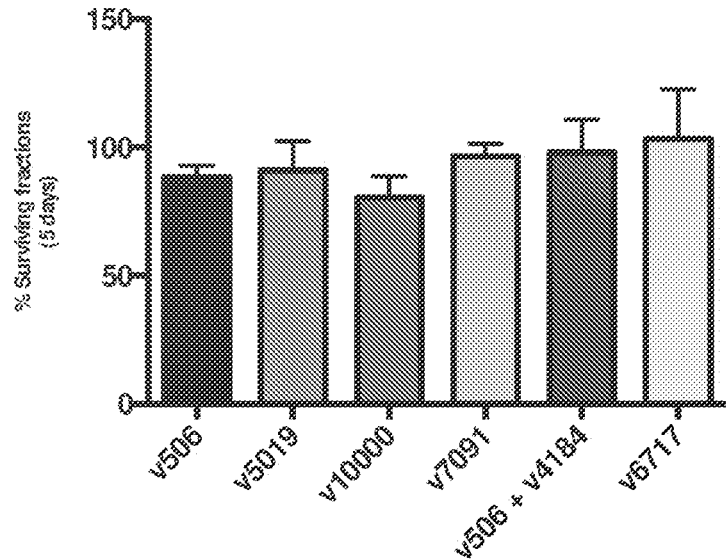
FIG. 46A depicts the effect of anti-HER2 biparatopic antibody format on the ability of antibodies to inhibit growth of HER2+ tumor cells.
Figure 46B:
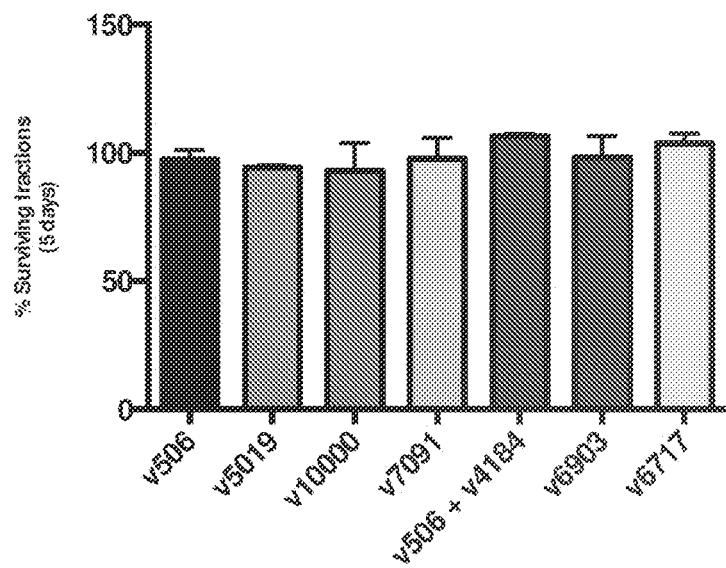
FIG. 46B depicts the effect of anti-HER2 biparatopic antibody format on the ability of antibodies to inhibit growth of HER2+ tumor cells.
Figure 46C:
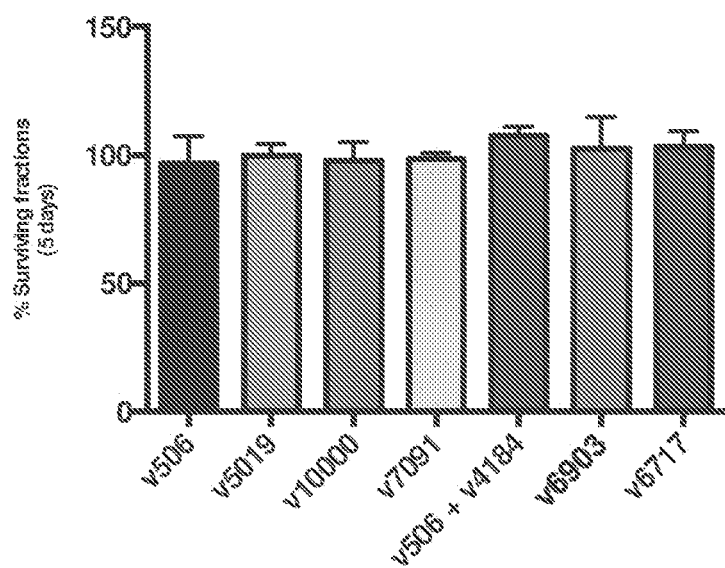
FIG. 46C depicts the effect of anti-HER2 biparatopic antibody format on the ability of antibodies to inhibit growth of HER2+ tumor cells.

The effect of anti-HER2 biparatopic antibody formats on survival of HER2+ cells is shown in FIG. 46, where FIG. 46A shows the result in the Trastuzumab sensitive SKOV3 HER2 2+/3+ cell line at 300 nM; FIG. 46B shows the result in JIMT-1 HER2 2+ (Trastuzumab resistant) cells at 300 nM, and FIG. 46C shows the result in MCF7 HER2 1+ cell line at 300 nM. In the SKOV3 cell line, little difference was observed among the biparatopic formats in the extent of growth inhibition, and no growth inhibition was observed by any of the test antibodies in JIMT-1 and MCF7 cells.

The data in FIG. 44 and FIG. 45 show that anti-HER2 ECD2×ECD4 biparatopic antibodies with the Fab-scFv and Fab-Fab formats (v5019, v7091, v10000, v6903) are capable of growth inhibition HER2 3+ tumor cells in the absence, and presence of EGF or HRG. In the HER2 3+ cell lines BT-474 and SKBR3, growth inhibition relative to the mock control rank ordered as follows, where v506+v4184>v6903>v7091>v10000>v5019>v506 v6717. The distance between antigen binding domains (Fab-Fab>Fab-scFv>scFv-scFv) correlates with the rank order of growth inhibition in the HER2 3+ tumor cells. Based on the data in trastuzumab-sensitive tumor cells, BT-474, and SKBr3, it may be expected that the growth inhibition difference among formats is significant at the HER2 3+ level but less so at the HER2 2+ or HER2 1+ levels.

Example 43: Evaluation of HER2 Binding Affinity and Kinetic at Varying Antibody Capture Levels The following experiment was conducted to compare HER2 binding kinetics (kd, off-rate) of exemplary anti-HER2 ECD2×ECD4 biparatopic antibodies when captured at varying surface densities by SPR. The correlation between a reduced (slower) off-rate with increasing antibody capture levels (surface density) is an indication of Trans binding (i.e. one antibody molecule binding to two HER2 molecules, described in Example 12). In this experiment the Fab-Fab format (v6903) was compared to the Fab-scFv format (v7091) to determine potential difference in Trans binding among the variants. Due to the larger spatial distance between antigen binding domains, it is hypothesized that the Fab-Fab format may be capable of Cis binding (engaging ECD 2 and 4 on one HER2 molecule); whereas, the Fab-scFv would not capable of Cis binding due to the shorter distance between the it's antigen binding domains. The anti-HER2 monospecific v506 was included as a control.

Figure 47A:
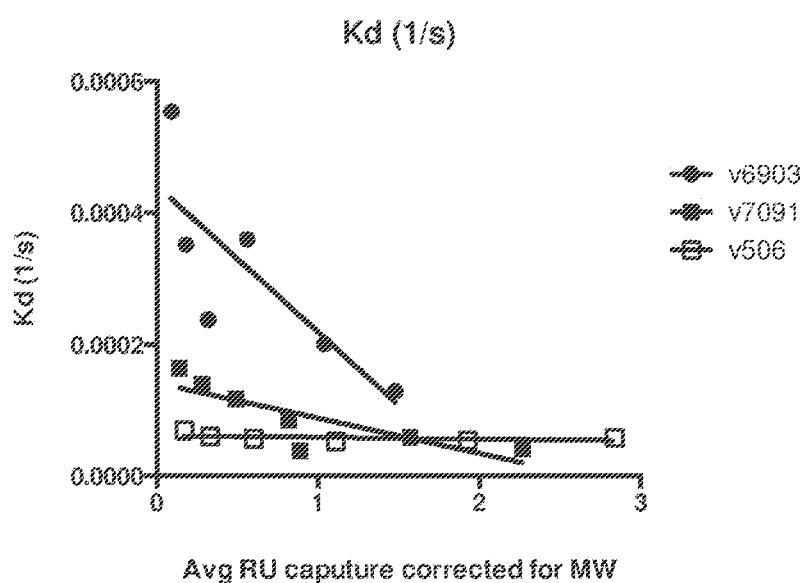

The experiment was conducted by SPR as described in Example 12. The data are shown in FIG. 47. FIG. 47A shows the plot and linear regression analysis for the kd (1/s) at different antibody capture levels with v6903 and v7091. Both v7091 and v6093 show a trend for decreasing off-rate with increasing surface capture levels; however, the correlation is significant with the Fab-scFv variant (v7091; P value=0.023) but not the Fab-Fab format (v6093; P value=0.053). The off-rate remained unchanged with varying antibody capture levels for the anti-HER2 monospecific control, v506.

Figure 47B:
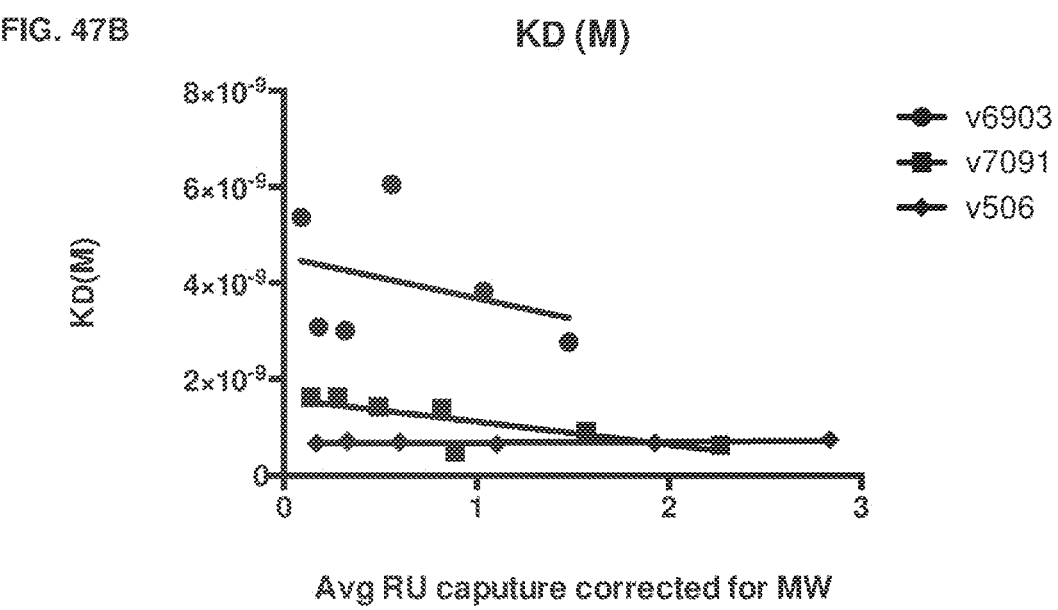

FIG. 47B shows the plot and linear regression analysis for the $K_D$ (M) at different antibody capture levels with v6903 and v7091. Similar to the off-rate comparison, both v7091 and v6093 show a trend for increasing affinity (lower $K_D$ value) with increasing surface capture levels. However, the correlation is significant with the Fab-scFv variant (v7091; P value=0.04) but not the Fab-Fab format (v6093; P value=0.51). The $K_D$ remained unchanged with varying antibody capture levels for the anti-HER2 monospecific control, v506. The data in FIG. 47 shows that the Fab-Fab and Fab-scFv anti-HER2 biparatopic antibody formats show trends of decreasing off-rates with increasing antibody surface capture levels; these trends are unique compared to a monospecific anti-Her2 antibody.

Example 44: Affinity and Stability Engineering of the Pertuzumab Fab

As indicated in Table 1, one variant (v10000) contains mutations in the Pertuzumab Fab. This Fab was derived from affinity and stability engineering in silico efforts, which were measured experimentally as monovalent or One-Armed Antibodies (OAAs).

Variant 9996: a monovalent anti-HER2 antibody, where the HER2 binding domain is a Fab derived from pertuzumab on chain A, with Y96A in VL region and T30A/A49G/L69F in VH region (Kabat numbering) and the Fc region is a heterodimer having the mutations T350V_L351Y_F405A_Y407V (EU numbering) in Chain A, T350V_T366L_K392L_T394W (EU numbering) in Chain B, and the hinge region of Chain B having the mutation C226S; the antigen binding domain binds to domain 4 of HER2.

Variant 10014: a monovalent anti-HER2 antibody, where the HER2 binding domain is a Fab derived from pertuzumab on chain A, with Y96A in VL region and T30A in VH region (Kabat numbering) and the Fc region is a heterodimer having the mutations T350V_L351Y_F405A_Y407V (EU numbering) in Chain A, T350V_T366L_K392L_T394W (EU numbering) in Chain B, and the hinge region of Chain B having the mutation C226S; the antigen binding domain binds to domain 4 of HER2.

Variant 10013: a monovalent anti-HER2 antibody, where the HER2 binding domain is a Fab derived from wild type pertuzumab on chain A, and the Fc region is a heterodimer having the mutations T350V_L351Y_F405A_Y407V (EU numbering) in Chain A, T350V_T366L_K392L_T394W (EU numbering) in Chain B, and the hinge region of Chain B having the mutation C226S; the antigen binding domain binds to domain 4 of HER2.

The following experiments were conducted to compare HER2 binding affinity and stability of the engineered Pertuzumab variants.

OAA variants were cloned and expressed as described in Example 1.

OAA were purified by protein A chromatography and Size Exclusion Chromatography, as described in Example 1.

Heterodimer purity (i.e. amount of OAA with a heterodimeric Fc) was assessed by non-reducing High Throughput Protein Express assay using Caliper LabChip GXII (Perkin Elmer #760499). Procedures were carried out according to HT Protein Express LabChip User Guide version2 LabChip GXII User Manual, with the following modifications. Heterodimer samples, at either 2 µl or 5 µl (concentration range 5-2000 ng/µl), were added to separate wells in 96 well plates (BioRad #HSP9601) along with 7 µl of HT Protein Express Sample Buffer (Perkin Elmer #760328). The heterodimer samples were then denatured at 70° C. for 15 mins. The LabChip instrument is operated using the HT Protein Express Chip (Perkin Elmer #760499) and the Ab-200 assay setting. After use, the chip was cleaned with MilliQ water and stored at 4° C.

The stability of the samples was assessed by measuring melting temperature or Tm, as determined by DSC with the protocol shown in example 24. The DSC was measured before and after SEC purification.

The affinity towards HER2 ECD of the samples was measured by SPR following the protocol from example 12. The SPR was measured before and after SEC purification. As summarized in Table 47A and 47B, the mutations in the variable domain have increased the HER2 affinity of the Fab compared to wild type pertuzumab, while maintaining WT stability. ([1] Purity determined by Caliper LabChip; [2] KD(WT)/KD(mut)

TABLE 47A

| OAA variant | Fab HC mutations | LC mut | Pr-A Yield (mg/L) | SPR pre-SEC KD AVE (nM) | SPR pre-SEC KD STDEV (nM) | n | Fold wrt WT[2] | Het purity post-SEC[1] | SPR post-SEC KD AVE (nM) | SPR post-SEC KD STDEV (nM) | n | Fold wrt WT |
|---|---|---|---|---|---|---|---|---|---|---|---|---|
| v9996 | T30A/A49G/L69F | Y96A | 22 | 1.7E−09 | 1.7E−10 | 5 | 9.6 | 93% | 1.8E−09 | 1.6E−11 | 2 | 8.4 |
| V10014 | T30A | Y96A | 20 | 2.0E−09 | 3.1E−10 | 4 | 8.1 | 81% | 2.1E−09 | 5.2E−10 | 3 | 7.0 |
| V10013 | WT | WT | 18 | 1.6E−08 | 5.1E−09 | 16 | 1.0 | 91% | 1.5E−08 | 3.5E−09 | 4 | 1.0 |

TABLE 47B

| OAA variant | DSC pre-SEC Tm (C.) | DSC pre-SEC ΔTm wrt WT (C.) | DSC post-SEC Tm (C.) | DSC post-SEC ΔTm wrt WT (C.) |
|---|---|---|---|---|
| v9996 | 77.2 | −0.2 | 77.2 | −0.7 |
| V10014 | 75.5 | −1.9 | 75.5 | −2.4 |
| V10013 | 77.4 | 0.0 | 77.9 | 0.0 |

The reagents employed in the examples are generally commercially available or can be prepared using commercially available instrumentation, methods, or reagents known in the art. The foregoing examples illustrate various aspects described herein and practice of the methods described herein. The examples are not intended to provide an exhaustive description of the many different embodiments of the invention. Thus, although the forgoing invention has been described in some detail by way of illustration and example for purposes of clarity of understanding, those of ordinary skill in the art will realize readily that many changes and modifications can be made thereto without departing from the spirit or scope of the appended claims.

All publications, patents and patent applications mentioned in this specification are herein incorporated by reference into the specification to the same extent as if each individual publication, patent or patent application was specifically and individually indicated to be incorporated herein by reference.

SEQUENCE TABLE

| Variant | H1 clone name | H2 clone name | L1 clone name | L2 clone name |
|---|---|---|---|---|
| 792 | 1011 | 1015 | −2 | −2 |
| 5019 | 3057 | 720 | 1811 | NA |
| 5020 | 719 | 3041 | NA | 1811 |
| 7091 | 3057 | 5244 | 1811 | NA |
| 10000 | 6586 | 5244 | 3382 | NA |

-continued

| Variant | H1 clone name | H2 clone name | L1 clone name | L2 clone name |
|---|---|---|---|---|
| 6903 | 5065 | 3468 | 5037 | 3904 |
| 6902 | 5065 | 3468 | 5034 | 3904 |
| 6717 | 3317 | 720 | NA | NA |
| 1040 | 4560 | 4553 | NA | 4561 |
| 630 | 719 | 716 | NA | NA |

-continued

| Variant | H1 clone name | H2 clone name | L1 clone name | L2 clone name |
|---|---|---|---|---|
| 4182 | 4560 | 3057 | NA | 1811 |
| 506 | 642 | 642 | −2 | −2 |
| 4184 | 3057 | 3041 | 1811 | 1811 |
| 9996 | 4372 | 6586 | NA | 3382 |

| SEQ ID NO. | Clone | Desc. | Sequence (amino acid or |
|---|---|---|---|
| 1 | 642 | Full | EVQLVESGGGLVQPGGSLRLSCAASGFNIKDTYIHWVRQAPGKGLEWVARIYPTNGYTRYADSVKGRF<br>TISADTSKNTAYLQMNSLRAEDTAVYYCSRWGGDGFYAMDYWGQGTLVTVSSASTKGPSVFPLAPSSK<br>STSGGTAALGCLVKDYFPEPVTVSWNSGALTSGVHTFPAVLQSSGLYSLSSVVTVPSSSLGTQTYICN<br>VNHKPSNTKVDKKVEPKSCDKTHTCPPCPAPELLGGPSVFLFPPKPKDTLMISRTPEVTCVVVDVSHE<br>DPEVKFNWYVDGVEVHNAKTKPREEQYNSTYRVVSVLTVLHQDWLNGKEYKCKVSNKALPAPIEKTIS<br>KAKGQPREPQVYTLPPSRDELTKNQVSLTCLVKGFYPSDIAVEWESNGQPENNYKTTPPVLDSDGSFF<br>LYSKLTVDKSRWQQGNVFSCSVMHEALHNHYTQKSLSLSPGK |
| 2 | 642 | Full | GAGGTGCAGCTGGTGGAAAGCGGAGGAGGACTGGTGCAGCCAGGAGGATCTCTGCGACTGAGTTGCGC<br>CGCTTCAGGATTCAACATCAAGGACACCTACATTCACTGGGTGCGACAGGCTCCAGGAAAAGGACTGG<br>AGTGGGTGGCTCGAATCTATCCCACTAATGGATACACCCGGTATGCCGACTCCGTGAAGGGGAGGTTT<br>ACTATTAGCGCCGATACATCCAAAAACACTGCTTACCTGCAGATGAACAGCCTGCGAGCCGAAGATAC<br>CGCTGTGTACTATTGCAGTCGATGGGGAGGAGACGGATTCTACGCTATGGATTATTGGGGACAGGGGA<br>CCCTGGTGACAGTGAGCTCCGCCTCTACCAAGGGCCCCAGTGTGTTTCCCCTGGCTCCTTCTAGTAAA<br>TCCACCTCTGGAGGGACAGCCGCTCTGGGATGTCTGGTGAAGGACTATTTCCCCGAGCCTGTGACCGT<br>GAGTTGGAACTCAGGCGCCCTGACAAGCGGAGTGCACACTTTTCCTGCTGTGCTGCAGTCAAGCGGGT<br>TGTACTCCCTGTCCTCTGTGGTGACAGTGCCAAGTTCAAGCCTGGGCACACAGACTTATATCTGCAAC<br>GTGAATCATAAGCCCTCAAATACAAAAGTGGACAAGAAAGTGGACCCAAGAGCTGTGATAAGCCCA<br>CACCTGCCCTCCCTGTCCAGCTCCAGAACTGCTGGGAGGACCTAGCGTGTTCCTGTTTCCCCCTAAGC<br>CAAAAGACACTCTGATGATTTCCAGGACTCCCGAGGTGACCTGCGTGGTGGTGGACGTGTCTCACGAG<br>GACCCCGAAGTGAAGTTCAACTGGTACGTGGATGGCGTGGAAGTGCATAATGCTAAGACAAAACCAAG<br>AGAGGAACAGTACAACTCCACTTATCGCGTCGTGAGCGTGCTGACCGTGCTGCACCAGGACTGGCTGA<br>ACGGGAAGGAGTATAAGTGCAAAGTCAGTAATAAGGCCCTGCCTGCTCCAATCGAAAAAACCATCTCT<br>AAGGCCAAAGGCCAGCCAAGGGAGCCCCAGGTGTACACACTGCCACCCAGCAGAGACGAACTGACCAA<br>GAACCAGGTGTCCCTGACATGTCTGGTGAAAGGCTTCTATCCTAGTGATATTGCTGTGGAGTGGGAAT<br>CAAATGGACAGCCAGAGAACAATTACAAGACCACACCTCCAGTGCTGGACAGCGATGGCAGCTTCTTC<br>CTGTATTCCAAGCTGACAGTGGATAAATCTCGATGGCAGCAGGGGAACGTGTTTACTTGTTCAGTGAT<br>GCATGAAGCCCTGCACAATCATTACACTCAGAAGAGCCTGTCCCTGTCTCCCGGCAAA |
| 3 | 642 | VH | EVQLVESGGGLVQPGGSLRLSCAASGFNIKDTYIHWVRQAPGKGLEWVARIYPTNGYTRYADSVKGRF<br>TISADTSKNTAYLQMNSLRAEDTAVYYCSRWGGDGFYAMDYWGQGTLVTVSS |
| 4 | 642 | VH | GAGGTGCAGCTGGTGGAAAGCGGAGGAGGACTGGTGCAGCCAGGAGGATCTCTGCGACTGAGTTGCGC<br>CGCTTCAGGATTCAACATCAAGGACACCTACATTCACTGGGTGCGACAGGCTCCAGGAAAAGGACTGG<br>AGTGGGTGGCTCGAATCTATCCCACTAATGGATACACCCGGTATGCCGACTCCGTGAAGGGGAGGTTT<br>ACTATTAGCGCCGATACATCCAAAAACACTGCTTACCTGCAGATGAACAGCCTGCGAGCCGAAGATAC<br>CGCTGTGTACTATTGCAGTCGATGGGGAGGAGACGGATTCTACGCTATGGATTATTGGGGACAGGGGA<br>CCCTGGTGACAGTGAGCTCC |
| 5 | 642 | H1 | GFNIKDTY |
| 6 | 642 | H1 | GGATTCAACATCAAGGACACCTAC |
| 7 | 642 | H3 | SRWGGDGFYAMDY |
| 8 | 642 | H3 | AGTCGATGGGGAGGAGACGGATTCTACGCTATGGATTAT |
| 9 | 642 | H2 | IYPTNGYT |
| 10 | 642 | H2 | ATCTATCCCACTAATGGATACACC |
| 11 | 642 | CH1 | ASTKGPSVFPLAPSSKSTSGGTAALGCLVKCYFPEPVTVSWNSGALTSGVHTFPAVLQSSGLYSLSSV<br>VTVPSSSLGTQTYICNVNHKPSNTKVDKKV |
| 12 | 642 | CH1 | GCCTCTACCAAGGGCCCCAGTGTGTTTCCCCTGGCTCCTTCTAGTAAATCCACCTCTGGAGGGACAGC<br>CGCTCTGGGATGTCTGGTGAAGGACTATTTCCCCGAGCCTGTGACCGTGAGTTGGAACTCAGGCGCC<br>TGACAAGCGGAGTGCACACTTTTCCTGCTGTGCTGCAGTCAAGCGGGTCTGTACTCCCTGTCCTCTGTG<br>GTGACAGTGCCAAGTTCAAGCCTGGGCACACAGACTTATATCTGCAACGTGAATCATAAGCCCTCAAA<br>TACAAAAGTGGACAAGAAAGTG |
| 13 | 642 | CH2 | APELLGGPSVFLFPPKPKDTLMISRTPEVTCVVVDVSHEDPEVKFNWYVDGVEVHNAKTKPREEQYNS<br>TYRVVSVLTVLHQDWLNGKEYKCKVSNKALPAPIEKTISKAK |

| SEQ ID NO. | Clone | Desc. | Sequence (amino acid or |
|---|---|---|---|
| 14 | 642 | CH2 | GCTCCAGAACTGCTGGGAGGACCTAGCGTGTTCCTGTTTCCCCCTAAGCCAAAAGACACTCTGATGAT<br>TTCCAGGACTCCCGAGGTGACCTGCGTGGTGGTGGACGTGTCTCACGAGGACCCCGAAGTGAAGTTCA<br>ACTGGTACGTGGATGGCGTGGAAGTGCATAATGCTAAGACAAAACCAAGAGAGGAACAGTACAACTCC<br>ACTTATCGCGTCGTGAGCGTGCTGACCGTGCTGCACCAGGACTGGCTGAACGGGAAGGAGTATAAGTG<br>CAAAGTCAGTAATAAGGCCCTGCCTGCTCCAATCGAAAAAACCATCTCTAAGGCCAAA |
| 15 | 642 | CH3 | GQPREPQVYTLPPSRDELTKNQVSLTCLVKGFYPSDIAVEWESNGQPENNYKTTPPVLDSDGSFFLYS<br>KLTVCKSRWQQGNVFSCSVMHEALHNHYTQKSLSLSPG |
| 16 | 642 | CH3 | GGCCAGCCAAGGGAGCCCCAGGTGTACACACTGCCACCCAGCAGAGACGAACTGACCAAGAACCAGGT<br>GTCCCTGACATGTCTGGTGAAAGGCTTCTATCCTAGTGATATTGCTGTGGAGTGGGAATCAAATGGAC<br>AGCCAGAGAACAATTACAAGACCACACCTCCAGTGCTGGACAGCGATGGCAGCTTCTTCCTGTATTCC<br>AAGCTGACAGTGGATAAATCTCGATGGCAGCAGGGGAACGTGTTTACTTGTTCAGTGATGCATGAAGC<br>CCTGCACAATCATTACACTCAGAAGAGCCTGTCCCTGTCTCCCGGC |
| 17 | 3468 | Full | EVQLVESGGGLVQPGGSLRLSCAASGFTFTDYTMDWVRQAPGKGLEWVADVNPNSGGSIYNQRFKGRF<br>TLSVDRSKNTLYLQMNSLRAEDTAVYYCARNLGPSFYFDYWGQGTLVTVSSASTKGPSVFPLAPSSKS<br>TSGGTAALGCLVKGYFPEPVTVSWNSGALTSGVHTFPAVLKSSGLYSLSSVVTVPSSSLGTQTYICNV<br>NHKPSNTKVDKKVEPKSCDKTHTCPPCPAPELLGGPSVFLFPPKPKDTLMISRTPEVTCVVVDVSHED<br>PEVKFNWYVDGVEVHNAKTKPREEQYNSTYRVVSVLTVLHQDWLNGKEYKCKVSNKALPAPIEKTISK<br>AKGQPREPQVYVLPPSRDELTKNQVSLLCLVKGFYPSDIAVEWESNGQPENNYLTWPPVLDSDGSFFL<br>YSKLTVDKSRWQQGNVFSCSVMHEALHNHYTQKSLSLSPG |
| 18 | 3468 | Full | GAAGTGCAGCTGGTCGAATCTGGAGGAGGACTGGTGCAGCCAGGAGGGTCCCTGCGCCTGTCTTGCGC<br>CGCTAGTGGCTTCACTTTTACCGACTACACCATGGATTGGGTGCGACAGGCACCTGGAAAGGGCCTGG<br>AGTGGGTCGCCGATGTGAACCCAAATAGCGGAGGCTCCATCTACAACCAGCGGTTCAAGGGCCGGTTC<br>ACCCTGTCAGTGGACCGGAGCAAAAACACCCTGTATCTGCAGATGAATAGCCTGCGAGCCGAAGATAC<br>TGCTGTGTACTATTGCGCCCGGAATCTGGGGCCCTCCTTCTACTTTGACTATTGGGGGCAGGGAACTC<br>TGGTCACCGTGAGCTCCGCCTCCACCAAGGGACCTTCTGTGTTCCCACTGGCTCCCTCTAGTAAATCC<br>ACATCTGGGGGAACTGCAGCCCTGGGCTGTCTGGTGAAGGGCTACTTCCCAGAGCCCGTCACAGTGTC<br>TTGGAACAGTGGCGCTCTGACTTCTGGGGTCCACACCTTTCCTGCAGTGCTGAAGTCAAGCGGGCTGT<br>ACAGCCTGTCCTCTGTGGTCACCGTGCCAAGTTCAAGCCTGGGAACACAGACTTATATCTGCAACGTG<br>AATCACAAGCCATCCAATACAAAAGTCGACAAGAAAGTGGAATCCAAGTCTTGTGATAAAACCCATAC<br>ATGCCCCCCTTGTCCTGCACCAGAGCTGCTGGGAGGACCAAGCGTGTTCCTGTTTCCACCCAAGCCTA<br>AAGATACACTGATGATTAGTAGGACCCCAGAAGTCACATGCGTGGTCGTGGACGTGAGCCACGAGGAC<br>CCCGAAGTCAAGTTTAACTGGTACGTGGACGGCGTCGAGGTGCATAATGCCAAGACTAAACCCAGGGA<br>GGAACAGTACAACAGTACCTATCGCGTCGTGTCAGTCCTGACAGTGCTGCATCAGGATTGGCTGAACG<br>GGAAAGAGTATAAGTGCAAAGTGAGCAATAAGGCTCTGCCCGCACCTATCGAGAAACAATTTCCAAG<br>GCAAAAGGACAGCCTAGAGAACCACAGGTGTACGTGCTGCCTCCATCAAGGGATGAGCTGACAAAGAA<br>CCAGGTCAGCCTGCTGTGTCTGGTGAAAGGATTCTATCCTCTGACATTGCTGTGGAGTGGGAAAGTA<br>ATGGCCAGCCTGAGAACAATTACCTGACCTGGCCCCCTGTGCTGGACTCAGATGGCAGCTTCTTTCTG<br>TATAGCAAGCTGACCGTCGACAAATCCCGGTGGCAGCAGGGGAATGTGTTTACTTGTTCAGTCATGCA<br>CGAGGCACTGCACAACCATTACACCCAGAAGTCACTGTCACTGTCACCAGGG |
| 19 | 3468 | VH | EVQLVESGGGLVQPGGSLRLSCAASGFTFTCYTMDWVRQAPGKGLEWVADVNPNSGGSIYNQRFKGRF<br>TLSVDRSKNTLYLQMNSLRAEDTAVYYCARNLGPSFYFDYWGQGTLVTVSS |
| 20 | 3468 | VH | GAAGTGCAGCTGGTCGAATCTGGAGGAGGACTGGTGCAGCCAGGAGGGTCCCTGCGCCTGTCTTGCGC<br>CGCTAGTGGCTTCACTTTTACCGACTACACCATGGATTGGGTGCGACAGGCACCTGGAAAGGGCCTGG<br>AGTGGGTCGCCGATGTGAACCCAAATAGCGGAGGCTCCATCTACAACCAGCGGTTCAAGGGCCGGTTC<br>ACCCTGTCAGTGGACCGGAGCAAAAACACCCTGTATCTGCAGATGAATAGCCTGCGAGCCGAAGATAC<br>TGCTGTGTACTATTGCGCCCGGAATCTGGGGCCCTCCTTCTACTTTGACTATTGGGGGCAGGGAACTC<br>TGGTCACCGTGAGCTCC |
| 21 | 3468 | H1 | GFTFTDYT |
| 22 | 3468 | H1 | GGCTTCACTTTTACCGACTACACC |
| 23 | 3468 | H3 | ARNLGPSFYFDY |
| 24 | 3468 | H3 | GCCCGGAATCTGGGGCCCTCCTTCTACTTTGACTAT |
| 25 | 3468 | H2 | VNPNSGGS |
| 26 | 3468 | H2 | GTGAACCCAAATAGCGGAGGCTCC |
| 27 | 3468 | CH1 | ASTKGPSVFPLAPSSKSTSGGTAALGCLVKGYFPEPVTVSWNSGALTSGVHTFPAVLKSSGLYSLSSV<br>VTVPSSSLGTQTYICNVNHKPSNTKVDKKV |
| 28 | 3468 | CH1 | GCCTCCACCAAGGGACCTTCTGTGTTCCCACTGGCTCCCTCTAGTAAATCCACATCTGGGGGAACTGC<br>AGCCCTGGGCTGTCTGGTGAAGGGCTACTTCCCAGAGCCCGTCACAGTGTCTTGGAACAGTGGCGCTC<br>TGACTTCTGGGGTCCACACCTTTCCTGCAGTGCTGAAGTCAAGCGGGCTGTACAGCCTGTCCTCTGTG<br>GTCACCGTGCCAAGTTCAAGCCTGGGAACACAGACTTATATCTGCAACGTGAATCACAAGCCATCCAA<br>TACAAAAGTCGACAAGAAAGTG |

| SEQ ID NO. | Clone | Desc. | Sequence (amino acid or |
|---|---|---|---|
| 29 | 3468 | CH2 | APELLGGPSVFLFPPKPKDTLMISRTPEVTCVVVDVSHEDPEVKFNWYVDGVEVHNAKTKPREEQYNS TYRVVSVLTVLHQDWLNGKEYKCKVSNKALPAPIEKTISKAK |
| 30 | 3468 | CH2 | GCACCAGAGCTGCTGGGAGGACCAAGCGTGTTCCTGTTTCCACCCAAGCCTAAAGATACACTGATGAT TAGTAGGACCCCAGAAGTCACATGCGTGGTCGTGGACGTGAGCCACGAGGACCCCGAAGTCAAGTTTA ACTGGTACGTGGACGGCGTCGAGGTGCATAATGCCAAGACTAAACCCAGGGAGGAACAGTACAACAGT ACCTATCGCGTCGTGTCAGTCCTGACAGTGCTGCATCAGGATTGGCTGAACGGGAAGAGTATAAGTG CAAAGTGAGCAATAAGGCTCTGCCCGCACCTATCGAGAAACAATTTCCAAGGCAAAA |
| 31 | 3468 | CH3 | GQPREPQVYVLPPSRDELTKNQVSLLCLVKGFYPSDTAVEWESNGQPENNYLTWPPVLDSDGSFFLYS KLTVDKSRWQQGNVFSCSVMHEALHNHYTQKSLSLSPG |
| 32 | 3468 | CH3 | GGACAGCCTAGAGAACCACAGGTGTACGTGCTGCCTCCATCAAGGGATGAGCTGACAAAGAACCAGGT CAGCCTGCTGTGTCTGGTGAAAGGATTCTATCCCTCTGACATTGCTGTGGAGTGGGAAAGTAATGGCC AGCCTGAGAACAATTACCTGACCTGGCCCCCTGTGCTGGACTCAGATGGCAGCTTCTTTCTGTATAGC AAGCTGACCGTCGACAAATCCCGGTGGCAGCAGGGGAATGTGTTTACTTGTTCAGTCATGCACGAGGC ACTGCACAACCATTACACCCAGAAGTCACTGTCACTGTCACCAGGG |
| 33 | 1811 | Full | DIQMTQSPSSLSASVGDRVTITCKASQDVSIGVAWYQQKPGKAPKLLIYSASYRYTGVPSRFSGSGSG TDFTLTISSLQPEDFATYYCQQYYIYPYTFGQGTKVEIKRTVAAPSVFIFPPSDEQLKSGTASVVCLL NNFYPREAKVQWKVDNALQSGNSQESVTEQDSKDSTYSLSSTLTLSKADYEKHKVYACEVTHQGLSSP VTKSFNRGEC |
| 34 | 1811 | Full | GATATTCAGATGACCCAGTCCCCAAGCTCCCTGAGTGCCTCAGTGGGCGACCGAGTCACCATCACATG CAAGGCTTCCCAGGATGTGTCTATTGGAGTCGCATGGTACCAGCAGAAGCCAGGCAAAGCACCCAAGC TGCTGATCTATAGCGCCTCCTACCGGTATACCGGCGTGCCCTCTAGATTCTCTGGCAGTGGGTCAGGA ACAGACTTTACTCTGACCATCTCTAGTCTGCAGCCTGAGGATTTCGCTACCTACTATTGCCAGCAGTA CTATATCTACCCATATACCTTTGGCCAGGGGACAAAAGTGGAGATCAAGAGGACTGTGGCCGCTCCCT CCGTCTTCATTTTTCCCCCTTCTGACGAACAGCTGAAAAGTGGCACAGCCAGCGTGGTCTGTCTGCTG AACAATTTCTACCCTCGCGAAGCCAAAGTGCAGTGGAAGGTCGATAACGCTCTGCAGAGCGGCAACAG CCAGGAGTCTGTGACTGAACAGGACAGTAAAGATTCAACCTATAGCCTGTCAAGCACACTGACTCTGA GCAAGGCAGACTACGAGAAGCACAAAGTGTATGCCTGCGAAGTCACACATCAGGGGCTGTCCTCTCCT GTGACTAAGAGCTTTAACAGAGGAGAGTGT |
| 35 | 1811 | VL | DIQMTQSPSSLSASVGDRVTITCKASQDVSIGVAWYQQKPGKAPKLLIYSASYRYTGVPSRFSGSGSG TDFTLTISSLQPEDFATYYCQQYYIYPYTFGQGTKVEIK |
| 36 | 1811 | VL | GATATTCAGATGACCCAGTCCCCAAGCTCCCTGAGTGCCTCAGTGGGCGACCGAGTCACCATCACATG CAAGGCTTCCCAGGATGTGTCTATTGGAGTCGCATGGTACCAGCAGAAGCCAGGCAAAGCACCCAAGC TGCTGATCTATAGCGCCTCCTACCGGTATACCGGCGTGCCCTCTAGATTCTCTGGCAGTGGGTCAGGA ACAGACTTTACTCTGACCATCTCTAGTCTGCAGCCTGAGGATTTCGCTACCTACTATTGCCAGCAGTA CTATATCTACCCATATACCTTTGGCCAGGGGACAAAAGTGGAGATCAAG |
| 37 | 1811 | L1 | QDVSIG |
| 38 | 1811 | L1 | CAGGATGTGTCTATTGGA |
| 39 | 1811 | L3 | QQYYIYPYT |
| 40 | 1811 | L3 | CAGCAGTACTATATCTACCCATATACC |
| 41 | 1811 | L2 | SAS |
| 42 | 1811 | L2 | AGCGCCTCC |
| 43 | 1811 | CL | RTVAAPSVFIFPPSDEQLKSGTASVVCLLNNFYPREAKVQWKVDNALQSGNSQESVTEQDSKDSTYSL SSTLTLSKADYEKHKVYACEVTHQGLSSPVTKSFNRGEC |
| 44 | 1811 | CL | AGGACTGTGGCCGCTCCCTCCGTCTTCATTTTTCCCCCTTCTGACGAACAGCTGAAAAGTGGCACAGC CAGCGTGGTCTGTCTGCTGAACAATTTCTACCCTCGCGAAGCCAAAGTGCAGTGGAAGGTCGATAACG CTCTGCAGAGCGGCAACAGCCAGGAGTCTGTGACTGAACAGGACAGTAAAGATTCAACCTATAGCCTG TCAAGCACACTGACTCTGAGCAAGGCAGACTACGAGAAGCACAAAGTGTATGCCTGCGAAGTCACACA TCAGGGGCTGTCCTCTCCTGTGACTAAGAGCTTTAACAGAGGAGAGTGT |
| 45 | 5034 | Full | DYKDDDDKDIQMTQSPSSLSASVGDRVTITCRASQDVNTAVAWYQQKPGKAPKLLIYSASFLYSGVPS RFSGSRSGTDFTLTISSLQPEDFATYYCQQHYTTPPTFGQGTKVEIKRTVAAPSVFIFPPSDERLKSG TASVVCLLNNFYPREAKVQWKVDNALQSGNSQESVTEQDSKDSTYSLSSTLTLSKADYEKHKVYACEV THQGLSSPVTKSFNRGEC |
| 46 | 5034 | Full | GACTACAAAGACGACGATGACAAAGATATCCAGATGACCCAGTCCCCTAGCTCCCTGTCCGCTTCTGT GGGCGATAGGGTCACTATTACCTGCCGCGCATCTCAGGACGTGAACACCGCAGTCGCCTGGTACCAGC AGAAGCCTGGGAAAGCTCCAAAGCTGCTGATCTACAGTGCATCATTCCTGTATTCAGGAGTGCCCAGC CGGTTTAGCGGCAGCAGATCTGGCACCGATTTCACACTGACTATTTCTAGTCTGCAGCCTGAGGACTT TGCCACATACTATTGCCAGCAGCACTATACCACACCCCCTACTTTCGGCCAGGGGACCAAAGTGGAGA |

| SEQ ID NO. | Clone | Desc. | Sequence (amino acid or |
|---|---|---|---|
| | | | TCAAGCGAACTGTGGCCGCTCCAAGTGTCTTCATTTTTCCACCCAGCGATGAAAGACTGAAGTCCGGC<br>ACAGCTTCTGTGGTCTGTCTGCTGAACAATTTTTACCCCAGAGAGGCCAAAGTGCAGTGGAAGGTCGA<br>CAACGCTCTGCAGAGTGGCAACAGCCAGGAGAGCGTGACAGAACAGGATTCCAAAGACTCTACTTATA<br>GTCTGTCAAGCACCCTGACACTGAGCAAGGCAGACTACGAAAAGCATAAAGTGTATGCCTGTGAGGTC<br>ACACATCAGGGGCTGTCATCACCAGTCACCAAATATTCCAATCGGGGGAGTGC |
| 47 | 5034 | VL | DIQMTQSPSSLSASVGDRVTITCRASQDVNTAVAWYQQKPGKAPKLLIYSASFLYSGVPSRFSGSRSG<br>TDFTLTISSLQPEDFATYYCQQHYTTPPTFGQGTKVEIK |
| 48 | 5034 | VL | GATATCCAGATGACCCAGTCCCCTAGCTCCCTGTCCGCTTCTGTGGGCGATAGGGTCACTATTACCTG<br>CCGCGCATCTCAGGACGTGAACACCGCAGTCGCCTGGTACCAGCAGAAGCCTGGGAAAGCTCCAAAGC<br>TGCTGATCTACAGTGCATCATTCCTGTATTCAGGAGTGCCCAGCCGGTTTAGCGGCAGCAGATCTGGC<br>ACCGATTTCACACTGACTATTTCTAGTCTGCAGCCTGAGGACTTTGCCACATACTATTGCCAGCAGCA<br>CTATACCACACCCCCTACTTTCGGCCAGGGGACCAAAGTGGAGATCAAG |
| 49 | 5034 | L1 | QDVNTA |
| 50 | 5034 | L1 | CAGGACGTGAACACCGCA |
| 51 | 5034 | L3 | QQHYTTPPT |
| 52 | 5034 | L3 | CAGCAGCACTATACCACACCCCCTACT |
| 53 | 5034 | L2 | SAS |
| 54 | 5034 | L2 | AGTGCATCA |
| 55 | 5034 | CL | RTVAAPSVFIFPPSDERLKSGTASVVCLLNNFYPREAKVQWKVDNALQSGNSQESVTEQDSKDSTYSL<br>SSTLTLSKADYEKHKVYACEVTHQGLSSPVTKSFNRGEC |
| 56 | 5034 | CL | CGAACTGTGGCCGCTCCAAGTGTCTTCATTTTTCCACCCAGCGATGAAAGACTGAAGTCCGGCACAGC<br>TTCTGTGGTCTGTCTGCTGAACAATTTTTACCCCAGAGAGGCCAAAGTGCAGTGGAAGGTCGACAACG<br>CTCTGCAGAGTGGCAACAGCCAGGAGAGCGTGACAGAACAGGATTCCAAAGACTCTACTTATAGTCTG<br>TCAAGCACCCTGACACTGAGCAAGGCAGACTACGAAAAGCATAAAGTGTATGCCTGTGAGGTCACACA<br>TCAGGGGCTGTCATCACCAGTCACCAAATATTCCAATCGGGGGAGTGC |
| 57 | 5037 | Full | DYKDDDDKDIQMTQSPSSLSASVGDRVTITCRASQDVNTAVAWYQQKPGKAPKLLIYSASFLYSGVPS<br>RFSGSRSGTDFTLTISSLQPEDFATYYCQQHYTTPPTFGQGTKVEIKRTVAAPSVFIFPPSDERLKSG<br>TASVVCLLNNFYPREAKVQWKVDNALQSGNSKESVTEQDSKDSTYSLSSRLTLSKADYEKHKVYACEV<br>THQGLSSPVTKSFNRGEC |
| 58 | 5037 | Full | GACTACAAAGACGACGATGACAAAGATATCCAGATGACCCAGTCCCCTAGCTCCCTGTCCGCTTCTGT<br>GGGCGATAGGGTCACTATTACCTGCCGCGCATCTCAGGACGTGAACACCGCAGTCGCCTGGTACCAGC<br>AGAAGCCTGGGAAAGCTCCAAAGCTGCTGATCTACAGTGCATCATTCCTGTATTCAGGAGTGCCCAGC<br>CGGTTTAGCGGCAGCAGATCTGGCACCGATTTCACACTGACTATTTCTAGTCTGCAGCCTGAGGACTT<br>TGCCACATACTATTGCCAGCAGCACTATACCACACCCCCTACTTTCGGCCAGGGGACCAAAGTGGAGA<br>TCAAGCGAACTGTGGCCGCTCCAAGTGTCTTCATTTTTCCACCCAGCGATGAAAGACTGAAGTCCGGC<br>ACAGCTTCTGTGGTCTGTCTGCTGAACAATTTTTACCCCAGAGAGGCCAAAGTGCAGTGGAAGGTCGA<br>CAACGCTCTGCAGAGTGGCAACAGCAAGGAGAGCGTGACAGAACAGGATTCCAAAGACTCTACTTATA<br>GTCTGTCAAGCAGACTGACACTGAGCAAGGCAGACTACGAAAAGCATAAAGTGTATGCCTGTGAGGTC<br>ACACATCAGGGGCTGTCATCACCAGTCACCAAATATTCCAATCGGGGGAGTGC |
| 59 | 5037 | VL | DIQMTQSPSSLSASVGDRVTITCRASQDVNTAVAWYQQKPGKAPKLLIYSASFLYSGVPSRFSGSRSG<br>TDFTLTISSLQPEDFATYYCQQHYTTPPTFGQGTKVEIK |
| 60 | 5037 | VL | GATATCCAGATGACCCAGTCCCCTAGCTCCCTGTCCGCTTCTGTGGGCGATAGGGTCACTATTACCTG<br>CCGCGCATCTCAGGACGTGAACACCGCAGTCGCCTGGTACCAGCAGAAGCCTGGGAAAGCTCCAAAGC<br>TGCTGATCTACAGTGCATCATTCCTGTATTCAGGAGTGCCCAGCCGGTTTAGCGGCAGCAGATCTGGC<br>ACCGATTTCACACTGACTATTTCTAGTCTGCAGCCTGAGGACTTTGCCACATACTATTGCCAGCAGCA<br>CTATACCACACCCCCTACTTTCGGCCAGGGGACCAAAGTGGAGATCAAG |
| 61 | 5037 | L1 | QDVNTA |
| 62 | 5037 | L1 | CAGGACGTGAACACCGCA |
| 63 | 5037 | L3 | QQHYTTPPT |
| 64 | 5037 | L3 | CAGCAGCACTATACCACACCCCCTACT |
| 65 | 5037 | L2 | SAS |
| 66 | 5037 | L2 | AGTGCATCA |
| 67 | 5037 | CL | RTVAAPSVFIFPPSDERLKSGTASVVCLLNNFYPREAKVQWKVDNALQSGNSKESVTEQDSKDSTYSL<br>SSRLTLSKADYEKHKVYACEVTHQGLSSPVTKSFNRGEC |

| SEQ ID NO. | Clone | Desc. | Sequence (amino acid or |
|---|---|---|---|
| 68 | 5037 | CL | CGAACTGTGGCCGCTCCAAGTGTCTTCATTTTTCCACCCAGCGATGAAAGACTGAAGTCCGGCACAGC<br>TTCTGTGGTCTGTCTGCTGAACAATTTTTACCCCAGAGAGGCCAAAGTGCAGTGGAAGGTCGACAACG<br>CTCTGCAGAGTGGCAACAGCAAGGAGAGCGTGACAGAACAGGATTCCAAAGACTCTACTTATAGTCTG<br>TCAAGCAGACTGACACTGAGCAAGGCAGACTACGAAAGCATAAAGTGTATGCCTGTGAGGTCACACA<br>TCAGGGGCTGTCATCACCAGTCACCAAATATTCCAATCGGGGGGAGTGC |
| 69 | 3382 | Full | DIQMTQSPSSLSASVGDRVTITCKASQDVSIGVAWYQQKPGKAPKLLIYSASYRYTGVPSRFSGSGSG<br>TDFTLTISSLQPEDFATYYCQQYYIYPATFGQGTKVEIKRTVAAPSVFIFPPSDEQLKSGTASVVCLL<br>NNFYPREAKVQWKVDNALQSGNSQESVTEQCSKDSTYSLSSTLTLSKADYEKHKVYACEVTHQGLSSP<br>VTKSFNRGEC |
| 70 | 3382 | Full | GATATTCAGATGACCCAGTCCCCAAGCTCCCTGAGTGCCTCAGTGGGCGACCGAGTCACCATCACATG<br>CAAGGCTTCCCAGGATGTGTCTATTGGAGTCGCATGGTACCAGCAGAAGCCAGGCAAAGCACCCAAGC<br>TGCTGATCTATAGCGCCTCCTACCGGTATACCGGCGTGCCCTCTAGATTCTCTGGCAGTGGGTCAGGA<br>ACAGACTTTACTCTGACCATCTCTAGTCTGCAGCCTGAGGATTTCGCTACCTACTATTGCCAGCAGTA<br>CTATATCTACCCAGCCACCTTTGGCCAGGGGACAAAAGTGGAGATCAAGAGGACTGTGGCCGCTCCCT<br>CCGTCTTCATTTTTCCCCCTTCTGACGAACAGCTGAAAAGTGGCACAGCCAGCGTGGTCTGTCTGCTG<br>AACAATTTCTACCCTCGCGAAGCCAAAGTGCAGTGGAAGGTCGATAACGCTCTGCAGAGCGGCAACAG<br>CCAGGAGTCTGTGACTGAACAGGACAGTAAAGATTCAACCTATAGCCTGTCAAGCACACTGACTCTGA<br>GCAAGGCAGACTACGAGAAGCACAAAGTGTATGCCTGCGAAGTCACACATCAGGGGCTGTCCTCTCCT<br>GTGACTAAGAGCTTTAACAGAGGAGAGTGT |
| 71 | 3382 | VL | DIQMTQSPSSLSASVGDRVTITCKASQDVSIGVAWYQQKPGKAPKLLIYSASYRYTGVPSRFSGSGSG<br>TDFTLTISSLQPEDFATYYCQQYYIYPATFGQGTKVEIK |
| 72 | 3382 | VL | GATATTCAGATGACCCAGTCCCCAAGCTCCCTGAGTGCCTCAGTGGGCGACCGAGTCACCATCACATG<br>CAAGGCTTCCCAGGATGTGTCTATTGGAGTCGCATGGTACCAGCAGAAGCCAGGCAAAGCACCCAAGC<br>TGCTGATCTATAGCGCCTCCTACCGGTATACCGGCGTGCCCTCTAGATTCTCTGGCAGTGGGTCAGGA<br>ACAGACTTTACTCTGACCATCTCTAGTCTGCAGCCTGAGGATTTCGCTACCTACTATTGCCAGCAGTA<br>CTATATCTACCCAGCCACCTTTGGCCAGGGGACAAAAGTGGAGATCAAG |
| 73 | 3382 | L1 | QDVSIG |
| 74 | 3382 | L1 | CAGGATGTGTCTATTGGA |
| 75 | 3382 | L3 | QQYYIYPAT |
| 76 | 3382 | L3 | CAGCAGTACTATATCTACCCAGCCACC |
| 77 | 3382 | L2 | SAS |
| 78 | 3382 | L2 | AGCGCCTCC |
| 79 | 3382 | CL | RTVAAPSVFIFPPSDEQLKSGTASVVCLLNNFYPREAKVQWKVDNALQSGNSQESVTEQDSKDSTYSL<br>SSTLTLSKADYEKHKVYACEVTHQGLSSPVTKSFNRGEC |
| 80 | 3382 | CL | AGGACTGTGGCCGCTCCCTCCGTCTTCATTTTTCCCCCTTCTGACGAACAGCTGAAAAGTGGCACAGC<br>CAGCGTGGTCTGTCTGCTGAACAATTTCTACCCTCGCGAAGCCAAAGTGCAGTGGAAGGTCGATAACG<br>CTCTGCAGAGCGGCAACAGCCAGGAGTCTGTGACTGAACAGGACAGTAAAGATTCAACCTATAGCCTG<br>TCAAGCACACTGACTCTGAGCAAGGCAGACTACGAGAAGCACAAAGTGTATGCCTGCGAAGTCACACA<br>TCAGGGGCTGTCCTCTCCTGTGACTAAGAGCTTTAACAGAGGAGAGTGT |
| 81 | 5065 | Full | EVQLVESGGGLVQPGGSLRLSCAASGFNIKDTYIHWVRQAPGKGLEWVARIYPTNGYTRYADSVKGRF<br>TISADTSKNTAYLQMNSLRAEDTAVYYCSRWGGDGFYAMDYWGQGTLVTVSSASTKGPSVFPLAPSSK<br>STSGGTAALGCEVTDYFPEPVTVSWNSGALTSGVHTFPAVLQSSGLYSLSSVVTVPSSSLGTQTYICN<br>VNHKPSNTKVDKKVEPKSCDKTHTCPPCPAPELLGGPSVFLFPPKPKDTLMISRTPEVTCVVVDVSHE<br>DPEVKFNWYVDGVEVHNAKTKPREEQYNSTYRVVSVLTVLHQDWLNGKEYKCKVSNKALPAPIEKTIS<br>KAKGQPREPQVYVYPPSRDELTKNQVSLTCLVKGFYPSDIAVEWESNGQPENNYKTTPPVLDSDGSFA<br>LVSKLTVDKSRWQQGNVFSCSVMHEALHNHYTQKSLSLSPG |
| 82 | 5065 | Full | GAGGTGCAGCTGGTCGAAAGCGGAGGAGGACTGGTGCAGCCAGGAGGGTCACTGCGACTGAGCTGCGC<br>AGCTTCCGGCTTCAACATCAAGGACACCTACATTCACTGGGTCCGCCAGGCTCCTGGAAAAGGCCTGG<br>AGTGGGTGGCACGAATCTATCCAACTAATGGATACACCCGGTATGCCGACTCCGTGAAGGGCCGGTTC<br>ACCATTTCTGCAGATACAAGTAAAAACACTGCCTACCTGCAGATGAACAGCCTGCGAGCCGAAGATAC<br>AGCCGTGTACTATTGCAGCCGATGGGGAGGCGACGGCTTCTACGCTATGGATTATTGGGGGCAGGGAA<br>CCCTGGTCACAGTGAGCTCCGCATCAACAAAGGGGCCTAGCGTGTTTCCACTGGCCCCCTCTAGTAAA<br>TCCACCTCTGGGGGAACAGCAGCCCTGGGATGTGAGGTGACCGACTACTTCCCAGAGCCCGTCACTGT<br>GAGCTGGAACTCCGGCGCCCTGACATCTGGGGTCCATACTTTTCCTGCTGTGCTGCAGTCAAGCGGCC<br>TGTACAGCCTGTCCTCTGTGGTCACTGTGCCAAGTTCAAGCCTGGGGACTCAGACCTATATCTGCAAC<br>GTGAATCACAAGCCATCCAATACCAAAGTCGACAAGAAAGTGGAACCCAAGTCTTGTGATAAAACACA<br>TACTTGCCCCCCTTGTCCTGCACCAGAGCTGCTGGGAGGACCAAGCGTGTTCCTGTTTCCACCCAAGC<br>CTAAAGACACCCTGATGATTAGTAGGACTCCAGAAGTCACCTGCGTGGTCGTGGACGTGAGCCACGAG<br>GACCCCGAAGTCAAGTTCAACTGGTACGTGGATGGCGTCGAGGTGCATAATGCCAAGACAAAACCCAG<br>GGAGGAACAGTACAACTCCACTTATCGCGTCGTGTCTGTCCTGACCGTGCTGCACCAGGACTGGCTGA |

| SEQ ID NO. | Clone | Desc. | Sequence (amino acid or |
|---|---|---|---|
| | | | ACGGCAAGGAGTATAAGTGCAAAGTGAGCAATAAGGCTCTGCCCGCACCTATCGAGAAAACAATTTCC<br>AAGGCTAAAGGGCAGCCTAGAGAACCACAGGTGTACGTGTACCCTCCATCTAGGGACGAGCTGACCAA<br>GAACCAGGTCAGTCTGACATGTCTGGTGAAAGGGTTCTATCCCAGCGATATCGCAGTGGAGTGGGAAT<br>CCAATGGACAGCCTGAGAACAATTACAAGACCACACCCCTGTGCTGGACTCTGATGGAAGTTTCGCC<br>CTGGTGAGTAAGCTGACCGTCGATAAATCACGGTGGCAGCAGGGCAACGTGTTCAGCTGTTCAGTGAT<br>GCACGAAGCACTGCACAACCACTACACCCAGAAAAGCCTGTCCCTGTCCCCCGGC |
| 83 | 5065 | VH | EVQLVESGGGLVQPGGSLRLSCAASGFNIKDTYIHWVRQAPGKGLEWVARIYPTNGYTRYADSVKGRF<br>TISADTSKNTAYLQMNSLRAEDTAVYYCSRWGGDGFYAMDYWGQGTLVTVSS |
| 84 | 5065 | VH | GAGGTGCAGCTGGTCGAAAGCGGAGGAGGACTGGTGCAGCCAGGAGGGTCACTGCGACTGAGCTGCGC<br>AGCTTCCGGCTTCAACATCAAGGACACCTACATTCACTGGGTCCGCCAGGCTCCTGGAAAAGGCCTGG<br>AGTGGGTGGCACGAATCTATCCAACTAATGGATACACCCGGTATGCCGACTCCGTGAAGGGCCGGTTC<br>ACCATTTCTGCAGATACAAGTAAAAACACTGCCTACCTGCAGATGAACAGCCTGCAGCCGAAGATAC<br>AGCCGTGTACTATTGCAGCCGATGGGGAGGCGACGGCTTCTACGCTATGGATTATTGGGGCAGGGAA<br>CCCTGGTCACAGTGAGCTCC |
| 85 | 5065 | H1 | GFNIKDTY |
| 86 | 5065 | H1 | GGCTTCAACATCAAGGACACCTAC |
| 87 | 5065 | H3 | SRWGGDGFYAMDY |
| 88 | 5065 | H3 | AGCCGATGGGGAGGCGACGGCTTCTACGCTATGGATTAT |
| 89 | 5065 | H2 | IYPTNGYT |
| 90 | 5065 | H2 | ATCTATCCAACTAATGGATACACC |
| 91 | 5065 | CH1 | ASTKGPSVFPLAPSSKSTSGGTAALGCEVTDYFPEPVTVSWNSGALTSGVHTFPAVLQSSGLYSLSSV<br>VTVPSSSLGTQTYICNVNHKPSNTKVDKKV |
| 92 | 5065 | CH1 | GCATCAACAAAGGGGCCTAGCGTGTTTCCACTGGCCCCCTCTAGTAAATCCACCTCTGGGGGAACAGC<br>AGCCCTGGGATGTGAGGTGACCGACTACTTCCCAGAGCCCGTCACTGTGAGCTGGAACTCCGGCGCC<br>TGACATCTGGGGTCCATACTTTTCCTGCTGTGCTGCAGTCAAGCGGCCTGTACAGCCTGTCCTCTGTG<br>GTCACTGTGCCAAGTTCAAGCCTGGGGACTCAGACCTATATCTGCAACGTGAATCACAAGCCATCCAA<br>TACCAAAGTCGACAAGAAAGTG |
| 93 | 5065 | CH2 | APELLGGPSVFLFPPKPKDTLMISRTPEVTCVVVDVSHEDPEVKFNWYVDGVEVHNAKTKPREEQYNS<br>TYRVVSVLTVLHQDWLNGKEYKCKVSNKALPAPIEKTISKAK |
| 94 | 5065 | CH2 | GCACCAGAGCTGCTGGGAGGACCAAGCGTGTTCCTGTTTCCACCCAAGCCTAAAGACACCCTGATGAT<br>TAGTAGGACTCCAGAAGTCACCTGCGTGGTCGTGGACGTGAGCCACGAGGACCCCGAAGTCAAGTTCA<br>ACTGGTACGTGGATGGCGTCGAGGTGCATAATGCCAAGACAAAACCCAGGGAGGAACAGTACAACTCC<br>ACTTATCGCGTCGTGTCTGTCCTGACCGTGCTGCACCAGGACTGGCTGAACGGCAAGGAGTATAAGTG<br>CAAAGTGAGCAATAAGGCTCTGCCCGCACCTATCGAGAAAACAATTTCCAAGGCTAAA |
| 95 | 5065 | CH3 | GQPREPQVYVYPPSRDELTKNQVSLTCLVKGFYPSDIAVEWESNGQPENNYKTTPPVLDSDGSFALVS<br>KLTVDKSRWQQGNVFSCSVMHEALHNHYTQKSLSLSPG |
| 96 | 5065 | CH3 | GGGCAGCCTAGAGAACCACAGGTGTACGTGTACCCTCCATCTAGGGACGAGCTGACCAAGAACCAGGT<br>CAGTCTGACATGTCTGGTGAAAGGGTTCTATCCCAGCGATATCGCAGTGGAGTGGGAATCCAATGGAC<br>AGCCTGAGAACAATTACAAGACCACACCCCTGTGCTGGACTCTGATGGAAGTTTCGCCCTGGTGAGT<br>AAGCTGACCGTCGATAAATCACGGTGGCAGCAGGGCAACGTGTTCAGCTGTTCAGTGATGCACGAAGC<br>ACTGCACAACCACTACACCCAGAAAAGCCTGTCCCTGTCCCCCGGC |
| 97 | 6586 | Full | EVQLVESGGGLVQPGGSLRLSCAASGFTFADYTMDWVRQAPGKGLEWVGDVNPNSGGSIYNQRFKGRF<br>TFSVDRSKNTLYLQMNSLRAEDTAVYYCARNLGPSFYFDYWGQGTLVTVSSASTKGPSVFPLAPSSKS<br>TSGGTAALGCLVKDYFPEPVTVSWNSGALTSGVHTFPAVLQSSGLYSLSSVVTVPSSSLGTQTYICNV<br>NHKPSNTKVDKKVEPKSCDKTHTCPPCPAPELLGGPSVFLFPPKPKDTLMISRTPEVTCVVVDVSHED<br>PEVKFNWYVDGVEVHNAKTKPREEQYNSTYRVVSVLTVLHQDWLNGKEYKCKVSNKALPAPIEKTISK<br>AKGQPREPQVYVYPPSRDELTKNQVSLTCLVKGFYPSDIAVEWESNGQPENNYKTTPPVLDSDGSFAL<br>VSKLTVDKSRWQQGNVFSCSVMHEALHNHYTQKSLSLSPG |
| 98 | 6586 | Full | GAGGTGCAGCTGGTGGAATCAGGAGGGGCCTGGTGCAGCCCGGAGGGTCTCTGCGACTGTCATGTGC<br>CGCTTCTGGGTTCACTTTCGCAGACTACACAATGGATTGGGTGCGACAGGCCCCCGGAAAGGGACTGG<br>AGTGGGTGGCGATGTCAACCCTAATTCTGGCGGGAGTATCTACAACCAGCGGTTCAAGGGGAGATTC<br>ACTTTTTCAGTGGACAGAAGCAAAAACACCCTGTATCTGCAGATGAACAGCCTGAGGGCCGAAGATAC<br>CGCTGTCTACTATTGCGCTCGCAATCTGGGCCCCAGTTTCTACTTTGACTATTGGGGGCAGGGAACCC<br>TGGTCACAGTCAGCTCCGCTAGCACTAAGGGGCCTTCCGTGTTTCCACTGGCTCCCTCTAGTAAATCC<br>ACCTCTGGAGGCACAGCTGCACTGGGATGTCTGGTGAAGGATTACTTCCCTGAACCAGTCACAGTGAG<br>TTGGAACTCAGGGGCTCTGACAAGTGGAGTCCATACTTTTCCCGCAGTGCTGCAGTCAAGCGGACTGT<br>ACTCCCTGTCCTCTGTGGTCACCGTGCCTAGTTCAAGCCTGGGCACCCAGACATATATCTGCAACGTG<br>AATCACAAGCCATCAAATACAAAGTCGACAAGAAAGTGGAGCCCAAGAGCTGTGATAAAACTCATAC<br>CTGCCCACCTTGTCCGGCGCCAGAACTGCTGGGAGGACCAAGCGTGTTCCTGTTTCCACCCAAGCCTA |

| SEQ ID NO. | Clone | Desc. | Sequence (amino acid or |
|---|---|---|---|
| | | | AAGACACCCTGATGATTTCCCGGACTCCTGAGGTCACCTGCGTGGTCGTGGACGTGTCTCACGAGGAC<br>CCCGAAGTCAAGTTCAACTGGTACGTGGATGGCGTCGAAGTGCATAATGCCAAGACCAAACCCCGGGA<br>GGAACAGTACAACTCTACCTATAGAGTCGTGAGTGTCCTGACAGTGCTGCACCAGGACTGGCTGAATG<br>GGAAGGAGTATAAGTGTAAAGTGAGCAACAAAGCCCTGCCCGCCCCAATCGAAAAACAATCTCTAAA<br>GCAAAAGGACAGCCTCGCGAACCACAGGTCTACGTCTACCCCCCATCAAGAGATGAACTGACAAAAAA<br>TCAGGTCTCTCTGACATGCCTGGTCAAAGGATTCTACCCTTCCGACATCGCCGTGGAGTGGGAAAGTA<br>ACGGCCAGCCCGAGAACAATTACAAGACCACACCCCTGTCCTGGACTCTGATGGGAGTTTCGCTCTG<br>GTGTCAAAGCTGACCGTCGATAAAAGCCGGTGGCAGCAGGGCAATGTGTTTAGCTGCTCCGTCATGCA<br>CGAAGCCCTGCACAATCACTACACACAGAAGTCCCTGAGCCTGAGCCCTGGC |
| 99 | 6586 | VH | EVQLVESGGGLVQPGGSLRLSCAASGFTFADYTMDWVRQAPGKGLEWVGDVNPNSGGSIYNQRFKGRF<br>TFSVDRSKNTLYLQMNSLRAEDTAVYYCARNLGPSFYFDYWGQGTLVTVSS |
| 100 | 6586 | VH | GAGGTGCAGCTGGTGGAATCAGGAGGGGGCCTGGTGCAGCCCGGAGGGTCTCTGCGACTGTCATGTGC<br>CGCTTCTGGGTTCACTTTCGCAGACTACACAATGGATTGGGTGCGACAGGCCCCCGGAAAGGGACTGG<br>AGTGGGTGGGCGATGTCAACCCTAATTCTGGCGGGAGTATCTACAACCAGCGGTTCAAGGGGAGATTC<br>ACTTTTTCAGTGGACAGAAGCAAAAACACCCTGTATCTGCAGATGAACAGCCTGAGGGCCGAAGATAC<br>CGCTGTCTACTATTGCGCTCGCAATCTGGGCCCCAGTTTCTACTTTGACTATTGGGGGCAGGGAACCC<br>TGGTGACAGTCAGCTCC |
| 101 | 6586 | H1 | GFTFADYT |
| 102 | 6586 | H1 | GGGTTCACTTTCGCAGACTACACA |
| 103 | 6586 | H3 | ARNLGPSFYFDY |
| 104 | 6586 | H3 | GCTCGCAATCTGGGCCCCAGTTTCTACTTTGACTAT |
| 105 | 6586 | H2 | VNPNSGGS |
| 106 | 6586 | H2 | GTCAACCCTAATTCTGGCGGGAGT |
| 107 | 6586 | CH1 | ASTKGPSVFPLAPSSKSTSGGTAALGCLVKDYFPEPVTVSWNSGALTSGVHTFPAVLQSSGLYSLSSV<br>VTVPSSSLGTQTYICNVNHKPSNTKVDKKV |
| 108 | 6586 | CH1 | GCTAGCACTAAGGGGCCTTCCGTGTTTCCACTGGCTCCCTCTAGTAAATCCACCTCTGGAGGCACAGC<br>TGCACTGGGATGTCTGGTGAAGGATTACTTCCCTGAACCAGTCACAGTGAGTTGGAACTCAGGGGCTC<br>TGACAAGTGGAGTCCATACTTTTCCCGCAGTGCTGCAGTCAAGCGGACTGTACTCCCTGTCCTCTGTG<br>GTCACCGTGCCTAGTTCAAGCCTGGGCACCCAGACATATATCTGCAACGTGAATCACAAGCCATCAAA<br>TACAAAAGTCGACAAGAAAGTG |
| 109 | 6586 | CH2 | APELLGGPSVFLFPPKPKDTLMISRTPEVTCVVVDVSHEDPEVKFNWYVDGVEVHNAKTKPREEQYNS<br>TYRVVSVLTVLHQDWLNGKEYKCKVSNKALPAPIEKTISKAK |
| 110 | 6586 | CH2 | GCGCCAGAACTGCTGGGAGGACCAAGCGTGTTCCTGTTTCCACCCAAGCCTAAAGACACCCTGATGAT<br>TTCCCGGACTCCTGAGGTCACCTGCGTGGTCGTGGACGTGTCTCACGAGGACCCCGAAGTCAAGTTCA<br>ACTGGTACGTGGATGGCGTCGAAGTGCATAATGCCAAGACCAAACCCCGGGAGGAACAGTACAACTCT<br>ACCTATAGAGTCGTGAGTGTCCTGACAGTGCTGCACCAGGACTGGCTGAATGGGAAGGAGTATAAGTG<br>TAAAGTGAGCAACAAAGCCCTGCCCGCCCCAATCGAAAAACAATCTCTAAAGCAAAA |
| 111 | 6586 | CH3 | GQPREPQVYVYPPSRDELTKNQVSLTCLVKGFYPSDIAVEWESNGQPENNYKTTPPVLDSDGSFALVS<br>KLTVCKSRWQQGNVFSCSVMHEALHNHYTQKSLSLSPG |
| 112 | 6586 | CH3 | GGACAGCCTCGCGAACCACAGGTCTACGTCTACCCCCCATCAAGAGATGAACTGACAAAAAATCAGGT<br>CTCTCTGACATGCCTGGTCAAAGGATTCTACCCTTCCGACATCGCCGTGGAGTGGGAGTTTCGCTCTGGTGTCA<br>AGCTGACCGTCGATAAAAGCCGGTGGCAGCAGGGCAATGTGTTTAGCTGCTCCGTCATGCACGAAGC<br>CCTGCACAATCACTACACACAGAAGTCCCTGAGCCTGAGCCCTGGC |
| 113 | 3904 | Full | YPYDVPDYATGSDIQMTQSPSSLSASVGDRVTITCKASQDVSIGVAWYQQKPGKAPKLLIYSASYRYT<br>GVPSRFSGSGSGTDFTLTISSLQPEDFATYYCQQYYIYPYTFGQGTKVEIKRTVAAPSVFIFPPSDEE<br>LKSGTASVVCLLNNEYPREAKVQWKVDNALQSGNSEESVTEQDSKDSTYSLSSTLELSKADYEKHKVY<br>ACEVTHQGLSSPVTKSFNRGEC |
| 114 | 3904 | Full | TATCCCTACGATGTGCCTGACTACGCTACTGGCTCCGATATCCAGATGACCCAGTCTCCAAGCTCCCT<br>GAGTGCATCAGTGGGGACCGAGTCACCATCACATGCAAGGCTTCCCAGGATGTGTCTATTGGAGTCG<br>CATGGTACCAGCAGAAGCCAGGCAAAGCACCCAAGCTGCTGATCTACAGCGCCTCCTACCGGTATACT<br>GGGGTGCCTTCCAGATTCTCTGGCAGTGGGTCAGGAACCGACTTTACTCTGACCATCTCTAGTCTGCA<br>GCCCGAGGATTTCGCCACCTACTATTGCCAGCAGTACTATATCTACCCTTATACCTTTGGCCAGGGGA<br>CAAAGTGGAGATCAAGAGGACAGTGGCCGCTCCAAGTGTCTTCATTTTTCCCCCTTCCGACGAAGAG<br>CTGAAAAGTGGAACTGCTTCAGTGGTCTGTCTGCTGAACAATTTCTACCCCGCGAAGCCAAAGTGCA<br>GTGGAAGGTCGATAACGCTCTGCAGAGCGGCAATTCCGAGGAGTCTGTGACAGAACAGGACAGTAAAG<br>ATTCAACTTATAGCCTGTCAAGCACACTGGAGCTGTCTAAGGCAGACTACGAGAAGCACAAAGTGTAT<br>GCCTGCGAAGTCACCCATCAGGGGCTGTCCTCTCCCGTGACAAAGAGCTTTAACAGAGGAGAGTGT |

| SEQ ID NO. | Clone | Desc. | Sequence (amino acid or |
|---|---|---|---|
| 115 | 3904 | VL | DIQMTQSPSSLSASVGDRVTITCKASQDVSIGVAWYQQKPGKAPKLLIYSASYRYTGVPSRFSGSGSG TDFTLTISSLQPEDFATYYCQQYYIYPYTFGQGTKVEIK |
| 116 | 3904 | VL | GATATCCAGATGACCCAGTCTCCAAGCTCCCTGAGTGCATCAGTGGGGGACCGAGTCACCATCACATG CAAGGCTTCCCAGGATGTGTCTATTGGAGTCGCATGGTACCAGCAGAAGCCAGGCAAAGCACCCAAGC TGCTGATCTACAGCGCCTCCTACCGGTATACTGGGGTGCCTTCCAGATTCTCTGGCAGTGGGTCAGGA ACCGACTTTACTCTGACCATCTCTAGTCTGCAGCCCGAGGATTTCGCCACCTACTATTGCCAGCAGTA CTATATCTACCCTTATACCTTTGGCCAGGGGACAAAAGTGGAGATCAAG |
| 117 | 3904 | L1 | QDVSIG |
| 118 | 3904 | L1 | CAGGATGTGTCTATTGGA |
| 119 | 3904 | L3 | QQYYIYPYT |
| 120 | 3904 | L3 | CAGCAGTACTATATCTACCCTTATACC |
| 121 | 3904 | L2 | SAS |
| 122 | 3904 | L2 | AGCGCCTCC |
| 123 | 3904 | CL | RTVAAPSVFIFPPSDEELKSGTASVVCLLNNFYPREAKVQWKVDNALQSGNSEESVTEQDSKDSTYSL SSTLTLSKADYEKHKVYACEVTHQGLSSPVTKSFNRGEC |
| 124 | 3904 | CL | AGGACAGTGGCCGCTCCAAGTGTCTTCATTTTTCCCCCTTCCGACGAAGAGCTGAAAAGTGGAACTGC TTCAGTGGTCTGTCTGCTGAACAATTTCTACCCCCGCGAAGCCAAAGTGCAGTGGAAGGTCGATAACG CTCTGCAGAGCGGCAATTCCGAGGAGTCTGTGACAGAACAGGACAGTAAAGATTCAACTTATAGCCTG TCAAGCACACTGGAGCTGTCTAAGGCAGACTACGAGAAGCACAAAGTGTATGCCTGCGAAGTCACCCA TCAGGGGCTGTCCTCTCCCGTGACAAAGAGCTTTAACAGAGGAGAGTGT |
| 125 | 4553 | Full | EVQLVESGGGLVQPGGSLRLSCAASGFNIKDTYIHWVRQAPGKGLEWVARIYPTNGYTRYADSVKGRF TISADTSKNTAYLQMNSLRAEDTAVYYCSRWGGDGFYAMDYWGQGTLVTVSSASTKGPSVFPLAPSSK STSGGTAALGCLVKDYFPEPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTLMISRTPEVTCVVVDVSHE DPEVKFNWYVDGVEVHNAKTKPREEQYNSTYRVVSVLTVLHQDWLNGKEYKCKVSNKALPAPIEKTIS KAKGQPREPQVYVYPPSRDELTKNQVSLTCLVKGFYPSDIAVEWESNGQPENNYKTTPPVLDSDGSFA LVSKLTVDKSRWQQGNVFSCSVMHEALHNHYTQKSLSLSPGK |
| 126 | 4553 | Full | GAAGTCCAGCTGGTCGAAAGCGGAGGAGGACTGGTGCAGCCAGGAGGGTCTCTGCGACTGAGTTGCGC CGCTTCAGGCTTCAACATCAAGGACACCTACATTCACTGGGTGCGCCAGGCTCCTGGAAAAGGCCTGG AGTGGGTGGCACGAATCTATCCAACTAATGGATACACCCGGTATGCAGACAGCGTGAAGGGCCGGTTC ACCATTAGCGCAGATACATCCAAAAACACTGCCTACCTGCAGATGAACAGCCTGCGAGCCGAAGATAC TGCTGTGTACTATTGCAGTCGGTGGGGAGGCGACGGCTTCTACGCTATGGATTATTGGGGGCAGGGAA CCCTGGTCACAGTGAGCTCCGCATCTACAAAGGGGCCTAGTGTGTTTCCACTGGCCCCCTCTAGTAAA TCCACCTCTGGGGGAACAGCAGCCCTGGGATGTCTGGTGAAGGACTATTTCCCAGAGCCCGTCACTGT GAGTTGGAACTCAGGCGCCCTGACATCCGGGGTCCATACTTTTCCTGCTGTGCTGCAGTCAAGCGGCC TGTACTCTCTGTCCTCTGTGGTCACCGTGCCAAGTTCAAGCCTGGGGACTCAGACCTATATCTGCAAC GTGAATCACAAGCCAAGCAATACAAAAGTCGACAAGAAAGTGGAACCCAAGAGCTGTGATAAAACACA TACTTGCCCCCCTTGTCCTGCACCAGAGCTGCTGGGAGGACCATCCGTGTTCCTGTTTCCACCCAAGC CTAAAGACACCCTGATGATTTCCAGGACTCCAGAAGTCACCTGCGTGGTCGTGGACGTGTCTCACGAG GACCCCGAAGTCAAGTTCAACTGGTACGTGGATGGCGTCGAGGTGCATAATGCCAAGACAAAACCCAG GGAGGAACAGTACAACTCAACTTATCGCGTCGTGAGCGTCCTGACCGTGCTGCACCAGGACTGGCTGA ACGGCAAGGAGTATAAGTGCAAAGTGAGCAATAAGGCTCTGCCCGCACCTATCGAGAAAACCATTAGC AAGGCCAAAGGGCAGCCTAGAGAACCACAGGTCTACGTGTATCCTCCAAGCAGGGACGAGCTGACCAA GAACCAGGTCTCCCTGACATGTCTGGTGAAAGGGTTTTACCCCAGTGATATCGCTGTGGAGTGGGAAT CAAATGGACAGCCTGAAAACAATTATAAGACCACACCCCCTGTGCTGGACAGCGATGGCAGCTTCGCT CTGGTCTCCAAGCTGACTGTGGATAAATCTCGGTGGCAGCAGGGCAACGTCTTTAGTTGTTCAGTGAT GCATGAGGCACTGCACAATCATTACACCCAGAAGAGCCTGTCCCTGTCTCCGGCAAA |
| 127 | 4553 | VH | EVQLVESGGGLVQPGGSLRLSCAASGFNIKDTYIHWVRQAPGKGLEWVARIYPTNGYTRYADSVKGRF TISADTSKNTAYLQMNSLRAEDTAVYYCSRWGGDGFYAMDYWGQGTLVTVSS |
| 128 | 4553 | VH | GAAGTCCAGCTGGTCGAAAGCGGAGGAGGACTGGTGCAGCCAGGAGGGTCTCTGCGACTGAGTTGCGC CGCTTCAGGCTTCAACATCAAGGACACCTACATTCACTGGGTGCGCCAGGCTCCTGGAAAAGGCCTGG AGTGGGTGGCACGAATCTATCCAACTAATGGATACACCCGGTATGCAGACAGCGTGAAGGGCCGGTTC ACCATTAGCGCAGATACATCCAAAAACACTGCCTACCTGCAGATGAACAGCCTGCGAGCCGAAGATAC TGCTGTGTACTATTGCAGTCGGTGGGGAGGCGACGGCTTCTACGCTATGGATTATTGGGGGCAGGGAA CCCTGGTCACAGTGAGCTCC |
| 129 | 4553 | H1 | GFNIKDTY |
| 130 | 4553 | H1 | GGCTTCAACATCAAGGACACCTAC |
| 131 | 4553 | H3 | SRWGGDGFYAMDY |

| SEQ ID NO. | Clone | Desc. | Sequence (amino acid or |
|---|---|---|---|
| 132 | 4553 | H3 | AGTCGGTGGGGAGGCGACGGCTTCTACGCTATGGATTAT |
| 133 | 4553 | H2 | IYPTNGYT |
| 134 | 4553 | H2 | ATCTATCCAACTAATGGATACACC |
| 135 | 4553 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV |
| 136 | 4553 | CH1 | GCATCTACAAAGGGGCCTAGTGTGTTTCCACTGGCCCCCTCTAGTAAATCCACCTCTGGGGGAACAGC AGCCCTGGGATGTCTGGTGAAGGACTATTTCCCAGAGCCCGTCACTGTGAGTTGGAACTCAGGCGCCC TGACATCCGGGGTCCATACTTTTCCTGCTGTGCTGCAGTCAAGCGGCCTGTACTCTCTGTCCTCTGTG GTCACCGTGCCAAGTTCAAGCCTGGGGACTCAGACCTATATCTGCAACGTGAATCACAAGCCAAGCAA TACAAAAGTCGACAAGAAAGTG |
| 137 | 4553 | CH2 | APELLGGPSVFLFPPKPKDTLMISRTPEVTCVVVDVSHEDPEVKFNWYVDGVEVHNAKTKPREEQYNS TYRVVSVLTVLHQDWLNGKEYKCKVSNKALPAPIEKTISKAK |
| 138 | 4553 | CH2 | GCACCAGAGCTGCTGGGAGGACCATCCGTGTTCCTGTTTCCACCCAAGCCTAAAGACACCCTGATGAT TTCCAGGACTCCAGAAGTCACCTGCGTGGTCGTGGACGTGTCTCACGAGGACCCCGAAGTCAAGTTCA ACTGGTACGTGGATGGCGTCGAGGTGCATAATGCCAAGACAAAACCCAGGGAGGAACAGTACAACTCA ACTTATCGCGTCGTGAGCGTCCTGACCGTGCTGCACCAGGACTGGCTGAACGGCAAGGAGTATAAGTG CAAAGTGAGCAATAAGGCTCTGCCCGCACCTATCGAGAAACCATTAGCAAGGCCAAA |
| 139 | 4553 | CH3 | GQPREPQVYVYPPSRDELTKNQVSLTCLVKGFYPSDIAVEWESNGQPENNYKTTPPVLDSDGSFALVS KLTVCKSRWQQGNVFSCSVMHEALHNHYTQKSLSLSPG |
| 140 | 4553 | CH3 | GGGCAGCCTAGAGAACCACAGGTCTACGTGTATCCTCCAAGCAGGGACGAGCTGACCAAGAACCAGGT CTCCCTGACATGTCTGGTGAAAGGGTTTTACCCCAGTGATATCGCTGTGGAGTGGGAATCAAATGGAC AGCCTGAAAACAATTATAAGACCACACCCCCTGTGCTGGACAGCGATGGCAGCTTCGCTCTGGTCTCC AAGCTGACTGTGGATAAATCTCGGTGGCAGCAGGGCAACGTCTTTACTTGTTCAGTGATGCATGAGGC ACTGCACAATCATTACACCCAGAAGAGCCTGTCCCTGTCTCCCGGC |
| 141 | 716 | Full | EPKSSDKTHTCPPCPAPELLGGPSVFLFPPKPKDTLMISRTPEVTCVVVDVSHEDPEVKFNWYVDGVE VHNAKTKPREEQYNSTYRVVSVLTVLHQDWLNGKEYKCKVSNKALPAPIEKTISKAKGQPREPQVYTL PPSRDELTKNQVSLICLVKGFYPSDIAVEWESNGQPENRYMTWPPVLDSCGSFFLYSKLTVDKSRWQQ GNVFSCSVMHEALHNHYTQKSLSLSPGK |
| 142 | 716 | Full | GAGCCCAAGAGCAGCGATAAGACCCACACCTGCCCTCCCTGTCCAGCTCCAGAACTGCTGGGAGGACC TAGCGTGTTCCTGTTTCCCCCTAAGCCAAAAGACACTCTGATGATTTCCAGGACTCCCGAGGTGACCT GCGTGGTGGTGGACGTGTCTCACGAGGACCCCGAAGTGAAGTTCAACTGGTACGTGGATGGCGTGGAA GTGCATAATGCTAAGACAAAACCAAGAGAGGAACAGTACAACTCCACTTATCGCGTCGTGAGCGTGCT GACCGTGCTGCACCAGGACTGGCTGAACGGGAAGGAGTATAAGTGCAAAGTCAGTAATAAGGCCCTGC CTGCTCCAATCGAAAAAACCATCTCTAAGGCCAAAGGCCAGCCAAGGGAGCCCCAGGTGTACACACTG CCACCCAGCAGAGACGAACTGACCAAGAACCAGGTGTCCCTGATCTGTCTGGTGAAAGGCTTCTATCC TAGTGATATTGCTGTGGAGTGGGAATCAAATGGACAGCCAGAGAACAGATACATGACCTGGCCTCCAG TGCTGGACAGCGATGGCAGCTTCTTCCTGTATTCCAAGCTGACAGTGGATAAATCTCGATGGCAGCAG GGGAACGTGTTTAGTTGTTCAGTGATGCATGAAGCCCTGCACAATCATTACACTCAGAAGAGCCTGTC CCTGTCTCCCGGCAAA |
| 143 | 716 | CH2 | APELLGGPSVFLFPPKPKDTLMISRTPEVTCVVVDVSHEDPEVKFNWYVDGVEVHNAKTKPREEQYNS TYRVVSVLTVLHQDWLNGKEYKCKVSNKALPAPIEKTISKAK |
| 144 | 716 | CH2 | GCTCCAGAACTGCTGGGAGGACCTAGCGTGTTCCTGTTTCCCCCTAAGCCAAAAGACACTCTGATGAT TTCCAGGACTCCCGAGGTGACCTGCGTGGTGGTGGACGTGTCTCACGAGGACCCCGAAGTGAAGTTCA ACTGGTACGTGGATGGCGTGGAAGTGCATAATGCTAAGACAAAACCAAGAGAGGAACAGTACAACTCC ACTTATCGCGTCGTGAGCGTGCTGACCGTGCTGCACCAGGACTGGCTGAACGGGAAGGAGTATAAGTG CAAAGTCAGTAATAAGGCCCTGCCTGCTCCAATCGAAAAAACCATCTCTAAGGCCAAA |
| 145 | 716 | CH3 | GQPREPQVYTLPPSRDELTKNQVSLICLVKGFYPSDIAVEWESNGQPENRYMTWPPVLDSDGSFFLYS KLTVDKSRWQQGNVFSCSVMHEALHNHYTQKSLSLSPG |
| 146 | 716 | CH3 | GGCCAGCCAAGGGAGCCCCAGGTGTACACACTGCCACCCAGCAGAGACGAACTGACCAAGAACCAGGT GTCCCTGATCTGTCTGGTGAAAGGCTTCTATCCTAGTGATATTGCTGTGGAGTGGGAATCAAATGGAC AGCCAGAGAACAGATACATGACCTGGCCTCCAGTGCTGGACAGCGATGGCAGCTTCTTCCTGTATTCC AAGCTGACAGTGGATAAATCTCGATGGCAGCAGGGGAACGTGTTTACTTGTTCAGTGATGCATGAAGC CCTGCACAATCATTACACTCAGAAGAGCCTGTCCCTGTCTCCCGGC |
| 147 | 719 | Full | DIQMTQSPSSLSASVGDRVTITCRASQDVNTAVAWYQQKPGKAPKLLIYSASFLYSGVPSRFSGSRSG TDFTLTISSLQPEDFATYYCQQHYTTPPTFGQGTKVEIKGGSGGGSGGGSGGGSGGGSGEVQLVESGG GLVQPGGSLRLSCAASGFNIKDTYIHWVRQAPGKGLEWVARIYPTNGYTRYADSVKGRFTISADTSKN TAYLQMNSLRAEDTAVYYCSRWGGDGFYAMDYWGQGTLVTVSSAAEPKSSDKTHTCPPCPAPELLGGP SVFLFPPKPKDTLMISRTPEVTCVVVDVSHEDPEVKFNWYVDGVEVHNAKTKPREEQYNSTYRVVSVL |

| SEQ ID NO. | Clone | Desc. | Sequence (amino acid or |
|---|---|---|---|
| | | | TVLHQDWLNGKEYKCKVSNKALPAPIEKTISKAKGQPREPQVYTYPPSRDELTKNQVSLTCLVKGFYP SDIAVEWESNGQPENNYKTTPPVLDEDGSFALVSKLTVDKSRWQQGNVFSCSVMHEALHNHYTQKSLS LSPGK |
| 148 | 719 | Full | GACATCCAGATGACCCAGTCTCCATCCTCCCTGTCTGCATCTGTAGGAGACAGAGTCACCATCACTTG CCGGGCAAGTCAGGACGTTAACACCGCTGTAGCTTGGTATCAGCAGAAACCAGGGAAAGCCCCTAAGC TCCTGATCTATTCTGCATCCTTTTTGTACAGTGGGGTCCCATCAAGGTTCAGTGGCAGTCGATCTGGG ACAGATTTCACTCTCACCATCAGCAGTCTGCAACCTGAAGATTTTGCAACTTACTACTGTCAACAGCA TTACACTACCCCACCCACTTTCGGCCAAGGGACCAAAGTGGAGATCAAAGGTGGTTCTGGTGGTGGTT CTGGTGGTGGTTCTGGTGGTGGTTCTGGTGAAGTGCAGCTGGTGGAGTCTGGGGGA GGCTTGGTACAGCCTGGCGGGTCCCTGAGACTCTCCTGTGCAGCCTCTGGATTCAACATTAAAGATAC TTATATCCACTGGGTCCGGCAAGCTCCAGGGAAGGGCCTGGAGTGGGTCGCACGTATTTATCCCACAA ATGGTTACACACGGTATGCGGACTCTGTGAAGGGCCGATTCACCATCTCCGCAGACACTTCCAAGAAC ACCGCGTATCTGCAAATGAACAGTCTGAGAGCTGAGGACACGGCCGTTTATTACTGTTCAAGATGGGG CGGAGACGGTTTCTACGCTATGGACTACTGGGGCCAAGGGACCCTGGTCACCGTCTCCTCAGCCGCCG AGCCCAAGAGCAGCGATAAGACCCACACCTGCCCTCCTGTCCAGCTCCAGAACTGCTGGGAGGACCT AGCGTGTTCCTGTTTCCCCCTAAGCCAAAAGACACTCTGATGATTTCCAGGACTCCCGAGGTGACCTG CGTGGTGGTGGACGTGTCTCACGAGGACCCCGAAGTGAAGTTCAACTGGTACGTGGATGGCGTGGAAG TGCATAATGCTAAGACAAAACCAAGAGAGGAACAGTACAACTCCACTTATCGCGTCGTGAGCGTGCTG ACCGTGCTGCACCAGGACTGGCTGAACGGGAAGGAGTATAAGTGCAAAGTCAGTAATAAGGCCCTGCC TGCTCCAATCGAAAAAACCATCTCTAAGGCCAAAGGCCAGCCAAGGGAGCCCCAGGTGTACACATACC CACCCAGCAGAGACGAACTGACCAAGAACCAGGTGTCCCTGACATGTCTGGTGAAAGGCTTCTATCCT AGTGATATTGCTGTGGAGTGGGAATCAAATGGACAGCCAGAGAACAATTACAAGACCACACCTCCAGT GCTGGACGAGGATGGCAGCTTCGCCCTGGTGTCAAGCTGACAGTGGATAAATCTCGATGGCAGCAGG GGAACGTGTTTACTTGTTCAGTGATGCATGAAGCCCTGCACAATCATTACACTCAGAAGAGCCTGTCC CTGTCTCCCGGCAAA |
| 149 | 719 | VL | DIQMTQSPSSLSASVGDRVTITCRASQDVNTAVAWYQQKPGKAPKLLIYSASFLYSGVPSRFSGSRSG TDFTLTISSLQPEDFATYYCQQHYTTPPTFGQGTKVEIK |
| 150 | 719 | VL | GACATCCAGATGACCCAGTCTCCATCCTCCCTGTCTGCATCTGTAGGAGACAGAGTCACCATCACTTG CCGGGCAAGTCAGGACGTTAACACCGCTGTAGCTTGGTATCAGCAGAAACCAGGGAAAGCCCCTAAGC TCCTGATCTATTCTGCATCCTTTTTGTACAGTGGGGTCCCATCAAGGTTCAGTGGCAGTCGATCTGGG ACAGATTTCACTCTCACCATCAGCAGTCTGCAACCTGAAGATTTTGCAACTTACTACTGTCAACAGCA TTACACTACCCCACCCACTTTCGGCCAAGGGACCAAAGTGGAGATCAAA |
| 151 | 719 | L1 | QDVNTA |
| 152 | 719 | L1 | CAGGACGTTAACACCGCT |
| 153 | 719 | L3 | QQHYTTPPT |
| 154 | 719 | L3 | CAACAGCATTACACTACCCCACCCACT |
| 155 | 719 | L2 | SAS |
| 156 | 719 | L2 | TCTGCATCC |
| 157 | 719 | VH | EVQLVESGGGLVQPGGSLRLSCAASGFNIKDTYIHWVRQAPGKGLEWVARIYPTNGYTRYADSVKGRF TISADTSKNTAYLQMNSLRAEDTAVYYCSRWGGDGFYAMDYWGQGTLVTVSS |
| 158 | 719 | VH | GAAGTGCAGCTGGTGGAGTCTGGGGGAGGCTTGGTACAGCCTGGCGGGTCCCTGAGACTCTCCTGTGC AGCCTCTGGATTCAACATTAAAGATACTTATATCCACTGGGTCCGGCAAGCTCCAGGGAAGGGCCTGG AGTGGGTCGCACGTATTTATCCCACAAATGGTTACACACGGTATGCGGACTCTGTGAAGGGCCGATTC ACCATCTCCGCAGACACTTCCAAGAACACCGCGTATCTGCAAATGAACAGTCTGAGAGCTGAGGACAC GGCCGTTTATTACTGTTCAAGATGGGGCGGAGACGGTTTCTACGCTATGGACTACTGGGGCCAAGGGA CCCTGGTCACCGTCTCCTCA |
| 159 | 719 | H1 | GFNIKDTY |
| 160 | 719 | H1 | GGATTCAACATTAAAGATACTTAT |
| 161 | 719 | H3 | SRWGGDGFYAMDY |
| 162 | 719 | H3 | TCAAGATGGGGCGGAGACGGTTTCTACGCTATGGACTAC |
| 163 | 719 | H2 | IYPTNGYT |
| 164 | 719 | H2 | ATTTATCCCACAAATGGTTACACA |
| 165 | 719 | CH2 | APELLGGPSVFLFPPKPKDTLMISRTPEVTCVVVDVSHEDPEVKFNWYVDGVEVHNAKTKPREEQYNS TYRVVSVLTVLHQDWLNGKEYKCKVSNKALPAPIEKTISKAK |
| 166 | 719 | CH2 | GCTCCAGAACTGCTGGGAGGACCTAGCGTGTTCCTGTTTCCCCCTAAGCCAAAAGACACTCTGATGAT TTCCAGGACTCCCGAGGTGACCTGCGTGGTGGTGGACGTGTCTCACGAGGACCCCGAAGTGAAGTTCA |

| SEQ ID NO. | Clone | Desc. | Sequence (amino acid or |
|---|---|---|---|
| | | | ACTGGTACGTGGATGGCGTGGAAGTGCATAATGCTAAGACAAAACCAAGAGAGGAACAGTACAACTCC ACTTATCGCGTCGTGAGCGTGCTGACCGTGCTGCACCAGGACTGGCTGAACGGGAAGGAGTATAAGTG CAAAGTCAGTAATAAGGCCCTGCCTGCTCCAATCGAAAAAACCATCTCTAAGGCCAAA |
| 167 | 719 | CH3 | GQPREPQVYTYPPSRDELTKNQVSLTCLVKGFYPSDIAVEWESNGQPENNYKTTPPVLDEDGSFALVS KLTVDKSRWQQGNVFSCSVMHEALHNHYTQKSLSLSPG |
| 168 | 719 | CH3 | GGCCAGCCAAGGGAGCCCCAGGTGTACACATACCCACCCAGCAGAGACGAACTGACCAAGAACCAGGT GTCCCTGACATGTCTGGTGAAAGGCTTCTATCCTAGTGATATTGCTGTGGAGTGGGAATCAAATGGAC AGCCAGAGAACAATTACAAGACCACACCTCCAGTGCTGGACGAGGATGGCAGCTTCGCCCTGGTGTCC AAGCTGACAGTGGATAAATCTCGATGGCAGCAGGGGAACGTGTTTACTTGTTCAGTGATGCATGAAGC CCTGCACAATCATTACACTCAGAAGAGCCTGTCCCTGTCTCCCGGC |
| 169 | 720 | Full | DIQMTQSPSSLSASVGDRVTITCRASQDVNTAVAWYQQKPGKAPKLLIYSASFLYSGVPSRFSGSRSG TDFTLTISSLQPEDFATYYCQQHYTTPPTFGQGTKVEIKGGSGGGSGGGSGGGSGGGSGEVQLVESGG GLVQPGGSLRLSCAASGFNIKDTYIHWVRQAPGKGLEWVARIYPTNGYTRYADSVKGRFTISADTSKN TAYLQMNSLRAEDTAVYYCSRWGGDGFYAMDYWGQGTLVTVSSAAEPKSSDKTHTCPPCPAPELLGGP SVFLFPPKPKDTLMISRTPEVTCVVVDVSHEDPEVKFNWYVDGVEVHNAKTKPREEQYNSTYRVVSVL TVLHQDWLNGKEYKCKVSNKALPAPIEKTISKAKGQPREPQVYTLPPSRDELTKNQVSLICLVKGFYP SDIAVEWESNGQPENRYMTWPPVLDSCGSFFLYSKLTVDKSRWQQGNVFSCSVMHEALHNHYTQKSLS LSPGK |
| 170 | 720 | Full | GACATCCAGATGACCCAGTCTCCATCCTCCCTGTCTGCATCTGTAGGAGACAGAGTCACCATCACTTG CCGGGCAAGTCAGGACGTTAACACCGCTGTAGCTTGGTATCAGCAGAAACCAGGGAAAGCCCCTAAGC TCCTGATCTATTCTGCATCCTTTTTGTACAGTGGGGTCCCATCAAGGTTCAGTGGCAGTCGATCTGGG ACAGATTTCACTCTCACCATCAGCAGTCTGCAACCTGAAGATTTTGCAACTTACTACTGTCAACAGCA TTACACTACCCCACCCACTTTCGGCCAAGGGACCAAAGTGGAGATCAAAGGTGGTTCTGGTGGTGGTT CTGGTGGTGGTTCTGGTGGTGGTTCTGGTGGTGGTTCTGGTGAAGTGCAGCTGGTGGAGTCTGGGGGA GGCTTGGTACAGCCTGGCGGGTCCCTGAGACTCTCCTGTGCAGCCTCTGGATTCAACATTAAAGATAC TTATATCCACTGGGTCCGGCAAGCTCCAGGGAAGGGCCTGGAGTGGGTCGCACGTATTTATCCCACAA ATGGTTACACACGGTATGCGGACTCTGTGAAGGGCCGATTCACCATCTCCGCAGACACTTCCAAGAAC ACCGCGTATCTGCAAATGAACAGTCTGAGAGCTGAGGACACGGCCGTTTATTACTGTTCAAGATGGGG CGGAGACGGTTTCTACGCTATGGACTACTGGGGCCAAGGGACCCTGGTCACCGTCTCCTCAGCCGCCG AGCCCAAGAGCAGCGATAAGACCCACACCTGCCCTCCCTGTCCAGCTCCAGAACTGCTGGGAGGACCT AGCGTGTTCCTGTTTCCCCCTAAGCCAAAAGACACTCTGATGATTTCCAGGACTCCCGAGGTGACCTG CGTGGTGGTGGACGTGTCTCACGAGGACCCCGAAGTGAAGTTCAACTGGTACGTGGATGGCGTGGAAG TGCATAATGCTAAGACAAAACCAAGAGAGGAACAGTACAACTCCACTTATCGCGTCGTGAGCGTGCTG ACCGTGCTGCACCAGGACTGGCTGAACGGGAAGGAGTATAAGTGCAAAGTCAGTAATAAGGCCCTGCC TGCTCCAATCGAAAAAACCATCTCTAAGGCCAAGGGACAGCCAAGGGAGCCCCAGGTGTACACACTGC CACCCAGCAGAGACGAACTGACCAAGAACCAGGTGTCCCTGATCTGTCTGGTGAAAGGCTTCTATCCT AGTGATATTGCTGTGGAGTGGGAATCAAATGGACAGCCAGAGAACAGATACATGACCTGGCCTCCAGT GCTGGACAGCGATGGCAGCTTCTTCCTGTATTCCAAGCTGACAGTGGATAAATCTCGATGGCAGCAGG GGAACGTGTTTACTTGTTCAGTGATGCATGAAGCCCTGCACAATCATTACACTCAGAAGAGCCTGTCC CTGTCTCCCGGCAAA |
| 171 | 720 | VL | DIQMTQSPSSLSASVGDRVTITCRASQDVNTAVAWYQQKPGKAPKLLIYSASFLYSGVPSRFSGSRSG TDFTLTISSLQPEDFATYYCQQHYTTPPTFGQGTKVEIK |
| 172 | 720 | VL | GACATCCAGATGACCCAGTCTCCATCCTCCCTGTCTGCATCTGTAGGAGACAGAGTCACCATCACTTG CCGGGCAAGTCAGGACGTTAACACCGCTGTAGCTTGGTATCAGCAGAAACCAGGGAAAGCCCCTAAGC TCCTGATCTATTCTGCATCCTTTTTGTACAGTGGGGTCCCATCAAGGTTCAGTGGCAGTCGATCTGGG ACAGATTTCACTCTCACCATCAGCAGTCTGCAACCTGAAGATTTTGCAACTTACTACTGTCAACAGCA TTACACTACCCCACCCACTTTCGGCCAAGGGACCAAAGTGGAGATCAAA |
| 173 | 720 | L1 | QDVNTA |
| 174 | 720 | L1 | CAGGACGTTAACACCGCT |
| 175 | 720 | L3 | QQHYTTPPT |
| 176 | 720 | L3 | CAACAGCATTACACTACCCCACCCACT |
| 177 | 720 | L2 | SAS |
| 178 | 720 | L2 | TCTGCATCC |
| 179 | 720 | VH | EVQLVESGGGLVQPGGSLRLSCAASGFNIKDTYIHWVRQAPGKGLEWVARIYPTNGYTRYADSVKGRF TISADTSKNTAYLQMNSLRAEDTAVYYCSRWGGDGFYAMDYWGQGTLVTVSS |
| 180 | 720 | VH | GAAGTGCAGCTGGTGGAGTCTGGGGGAGGCTTGGTACAGCCTGGCGGGTCCCTGAGACTCTCCTGTGC AGCCTCTGGATTCAACATTAAAGATACTTATATCCACTGGGTCCGGCAAGCTCCAGGGAAGGGCCTGG AGTGGGTCGCACGTATTTATCCCACAAATGGTTACACACGGTATGCGGACTCTGTGAAGGGCCGATTC ACCATCTCCGCAGACACTTCCAAGAACACCGCGTATCTGCAAATGAACAGTCTGAGAGCTGAGGACAC GGCCGTTTATTACTGTTCAAGATGGGGCGGAGACGGTTTCTACGCTATGGACTACTGGGGCCAAGGGA CCCTGGTCACCGTCTCCTCA |

| SEQ ID NO. | Clone | Desc. | Sequence (amino acid or |
|---|---|---|---|
| 181 | 720 | H1 | GFNIKDTY |
| 182 | 720 | H1 | GGATTCAACATTAAAGATACTTAT |
| 183 | 720 | H3 | SRWGGDGFYAMDY |
| 184 | 720 | H3 | TCAAGATGGGCGGAGACGGTTTCTACGCTATGGACTAC |
| 185 | 720 | H2 | IYPTNGYT |
| 186 | 720 | H2 | ATTTATCCCACAAATGGTTACACA |
| 187 | 720 | CH2 | APELLGGPSVFLFPPKPKDTLMISRTPEVTCVVVDVSHEDPEVKFNWYVDGVEVHNAKTKPREEQYNS TYRVVSVLTVLHQDWLNGKEYKCKVSNKALPAPIEKTISKAK |
| 188 | 720 | CH2 | GCTCCAGAACTGCTGGGAGGACCTAGCGTGTTCCTGTTTCCCCCTAAGCCAAAAGACACTCTGATGAT TTCCAGGACTCCCGAGGTGACCTGCGTGGTGGTGGACGTGTCTCACGAGGACCCCGAAGTGAAGTTCA ACTGGTACGTGGATGGCGTGGAAGTGCATAATGCTAAGACAAAACCAAGAGAGGAACAGTACAACTCC ACTTATCGCGTCGTGAGCGTGCTGACCGTGCTGCACCAGGACTGGCTGAACGGGAAGGAGTATAAGTG CAAAGTCAGTAATAAGGCCCTGCCTGCTCCAATCGAAAAAACCATCTCTAAGGCCAAA |
| 189 | 720 | CH3 | GQPREPQVYTLPPSRDELTKNQVSLICLVKGFYPSDIAVEWESNGQPENRYMTWPPVLDSDGSFFLYS KLTVCKSRWQQGNVFSCSVMHEALHNHYTQKSLSLSPG |
| 190 | 720 | CH3 | GGCCAGCCAAGGGAGCCCCAGGTGTACACACTGCCACCCAGCAGAGACGAACTGACCAAGAACCAGGT GTCCCTGATCTGTCTGGTGAAAGGCTTCTATCCTAGTGATATTGCTGTGGAGTGGGAATCAAATGGAC AGCCAGAGAACAGATACATGACCTGGCCTCCAGTGCTGGACAGCGATGGCAGCTTCTTCCTGTATTCC AAGCTGACAGTGGATAAATCTCGATGGCAGCAGGGGAACGTGTTTACTTGTTCAGTGATGCATGAAGC CCTGCACAATCATTACACTCAGAAGAGCCTGTCCCTGTCTCCCGGC |
| 191 | 4561 | Full | DIQMTQSPSSLSASVGDRVTITCRASQDVNTAVAWYQQKPGKAPKLLIYSASFLYSGVPSRFSGSRSG TDFTLTISSLQPEDFATYYCQQHYTTPPTFGQGTKVEIKRTVAAPSVFIFPPSDEQLKSGTASVVCLL NNFYPREAKVQWKVDNALQSGNSQESVTEQCSKDSTYSLSSTLTLSKADYEKHKVYACEVTHQGLSSP VTKSFNRGEC |
| 192 | 4561 | Full | GATATTCAGATGACCCAGTCCCCTAGCTCCCTGTCCGCTTCTGTGGGCGACAGGGTCACTATCACCTG CCGCGCATCTCAGGATGTGAACACCGCAGTCGCCTGGTACCAGCAGAAGCCTGGGAAAGCTCCAAAGC TGCTGATCTACAGTGCATCATTCCTGTATTCAGGAGTGCCCAGCCGGTTTAGCGGCAGCAGATCTGGC ACCGACTTCACACTGACTATCTCTAGTCTGCAGCCTGAGGATTTTGCCACATACTATTGCCAGCAGCA CTATACCACACCCCCTACTTTCGGCCAGGGGACCAAAGTGGAGATCAAGCGAACTGTGGCCGCTCCAA GTGTCTTCATTTTTCCACCCAGCGACGAACAGCTGAAATCCGGCACAGCTTCTGTGGTCTGTCTGCTG AACAACTTCTACCCCAGAGAGGCCAAAGTGCAGTGGAAGGTCGATAACGCTCTGCAGAGTGGCAACAG CCAGGAGAGCGTGACAGAACAGGACTCCAAAGATTCTACTTATAGTCTGTCAAGCACCCTGACACTGA GCAAGGCAGACTACGAAAAGCATAAAGTGTATGCCTGTGAGGTGACCCATCAGGGGCTGTCTTCTCCC GTGACCAAGTCTTTCAACCGAGGCGAATGT |
| 193 | 4561 | VL | DIQMTQSPSSLSASVGDRVTITCRASQDVNTAVAWYQQKPGKAPKLLIYSASFLYSGVPSRFSGSRSG TDFTLTISSLQPEDFATYYCQQHYTTPPTFGQGTKVEIK |
| 194 | 4561 | VL | GATATTCAGATGACCCAGTCCCCTAGCTCCCTGTCCGCTTCTGTGGGCGACAGGGTCACTATCACCTG CCGCGCATCTCAGGATGTGAACACCGCAGTCGCCTGGTACCAGCAGAAGCCTGGGAAAGCTCCAAAGC TGCTGATCTACAGTGCATCATTCCTGTATTCAGGAGTGCCCAGCCGGTTTAGCGGCAGCAGATCTGGC ACCGACTTCACACTGACTATCTCTAGTCTGCAGCCTGAGGATTTTGCCACATACTATTGCCAGCAGCA CTATACCACACCCCCTACTTTCGGCCAGGGGACCAAAGTGGAGATCAAG |
| 195 | 4561 | L1 | QDVNTA |
| 196 | 4561 | L1 | CAGGATGTGAACACCGCA |
| 197 | 4561 | L3 | QQHYTTPPT |
| 198 | 4561 | L3 | CAGCAGCACTATACCACACCCCCTACT |
| 199 | 4561 | L2 | SAS |
| 200 | 4561 | L2 | AGTGCATCA |
| 201 | 4561 | CL | RTVAAPSVFIFPPSDEQLKSGTASVVCLLNNFYPREAKVQWKVDNALQSGNSQESVTEQDSKDSTYSL SSTLTLSKADYEKHKVYACEVTHQGLSSPVTKSFNRGEC |
| 202 | 4561 | CL | CGAACTGTGGCCGCTCCAAGTGTCTTCATTTTTCCACCCAGCGACGAACAGCTGAAATCCGGCACAGC TTCTGTGGTCTGTCTGCTGAACAACTTCTACCCCAGAGAGGCCAAAGTGCAGTGGAAGGTCGATAACG CTCTGCAGAGTGGCAACAGCCAGGAGAGCGTGACAGAACAGGACTCCAAAGATTCTACTTATAGTCTG |

| SEQ ID NO. | Clone | Desc. | Sequence (amino acid or |
|---|---|---|---|
| | | | TCAAGCACCCTGACACTGAGCAAGGCAGACTACGAAAAGCATAAAGTGTATGCCTGTGAGGTGACCCA<br>TCAGGGGCTGTCTTCTCCCGTGACCAAGTCTTTCAACCGAGGCGAATGT |
| 203 | 3041 | Full | EVQLVESGGGLVQPGGSLRLSCAASGFTFTCYTMDWVRQAPGKGLEWVADVNPNSGGSIYNQRFKGRF<br>TLSVDRSKNTLYLQMNSLRAEDTAVYYCARNLGPSFYFDYWGQGTLVTVSSASTKGPSVFPLAPSSKS<br>TSGGTAALGCLVKCYFPEPVTVSWNSGALTSGVHTFPAVLQSSGLYSLSSVVTVPSSSLGTQTYICNV<br>NHKPSNTKVDKKVEPKSCDKTHTCPPCPAPELLGGPSVFLFPPKPKDTLMISRTPEVTCVVVDVSHED<br>PEVKFNWYVDGVEVHNAKTKPREEQYNSTYRVVSVLTVLHQDWLNGKEYKCKVSNKALPAPIEKTISK<br>AKGQPREPQVYVLPPSRDELTKNQVSLLCLVKGFYPSDIAVEWESNGQPENNYLTWPPVLDSDGSFFL<br>YSKLTVDKSRWQQGNVFSCSVMHEALHNHYTQKSLSLSPG |
| 204 | 3041 | Full | GAAGTGCAGCTGGTCGAATCTGGAGGAGGACTGGTGCAGCCAGGAGGGTCCCTGCGCCTGTCTTGCGC<br>CGCTAGTGGCTTCACTTTTACCGACTACACCATGGATTGGGTGCGACAGGCACCTGGAAAGGGCCTGG<br>AGTGGGTCGCCGATGTGAACCCAAATAGCGGAGGCTCCATCTACAACCAGCGGTTCAAGGGCCGGTTC<br>ACCCTGTCAGTGGACCGGAGCAAAAACACCCTGTATCTGCAGATGAATAGCCTGCGAGCCGAAGATAC<br>TGCTGTGTACTATTGCGCCCGGAATCTGGGGCCCTCCTTCTACTTTGACTATTGGGGGCAGGGAACTC<br>TGGTCACCGTGAGCTCCGCCTCCACCAAGGGACCTTCTGTGTTCCCACTGGCTCCCTCTAGTAAATCC<br>ACATCTGGGGGAACTGCAGCCCTGGGCTGTCTGGTGAAGGACTACTTCCCAGAGCCCGTCACAGTGTC<br>TTGGAACAGTGGCGCTCTGACTTCTGGGGTCCACACCTTTCCTGCAGTGCTGCAGTCAAGCGGGCTGT<br>ACAGCCTGTCCTCTGTGGTCACCGTGCCAAGTTCAAGCCTGGGAACACAGACTTATATCTGCAACGTG<br>AATCACAAGCCATCCAATACAAAAGTCGACAAGAAAGTGGAACCCAAGTCTTGTGATAAACCCATAC<br>ATGCCCCCCTTGTCCTGCACCAGAGCTGCTGGGAGGACCAAGCGTGTTCCTGTTTCCACCCAAGCCTA<br>AAGATACACTGATGATTAGTAGGACCCCAGAAGTCACATGCGTGGTCGTGGACGTGAGCCACGAGGAC<br>CCCGAAGTCAAGTTTAACTGGTACGTGGACGGCGTCGAGGTGCATAATGCCAAGACTAAACCCAGGGA<br>GGAACAGTACAACAGTACCTATCGCGTCGTGTCAGTCCTGACAGTGCTGCATCAGGATTGGCTGAACG<br>GGAAAGAGTATAAGTGCAAAGTGAGCAATAAGGCTCTGCCCGCACCTATCGAGAAAACAATTTCCAAG<br>GCAAAAGGACAGCCTAGAGAACCACAGGTGTACGTGCTGCCTCCATCAAGGGATGAGCTGACAAAGAA<br>CCAGGTCAGCCTGCTGTGTCTGGTGAAAGGATTCTATCCCTCTGACATTGCTGTGGAGTGGGAAAGTA<br>ATGGCCAGCCTGAGAACAATTACCTGACCTGGCCCCTGTGCTGGACTCAGATGGCAGCTTCTTTCTG<br>TATAGCAAGCTGACCGTCGACAAATCCCGGTGGCAGCAGGGGAATGTGTTTACTTGTTCAGTCATGCA<br>CGAGGCACTGCACAACCATTACACCCAGAAGTCACTGTCACTGTCACCAGGG |
| 205 | 3041 | VH | EVQLVESGGGLVQPGGSLRLSCAASGFTFTDYTMDWVRQAPGKGLEWVADVNPNSGGSIYNQRFKGRF<br>TLSVDRSKNTLYLQMNSLRAEDTAVYYCARNLGPSFYFDYWGQGTLVTVSS |
| 206 | 3041 | VH | GAAGTGCAGCTGGTCGAATCTGGAGGAGGACTGGTGCAGCCAGGAGGGTCCCTGCGCCTGTCTTGCGC<br>CGCTAGTGGCTTCACTTTTACCGACTACACCATGGATTGGGTGCGACAGGCACCTGGAAAGGGCCTGG<br>AGTGGGTCGCCGATGTGAACCCAAATAGCGGAGGCTCCATCTACAACCAGCGGTTCAAGGGCCGGTTC<br>ACCCTGTCAGTGGACCGGAGCAAAAACACCCTGTATCTGCAGATGAATAGCCTGCGAGCCGAAGATAC<br>TGCTGTGTACTATTGCGCCCGGAATCTGGGGCCCTCCTTCTACTTTGACTATTGGGGGCAGGGAACTC<br>TGGTCACCGTGAGCTCC |
| 207 | 3041 | H1 | GFTFTCYT |
| 208 | 3041 | H1 | GGCTTCACTTTTACCGACTACACC |
| 209 | 3041 | H3 | ARNLGPSFYFDY |
| 210 | 3041 | H3 | GCCCGGAATCTGGGGCCCTCCTTCTACTTTGACTAT |
| 211 | 3041 | H2 | VNPNSGGS |
| 212 | 3041 | H2 | GTGAACCCAAATAGCGGAGGCTCC |
| 213 | 3041 | CH1 | ASTKGPSVFPLAPSSKSTSGGTAALGCLVKDYFPEPVTVSWNSGALTSGVHTFPAVLQSSGLYSLSSV<br>VTVPSSSLGTQTYICNVNHKPSNTKVDKKV |
| 214 | 3041 | CH1 | GCCTCCACCAAGGGACCTTCTGTGTTCCCACTGGCTCCCTCTAGTAAATCCACATCTGGGGGAACTGC<br>AGCCCTGGGCTGTCTGGTGAAGGACTACTTCCCAGAGCCCGTCACAGTGTCTTGGAACAGTGGCGCTC<br>TGACTTCTGGGGTCCACACCTTTCCTGCAGTGCTGCAGTCAAGCGGGCTGTACAGCCTGTCCTCTGTG<br>GTCACCGTGCCAAGTTCAAGCCTGGGAACACAGACTTATATCTGCAACGTGAATCACAAGCCATCCAA<br>TACAAAAGTCGACAAGAAAGTG |
| 215 | 3041 | CH2 | APELLGGPSVFLFPPKPKDTLMISRTPEVTCVVVDVSHEDPEVKFNWYVDGVEVHNAKTKPREEQYNS<br>TYRVVSVLTVLHQDWLNGKEYKCKVSNKALPAPIEKTISKAK |
| 216 | 3041 | CH2 | GCACCAGAGCTGCTGGGAGGACCAAGCGTGTTCCTGTTTCCACCCAAGCCTAAAGATACACTGATGAT<br>TAGTAGGACCCCAGAAGTCACATGCGTGGTCGTGGACGTGAGCCACGAGGACCCCGAAGTCAAGTTTA<br>ACTGGTACGTGGACGGCGTCGAGGTGCATAATGCCAAGACTAAACCCAGGGAGGAACAGTACAACAGT<br>ACCTATCGCGTCGTGTCAGTCCTGACAGTGCTGCATCAGGATTGGCTGAACGGGAAAGAGTATAAGTG<br>CAAAGTGAGCAATAAGGCTCTGCCCGCACCTATCGAGAAAACAATTTCCAAGGCAAAA |
| 217 | 3041 | CH3 | GQPREPQVYVLPPSRDELTKNQVSLLCLVKGFYPSDIAVEWESNGQPENNYLTWPPVLDSDGSFFLYS<br>KLTVDKSRWQQGNVFSCSVMHEALHNHYTQKSLSLSPG |

| SEQ ID NO. | Clone | Desc. | Sequence (amino acid or |
|---|---|---|---|
| 218 | 3041 | CH3 | GGACAGCCTAGAGAACCACAGGTGTACGTGCTGCCTCCATCAAGGGATGAGCTGACAAAGAACCAGGT<br>CAGCCTGCTGTGTCTGGTGAAAGGATTCTATCCCTCTGACATTGCTGTGGAGTGGGAAAGTAATGGCC<br>AGCCTGAGAACAATTACCTGACCTGGCCCCCTGTGCTGGACTCAGATGGCAGCTTCTTTCTGTATAGC<br>AAGCTGACCGTCGACAAATCCCGGTGGCAGCAGGGGAATGTGTTTACTTGTTCAGTCATGCACGAGGC<br>ACTGCACAACCATTACACCCAGAAGTCACTGTCACTGTCACCAGGG |
| 219 | 3057 | Full | EVQLVESGGGLVQPGGSLRLSCAASGFTFTDYTMDWVRQAPGKGLEWVADVNPNSGGSIYNQRFKGRF<br>TLSVDRSKNTLYLQMNSLRAEDTAVYYCARNLGPSFYFDYWGQGTLVTVSSASTKGPSVFPLAPSSKS<br>TSGGTAALGCLVKDYFPEPVTVSWNSGALTSGVHTFPAVLQSSGLYSLSSVVTVPSSSLGTQTYICNV<br>NHKPSNTKVDKKVEPKSCDKTHTCPPCPAPELLGGPSVFLFPPKPKDTLMISRTPEVTCVVVDVSHED<br>PEVKFNWYVDGVEVHNAKTKPREEQYNSTYRVVSVLTVLHQDWLNGKEYKCKVSNKALPAPIEKTISK<br>AKGQPREPQVYVYPPSRDELTKNQVSLTCLVKGFYPSDIAVEWESNGQPENNYKTTPPVLDSDGSFAL<br>VSKLTVDKSRWQQGNVFSCSVMHEALHNHYTQKSLSLSPG |
| 220 | 3057 | Full | GAAGTGCAGCTGGTCGAATCTGGAGGAGGACTGGTGCAGCCAGGAGGGTCCCTGCGCCTGTCTTGCGC<br>CGCTAGTGGCTTCACTTTTACCGACTACACCATGGATTGGGTGCGACAGGCACCTGGAAAGGGCCTGG<br>AGTGGGTCGCCGATGTGAACCCAAATAGCGGAGGCTCCATCTACAACCAGCGGTTCAAGGGCCGGTTC<br>ACCCTGTCAGTGGACCGGAGCAAAAACACCCTGTATCTGCAGATGAATAGCCTGCGAGCCGAAGATAC<br>TGCTGTGTACTATTGCGCCCGGAATCTGGGGCCCTCCTTCTACTTTGACTATTGGGGGCAGGGAACTC<br>TGGTCACCGTGAGCTCCGCCTCCACCAAGGGACCTTCTGTGTTCCCACTGGCTCCCTCTAGTAAATCC<br>ACATCTGGGGGAACTGCAGCCCTGGGCTGTCTGGTGAAGGACTACTTCCCAGAGCCCGTCACAGTGTC<br>TTGGAACAGTGGCGCTCTGACTTCTGGGGTCCACACCTTTCCTGCAGTGCTGCAGTCAAGCGGGCTGT<br>ACAGCCTGTCCTCTGTGGTCACCGTGCCAAGTTCAAGCCTGGGAACACAGACTTATATCTGCAACGTG<br>AATCACAAGCCATCCAATACAAAAGTCGACAAGAAAGTGGAACCCAAGTCTTGTGATAAAACCCATAC<br>ATGCCCCCCTTGTCCTGCACCAGAGCTGCTGGGAGGACCAAGCGTGTTCCTGTTTCCACCCAAGCCTA<br>AAGATACACTGATGATTAGTAGGACCCCAGAAGTCACATGCGTGGTCGTGGACGTGAGCCACGAGGAC<br>CCCGAAGTCAAGTTTAACTGGTACGTGGACGGCGTCGAGGTGCATAATGCCAAGACTAAACCCAGGGA<br>GGAACAGTACAACAGTACCTATCGCGTCGTGTCAGTCCTGACAGTGCTGCATCAGGATTGGCTGAACG<br>GGAAAGAGTATAAGTGCAAAGTGAGCAATAAGGCTCTGCCCGCACCTATCGAGAAAACAATTTCCAAG<br>GCAAAAGGACAGCCTAGAGAACCACAGGTGTACGTGTATCCTCCATCAAGGGATGAGCTGACAAAGAA<br>CCAGGTCAGCCTGACTTGTCTGGTGAAAGGATTCTATCCCTCTGACATTGCTGTGGAGTGGGAAAGTA<br>ATGGCCAGCCTGAGAACAATTACAAGACCACACCCCTGTGCTGGACTCAGATGGCAGCTTCGCGCTG<br>GTGAGCAAGCTGACCGTCGACAAATCCCGGTGGCAGCAGGGGAATGTGTTTACTTGTTCAGTCATGCA<br>CGAGGCACTGCACAACCATTACACCCAGAAGTCACTGTCACTGTCACCAGGG |
| 221 | 3057 | VH | EVQLVESGGGLVQPGGSLRLSCAASGFTFTDYTMDWVRQAPGKGLEWVADVNPNSGGSIYNQRFKGRF<br>TLSVDRSKNTLYLQMNSLRAEDTAVYYCARNLGPSFYFDYWGQGTLVTVSS |
| 222 | 3057 | VH | GAAGTGCAGCTGGTCGAATCTGGAGGAGGACTGGTGCAGCCAGGAGGGTCCCTGCGCCTGTCTTGCGC<br>CGCTAGTGGCTTCACTTTTACCGACTACACCATGGATTGGGTGCGACAGGCACCTGGAAAGGGCCTGG<br>AGTGGGTCGCCGATGTGAACCCAAATAGCGGAGGCTCCATCTACAACCAGCGGTTCAAGGGCCGGTTC<br>ACCCTGTCAGTGGACCGGAGCAAAAACACCCTGTATCTGCAGATGAATAGCCTGCGAGCCGAAGATAC<br>TGCTGTGTACTATTGCGCCCGGAATCTGGGGCCCTCCTTCTACTTTGACTATTGGGGGCAGGGAACTC<br>TGGTCACCGTGAGCTCC |
| 223 | 3057 | H1 | GFTFTDYT |
| 224 | 3057 | H1 | GGCTTCACTTTTACCGACTACACC |
| 225 | 3057 | H3 | ARNLGPSFYFDY |
| 226 | 3057 | H3 | GCCCGGAATCTGGGGCCCTCCTTCTACTTTGACTAT |
| 227 | 3057 | H2 | VNPNSGGS |
| 228 | 3057 | H2 | GTGAACCCAAATAGCGGAGGCTCC |
| 229 | 3057 | CH1 | ASTKGPSVFPLAPSSKSTSGGTAALGCLVKDYFPEPVTVSWNSGALTSGVHTFPAVLQSSGLYSLSSV<br>VTVPSSSLGTQTYICNVNHKPSNTKVDKKV |
| 230 | 3057 | CH1 | GCCTCCACCAAGGGACCTTCTGTGTTCCCACTGGCTCCCTCTAGTAAATCCACATCTGGGGGAACTGC<br>AGCCCTGGGCTGTCTGGTGAAGGACTACTTCCCAGAGCCCGTCACAGTGTCTTGGAACAGTGGCGCTC<br>TGACTTCTGGGGTCCACACCTTTCCTGCAGTGCTGCAGTCAAGCGGGCTGTACAGCCTGTCCTCTGTG<br>GTCACCGTGCCAAGTTCAAGCCTGGGAACACAGACTTATATCTGCAACGTGAATCACAAGCCATCCAA<br>TACAAAAGTCGACAAGAAAGTG |
| 231 | 3057 | CH2 | APELLGGPSVFLFPPKPKDTLMISRTPEVTCVVVDVSHEDPEVKFNWYVDGVEVHNAKTKPREEQYNS<br>TYRVVSVLTVLHQDWLNGKEYKCKVSNKALPAPIEKTISKAK |
| 232 | 3057 | CH2 | GCACCAGAGCTGCTGGGAGGACCAAGCGTGTTCCTGTTTCCACCCAAGCCTAAAGATACACTGATGAT<br>TAGTAGGACCCCAGAAGTCACATGCGTGGTCGTGGACGTGAGCCACGAGGACCCCGAAGTCAAGTTTA<br>ACTGGTACGTGGACGGCGTCGAGGTGCATAATGCCAAGACTAAACCCAGGGAGGAACAGTACAACAGT<br>ACCTATCGCGTCGTGTCAGTCCTGACAGTGCTGCATCAGGATTGGCTGAACGGGAAAGAGTATAAGTG<br>CAAAGTGAGCAATAAGGCTCTGCCCGCACCTATCGAGAAAACAATTTCCAAGGCAAAA |

| SEQ ID NO. | Clone | Desc. | Sequence (amino acid or |
|---|---|---|---|
| 233 | 3057 | CH3 | GQPREPQVYVYPPSRDELTKNQVSLTCLVKGFYPSDIAVEWESNGQPENNYKTTPPVLDSCGSFALVS KLTVCKSRWQQGNVFSCSVMHEALHNHYTQKSLSLSPG |
| 234 | 3057 | CH3 | GGACAGCCTAGAGAACCACAGGTGTACGTGTATCCTCCATCAAGGGATGAGCTGACAAAGAACCAGGT CAGCCTGACTTGTCTGGTGAAAGGATTCTATCCCTCTGACATTGCTGTGGAGTGGGAAAGTAATGGCC AGCCTGAGAACAATTACAAGACCACACCCCCTGTGCTGGACTCAGATGGCAGCTTCGCGCTGGTGAGC AAGCTGACCGTCGACAAATCCCGGTGGCAGCAGGGGAATGTGTTTACTTGTTCAGTCATGCACGAGGC ACTGCACAACCATTACACCCAGAAGTCACTGTCACTGTCACCAGGG |
| 235 | 1011 | Full | EVQLVESGGGLVQPGGSLRLSCAASGFNIKDTYIHWVRQAPGKGLEWVARIYPTNGYTRYADSVKGRF TISADTSKNTAYLQMNSLRAEDTAVYYCSRWGGDGFYAMDYWGQGTLVTVSSASTKGPSVFPLAPSSK STSGGTAALGCLVKDYFPEPVTVSWNSGALTSGVHTFPAVLQSSGLYSLSSVVTVPSSSLGTQTYICN VNHKPSNTKVDKKVEPKSCDKTHTCPPCPAPELLGGPSVFLFPPKPKDTLMISRTPEVTCVVVDVSHE DPEVKFNWYVDGVEVHNAKTKPREEQYNSTYRVVSVLTVLHQDWLNGKEYKCKVSNKALPAPIEKTIS KAKGQPREPQVYVYPPSRDELTKNQVSLTCLVKGFYPSDIAVEWESNGQPENNYKTTPPVLDSCGSFA LVSKLTVCKSRWQQGNVFSCSVMHEALHNHYTQKSLSLSPGK |
| 236 | 1011 | Full | GAGGTGCAGCTGGTGGAAAGCGGAGGAGGACTGGTGCAGCCAGGAGGATCTCTGCGACTGAGTTGCGC CGCTTCAGGATTCAACATCAAGGACACCTACATTCACTGGGTGCGACAGGCTCCAGGAAAAGGACTGG AGTGGGTGGCTCGAATCTATCCCACTAATGGATACACCCGGTATGCCGACTCCGTGAAGGGGAGGTTT ACTATTAGCGCCGATACATCCAAAAACACTGCTTACCTGCAGATGAACAGCCTGCGAGCCGAAGATAC CGCTGTGTACTATTGCAGTCGATGGGGAGGAGACGGATTCTACGCTATGGATTATTGGGGACAGGGGA CCCTGGTGACAGTGAGCTCCGCCTCTACCAAGGGCCCCAGTGTGTTTCCCCTGGCTCCTTCTAGTAAA TCCACCTCTGGAGGGACAGCCGCTCTGGGATGTCTGGTGAAGGACTATTTCCCCGAGCCTGTGACCGT GAGTTGGAACTCAGGCGCCCTGACAAGCGGAGTGCACACTTTTCCTGCTGTGCTGCAGTCAAGCGGGC TGTACTCCCTGTCCTCTGTGGTGACAGTGCCAAGTTCAAGCCTGGGCACACAGACTTATATCTGCAAC GTGAATCATAAGCCCTCAAATACAAAAGTGGACAAGAAAGTGGAGCCCAAGAGCTGTGATAAGACCCA CACCTGCCCTCCCTGTCCAGCTCCAGAACTGCTGGGAGGACCTAGCGTGTTCCTGTTTCCCCCTAAGC CAAAAGACACTCTGATGATTTCCAGGACTCCCGAGGTGACCTGCGTGGTGGTGGACGTGTCTCACGAG GACCCCGAAGTGAAGTTCAACTGGTACGTGGATGGCGTGGAAGTGCATAATGCTAAGACAAACCAAG AGAGGAACAGTACAACTCCACTTATCGCGTCGTGAGCGTGCTGACCGTGCTGCACCAGGACTGGCTGA ACGGGAAGGAGTATAAGTGCAAAGTCAGTAATAAGGCCCTGCCTGCTCCAATCGAAAAAACCATCTCT AAGGCCAAAGGCCAGCCAAGGGAGCCCCAGGTGTACGTGTACCCACCCAGCAGAGACGAACTGACCAA GAACCAGGTGTCCCTGACATGTCTGGTGAAAGGCTTCTATCCTAGTGATATTGCTGTGGAGTGGGAAT CAAATGGACAGCCAGAGAACAATTACAAGACCACACCTCCAGTGCTGGACAGCGATGGCAGCTTCGCC CTGGTGTCCAAGCTGACAGTGGATAAATCTCGATGGCAGCAGGGGAACGTGTTTACTTGTTCAGTGAT GCATGAAGCCCTGCACAATCATTACACTCAGAAGAGCCTGTCCCTGTCCCCGGCAAA |
| 237 | 1011 | VH | EVQLVESGGGLVQPGGSLRLSCAASGFNIKDTYIHWVRQAPGKGLEWVARIYPTNGYTRYADSVKGRF TISADTSKNTAYLQMNSLRAEDTAVYYCSRWGGDGFYAMDYWGQGTLVTVSS |
| 238 | 1011 | VH | GAGGTGCAGCTGGTGGAAAGCGGAGGAGGACTGGTGCAGCCAGGAGGATCTCTGCGACTGAGTTGCGC CGCTTCAGGATTCAACATCAAGGACACCTACATTCACTGGGTGCGACAGGCTCCAGGAAAAGGACTGG AGTGGGTGGCTCGAATCTATCCCACTAATGGATACACCCGGTATGCCGACTCCGTGAAGGGGAGGTTT ACTATTAGCGCCGATACATCCAAAAACACTGCTTACCTGCAGATGAACAGCCTGCGAGCCGAAGATAC CGCTGTGTACTATTGCAGTCGATGGGGAGGAGACGGATTCTACGCTATGGATTATTGGGGACAGGGGA CCCTGGTGACAGTGAGCTCC |
| 239 | 1011 | H1 | GFNIKDTY |
| 240 | 1011 | H1 | GGATTCAACATCAAGGACACCTAC |
| 241 | 1011 | H3 | SRWGGDGFYAMDY |
| 242 | 1011 | H3 | AGTCGATGGGGAGGAGACGGATTCTACGCTATGGATTAT |
| 243 | 1011 | H2 | IYPTNGYT |
| 244 | 1011 | H2 | ATCTATCCCACTAATGGATACACC |
| 245 | 1011 | CH1 | ASTKGPSVFPLAPSSKSTSGGTAALGCLVKDYFPEPVTVSWNSGALTSGVHTFPAVLQSSGLYSLSSV VTVPSSSLGTQTYICNVNHKPSNTKVDKKV |
| 246 | 1011 | CH1 | GCCTCTACCAAGGGCCCCAGTGTGTTTCCCCTGGCTCCTTCTAGTAAATCCACCTCTGGAGGGACAGC CGCTCTGGGATGTCTGGTGAAGGACTATTTCCCCGAGCCTGTGACCGTGAGTTGGAACTCAGGCGCCC TGACAAGCGGAGTGCACACTTTTCCTGCTGTGCTGCAGTCAAGCGGGCTGTACTCCCTGTCCTCTGTG GTGACAGTGCCAAGTTCAAGCCTGGGCACACAGACTTATATCTGCAACGTGAATCATAAGCCCTCAAA TACAAAAGTGGACAAGAAAGTG |
| 247 | 1011 | CH2 | APELLGGPSVFLFPPKPKDTLMISRTPEVTCVVVDVSHEDPEVKFNWYVDGVEVHNAKTKPREEQYNS TYRVVSVLTVLHQDWLNGKEYKCKVSNKALPAPIEKTISKAK |
| 248 | 1011 | CH2 | GCTCCAGAACTGCTGGGAGGACCTAGCGTGTTCCTGTTTCCCCCTAAGCCAAAAGACACTCTGATGAT TTCCAGGACTCCCGAGGTGACCTGCGTGGTGGTGGACGTGTCTCACGAGGACCCCGAAGTGAAGTTCA ACTGGTACGTGGATGGCGTGGAAGTGCATAATGCTAAGACAAAACCAAGAGAGGAACAGTACAACTCC |

| SEQ ID NO. | Clone | Desc. | Sequence (amino acid or |
|---|---|---|---|
| | | | ACTTATCGCGTCGTGAGCGTGCTGACCGTGCTGCACCAGGACTGGCTGAACGGGAAGGAGTATAAGTG<br>CAAAGTCAGTAATAAGGCCCTGCCTGCTCCAATCGAAAAAACCATCTCTAAGGCCAAA |
| 249 | 1011 | CH3 | GQPREPQVYVYPPSRDELTKNQVSLTCLVKGFYPSDIAVEWESNGQPENNYKTTPPVLDSDGSFALVS<br>KLTVDKSRWQQGNVFSCSVMHEALHNHYTQKSLSLSPG |
| 250 | 1011 | CH3 | GGCCAGCCAAGGGAGCCCCAGGTGTACGTGTACCCACCCAGCAGAGACGAACTGACCAAGAACCAGGT<br>GTCCCTGACATGTCTGGTGAAAGGCTTCTATCCTAGTGATATTGCTGTGGAGTGGGAATCAAATGGAC<br>AGCCAGAGAACAATTACAAGACCACACCTCCAGTGCTGGACAGCGATGGCAGCTTCGCCCTGGTGTCC<br>AAGCTGACAGTGGATAAATCTCGATGGCAGCAGGGGAACGTGTTTACTTGTTCAGTGATGCATGAAGC<br>CCTGCACAATCATTACACTCAGAAGAGCCTGTCCCTGTCTCCCGGC |
| 251 | 4560 | Full | EPKSSDKTHTCPPCPAPELLGGPSVFLFPPKPKDTLMISRTPEVTCVVVDVSHEDPEVKFNWYVDGVE<br>VHNAKTKPREEQYNSTYRVVSVLTVLHQDWLNGKEYKCKVSNKALPAPIEKTISKAKGQPREPQVYVL<br>PPSRDELTKNQVSLLCLVKGFYPSDIAVEWESNGQPENNYLTWPPVLDSDGSFFLYSKLTVDKSRWQQ<br>GNVFSCSVMHEALHNHYTQKSLSLSPGK |
| 252 | 4560 | Full | GAACCTAAAAGCAGCGACAAGACCCACACATGCCCCCCTTGTCCAGCTCCAGAACTGCTGGGAGGACC<br>AAGCGTGTTCCTGTTTCCACCCAAGCCCAAAGATACACTGATGATCAGCCGAACTCCCGAGGTCACCT<br>GCGTGGTCGTGGACGTGTCCCACGAGGACCCCGAAGTCAAGTTCAACTGGTACGTGGACGGCGTCGAA<br>GTGCATAATGCAAAGACTAAACCACGGGAGGAACAGTACAACTCTACATATAGAGTCGTGAGTGTCCT<br>GACTGTGCTGCATCAGGATTGGCTGAACGGCAAAGAGTATAAGTGCAAAGTGTCTAATAAGGCCCTGC<br>CTGCTCCAATCGAGAAAACTATTAGTAAGGCAAAAGGGCAGCCCAGGGAACCTCAGGTCTACGTGCTG<br>CCTCCAAGTCGCGACGAGCTGACCAAGAACCAGGTCTCACTGCTGTGTCTGGTGAAAGGATTCTATCC<br>TTCCGATATTGCCGTGGAGTGGGAATCTAATGGCCAGCCAGAGAACAATTACCTGACCTGGCCCCCTG<br>TGCTGGACAGCGATGGGTCCTTCTTTCTGTATTCAAAGCTGACAGTGGACAAAAGCAGATGGCAGCAG<br>GGAAACGTCTTTAGCTGTTCCGTGATGCACGAAGCCCTGCACAATCATTACACCCAGAAGTCTCTGAG<br>TCTGTCACCTGGCAAA |
| 253 | 4560 | CH2 | APELLGGPSVFLFPPKPKDTLMISRTPEVTCVVVDVSHEDPEVKFNWYVDGVEVHNAKTKPREEQYNS<br>TYRVVSVLTVLHQDWLNGKEYKCKVSNKALPAPIEKTISKAK |
| 254 | 4560 | CH2 | GCTCCAGAACTGCTGGGAGGACCAAGCGTGTTCCTGTTTCCACCCAAGCCCAAAGATACACTGATGAT<br>CAGCCGAACTCCCGAGGTCACCTGCGTGGTCGTGGACGTGTCCCACGAGGACCCCGAAGTCAAGTTCA<br>ACTGGTACGTGGACGGCGTCGAAGTGCATAATGCAAAGACTAAACCACGGGAGGAACAGTACAACTCT<br>ACATATAGAGTCGTGAGTGTCCTGACTGTGCTGCATCAGGATTGGCTGAACGGCAAAGAGTATAAGTG<br>CAAAGTGTCTAATAAGGCCCTGCCTGCTCCAATCGAGAAAACTATTAGTAAGGCAAAA |
| 255 | 4560 | CH3 | GQPREPQVYVLPPSRDELTKNQVSLLCLVKGFYPSDIAVEWESNGQPENNYLTWPPVLDSDGSFELYS<br>KLTVDKSRWQQGNVFSCSVMHEALHNHYTQKSLSLSPG |
| 256 | 4560 | CH3 | GGGCAGCCCAGGGAACCTCAGGTCTACGTGCTGCCTCCAAGTCGCGACGAGCTGACCAAGAACCAGGT<br>CTCACTGCTGTGTCTGGTGAAAGGATTCTATCCTTCCGATATTGCCGTGGAGTGGGAATCTAATGCC<br>AGCCAGAGAACAATTACCTGACCTGGCCCCCTGTGCTGGACAGCGATGGGTCCTTCTTTCTGTATTCA<br>AAGCTGACAGTGGACAAAAGCAGATGGCAGCAGGGAAACGTCTTTAGCTGTTCCGTGATGCACGAAGC<br>CCTGCACAATCATTACACCCAGAAGTCTCTGAGTCTGTCACCTGGC |
| 257 | 3317 | Full | DIQMTQSPSSLSASVGDRVTITCKASQDVSIGVAWYQQKPGKAPKLLIYSASYRYTGVPSRFSGSGSG<br>TDFTLTISSLQPEDFATYYCQQYYIYPYTFGQGTKVEIKGGGGSGGGGSGGGGSEVQLVESGGGLVQP<br>GGSLRLSCAASGFTFTDYTMDWVRQAPGKGLEWVADVNPNSGGSIYNQRFKGRFTLSVDRSKNTLYLQ<br>MNSLRAEDTAVYYCARNLGPSFYFDYWGQGTLVTVSSAAEPKSSDKTHTCPPCPAPELLGGPSVFLFP<br>PKPKDTLMISRTPEVTCVVVDVSHEDPEVKFNWYVDGVEVHNAKTKPREEQYNSTYRVVSVLTVLHQD<br>WLNGKEYKCKVSNKALPAPIEKTISKAKGQPREPQVYVYPPSRDELTKNQVSLTCLVKGFYPSDIAVE<br>WESNGQPENNYKTTPPVLDSDGSFALVSKLTVDKSRWQQGNVFSCSVMHEALHNHYTQKSLSLSPGK |
| 258 | 3317 | Full | GACATTCAGATGACCCAGAGCCCTAGCTCCCTGAGTGCCTCAGTCGGGGACAGGGTGACTATCACCTG<br>CAAGGCTTCACAGGATGTCAGCATTGGCGTGGCATGGTACCAGCAGAAGCCAGGGAAAGCACCCAAGC<br>TGCTGATCTATAGCGCCTCCTACAGGTATACAGGCGTGCCATCCCGCTTCTCTGGCAGTGGGTCAGGA<br>ACTGACTTTACACTGACTATTTCTAGTCTGCAGCCCGAAGATTTCGCCACATACTATTGCCAGCAGTA<br>CTATATCTACCCTTATACTTTTGGCCAGGGGACCAAAGTGGAGATTAAGGGCGGAGGAGGCTCCGGAG<br>GAGGAGGGTCTGGAGGAGGAGGAAGTGAGGTCCAGCTGGTGGAATCGGAGGAGGACTGGTGCAGCCA<br>GGAGGGTCCCTGAGGCTGTCTTGTGCCGCTAGTGGCTTCACCTTTACAGACTACACAATGGATTGGGT<br>GCGCCAGGCACCAGGAAAGGGACTGGAATGGGTCGCTGATGTGAACCCTAATAGCGGAGGCTCCATCT<br>ACAACCAGCGGTTCAAAGGACGGTTCACCCTGTCAGTGGACCGGAGCAAGAACACCCTGTATCTGCAG<br>ATGAACAGCCTGAGAGCCGAGGATACTGCTGTGTACTATTGCGCCAGGAATCTGGGCCCAAGCTTCTA<br>CTTTGACTATTGGGGGCAGGGAACACTGGTCACTGTGTCAAGCGCAGCCGAACCCAAATCCTCTGATA<br>AGACTCACACCTGCCCACCTTGTCCAGCTCCAGAGCTGCTGGGAGGACCTAGCGTGTTCCTGTTTCCA<br>CCCAAGCCAAAAGACACTCTGATGATTTCTAGAACCCCTGAGGTGACATGTGTGGTCGTGGACGTCAG<br>TCACGAGGACCCCGAAGTCAAATTCAACTGGTACGTGGATGGCGTCGAGGTGCATAATGCCAAGACCA<br>AACCCCGAGAGGAACAGTACAACTCAACCTATCGGGTCGTGAGCGTCCTGACAGTGCTGCATCAGGAC<br>TGGCTGAACGGCAAGGAGTATAAGTGCAAAGTGAGCAACAAGGCTCTGCCTGCACCAATCGAGAAGAC<br>CATTTCCAAGGCTAAAGGCAGCCCCGCGAACCTCAGGTCTACGTGTATCCTCCAAGCCGAGATGAGC<br>TGACAAAAAACCAGGTCTCCCTGACTTGTCTGGTGAAGGATTTTACCCAAGTGACATCGCAGTGGAG<br>TGGGAATCAAATGGCCAGCCCGAAAACAATTATAAGACCACACCCCCTGTGCTGGACTCTGATGGGAG |

| SEQ ID NO. | Clone | Desc. | Sequence (amino acid or |
|---|---|---|---|
| | | | TTTCGCACTGGTCTCCAAACTGACCGTGGACAAGTCTCGGTGGCAGCAGGGAAACGTCTTTAGCTGTT<br>CCGTGATGCACGAGGCCCTGCACAATCATTACACACAGAAATCTCTGAGTCTGTCACCTGGCAAG |
| 259 | 3317 | VL | DIQMTQSPSSLSASVGDRVTITCKASQDVSIGVAWYQQKPGKAPKLLIYSASYRYTGVPSRFSGSGSG<br>TDFTLTISSLQPEDFATYYCQQYYIYPYTFGQGTKVEIK |
| 260 | 3317 | VL | GACATTCAGATGACCCAGAGCCCTAGCTCCCTGAGTGCCTCAGTCGGGGACAGGGTGACTATCACCTG<br>CAAGGCTTCACAGGATGTCAGCATTGGCGTGGCATGGTACCAGCAGAAGCCAGGGAAAGCACCCAAGC<br>TGCTGATCTATAGCGCCTCCTACAGGTATACAGGCGTGCCATCCCGCTTCTCTGGCAGTGGGTCAGGA<br>ACTGACTTTACACTGACTATTTCTAGTCTGCAGCCCGAAGATTTCGCCACATACTATTGCCAGCAGTA<br>CTATATCTACCCTTATACTTTTGGCCAGGGGACCAAAGTGGAGATTAAG |
| 261 | 3317 | L1 | QDVSIG |
| 262 | 3317 | L1 | CAGGATGTCAGCATTGGC |
| 263 | 3317 | L3 | QQYYIYPYT |
| 264 | 3317 | L3 | CAGCAGTACTATATCTACCCTTATACT |
| 265 | 3317 | L2 | SAS |
| 266 | 3317 | L2 | AGCGCCTCC |
| 267 | 3317 | VH | EVQLVESGGGLVQPGGSLRLSCAASGFTFTDYTMDWVRQAPGKGLEWVADVNPNSGGSIYNQRFKGRF<br>TLSVDRSKNTLYLQMNSLRAEDTAVYYCARNLGPSFYFDYWGQGTLVTVSS |
| 268 | 3317 | VH | GAGGTCCAGCTGGTGGAATCTGGAGGAGGACTGGTGCAGCCAGGAGGGTCCCTGAGGCTGTCTTGTGC<br>CGCTAGTGGCTTCACCTTTACAGACTACACAATGGATTGGGTGCGCCAGGCACCAGGAAAGGGACTGG<br>AATGGGTCGCTGATGTGAACCCTAATAGCGGAGGCTCCATCTACAACCAGCGGTTCAAAGGACGGTTC<br>ACCCTGTCAGTGGACCGGAGCAAGAACACCCTGTATCTGCAGATGAACAGCCTGAGAGCCGAGGATAC<br>TGCTGTGTACTATTGCGCCAGGAATCTGGGCCCAAGCTTCTACTTTGACTATTGGGGGCAGGGAACAC<br>TGGTCACTGTGTCAAGC |
| 269 | 3317 | H1 | GFTFTDYT |
| 270 | 3317 | H1 | GGCTTCACCTTTACAGACTACACA |
| 271 | 3317 | H3 | ARNLGPSFYFDY |
| 272 | 3317 | H3 | GCCAGGAATCTGGGCCCAAGCTTCTACTTTGACTAT |
| 273 | 3317 | H2 | VNPNSGGS |
| 274 | 3317 | H2 | GTGAACCCTAATAGCGGAGGCTCC |
| 275 | 3317 | CH2 | APELLGGPSVFLFPPKPKDTLMISRTPEVTCVVVDVSHEDPEVKFNWYVDGVEVHNAKTKPREEQYNS<br>TYRVVSVLTVLHQDWLNGKEYKCKVSNKALPAPIEKTISKAK |
| 276 | 3317 | CH2 | GCTCCAGAGCTGCTGGGAGGACCTAGCGTGTTCCTGTTTCCACCCAAGCCAAAAGACACTCTGATGAT<br>TTCTAGAACCCCTGAAGTGACATGTGTGGTCGTGGACGTCAGTCACGAGGACCCCGAAGTCAAATTCA<br>ACTGGTACGTGGATGGCGTCGAGGTGCATAATGCCAAGACCAAACCCCGAGAGGAACAGTACAACTCA<br>ACCTATCGGGTCGTGAGCGTCCTGACAGTGCTGCATCAGGACTGGCTGAACGGCAAGGAGTATAAGTG<br>CAAAGTGAGCAACAAGGCTCTGCCTGCACCAATCGAGAAGACCATTTCCAAGGCTAAA |
| 277 | 3317 | CH3 | GQPREPQVYVYPPSRDELTKNQVSLTCLVKGFYPSDIAVEWESNGQPENNYKTTPPVLDSDGSFALVS<br>KLTVDKSRWQQGNVFSCSVMHEALHNHYTQKSLSLSPG |
| 278 | 3317 | CH3 | GGGCAGCCCCGCGAACCTCAGGTCTACGTGTATCCTCCAAGCCGAGATGAGCTGACAAAAAACCAGGT<br>CTCCCTGACTTGTCTGGTGAAGGGATTTTACCCAAGTGACATCGCAGTGGAGTGGGAATCAAATGGCC<br>AGCCCGAAAACAATTATAAGACCACACCCCCTGTGCTGGACTCTGATGGGAGTTTCGCACTGGTCTCC<br>AAACTGACCGTGGACAAGTCTCGGTGGCAGCAGGGAAACGTCTTTAGCTGTTCCGTGATGCACGAGGC<br>CCTGCACAATCATTACACACAGAAATCTCTGAGTCTGTCACCTGGC |
| 279 | 1015 | Full | EVQLVESGGGLVQPGGSLRLSCAASGFNIKDTYIHWVRQAPGKGLEWVARIYPTNGYTRYADSVKGRF<br>TISADTSKNTAYLQMNSLRAEDTAVYYCSRWGGDGFYAMDYWGQGTLVTVSSASTKGPSVFPLAPSSK<br>STSGGTAALGCLVKDYFPEPVTVSWNSGALTSGVHTFPAVLQSSGLYSLSSVVTVPSSSLGTQTYICN<br>VNHKPSNTKVDKKVEPKSCDKTHTCPPCPAPELLGGPSVFLFPPKPKDTLMISRTPEVTCVVVDVSHE<br>DPEVKFNWYVDGVEVHNAKTKPREEQYNSTYRVVSVLTVLHQDWLNGKEYKCKVSNKALPAPIEKTIS<br>KAKGQPREPQVYVLPPSRDELTKNQVSLLCLVKGFYPSDIAVEWESNGQPENNYLTWPPVLDSCGSFF<br>LYSKLTVCKSRWQQGNVFSCSVMHEALHNHYTQKSLSLSPGK |
| 280 | 1015 | Full | GAGGTGCAGCTGGTGGAAAGCGGAGGAGGACTGGTGCAGCCAGGAGGATCTCTGCGACTGAGTTGCGC<br>CGCTTCAGGATTCAACATCAAGGACACCTACATTCACTGGGTGCGACAGGCTCCAGGAAAGGACTGG<br>AGTGGGTGGCTCGAATCTATCCCACTAATGGATACACCCGGTATGCCGACTCCGTGAAGGGGAGGTTT |

| SEQ ID NO. | Clone | Desc. | Sequence (amino acid or |
|---|---|---|---|
| | | | ACTATTAGCGCCGATACATCCAAAAACACTGCTTACCTGCAGATGAACAGCCTGCGAGCCGAAGATAC<br>CGCTGTGTACTATTGCAGTCGATGGGGAGGAGACGGATTCTACGCTATGGATTATTGGGGACAGGGGA<br>CCCTGGTGACAGTGAGCTCCGCCTCTACCAAGGGCCCCAGTGTGTTTCCCCTGGCTCCTTCTAGTAAA<br>TCCACCTCTGGAGGGACAGCCGCTCTGGGATGTCTGGTGAAGGACTATTTCCCCGAGCCTGTGACCGT<br>GAGTTGGAACTCAGGCGCCCTGACAAGCGGAGTGCACACTTTTCCTGCTGTGCTGCAGTCAAGCGGGC<br>TGTACTCCCTGTCCTCTGTGGTGACAGTGCCAAGTTCAAGCCTGGGCACACAGACTTATATCTGCAAC<br>GTGAATCATAAGCCCTCAAATACAAAAGTGGACAAGAAAGTGGAGCCCAAGAGCTGTGATAAGACCCA<br>CACCTGCCCTCCCTGTCCAGCTCCAGAACTGCTGGGAGGACCTAGCGTGTTCCTGTTTCCCCCTAAGC<br>CAAAAGACACTCTGATGATTTCCAGGACTCCCGAGGTGACCTGCGTGGTGGTGGACGTGTCTCACGAG<br>GACCCCGAAGTGAAGTTCAACTGGTACGTGGATGGCGTGGAAGTGCATAATGCTAAGACAAAACCAAG<br>AGAGGAACAGTACAACTCCACTTATCGCGTCGTGAGCGTGCTGACCGTGCTGCACCAGGACTGGCTGA<br>ACGGGAAGGAGTATAAGTGCAAAGTCAGTAATAAGGCCCTGCCTGCTCCAATCGAAAAAACCATCTCT<br>AAGGCCAAAGGCCAGCCAAGGGAGCCCCAGGTATACGTGCTGCCACCCAGCAGAGACGAACTGACCAA<br>GAACCAGGTGTCCCTGCTGTGTCTGGTGAAAGGCTTCTATCCTAGTGATATTGCTGTGGAGTGGGAAT<br>CAAATGGACAGCCAGAGAACAATTACCTGACCTGGCCTCCAGTGCTGGACAGCGATGGCAGCTTCTTC<br>CTGTATTCCAAGCTGACAGTGGATAAATCTCGATGGCAGCAGGGGAACGTGTTTAGTTGTTCAGTGAT<br>GCATGAAGCCCTGCACAATCATTACACTCAGAAGAGCCTGTCCCTGTCTCCGGCAAA |
| 281 | 1015 | VH | EVQLVESGGGLVQPGGSLRLSCAASGFNIKDTYIHWVRQAPGKGLEWVARIYPTNGYTRYADSVKGRF<br>TISADTSKNTAYLQMNSLRAEDTAVYYCSRWGGDGFYAMDYWGQGTLVTVSS |
| 282 | 1015 | VH | GAGGTGCAGCTGGTGGAAAGCGGAGGAGGACTGGTGCAGCCAGGAGGATCTCTGCGACTGAGTTGCGC<br>CGCTTCAGGATTCAACATCAAGGACACCTACATTCACTGGGTGCGACAGGCTCCAGGAAAAGGACTGG<br>AGTGGGTGGCTCGAATCTATCCCACTAATGGATACACCCGGTATGCCGACTCCGTGAAGGGGAGGTTT<br>ACTATTAGCGCCGATACATCCAAAAACACTGCTTACCTGCAGATGAACAGCCTGCGAGCCGAAGATAC<br>CGCTGTGTACTATTGCAGTCGATGGGGAGGAGACGGATTCTACGCTATGGATTATTGGGGACAGGGGA<br>CCCTGGTGACAGTGAGCTCC |
| 283 | 1015 | H1 | GFNIKDTY |
| 284 | 1015 | H1 | GGATTCAACATCAAGGACACCTAC |
| 285 | 1015 | H3 | SRWGGDGFYAMDY |
| 286 | 1015 | H3 | AGTCGATGGGGAGGAGACGGATTCTACGCTATGGATTAT |
| 287 | 1015 | H2 | IYPTNGYT |
| 288 | 1015 | H2 | ATCTATCCCACTAATGGATACACC |
| 289 | 1015 | CH1 | ASTKGPSVFPLAPSSKSTSGGTAALGCLVKDYFPEPVTVSWNSGALTSGVHTFPAVLQSSGLYSLSSV<br>VTVPSSSLGTQTYICNVNHKPSNTKVDKKV |
| 290 | 1015 | CH1 | GCCTCTACCAAGGGCCCCAGTGTGTTTCCCCTGGCTCCTTCTAGTAAATCCACCTCTGGAGGGACAGC<br>CGCTCTGGGATGTCTGGTGAAGGACTATTTCCCCGAGCCTGTGACCGTGAGTTGGAACTCAGGCGCCC<br>TGACAAGCGGAGTGCACACTTTTCCTGCTGTGCTGCAGTCAAGCGGGCTGTACTCCCTGTCCTCTGTG<br>GTGACAGTGCCAAGTTCAAGCCTGGGCACACAGACTTATATCTGCAACGTGAATCATAAGCCCTCAAA<br>TACAAAAGTGGACAAGAAAGTG |
| 291 | 1015 | CH2 | APELLGGPSVFLFPPKPKDTLMISRTPEVTCVVVDVSHEDPEVKFNWYVDGVEVHNAKTKPREEQYNS<br>TYRVVSVLTVLHQDWLNGKEYKCKVSNKALPAPIEKTISKAK |
| 292 | 1015 | CH2 | GCTCCAGAACTGCTGGGAGGACCTAGCGTGTTCCTGTTTCCCCCTAAGCCAAAAGACACTCTGATGAT<br>TTCCAGGACTCCCGAGGTGACCTGCGTGGTGGTGGACGTGTCTCACGAGGACCCCGAAGTGAAGTTCA<br>ACTGGTACGTGGATGGCGTGGAAGTGCATAATGCTAAGACAAAACCAAGAGAGGAACAGTACAACTCC<br>ACTTATCGCGTCGTGAGCGTGCTGACCGTGCTGCACCAGGACTGGCTGAACGGGAAGGAGTATAAGTG<br>CAAAGTCAGTAATAAGGCCCTGCCTGCTCCAATCGAAAAAACCATCTCTAAGGCCAAA |
| 293 | 1015 | CH3 | GQPREPQVYVLPPSRDELTKNQVSLLCLVKGFYPSDIAVEWESNGQPENNYLTWPPVLDSDGSFELYS<br>KLTVDKSRWQQGNVFSCSVMHEALHNHYTQKSLSLSPG |
| 294 | 1015 | CH3 | GGCCAGCCAAGGGAGCCCCAGGTGTACGTGCTGCCACCCAGCAGAGACGAACTGACCAAGAACCAGGT<br>GTCCCTGCTGTGTCTGGTGAAAGGCTTCTATCCTAGTGATATTGCTGTGGAGTGGGAATCAAATGGAC<br>AGCCAGAGAACAATTACCTGACCTGGCCTCCAGTGCTGGACAGCGATGGCAGCTTCTTCCTGTATTCC<br>AAGCTGACAGTGGATAAATCTCGATGGCAGCAGGGGAACGTGTTTACTTGTTCAGTGATGCATGAAGC<br>CCTGCACAATCATTACACTCAGAAGAGCCTGTCCCTGTCTCCGGC |
| 295 | 5244 | Full | DIQMTQSPSSLSASVGDRVTITCRASQDVNTAVAWYQQKPGKAPKLLIYSASFLYSGVPSRFSGSRSG<br>TDFTLTISSLQPEDFATYYCQQHYTTPPTFGQGTKVEIKGGSGGSGGSGGSGGSGGSGEVQLVESGG<br>GLVQPGGSLRLSCAASGFNIKDTYIHWVRQAPGKGLEWVARIYPTNGYTRYADSVKGRFTISADTSKN<br>TAYLQMNSLRAEDTAVYYCSRWGGDGFYAMDYWGQGTLVTVSSAAEPKSSDKTHTCPPCPAPELLGGP<br>SVFLFPPKPKDTLMISRTPEVTCVVVDVSHEDPEVKFNWYVDGVEVHNAKTKPREEQYNSTYRVVSVL<br>TVLHQDWLNGKEYKCKVSNKALPAPIEKTISKAKGQPREPQVYVLPPSRDELTKNQVSLLCLVKGFYP<br>SDIAVEWESNGQPENNYLTWPPVLDSDGSFFLYSKLTVDKSRWQQGNVFSCSVMHEALHNHYTQKSLS<br>LSPG |

| SEQ ID NO. | Clone | Desc. | Sequence (amino acid or |
|---|---|---|---|
| 296 | 5244 | Full | GACATTCAGATGACACAGAGCCCCAGCTCCCTGAGTGCTTCAGTCGGCGACAGGGTGACTATCACCTG<br>CCGCGCATCCCAGGATGTCAACACCGCTGTGGCATGGTACCAGCAGAAGCCTGGAAAAGCCCCAAAGC<br>TGCTGATCTACAGCGCTTCCTTCCTGTATTCTGGCGTGCCAAGTCGGTTTTCTGGAAGTAGATCAGGC<br>ACTGACTTCACACTGACTATCTCTAGTCTGCAGCCCGAAGATTTTGCCACCTACTATTGCCAGCAGCA<br>CTATACCACACCCCCTACATTCGGACAGGGCACTAAAGTGGAGATTAAGGGCGGGTCAGGCGGAGGGA<br>GCGGAGGAGGGTCCGGAGGAGGGTCTGGAGGAGGGAGTGGAGAGGTCCAGCTGGTGGAATCTGGAGGA<br>GGACTGGTGCAGCCTGGAGGCTCACTGCGACTGAGCTGTGCCGCTTCCGGCTTTAACATCAAAGACAC<br>ATACATTCATTGGGTCAGGCAGGCACCAGGGAAGGGACTGGAATGGGTGGCCCGCATCTATCCCACAA<br>ATGGGTACACTCGATATGCCGACAGCGTGAAAGGACGGTTTACCATTTCTGCTGATACCAGTAAGAAC<br>ACAGCATACCTGCAGATGAACAGCCTGCGCGCAGAGGATACAGCCGTGTACTATTGCAGTCGATGGGG<br>GGGAGACGGCTTCTACGCCATGGATTATTGGGGCCAGGGGACTCTGGTCACCGTGTCAAGCGCAGCCG<br>AACCTAAATCCTCTGACAAGACCCACACATGCCCACCCTGTCCTGCTCCAGAGCTGCTGGGAGGACCA<br>TCCGTGTTCCTGTTTCCTCCAAAGCCTAAAGATACACTGATGATTAGCCGCACTCCCGAAGTCACCTG<br>TGTGGTCGTGGACGTGTCCCACGAGGACCCCGAAGTCAAGTTCAACTGGTACGTGGACGGCGTCGAGG<br>TGCATAATGCCAAGACTAAACCAAGAGAGGAACAGTACAATTCAACCTATAGGGTCGTGAGCGTCCTG<br>ACAGTGCTGCATCAGGATTGGCTGAACGGCAAGGAGTATAAGTGCAAAGTGTCTAACAAGGCCCTGCC<br>CGCTCCTATCGAGAAGACTATTAGCAAGGCAAAAGGGCAGCCACGGGAACCCCAGGTCTACGTGCTGC<br>CCCCTAGCAGAGACGAGCTGACCAAAAACCAGGTCTCCCTGCTGTGTCTGGTGAAGGGCTTTTATCCT<br>AGTGATATCGCTGTGGAGTGGGAATCAAATGGGCAGCCAGAAAACAATTACCTGACATGGCCACCCGT<br>GCTGGACAGCGATGGGTCCTTCTTTCTGTATTCCAAACTGACTGTGGACAAGTCTAGATGGCAGCAGG<br>GAAACGTCTTCAGCTGTTCCGTGATGCACGAGGCCCTGCACAATCATTACACCCAGAAGTCTCTGAGT<br>CTGTCACCCGGC |
| 297 | 5244 | VL | DIQMTQSPSSLSASVGDRVTITCRASQDVNTAVAWYQQKPGKAPKLLIYSASFLYSGVPSRFSGSRSG<br>TDFTLTISSLQPEDFATYYCQQHYTTPPTFGQGTKVEIK |
| 298 | 5244 | VL | GACATTCAGATGACACAGAGCCCCAGCTCCCTGAGTGCTTCAGTCGGCGACAGGGTGACTATCACCTG<br>CCGCGCATCCCAGGATGTCAACACCGCTGTGGCATGGTACCAGCAGAAGCCTGGAAAAGCCCCAAAGC<br>TGCTGATCTACAGCGCTTCCTTCCTGTATTCTGGCGTGCCAAGTCGGTTTTCTGGAAGTAGATCAGGC<br>ACTGACTTCACACTGACTATCTCTAGTCTGCAGCCCGAAGATTTTGCCACCTACTATTGCCAGCAGCA<br>CTATACCACACCCCCTACATTCGGACAGGGCACTAAAGTGGAGATTAAG |
| 299 | 5244 | L1 | QDVNTA |
| 300 | 5244 | L1 | CAGGATGTCAACACCGCT |
| 301 | 5244 | L3 | QQHYTTPPT |
| 302 | 5244 | L3 | CAGCAGCACTATACCACACCCCCTACA |
| 303 | 5244 | L2 | SAS |
| 304 | 5244 | L2 | AGCGCTTCC |
| 305 | 5244 | VH | EVQLVESGGGLVQPGGSLRLSCAASGFNIKDTYIHWVRQAPGKGLEWVARIYPTNGYTRYADSVKGRF<br>TISADTSKNTAYLQMNSLRAEDTAVYYCSRWGGDGFYAMDYWGQGTLVTVSS |
| 306 | 5244 | VH | GAGGTCCAGCTGGTGGAATCTGGAGGAGGACTGGTGCAGCCTGGAGGCTCACTGCGACTGAGCTGTGC<br>CGCTTCCGGCTTTAACATCAAAGACACATACATTCATTGGGTCAGGCAGGCACCAGGGAAGGGACTGG<br>AATGGGTGGCCCGCATCTATCCCACAAATGGGTACACTCGATATGCCGACAGCGTGAAAGGACGGTTT<br>ACCATTTCTGCTGATACCAGTAAGAACACAGCATACCTGCAGATGAACAGCCTGCGCGCAGAGGATAC<br>AGCCGTGTACTATTGCAGTCGATGGGGGGGAGACGGCTTCTACGCCATGGATTATTGGGGCCAGGGGA<br>CTCTGGTCACCGTGTCAAGC |
| 307 | 5244 | H1 | GFNIKDTY |
| 308 | 5244 | H1 | GGCTTTAACATCAAAGACACATAC |
| 309 | 5244 | H3 | SRWGGDGFYAMDY |
| 310 | 5244 | H3 | AGTCGATGGGGGGAGACGGCTTCTACGCCATGGATTAT |
| 311 | 5244 | H2 | IYPTNGYT |
| 312 | 5244 | H2 | ATCTATCCCACAAATGGGTACACT |
| 313 | 5244 | CH2 | APELLGGPSVFLFPPKPKDTLMISRTPEVTCVVVDVSHEDPEVKFNWYVDGVEVHNAKTKPREEQYNS<br>TYRVVSVLTVLHQDWLNGKEYKCKVSNKALPAPIEKTISKAK |
| 314 | 5244 | CH2 | GCTCCAGAGCTGCTGGGAGGACCATCCGTGTTCCTGTTTCCTCCAAAGCCTAAAGATACACTGATGAT<br>TAGCCGCACTCCCGAAGTCACCTGTGTGGTCGTGGACGTGTCCCACGAGGACCCCGAAGTCAAGTTCA<br>ACTGGTACGTGGACGGCGTCGAGGTGCATAATGCCAAGACTAAACCAAGAGAGGAACAGTACAATTCA<br>ACCTATAGGGTCGTGAGCGTCCTGACAGTGCTGCATCAGGATTGGCTGAACGGCAAGGAGTATAAGTG<br>CAAAGTGTCTAACAAGGCCCTGCCCGCTCCTATCGAGAAGACTATTAGCAAGGCAAAA |

| SEQ ID NO. | Clone | Desc. | Sequence (amino acid or |
|---|---|---|---|
| 315 | 5244 | CH3 | GQPREPQVYVLPPSRDELTKNQVSLLCLVKGFYPSDIAVEWESNGQPENNYLTWPPVLDSDGSFFLYS<br>KLTVDKSRWQQGNVFSCSVMHEALHNHYTQKSLSLSPG |
| 316 | 5244 | CH3 | GGGCAGCCACGGGAACCCCAGGTCTACGTGCTGCCCCCTAGCAGAGACGAGCTGACCAAAAACCAGGT<br>CTCCCTGCTGTGTCTGGTGAAGGGCTTTTATCCTAGTGATATCGCTGTGGAGTGGGAATCAAATGGGC<br>AGCCAGAAAACAATTACCTGACATGGCCACCCGTGCTGGACAGCGATGGGTCCTTCTTTCTGTATTCC<br>AAACTGACTGTGGACAAGTCTAGATGGCAGCAGGGAAACGTCTTCAGCTGTTCCGTGATGCACGAGGC<br>CCTGCACAATCATTACACCCAGAAGTCTCTGAGTCTGTCACCCGGC |
| 317 | -2 | Full | DIQMTQSPSSLSASVGDRVTITCRASQDVNTAVAWYQQKPGKAPKLLIYSASFLYSGVPSRFSGSRSG<br>TDFTLTISSLQPEDFATYYCQQHYTTPPTFGQGTKVEIKRTVAAPSVFIFPPSDEQLKSGTASVVCLL<br>NNFYPREAKVQWKVDNALQSGNSQESVTEQDSKDSTYSLSSTLTLSKADYEKHKVYACEVTHQGLSSP<br>VTKSFNRGEC |
| 318 | -2 | Full | GACATCCAGATGACCCAGTCTCCATCCTCCCTGTCTGCATCTGTAGGAGACAGAGTCACCATCACTTG<br>CCGGGCAAGTCAGGACGTTAACACCGCTGTAGCTTGGTATCAGCAGAAACCAGGGAAAGCCCCTAAGC<br>TCCTGATCTATTCTGCATCCTTTTTGTACAGTGGGGTCCCATCAAGGTTCAGTGGCAGTCGATCTGGG<br>ACAGATTTCACTCTCACCATCAGCAGTCTGCAACCTGAAGATTTTGCAACTTACTACTGTCAACAGCA<br>TTACACTACCCCACCCACTTTCGGCCAAGGGACCAAAGTGGAGATCAAACGAACTGTGGCTGCACCAT<br>CTGTCTTCATCTTCCCGCCATCTGATGAGCAGTTGAAATCTGGAACTGCCTCTGTTGTGTGCCTGCTG<br>AATAACTTCTATCCCAGAGAGGCCAAAGTACAGTGGAAGGTGGATAACGCCCTCCAATCGGGTAACTC<br>CCAAGAGAGTGTCACAGAGCAGGACAGCAAGGACAGCACCTACAGCCTCAGCAGCACCCTGACGCTGA<br>GCAAAGCAGACTACGAGAAACACAAAGTCTACGCCTGCGAAGTCACCCATCAGGGCCTGAGCTCGCCC<br>GTCACAAAGAGCTTCAACAGGGGAGAGTGT |
| 319 | -2 | VL | DIQMTQSPSSLSASVGDRVTITCRASQDVNTAVAWYQQKPGKAPKLLIYSASFLYSGVPSRFSGSRSG<br>TDFTLTISSLQPEDFATYYCQQHYTTPPTFGQGTKVEIK |
| 320 | -2 | VL | GACATCCAGATGACCCAGTCTCCATCCTCCCTGTCTGCATCTGTAGGAGACAGAGTCACCATCACTTG<br>CCGGGCAAGTCAGGACGTTAACACCGCTGTAGCTTGGTATCAGCAGAAACCAGGGAAAGCCCCTAAGC<br>TCCTGATCTATTCTGCATCCTTTTTGTACAGTGGGGTCCCATCAAGGTTCAGTGGCAGTCGATCTGGG<br>ACAGATTTCACTCTCACCATCAGCAGTCTGCAACCTGAAGATTTTGCAACTTACTACTGTCAACAGCA<br>TTACACTACCCCACCCACTTTCGGCCAAGGGACCAAAGTGGAGATCAAA |
| 321 | -2 | L1 | QDVNTA |
| 322 | -2 | L1 | CAGGACGTTAACACCGCT |
| 323 | -2 | L3 | QQHYTTPPT |
| 324 | -2 | L3 | CAACAGCATTACACTACCCCACCCACT |
| 325 | -2 | L2 | SAS |
| 326 | -2 | L2 | TCTGCATCC |
| 327 | -2 | CL | RTVAAPSVFIFPPSDEQLKSGTASVVCLLNNFYPREAKVQWKVDNALQSGNSQESVTEQDSKDSTYSL<br>SSTLTLSKADYEKHKVYACEVTHQGLSSPVTKSFNRGEC |
| 328 | -2 | CL | CGAACTGTGGCTGCACCATCTGTCTTCATCTTCCCGCCATCTGATGAGCAGTTGAAATCTGGAACTGC<br>CTCTGTTGTGTGCCTGCTGAATAACTTCTATCCCAGAGAGGCCAAAGTACAGTGGAAGGTGGATAACG<br>CCCTCCAATCGGGTAACTCCCAAGAGAGTGTCACAGAGCAGGACAGCAAGGACAGCACCTACAGCCTC<br>AGCAGCACCCTGACGCTGAGCAAAGCAGACTACGAGAAACACAAAGTCTACGCCTGCGAAGTCACCCA<br>TCAGGGCCTGAGCTCGCCCGTCACAAAGAGCTTCAACAGGGGAGAGTGT |
| 329 | 4372 | Full | EPKSSDKTHTCPPCPAPELLGGPSVFLFPPKPKDTLMISRTPEVTCVVVDVSHEDPEVKFNWYVDGVE<br>VHNAKTKPREEQYNSTYRVVSVLTVLHQDWLNGKEYKCKVSNKALPAPIEKTISKAKGQPREPQVYVL<br>PPSRDELTKNQVSLLCLVKGFYPSDIAVEWESNGQPENNYLTWPPVLDSDGSFFLYSKLTVDKSRWQQ<br>GNVFSCSVMHEALHNHYTQKSLSLSPG |
| 330 | 4372 | Full | GAACCTAAATCCAGCGACAAGACCCACACATGCCCCCCTTGTCCAGCTCCAGAACTGCTGGGAGGACC<br>AAGCGTGTTCCTGTTTCCACCCAAGCCCAAAGATACACTGATGATCAGCCGAACTCCCGAGGTCACCT<br>GCGTGGTCGTGGACGTGTCCCACGAGGACCCCGAAGTCAAGTTCAACTGGTACGTGGACGGCGTGGAA<br>GTGCATAATGCAAAGACTAAACCACGGGAGGAACAGTACAACTCTACATATAGAGTCGTGAGTGTCCT<br>GACTGTGCTGCATCAGGATTGGCTGAACGGCAAAGAGTATAAGTGCAAAGTGTCTAATAAGGCCCTGC<br>CTGCTCCAATCGAGAAACTATTAGTAAGGCAAAGGGCAGCCCAGGGAACCTCAGGTCTACGTGCTG<br>CCTCCAAGTCGCGACGAGCTGACCAAGAACCAGGTCTCACTGCTGTGTCTGGTGAAAGGATTCTATCC<br>TTCCGATATTGCCGTGGAGTGGGAATCTAATGGCCAGCCAGAGAACAATTACCTGACCTGGCCCGTGC<br>TGCTGGACAGCGATGGGTCCTTCTTTCTGTATTCAAAGCTGACAGTGGACAAAAGCAGATGGCAGCAG<br>GGAAACGTCTTTAGCTGTTCCGTGATGCACGAAGCCCTGCACAATCATTACACCCAGAAGTCTCTGAG<br>TCTGTCACCTGGC |
| 331 | 4372 | CH2 | APELLGGPSVFLFPPKPKDTLMISRTPEVTCVVVDVSHEDPEVKFNWYVDGVEVHNAKTKPREEQYNS<br>TYRVVSVLTVLHQDWLNGKEYKCKVSNKALPAPIEKTISKAK |

| SEQ ID NO. | Clone | Desc. | Sequence (amino acid or |
|---|---|---|---|
| 332 | 4372 | CH2 | GCTCCAGAACTGCTGGGAGGACCAAGCGTGTTCCTGTTTCCACCCAAGCCCAAAGATACACTGATGAT<br>CAGCCGAACTCCCGAGGTCACCTGCGTGGTCGTGGACGTGTCCCACGAGGACCCCGAAGTCAAGTTCA<br>ACTGGTACGTGGACGGCGTCGAAGTGCATAATGCAAAGACTAAACCACGGGAGGAACAGTACAACTCT<br>ACATATAGAGTCGTGAGTGTCCTGACTGTGCTGCATCAGGATTGGCTGAACGGCAAGAGTATAAGTG<br>CAAAGTGTCTAATAAGGCCCTGCCTGCTCCAATCGAGAAAACTATTAGTAAGGCAAAA |
| 333 | 4372 | CH3 | GQPREPQVYVLPPSRDELTKNQVSLLCLVKGFYPSDIAVEWESNGQPENNYLTWPPVLDSDGSFELYS<br>KLTVCKSRWQQGNVFSCSVMHEALHNHYTQKSLSLSPG |
| 334 | 4372 | CH3 | GGGCAGCCCAGGGAACCTCAGGTCTACGTGCTGCCTCCAAGTCGCGACGAGCTGACCAAGAACCAGGT<br>CTCACTGCTGTGTCTGGTGAAAGGATTCTATCCTTCCGATATTGCCGTGGAGTGGGAATCTAATGGCC<br>AGCCAGAGAACAATTACCTGACCTGGCCCCCTGTGCTGGACAGCGATGGGTCCTTCTTTCTGTATTCA<br>AAGCTGACAGTGGACAAAAGCAGATGGCAGCAGGGAAACGTCTTTAGCTGTTCCGTGATGCACGAAGC<br>CCTGCACAATCATTACACCCAGAAGTCTCTGAGTCTGTCACCTGGC |

| SEQ ID NO: | Pertuzumab WT CDR | sequences |
|---|---|---|
| 335 | CDR-H2 | VNPNSGGS |
| 336 | CDR-H3 | ARNLGPSFYFDY |
| 337 | CDR-H1 | GFTFTDYT |
| 338 | CDR-L2 | SAS |
| 339 | CDR-L3 | QQYYIYPYT |
| 340 | CDR-L1 | QDVSIG |

| SEQ ID NO: | Trastuzumab WT CDR | sequences |
|---|---|---|
| 341 | CDR-H2 | IYPTNGYT |
| 342 | CDR-H3 | SRWGGDGFYAMDY |
| 343 | CDR-H1 | GFNIKDTY |
| 344 | CDR-L2 | SAS |
| 345 | CDR-L3 | QQHYTTPPT |
| 346 | CDR-L1 | QDVNTA |

Pertuzumab variant CDR-L3: QQYYIYPAT
Clone 3382, variant 10000 (SEQ ID NO: 347)
Pertuzumab variant CDR-H1: GFTFADYT
Clone 6586, variant 10000 (SEQ ID NO:348)

What is claimed:

1. An isolated antigen binding construct comprising:
   (a) a first antigen-binding polypeptide construct which specifically binds a HER2 (human epidermal growth factor receptor 2) ECD2 (extracellular domain 2) antigen on a HER2-expressing cell, wherein the first antigen binding polypeptide construct comprises a first heavy chain variable region (VH1) and a first light chain variable region (VL1), wherein the VH1 comprises the sequence shown in SEQ ID NO:99 and the VL1 comprises the sequence shown in SEQ ID NO:71; and
   (b) a second antigen binding polypeptide construct which specifically binds a HER2 ECD4 (extracellular domain 4) antigen on a HER2-expressing cell, wherein the second antigen binding polypeptide construct comprises a second heavy chain variable domain (VH2) and a second light chain variable domain (VL2), wherein the VH2 comprises the sequence shown in SEQ ID NO: 305 and the VL2 comprises the sequence shown in SEQ ID NO:297, and wherein the second antigen binding polypeptide construct is operably linked to the first antigen binding polypeptide construct.

2. The isolated construct of claim 1, wherein the first antigen binding polypeptide is a Fab and the second antigen binding polypeptide is a scFv.

3. The isolated construct of claim 1, wherein the first antigen binding polypeptide is an scFv and the second antigen binding polypeptide is a Fab.

4. The isolated construct of claim 2, wherein the first antigen binding polypeptide construct comprises a first heavy chain (H1) comprising the VH1 and a first light chain (L1) comprising the VL1, and the H1 comprises the sequence shown in SEQ ID NO:97 and the L1 comprises the sequence shown in SEQ ID NO:69; and the second antigen binding polypeptide construct comprises the sequence shown in SEQ ID NO:295.

5. The isolated construct of claim 1, further comprising a heterodimeric Fc, wherein the heterodimeric Fc is a human IgG1 Fc comprising a first Fc polypeptide and a second Fc polypeptide, the first Fc polypeptide comprising a first CH3 sequence and the second Fc polypeptide comprising a second CH3 sequence;
   wherein the first Fc polypeptide is operably linked to the first antigen-binding polypeptide construct and the second Fc polypeptide is operably linked to the second antigen-binding polypeptide construct; and
   wherein the first CH3 sequence comprises T350V_L351Y_F405A_Y407V in the first Fc polypeptide, and the second CH3 sequence comprises T350V_T366L_K392L_T394W according to EU numbering compared to a wild-type homodimeric human IgG1 Fc.

6. An isolated polynucleotide or set of isolated polynucleotides that encode(s):
   (a) a first antigen-binding polypeptide construct which specifically binds a HER2 (human epidermal growth factor receptor 2) ECD2 (extracellular domain 2) antigen on a HER2-expressing cell, wherein the first antigen binding polypeptide construct comprises a first heavy chain variable region (VH1) and a first light chain variable region (VL1), wherein the VH1 comprises the sequence shown in SEQ ID NO:99 and the VL1 comprises the sequence shown in SEQ ID NO:71; and
   (b) a second antigen binding polypeptide construct which specifically binds a HER2 ECD4 (extracellular domain 4) antigen on a HER2-expressing cell, wherein the second antigen binding polypeptide construct comprises a second heavy chain variable domain (VH2) and a second light chain variable domain (VL2), wherein the VH2 comprises the sequence shown in SEQ ID NO:305 and the VL2 comprises the sequence shown in SEQ ID NO:297.

7. The isolated polynucleotide or set of isolated polynucleotides of claim 6, wherein the first antigen binding polypeptide construct comprises a first heavy chain (H1) comprising the VH1 and a first light chain (L1) comprising the VL1, and the H1 comprises the sequence shown in SEQ ID NO:97 and the L1 comprises the sequence shown in SEQ ID NO:69.

8. The isolated polynucleotide or set of isolated polynucleotides of claim 6, wherein the second antigen binding polypeptide construct comprises the sequence shown in SEQ ID NO:295.

9. The isolated polynucleotide or set of isolated polynucleotides of claim 7, wherein the second antigen binding polypeptide construct comprises the sequence shown in SEQ ID NO:295.

10. The isolated polynucleotide or set of isolated polynucleotides of claim 6, further encoding a heterodimeric Fc, wherein the heterodimeric Fc is a human IgG1 Fc comprising a first Fc polypeptide and a second Fc polypeptide, the first Fc polypeptide comprising a first CH3 sequence and the second Fc polypeptide comprising a second CH3 sequence, wherein the first CH3 sequence comprises T350V_L351Y_F405A_Y407V in the first Fc polypeptide, and the second CH3 sequence comprises T350V_T366L_K392L_T394W according to EU numbering compared to a wild-type homodimeric human IgG1 Fc.

11. The isolated polynucleotide or set of isolated polynucleotides of claim 9, further encoding a heterodimeric Fc, wherein the heterodimeric Fc is a human IgG1 Fc comprising a first Fc polypeptide and a second Fc polypeptide, the first Fc polypeptide comprising a first CH3 sequence and the second Fc polypeptide comprising a second CH3 sequence, wherein the first CH3 sequence comprises T350V_L351Y_F405A_Y407V in the first Fc polypeptide, and the second CH3 sequence comprises T350V_T366L_K392L_T394W according to EU numbering compared to a wild-type homodimeric human IgG1 Fc.

12. A vector or set of vectors comprising an isolated polynucleotide or set of isolated polynucleotides that encode(s):
   (a) a first antigen-binding polypeptide construct which specifically binds a HER2 (human epidermal growth factor receptor 2) ECD2 (extracellular domain 2) antigen on a HER2-expressing cell, wherein the first antigen binding polypeptide construct comprises a first heavy chain variable region (VH1) and a first light chain variable region (VL1), wherein the VH1 comprises the sequence shown in SEQ ID NO:99 and the VL1 comprises the sequence shown in SEQ ID NO:71; and (b) a second antigen binding polypeptide construct which specifically binds a HER2 ECD4 (extracellular domain 4) antigen on a HER2-expressing cell, wherein the second antigen binding polypeptide construct comprises a second heavy chain variable domain (VH2) and a second light chain variable domain (VL2), wherein the VH2 comprises the sequence shown in SEQ ID NO:305 and the VL2 comprises the sequence shown in SEQ ID NO:297.

13. The vector or set of vectors of claim 12, wherein the first antigen binding polypeptide construct comprises a first heavy chain (H1) comprising the VH1 and a first light chain (L1) comprising the VL1, and the H1 comprises the sequence shown in SEQ ID NO:97 and the L1 comprises the sequence shown in SEQ ID NO:69.

14. The vector or set of vectors of claim 12, wherein the second antigen binding polypeptide construct comprises the sequence shown in SEQ ID NO:295.

15. The vector or set of vectors of claim 13, wherein the second antigen binding polypeptide construct comprises the sequence shown in SEQ ID NO:295.

16. The vector or set of vectors of claim 12, where the isolated polynucleotide or set of isolated polynucleotides further encode(s) a heterodimeric Fc, wherein the heterodimeric Fc is a human IgG1 Fc comprising a first Fc polypeptide and a second Fc polypeptide, the first Fc polypeptide comprising a first CH3 sequence and the second Fc polypeptide comprising a second CH3 sequence, wherein the first CH3 sequence comprises T350V_L351Y_F405A_Y407V in the first Fc polypeptide, and the second CH3 sequence comprises T350V_T366L_K392L_T394W according to EU numbering compared to a wild-type homodimeric human IgG1 Fc.

17. The vector or set of vectors of claim 15, where the isolated polynucleotide or set of isolated polynucleotides further encode(s) a heterodimeric Fc, wherein the heterodimeric Fc is a human IgG1 Fc comprising a first Fc polypeptide and a second Fc polypeptide, the first Fc polypeptide comprising a first CH3 sequence and the second Fc polypeptide comprising a second CH3 sequence, wherein the first CH3 sequence comprises T350V_L351Y_F405A_Y407V in the first Fc polypeptide, and the second CH3 sequence comprises T350V_T366L_K392L_T394W.

18. An isolated cell comprising the isolated polynucleotide or set of isolated polynucleotides of claim 6.

19. An isolated cell comprising the isolated polynucleotide or set of isolated polynucleotides of claim 7.

20. An isolated cell comprising the isolated polynucleotide or set of isolated polynucleotides of claim 8.

21. An isolated cell comprising the isolated polynucleotide or set of isolated polynucleotides of claim 9.

22. An isolated cell comprising the isolated polynucleotide or set of isolated polynucleotides of claim 10.

23. An isolated cell comprising the isolated polynucleotide or set of isolated polynucleotides of claim 11.

\* \* \* \* \*

SEQUENCE LISTING

<160> NUMBER OF SEQ ID NOS: 350

<210> SEQ ID NO 1
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
                100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 2
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
gaggtgcagc tggtggaaag cggaggagga ctggtgcagc caggaggatc tctgcgactg      60
agttgcgccg cttcaggatt caacatcaag gacacctaca ttcactgggt gcgacaggct     120
ccaggaaaag gactggagtg ggtggctcga atctatccca ctaatggata cacccggtat     180
gccgactccg tgaagggggag gtttactatt agcgccgata catccaaaaa cactgcttac     240
ctgcagatga acagcctgcg agccgaagat accgctgtgt actattgcag tcgatgggga     300
ggagacggat tctacgctat ggattattgg ggacagggga ccctggtgac agtgagctcc     360
gcctctacca agggcccag tgtgtttccc ctggctcctt ctagtaaatc cacctctgga     420
gggacagccg ctctgggatg tctggtgaag gactatttcc ccgagcctgt gaccgtgagt     480
tggaactcag gcgccctgac aagcggagtg cacacttttc ctgctgtgct gcagtcaagc     540
gggctgtact ccctgtcctc tgtggtgaca gtgccaagtt caagcctggg cacacagact     600
tatatctgca acgtgaatca taagccctca aatacaaaag tggacaagaa agtggagccc     660
aagagctgtg ataagaccca cacctgccct ccctgtccag ctccagaact gctgggagga     720
cctagcgtgt tcctgttttcc ccctaagcca aaagacactc tgatgatttc caggactccc     780
gaggtgacct gcgtggtggt ggacgtgtct cacgaggacc ccgaagtgaa gttcaactgg     840
tacgtggatg gcgtggaagt gcataatgct aagacaaaac caagagagga acagtacaac     900
tccacttatc gcgtcgtgag cgtgctgacc gtgctgcacc aggactggct gaacgggaag     960
gagtataagt gcaaagtcag taataaggcc ctgcctgctc caatcgaaaa aaccatctct    1020
aaggccaaag ccagccaag ggagcccag tgtacacac tgccacccag cagagacgaa    1080
ctgaccaaga accaggtgtc cctgacatgt ctggtgaaag gcttctatcc tagtgatatt    1140
gctgtggagt gggaatcaaa tggacagcca gagaacaatt acaagaccac acctccagtg    1200
ctggacagcg atggcagctt cttcctgtat tccaagctga cagtggataa atctcgatgg    1260
cagcagggga acgtgtttag ttgttcagtg atgcatgaag ccctgcacaa tcattacact    1320
cagaagagcc tgtccctgtc tcccggcaaa                                    1350

<210> SEQ ID NO 3
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110
```

Gly Thr Leu Val Thr Val Ser Ser
        115                 120

<210> SEQ ID NO 4
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
gaggtgcagc tggtggaaag cggaggagga ctggtgcagc caggaggatc tctgcgactg     60
agttgcgccg cttcaggatt caacatcaag gacacctaca ttcactgggt gcgacaggct    120
ccaggaaaag gactggagtg ggtggctcga atctatccca ctaatggata cacccggtat    180
gccgactccg tgaaggggag gtttactatt agcgccgata catccaaaaa cactgcttac    240
ctgcagatga acagcctgcg agccgaagat accgctgtgt actattgcag tcgatgggga    300
ggagacggat tctacgctat ggattattgg ggacagggga ccctggtgac agtgagctcc    360

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Phe Asn Ile Lys Asp Thr Tyr
1               5

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggattcaaca tcaaggacac ctac                                            24

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Arg Trp Gly Gly Asp Gly Phe Tyr Ala Met Asp Tyr
1               5                   10

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
agtcgatggg gaggagacgg attctacgct atggattat                            39

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ile Tyr Pro Thr Asn Gly Tyr Thr
1               5

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
atctatccca ctaatggata cacc                                                24

<210> SEQ ID NO 11
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 12
<211> LENGTH: 294
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
gcctctacca agggcccag tgtgtttccc ctggctcctt ctagtaaatc cacctctgga        60
gggacagccg ctctgggatg tctggtgaag gactatttcc ccgagcctgt gaccgtgagt      120
tggaactcag gcgccctgac aagcggagtg cacacttttc ctgctgtgct gcagtcaagc      180
gggctgtact ccctgtcctc tgtggtgaca gtgccaagtt caagcctggg cacacagact      240
tatatctgca acgtgaatca taagccctca aatacaaaag tggacaagaa agtg            294

-continued

<210> SEQ ID NO 13
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 14
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
gctccagaac tgctgggagg acctagcgtg ttcctgtttc cccctaagcc aaaagacact      60
ctgatgattt ccaggactcc cgaggtgacc tgcgtggtgg tggacgtgtc tcacgaggac     120
cccgaagtga agttcaactg gtacgtggat ggcgtggaag tgcataatgc taagacaaaa     180
ccaagagagg aacagtacaa ctccacttat cgcgtcgtga gcgtgctgac cgtgctgcac     240
caggactggc tgaacgggaa ggagtataag tgcaaagtca gtaataaggc cctgcctgct     300
ccaatcgaaa aaaccatctc taaggccaaa                                      330

<210> SEQ ID NO 15
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

```
Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly
            100                 105

<210> SEQ ID NO 16
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
ggccagccaa gggagcccca ggtgtacaca ctgccaccca gcagagacga actgaccaag      60
aaccaggtgt ccctgacatg tctggtgaaa ggcttctatc ctagtgatat tgctgtggag     120
tgggaatcaa atggacagcc agagaacaat tacaagacca cacctccagt gctggacagc     180
gatggcagct tcttcctgta ttccaagctg acagtggata atctcgatg gcagcagggg      240 aacgtgttta gttgttcagt gatgcatgaa gccctgcaca tcattacac tcagaagagc      300 ctgtccctgt ctcccggc                                                    318

<210> SEQ ID NO 17
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
             20                  25                  30

Thr Met Asp Trp Val Arg Gln Ala Pro Gly Lys Gly Leu Glu Trp Val
         35                  40                  45

Ala Asp Val Asn Pro Asn Ser Gly Gly Ser Ile Tyr Asn Gln Arg Phe
 50                  55                  60

Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Gly Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Lys Ser Ser Gly Leu Tyr Ser Leu Ser Ser Val Val Thr Val Pro Ser
            180                 185                 190
```

```
Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Val
            340                 345                 350

Leu Pro Pro Ser Arg Asp Glu Leu Thr Lys Asn Gln Val Ser Leu Leu
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Leu Thr Trp Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 18
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
gaagtgcagc tggtcgaatc tggaggagga ctggtgcagc caggagggtc cctgcgcctg      60
tcttgcgccg ctagtggctt cacttttacc gactacacca tggattgggt cgacaggca     120 cctggaaagg gcctggagtg ggtcgccgat gtgaacccaa atagcggagg ctccatctac     180
aaccagcggt tcaagggccg gttcaccctg tcagtggacc ggagcaaaaa caccctgtat     240
ctgcagatga atagcctgcg agccgaagat actgctgtgt actattgcgc ccggaatctg     300
gggccctcct tctactttga ctattggggg cagggaactc tggtcaccgt gagctccgcc     360
tccaccaagg gccttctgt gttcccactg gctccctcta gtaaatccac atctggggga     420
actgcagccc tgggctgtct ggtgaagggc tacttcccag agcccgtcac agtgtcttgg     480
aacagtggcg ctctgacttc tggggtccac acctttcctg cagtgctgaa gtcaagcggg     540
ctgtacagcc tgtcctctgt ggtcaccgtg ccaagttcaa gcctgggaac acagacttat     600
```

```
atctgcaacg tgaatcacaa gccatccaat acaaaagtcg acaagaaagt ggaacccaag      660
tcttgtgata aaacccatac atgccccct tgtcctgcac cagagctgct gggaggacca       720
agcgtgttcc tgtttccacc caagcctaaa gatacactga tgattagtag gaccccagaa     780
gtcacatgcg tggtcgtgga cgtgagccac gaggaccccg aagtcaagtt taactggtac     840
gtggacggcg tcgaggtgca taatgccaag actaaaccca gggaggaaca gtacaacagt     900
acctatcgcg tcgtgtcagt cctgacagtg ctgcatcagg attggctgaa cgggaaagag     960
tataagtgca aagtgagcaa taaggctctg cccgcaccta tcgagaaaac aatttccaag    1020
gcaaaaggac agcctagaga accacaggtg tacgtgctgc ctccatcaag ggatgagctg    1080
acaaagaacc aggtcagcct gctgtgtctg gtgaaaggat tctatccctc tgacattgct    1140
gtggagtggg aaagtaatgg ccagcctgag aacaattacc tgacctggcc ccctgtgctg    1200
gactcagatg gcagcttctt tctgtatagc aagctgaccg tcgacaaatc ccggtggcag    1260
caggggaatg tgtttagttg ttcagtcatg cacgaggcac tgcacaacca ttacacccag    1320
aagtcactgt cactgtcacc aggg                                           1344
```

<210> SEQ ID NO 19
<211> LENGTH: 119
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 19

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115
```

<210> SEQ ID NO 20
<211> LENGTH: 357
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 20

```
gaagtgcagc tggtcgaatc tggaggagga ctggtgcagc caggagggtc cctgcgcctg      60
tcttgcgccg ctagtggctt cacttttacc gactacacca tggattgggt gcgacaggca     120
cctggaaagg gcctggagtg ggtcgccgat gtgaacccaa atagcggagg ctccatctac     180
aaccagcggt tcaagggccg gttcacccta tcagtggacc ggagcaaaaa caccctgtat     240
```

```
ctgcagatga atagcctgcg agccgaagat actgctgtgt actattgcgc ccggaatctg      300
gggccctcct tctactttga ctattggggg cagggaactc tggtcaccgt gagctcc        357
```

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Phe Thr Phe Thr Asp Tyr Thr
1               5

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ggcttcactt ttaccgacta cacc                                             24

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Arg Asn Leu Gly Pro Ser Phe Tyr Phe Asp Tyr
1               5                   10

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gcccggaatc tggggccctc cttctacttt gactat                                36

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Val Asn Pro Asn Ser Gly Gly Ser
1               5

<210> SEQ ID NO 26
<211> LENGTH: 24
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 26
gtgaacccaa atagcggagg ctcc                                            24

<210> SEQ ID NO 27
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Gly Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Lys Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 28
<211> LENGTH: 294
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
gcctccacca agggaccttc tgtgttccca ctggctccct ctagtaaatc cacatctggg     60
ggaactgcag ccctgggctg tctggtgaag ggctacttcc cagagcccgt cacagtgtct    120
tggaacagtg gcgctctgac ttctggggtc cacacctttc ctgcagtgct gaagtcaagc    180
gggctgtaca gcctgtcctc tgtggtcacc gtgccaagtt caagcctggg aacacagact    240
tatatctgca acgtgaatca caagccatcc aatacaaaag tcgacaagaa agtg          294

<210> SEQ ID NO 29
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45
```

```
Val Asp Gly Val Glu Val His Asn Ala Lys Thr Lys Pro Arg Glu Glu
 50                  55                  60
Gln Tyr Asn Ser Thr Tyr Arg Val Val Ser Val Leu Thr Val Leu His
 65                  70                  75                  80
Gln Asp Trp Leu Asn Gly Lys Glu Tyr Lys Cys Lys Val Ser Asn Lys
                 85                  90                  95
Ala Leu Pro Ala Pro Ile Glu Lys Thr Ile Ser Lys Ala Lys
            100                 105                 110
```

<210> SEQ ID NO 30
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

```
gcaccagagc tgctgggagg accaagcgtg ttcctgtttc cacccaagcc taaagataca    60
ctgatgatta gtaggacccc agaagtcaca tgcgtggtcg tggacgtgag ccacgaggac   120
cccgaagtca agtttaactg gtacgtggac ggcgtcgagg tgcataatgc aagactaaa    180 cccagggagg aacagtacaa cagtacctat cgcgtcgtgt cagtcctgac agtgctgcat   240
caggattggc tgaacgggaa agagtataag tgcaaagtga gcaataaggc tctgcccgca   300
cctatcgaga aaacaatttc caaggcaaaa                                    330
```

<210> SEQ ID NO 31
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

```
Gly Gln Pro Arg Glu Pro Gln Val Tyr Val Leu Pro Pro Ser Arg Asp
 1               5                  10                  15
Glu Leu Thr Lys Asn Gln Val Ser Leu Leu Cys Leu Val Lys Gly Phe
             20                  25                  30
Tyr Pro Ser Asp Ile Ala Val Glu Trp Glu Ser Asn Gly Gln Pro Glu
         35                  40                  45
Asn Asn Tyr Leu Thr Trp Pro Pro Val Leu Asp Ser Asp Gly Ser Phe
 50                  55                  60
Phe Leu Tyr Ser Lys Leu Thr Val Asp Lys Ser Arg Trp Gln Gln Gly
 65                  70                  75                  80
Asn Val Phe Ser Cys Ser Val Met His Glu Ala Leu His Asn His Tyr
                 85                  90                  95
Thr Gln Lys Ser Leu Ser Leu Ser Pro Gly
            100                 105
```

<210> SEQ ID NO 32
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
ggacagccta gagaaccaca ggtgtacgtg ctgcctccat caagggatga gctgacaaag    60
```

```
aaccaggtca gcctgctgtg tctggtgaaa ggattctatc cctctgacat tgctgtggag   120
tgggaaagta atggccagcc tgagaacaat tacctgacct ggccccctgt gctggactca   180
gatggcagct tctttctgta tagcaagctg accgtcgaca atcccggtg gcagcagggg    240 aatgtgttta gttgttcagt catgcacgag gcactgcaca accattacac ccagaagtca   300
ctgtcactgt caccaggg                                                 318
```

<210> SEQ ID NO 33
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 34
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34

```
gatattcaga tgacccagtc cccaagctcc ctgagtgcct cagtgggcga ccgagtcacc    60
atcacatgca aggcttccca ggatgtgtct attggagtcg catggtacca gcagaagcca   120
```

```
ggcaaagcac ccaagctgct gatctatagc gcctcctacc ggtataccgg cgtgccctct    180
agattctctg gcagtgggtc aggaacagac tttactctga ccatctctag tctgcagcct    240
gaggatttcg ctacctacta ttgccagcag tactatatct acccatatac ctttggccag    300
gggacaaaag tggagatcaa gaggactgtg gccgctccct ccgtcttcat ttttcccct    360 tctgacgaac agctgaaaag tggcacagcc agcgtggtct gtctgctgaa caatttctac    420
cctcgcgaag ccaaagtgca gtggaaggtc gataacgctc tgcagagcgg caacagccag    480
gagtctgtga ctgaacagga cagtaaagat tcaacctata gcctgtcaag cacactgact    540
ctgagcaagg cagactacga aagcacaaa gtgtatgcct gcgaagtcac acatcagggg    600
ctgtcctctc ctgtgactaa gagctttaac agaggagagt gt                      642
```

```
<210> SEQ ID NO 35
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35
```

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105

```
<210> SEQ ID NO 36
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
gatattcaga tgacccagtc cccaagctcc ctgagtgcct cagtgggcga ccgagtcacc     60
atcacatgca aggcttccca ggatgtgtct attggagtcg catggtacca gcagaagcca    120
ggcaaagcac ccaagctgct gatctatagc gcctcctacc ggtataccgg cgtgccctct    180
agattctctg gcagtgggtc aggaacagac tttactctga ccatctctag tctgcagcct    240
gaggatttcg ctacctacta ttgccagcag tactatatct acccatatac ctttggccag    300
gggacaaaag tggagatcaa g                                              321
```

```
<210> SEQ ID NO 37
<211> LENGTH: 6
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 37

Gln Asp Val Ser Ile Gly
1               5

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
caggatgtgt ctattgga                                                 18

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Gln Tyr Tyr Ile Tyr Pro Tyr Thr
1               5

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
cagcagtact atatctaccc atatacc                                       27

<210> SEQ ID NO 41
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ser Ala Ser
1

<210> SEQ ID NO 42
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42 agcgcctcc                                                            9

<210> SEQ ID NO 43
<211> LENGTH: 107
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 43

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 44
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 44

```
aggactgtgg ccgctccctc cgtcttcatt tttccccctt ctgacgaaca gctgaaaagt    60
ggcacagcca gcgtggtctg tctgctgaac aatttctacc ctcgcgaagc caaagtgcag   120
tggaaggtcg ataacgctct gcagagcggc aacagccagg agtctgtgac tgaacaggac   180
agtaaagatt caacctatag cctgtcaagc acactgactc tgagcaaggc agactacgag   240
aagcacaaag tgtatgcctg cgaagtcaca catcaggggc tgtcctctcc tgtgactaag   300
agctttaaca gaggagagtg t                                              321
```

<210> SEQ ID NO 45
<211> LENGTH: 222
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 45

```
Asp Tyr Lys Asp Asp Asp Asp Lys Asp Ile Gln Met Thr Gln Ser Pro
1               5                   10                  15

Ser Ser Leu Ser Ala Ser Val Gly Asp Arg Val Thr Ile Thr Cys Arg
            20                  25                  30

Ala Ser Gln Asp Val Asn Thr Ala Val Ala Trp Tyr Gln Gln Lys Pro
        35                  40                  45

Gly Lys Ala Pro Lys Leu Leu Ile Tyr Ser Ala Ser Phe Leu Tyr Ser
    50                  55                  60

Gly Val Pro Ser Arg Phe Ser Gly Ser Arg Ser Gly Thr Asp Phe Thr
65                  70                  75                  80

Leu Thr Ile Ser Ser Leu Gln Pro Glu Asp Phe Ala Thr Tyr Tyr Cys
                85                  90                  95
```

Gln Gln His Tyr Thr Thr Pro Pro Thr Phe Gly Gln Gly Thr Lys Val
            100                 105                 110

Glu Ile Lys Arg Thr Val Ala Ala Pro Ser Val Phe Ile Phe Pro Pro
        115                 120                 125

Ser Asp Glu Arg Leu Lys Ser Gly Thr Ala Ser Val Val Cys Leu Leu
    130                 135                 140

Asn Asn Phe Tyr Pro Arg Glu Ala Lys Val Gln Trp Lys Val Asp Asn
145                 150                 155                 160

Ala Leu Gln Ser Gly Asn Ser Gln Glu Ser Val Thr Glu Gln Asp Ser
                165                 170                 175

Lys Asp Ser Thr Tyr Ser Leu Ser Thr Leu Thr Leu Ser Lys Ala
            180                 185                 190

Asp Tyr Glu Lys His Lys Val Tyr Ala Cys Glu Val Thr His Gln Gly
        195                 200                 205

Leu Ser Ser Pro Val Thr Lys Ser Phe Asn Arg Gly Glu Cys
    210                 215                 220

<210> SEQ ID NO 46
<211> LENGTH: 666
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
gactacaaag acgacgatga caaagatatc cagatgaccc agtcccctag ctccctgtcc     60
gcttctgtgg gcgatagggt cactattacc tgccgcgcat ctcaggacgt gaacaccgca    120
gtcgcctggt accagcagaa gcctgggaaa gctccaaagc tgctgatcta cagtgcatca    180
ttcctgtatt caggagtgcc cagccggttt agcggcagca gatctggcac cgatttcaca    240
ctgactattt ctagtctgca gcctgaggac tttgccacat actattgcca gcagcactat    300
accacacccc ctactttcgg ccaggggacc aaagtggaga tcaagcgaac tgtggccgct    360
ccaagtgtct tcattttttcc acccagcgat gaaagactga gtccggcac agcttctgtg    420 gtctgtctgc tgaacaattt ttaccccaga gaggccaaag tgcagtggaa ggtcgacaac    480
gctctgcaga gtggcaacag ccaggagagc gtgacagaac aggattccaa agactctact    540
tatagtctgt caagcaccct gacactgagc aaggcagact acgaaaagca taagtgtat    600 gcctgtgagg tcacacatca ggggctgtca tcaccagtca ccaaatcatt caatcggggg    660
gagtgc                                                               666

<210> SEQ ID NO 47
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
            50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys
            100                 105

<210> SEQ ID NO 48
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
gatatccaga tgacccagtc ccctagctcc ctgtccgctt ctgtgggcga tagggtcact        60
attacctgcc gcgcatctca ggacgtgaac accgcagtcg cctggtacca gcagaagcct      120
gggaaagctc caaagctgct gatctacagt gcatcattcc tgtattcagg agtgcccagc      180
cggtttagcg gcagcagatc tggcaccgat tcacactga ctatttctag tctgcagcct       240
gaggactttg ccacatacta ttgccagcag cactatacca cccccctac tttcggccag       300 gggaccaaag tggagatcaa g                                                321

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gln Asp Val Asn Thr Ala
1               5

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
caggacgtga acaccgca                                                     18

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Gln His Tyr Thr Thr Pro Pro Thr
1               5

<210> SEQ ID NO 52

```
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
cagcagcact ataccacacc ccctact                                              27

<210> SEQ ID NO 53
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ser Ala Ser
1

<210> SEQ ID NO 54
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54 agtgcatca                                                                    9

<210> SEQ ID NO 55
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Arg Thr Val Ala Ala Pro Ser Val Phe Ile Phe Pro Pro Ser Asp Glu
1               5                   10                  15

Arg Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 56
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 56

```
cgaactgtgg ccgctccaag tgtcttcatt tttccaccca gcgatgaaag actgaagtcc      60
ggcacagctt ctgtggtctg tctgctgaac aatttttacc ccagagaggc caaagtgcag     120
tggaaggtcg acaacgctct gcagagtggc aacagccagg agagcgtgac agaacaggat     180
tccaaagact ctacttatag tctgtcaagc accctgacac tgagcaaggc agactacgaa     240
aagcataaag tgtatgcctg tgaggtcaca catcaggggc tgtcatcacc agtcaccaaa     300
tcattcaatc gggggagtg c                                                321
```

<210> SEQ ID NO 57
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

```
Asp Tyr Lys Asp Asp Asp Lys Asp Ile Gln Met Thr Gln Ser Pro
1               5                   10                  15

Ser Ser Leu Ser Ala Ser Val Gly Asp Arg Val Thr Ile Thr Cys Arg
            20                  25                  30

Ala Ser Gln Asp Val Asn Thr Ala Val Ala Trp Tyr Gln Gln Lys Pro
        35                  40                  45

Gly Lys Ala Pro Lys Leu Leu Ile Tyr Ser Ala Ser Phe Leu Tyr Ser
    50                  55                  60

Gly Val Pro Ser Arg Phe Ser Gly Ser Arg Ser Gly Thr Asp Phe Thr
65                  70                  75                  80

Leu Thr Ile Ser Ser Leu Gln Pro Glu Asp Phe Ala Thr Tyr Tyr Cys
                85                  90                  95

Gln Gln His Tyr Thr Thr Pro Pro Thr Phe Gly Gln Gly Thr Lys Val
            100                 105                 110

Glu Ile Lys Arg Thr Val Ala Ala Pro Ser Val Phe Ile Phe Pro Pro
        115                 120                 125

Ser Asp Glu Arg Leu Lys Ser Gly Thr Ala Ser Val Val Cys Leu Leu
    130                 135                 140

Asn Asn Phe Tyr Pro Arg Glu Ala Lys Val Gln Trp Lys Val Asp Asn
145                 150                 155                 160

Ala Leu Gln Ser Gly Asn Ser Lys Glu Ser Val Thr Glu Gln Asp Ser
                165                 170                 175

Lys Asp Ser Thr Tyr Ser Leu Ser Ser Arg Leu Thr Leu Ser Lys Ala
            180                 185                 190

Asp Tyr Glu Lys His Lys Val Tyr Ala Cys Glu Val Thr His Gln Gly
        195                 200                 205

Leu Ser Ser Pro Val Thr Lys Ser Phe Asn Arg Gly Glu Cys
    210                 215                 220
```

<210> SEQ ID NO 58
<211> LENGTH: 666
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58

```
gactacaaag acgacgatga caaagatatc cagatgaccc agtcccctag ctccctgtcc      60
```

```
gcttctgtgg gcgatagggt cactattacc tgccgcgcat ctcaggacgt gaacaccgca    120
gtcgcctggt accagcagaa gcctgggaaa gctccaaagc tgctgatcta cagtgcatca    180
ttcctgtatt caggagtgcc cagccggttt agcggcagca gatctggcac cgatttcaca    240
ctgactattt ctagtctgca gcctgaggac tttgccacat actattgcca gcagcactat    300
accacacccc ctactttcgg ccaggggacc aaagtggaga tcaagcgaac tgtggccgct    360
ccaagtgtct catttttcc acccagcgat gaaagactga agtccggcac agcttctgtg    420
gtctgtctgc tgaacaattt ttaccccaga gaggccaaag tgcagtggaa ggtcgacaac    480
gctctgcaga gtggcaacag caaggagagc gtgacagaac aggattccaa agactctact    540
tatagtctgt caagcagact gacactgagc aaggcagact acgaaaagca taaagtgtat    600
gcctgtgagg tcacacatca ggggctgtca tcaccagtca ccaaatcatt caatcggggg    660
gagtgc                                                               666

<210> SEQ ID NO 59
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 60
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
gatatccaga tgacccagtc ccctagctcc ctgtccgctt ctgtgggcga tagggtcact    60
attacctgcc gcgcatctca ggacgtgaac accgcagtcg cctggtacca gcagaagcct    120
gggaaagctc caaagctgct gatctacagt gcatcattcc tgtattcagg agtgcccagc    180
cggtttagcg gcagcagatc tggcaccgat ttcacactga ctatttctag tctgcagcct    240
gaggactttg ccacatacta ttgccagcag cactatacca caccccctac tttcggccag    300
gggaccaaag tggagatcaa g                                              321
```

```
<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gln Asp Val Asn Thr Ala
1               5

<210> SEQ ID NO 62
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
caggacgtga acaccgca                                                   18

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Gln His Tyr Thr Thr Pro Pro Thr
1               5

<210> SEQ ID NO 64
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
cagcagcact ataccacacc ccctact                                         27

<210> SEQ ID NO 65
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ser Ala Ser
1

<210> SEQ ID NO 66
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66 agtgcatca                                                              9
```

<210> SEQ ID NO 67
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Arg Thr Val Ala Ala Pro Ser Val Phe Ile Phe Pro Pro Ser Asp Glu
1               5                   10                  15

Arg Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Lys Glu Ser Val Thr Glu Gln Asp Ser Lys Asp Ser
    50                  55                  60

Thr Tyr Ser Leu Ser Ser Arg Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 68
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
cgaactgtgg ccgctccaag tgtcttcatt tttccaccca gcgatgaaag actgaagtcc       60
ggcacagctt ctgtggtctg tctgctgaac aattttttacc ccagagaggc caaagtgcag    120
tggaaggtcg acaacgctct gcagagtggc aacagcaagg agagcgtgac agaacaggat    180
tccaaagact ctacttatag tctgtcaagc agactgacac tgagcaaggc agactacgaa    240
aagcataaag tgtatgcctg tgaggtcaca catcaggggc tgtcatcacc agtcaccaaa    300
tcattcaatc gggggagtg c                                                321

<210> SEQ ID NO 69
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ile Tyr Pro Ala
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 70
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70

```
gatattcaga tgacccagtc cccaagctcc ctgagtgcct cagtgggcga ccgagtcacc    60
atcacatgca aggcttccca ggatgtgtct attggagtcg catggtacca gcagaagcca   120
ggcaaagcac ccaagctgct gatctatagc gcctcctacc ggtataccgg cgtgccctct   180
agattctctg gcagtgggtc aggaacagac tttactctga ccatctctag tctgcagcct   240
gaggatttcg ctacctacta ttgccagcag tactatatct acccagccac ctttggccag   300
gggacaaaag tggagatcaa gaggactgtg gccgctccct ccgtcttcat ttttccccct   360
tctgacgaac agctgaaaag tggcacagcc agcgtggtct gtctgctgaa caatttctac   420
cctcgcgaag ccaaagtgca gtggaaggtc gataacgctc tgcagagcgg caacagccag   480
gagtctgtga ctgaacagga cagtaaagat tcaacctata gcctgtcaag cacactgact   540
ctgagcaagg cagactacga gaagcacaaa gtgtatgcct gcgaagtcac acatcagggg   600
ctgtcctctc ctgtgactaa gagctttaac agaggagagt gt                      642
```

<210> SEQ ID NO 71
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

```
Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Ser Ile Gly
             20                  25                  30
```

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Ala
                85                  90                  95

Thr Phe Gly Gln Gly Thr Lys Val Glu Ile Lys
            100                 105

<210> SEQ ID NO 72
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72
gatattcaga tgacccagtc cccaagctcc ctgagtgcct cagtgggcga ccgagtcacc      60
atcacatgca aggcttccca ggatgtgtct attggagtcg catggtacca gcagaagcca     120
ggcaaagcac ccaagctgct gatctatagc gcctcctacc ggtataccgg cgtgccctct     180
agattctctg gcagtgggtc aggaacagac tttactctga ccatctctag tctgcagcct     240
gaggatttcg ctacctacta ttgccagcag tactatatct acccagccac ctttggccag     300
gggacaaaag tggagatcaa g                                               321

<210> SEQ ID NO 73
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gln Asp Val Ser Ile Gly
1               5

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
caggatgtgt ctattgga                                                    18

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gln Gln Tyr Tyr Ile Tyr Pro Ala Thr
1               5

<210> SEQ ID NO 76
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
cagcagtact atatctaccc agccacc                                        27

<210> SEQ ID NO 77
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ser Ala Ser
1

<210> SEQ ID NO 78
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78 agcgcctcc                                                             9

<210> SEQ ID NO 79
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 80
<211> LENGTH: 321
<212> TYPE: DNA
<213> ORGANISM: Artificial Sequence
<220> FEATURE:

<223> OTHER INFORMATION: Description of Artificial Sequence: Synthetic
    polynucleotide

<400> SEQUENCE: 80

```
aggactgtgg ccgctccctc cgtcttcatt tttccccctt ctgacgaaca gctgaaaagt      60
ggcacagcca gcgtggtctg tctgctgaac aatttctacc ctcgcgaagc caaagtgcag     120
tggaaggtcg ataacgctct gcagagcggc aacagccagg agtctgtgac tgaacaggac     180
agtaaagatt caacctatag cctgtcaagc acactgactc tgagcaaggc agactacgag     240
aagcacaaag tgtatgcctg cgaagtcaca catcagggc tgtcctctcc tgtgactaag     300
agctttaaca gaggagagtg t                                               321
```

<210> SEQ ID NO 81
<211> LENGTH: 449
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 81

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Glu Val Thr Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270
```

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Val Tyr Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Ala Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 82
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82
gaggtgcagc tggtcgaaag cggaggagga ctggtgcagc caggagggtc actgcgactg      60
agctgcgcag cttccggctt caacatcaag gacacctaca ttcactgggt ccgccaggct     120
cctggaaaag gcctggagtg ggtggcacga atctatccaa ctaatggata cacccggtat     180
gccgactccg tgaagggccg gttcaccatt tctgcagata caagtaaaaa cactgcctac     240
ctgcagatga acagcctgcg agccgaagat acagccgtgt actattgcag ccgatgggga     300
ggcgacggct tctacgctat ggattattgg ggcagggaa ccctggtcac agtgagctcc      360
gcatcaacaa aggggcctag cgtgtttcca ctggcccct ctagtaaatc cacctctggg      420
ggaacagcag ccctgggatg tgaggtgacc gactacttcc cagagcccgt cactgtgagc     480
tggaactccg gcgccctgac atctggggtc catactttc ctgctgtgct gcagtcaagc      540
ggcctgtaca gcctgtcctc tgtggtcact gtgccaagtt caagcctggg gactcagacc     600
tatatctgca acgtgaatca caagcccatcc aataccaaag tcgacaagaa agtggaaccc    660
aagtcttgtg ataaaacaca tacttgcccc ccttgtcctg caccagagct gctgggagga    720
ccaagcgtgt tcctgtttcc acccaagcct aaagacaccc tgatgattag taggactcca    780
gaagtcacct gcgtggtcgt ggacgtgagc cacgaggacc ccgaagtcaa gttcaactgg    840
tacgtggatg gcgtcgaggt gcataatgcc aagacaaaac ccaggagga acagtacaac     900 tccactatc gcgtcgtgtc tgtcctgacc gtgctgcacc aggactggct gaacggcaag    960
gagtataagt gcaaagtgag caataaggct ctgccccgcac ctatcgagaa aacaatttcc    1020

```
aaggctaaag ggcagcctag agaaccacag gtgtacgtgt accctccatc tagggacgag    1080
ctgaccaaga accaggtcag tctgacatgt ctggtgaaag ggttctatcc cagcgatatc    1140
gcagtggagt gggaatccaa tggacagcct gagaacaatt acaagaccac accccctgtg    1200
ctggactctg atggaagttt cgccctggtg agtaagctga ccgtcgataa atcacggtgg    1260
cagcagggca acgtgttcag ctgttcagtg atgcacgaag cactgcacaa ccactacacc    1320
cagaaaagcc tgtccctgtc ccccggc                                        1347
```

<210> SEQ ID NO 83
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120
```

<210> SEQ ID NO 84
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84

```
gaggtgcagc tggtcgaaag cggaggagga ctggtgcagc caggagggtc actgcgactg     60
agctgcgcag cttccggctt caacatcaag gacacctaca ttcactgggt ccgccaggct    120
cctggaaaag gcctggagtg ggtggcacga atctatccaa ctaatggata cacccggtat    180
gccgactccg tgaagggccg gttcaccatt tctgcagata caagtaaaaa cactgcctac    240
ctgcagatga acagcctgcg agccgaagat acagccgtgt actattgcag ccgatgggga    300
ggcgacggct ctacgctat ggattattgg gggcagggaa ccctggtcac agtgagctcc    360
```

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 85

Gly Phe Asn Ile Lys Asp Thr Tyr
1               5

<210> SEQ ID NO 86
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
ggcttcaaca tcaaggacac ctac                                          24

<210> SEQ ID NO 87
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ser Arg Trp Gly Gly Asp Gly Phe Tyr Ala Met Asp Tyr
1               5                   10

<210> SEQ ID NO 88
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
agccgatggg gaggcgacgg cttctacgct atggattat                          39

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ile Tyr Pro Thr Asn Gly Tyr Thr
1               5

<210> SEQ ID NO 90
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
atctatccaa ctaatggata cacc                                          24

<210> SEQ ID NO 91
<211> LENGTH: 98
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 91

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Glu Val Thr Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 92
<211> LENGTH: 294
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
gcatcaacaa aggggcctag cgtgtttcca ctggccccct ctagtaaatc cacctctggg      60
ggaacagcag ccctgggatg tgaggtgacc gactacttcc agagcccgt cactgtgagc     120 tggaactccg gcgccctgac atctggggtc catactttc ctgctgtgct gcagtcaagc     180
ggcctgtaca gcctgtcctc tgtggtcact gtgccaagtt caagcctggg gactcagacc     240
tatatctgca acgtgaatca caagccatcc aataccaaag tcgacaagaa agtg            294

<210> SEQ ID NO 93
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 94
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94
gcaccagagc tgctgggagg accaagcgtg ttcctgtttc cacccaagcc taaagacacc    60
ctgatgatta gtaggactcc agaagtcacc tgcgtggtcg tggacgtgag ccacgaggac   120
cccgaagtca agttcaactg gtacgtggat ggcgtcgagg tgcataatgc caagacaaaa   180
cccagggagg aacagtacaa ctccacttat cgcgtcgtgt ctgtcctgac cgtgctgcac   240
caggactggc tgaacggcaa ggagtataag tgcaaagtga gcaataaggc tctgcccgca   300
cctatcgaga aacaatttc caaggctaaa                                     330

<210> SEQ ID NO 95
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gly Gln Pro Arg Glu Pro Gln Val Tyr Val Tyr Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Ala Leu Val Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 96
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
gggcagccta gagaaccaca ggtgtacgtg taccctccat ctagggacga gctgaccaag    60
aaccaggtca gtctgacatg tctggtgaaa gggttctatc ccagcgatat cgcagtggag   120
tgggaatcca atggacagcc tgagaacaat tacaagacca cccccctgt gctggactct    180 gatggaagtt tcgccctggt gagtaagctg accgtcgata atcacggtg gcagcagggc   240 aacgtgttca gctgttcagt gatgcacgaa gcactgcaca accactacac ccagaaaagc   300
ctgtccctgt ccccggc                                                 318

<210> SEQ ID NO 97

<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ala Asp Tyr
            20                  25                  30

Thr Met Asp Trp Val Arg Gln Ala Pro Gly Lys Gly Leu Glu Trp Val
        35                  40                  45

Gly Asp Val Asn Pro Asn Ser Gly Ser Ile Tyr Asn Gln Arg Phe
    50                  55                  60

Lys Gly Arg Phe Thr Phe Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Val
            340                 345                 350

Tyr Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu

```
                370                 375                 380
Ser Asn Gly Gln Pro Glu Asn Asn Tyr Lys Thr Thr Pro Pro Val Leu
385                 390                 395                 400

Asp Ser Asp Gly Ser Phe Ala Leu Val Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445
```

<210> SEQ ID NO 98
<211> LENGTH: 1344
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 98

```
gaggtgcagc tggtggaatc aggagggggc tggtgcagc cggagggtc tctgcgactg       60
tcatgtgccg cttctgggtt cactttcgca gactacacaa tggattgggt gcgacaggcc    120
cccggaaagg gactggagtg ggtgggcgat gtcaacccta ttctggcgg gagtatctac    180
aaccagcggt tcaaggggag attcactttt tcagtggaca gagcaaaaa caccctgtat    240
ctgcagatga acagcctgag gccgaagat accgctgtct actattgcgc tcgcaatctg    300
ggccccagtt tctactttga ctattggggg cagggaaccc tggtgacagt cagctccgct    360
agcactaagg ggccttccgt gtttccactg gctccctcta gtaaatccac ctctggaggc    420
acagctgcac tgggatgtct ggtgaaggat tacttccctg aaccagtcac agtgagttgg    480
aactcagggg ctctgacaag tggagtccat acttttcccg cagtgctgca gtcaagcgga    540
ctgtactccc tgtcctctgt ggtcaccgtg cctagttcaa gcctgggcac ccagacatat    600
atctgcaacg tgaatcacaa gccatcaaat acaaaagtcg acaagaaagt ggagcccaag    660
agctgtgata aaactcatac ctgcccacct tgtccggcgc cagaactgct gggaggacca    720
agcgtgttcc tgtttccacc caagcctaaa gacaccctga tgatttcccg gactcctgag    780
gtcacctgcg tggtcgtgga cgtgtctcac gaggaccccg aagtcaagtt caactggtac    840
gtggatggcg tcgaagtgca taatgccaag accaaacccc gggaggaaca gtacaactct    900
acctatagag tcgtgagtgt cctgacagtg ctgcaccagg actggctgaa tgggaaggag    960
tataagtgta agtgagcaa caaagccctg cccgccccaa tcgaaaaaac aatctctaaa   1020
gcaaaaggac agcctcgcga accacaggtc tacgtctacc ccccatcaag agatgaactg   1080
acaaaaaatc aggtctctct gacatgcctg gtcaaaggat tctacccttc cgacatcgcc   1140
gtggagtggg aaagtaacgg ccagcccgag aacaattaca agaccacacc ccctgtcctg   1200
gactctgatg ggagttttgc tctggtgtca aagctgaccg tcgataaaag ccggtggcag   1260
cagggcaatg tgttagctg ctccgtcatg cacgaagccc tgcacaatca ctacacacag   1320
aagtccctga gcctgagccc tggc                                         1344
```

<210> SEQ ID NO 99
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 99

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Ala Asp Tyr
            20                  25                  30

Thr Met Asp Trp Val Arg Gln Ala Pro Gly Lys Gly Leu Glu Trp Val
        35                  40                  45

Gly Asp Val Asn Pro Asn Ser Gly Gly Ser Ile Tyr Asn Gln Arg Phe
    50                  55                  60

Lys Gly Arg Phe Thr Phe Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

<210> SEQ ID NO 100
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100
gaggtgcagc tggtggaatc aggagggggc ctggtgcagc ccggagggtc tctgcgactg      60
tcatgtgccg cttctgggtt cactttcgca gactacacaa tggattgggt gcgacaggcc     120
cccggaaagg gactggagtg ggtgggcgat gtcaacccta attctggcgg gagtatctac     180
aaccagcggt tcaaggggag attcactttt tcagtggaca gaagcaaaaa cacccctgtat    240 ctgcagatga acagcctgag ggccgaagat accgctgtct actattgcgc tcgcaatctg    300
ggccccagtt tctactttga ctattggggg cagggaaccc tggtgacagt cagctcc       357

<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Phe Thr Phe Ala Asp Tyr Thr
1               5

<210> SEQ ID NO 102
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
gggttcactt tcgcagacta caca                                              24

<210> SEQ ID NO 103

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ala Arg Asn Leu Gly Pro Ser Phe Tyr Phe Asp Tyr
1               5                   10

<210> SEQ ID NO 104
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
gctcgcaatc tgggcccag tttctacttt gactat                              36

<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Val Asn Pro Asn Ser Gly Gly Ser
1               5

<210> SEQ ID NO 106
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
gtcaaccctA attctggcgg gagt                                          24

<210> SEQ ID NO 107
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
```

-continued

```
                 85                  90                  95

Lys Val

<210> SEQ ID NO 108
<211> LENGTH: 294
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108
gctagcacta aggggccttc cgtgtttcca ctggctccct ctagtaaatc cacctctgga      60
ggcacagctg cactgggatg tctggtgaag gattacttcc ctgaaccagt cacagtgagt     120
tggaactcag gggctctgac aagtggagtc catacttttc ccgcagtgct gcagtcaagc     180
ggactgtact ccctgtcctc tgtggtcacc gtgcctagtt caagcctggg cacccagaca     240
tatatctgca acgtgaatca caagccatca aatacaaaag tcgacaagaa agtg           294

<210> SEQ ID NO 109
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 110
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 110
gcgccagaac tgctgggagg accaagcgtg ttcctgtttc acccaagcc taaagacacc       60 ctgatgattt cccggactcc tgaggtcacc tgcgtggtcg tggacgtgtc tcacgaggac     120
cccgaagtca agttcaactg gtacgtggat ggcgtcgaag tgcataatgc caagaccaaa     180 ccccggagg aacagtacaa ctctacctat agagtcgtga gtgtcctgac agtgctgcac      240
caggactggc tgaatgggaa ggagtataag tgtaaagtga gcaacaaagc cctgcccgcc     300
ccaatcgaaa aaacaatctc taaagcaaaa                                     330
```

<210> SEQ ID NO 111
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Gly Gln Pro Arg Glu Pro Gln Val Tyr Val Tyr Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Ala Leu Val Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 112
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 112
ggacagcctc gcgaaccaca ggtctacgtc tacccccat caagagatga actgacaaaa     60
aatcaggtct ctctgacatg cctggtcaaa ggattctacc cttccgacat cgccgtggag    120
tgggaaagta acggccagcc cgagaacaat tacaagacca cccccctgt cctggactct     180 gatgggagtt tcgctctggt gtcaaagctg accgtcgata aaagccggtg gcagcagggc    240
aatgtgttta gctgctccgt catgcacgaa gccctgcaca tcactacac acagaagtcc    300 ctgagcctga gccctggc                                                  318

<210> SEQ ID NO 113
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Tyr Pro Tyr Asp Val Pro Asp Tyr Ala Thr Gly Ser Asp Ile Gln Met
1               5                   10                  15

Thr Gln Ser Pro Ser Ser Leu Ser Ala Ser Val Gly Asp Arg Val Thr
            20                  25                  30

Ile Thr Cys Lys Ala Ser Gln Asp Val Ser Ile Gly Val Ala Trp Tyr
        35                  40                  45

Gln Gln Lys Pro Gly Lys Ala Pro Lys Leu Leu Ile Tyr Ser Ala Ser
    50                  55                  60

```
Tyr Arg Tyr Thr Gly Val Pro Ser Arg Phe Ser Gly Ser Gly Ser Gly
 65                  70                  75                  80

Thr Asp Phe Thr Leu Thr Ile Ser Ser Leu Gln Pro Glu Asp Phe Ala
                 85                  90                  95

Thr Tyr Tyr Cys Gln Gln Tyr Tyr Ile Tyr Pro Tyr Thr Phe Gly Gln
            100                 105                 110

Gly Thr Lys Val Glu Ile Lys Arg Thr Val Ala Ala Pro Ser Val Phe
        115                 120                 125

Ile Phe Pro Pro Ser Asp Glu Leu Lys Ser Gly Thr Ala Ser Val
130                 135                 140

Val Cys Leu Leu Asn Asn Phe Tyr Pro Arg Glu Ala Lys Val Gln Trp
145                 150                 155                 160

Lys Val Asp Asn Ala Leu Gln Ser Gly Asn Ser Glu Glu Ser Val Thr
                165                 170                 175

Glu Gln Asp Ser Lys Asp Ser Thr Tyr Ser Leu Ser Ser Thr Leu Glu
            180                 185                 190

Leu Ser Lys Ala Asp Tyr Glu Lys His Lys Val Tyr Ala Cys Glu Val
        195                 200                 205

Thr His Gln Gly Leu Ser Ser Pro Val Thr Lys Ser Phe Asn Arg Gly
210                 215                 220

Glu Cys
225

<210> SEQ ID NO 114
<211> LENGTH: 678
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 114
tatccctacg atgtgcctga ctacgctact ggctccgata tccagatgac ccagtctcca      60
agctccctga gtgcatcagt gggggaccga gtcaccatca catgcaaggc ttcccaggat     120
gtgtctattg agtcgcatg gtaccagcag aagccaggca agcacccaa gctgctgatc       180 tacagcgcct cctaccggta tactggggtg ccttccagat tctctggcag tgggtcagga     240
accgacttta ctctgaccat ctctagtctg cagcccgagg atttcgccac ctactattgc     300
cagcagtact atatctaccc ttatacctt ggccagggga caaaagtgga gatcaagagg      360
acagtggccg ctccaagtgt cttcattttt ccccttccg acgaagagct gaaaagtgga      420
actgcttcag tggtctgtct gctgaacaat ttctacccc gcgaagccaa agtgcagtgg     480
aaggtcgata acgctctgca gagcggcaat tccgaggagt ctgtgacaga acaggacagt     540
aaagattcaa cttatagcct gtcaagcaca ctggagctgt ctaaggcaga ctacgagaag     600
cacaaagtgt atgcctgcga agtcacccat caggggctgt cctctcccgt gacaaagagc     660
tttaacagag gagagtgt                                                    678

<210> SEQ ID NO 115
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115
```

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105

<210> SEQ ID NO 116
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116
gatatccaga tgacccagtc tccaagctcc ctgagtgcat cagtggggga ccgagtcacc      60
atcacatgca aggcttccca ggatgtgtct attggagtcg catggtacca gcagaagcca     120
ggcaaagcac ccaagctgct gatctacagc gcctcctacc ggtatactgg ggtgccttcc     180
agattctctg gcagtgggtc aggaaccgac tttactctga ccatctctag tctgcagccc     240
gaggatttcg ccacctacta ttgccagcag tactatatct acccttatac ctttggccag     300
gggacaaaag tggagatcaa g                                               321

<210> SEQ ID NO 117
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gln Asp Val Ser Ile Gly
1               5

<210> SEQ ID NO 118
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
caggatgtgt ctattgga                                                    18

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gln Gln Tyr Tyr Ile Tyr Pro Tyr Thr
1               5

<210> SEQ ID NO 120
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
cagcagtact atatctaccc ttatacc                                              27

<210> SEQ ID NO 121
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ser Ala Ser
1

<210> SEQ ID NO 122
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122 agcgcctcc                                                                   9

<210> SEQ ID NO 123
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Arg Thr Val Ala Ala Pro Ser Val Phe Ile Phe Pro Pro Ser Asp Glu
1               5                   10                  15

Glu Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Glu Glu Ser Val Thr Glu Gln Asp Ser Lys Asp Ser
    50                  55                  60

Thr Tyr Ser Leu Ser Ser Thr Leu Glu Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 124
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124
aggacagtgg ccgctccaag tgtcttcatt tttccccctt ccgacgaaga gctgaaaagt       60
ggaactgctt cagtggtctg tctgctgaac aatttctacc ccgcgaagc caaagtgcag      120 tggaaggtcg ataacgctct gcagagcggc aattccgagg agtctgtgac agaacaggac     180
agtaaagatt caacttatag cctgtcaagc acactggagc tgtctaaggc agactacgag     240
aagcacaaag tgtatgcctg cgaagtcacc catcaggggc tgtcctctcc cgtgacaaag     300
agctttaaca gaggagagtg t                                                321

<210> SEQ ID NO 125
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile

```
            245                 250                 255
Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Val Tyr Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Ala Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 126
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126
gaagtccagc tggtcgaaag cggaggagga ctggtgcagc caggagggtc tctgcgactg      60
agttgcgccg cttcaggctt caacatcaag gacacctaca ttcactgggt gcgccaggct     120
cctggaaaag gcctggagtg ggtggcacga atctatccaa ctaatggata cacccggtat     180
gcagacagcg tgaagggccg gttcaccatt agcgcagata catccaaaaa cactgcctac     240
ctgcagatga acagcctgcg agccgaagat actgctgtgt actattgcag tcggtgggga     300
ggcgacggct tctacgctat ggattattgg ggcagggaa ccctggtcac agtgagctcc      360
gcatctacaa aggggcctag tgtgtttcca ctggccccct ctagtaaatc cacctctggg     420
ggaacagcag ccctgggatg tctggtgaag gactatttcc cagagcccgt cactgtgagt     480
tggaactcag gcgccctgac atccggggtc atacttttc ctgctgtgct gcagtcaagc     540
ggcctgtact ctctgtcctc tgtggtcacc gtgccaagtt caagcctggg gactcagacc     600
tatatctgca acgtgaatca caagccaagc aatacaaaag tcgacaagaa agtggaaccc     660
aagagctgtg ataaaacaca tacttgcccc ccttgtcctg caccagagct gctgggagga     720
ccatccgtgt tcctgtttcc acccaagcct aagacaccc tgatgatttc caggactcca     780
gaagtcacct gcgtggtcgt ggacgtgtct cacgaggacc ccgaagtcaa gttcaactgg     840
```

```
tacgtggatg gcgtcgaggt gcataatgcc aagacaaaac ccagggagga acagtacaac    900
tcaacttatc gcgtcgtgag cgtcctgacc gtgctgcacc aggactggct gaacggcaag    960
gagtataagt gcaaagtgag caataaggct ctgcccgcac ctatcgagaa aaccattagc    1020
aaggccaaag ggcagcctag agaaccacag gtctacgtgt atcctccaag cagggacgag    1080
ctgaccaaga accaggtctc cctgacatgt ctggtgaaag gttttaccc cagtgatatc     1140 gctgtggagt gggaatcaaa tggacagcct gaaaacaatt ataagaccac accccctgtg    1200
ctggacagcg atggcagctt cgctctggtc tccaagctga ctgtggataa atctcggtgg    1260
cagcagggca acgtctttag ttgttcagtg atgcatgagg cactgcacaa tcattacacc    1320
cagaagagcc tgtccctgtc tcccggcaaa                                    1350
```

<210> SEQ ID NO 127
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide <400> SEQUENCE: 127

```
Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120
```

<210> SEQ ID NO 128
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide <400> SEQUENCE: 128

```
gaagtccagc tggtcgaaag cggaggagga ctggtgcagc caggagggtc tctgcgactg    60
agttgcgccg cttcaggctt caacatcaag gacacctaca ttcactgggt gcgccaggct    120
cctggaaaag gcctggagtg ggtggcacga atctatccaa ctaatggata cacccggtat    180
gcagacagcg tgaagggccg gttcaccatt agcgcagata catccaaaaa cactgcctac    240
ctgcagatga acagcctgcg agccgaagat actgctgtgt actattgcag tcggtgggga    300
ggcgacggct tctacgctat ggattattgg gggcagggaa ccctggtcac agtgagctcc    360
```

<210> SEQ ID NO 129

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gly Phe Asn Ile Lys Asp Thr Tyr
1               5

<210> SEQ ID NO 130
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
ggcttcaaca tcaaggacac ctac                                           24

<210> SEQ ID NO 131
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ser Arg Trp Gly Gly Asp Gly Phe Tyr Ala Met Asp Tyr
1               5                   10

<210> SEQ ID NO 132
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
agtcggtggg gaggcgacgg cttctacgct atggattat                           39

<210> SEQ ID NO 133
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ile Tyr Pro Thr Asn Gly Tyr Thr
1               5

<210> SEQ ID NO 134
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
atctatccaa ctaatggata cacc                                           24
```

<210> SEQ ID NO 135
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 136
<211> LENGTH: 294
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136
gcatctacaa aggggcctag tgtgtttcca ctggccccct ctagtaaatc cacctctggg      60
ggaacagcag ccctgggatg tctggtgaag gactatttcc cagagcccgt cactgtgagt    120
tggaactcag gcgccctgac atccggggtc catactttc ctgctgtgct gcagtcaagc    180
ggcctgtact ctctgtcctc tgtggtcacc gtgccaagtt caagcctggg gactcagacc    240
tatatctgca acgtgaatca caagccaagc aatacaaaag tcgacaagaa agtg          294

<210> SEQ ID NO 137
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys

```
                    85                  90                  95
Ala Leu Pro Ala Pro Ile Glu Lys Thr Ile Ser Lys Ala Lys
            100                 105                 110

<210> SEQ ID NO 138
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 138
gcaccagagc tgctgggagg accatccgtg ttcctgtttc acccaagcc taaagacacc      60 ctgatgattt ccaggactcc agaagtcacc tgcgtggtcg tggacgtgtc tcacgaggac     120
cccgaagtca agttcaactg gtacgtggat ggcgtcgagg tgcataatgc caagacaaaa    180
cccagggagg aacagtacaa ctcaacttat cgcgtcgtga cgtcctgac cgtgctgcac     240 caggactggc tgaacggcaa ggagtataag tgcaaagtga gcaataaggc tctgcccgca    300
cctatcgaga aaaccattag caaggccaaa                                     330

<210> SEQ ID NO 139
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Gly Gln Pro Arg Glu Pro Gln Val Tyr Val Tyr Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Ala Leu Val Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 140
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 140
gggcagccta gagaaccaca ggtctacgtg tatcctccaa gcagggacga gctgaccaag     60
aaccaggtct ccctgacatg tctggtgaaa gggttttacc ccagtgatat cgctgtggag    120
tgggaatcaa atggacagcc tgaaaacaat tataagacca caccccctgt gctggacagc    180
gatggcagct tcgctctggt ctccaagctg actgtggata aatctcggtg gcagcagggc    240
```

```
aacgtcttta gttgttcagt gatgcatgag gcactgcaca atcattacac ccagaagagc    300
ctgtccctgt ctcccggc                                                  318
```

<210> SEQ ID NO 141
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

```
Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Ile Cys Leu Val Lys Gly Phe Tyr Pro Ser
145                 150                 155                 160

Asp Ile Ala Val Glu Trp Glu Ser Asn Gly Gln Pro Glu Asn Arg Tyr
                165                 170                 175

Met Thr Trp Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 142
<211> LENGTH: 696
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 142

```
gagcccaaga gcagcgataa gacccacacc tgccctccct gtccagctcc agaactgctg    60
ggaggaccta gcgtgttcct gtttccccct aagccaaaag acactctgat gatttccagg   120
actcccgagg tgacctgcgt ggtggtggac gtgtctcacg aggaccccga agtgaagttc   180
aactggtacg tggatggcgt ggaagtgcat aatgctaaga caaaaccaag agaggaacag   240
```

```
tacaactcca cttatcgcgt cgtgagcgtg ctgaccgtgc tgcaccagga ctggctgaac      300
gggaaggagt ataagtgcaa agtcagtaat aaggccctgc ctgctccaat cgaaaaaacc      360
atctctaagg ccaaaggcca gccaagggag ccccaggtgt acacactgcc acccagcaga      420
gacgaactga ccaagaacca ggtgtccctg atctgtctgg tgaaaggctt ctatcctagt      480
gatattgctg tggagtggga atcaaatgga cagccagaga acagatacat gacctggcct      540
ccagtgctgg acagcgatgg cagcttcttc ctgtattcca agctgacagt ggataaatct      600
cgatggcagc aggggaacgt gtttagttgt tcagtgatgc atgaagccct gcacaatcat      660
tacactcaga agagcctgtc cctgtctccc ggcaaa                                696
```

<210> SEQ ID NO 143
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110
```

<210> SEQ ID NO 144
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 144

```
gctccagaac tgctgggagg acctagcgtg ttcctgtttc cccctaagcc aaaagacact      60
ctgatgattt ccaggactcc cgaggtgacc tgcgtggtgg tggacgtgtc tcacgaggac      120
cccgaagtga agttcaactg gtacgtggat ggcgtggaag tgcataatgc taagacaaaa      180
ccaagagagg aacagtacaa ctccacttat cgcgtcgtga gcgtgctgac cgtgctgcac      240
caggactggc tgaacgggaa ggagtataag tgcaaagtca gtaataaggc cctgcctgct      300
ccaatcgaaa aaaccatctc taaggccaaa                                       330
```

<210> SEQ ID NO 145
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Gly Gln Pro Arg Glu Pro Gln Val Tyr Thr Leu Pro Pro Ser Arg Asp
1               5                   10                  15

Glu Leu Thr Lys Asn Gln Val Ser Leu Ile Cys Leu Val Lys Gly Phe
            20                  25                  30

Tyr Pro Ser Asp Ile Ala Val Glu Trp Glu Ser Asn Gly Gln Pro Glu
        35                  40                  45

Asn Arg Tyr Met Thr Trp Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 146
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 146
ggccagccaa gggagcccca ggtgtacaca ctgccaccca gcagagacga actgaccaag      60
aaccaggtgt ccctgatctg tctggtgaaa ggcttctatc ctagtgatat tgctgtggag     120
tgggaatcaa atggacagcc agagaacaga tacatgacct ggcctccagt gctggacagc     180
gatggcagct tcttcctgta ttccaagctg acagtggata aatctcgatg gcagcagggg     240
aacgtgttta gttgttcagt gatgcatgaa gccctgcaca atcattacac tcagaagagc     300
ctgtccctgt ctcccggc                                                   318

<210> SEQ ID NO 147
<211> LENGTH: 481
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Ser Gly Gly
            100                 105                 110

Gly Ser Gly Gly Ser Gly Gly Ser Gly Gly Ser Gly Glu
        115                 120                 125

Val Gln Leu Val Glu Ser Gly Gly Leu Val Gln Pro Gly Gly Ser
130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Gly Leu Glu Trp Val Ala
                165                 170                 175

Arg Ile Tyr Pro Thr Asn Gly Tyr Thr Arg Tyr Ala Asp Ser Val Lys
            180                 185                 190

Gly Arg Phe Thr Ile Ser Ala Asp Thr Ser Lys Asn Thr Ala Tyr Leu
        195                 200                 205

Gln Met Asn Ser Leu Arg Ala Glu Asp Thr Ala Val Tyr Tyr Cys Ser
210                 215                 220

Arg Trp Gly Gly Asp Gly Phe Tyr Ala Met Asp Tyr Trp Gly Gln Gly
225                 230                 235                 240

Thr Leu Val Thr Val Ser Ser Ala Ala Glu Pro Lys Ser Ser Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
370                 375                 380

Tyr Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Glu Asp Gly Ser Phe Ala Leu Val Ser Lys Leu Thr Val Asp Lys
        435                 440                 445

Ser Arg Trp Gln Gln Gly Asn Val Phe Ser Cys Ser Val Met His Glu
450                 455                 460

Ala Leu His Asn His Tyr Thr Gln Lys Ser Leu Ser Leu Ser Pro Gly
465                 470                 475                 480

Lys

<210> SEQ ID NO 148
<211> LENGTH: 1443
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 148

```
gacatccaga tgacccagtc tccatcctcc ctgtctgcat ctgtaggaga cagagtcacc      60
atcacttgcc gggcaagtca ggacgttaac accgctgtag cttggtatca gcagaaacca     120
gggaaagccc ctaagctcct gatctattct gcatcctttt tgtacagtgg ggtcccatca     180
aggttcagtg gcagtcgatc tgggacagat ttcactctca ccatcagcag tctgcaacct     240
gaagattttg caacttacta ctgtcaacag cattacacta ccccacccac tttcggccaa     300
gggaccaaag tggagatcaa aggtggttct ggtggtggtt ctggtggtgg ttctggtggt     360
ggttctggtg gtggttctgg tgaagtgcag ctggtggagt ctgggggagg cttggtacag     420
cctggcgggt ccctgagact ctcctgtgca gcctctggat tcaacattaa agatacttat     480
atccactggg tccggcaagc tccagggaag gcctggagt gggtcgcacg tatttatccc      540
acaaatggtt acacacggta tgcggactct gtgaagggcc gattcaccat ctccgcagac     600
acttccaaga acaccgcgta tctgcaaatg aacagtctga gagctgagga cacggccgtt     660
tattactgtt caagatgggg cggagacggt ttctacgcta tggactactg gggccaaggg     720
accctggtca ccgtctcctc agccgccgag cccaagagca cgataagac ccacacctgc      780
cctccctgtc cagctccaga actgctggga ggacctagcg tgttcctgtt tcccccctaag    840
ccaaaagaca ctctgatgat ttccaggact cccgaggtga cctgcgtggt ggtggacgtg     900
tctcacgagg accccgaagt gaagttcaac tggtacgtgg atggcgtgga agtgcataat     960
gctaagacaa aaccaagaga ggaacagtac aactccactt atcgcgtcgt gagcgtgctg    1020
accgtgctgc accaggactg gctgaacggg aaggagtata agtgcaaagt cagtaataag    1080
gccctgcctg ctccaatcga aaaaaccatc tctaaggcca aaggccagcc aagggagccc    1140
caggtgtaca cataccccacc cagcagagac gaactgacca gaaccaggt gtccctgaca    1200
tgtctggtga aaggcttcta tcctagtgat attgctgtgg agtgggaatc aaatggacag    1260
ccagagaaca attacaagac cacacctcca gtgctggacg aggatggcag cttcgccctg    1320
gtgtccaagc tgacagtgga taatctcga tggcagcagg ggaacgtgtt tagttgttca    1380
gtgatgcatg aagccctgca caatcattac actcagaaga gcctgtccct gtctcccggc    1440
aaa                                                                  1443
```

<210> SEQ ID NO 149
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 149

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80
```

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 150
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 150
gacatccaga tgacccagtc tccatcctcc ctgtctgcat ctgtaggaga cagagtcacc      60
atcacttgcc gggcaagtca ggacgttaac accgctgtag cttggtatca gcagaaacca     120
gggaaagccc ctaagctcct gatctattct gcatcctttt tgtacagtgg ggtcccatca     180
aggttcagtg gcagtcgatc tgggacagat ttcactctca ccatcagcag tctgcaacct     240
gaagattttg caacttacta ctgtcaacag cattacacta ccccacccac tttcggccaa     300
gggaccaaag tggagatcaa a                                               321

<210> SEQ ID NO 151
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gln Asp Val Asn Thr Ala
1               5

<210> SEQ ID NO 152
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
caggacgtta acaccgct                                                    18

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Gln Gln His Tyr Thr Thr Pro Pro Thr
1               5

<210> SEQ ID NO 154
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
caacagcatt acactacccc acccact                                                27

<210> SEQ ID NO 155
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Ser Ala Ser
1

<210> SEQ ID NO 156
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156 tctgcatcc                                                                    9

<210> SEQ ID NO 157
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 158
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 158
gaagtgcagc tggtggagtc tgggggaggc ttggtacagc ctggcgggtc cctgagactc           60

```
tcctgtgcag cctctggatt caacattaaa gatacttata tccactgggt ccggcaagct      120
ccagggaagg gcctggagtg ggtcgcacgt atttatccca caaatggtta cacacggtat      180
gcggactctg tgaagggccg attcaccatc tccgcagaca cttccaagaa caccgcgtat      240
ctgcaaatga acagtctgag agctgaggac acggccgttt attactgttc aagatggggc      300
ggagacggtt tctacgctat ggactactgg ggccaaggga ccctggtcac cgtctcctca      360
```

<210> SEQ ID NO 159
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Gly Phe Asn Ile Lys Asp Thr Tyr
1               5

<210> SEQ ID NO 160
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
ggattcaaca ttaaagatac ttat                                              24

<210> SEQ ID NO 161
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Ser Arg Trp Gly Gly Asp Gly Phe Tyr Ala Met Asp Tyr
1               5                   10

<210> SEQ ID NO 162
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
tcaagatggg gcggagacgg tttctacgct atggactac                              39

<210> SEQ ID NO 163
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Ile Tyr Pro Thr Asn Gly Tyr Thr
1               5

```
<210> SEQ ID NO 164
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
atttatccca caaatggtta caca                                             24

<210> SEQ ID NO 165
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165
```

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

```
<210> SEQ ID NO 166
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 166
gctccagaac tgctgggagg acctagcgtg ttcctgtttc cccctaagcc aaaagacact      60
ctgatgattt ccaggactcc cgaggtgacc tgcgtggtgg tggacgtgtc tcacgaggac     120
cccgaagtga agttcaactg gtacgtggat ggcgtggaag tgcataatgc taagacaaaa     180
ccaagagagg aacagtacaa ctccacttat cgcgtcgtga gcgtgctgac cgtgctgcac     240
caggactggc tgaacgggaa ggagtataag tgcaaagtca gtaataaggc cctgcctgct     300
ccaatcgaaa aaaccatctc taaggccaaa                                     330

<210> SEQ ID NO 167
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167
```

Gly Gln Pro Arg Glu Pro Gln Val Tyr Thr Tyr Pro Pro Ser Arg Asp

```
 1               5                  10                  15
Glu Leu Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
                35                  40                  45

Asn Asn Tyr Lys Thr Thr Pro Pro Val Leu Asp Glu Asp Gly Ser Phe
 50                  55                  60

Ala Leu Val Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
                100                 105

<210> SEQ ID NO 168
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 168
ggccagccaa gggagcccca ggtgtacaca tacccaccca gcagagacga actgaccaag      60
aaccaggtgt ccctgacatg tctggtgaaa ggcttctatc ctagtgatat tgctgtggag     120
tgggaatcaa atggacagcc agagaacaat tacaagacca cacctccagt gctggacgag     180
gatggcagct tcgccctggt gtccaagctg acagtggata aatctcgatg gcagcagggg     240
aacgtgttta gttgttcagt gatgcatgaa gccctgcaca atcattacac tcagaagagc     300
ctgtccctgt ctcccggc                                                   318

<210> SEQ ID NO 169
<211> LENGTH: 481
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
                35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Ser Gly Gly
                100                 105                 110

Gly Ser Gly Gly Gly Ser Gly Gly Ser Gly Gly Ser Gly Glu
        115                 120                 125

Val Gln Leu Val Glu Ser Gly Gly Gly Leu Val Gln Pro Gly Gly Ser
```

```
        130                 135                 140
Leu Arg Leu Ser Cys Ala Ala Ser Gly Phe Asn Ile Lys Asp Thr Tyr
145                 150                 155                 160

Ile His Trp Val Arg Gln Ala Pro Gly Lys Gly Leu Glu Trp Val Ala
                165                 170                 175

Arg Ile Tyr Pro Thr Asn Gly Tyr Thr Arg Tyr Ala Asp Ser Val Lys
            180                 185                 190

Gly Arg Phe Thr Ile Ser Ala Asp Thr Ser Lys Asn Thr Ala Tyr Leu
        195                 200                 205

Gln Met Asn Ser Leu Arg Ala Glu Asp Thr Ala Val Tyr Tyr Cys Ser
    210                 215                 220

Arg Trp Gly Gly Asp Gly Phe Tyr Ala Met Asp Tyr Trp Gly Gln Gly
225                 230                 235                 240

Thr Leu Val Thr Val Ser Ser Ala Ala Glu Pro Lys Ser Ser Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Ile
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Arg Tyr Met Thr Trp Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Lys
```

<210> SEQ ID NO 170
<211> LENGTH: 1443
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 170
gacatccaga tgacccagtc tccatcctcc ctgtctgcat ctgtaggaga cagagtcacc          60

```
atcacttgcc gggcaagtca ggacgttaac accgctgtag cttggtatca gcagaaacca      120
gggaaagccc ctaagctcct gatctattct gcatcctttt tgtacagtgg ggtcccatca      180
aggttcagtg gcagtcgatc tgggacagat ttcactctca ccatcagcag tctgcaacct      240
gaagattttg caacttacta ctgtcaacag cattacacta ccccacccac tttcggccaa      300
gggaccaaag tggagatcaa aggtggttct ggtggtggtt ctggtggtgg ttctggtggt      360
ggttctggtg gtggttctgg tgaagtgcag ctggtggagt ctgggggagg cttggtacag      420
cctggcgggt ccctgagact ctcctgtgca gcctctggat tcaacattaa agatacttat      480
atccactggg tccggcaagc tccagggaag gcctggagt gggtcgcacg tatttatccc      540
acaaatggtt acacacggta tgcggactct gtgaagggcc gattcaccat ctccgcagac      600
acttccaaga acaccgcgta tctgcaaatg aacagtctga gagctgagga cacggccgtt      660
tattactgtt caagatgggg cggagacggt ttctacgcta tggactactg gggccaaggg      720
accctggtca ccgtctcctc agccgccgag cccaagagca cgataagac ccacacctgc      780
cctccctgtc cagctccaga actgctggga ggacctagcg tgttcctgtt tccccctaag      840
ccaaaagaca ctctgatgat ttccaggact cccgaggtga cctgcgtggt ggtggacgtg      900
tctcacgagg accccgaagt gaagttcaac tggtacgtgg atggcgtgga agtgcataat      960
gctaagacaa aaccaagaga ggaacagtac aactccactt atcgcgtcgt gagcgtgctg     1020
accgtgctgc accaggactg gctgaacggg aaggagtata agtgcaaagt cagtaataag     1080
gccctgcctg ctccaatcga aaaaccatc tctaaggcca aaggccagcc aagggagccc     1140
caggtgtaca cactgccacc cagcagagac gaactgacca gaaccaggt gtccctgatc     1200
tgtctggtga aaggcttcta tcctagtgat attgctgtgg agtgggaatc aaatggacag     1260
ccagagaaca gatacatgac ctggcctcca gtgctggaca gcgatggcag cttcttcctg     1320
tattccaagc tgacagtgga taaatctcga tggcagcagg ggaacgtgtt tagttgttca     1380
gtgatgcatg aagccctgca caatcattac actcagaaga gcctgtccct gtctcccggc     1440
aaa                                                                    1443
```

<210> SEQ ID NO 171
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 171

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 172
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 172
gacatccaga tgacccagtc tccatcctcc ctgtctgcat ctgtaggaga cagagtcacc      60
atcacttgcc gggcaagtca ggacgttaac accgctgtag cttggtatca gcagaaacca     120
gggaaagccc ctaagctcct gatctattct gcatcctttt tgtacagtgg ggtcccatca     180
aggttcagtg gcagtcgatc tgggacagat ttcactctca ccatcagcag tctgcaacct     240
gaagattttg caacttacta ctgtcaacag cattacacta ccccacccac tttcggccaa     300
gggaccaaag tggagatcaa a                                               321

<210> SEQ ID NO 173
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Gln Asp Val Asn Thr Ala
1               5

<210> SEQ ID NO 174
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
caggacgtta acaccgct                                                    18

<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Gln Gln His Tyr Thr Thr Pro Pro Thr
1               5

<210> SEQ ID NO 176
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
caacagcatt acactacccc acccact                                          27

<210> SEQ ID NO 177
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Ser Ala Ser
1

<210> SEQ ID NO 178
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178 tctgcatcc                                                                 9

<210> SEQ ID NO 179
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 180
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 180
gaagtgcagc tggtggagtc tgggggaggc ttggtacagc ctggcgggtc cctgagactc     60
tcctgtgcag cctctggatt caacattaaa gatacttata tccactgggt ccggcaagct    120
ccagggaagg gcctggagtg ggtcgcacgt atttatccca caaatggtta cacacggtat    180

```
gcggactctg tgaagggccg attcaccatc tccgcagaca cttccaagaa caccgcgtat        240
ctgcaaatga acagtctgag agctgaggac acggccgttt attactgttc aagatggggc        300
ggagacggtt tctacgctat ggactactgg ggccaaggga ccctggtcac cgtctcctca        360

<210> SEQ ID NO 181
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Gly Phe Asn Ile Lys Asp Thr Tyr
1               5

<210> SEQ ID NO 182
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
ggattcaaca ttaaagatac ttat                                               24

<210> SEQ ID NO 183
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Ser Arg Trp Gly Gly Asp Gly Phe Tyr Ala Met Asp Tyr
1               5                   10

<210> SEQ ID NO 184
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
tcaagatggg gcggagacgg tttctacgct atggactac                               39

<210> SEQ ID NO 185
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Ile Tyr Pro Thr Asn Gly Tyr Thr
1               5

<210> SEQ ID NO 186
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 186
atttatccca caaatggtta caca                                                 24

<210> SEQ ID NO 187
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187
```

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

```
<210> SEQ ID NO 188
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 188
gctccagaac tgctgggagg acctagcgtg ttcctgtttc cccctaagcc aaaagacact        60
ctgatgattt ccaggactcc cgaggtgacc tgcgtggtgg tggacgtgtc tcacgaggac       120
cccgaagtga agttcaactg gtacgtggat ggcgtggaag tgcataatgc taagacaaaa       180
ccaagagagg aacagtacaa ctccacttat cgcgtcgtga gcgtgctgac cgtgctgcac       240
caggactggc tgaacgggaa ggagtataag tgcaaagtca gtaataaggc cctgcctgct       300
ccaatcgaaa aaaccatctc taaggccaaa                                        330

<210> SEQ ID NO 189
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189
```

Gly Gln Pro Arg Glu Pro Gln Val Tyr Thr Leu Pro Pro Ser Arg Asp
1               5                   10                  15

Glu Leu Thr Lys Asn Gln Val Ser Leu Ile Cys Leu Val Lys Gly Phe
            20                  25                  30

Tyr Pro Ser Asp Ile Ala Val Glu Trp Glu Ser Asn Gly Gln Pro Glu
            35                  40                  45

Asn Arg Tyr Met Thr Trp Pro Val Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly
            100                 105

<210> SEQ ID NO 190
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 190
ggccagccaa gggagcccca ggtgtacaca ctgccaccca gcagagacga actgaccaag      60
aaccaggtgt ccctgatctg tctggtgaaa ggcttctatc ctagtgatat tgctgtggag    120
tgggaatcaa atggacagcc agagaacaga tacatgacct ggcctccagt gctggacagc    180
gatggcagct tcttcctgta ttccaagctg acagtggata atctcgatg gcagcagggg     240 aacgtgttta gttgttcagt gatgcatgaa gccctgcaca atcattacac tcagaagagc    300
ctgtccctgt ctcccggc                                                   318

<210> SEQ ID NO 191
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

```
Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 192
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 192
gatattcaga tgacccagtc ccctagctcc ctgtccgctt ctgtgggcga cagggtcact      60
atcacctgcc gcgcatctca ggatgtgaac accgcagtcg cctggtacca gcagaagcct    120
gggaaagctc caaagctgct gatctacagt gcatcattcc tgtattcagg agtgcccagc    180
cggtttagcg gcagcagatc tggcaccgac ttcacactga ctatctctag tctgcagcct    240
gaggattttg ccacatacta ttgccagcag cactatacca cccccctac tttcggccag     300 gggaccaaag tggagatcaa gcgaactgtg gccgctccaa gtgtcttcat ttttccaccc    360
agcgacgaac agctgaaatc cggcacagct tctgtggtct gtctgctgaa caacttctac    420
cccagagagg ccaaagtgca gtggaaggtc gataacgctc tgcagagtgg aacagccag    480 gagagcgtga cagaacagga ctccaaagat tctacttata gtctgtcaag caccctgaca    540
ctgagcaagg cagactacga aaagcataaa gtgtatgcct gtgaggtgac ccatcagggg    600
ctgtcttctc ccgtgaccaa gtctttcaac cgaggcgaat gt                       642

<210> SEQ ID NO 193
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

```
<210> SEQ ID NO 194
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 194
gatattcaga tgacccagtc ccctagctcc ctgtccgctt ctgtgggcga cagggtcact      60
atcacctgcc gcgcatctca ggatgtgaac accgcagtcg cctggtacca gcagaagcct     120
gggaaagctc caaagctgct gatctacagt gcatcattcc tgtattcagg agtgcccagc     180
cggtttagcg gcagcagatc tggcaccgac ttcacactga ctatctctag tctgcagcct     240
gaggattttg ccacatacta ttgccagcag cactatacca cccccctac tttcggccag      300 gggaccaaag tggagatcaa g                                                321

<210> SEQ ID NO 195
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Gln Asp Val Asn Thr Ala
1               5

<210> SEQ ID NO 196
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
caggatgtga acaccgca                                                    18

<210> SEQ ID NO 197
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Gln Gln His Tyr Thr Thr Pro Pro Thr
1               5

<210> SEQ ID NO 198
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
cagcagcact ataccacacc ccctact                                          27

<210> SEQ ID NO 199
<211> LENGTH: 3
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Ser Ala Ser
1

<210> SEQ ID NO 200
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200 agtgcatca                                                                  9

<210> SEQ ID NO 201
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 202
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 202
cgaactgtgg ccgctccaag tgtcttcatt tttccaccca gcgacgaaca gctgaaatcc      60
ggcacagctt ctgtggtctg tctgctgaac aacttctacc ccagagaggc caaagtgcag     120
tggaaggtcg ataacgctct gcagagtggc aacagccagg agagcgtgac agaacaggac     180
tccaaagatt ctacttatag tctgtcaagc accctgacac tgagcaaggc agactacgaa     240
aagcataaag tgtatgcctg tgaggtgacc catcaggggc tgtcttctcc cgtgaccaag     300
tctttcaacc gaggcgaatg t                                               321

<210> SEQ ID NO 203
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 203

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Val
            340                 345                 350

Leu Pro Pro Ser Arg Asp Glu Leu Thr Lys Asn Gln Val Ser Leu Leu
        355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Leu Thr Trp Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

<210> SEQ ID NO 204
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 204
gaagtgcagc tggtcgaatc tggaggagga ctggtgcagc caggagggtc cctgcgcctg      60
tcttgcgccg ctagtggctt cacttttacc gactacacca tggattgggt gcgacaggca     120
cctggaaagg gcctggagtg ggtcgccgat gtgaacccaa atagcggagg ctccatctac     180
aaccagcggt tcaagggccg gttcaccctg tcagtggacc ggagcaaaaa caccctgtat     240
ctgcagatga atagcctgcg agccgaagat actgctgtgt actattgcgc ccggaatctg     300
gggccctcct tctactttga ctattggggg cagggaactc tggtcaccgt gagctccgcc     360
tccaccaagg gaccttctgt gttcccactg gctccctcta gtaaatccac atctggggga     420
actgcagccc tgggctgtct ggtgaaggac tacttcccag agcccgtcac agtgtcttgg     480
aacagtggcg ctctgacttc tggggtccac acctttcctg cagtgctgca gtcaagcggg     540
ctgtacagcc tgtcctctgt ggtcaccgtg ccaagttcaa gcctgggaac acagacttat     600
atctgcaacg tgaatcacaa gccatccaat acaaaagtcg acaagaaagt ggaacccaag     660
tcttgtgata aacccatac atgccccct tgtcctgcac cagagctgct gggaggacca      720
agcgtgttcc tgtttccacc caagcctaaa gatacactga tgattagtag gacccagaa      780 gtcacatgcg tggtcgtgga cgtgagccac gaggaccccg aagtcaagtt taactggtac     840
gtggacggcg tcgaggtgca taatgccaag actaaaccca gggaggaaca gtacaacagt     900
acctatcgcg tcgtgtcagt cctgacagtg ctgcatcagg attggctgaa cgggaaagag     960
tataagtgca agtgagcaa taaggctctg cccgcaccta tcgagaaaac aatttccaag    1020
gcaaaaggac agcctagaga accacaggtg tacgtgctgc ctccatcaag ggatgagctg    1080
acaaagaacc aggtcagcct gctgtgtctg gtgaaaggat tctatccctc tgacattgct    1140
gtggagtggg aaagtaatgg ccagcctgag aacaattacc tgacctggcc ccctgtgctg    1200
gactcagatg gcagcttctt tctgtatagc aagctgaccg tcgacaaatc ccggtggcag    1260
caggggaatg tgtttagttg ttcagtcatg cacgaggcac tgcacaacca ttacacccag    1320
aagtcactgt cactgtcacc aggg                                           1344

<210> SEQ ID NO 205
<211> LENGTH: 119
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 205

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

<210> SEQ ID NO 206
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 206
gaagtgcagc tggtcgaatc tggaggagga ctggtgcagc caggagggtc cctgcgcctg      60
tcttgcgccg ctagtggctt cacttttacc gactacacca tggattgggt gcgacaggca     120
cctggaaagg gcctggagtg ggtcgccgat gtgaacccaa atagcggagg ctccatctac     180
aaccagcggt tcaagggccg gttcacccta tcagtggacc ggagcaaaaa caccctgtat     240
ctgcagatga atagcctgcg agccgaagat actgctgtgt actattgcgc ccggaatctg     300
gggccctcct tctactttga ctattggggg cagggaactc tggtcaccgt gagctcc       357

<210> SEQ ID NO 207
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 207

Gly Phe Thr Phe Thr Asp Tyr Thr
1               5

<210> SEQ ID NO 208
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 208
ggcttcactt ttaccgacta cacc       24

<210> SEQ ID NO 209
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Ala Arg Asn Leu Gly Pro Ser Phe Tyr Phe Asp Tyr
1               5                   10

<210> SEQ ID NO 210
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
gcccggaatc tggggccctc cttctacttt gactat                                 36

<210> SEQ ID NO 211
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Val Asn Pro Asn Ser Gly Gly Ser
1               5

<210> SEQ ID NO 212
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
gtgaacccaa atagcggagg ctcc                                              24

<210> SEQ ID NO 213
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val

<210> SEQ ID NO 214
<211> LENGTH: 294
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 214
gcctccacca agggaccttc tgtgttccca ctggctccct ctagtaaatc cacatctggg     60
ggaactgcag ccctgggctg tctggtgaag gactacttcc cagagcccgt cacagtgtct    120
tggaacagtg gcgctctgac ttctggggtc cacacctttc ctgcagtgct gcagtcaagc    180
gggctgtaca gcctgtcctc tgtggtcacc gtgccaagtt caagcctggg aacacagact    240
tatatctgca acgtgaatca caagccatcc aatacaaaag tcgacaagaa agtg          294

<210> SEQ ID NO 215
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 216
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 216
gcaccagagc tgctgggagg accaagcgtg ttcctgtttc cacccaagcc taaagataca     60
ctgatgatta gtaggacccc agaagtcaca tgcgtggtcg tggacgtgag ccacgaggac    120
cccgaagtca agtttaactg gtacgtggac ggcgtcgagg tgcataatgc caagactaaa    180
cccagggagg aacagtacaa cagtacctat cgcgtcgtgt cagtcctgac agtgctgcat    240
caggattggc tgaacgggaa agagtataag tgcaaagtga gcaataaggc tctgcccgca    300

```
cctatcgaga aaacaatttc caaggcaaaa                                      330
```

<210> SEQ ID NO 217
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Gly Gln Pro Arg Glu Pro Gln Val Tyr Val Leu Pro Pro Ser Arg Asp
1               5                   10                  15

Glu Leu Thr Lys Asn Gln Val Ser Leu Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Leu Thr Trp Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 218
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 218

```
ggacagccta gagaaccaca ggtgtacgtg ctgcctccat caagggatga gctgacaaag    60
aaccaggtca gcctgctgtg tctggtgaaa ggattctatc cctctgacat tgctgtggag   120
tgggaaagta atggccagcc tgagaacaat tacctgacct ggcccctgt gctggactca    180 gatggcagct ctttctgta tagcaagctg accgtcgaca atcccggtgc agcagggg      240 aatgtgttta gttgttcagt catgcacgag gcactgcaca accattacac ccagaagtca   300
ctgtcactgt caccaggg                                                  318
```

<210> SEQ ID NO 219
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
```

```
                50                  55                  60
Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Leu Gly Pro Ser Phe Tyr Phe Asp Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
                210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Val
                340                 345                 350

Tyr Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Ala Leu Val Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

<210> SEQ ID NO 220
<211> LENGTH: 1344
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 220

```
gaagtgcagc tggtcgaatc tggaggagga ctggtgcagc caggagggtc cctgcgcctg    60
tcttgcgccg ctagtggctt cactttacc gactacacca tggattgggt gcgacaggca    120
cctggaaagg gcctggagtg ggtcgccgat gtgaacccaa atagcggagg ctccatctac   180
aaccagcggt tcaagggccg gttcaccctg tcagtggacc ggagcaaaaa caccctgtat   240
ctgcagatga atagcctgcg agccgaagat actgctgtgt actattgcgc ccggaatctg   300
gggccctcct tctactttga ctattggggg cagggaactc tggtcaccgt gagctccgcc   360
tccaccaagg gaccttctgt gttcccactg gctccctcta gtaaatccac atctggggga   420
actgcagccc tgggctgtct ggtgaaggac tacttcccag agcccgtcac agtgtcttgg   480
aacagtggcg ctctgacttc tggggtccac acctttcctg cagtgctgca gtcaagcggg   540
ctgtacagcc tgtcctctgt ggtcaccgtg ccaagttcaa gctgggaac acagacttat    600
atctgcaacg tgaatcacaa gccatccaat acaaaagtcg acaagaaagt ggaacccaag   660
tcttgtgata aacccatac atgcccccct tgtcctgcac cagagctgct gggaggacca    720
agcgtgttcc tgtttccacc caagcctaaa gatacactga tgattagtag gaccccagaa   780
gtcacatgcg tggtcgtgga cgtgagccac gaggaccccg aagtcaagtt taactggtac   840
gtggacggcg tcgaggtgca taatgccaag actaaaccca gggaggaaca gtacaacagt   900
acctatcgcg tcgtgtcagt cctgacagtg ctgcatcagg attggctgaa cgggaaagag   960
tataagtgca agtgagcaa taaggctctg cccgcaccta tcgagaaaac aatttccaag   1020
gcaaaaggac agcctagaga accacaggtg tacgtgtatc ctccatcaag ggatgagctg   1080
acaaagaacc aggtcagcct gacttgtctg gtgaaaggat tctatccctc tgacattgct   1140
gtggagtggg aaagtaatgg ccagcctgag aacaattaca agaccacacc ccctgtgctg   1200
gactcagatg gcagcttcgc gctggtgagc aagctgaccg tcgacaaatc ccggtggcag   1260
caggggaatg tgtttagttg ttcagtcatg cacgaggcac tgcacaacca ttacacccag   1320
aagtcactgt cactgtcacc aggg                                          1344
```

<210> SEQ ID NO 221
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
```

```
                    85                  90                  95
Ala Arg Asn Leu Gly Pro Ser Phe Tyr Phe Asp Tyr Trp Gly Gln Gly
            100                 105                 110

Thr Leu Val Thr Val Ser Ser
        115

<210> SEQ ID NO 222
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 222
gaagtgcagc tggtcgaatc tggaggagga ctggtgcagc caggagggtc cctgcgcctg      60
tcttgcgccg ctagtggctt cactttacc gactacacca tggattgggt gcgacaggca     120
cctggaaagg gcctggagtg ggtcgccgat gtgaacccaa atagcggagg ctccatctac    180
aaccagcggt tcaagggccg gttcaccctg tcagtggacc ggagcaaaaa caccctgtat    240
ctgcagatga atagcctgcg agccgaagat actgctgtgt actattgcgc ccggaatctg    300
gggccctcct tctactttga ctattggggg cagggaactc tggtcaccgt gagctcc       357

<210> SEQ ID NO 223
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Gly Phe Thr Phe Thr Asp Tyr Thr
1               5

<210> SEQ ID NO 224
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
ggcttcactt ttaccgacta cacc                                            24

<210> SEQ ID NO 225
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Ala Arg Asn Leu Gly Pro Ser Phe Tyr Phe Asp Tyr
1               5                  10

<210> SEQ ID NO 226
<211> LENGTH: 36
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 226
gcccggaatc tggggccctc cttctacttt gactat                               36

<210> SEQ ID NO 227
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Val Asn Pro Asn Ser Gly Gly Ser
1               5

<210> SEQ ID NO 228
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
gtgaacccaa atagcggagg ctcc                                            24

<210> SEQ ID NO 229
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 230
<211> LENGTH: 294
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 230
gcctccacca aggaccttc tgtgttccca ctggctccct ctagtaaatc cacatctggg      60
ggaactgcag ccctgggctg tctggtgaag gactacttcc cagagcccgt cacagtgtct    120

```
tggaacagtg gcgctctgac ttctggggtc cacaccttc ctgcagtgct gcagtcaagc      180
gggctgtaca gcctgtcctc tgtggtcacc gtgccaagtt caagcctggg aacacagact      240
tatatctgca acgtgaatca caagccatcc aatacaaaag tcgacaagaa agtg            294
```

<210> SEQ ID NO 231
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110
```

<210> SEQ ID NO 232
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 232

```
gcaccagagc tgctgggagg accaagcgtg ttcctgtttc cacccaagcc taaagataca      60
ctgatgatta gtaggacccc agaagtcaca tgcgtggtcg tggacgtgag ccacgaggac     120
cccgaagtca agtttaactg gtacgtggac ggcgtcgagg tgcataatgc aagactaaa     180 cccagggagg aacagtacaa cagtacctat cgcgtcgtgt cagtcctgac agtgctgcat     240
caggattggc tgaacgggaa agagtataag tgcaaagtga gcaataaggc tctgcccgca     300
cctatcgaga aaacaatttc caaggcaaaa                                      330
```

<210> SEQ ID NO 233
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

```
Gly Gln Pro Arg Glu Pro Gln Val Tyr Val Tyr Pro Pro Ser Arg Asp
1               5                   10                  15

Glu Leu Thr Lys Asn Gln Val Ser Leu Thr Cys Leu Val Lys Gly Phe
                20                  25                  30

Tyr Pro Ser Asp Ile Ala Val Glu Trp Glu Ser Asn Gly Gln Pro Glu
```

```
                35                  40                  45
Asn Asn Tyr Lys Thr Thr Pro Pro Val Leu Asp Ser Asp Gly Ser Phe
 50                  55                  60
Ala Leu Val Ser Lys Leu Thr Val Asp Lys Ser Arg Trp Gln Gln Gly
 65                  70                  75                  80
Asn Val Phe Ser Cys Ser Val Met His Glu Ala Leu His Asn His Tyr
                 85                  90                  95
Thr Gln Lys Ser Leu Ser Leu Ser Pro Gly
            100                 105

<210> SEQ ID NO 234
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 234
ggacagccta gagaaccaca ggtgtacgtg tatcctccat caagggatga gctgacaaag     60
aaccaggtca gcctgacttg tctggtgaaa ggattctatc cctctgacat tgctgtggag    120
tgggaaagta atggccagcc tgagaacaat tacaagacca cccccctgt gctggactca     180 gatggcagct tcgcgctggt gagcaagctg accgtcgaca atcccggtg cagcagggg     240 aatgtgttta gttgttcagt catgcacgag gcactgcaca accattacac ccagaagtca    300
ctgtcactgt caccaggg                                                   318

<210> SEQ ID NO 235
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Asn Ile Lys Asp Thr
             20                  25                  30
Tyr Ile His Trp Val Arg Gln Ala Pro Gly Lys Gly Leu Glu Trp Val
         35                  40                  45
Ala Arg Ile Tyr Pro Thr Asn Gly Tyr Thr Arg Tyr Ala Asp Ser Val
 50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ser Arg Trp Gly Gly Asp Gly Phe Tyr Ala Met Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
```

```
                165                 170                 175
Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Val Tyr Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Ala Leu Val Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 236
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 236
gaggtgcagc tggtggaaag cggaggagga ctggtgcagc caggaggatc tctgcgactg      60
agttgcgccg cttcaggatt caacatcaag gacacctaca ttcactgggt gcgacaggct     120
ccaggaaaag gactggagtg gtggctcgaa tctatcccta atggatatac acccggtat     180 gccgactccg tgaaggggag gtttactatt agcgccgata catccaaaaa cactgcttac     240
ctgcagatga acagcctgcg agccgaagat accgctgtgt actattgcag tcgatgggga     300
ggagacggat tctacgctat ggattattgg ggacagggga ccctggtgac agtgagctcc     360
```

```
gcctctacca agggccccag tgtgtttccc ctggctcctt ctagtaaatc cacctctgga    420
gggacagccg ctctgggatg tctggtgaag gactatttcc ccgagcctgt gaccgtgagt    480
tggaactcag gcgccctgac aagcggagtg cacacttttc ctgctgtgct gcagtcaagc    540
gggctgtact ccctgtcctc tgtggtgaca gtgccaagtt caagcctggg cacacagact    600
tatatctgca acgtgaatca taagccctca aatacaaaag tggacaagaa agtggagccc    660
aagagctgtg ataagaccca cacctgccct ccctgtccag ctccagaact gctgggagga    720
cctagcgtgt tcctgtttcc ccctaagcca aaagacactc tgatgatttc caggactccc    780
gaggtgacct gcgtggtggt ggacgtgtct cacgaggacc ccgaagtgaa gttcaactgg    840
tacgtggatg gcgtggaagt gcataatgct aagacaaaac caagagagga acagtacaac    900
tccacttatc gcgtcgtgag cgtgctgacc gtgctgcacc aggactggct gaacgggaag    960
gagtataagt gcaaagtcag taataaggcc ctgcctgctc aatcgaaaa aaccatctct   1020
aaggccaaag gccagccaag ggagccccag gtgtacgtgt acccaccag cagagacgaa   1080
ctgaccaaga accaggtgtc cctgacatgt ctggtgaaag gcttctatcc tagtgatatt   1140
gctgtggagt gggaatcaaa tggacagcca gagaacaatt acaagaccac acctccagtg   1200
ctggacagcg atggcagctt cgccctggtg tccaagctga cagtggataa atctcgatgg   1260
cagcagggga acgtgtttag ttgttcagtg atgcatgaag ccctgcacaa tcattacact   1320
cagaagagcc tgtccctgtc tcccggcaaa                                   1350
```

<210> SEQ ID NO 237
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 238
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 238

```
gaggtgcagc tggtggaaag cggaggagga ctggtgcagc caggaggatc tctgcgactg      60
agttgcgccg cttcaggatt caacatcaag gacacctaca ttcactgggt cgacaggct      120 ccaggaaaag gactggagtg ggtggctcga atctatccca ctaatggata cacccggtat     180
gccgactccg tgaaggggag gtttactatt agcgccgata catccaaaaa cactgcttac    240
ctgcagatga acagcctgcg agccgaagat accgctgtgt actattgcag tcgatgggga    300
ggagacggat tctacgctat ggattattgg ggacagggga ccctggtgac agtgagctcc    360
```

<210> SEQ ID NO 239
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Gly Phe Asn Ile Lys Asp Thr Tyr
1               5

<210> SEQ ID NO 240
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240

```
ggattcaaca tcaaggacac ctac                                              24
```

<210> SEQ ID NO 241
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Ser Arg Trp Gly Gly Asp Gly Phe Tyr Ala Met Asp Tyr
1               5                   10

<210> SEQ ID NO 242
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242

```
agtcgatggg gaggagacgg attctacgct atggattat                              39
```

<210> SEQ ID NO 243
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Ile Tyr Pro Thr Asn Gly Tyr Thr

-continued

```
<210> SEQ ID NO 244
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
atctatccca ctaatggata cacc                                          24

<210> SEQ ID NO 245
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245
```

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

```
<210> SEQ ID NO 246
<211> LENGTH: 294
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 246
gcctctacca agggcccag tgtgtttccc ctggctcctt ctagtaaatc cacctctgga     60
gggacagccg ctctgggatg tctggtgaag gactatttcc ccgagcctgt gaccgtgagt   120
tggaactcag gcgccctgac aagcggagtg cacacttttc ctgctgtgct gcagtcaagc   180
gggctgtact ccctgtcctc tgtggtgaca gtgccaagtt caagcctggg cacacagact   240
tatatctgca acgtgaatca taagccctca aatacaaaag tggacaagaa agtg         294

<210> SEQ ID NO 247
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247
```

Ala Pro Glu Leu Leu Gly Gly Pro Ser Val Phe Leu Phe Pro Pro Lys

```
1               5                   10                  15
Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
 50                 55                  60

Gln Tyr Asn Ser Thr Tyr Arg Val Val Ser Val Leu Thr Val Leu His
 65                 70                  75                  80

Gln Asp Trp Leu Asn Gly Lys Glu Tyr Lys Cys Lys Val Ser Asn Lys
            85                  90                  95

Ala Leu Pro Ala Pro Ile Glu Lys Thr Ile Ser Lys Ala Lys
            100                 105                 110
```

<210> SEQ ID NO 248
<211> LENGTH: 330
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 248

```
gctccagaac tgctgggagg acctagcgtg ttcctgtttc cccctaagcc aaaagacact      60
ctgatgattt ccaggactcc cgaggtgacc tgcgtggtgg tggacgtgtc tcacgaggac     120
cccgaagtga agttcaactg gtacgtggat ggcgtggaag tgcataatgc taagacaaaa     180
ccaagagagg aacagtacaa ctccacttat cgcgtcgtga gcgtgctgac cgtgctgcac     240
caggactggc tgaacgggaa ggagtataag tgcaaagtca gtaataaggc cctgcctgct     300
ccaatcgaaa aaccatctc taaggccaaa                                       330
```

<210> SEQ ID NO 249
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 249

```
Gly Gln Pro Arg Glu Pro Gln Val Tyr Val Tyr Pro Pro Ser Arg Asp
 1               5                  10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
 50                 55                  60

Ala Leu Val Ser Lys Leu Thr Val Asp Lys Ser Arg Trp Gln Gln Gly
 65                 70                  75                  80

Asn Val Phe Ser Cys Ser Val Met His Glu Ala Leu His Asn His Tyr
            85                  90                  95

Thr Gln Lys Ser Leu Ser Leu Ser Pro Gly
            100                 105
```

<210> SEQ ID NO 250
<211> LENGTH: 318
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 250
ggccagccaa gggagcccca ggtgtacgtg tacccaccca gcagagacga actgaccaag      60
aaccaggtgt ccctgacatg tctggtgaaa ggcttctatc ctagtgatat tgctgtggag     120
tgggaatcaa atggacagcc agagaacaat tacaagacca cacctccagt gctggacagc     180
gatggcagct tcgccctggt gtccaagctg acagtggata aatctcgatg gcagcagggg     240
aacgtgttta gttgttcagt gatgcatgaa gccctgcaca atcattacac tcagaagagc     300
ctgtccctgt ctcccggc                                                   318

<210> SEQ ID NO 251
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Val Leu Pro Pro Ser Arg Asp Glu Leu Thr
    130                 135                 140

Lys Asn Gln Val Ser Leu Leu Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Leu Thr Trp Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 252
<211> LENGTH: 696
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 252

```
gaacctaaaa gcagcgacaa gacccacaca tgccccccctt gtccagctcc agaactgctg    60
ggaggaccaa gcgtgttcct gtttccaccc aagcccaaag atacactgat gatcagccga   120
actcccgagg tcacctgcgt ggtcgtggac gtgtcccacg aggaccccga agtcaagttc   180
aactggtacg tggacggcgt cgaagtgcat aatgcaaaga ctaaaccacg ggaggaacag   240
tacaactcta catatagagt cgtgagtgtc ctgactgtgc tgcatcagga ttggctgaac   300
ggcaaagagt ataagtgcaa agtgtctaat aaggccctgc ctgctccaat cgagaaaact   360
attagtaagg caaaagggca gcccagggaa cctcaggtct acgtgctgcc tccaagtcgc   420
gacgagctga ccaagaacca ggtctcactg ctgtgtctgg tgaaaggatt ctatccttcc   480
gatattgccg tggagtggga atctaatggc cagccagaga caattacctg gacctggccc   540
cctgtgctgg acagcgatgg gtccttcttt ctgtattcaa agctgacagt ggacaaaagc   600
agatggcagc agggaaacgt ctttagctgt tccgtgatgc acgaagccct gcacaatcat   660
tacacccaga gtctctgagg tctgtcacct ggcaaa                              696
```

<210> SEQ ID NO 253
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 253

```
Ala Pro Glu Leu Leu Gly Gly Pro Ser Val Phe Leu Phe Pro Pro Lys
1               5                   10                  15
Pro Lys Asp Thr Leu Met Ile Ser Arg Thr Pro Glu Val Thr Cys Val
            20                  25                  30
Val Val Asp Val Ser His Glu Asp Pro Glu Val Lys Phe Asn Trp Tyr
        35                  40                  45
Val Asp Gly Val Glu Val His Asn Ala Lys Thr Lys Pro Arg Glu Glu
    50                  55                  60
Gln Tyr Asn Ser Thr Tyr Arg Val Val Ser Val Leu Thr Val Leu His
65                  70                  75                  80
Gln Asp Trp Leu Asn Gly Lys Glu Tyr Lys Cys Lys Val Ser Asn Lys
                85                  90                  95
Ala Leu Pro Ala Pro Ile Glu Lys Thr Ile Ser Lys Ala Lys
            100                 105                 110
```

<210> SEQ ID NO 254
<211> LENGTH: 330
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 254

```
gctccagaac tgctgggagg accaagcgtg ttcctgtttc cacccaagcc caaagataca    60
ctgatgatca gccgaactcc cgaggtcacc tgcgtggtcg tggacgtgtc ccacgaggac   120
cccgaagtca agttcaactg gtacgtggac ggcgtcgaag tgcataatgc aaagactaaa   180
```
ccacgggagg aacagtacaa ctctacatat agagtcgtga gtgtcctgac tgtgctgcat    240
caggattggc tgaacggcaa agagtataag tgcaaagtgt ctaataaggc cctgcctgct    300
ccaatcgaga aaactattag taaggcaaaa                                     330

<210> SEQ ID NO 255
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

Gly Gln Pro Arg Glu Pro Gln Val Tyr Val Leu Pro Pro Ser Arg Asp
1               5                   10                  15

Glu Leu Thr Lys Asn Gln Val Ser Leu Leu Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Leu Thr Trp Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 256
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 256
gggcagccca gggaacctca ggtctacgtg ctgcctccaa gtcgcgacga gctgaccaag    60
aaccaggtct cactgctgtg tctggtgaaa ggattctatc cttccgatat tgccgtggag    120
tgggaatcta atggccagcc agagaacaat tacctgacct ggccccctgt gctggacagc    180
gatgggtcct tctttctgta ttcaaagctg acagtggaca aaagcagatg gcagcaggga    240
aacgtcttta gctgttccgt gatgcacgaa gccctgcaca atcattacac ccagaagtct    300
ctgagtctgt cacctggc                                                  318

<210> SEQ ID NO 257
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 257

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
                35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Gly Gly Gly Gly Ser
                100                 105                 110

Gly Gly Gly Gly Ser Gly Gly Gly Ser Glu Val Gln Leu Val Glu
            115                 120                 125

Ser Gly Gly Gly Leu Val Gln Pro Gly Gly Ser Leu Arg Leu Ser Cys
    130                 135                 140

Ala Ala Ser Gly Phe Thr Phe Thr Asp Tyr Thr Met Asp Trp Val Arg
145                 150                 155                 160

Gln Ala Pro Gly Lys Gly Leu Glu Trp Val Ala Asp Val Asn Pro Asn
                165                 170                 175

Ser Gly Gly Ser Ile Tyr Asn Gln Arg Phe Lys Gly Arg Phe Thr Leu
            180                 185                 190

Ser Val Asp Arg Ser Lys Asn Thr Leu Tyr Leu Gln Met Asn Ser Leu
    195                 200                 205

Arg Ala Glu Asp Thr Ala Val Tyr Tyr Cys Ala Arg Asn Leu Gly Pro
210                 215                 220

Ser Phe Tyr Phe Asp Tyr Trp Gly Gln Gly Thr Leu Val Thr Val Ser
225                 230                 235                 240

Ser Ala Ala Glu Pro Lys Ser Ser Asp Lys Thr His Thr Cys Pro Pro
                245                 250                 255

Cys Pro Ala Pro Glu Leu Leu Gly Gly Pro Ser Val Phe Leu Phe Pro
                260                 265                 270

Pro Lys Pro Lys Asp Thr Leu Met Ile Ser Arg Thr Pro Glu Val Thr
    275                 280                 285

Cys Val Val Val Asp Val Ser His Glu Asp Pro Glu Val Lys Phe Asn
290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
    355                 360                 365

Gly Gln Pro Arg Glu Pro Gln Val Tyr Val Tyr Pro Pro Ser Arg Asp
370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Ala Leu Val Ser Lys Leu Thr Val Asp Lys Ser Arg Trp Gln Gln Gly
    435                 440                 445

Asn Val Phe Ser Cys Ser Val Met His Glu Ala Leu His Asn His Tyr

Thr Gln Lys Ser Leu Ser Leu Ser Pro Gly Lys
465          470              475

<210> SEQ ID NO 258
<211> LENGTH: 1425
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 258
gacattcaga tgacccagag ccctagctcc ctgagtgcct cagtcgggga cagggtgact      60
atcacctgca aggcttcaca ggatgtcagc attggcgtgg catggtacca gcagaagcca     120
gggaaagcac ccaagctgct gatctatagc gcctcctaca ggtatacagg cgtgccatcc     180
cgcttctctg gcagtgggtc aggaactgac tttacactga ctatttctag tctgcagccc     240
gaagatttcg ccacatacta ttgccagcag tactatatct acccttatac ttttggccag     300
gggaccaaag tggagattaa ggcggagga ggctccggag gaggagggtc tggaggagga     360
ggaagtgagg tccagctggt ggaatctgga ggaggactgg tgcagccagg agggtccctg     420
aggctgtctt gtgccgctag tggcttcacc tttacagact acacaatgga ttgggtgcgc     480
caggcaccag gaaagggact ggaatgggtc gctgatgtga cccctaatag cggaggctcc     540
atctacaacc agcggttcaa aggacggttc accctgtcag tggaccggag caagaacacc     600
ctgtatctgc agatgaacag cctgagagcc gaggatactg ctgtgtacta ttgcgccagg     660
aatctgggcc aagcttcta ctttgactat tgggggcagg aacactggt cactgtgtca     720
agcgcagccg aacccaaatc tctgataag actcacacct gcccaccttg tccagctcca     780
gagctgctgg aggacctag cgtgttcctg tttccaccca gccaaaaga cactctgatg     840
atttctagaa cccctgaagt gacatgtgtg gtcgtggacg tcagtcacga ggaccccgaa     900
gtcaaattca actggtacgt ggatggcgtc gaggtgcata atgccaagac caaaccccga     960
gaggaacagt acaactcaac ctatcgggtc gtgagcgtcc tgaccgtgct gcatcaggac    1020
tggctgaacg gcaaggagta taagtgcaaa gtgagcaaca aggctctgcc tgcaccaatc    1080
gagaagacca tttccaaggc taagggcag ccccgcgaac ctcaggtcta cgtgtatcct    1140
ccaagccgag atgagctgac aaaaaaccag gtctccctga cttgtctggt aagggatttt    1200
tacccaagtg acatcgcagt ggagtgggaa tcaaatggcc agcccgaaaa caattataag    1260
accacacccc ctgtgctgga ctctgatggg agtttcgcac tggtctccaa actgaccgtg    1320
gacaagtctc ggtggcagca gggaaacgtc tttagctgtt ccgtgatgca cgaggccctg    1380
cacaatcatt acacacagaa atctctgagt ctgtcacctg gcaag               1425

<210> SEQ ID NO 259
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly

```
            20                  25                  30
Val Ala Trp Tyr Gln Gln Lys Pro Gly Lys Ala Pro Lys Leu Leu Ile
         35                  40                  45

Tyr Ser Ala Ser Tyr Arg Tyr Thr Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ile Tyr Pro Tyr
                 85                  90                  95

Thr Phe Gly Gln Gly Thr Lys Val Glu Ile Lys
             100                 105

<210> SEQ ID NO 260
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 260
gacattcaga tgacccagag ccctagctcc ctgagtgcct cagtcgggga cagggtgact      60
atcacctgca aggcttcaca ggatgtcagc attggcgtgg catggtacca gcagaagcca     120
gggaaagcac ccaagctgct gatctatagc gcctcctaca ggtatacagg cgtgccatcc     180
cgcttctctg gcagtgggtc aggaactgac tttacactga ctatttctag tctgcagccc     240
gaagatttcg ccacatacta ttgccagcag tactatatct acccttatac ttttggccag     300
gggaccaaag tggagattaa g                                               321

<210> SEQ ID NO 261
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Gln Asp Val Ser Ile Gly
 1               5

<210> SEQ ID NO 262
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
caggatgtca gcattggc                                                    18

<210> SEQ ID NO 263
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Gln Gln Tyr Tyr Ile Tyr Pro Tyr Thr
```

```
<210> SEQ ID NO 264
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
cagcagtact atatctaccc ttatact                                          27

<210> SEQ ID NO 265
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Ser Ala Ser
1

<210> SEQ ID NO 266
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266 agcgcctcc                                                               9

<210> SEQ ID NO 267
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115

<210> SEQ ID NO 268
```

<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 268
gaggtccagc tggtggaatc tggaggagga ctggtgcagc caggagggtc cctgaggctg     60
tcttgtgccg ctagtggctt cacctttaca gactacacaa tggattgggt gcgccaggca    120
ccaggaaagg gactggaatg ggtcgctgat gtgaaccctc atagcggagg ctccatctac    180
aaccagcggt tcaaaggacg gttcaccctg tcagtggacc ggagcaagaa caccctgtat    240
ctgcagatga acagcctgag agccgaggat actgctgtgt actattgcgc caggaatctg    300
ggcccaagct ctactttga ctattgggggg cagggaacac tggtcactgt gtcaagc      357

<210> SEQ ID NO 269
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Gly Phe Thr Phe Thr Asp Tyr Thr
1               5

<210> SEQ ID NO 270
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
ggcttcacct ttacagacta caca                                            24

<210> SEQ ID NO 271
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Ala Arg Asn Leu Gly Pro Ser Phe Tyr Phe Asp Tyr
1               5                   10

<210> SEQ ID NO 272
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
gccaggaatc tgggcccaag cttctacttt gactat                               36

<210> SEQ ID NO 273
<211> LENGTH: 8
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 273

Val Asn Pro Asn Ser Gly Gly Ser
1               5

<210> SEQ ID NO 274
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274 gtgaaccta atagcggagg ctcc                                           24

<210> SEQ ID NO 275
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 276
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 276
gctccagagc tgctgggagg acctagcgtg ttcctgtttc cacccaagcc aaaagacact      60
ctgatgattt ctagaacccc tgaagtgaca tgtgtggtcg tggacgtcag tcacgaggac     120
cccgaagtca aattcaactg gtacgtggat ggcgtcgagg tgcataatgc caagaccaaa     180
ccccgagagg aacagtacaa ctcaacctat cgggtcgtga gcgtcctgac agtgctgcat     240
caggactggc tgaacggcaa ggagtataag tgcaaagtga gcaacaaggc tctgcctgca     300
ccaatcgaga agaccatttc caaggctaaa                                     330
```

```
<210> SEQ ID NO 277
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 277

Gly Gln Pro Arg Glu Pro Gln Val Tyr Val Tyr Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Ala Leu Val Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105

<210> SEQ ID NO 278
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 278
gggcagcccc gcgaacctca ggtctacgtg tatcctccaa gccgagatga gctgacaaaa      60
aaccaggtct ccctgacttg tctggtgaag ggattttacc caagtgacat cgcagtggag     120
tgggaatcaa atggccagcc cgaaaacaat tataagacca ccccctgt gctggactct      180 gatgggagtt tcgcactggt ctccaaactg accgtggaca gtctcggtg cagcaggga      240 aacgtcttta gctgttccgt gatgcacgag gccctgcaca atcattacac acagaaatct     300
ctgagtctgt cacctggc                                                   318

<210> SEQ ID NO 279
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 279

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80
```

Leu Gln Met Asn Ser Leu Arg Ala Glu Asp Thr Ala Val Tyr Tyr Cys
            85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Val Leu Pro Pro Ser Arg Asp Glu Leu Thr Lys Asn Gln Val Ser Leu
        355                 360                 365

Leu Cys Leu Val Lys Gly Phe Tyr Pro Ser Asp Ile Ala Val Glu Trp
370                 375                 380

Glu Ser Asn Gly Gln Pro Glu Asn Asn Tyr Leu Thr Trp Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 280
<211> LENGTH: 1350
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 280

```
gaggtgcagc tggtggaaag cggaggagga ctggtgcagc caggaggatc tctgcgactg      60
agttgcgccg cttcaggatt caacatcaag gacacctaca ttcactgggt gcgacaggct     120
ccaggaaaag gactggagtg ggtggctcga atctatccca ctaatggata cacccggtat     180
gccgactccg tgaaggggag gtttactatt agcgccgata catccaaaaa cactgcttac     240
ctgcagatga acagcctgcg agccgaagat accgctgtgt actattgcag tcgatgggga     300
ggagacggat tctacgctat ggattattgg ggacagggga ccctggtgac agtgagctcc     360
gcctctacca agggcccag tgtgtttccc ctggctcctt ctagtaaatc cacctctgga     420
gggacagccg ctctgggatg tctggtgaag gactatttcc ccgagcctgt gaccgtgagt     480
tggaactcag gcgccctgac aagcggagtg cacacttttc ctgctgtgct gcagtcaagc     540
gggctgtact ccctgtcctc tgtggtgaca gtgccaagtt caagcctggg cacacagact     600
tatatctgca acgtgaatca taagccctca aatacaaaag tggacaagaa agtggagccc     660
aagagctgtg ataagaccca cacctgcccc cctgtccag ctccagaact gctgggagga     720
cctagcgtgt tcctgtttcc ccctaagcca aaagacactc tgatgatttc caggactccc     780
gaggtgacct gcgtggtggt ggacgtgtct cacgaggacc ccgaagtgaa gttcaactgg     840
tacgtggatg gcgtggaagt gcataatgct aagacaaaac caagagagga acagtacaac     900
tccacttatc gcgtcgtgag cgtgctgacc gtgctgcacc aggactggct gaacgggaag     960
gagtataagt gcaaagtcag taataaggcc ctgcctgctc caatcgaaaa aaccatctct    1020
aaggccaaag ccagccaag ggagccccag gtgtacgtgc tgccacccag cagagacgaa    1080
ctgaccaaga accaggtgtc cctgctgtgt ctggtgaaag gcttctatcc tagtgatatt    1140
gctgtggagt gggaatcaaa tggacagcca gagaacaatt acctgacctg gcctccagtg    1200
ctggacagcg atggcagctt cttcctgtat tccaagctga cagtggataa atctcgatgg    1260
cagcagggga acgtgtttag ttgttcagtg atgcatgaag ccctgcacaa tcattacact    1320
cagaagagcc tgtccctgtc tcccggcaaa                                    1350
```

<210> SEQ ID NO 281
<211> LENGTH: 120
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 281

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 282
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 282
gaggtgcagc tggtggaaag cggaggagga ctggtgcagc caggaggatc tctgcgactg      60
agttgcgccg cttcaggatt caacatcaag gacacctaca ttcactgggt gcgacaggct     120
ccaggaaaag gactggagtg ggtggctcga atctatccca ctaatggata cacccggtat     180
gccgactccg tgaaggggag gtttactatt agcgccgata catccaaaaa cactgcttac     240
ctgcagatga acagcctgcg agccgaagat accgctgtgt actattgcag tcgatgggga     300
ggagacggat tctacgctat ggattattgg ggacagggga ccctggtgac agtgagctcc     360

<210> SEQ ID NO 283
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Gly Phe Asn Ile Lys Asp Thr Tyr
1               5

<210> SEQ ID NO 284
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
ggattcaaca tcaaggacac ctac      24

<210> SEQ ID NO 285
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Ser Arg Trp Gly Gly Asp Gly Phe Tyr Ala Met Asp Tyr
1               5                   10

<210> SEQ ID NO 286
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
agtcgatggg gaggagacgg attctacgct atggattat                              39

<210> SEQ ID NO 287
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Ile Tyr Pro Thr Asn Gly Tyr Thr
1               5

<210> SEQ ID NO 288
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 288
atctatccca ctaatggata cacc                                             24

<210> SEQ ID NO 289
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 290
<211> LENGTH: 294
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 290
gcctctacca agggcccag tgtgtttccc ctggctcctt ctagtaaatc cacctctgga        60
gggacagccg ctctgggatg tctggtgaag gactatttcc ccgagcctgt gaccgtgagt     120
tggaactcag gcgccctgac aagcggagtg cacactttc ctgctgtgct gcagtcaagc     180

```
gggctgtact ccctgtcctc tgtggtgaca gtgccaagtt caagcctggg cacacagact    240
tatatctgca acgtgaatca taagccctca aatacaaaag tggacaagaa agtg          294
```

<210> SEQ ID NO 291
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110
```

<210> SEQ ID NO 292
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 292

```
gctccagaac tgctgggagg acctagcgtg ttcctgtttc ccccttaagcc aaaagacact    60 ctgatgattt ccaggactcc cgaggtgacc tgcgtggtgg tggacgtgtc tcacgaggac    120
cccgaagtga agttcaactg gtacgtggat ggcgtggaag tgcataatgc aaagacaaaa    180
ccaagagagg aacagtacaa ctccacttat cgcgtcgtga gcgtgctgac cgtgctgcac    240
caggactggc tgaacgggaa ggagtataag tgcaaagtca gtaataaggc cctgcctgct    300
ccaatcgaaa aaaccatctc taaggccaaa                                     330
```

<210> SEQ ID NO 293
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 293

```
Gly Gln Pro Arg Glu Pro Gln Val Tyr Val Leu Pro Pro Ser Arg Asp
1               5                   10                  15

Glu Leu Thr Lys Asn Gln Val Ser Leu Leu Cys Leu Val Lys Gly Phe
            20                  25                  30

Tyr Pro Ser Asp Ile Ala Val Glu Trp Glu Ser Asn Gly Gln Pro Glu
        35                  40                  45
```

```
Asn Asn Tyr Leu Thr Trp Pro Pro Val Leu Asp Ser Asp Gly Ser Phe
        50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly
            100                 105
```

<210> SEQ ID NO 294
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 294

```
ggccagccaa gggagcccca ggtgtacgtg ctgccaccca gcagagacga actgaccaag      60
aaccaggtgt ccctgctgtg tctggtgaaa ggcttctatc ctagtgatat tgctgtggag     120
tgggaatcaa atggacagcc agagaacaat tacctgacct ggcctccagt gctggacagc     180
gatggcagct tcttcctgta ttccaagctg acagtggata atctcgatg gcagcagggg     240 aacgtgttta gttgttcagt gatgcatgaa gccctgcaca tcattacac tcagaagagc     300 ctgtccctgt ctcccggc                                                   318
```

<210> SEQ ID NO 295
<211> LENGTH: 480
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 295

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asn Thr Ala
             20                  25                  30

Val Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Gly Gly Ser Gly Gly
            100                 105                 110

Gly Ser Gly Gly Gly Ser Gly Gly Gly Ser Gly Gly Gly Ser Gly Glu
        115                 120                 125

Val Gln Leu Val Glu Ser Gly Gly Gly Leu Val Gln Pro Gly Gly Ser
    130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Gly Leu Glu Trp Val Ala
                165                 170                 175
```

Arg Ile Tyr Pro Thr Asn Gly Tyr Thr Arg Tyr Ala Asp Ser Val Lys
            180                 185                 190

Gly Arg Phe Thr Ile Ser Ala Asp Thr Ser Lys Asn Thr Ala Tyr Leu
        195                 200                 205

Gln Met Asn Ser Leu Arg Ala Glu Asp Thr Ala Val Tyr Tyr Cys Ser
    210                 215                 220

Arg Trp Gly Gly Asp Gly Phe Tyr Ala Met Asp Tyr Trp Gly Gln Gly
225                 230                 235                 240

Thr Leu Val Thr Val Ser Ser Ala Ala Glu Pro Lys Ser Ser Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Val
    370                 375                 380

Leu Pro Pro Ser Arg Asp Glu Leu Thr Lys Asn Gln Val Ser Leu Leu
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Leu Thr Trp Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

<210> SEQ ID NO 296
<211> LENGTH: 1440
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 296
gacattcaga tgacacagag ccccagctcc ctgagtgctt cagtcggcga cagggtgact      60
atcacctgcc gcgcatccca ggatgtcaac accgctgtgg catggtacca gcagaagcct    120
ggaaaagccc caaagctgct gatctacagc gcttccttcc tgtattctgg cgtgccaagt    180
cggttttctg gaagtagatc aggcactgac ttcacactga ctatctctag tctgcagccc    240
gaagattttg ccacctacta ttgccagcag cactatacca cacccctac attcggacag    300

-continued

```
ggcactaaag tggagattaa gggcgggtca ggcggaggga gcggaggagg gtccggagga    360
gggtctggag gagggagtgg agaggtccag ctggtggaat ctggaggagg actggtgcag    420
cctggaggct cactgcgact gagctgtgcc gcttccggct ttaacatcaa agacacatac    480
attcattggg tcaggcaggc caccagggaag gactggaat gggtggcccg catctatccc    540
acaaatgggt acactcgata tgccgacagc gtgaaggac ggtttaccat ttctgctgat    600
accagtaaga acacagcata cctgcagatg aacagcctgc gcgcagagga tacagccgtg    660
tactattgca gtcgatgggg gggagacggc ttctacgcca tggattattg gggccagggg    720
actctggtca ccgtgtcaag cgcagccgaa cctaaatcct ctgacaagac ccacacatgc    780
ccaccctgtc ctgctccaga gctgctggga ggaccatccg tgttcctgtt tcctccaaag    840
cctaaagata cactgatgat tagccgcact cccgaagtca cctgtgtggt cgtggacgtg    900
tcccacgagg accccgaagt caagttcaac tggtacgtgg acggcgtcga ggtgcataat    960
gccaagacta aaccaagaga ggaacagtac aattcaacct atagggtcgt gagcgtcctg   1020
acagtgctgc atcaggattg gctgaacggc aaggagtata agtgcaaagt gtctaacaag   1080
gccctgcccg ctcctatcga gaagactatt agcaaggcaa agggcagcc acgggaaccc   1140 caggtctacg tgctgccccc tagcagagac gagctgacca aaaaccaggt ctccctgctg   1200
tgtctggtga agggcttta tcctagtgat atcgctgtgg agtgggaatc aaatgggcag   1260
ccagaaaaca attcctgac atggccaccc gtgctggaca gcgatgggtc cttctttctg   1320
tattccaaac tgactgtgga caagtctaga tggcagcagg gaaacgtctt cagctgttcc   1380
gtgatgcacg aggccctgca caatcattac acccagaagt ctctgagtct gtcacccggc   1440
```

<210> SEQ ID NO 297
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105
```

<210> SEQ ID NO 298
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 298

```
gacattcaga tgacacagag ccccagctcc ctgagtgctt cagtcggcga cagggtgact    60
atcacctgcc gcgcatccca ggatgtcaac accgctgtgg catggtacca gcagaagcct   120
ggaaaagccc caaagctgct gatctacagc gcttccttcc tgtattctgg cgtgccaagt   180
cggttttctg gaagtagatc aggcactgac ttcacactga ctatctctag tctgcagccc   240
gaagattttg ccacctacta ttgccagcag cactatacca cccccctac attcggacag    300
ggcactaaag tggagattaa g                                             321
```

<210> SEQ ID NO 299
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Gln Asp Val Asn Thr Ala
1               5

<210> SEQ ID NO 300
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 300
caggatgtca acaccgct                                                  18

<210> SEQ ID NO 301
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Gln Gln His Tyr Thr Thr Pro Pro Thr
1               5

<210> SEQ ID NO 302
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
cagcagcact ataccacacc ccctaca                                        27

<210> SEQ ID NO 303
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Ser Ala Ser
1

<210> SEQ ID NO 304
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304 agcgcttcc                                                                9

<210> SEQ ID NO 305
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 305

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 306
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 306
gaggtccagc tggtggaatc tggaggagga ctggtgcagc ctggaggctc actgcgactg      60
agctgtgccg cttccggctt taacatcaaa gacacataca ttcattgggt caggcaggca     120
ccagggaagg gactggaatg gtggcccgc atctatccca caaatgggta cactcgatat      180
gccgacagcg tgaaaggacg gtttaccatt tctgctgata ccagtaagaa cacagcatac     240
ctgcagatga acagcctgcg cgcagaggat acagccgtgt actattgcag tcgatggggg     300
ggagacggct tctacgccat ggattattgg ggccagggga ctctggtcac cgtgtcaagc     360

<210> SEQ ID NO 307
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Gly Phe Asn Ile Lys Asp Thr Tyr
1               5

<210> SEQ ID NO 308
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
ggctttaaca tcaaagacac atac                                            24

<210> SEQ ID NO 309
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Ser Arg Trp Gly Gly Asp Gly Phe Tyr Ala Met Asp Tyr
1               5                   10

<210> SEQ ID NO 310
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
agtcgatggg ggggagacgg cttctacgcc atggattat                            39

<210> SEQ ID NO 311
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Ile Tyr Pro Thr Asn Gly Tyr Thr
1               5

<210> SEQ ID NO 312
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 312
atctatccca caaatgggta cact                                            24

<210> SEQ ID NO 313
<211> LENGTH: 110

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 313

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 314
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 314
gctccagagc tgctgggagg accatccgtg ttcctgtttc ctccaaagcc taaagataca     60
ctgatgatta gccgcactcc cgaagtcacc tgtgtggtcg tggacgtgtc ccacgaggac    120
cccgaagtca agttcaactg gtacgtggac ggcgtcgagg tgcataatgc aagactaaa    180 ccaagagagg aacagtacaa ttcaacctat agggtcgtga gcgtcctgac agtgctgcat    240
caggattggc tgaacggcaa ggagtataag tgcaaagtgt ctaacaaggc cctgcccgct    300
cctatcgaga agactattag caaggcaaaa                                     330

<210> SEQ ID NO 315
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 315

Gly Gln Pro Arg Glu Pro Gln Val Tyr Val Leu Pro Pro Ser Arg Asp
1               5                   10                  15

Glu Leu Thr Lys Asn Gln Val Ser Leu Leu Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Leu Thr Trp Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
```

```
                        85                  90                  95
Thr Gln Lys Ser Leu Ser Leu Ser Pro Gly
                   100                 105

<210> SEQ ID NO 316
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 316
gggcagccac gggaacccca ggtctacgtg ctgcccccta gcagagacga gctgaccaaa      60
aaccaggtct ccctgctgtg tctggtgaag ggcttttatc ctagtgatat cgctgtggag     120
tgggaatcaa atgggcagcc agaaaacaat tacctgacat ggccacccgt gctggacagc     180
gatgggtcct tctttctgta ttccaaactg actgtggaca gtctagatg gcagcaggga      240 aacgtcttca gctgttccgt gatgcacgag gccctgcaca tcattacac ccagaagtct      300 ctgagtctgt cacccggc                                                   318

<210> SEQ ID NO 317
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 317

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
```

<210> SEQ ID NO 318
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 318

```
gacatccaga tgacccagtc tccatcctcc ctgtctgcat ctgtaggaga cagagtcacc    60
atcacttgcc gggcaagtca ggacgttaac accgctgtag cttggtatca gcagaaacca   120
gggaaagccc ctaagctcct gatctattct gcatcctttt tgtacagtgg ggtcccatca   180
aggttcagtg gcagtcgatc tgggacagat ttcactctca ccatcagcag tctgcaacct   240
gaagattttg caacttacta ctgtcaacag cattacacta ccccacccac tttcggccaa   300
gggaccaaag tggagatcaa acgaactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccaa   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gt                      642
```

<210> SEQ ID NO 319
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 319

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 320
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 320

```
gacatccaga tgacccagtc tccatcctcc ctgtctgcat ctgtaggaga cagagtcacc    60
```

```
atcacttgcc gggcaagtca ggacgttaac accgctgtag cttggtatca gcagaaacca    120
gggaaagccc ctaagctcct gatctattct gcatcctttt tgtacagtgg ggtcccatca    180
aggttcagtg gcagtcgatc tgggacagat ttcactctca ccatcagcag tctgcaacct    240
gaagattttg caacttacta ctgtcaacag cattacacta ccccacccac tttcggccaa    300
gggaccaaag tggagatcaa a                                              321
```

<210> SEQ ID NO 321
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Gln Asp Val Asn Thr Ala
1               5

<210> SEQ ID NO 322
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
caggacgtta acaccgct                                                   18

<210> SEQ ID NO 323
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Gln Gln His Tyr Thr Thr Pro Pro Thr
1               5

<210> SEQ ID NO 324
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
caacagcatt acactacccc acccact                                         27

<210> SEQ ID NO 325
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Ser Ala Ser
1

<210> SEQ ID NO 326
<211> LENGTH: 9
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 326 tctgcatcc                                                                  9

<210> SEQ ID NO 327
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 327

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 328
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 328
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccaag agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg t                                                321

<210> SEQ ID NO 329
<211> LENGTH: 231
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 329

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
            85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Val Leu Pro Pro Ser Arg Asp Glu Leu Thr
130                 135                 140

Lys Asn Gln Val Ser Leu Leu Cys Leu Val Lys Gly Phe Tyr Pro Ser
145                 150                 155                 160

Asp Ile Ala Val Glu Trp Glu Ser Asn Gly Gln Pro Glu Asn Asn Tyr
            165                 170                 175

Leu Thr Trp Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
210                 215                 220

Ser Leu Ser Leu Ser Pro Gly
225                 230

<210> SEQ ID NO 330
<211> LENGTH: 693
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 330
gaacctaaat ccagcgacaa gacccacaca tgcccccctt gtccagctcc agaactgctg      60
ggaggaccaa gcgtgttcct gtttccaccc aagcccaaag atacactgat gatcagccga     120
actcccgagg tcacctgcgt ggtcgtggac gtgtcccacg aggacccccga agtcaagttc     180 aactggtacg tggacggcgt cgaagtgcat aatgcaaaga ctaaaccacg ggaggaacag     240
tacaactcta catatagagt cgtgagtgtc ctgactgtgc tgcatcagga ttggctgaac     300
ggcaaagagt ataagtgcaa agtgtctaat aaggccctgc ctgctccaat cgagaaaact     360
attagtaagg caaaagggca gcccagggaa cctcaggtct acgtgctgcc tccaagtcgc     420
gacgagctga ccaagaacca ggtctcactg ctgtgtctgg tgaaaggatt ctatccttcc     480
gatattgccg tggagtggga atctaatggc cagccagaga caattacct gacctggccc      540 cctgtgctgg acagcgatgg gtccttcttt ctgtattcaa agctgacagt ggacaaaagc     600
agatggcagc agggaaacgt ctttagctgt tccgtgatgc acgaagccct gcacaatcat     660
tacacccaga gtctctgag tctgtcacct ggc                                  693

<210> SEQ ID NO 331
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 331

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 332
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 332
gctccagaac tgctgggagg accaagcgtg ttcctgtttc cacccaagcc caaagataca    60
ctgatgatca gccgaactcc cgaggtcacc tgcgtggtcg tggacgtgtc ccacgaggac   120
cccgaagtca agttcaactg gtacgtggac ggcgtcgaag tgcataatgc aaagactaaa   180
ccacgggagg aacagtacaa ctctacatat agagtcgtga gtgtcctgac tgtgctgcat   240
caggattggc tgaacggcaa agagtataag tgcaaagtgt ctaataaggc cctgcctgct   300
ccaatcgaga aaactattag taaggcaaaa                                    330

<210> SEQ ID NO 333
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 333

Gly Gln Pro Arg Glu Pro Gln Val Tyr Val Leu Pro Pro Ser Arg Asp
1               5                   10                  15

Glu Leu Thr Lys Asn Gln Val Ser Leu Leu Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Leu Thr Trp Pro Pro Val Leu Asp Ser Asp Gly Ser Phe
    50                  55                  60

```
Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly
            100                 105

<210> SEQ ID NO 334
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 334
gggcagccca gggaacctca ggtctacgtg ctgcctccaa gtcgcgacga gctgaccaag      60
aaccaggtct cactgctgtg tctggtgaaa ggattctatc cttccgatat tgccgtggag     120
tgggaatcta atggccagcc agagaacaat tacctgacct ggccccctgt gctggacagc     180
gatgggtcct tctttctgta ttcaaagctg acagtggaca aaagcagatg gcagcaggga     240
aacgtcttta gctgttccgt gatgcacgaa gccctgcaca tcattacac ccagaagtct     300 ctgagtctgt cacctggc                                                  318

<210> SEQ ID NO 335
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Val Asn Pro Asn Ser Gly Gly Ser
1               5

<210> SEQ ID NO 336
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Ala Arg Asn Leu Gly Pro Ser Phe Tyr Phe Asp Tyr
1               5                   10

<210> SEQ ID NO 337
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Gly Phe Thr Phe Thr Asp Tyr Thr
1               5

<210> SEQ ID NO 338
<211> LENGTH: 3
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 338

Ser Ala Ser
1

<210> SEQ ID NO 339
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Gln Gln Tyr Tyr Ile Tyr Pro Tyr Thr
1               5

<210> SEQ ID NO 340
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Gln Asp Val Ser Ile Gly
1               5

<210> SEQ ID NO 341
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Ile Tyr Pro Thr Asn Gly Tyr Thr
1               5

<210> SEQ ID NO 342
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Ser Arg Trp Gly Gly Asp Gly Phe Tyr Ala Met Asp Tyr
1               5                   10

<210> SEQ ID NO 343
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Gly Phe Asn Ile Lys Asp Thr Tyr
1               5
```

```
<210> SEQ ID NO 344
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Ser Ala Ser
1

<210> SEQ ID NO 345
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Gln Gln His Tyr Thr Thr Pro Pro Thr
1               5

<210> SEQ ID NO 346
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Gln Asp Val Asn Thr Ala
1               5

<210> SEQ ID NO 347
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Gln Gln Tyr Tyr Ile Tyr Pro Ala Thr
1               5

<210> SEQ ID NO 348
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Gly Phe Thr Phe Ala Asp Tyr Thr
1               5

<210> SEQ ID NO 349
<211> LENGTH: 607
<212> TYPE: PRT
<213> ORGANISM: Homo sapiens

<400> SEQUENCE: 349

Thr Gln Val Cys Thr Gly Thr Asp Met Lys Leu Arg Leu Pro Ala Ser
```

-continued

```
1               5                   10                  15
Pro Glu Thr His Leu Asp Met Leu Arg His Leu Tyr Gln Gly Cys Gln
                20                  25                  30
Val Val Gln Gly Asn Leu Glu Leu Thr Tyr Leu Pro Thr Asn Ala Ser
                35                  40                  45
Leu Ser Phe Leu Gln Asp Ile Gln Glu Val Gln Gly Tyr Val Leu Ile
                50                  55                  60
Ala His Asn Gln Val Arg Gln Val Pro Leu Gln Arg Leu Arg Ile Val
65                  70                  75                  80
Arg Gly Thr Gln Leu Phe Glu Asp Asn Tyr Ala Leu Ala Val Leu Asp
                85                  90                  95
Asn Gly Asp Pro Leu Asn Asn Thr Thr Pro Val Thr Gly Ala Ser Pro
                100                 105                 110
Gly Gly Leu Arg Glu Leu Gln Leu Arg Ser Leu Thr Glu Ile Leu Lys
                115                 120                 125
Gly Gly Val Leu Ile Gln Arg Asn Pro Gln Leu Cys Tyr Gln Asp Thr
                130                 135                 140
Ile Leu Trp Lys Asp Ile Phe His Lys Asn Asn Gln Leu Ala Leu Thr
145                 150                 155                 160
Leu Ile Asp Thr Asn Arg Ser Arg Ala Cys His Pro Cys Ser Pro Met
                165                 170                 175
Cys Lys Gly Ser Arg Cys Trp Gly Glu Ser Ser Glu Asp Cys Gln Ser
                180                 185                 190
Leu Thr Arg Thr Val Cys Ala Gly Gly Cys Ala Arg Cys Lys Gly Pro
                195                 200                 205
Leu Pro Thr Asp Cys Cys His Glu Gln Cys Ala Ala Gly Cys Thr Gly
                210                 215                 220
Pro Lys His Ser Asp Cys Leu Ala Cys Leu His Phe Asn His Ser Gly
225                 230                 235                 240
Ile Cys Glu Leu His Cys Pro Ala Leu Val Thr Tyr Asn Thr Asp Thr
                245                 250                 255
Phe Glu Ser Met Pro Asn Pro Glu Gly Arg Tyr Thr Phe Gly Ala Ser
                260                 265                 270
Cys Val Thr Ala Cys Pro Tyr Asn Tyr Leu Ser Thr Asp Val Gly Ser
                275                 280                 285
Cys Thr Leu Val Cys Pro Leu His Asn Gln Glu Val Thr Ala Glu Asp
                290                 295                 300
Gly Thr Gln Arg Cys Glu Lys Cys Ser Lys Pro Cys Ala Arg Val Cys
305                 310                 315                 320
Tyr Gly Leu Gly Met Glu His Leu Arg Glu Val Arg Ala Val Thr Ser
                325                 330                 335
Ala Asn Ile Gln Glu Phe Ala Gly Cys Lys Lys Ile Phe Gly Ser Leu
                340                 345                 350
Ala Phe Leu Pro Glu Ser Phe Asp Gly Asp Pro Ala Ser Asn Thr Ala
                355                 360                 365
Pro Leu Gln Pro Glu Gln Leu Gln Val Phe Glu Thr Leu Glu Glu Ile
                370                 375                 380
Thr Gly Tyr Leu Tyr Ile Ser Ala Trp Pro Asp Ser Leu Pro Asp Leu
385                 390                 395                 400
Ser Val Phe Gln Asn Leu Gln Val Ile Arg Gly Arg Ile Leu His Asn
                405                 410                 415
Gly Ala Tyr Ser Leu Thr Leu Gln Gly Leu Gly Ile Ser Trp Leu Gly
                420                 425                 430
```

```
Leu Arg Ser Leu Arg Glu Leu Gly Ser Gly Leu Ala Leu Ile His His
            435                 440                 445

Asn Thr His Leu Cys Phe Val His Thr Val Pro Trp Asp Gln Leu Phe
450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
                    485                 490                 495

His Cys Trp Gly Pro Gly Pro Thr Gln Cys Val Asn Cys Ser Gln Phe
            500                 505                 510

Leu Arg Gly Gln Glu Cys Val Glu Cys Arg Val Leu Gln Gly Leu
            515                 520                 525

Pro Arg Glu Tyr Val Asn Ala Arg His Cys Leu Pro Cys His Pro Glu
            530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
                    565                 570                 575

Arg Cys Pro Ser Gly Val Lys Pro Asp Leu Ser Tyr Met Pro Ile Trp
            580                 585                 590

Lys Phe Pro Asp Glu Glu Gly Ala Cys Gln Pro Cys Pro Ile Asn
            595                 600                 605

<210> SEQ ID NO 350
<211> LENGTH: 217
<212> TYPE: PRT
<213> ORGANISM: Homo sapiens

<400> SEQUENCE: 350

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
```

```
                195                 200                 205
Lys Ser Leu Ser Leu Ser Pro Gly Lys
            210                 215
```